US008119631B2

(12) United States Patent
Batchelor et al.

(10) Patent No.: US 8,119,631 B2
(45) Date of Patent: Feb. 21, 2012

(54) INHIBITORS OF INTERLEUKIN-1β CONVERTING ENZYME

(75) Inventors: Mark James Batchelor, Cumnor Hill (GB); David Bebbington, Pewsey (GB); Guy W. Bemis, Arlington, MA (US); Wolf Herman Fridman, Paris (FR); Roger John Gillespie, Nr. Malmesbury (GB); Julian M. C. Golec, Swindon (GB); Yong Gu, Brookline, MA (US); David J. Lauffer, Stow, MA (US); David J. Livingston, Newtonville, MA (US); Saroop Singh Matharu, Cricklade (GB); Michael D. Mullican, Needham, MA (US); Mark A. Murcko, Holliston, MA (US); Robert Murdoch, Highworth (GB); Philip Nyce, Milbury, MA (US); Andrea L. C. Robidoux, Andover, MA (US); Michael Su, Newton, MA (US); M. Woods Wannamaker, Stow, MA (US); Keith P. Wilson, Hopkinton, MA (US); Robert E. Zelle, Stow, MA (US)

(73) Assignee: Vertex Pharmaceuticals Incorporated, Cambridge, MA (US)

(*) Notice: Subject to any disclaimer, the term of this patent is extended or adjusted under 35 U.S.C. 154(b) by 0 days.

(21) Appl. No.: 12/786,221

(22) Filed: May 24, 2010

(65) Prior Publication Data

US 2011/0178069 A1     Jul. 21, 2011

Related U.S. Application Data

(60) Division of application No. 11/655,938, filed on Jan. 18, 2007, now Pat. No. 7,790,713, which is a continuation of application No. 10/999,865, filed on Nov. 29, 2004, now abandoned, which is a division of application No. 10/058,522, filed on Jan. 28, 2002, now abandoned, which is a division of application No. 09/773,477, filed on Jan. 31, 2001, now Pat. No. 6,423,840, which is a division of application No. 08/761,483, filed on Dec. 6, 1996, now Pat. No. 6,204,261, and a continuation-in-part of application No. 08/712,878, filed on Sep. 12, 1996, now Pat. No. 5,985,863, which is a continuation-in-part of application No. 08/598,332, filed on Feb. 8, 1996, now Pat. No. 5,874,424, which is a continuation-in-part of application No. 08/575,641, filed on Dec. 20, 1995, now Pat. No. 6,008,217.

(60) Provisional application No. 60/031,495, filed on Nov. 26, 1996.

(51) Int. Cl.
*C07D 243/12* (2006.01)
*C07D 255/04* (2006.01)
*C07D 257/10* (2006.01)
*C07D 259/00* (2006.01)
*A61K 31/55* (2006.01)
*A61P 29/00* (2006.01)

(52) U.S. Cl. ......... 514/221; 540/501; 540/517; 540/518

(58) Field of Classification Search .................. 540/501, 540/517, 518; 514/221
See application file for complete search history.

(56) References Cited

U.S. PATENT DOCUMENTS

| | | |
|---|---|---|
| 4,276,298 A | 6/1981 | Jones |
| 4,369,183 A | 1/1983 | Jones |
| 4,499,295 A | 2/1985 | Mueller |
| 4,551,279 A | 11/1985 | Mueller |
| 4,584,387 A | 4/1986 | Mukaiyama |
| 4,584,397 A | 4/1986 | Mueller |
| 4,968,607 A | 11/1990 | Dower |
| 5,008,245 A | 4/1991 | Digenis |
| 5,055,451 A | 10/1991 | Krantz |
| 5,081,228 A | 1/1992 | Dower |
| 5,158,936 A | 10/1992 | Krantz |
| 5,180,812 A | 1/1993 | Dower |
| 5,374,623 A | 12/1994 | Zimmerman |
| 5,411,985 A | 5/1995 | Bills |
| 5,416,013 A | 5/1995 | Black |
| 5,430,128 A | 7/1995 | Chapman |

(Continued)

FOREIGN PATENT DOCUMENTS

AU        A-64514/94        12/1994

(Continued)

OTHER PUBLICATIONS

Ahmed et al., "A Role for Caspase-1 and -3 in the Pathology of Experimental Allergic Encephalomyelitis," American Journal of Pathology, 161:1577-1586 (2002).

(Continued)

*Primary Examiner* — Bruck Kifle
(74) *Attorney, Agent, or Firm* — Ropes & Gray LLP; James F. Haley, Jr.; Brian M. Gummow

(57) ABSTRACT

The present invention relates to novel classes of compounds which are inhibitors of interleukin-1β converting enzyme. The ICE inhibitors of this invention are characterized by specific structural and physicochemical features. This invention also relates to pharmaceutical compositions comprising these compounds. The compounds and pharmaceutical compositions of this invention are particularly well suited for inhibiting ICE activity and consequently, may be advantageously used as agents against IL-1-, apoptosis-, IGIF-, and IFN-γ-mediated diseases, inflammatory diseases, autoimmune diseases, destructive bone disorders, proliferative disorders, infectious diseases, degenerative diseases, and necrotic diseases. This invention also relates to methods for inhibiting ICE activity, for treating interleukin-1-, apoptosis-, IGIF- and IFN-γ-mediated diseases and decreasing IGIF and IFN-γ production using the compounds and compositions of this invention. This invention also relates to methods for preparing N-acylamino compounds.

15 Claims, 11 Drawing Sheets

U.S. PATENT DOCUMENTS

| | | | |
|---|---|---|---|
| 5,434,248 | A | 7/1995 | Chapman |
| 5,462,939 | A | 10/1995 | Dolle |
| 5,486,623 | A | 1/1996 | Zimmerman |
| 5,498,616 | A | 3/1996 | Mallamo |
| 5,498,695 | A | 3/1996 | Daumy |
| 5,552,400 | A | 9/1996 | Dolle |
| 5,565,430 | A | 10/1996 | Dolle |
| 5,585,357 | A | 12/1996 | Dolle |
| 5,585,486 | A | 12/1996 | Dolle |
| 5,639,745 | A | 6/1997 | Dolle |
| 5,656,627 | A | 8/1997 | Bemis |
| 5,670,494 | A | 9/1997 | Dolle |
| 5,716,929 | A | 2/1998 | Bemis |
| 5,756,466 | A | 5/1998 | Bemis |
| 5,847,135 | A | 12/1998 | Bemis |
| 5,874,424 | A | 2/1999 | Barchelor |
| 5,973,111 | A | 10/1999 | Bemis |
| 6,025,147 | A | 2/2000 | Bemis |
| 6,103,711 | A | 8/2000 | Bemis |
| 6,184,244 | B1 | 2/2001 | Karanewshky |
| 6,204,261 | B1 | 3/2001 | Batchelor |
| 6,258,948 | B1 | 7/2001 | Batchelor |
| 6,420,522 | B1 | 7/2002 | Bemis |
| 6,423,840 | B1 | 7/2002 | Batchelor |
| 7,288,624 | B2 | 10/2007 | Bemis |
| 2008/0039449 | A1 | 2/2008 | Batchelor |

FOREIGN PATENT DOCUMENTS

| | | |
|---|---|---|
| EP | A-0 135 349 | 9/1984 |
| EP | A-0 275 101 | 7/1988 |
| EP | A-0 410 411 | 1/1991 |
| EP | A-0 417 721 | 3/1991 |
| EP | A-0 479 489 | 4/1992 |
| EP | A-0 504 938 | 9/1992 |
| EP | A-0 519 748 | 12/1992 |
| EP | A-0 525 420 | 2/1993 |
| EP | A-0 528 487 | 2/1993 |
| EP | A-0 529 713 | 3/1993 |
| EP | A-0 533 226 | 3/1993 |
| EP | A-0 533 350 | 3/1993 |
| EP | A-0 547 699 | 6/1993 |
| EP | A-0 618 223 | 10/1994 |
| EP | A-0 623 592 | 11/1994 |
| EP | A-0 623 606 | 11/1994 |
| EP | A-0 628 550 | 12/1994 |
| EP | A-0 644 197 | 3/1995 |
| EP | A-0 644 198 | 3/1995 |
| WO | WO 90/13549 | 11/1990 |
| WO | WO 91/5577 | 10/1991 |
| WO | WO 91/18903 | 12/1991 |
| WO | WO 93/05071 | 3/1993 |
| WO | WO 93/09135 | 5/1993 |
| WO | WO 93/14777 | 8/1993 |
| WO | WO 93/16710 | 9/1993 |
| WO | WO 93/25683 | 12/1993 |
| WO | WO 93/25685 | 12/1993 |
| WO | WO 93/25694 | 12/1993 |
| WO | WO 94/00154 | 1/1994 |
| WO | WO 94/03480 | 2/1994 |
| WO | WO 95/00160 | 1/1995 |
| WO | WO 95/05192 | 2/1995 |
| WO | WO 95/16706 | 6/1995 |
| WO | WO 95/26958 | 10/1995 |
| WO | WO 95/29672 | 11/1995 |
| WO | WO 95/33751 | 12/1995 |
| WO | WO 95/33753 | 12/1995 |
| WO | WO 95/35308 | 12/1995 |
| WO | WO 96/03982 | 2/1996 |
| WO | WO 96/25408 | 8/1996 |

OTHER PUBLICATIONS

Alberg et al., "Structure-Based Design of a Cyclophilin-Calcineurin Bridging Ligand," Science, 262(5131):248-250 (1993).

Andrews, "Functional Groups, Drug-Receptor Interactions and Drug Design," Trends in Pharmacological Sciences, 7:148-151 (1986).

Antonopoulos et al., "Functional caspase-1 is required for Langerhans cell migration and optimal contact sensitization in mice," Journal of Immunology, 166:3672-3677(2001).

Appelt et al, "Design of Enzyme Inhibitors Using iterative Protein crystallographic Analysis," Journal of Medicinal Chemistry, 34(7):1925-1934 (1991).

Ator et al., "Interleukin-1β Converting Enzyme: Biology and the Chemistry of Inhibitors," Current Pharmaceutical Design, 1:191-210 (1995).

Ator, "Peptide and Non-peptide inhibitors of interleukin-1β Converting Enzyme," Cambridge Healthtech Institute (Inflammatory Cytokine Antagonists Targets, Strategies, and Indication), (1994).

Baker et al., "The Thiol Proteases: Structure and Mechanism," Biological Macromolecules and Assemblies, 3:313-368 (1987).

Baldwin et al., "Thienothiopyran-2-sulfonamides: Novel Topically Active Carbonic Anhydrase Inhibitors for the Treatment of Glaucoma," Journal of Medicinal Chemistry, 32(12):2510-2513 (1989).

Barinaga, "Death Gives Birth to the Nervous System, But How?," Science, 259(5096):762-763 (1993).

Bartlett et al., "Caveat: A Program to Facilitate the Structure-derived Design of Biologically Active Molecules," Molecular Recognition: Chemical and Biochemical Problems, 78:182-196 (1989).

Bender et al., "Pharmacological Modulation of Interleukin-1," Annual Reports in Medicinal Chemistry, 25:185-193 (1989).

Black et al., "Activation of Interleukin-1β by a Co-induced Protease," FEBS Letters, 247:386-390 (1989).

Boermeester et al., "Interleukin-1 Blockade Attenuates Mediator Release and Dysregulation of the Hemostatic Mechanism During Human Sepsis," Archivese of Surgery, 130:739-748 (1995).

Böhm, "The Computer Program LUDI: A New Method for the De Novo Design of Enzyme inhibitors," Journal of Computer-Aided Molecular Design, 6:61-78 (1992).

Bonifati et al., "Interleukin-1-beta, Interleukin-6, and Interferon-gamma in Suction Blister Fluids of Involved and Uninvolved skin and in Sera of Psoriatic Patients," Acta Derm Venerol (Stockh), Suppl. 186:23-24 (1994).

Breitner et al., "Inverse Association of Anti-inflammatory Treatments and Alzheimer's Disease: Initial Results of a Co-twin Control Study," Neurology, 44:227-232 (1994).

Brooks et al., "CHARMM: A Program for Macromolecular Energy, Minimization, and Dynamics Calculations," Journal of Computational Chemistry, 4:187-217 (1983).

Brünger et al., "Slow-Cooling Protocols for Crystallographic Refinement by Simulated Annealing," Acta Crystallographica, A46:585-593 (1990).

Brünger, "Extension of Molecular Replacement: A New Search Strategy Based on Patterson Correlation Refinement," Acta Crystallographica, A46:46-57 (1990).

Burkett et al., "Methods for the Computation of Molecular Geometry" Molecular Mechanics, 3: 59-78 (1982).

Carson, "Ribbons 2.0," Journal of Applied Crystallography, 24:958-961 (1991).

Casano et al., "The Structure and Complete Nucleotide Sequence of the Murine Gene Encoding Interleukin-1β Converting Enzyme (ICE)," Genomics,.20:474-481 (1994).

Cerretti et al., "Molecular Cloning of the Interleukin-1β Converting Enzyme," Bioorganic and Medicinal Chemistry Letters, 2:613-618 (1992).

Chapman, "Synthesis of a Potent, Reversible Inhibitor of Interleukin-1β Converting Enzyme," Bioorganic and Medicinal Chemistry Letters, 2:613-618 (1992).

Chubinskaya et al., "Chondrocyte Matrix Metalloproteinase-8: Up-regulation of Neutrophil Collagenase by Interleukin 1β in Human Cartilage from Knee and Ankle Joints," Laboratory Investigation, 74(1):232-249 (1996).

Cohen et al., "Molecular Modeling Software and Methods for Medicinal Chemistry," Journal of Medicinal Chemistry, 33:883-894 (1990).

Cohen, "Drug Design in Three Dimensions," Advances in Drug Research, 14:41-145 (1985).

Cohen, "Rational Drug Design and Molecular Modeling," Drugs of the Future, 10:311-328 (1985).

Cominelli et al., "Interleukin-1 and Interleukin-1 Receptor Antagonist in Inflammatory Bowel Disease," Alimentary Pharmacology and Therapeutics, 10(2):49-53 (1996).

Davies et al., "Protein Crystallization: Micro Techniques Involving Vapor Diffusion," Methods in Enzymology, 22:266-269 (1971).

Debets et al. "Enhanced production of biologically active interleukin-1α and interleuking-1β by psoriatic epidermal cells ex vivo: evidence of increased cytosolic interleukin-1β levels and facilitated interleukin-1 release." European Journal of Immunology, 25:1624-16:30 (1995).

Dill, "Dominant Forces in Protein Folding," Biochemistry, 29:7133-7155 (1990).

Dinarello et al., "Anticytokine Strategies in the Treatment of the Systemic Inflammatory Response Syndrome," Journal of the American Medical Association, 269:1829-1835 (1993).

Dinarello, "Role of Interleukin-1 in Infectious Diseases," Immunological Reviews, 127:119-146 (1992).

Dolle et al., "Aspartyl α-((1-Phenyl-3-(trifluoromethyl)-pyrazol-5-yl)oxy)methyl Ketones as Interleukin-1β Converting Enzyme Inhibitors. Significance of the P1 and P3 Amido Nitrogens for Enzyme-Peptide Inhibitor Binding," Journal of Medicinal Chemistry, 37:3863-3865 (1994).

Dolle et al., "Aspartyl α-((Diphenylphosphinyl)oxy)methyl Ketones as Novel Inhibitors of Interleukin-1β Converting Enzyme. Utility of the Diphenylphosphinic Acid Leaving Group for the Inhibition of Cysteine Proteases," Journal of Medicinal Chemistry, 38:220-222 (1995).

Dolle et al., "P1 Aspartate-Based Peptide α-((2,6-Dichlorobenzoyl)oxy)methyl Ketones as Potent Time-Dependent Inhibitors of Interleukin-1β-Converting Enzyme," Journal of Medicinal Chemistry, 37:563-564 (1994).

Dolle et al., "Pyridazinodiazepines as a high-affinity, P2-P3 peptidomimetic class of interleukin-1 beta-converting enzyme inhibitor," Journal of Medicinal Chemistry, 40(13):1941-1946 (1997).

Ealick et al., "Application of Crystallographic and Modeling Methods in the Design of Purine Nucleoside Phosphorylase Inhibitors," PNAS, 88:11540-11544 (1991).

Edwards et al., "Design, Synthesis, and Kinetic Evaluation of a Unique Class of Elastase Inhibitors, the Peptidyl α-Ketobenzoxazoles, and the X-ray Crystal Structure of the Covalent Complex between Porcine Pancreatic Elastase and Ac-Ala-Pro-Val-2-Benzoxazole," Journal of the American Chemistry Society, 114:1854-1863 (1992).

Eklund et al., "Three-dimensional Structure of Horse Liver Alcohol Dehydrogenase at 2.4 A Resolution," Journal of Molecular Biology, 102(1):27-59 (1976).

Elford et al., "Reduction of Inflammation and Pyrexia in the Rat by Oral Administration of SDZ 224-015, an Inhibitor of the Interleukin-1β Converting Enzyme," British journal of Pharmacology, 115:601-606 (1995).

Endres et al., "Attenuation of Delayed Neuronal Death After Mild Focal Ischemia in Mice by Inhibition of the Caspase Family," Journal of Cerebral Blood Flow & Metabolism, 18:238-247 (1998).

Erickson et al., "Design, Activity, and 2.8 A Crystal Structure of a C2 Symmetric inhibitor Complexed to HIV-1 Protease," Science, 249:527-533.

Estrov et al., "Role of Interleukin-1 β Converting Enzyme (ICE) in Acute Myelogenous Leukemia Cell Proliferation and Programmed Cell Death,", Leukemia & Lymphoma, 24:379-391 (1997).

Fan et al., "Stimulation of Angiogenesis by Substance P and Interleukin-1 in the Rat and Its Inhibition by NK1 or Interleukin-1 Receptor Antagonists," British Journal of Pharmacology, 110:43-49 (1993).

Fauszt et al., "Inhibition of Interleukin-1β Converting Enzyme by Peptide Derivatives," Proc. of the 13th Am. Peptide. Symp., Jun. 20-25, 1993, Hodges,.R.S. and Smith, J.A., Eds., Peptides, pp. 589-591 (1994).

Fletcher, et al., "A Synthetic Inhibitor of Interleukin-1β Converting Enzyme Prevents Endotoxin-Induced Interleukin-1β Production In Vitro and In Vivo,", Journal of Interferon and Cytokine Research, 15:243-248 (1995).

Friedlander et al., "Inhibition of ICE Slows ALS in Mice," Nature, 388:31.

Furlan et al., "Caspase-1 Regulates the inflammatory Process Leading to Autoimmune Demyelination," Journal of Immunology, 163:2403-2409 (1999).

Gagliardini et al., "Prevention of Vertebrate Neuronal Death by the crmA Gene," Science, 263:826-828 (1994).

Geiger et al., "Neutralization of Interleukin-1β Activity in vivo with a Monoclonal Antibody Alleviates Collagen-induced Arthritis in DBA/1 Mice and Prevents the Associated Acute-phase Response," Clinical and Experimental Rheumatology, 11:515-522 (1993).

Giannis et al., "Peptidomimetics for Receptor Ligands-Discovery, Development, and Medical Perspectives," Angewandte Chemie international Edition, 32:1244-1267 (1993).

Goodford, "A Computational Procedure for Determining Energetically Favorable Binding Sites on Biologically Important Macromolecules," Journal of Medicinal Chemistry, 28:849-857 (1985).

Goodsell et al., "Automated Docking of Substrates to Proteins by Simulated Annealing," Proteins: Structure, Function, and Genetics, 8:195-202 (1990).

Graybill et al., "Preparation and Evaluation of Peptide Aspartyl Hemiacetals as Reversible Inhibitors of Interleukin-1β Cnverting Enzyme (ICE)," International Journal of Peptide and Protein Research, 44:173-182 (1994).

Gray-Bill et al., "Synthesis and Evaluation of Diacylhydrazines as Inhibitors of the interleukin-1β Converting Enzyme (ICE)," Bioorganic and Medicinal Chemistry Letters, 5:1197-1202 (1995).

Graybill et al., "The Preparation and Evaluation of Peptidic Aspartyl Hemiacetals as Reversible Inhibitors of ICE," Am. Chem. Soc. Abs. (206th Natl. Mtg.), MEDI 235 (1993).

Griffin et al., "Brain interleukin 1 and S-100 Immunoreactivity are Elevated in Down Syndrome and Alzheimer Disease," PNAS, 86:7611-7615 (1989).

Grobmyer et al., "Peptidomimetic Fluoromethylketone Rescues Mice from Lethal Endotoxic Shock," Molecular Medicine, 5:585-594 (1999).

Hammerberg et al., "Interleukin-1 Receptor Antagonist in Normal and Psoriatic Epidermis," Journal of Clinical Investigation, 90:571-583 (1992).

Hanessian et al., "Design and Synthesis of a Prototype Model Antagonist of Tachykinin NK-2 Receptor," Biorganic Medicinal Chemistry Letters, 3:2689-2692 (1993).

Harris, "Rheumatoid Arthritis: Pathophysiology and Implications for Therapy," New England Journal of Medicine, 322:1277-1289 (1990).

Hendrickson et al., "Selenomethionyl Proteins Produced for Analysis by Multiwavelength Anomalous Diffraction (MAD): A Vehicle for Direct Determination of Three-dimensional Structure," EMBO Journal, 9:1665-1672.

Hirschmann et al., "Nonpeptidal Peptidornimetics with a β-D-Glucose Scaffolding. A Partial Somatostatin Agonist Bearing a Close Structural Relationship to a Potent, Selective Substance P Antagonist," Journal of the American Chemical Society, 114:9217-9218 (1992).

Hirschmann et al., "The First Design and Synthesis of a Steroidal Peptidomimetic. The Potential Value of Peptidomimeties in Elucidating the Bioactive Conformation of Peptide Ligands," Journal of the American Chemical Society, 114:9699-9701 (1992).

Holmgren et al., "Three-dimensional Structure of *Escherichia coli* Thioredoxin-S2 to 2.8 A Resolution," PNAS, 72(6):2305-2309 (1975).

Hopfinger et al., "Molecular Shape Analysis: A Formalism to Quantitatively Establish Spatial Molecular Similarity," in Concepts and Applications of Molecular Similarity, pp. 173-209 (M. Johnson & G. Maggiora eds., 1990).

Hopfinger, "Computer-Assisted Drug Design," Journal of Medicinal Chemistry, 28:1133-1139 (1985).

Howard et al., "IL-1-Converting Enzyme Requires Aspartic Acid Residues for Processing of the IL-1β Precursor at Two Distinct Sites and Does Not Cleave 31-kDa IL-1α," Journal of Immunology, 147:2964-2969 (1991).

Howard et al., "High-Level Production and Characterization of Functional Human Interleukin-1β Converting Enzyme in Baculovirus and E. coli Expression Systems," Journal of Cellular Biochemistry Supplement, 17B,146 (1993).

Howard et al., "Human interleukin-1β Converting Enzyme: A Mutational Analysis of Proenzyme Activation," Journal of Cellular Biochemistry Supplement, 17B:113 (1993).

Ilzecka et al., "Interleukin-1β Converting Enzyme/Caspase-1 (ICE/Caspase-1) and Soluble APO-1/Fas/CD 95 Receptor in Amyotrophic Lateral Sclerosis Patients," Acta Neurologica Scandinavica., 103:255-258 (2001).

Kamphuis et al., "Thiol Proteases: Comparative Studies Based on the High-resolution Structures of Papain and Actinidin, and on Amino Acid Sequence Information for Cathepsins B and H, and Stein Bromelain," Journal of Molecular Biology, 182:317-329(1985).

Knowles, "Tinkering with Enzymes: What are We Learning?," Science, 236:1252-1258 (1987).

Kostura et al., "Identification of a Monocyte Specific Pre-interleukin 1β Convertase Activity," PNAS, 86:5227-5231 (1989).

Ku et al., "IL-1β Converting Enzyme Inhibition Blocks Progression of Type II Collagen-Induced Arthritis in Mice," Cytokine, 8:377-386 (1996).

Kuida et al., "Altered Cytokine Export and Apoptosis in Mice Deficient in Interleukin-1β Converting Enzyme," Science, 267:2000-2003 (1995).

Kuntz et al., "A Geometric Approach to Macromolecule-Ligand Interactions," Journal of Molecular Biology, 161:269-288 (1982).

Lan et al., "Interleukin-1 Receptor Antagonist halts the Progression of Established Crescentic Glomerulonephritis in the Rat," Kidney international, 47:1303-1309 (1995).

Lattman, "Use of the Rotation and Translation Functions," Methods in Enzymology, 115:55-77(1985).

Li et al., "Mice Deficient in IL-1β-Converting Enzyme are Defective in Production of Mature IL-1β and Resistant to Endotoxic Shock," Cell, 80:401-411 (1995).

Li et al., "Functional Role of Caspase-1 and Caspase-3 in an ALS Transgenic Mouse Model," Science, 288:335-339 (2000).

Lipinski, "Bioisosterisrn in Drug Design," Annual Reports in Medicinal Chemistry, 21:283-291 (1986).

Loher et al., "The interleukin-1beta-converting enzyme inhibitor pralnacasan reduces dextran sunte sodium-induced murine colitis and T helper 1 T-cell activation," Journal of Pharmacology and Experimental Therapeutics, 308:583-590 (2004).

Lonnemann et al., "Differences in the Synthesis and Kinetics of Release of Interleukin 1α, Interleukin 1β and Tumor Necrosis Factor from Human Mononuclear Cells," European Journal of Immunology, 19:1531-1536 (1989).

MacKenzie et al., "An Inhibitor of the Interteukin-1β-Processing Enzyme Blocks IL-1 Release and Reduces Pyrexia and Acute Inflammation,", Inflammation Research Association (7th International. Conference.), W42 (1994).

Mandrup-Poulsen et al., "Involvement of interleukin 1 and Interleukin 1 Antagonist in Pancreatic β-Cell Destruction in Insulindependent Diabetes Mellitus," Cytokine, 5:185-191 (1993).

March et al., "Cloning, Sequence and Expression of Two Distinct Human Interleukin-1 Complementary DNAs," Nature, 315:641-647 (1985).

Marshall et al,, "Approaches to the Conformation of the Drug Bound to the Receptor," Molecular Graphics and Drug Design, pp. 115-156 (A. Burgen et al. eds., 1986).

Marshall, "Computer-Aided Drug Design," Annual Review of Pharmacology Toxicology, 27:193-213 (1987).

Martin, "3D Database Searching in Drug Design," Journal of Medicinal Chemistry, 35:2145-2154 (1992).

Marx, "Cell Death Studies Yield Cancer Clues," Science, 259:760-761 (1993).

Mayer et al., "A Unique Geometry of the Active Site of Angiotensin-Converting Enzyme Consistent with Structure-Activity Studies," Journal of Computer-Aided Molecular Design, 1:3-16 (1987).

McCarthy et al., "Inhibition of Interleukin-1 by an Interleukin-1 Receptor Antagonist Prevents Graft-Versus Host Disease," Blood, 78:1915-1918 (1991).

Ménard et al., "Contribution of the Glutamine 19 Side Chain to Transition-State Stabilization in the Oxyanion Hole of Papain," Biochemistry, 30:8924-8928 (1991).

Ménard et al., "Importance of Hydrogen-Bonding Interactions Involving the Side Chain of Asp 158 in the Catalytic Mechanism of Papain," Biochemistry, 30:5531-5538 (1991).

Meng et al., "Automated Docking with Grid-Based Energy Evaluation," Journal of Computational Chemistry., 13:505-524 (1992).

Miller et al., "Inhibition of Mature IL-1β Production in Murine Macrophages and a Murine Model of Inflammation by WIN 67694. an Inhibitor of IL-1β Converting Enzyme," Journal of Immunology, 154:1331-1338 (1995).

Miller et al., "The Accessible Surface Area and Stability of Oligomeric Proteins," Nature, 328:834-836 (1987).

Miller et al., "The IL-1β Converting Enzyme as a Therapeutic Target," Ann. New York Academy of Sciences, 696:133-148 (1993).

Ming et al., "Caspase-1 Expression in Multiple Sclerosis Plaques and Cultured Glial Cells," Journal of the Neurological Sciences, 197:9-18 (2002).

Miranker et al., "Functionality Maps of Binding Sites: A Multiple Copy Simultaneous Search Method," Proteins: Structure, Function, and Genetics, 11:29-34 (1991).

Miura et al., "Induction of Apoptosis in Fibroblasts by IL-1β-Converting Enzyme, a Mammalian Homolog of the Celegans Cell Death Gene ced-3," Cell, 75:653-660 (1993).

Mjalli et al., "Activated Ketones as Potent Reversible Inhibitors of Interleukin-1β Converting Enzyme," Biorganic Medicinal Chemistry Letters, 4:1965-1968 (1994).

Mjalli et al., "Phenylalkyl Ketones as Potent Reversible Inhibitors of Interleukin-1β Converting Enzyme," Biorganic Medicinal Chemistry Letters, 3:2689-2692 (1993).

Molineaux et al., "Interleukin 1β (IL-1β) Processing in Murine Macrophages Requires a Structurally Conserved Homologue of Human IL-1β Converting Enzyme," PNAS, 90:1809-1813 (1993).

Mosley et al., "Determination of the Minimum Polypeptide Lengths of the Functionally Active Sites of Human Interleukins 1α and 1β," PNAS, 84:4572-4576 (1987).

Mullican et al.. "The Synthesis and Evaluation of Peptidyl Aspartyl Aldehydes as inhibitors of ICE," Biorganic Medicinal Chemistry Letters, 4:2359-2364 (1994).

Nalin, "Apoptosis Research Enters the ICE Age," Structure, 3:143-145 (1995).

Navia et al., "Use of Structural Information in Drug Design," Current Opinion in Structural Biology, 2:202-210 (1992).

Nett et al., "Molecular Cloning of the Murine 1L-1β Converting Enzyme cDNA," Journal of Immunology, 149:3254-3259 (1992).

Nett-Fiordalisi et al., "Characterization and Activation of the Murine Interleukin-1β (IL-1β) Converting Enzyme," Journal of Cellular Biochemistry, Supplement, 17B:117 (1993).

Nishibata et al., "Automatic Creation of Drug Candidate Structures Based on Receptor Structure. Starting Point for Artificial Lead Generation," Tetrahedron, 47:8985-8990 (1991).

Noren et al., "A General Method for Site-Specific Incorporation of Unnatural Amino Acids into Proteins," Science, 244:182-188 (1989).

Norman et al., "Decreased Mortality of Severe Acute Pancreatitis After Proximal Cytokine Blockade," Annals of Surgery, 221(6):625-634 (1995).

Norman et al., "Severity and Mortality of Experimental Pancreatitis are Dependent on lnterleukin-1 Converting Enzyme (ICE)," Journal of Interferon and Cytokine Research, 17:113-118 (1997).

Noronha et al., "In situ Production of TNF-α, IL- 1β and IL-2R in ANCA-positive Glomerulonephritis," Kidney International, 43:682-692 (1993).

Office Action dated Dec. 15, 2008 in U.S. Appl. No. 11/655,938, filed Jan. 18, 2007 and published as US 2008-0039449 A1.

Office Action dated Jun. 26, 2009 in U.S. Appl. No. 11/901,843.

Ohlsson et al., "Interleukin-1 Receptor Antagonist Reduces Mortality from Endotoxin Shock," Nature, 348:550-552 (1990).

Oppenheim et al., "There is More than One Interleukin 1," Immunology. Today, 7:45-55 (1986).

Pennington et al., "Synthesis of a Fluorogenic Interleukin-1β Convening Enzyme Substrate Based on Resonance Energy Transfer," Peptide Research, 7(2):72-76 (1994).

Peters et al., "Three-Dimensional Modeling and Drug Development: Has "Rational" Drug Design Arrived?" Biotechnology (N Y), 12:147-150 (1994).

Plattner et al., "Obstacles to Drug Development from Peptide Leads," Drug Discovery Technologies, 51: 92-126 (C. Clark & W. Moss eds., 1990).

Polgár, "On the Mode of Activation of the Catalytically Essential Sulfhydryl Group of Papain," European Journal of Biochemistry, 33(1):104-109 (1973).

Pomerantz et al., "Inhibition of Caspase 1 Reduces Human Myocardial Ischemic Dysfunction via inhibition of IL-18 and IL-1β," PNAS, 98:2871-2876 (2001).

Prasad et al., "P1 Aspartate-Based Peptide α-Arylacyloxy- and α-Aryloxymethyl Ketones as Potent Time-Dependent Inhibitors of Interleukin 1β Converting Enzyme," Am. Chem. Soc. Abs. (24th Med. Chem. Symp.), 66 (1994).

Randle et al., "Interleukin-1 Converting Enzyme (Caspase-1) Inhibition with VX-765 Reduces Inflammation and Cytokine Levels in Murine Oxazoline-induced Dermatitis," Poster 856, The Society for Investigative Dermatology, 62nd Annual Meeting, Washington, D.C., May 9-12, 2001.

Ray et al., "Viral Inhibition of inflammation; Cowpox Virus Encodes an Inhibitor of the Interleukin-1β Converting Enzyme," Cell, 69;597-604 (1992).

Reiter, "Peptidic p-Nitroanilide Substrates of Interleukin-1β-Converting Enzyme," International Journal of Peptide and Protein Research, 43:87-96 (1994).

Revesz et al., "Synthesis of P1 Aspartate-Based Peptide Acyloxymethyl and Fluoromethyl Ketones as Inhibitors of Interleukin-1β-Converting Enzyme,", Tetrahedron Letters, 35:9693-9696 (1994).

Ring et al., "Structure-based Inhibitor Design by Using Protein Models for the Development of Antiparasitic Agents," PNAS, 90:3583-3587 (1993).

Robinson et al., "Synthesis of a Peptidyl Difluoro Ketone Bearing the Aspartic Acid Side Chain: An inhibitor of Interleukin-1β Converting Enzyme," Journal of Organic Chemistry, 57:7309-7314 (1992).

Rouquet et al., "ICE inhibitor YVADcmk is a Potent Therapeutic Agent Against In Vivo Liver Apoptosis," Current Biology, 6:1192-1195 (1996).

Salvatore et al., "L-741,494, A Fungal Metabolite that is an Inhibitor of Interleukin-1β Converting Enzyme," Journal National Products, 57:755-760 (1994).

Sandberg et al., "Treatment with an Interleukin-1 Receptor Antagonist Protein Prolongs Mouse Islet Allograft Survival," Diabetes, 42:1845-1851 (1993).

Schecter et al., "On the Size of the Active Site in Proteases. I. Papain," Biochemical and Biophysical Research Communication, 27:157-162 (1967).

Schmidt et al., "Synthesis and Evaluation of Aspartyl α-Chloro-, α-Aryloxy-, and α-Arylacyloxymehyl Ketones as Inhibitors of Interleukin-1β Converting Enzyme," Am. Chem. Soc. Abs. (208th Natl. Mtg.), MEDI 4 (1994).

Shivers et al., "Molecular Cloning of Rat Interleukin-1β-Converting Enzyme: Distribution and Regulation," Journal of Cellular Biochemistry Supplement, 17B:119 (1993).

Siegmund, "Interleukin-1β Converting Enzyme (Caspase-1) in Intestinal Inflammation," Biochemical Pharmacology, 64:1-8 (2002).

Singer et al., "Interleukin 1β is Localized in the Cytoplasmic Ground Substance but is Largely Absent from the Golgi Apparatus and Plasma Membranes of Stimulated Human Monocytes," Journal of Experimental Medicine, 167:389-407 (1988).

Sleath et al,, "Substrate Specificity of the Protease that Processes Human Interleukin-1β," Journal of Biological Chemistry, 265:14526-14528 (1990).

Spatola, Chemistry and Biochemistry of Amino Acids, Peptides and Proteins, vol. 7, B. Weinstein, ed., Marcel Dekker Inc., ch. 5, pp. 267-281 (1983).

Steinman et al., "How to Successfully Apply Animal Studies in Experimental Allergic Enchepalomyelitis to Research on Multiple Scleroris," Annals of Neurology, 60:12-21 (2006).

Taylor et al., "Hydrogen-Bond Geometry in Organic Crystals," Accounts of Chemical Research 17:320-326 (1984).

Thornber, "Isosterism, and Molecular Modification in Drug Design," Chemical Society Reviews, 8:563-580 (1979).

Thornberry et al., "A Novel Heterodimeric Cysteine Protease is Required for Interleukin-1β Processing in Monocytes," Nature, 356:768-774 (1992).

Thornberry et al., "Inactivation of Interleukin-1β Converting Enzyme by Peptide (Acyloxy)methyl Ketones," Biochemistry, 33:3934-3940 (1994).

Travis, "Proteins and Organic Solvents Make an Eye-Opening Mix," Science, 262:1374 (1993).

Uhl et al., "Secretion of Human Monocyte Mature IL-1β: Optimization of Culture Conditions and Inhibition by ICE Inhibitors," Inflammation Research Association (7th International Conference.), W41 (1994).

Vertex Pharmaceuticals, Inc., Jan. 8, 2002 Press Release.

Walker et al., "Crystal Structure of the Cysteine Protease Interleukin-1β-Converting Enzyme: A (p20/p10)2 Homodimer," Cell, 78:343-352 (1994).

Warner, et al., "Pyridoue HLE Inhibitors: Variation of the 3 and 5 Substituents," Royal Soc. Chem. Abs. (7th RSC-SCI Medicinal Chemistry Symposium.), P23 (1993).

Weiner et al., "A New Force Field for Molecular Mechanical Simulation of Nucleic Acids and Proteins," Journal of the American Chemical Society, 106:765-784 (1984).

Wilson et al., "Structure and Mechanism of Interleukin-1β Converting Enzyme," Nature, 370:270-275 (1994).

Wong et al., "Dynamics and Design of Enzymes and Inhibitors," Journal of the American Chemical Society, 108:3830-3832 (1986).

Wooley et al., "The Effect of an Interleukin-1 Receptor Antagonist Protein on Type II Collagen-induced Arthritis and Antigen-induced Arthritis in Mice," Arthritis and Rheumatism, 36(9):1305-1314 (1993).

Yaoita et al., "Attenuation of Ischemia/Reperfusion Injury in Rats by a Caspase Inhibitor," Circulation, 97:276-281 (1998).

Yuan et aL, "The C.elegans Cell Death Gene ced-3 Encodes a Protein Similar to Mammalian Interleukin-1β-Converting Enzyme," Cell, 75: 641-652 (1993).

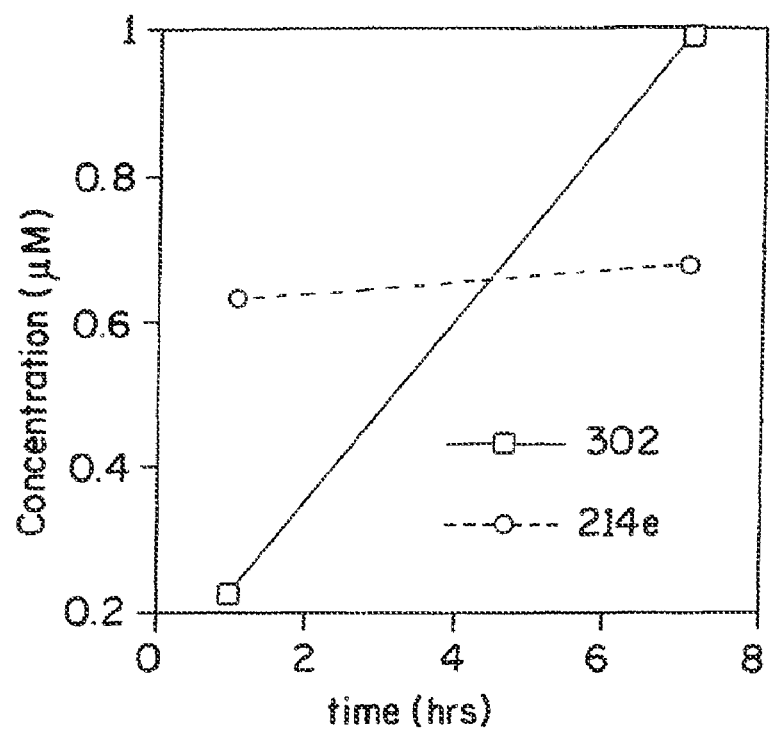
FIG. 11
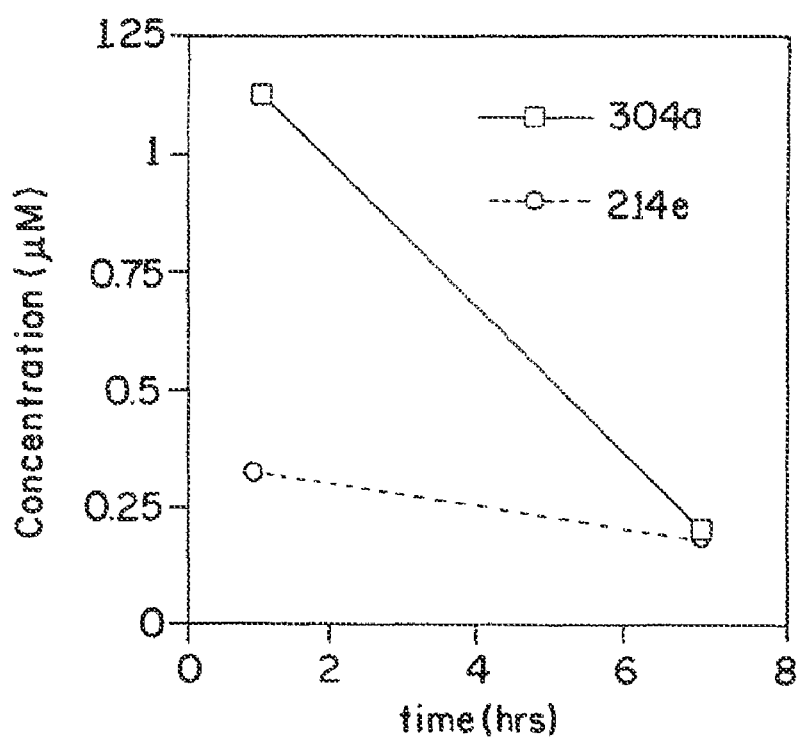

INHIBITORS OF INTERLEUKIN-1β CONVERTING ENZYME

CROSS-REFERENCE TO RELATED APPLICATIONS

This application is a divisional of patent application Ser. No. 11/655,938, filed Jan. 18, 2007, which is a continuation of patent application Ser. No. 10/999,865, filed Nov. 29, 2004, which is a divisional of patent application Ser. No. 10/058,522, filed Jan. 28, 2002, which is a divisional of patent application Ser. No. 09/773,477, filed Jan. 31, 2001, now U.S. Pat. No. 6,423,840, which is a divisional of patent application Ser. No. 08/761,483, filed Dec. 6, 1996, now U.S. Pat. No. 6,204,261, which claims priority to provisional patent application No. 60/031,495, filed Nov. 26, 1996. Patent application Ser. No. 08/761,483 is also a continuation-in-part of patent application Ser. No. 08/712,878, filed Sep. 12, 1996, now U.S. Pat. No. 5,985,863, which is a continuation-in-part of patent application Ser. No. 08/598,332, filed Feb. 8, 1996, now U.S. Pat. No. 5,874,424, which is a continuation-in-part of patent application Ser. No. 08/575,641, filed Dec. 20, 1995, now U.S. Pat. No. 6,008,217. The entire disclosures of each of the above applications is incorporated by reference herein.

The Sequence Listing associated with this application is provided in text format in lieu of a paper copy, and is hereby incorporated by reference into the specification. The name of the text file containing the Sequence Listing is Sequence_Listing.txt. The text file is 4,301 bytes in size, was created on Feb. 8, 2011, and is being submitted electronically via EFS-Web.

TECHNICAL FIELD OF THE INVENTION

The present invention relates to novel classes of compounds which are inhibitors of interleukin-1β converting enzyme ("ICE"). This invention also relates to pharmaceutical compositions comprising these compounds. The compounds and pharmaceutical compositions of this invention are particularly well suited for inhibiting ICE activity and consequently, may be advantageously used as agents against interleukin-1- ("IL-1"), apoptosis-, interferon gamma inducing factor- ("IGIF") and interferon-γ- ("IFN-γ") mediated diseases, including inflammatory diseases, autoimmune diseases, destructive bone, proliferative disorders, infectious diseases and degenerative diseases. This invention also relates to methods for inhibiting ICE activity, and decreasing IGIF production and IFN-γ production and methods for treating interleukin-1-, apoptosis-, IGIF- and IFN-γ-mediated diseases using the compounds and compositions of this invention. This invention also relates to methods of preparing N-acylamino compounds.

BACKGROUND OF THE INVENTION

Interleukin 1 ("IL-1") is a major pro-inflammatory and immunoregulatory protein that stimulates fibroblast differentiation and proliferation, the production of prostaglandins, collagenase and phospholipase by synovial cells and chondrocytes, basophil and eosinophil degranulation and neutrophil activation. Oppenheim, J. H. et al, *Immunology Today*, 7, pp. 45-56 (1986). As such, it is involved in the pathogenesis of chronic and acute inflammatory and autoimmune diseases. For example, in rheumatoid arthritis, IL-1 is both a mediator of inflammatory symptoms and of the destruction of the cartilage proteoglycan in afflicted joints. Wood, D. D. et al., *Arthritis Rheum.* 26, 975, (1983); Pettipher, E. J. et al., *Proc. Natl. Acad. Sci. UNITED STATES OF AMERICA* 71, 295 (1986); Arend, W. P. and Dayer, J. M., *Arthritis Rheum.* 38, 151 (1995). IL-1 is also a highly potent bone resorption agent. Jandiski, J. J., *J. Oral Path* 17, 145 (1988); Dewhirst, F. E. et al., *J. Immunol.* 8, 2562 1985). It is alternately referred to as "osteoclast activating factor" in destructive bone diseases such as osteoarthritis and multiple myeloma. Bataille, R. et al., *Int. J. Clin. Lab. Res.* 21(4), 283 (1992). In certain proliferative disorders, such as acute myelogenous leukemia and multiple myeloma, IL-1 can promote tumor cell growth and adhesion. Bani, M. R., *J. Natl. Cancer Inst.* 83, 123 (1991); Vidal-Vanaclocha, F., *Cancer Res.* 54, 2667 (1994). In these disorders, IL-1 also stimulates production of other cytokines such as IL-6, which can modulate tumor development (Tartour et al., *Cancer Res.* 54, 6243 (1994). IL-1 is predominantly produced by peripheral blood monocytes as part of the inflammatory response and exists in two distinct agonist forms, IL-1α and IL-1β. Mosely, B. S. et al., *Proc. Nat, Acad. Sci.*, 84, pp. 4572-4576 (1987); Lonnemann, G. et al., *Eur. J. Immunol.*, 19, pp. 1531-1536 (1989).

IL-1β is synthesized as a biologically inactive precursor, pIL-1β. pIL-1β lacks a conventional leader sequence and is not processed by a signal peptidase. March, C. J., *Nature*, 315, pp. 641-647 (1985). Instead, pIL-1β is cleaved by interleukin-1β converting enzyme ("ICE") between Asp-116 and Ala-117 to produce the biologically active C-terminal fragment found in human serum and synovial fluid. Sleath, P. R., et al., *J. Biol. Chem.*, 265, pp. 14526-14528 (1992); A. D. Howard et al., *J. Immunol.*, 147, pp. 2964-2969 (1991). ICE is a cysteine protease localized primarily in monocytes. It converts precursor IL-43 to the mature form. Black, R. A. et al., *FEBS Lett.*, 247, pp. 386-390 (1989); Kostura, M. J. et al., *Proc. Natl. Acad. Sci. UNITED STATES OF AMERICA*, 86, pp. 5227-5231 (1989). Processing by ICE is also necessary for the transport of mature IL-1β through the cell membrane.

ICE, or its homologs, also appears to be involved in the regulation of programmed cell death or apoptosis. Yuan, J. et al., *Cell*, 75, pp. 641-652 (1993); Miura, M. et al., *Cell*, 75, pp. 653-660 (1993); Nett-Fiordalisi, M. A. et al., *J. Cell Biochem.*, 17B, p. 117 (1993). In particular, ICE or ICE homologs are thought to be associated with the regulation of apoptosis in neurodegenerative diseases, such as Alzheimer's and Parkinson's disease. Marx, J. and M. Baringa, *Science*, 259, pp. 760-762 (1993); Gagliardini, V. et al., *Science*, 263, pp. 826-828 (1994). Therapeutic applications for inhibition of apoptosis may include treatment of Alzheimer's disease, Parkinson's disease, stroke, myocardial infarction, spinal atrophy, and aging.

ICE has been demonstrated to mediate apoptosis (programmed cell death) in certain tissue types. Steller, H., *Science*, 267, p. 1445 (1995); Whyte, M. and Evan, G., *Nature*, 376, p. 17 (1995); Martin, S. J. and Green, D. R., *Cell*, 82, p. 349 (1995); Alnemri, E. S., et al., *J. Biol. Chem.*, 270, p. 4312 (1995); Yuan, J. *Curr. Opin. Cell Biol.*, 7, p. 211 (1995). A transgenic mouse with a disruption of the ICE gene is deficient in Fas-mediated apoptosis (Kuida, K. et al., *Science* 267, 2000 (1995)). This activity of ICE is distinct from its role as the processing enzyme for pro-IL1β. It is conceivable that in certain tissue types, inhibition of ICE may not affect secretion of mature IL-1β, but may inhibit apoptosis.

Enzymatically active ICE has been previously described as a heterodimer composed of two subunits, p20 and p10 (20 kDa and 10 kDa molecular weight, respectively). These subunits are derived from a 45 kDa proenzyme (p45) by way of a p30 form, through an activation mechanism that is autocatalytic. Thornberry, N. A. et al., *Nature*, 356, pp. 768-774 (1992). The ICE proenzyme has been divided into several functional domains: a prodomain (p14), a p22/20 subunit, a polypeptide linker and a p10 subunit. Thornberry et al., supra; Casano et al., *Genomics*, 20, pp. 474-481 (1994).

Full length p45 has been characterized by its cDNA and amino acid sequences. PCT patent applications WO 91/15577 and WO 94/00154. The p20 and p10 cDNA and amino acid sequences are also known. Thornberry et al., supra. Murine and rat ICE have also been sequenced and cloned. They have high amino acid and nucleic acid sequence homology to human ICE. Miller, D. K. et al., *Ann. N.Y. Acad. Sci.*, 696, pp. 133-148 (1993); Molineaux, S. M. et al., *Proc. Nat. Acad. Sci.*, 90, pp. 1809-1813 (1993). The three-dimensional structure of ICE has been determined at atomic resolution by X-ray crystallography. Wilson, K. P., et al., *Nature*, 370, pp. 270-275 (1994). The active enzyme exists as a tetramer of two p20 and two p10 subunits.

Additionally, there exist human homologs of ICE with sequence similarities in the active site regions of the enzymes. Such homologs include TX (or $ICE_{rel-II}$ or ICH-2) (Faucheu, et al., *EMBO J.*, 14, p. 1914 (1995); Kamens J., et al., *J. Biol. Chem.*, 270, p. 15250 (1995); Nicholson et al., *J. Biol. Chem.*, 270 15870 (1995)), TY (or $ICE_{rel-II}$) (Nicholson et al., *J. Biol. Chem.*, 270, p. 15870 (1995); ICH-1 (or Nedd-2) (Wang, L. et al., *Cell*, 78, p. 739 (1994)), MCH-2, (Fernandes-Alnemri, T. et al., *Cancer Res.*, 55, p. 2737 (1995), CPP32 (or YAMA or apopain) (Fernandes-Alnemri, T. et al., *J. Biol. Chem.*, 269, p. 30761 (1994); Nicholson, D. W. et al., *Nature*, 376, p. 37 (1995)), and CMH-1 (or MCH-3) (Lippke, et al., *J. Biol. Chem.*, (1996); Fernandes-Alnemri, T. et al., *Cancer Res.*, (1995)). Each of these ICE homologs, as well as ICE itself, is capable of inducing apoptosis when overexpressed in transfected cell lines. Inhibition of one or more of these homologs with the peptidyl ICE inhibitor Tyr-Val-Ala-Asp-chloromethylketone (SEQ ID NO: 1) results in inhibition of apoptosis in primary cells or cell lines. Lazebnik et al., *Nature*, 371, p. 346 (1994). The compounds described herein are also capable of inhibiting one or more homologs of ICE (see Example 5). Therefore, these compounds may be used to inhibit apoptosis in tissue types that contain ICE homologs, but which do not contain active ICE or produce mature IL-1β.

Interferon-gamma inducing factor (IGIF) is an approximately 18-kDa polypeptide that stimulates T-cell production of interferon-gamma (IFN-γ). IGIF is produced by activated Kupffer cells and macrophages in vivo and is exported out of such cells upon endotoxin stimulation. Thus, a compound that decreases IGIF production would be useful as an inhibitor of such T-cell stimulation which in turn would reduce the levels of IFN-γ production by those cells.

IFN-γ is a cytokine with immunomodulatory effects on a variety of immune cells. In particular, IFN-γ is involved in macrophage activation and Th1 cell selection (F. Belardelli, *APMIS*, 103, p. 161 (1995)). IFN-γ exerts its effects in part by modulating the expression of genes through the STAT and IRF pathways (C. Schindler and J. E. Darnell, *Ann. Rev. Biochem.*, 64, p. 621 (1995); T. Taniguchi, *J. Cancer Res. Clin. Oncol.*, 121, p. 516 (1995)).

Mice lacking IFN-γ or its receptor have multiple defects in immune cell function and are resistant to endotoxic shock (S. Huang et al., *Science*, 259, p. 1742 (1993); D. Dalton et al., *Science*, 259, p. 1739 (1993); B. D. Car et al., *J. Exp. Med.*, 179, p. 1437 (1994)). Along with IL-12, IGIF appears to be a potent inducer of IFN-γ production by T cells (H. Okamura et al., *Infection and Immunity*, 63, p. 3966 (1995); H. Okamura et al., *Nature*, 378, p. 88 (1995); S. Ushio et al., *J. Immunol.*, 156, p. 4274 (1996)).

IFN-γ has been shown to contribute to the pathology associated with a variety of inflammatory, infectious and autoimmune disorders and diseases. Thus, compounds capable of decreasing IFN-γ production would be useful to ameliorate the effects of IFN-γ related pathologies.

The biological regulation of IGIF and thus IFN-γ has not been elucidated. It is known that IGIF is synthesized as a precursor protein, called "pro-IGIF". It has been unclear, however, how pro-IGIF is cleaved and whether its processing has biological importance.

Accordingly, compositions and methods capable of regulating the conversion of pro-IGIF to IGIF would be useful for decreasing IGIF and IFN-γ production in vivo, and thus for ameliorating the detrimental effects of these proteins which contribute to human disorders and diseases.

However, ICE and other members of the ICE/CED-3 family have not previously been linked to the conversion of pro-IGIF to IGIF or to IFN-γ production in vivo.

ICE inhibitors represent a class of compounds useful for the control of inflammation or apoptosis or both. Peptide and peptidyl inhibitors of ICE have been described. PCT patent applications WO 91/15577; WO 93/05071; WO 93/09135; WO 93/14777 and WO 93/16710; and European patent application 0 547 699. Such peptidyl inhibitors of ICE has been observed to block the production of mature IL-1β in a mouse model of inflammation (vide infra) and to suppress growth of leukemia cells in vitro (Estrov et al., *Blood* 84, 380a (1994)). However, due to their peptidic nature, such inhibitors are typically characterized by undesirable pharmacologic properties, such as poor cellular penetration and cellular activity, poor oral absorption, poor stability and rapid metabolism. Plattner, J. J. and D. W. Norbeck, in *Drug Discovery Technologies*, C. R. Clark and W. H. Moos, Eds. (Ellis Horwood, Chichester, England, 1990), pp. 92-126. This has hampered their development into effective drugs.

Non-peptidyl compounds have also been reported to inhibit ICE in vitro. PCT patent application WO 95/26958; U.S. Pat. No. 5,552,400; Dolle et al., *J. Med. Chem.*, 39, pp. 2438-2440 (1996); However, it is not clear whether these compounds have the appropriate pharmacological profile to be therapeutically useful.

Additionally, current methods for the preparation of such compounds are not advantageous. These methods use tributyltin hydride, a toxic, moisture sensitive reagent. Thus, these methods are inconvenient to carry out, pose a health risk and create toxic-waste disposal problems. Furthermore, it is difficult to purify compounds prepared by these methods.

Accordingly, the need exists for compounds that can effectively inhibit the action of ICE in vivo, for use as agents for preventing and treating chronic and acute forms of IL-1-mediated diseases, apoptosis-, IGIF-, or IFN-γ-mediated diseases, as well as inflammatory, autoimmune, destructive bone, proliferative, infectious, or degenerative diseases. The need also exists for methods of preparing such compounds.

SUMMARY OF THE INVENTION

The present invention provides novel classes of compounds, and pharmaceutically acceptable derivatives thereof, that are useful as inhibitors of ICE. These compounds can be used alone or in combination with other therapeutic or prophylactic agents, such as antibiotics, immunomodulators or other anti-inflammatory agents, for the treatment or prophylaxis of diseases mediated by IL-1, apoptosis, IGIF or IFN-γ. According to a preferred embodiment, the compounds of this invention are capable of binding to the active site of ICE and inhibiting the activity of that enzyme. Additionally, they have improved cellular potency, improved pharmacokinetics, and/or improved oral bioavailability compared to peptidyl ICE inhibitors.

It is a principal object of this invention to provide novel classes of compounds which are inhibitors of ICE represented by formulas:

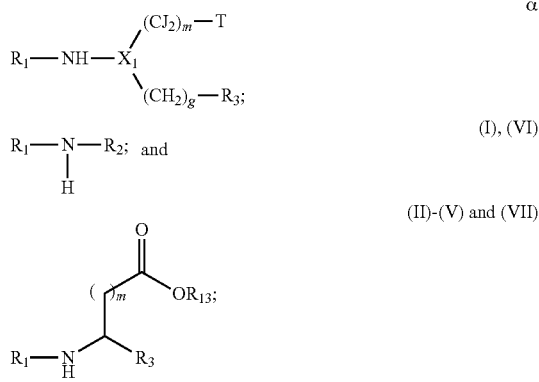

wherein the various substituents are described herein.

It is a further object of this invention to provide a process of preparing N-acylamino compounds by coupling a carboxylic acid with an alloc-protected amine.

BRIEF DESCRIPTION OF THE DRAWINGS

FIG. 11 Compounds 302 and 304a show detectable blood levels when administered orally (50 mg/kg, in 0.5% carboxymethylcellulose) to mice. Blood samples were collected at 1 and 7 hours after dosing. Compounds 302 and 304a are prodrugs of 214e and are metabolized to 214e in vivo. Compound 214e shows no blood levels above 0.10 μg/ml when administered orally (Example 8).

ABBREVIATIONS AND DEFINITIONS

Figure 1A:
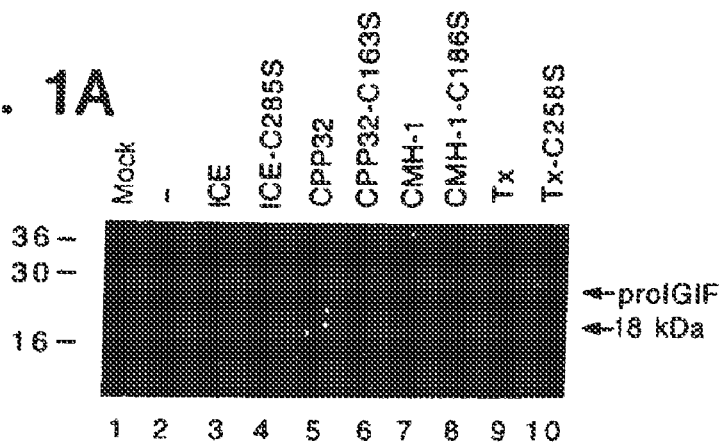
FIG. 1A ICE cleaves pro-IGIF in vivo. Cell lysates from Cos cells transfected with the various indicated expression plasmids or controls were analyzed for the presence of IGIF by separating proteins by SDS-PAGE and immunoblotting with anti-IGIF antisera (lane 1, mock transfected cells; lane 2, pro-IGIF alone; lanes 3-12, pro-IGIF in combination with ICE, ICE-C285S, CPP32, CPP32-C163S, CMH-1, CMH-1-C186S, Tx, Tx-C258S, respectively). Mobilities of pro-IGIF and the 18-kDa mature IGIF are indicated on the right. Molecular weight markers in kDa are shown on the left (Example 23).

| Abbreviations | |
|---|---|
| Designation | Reagent or Fragment |
| Ala | alanine |
| Arg | arginine |
| Asn | asparagine |
| Asp | aspartic acid |
| Cys | cysteine |
| Gln | glutamine |
| Glu | glutamic acid |
| Gly | glycine |
| His | histidine |
| Ile | isoleucine |
| Leu | leucine |
| Lys | lysine |
| Met | methionine |
| Phe | phenylalanine |
| Pro | proline |
| Ser | serine |
| Thr | threonine |
| Trp | tryptophan |
| Tyr | tyrosine |
| Val | valine |
| Ac$_2$O | acetic anhydride |
| n-Bu | normal-butyl |
| DMF | dimethylformamide |
| DIEA | N,N-diisopropylethylamine |
| EDC | 1-(3-Dimethylaminopropyl)-3-ethylcarbodiimide hydrochloride |
| Et$_2$O | diethyl ether |
| EtOAC | ethyl acetate |
| Fmoc | 9-fluorenylmethyoxycarbonyl |
| HBTU | O-benzotriazol-1-yl-N,N,N',N'-tetramethyluronium hexafluorophosphate |
| HOBT | 1-hydroxybenzotriazole hydrate |
| MeOH | methanol |
| TFA | trifluoroacetic acid |
| Alloc | allyloxycarbonyl |

Definitions

The following terms are employed herein:

The term "interferon gamma inducing factor" or "IGIF" refers to a factor which is capable of stimulating the endogenous production of IFN-γ.

The term "ICE inhibitor" refers to a compound which is capable of inhibiting the ICE enzyme. ICE inhibition may be determined using the methods described and incorporated by reference herein. The skilled practitioner realizes that an in vivo ICE inhibitor is not necessarily an in vitro ICE inhibitor. For example, a prodrug form of a compound typically demonstrates little or no activity in in vitro assays. Such prodrug forms may be altered by metabolic or other biochemical processes in the patient to provide an vivo ICE inhibitor.

The term "cytokine" refers to a molecule which mediates interactions between cells.

The term "condition" refers to any disease, disorder or effect that produces deleterious biological consequences in a subject.

The term "subject" refers to an animal, or to one or more cells derived from an animal. Preferably, the animal is a mammal, most preferably a human. Cells may be in any form, including but not limited to cells retained in tissue, cell clusters, immortalized cells, transfected or transformed cells, and cells derived from an animal that have been physically or phenotypically altered.

The term "active site" refers to any or all of the following sites in ICE: the substrate binding site, the site where an inhibitor binds and the site where the cleavage of substrate occurs.

The term "heterocycle" or "heterocyclic" refers to a stable mono- or polycyclic compound which may optionally contain one or two double bonds or may optionally contain one or more aromatic rings. Each heterocycle consists of carbon atoms and from one to four heteroatoms independently selected from a group including nitrogen, oxygen, and sulfur. As used herein, the terms "nitrogen heteroatoms" and "sulphur heteroatoms" include any oxidized form of nitrogen or sulfur and the quaternized form of any basic nitrogen. Heterocycles defined above include, for example, pyrimidinyl, tetrahydroquinolyl, tetrahydroisoquinonlinyl, purinyl, pyrimidyl, indolinyl, benzimidazolyl, imidazolyl, imidazolinoyl, imidazolidinyl, quinolyl, isoquinolyl, indolyl, pyridyl, pyrrolyl, pyrrolinyl, pyrazolyl, pyrazinyl, quinoxolyl, piperidinyl, morpholinyl, thiamorpholinyl, furyl, thienyl, triazolyl, thiazolyl, β-carbolinyl, tetrazolyl, thiazolidinyl, benzofuranoyl, thiamorpholinyl sulfone, benzoxazolyl, oxopiperidinyl, oxopyrroldinyl, oxoazepinyl, azepinyl, isoxazolyl, tetrahydropyranyl, tetrahydrofuranyl, thiadiazolyl, benzodioxolyl, benzothienyl, tetrahydrothiophenyl and sulfolanyl. Further heterocycles are described in A. R. Katritzky and C. W. Rees, eds., *Comprehensive Heterocyclic Chemistry The Structure. Reactions. Synthesis and Use of Heterocyclic Compounds*, Vol. 1-8, Pergamon Press, NY (1984).

The term "cycloalkyl" refers to a mono- or polycyclic group which contains 3 to 15 carbons and may optionally contain one or two double bonds. Examples include cyclohexyl, adamantyl and norbornyl.

The term "aryl" refers to a mono- or polycyclic group which contains 6, 10, 12, or 14 carbons in which at least one ring is aromatic. Examples include phenyl, naphthyl, and tetrahydronaphthalene.

The term "heteroaromatic" refers to a mono- or polycyclic group which contains 1 to 15 carbon atoms and from 1 to 4 heteroatoms, each of which is selected independently from a group including sulphur, nitrogen and oxygen, and which additionally contains from 1 to 3 five or six membered rings, at least one of which is aromatic.

The term "alpha-amino acid" (α-amino acid) refers to both the naturally occurring amino acids and other "non-protein" α-amino acids commonly utilized by those in the peptide chemistry arts when preparing synthetic analogues of naturally occurring peptides, including D and L forms. The naturally occurring amino acids are glycine, alanine, valine, leucine, iso-leucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. Examples of "non-protein" alpha-amino acids include hydroxylysine, homoserine, homotyrosine, homo-phenylalanine, citrulline, kynurenine, 4-amino-phenylalanine, 3-(2-naphthyl)-alanine, 3-(1-naphthyl)-alanine, methionine sulfone, t-butyl-alanine, t-butylglycine, 4-hydroxyphenylglycine, aminoalanine, phenylglycine, vinylalanine, propargyl-glycine, 1,2,4-triazolo-3-alanine, 4,4,4-trifluoro-threonine, thyronine, 6-hydroxytryptophan, 5-hydro-xytryptophan, 3-hydroxykynurenine, 3-aminotyrosine, trifluoromethyl-alanine, 2-thienylalanine, (2-(4-pyridyl)ethyl)-cysteine, 3,4-dimethoxy-phenylalanine, 3-(2-thiazolyl)-alanine, ibotenic acid, 1-amino-1-cyclopentanecarboxylic acid, 1-amino-1-cyclohexanecarboxylic acid, quisqualic acid, 3-trifluoromethylphenylalanine, 4-trifluoromethylphenylalanine, cyclohexylalanine, cyclo-hexylglycine, thiohistidine, 3-methoxytyrosine, elastatinal, norleucine, norvaline, alloisoleucine, homoarginine, thioproline, dehydroproline, hydroxy-proline, isonipectotic acid, homoproline, cyclohexyl-glycine, α-amino-n-butyric acid, cyclohexylalanine, aminophenylbutyric acid, phenylalanines substituted at the ortho, meta, or para position of the phenyl moiety with one or two of the following: a ($C_1$-$C_4$) alkyl, a ($C_1$-$C_4$) alkoxy, halogen or nitro groups or substituted with a methylenedioxy group; β-2- and 3-thienyl-alanine, β-2- and 3-furanylalanine, β-2-, 3- and 4-pyridylalanine, β-(benzothienyl-2- and 3-yl)alanine, β-(1- and 2-naphthyl)alanine, O-alkylated derivatives of serine, threonine or tyrosine, S-alkylated cysteine, S-alkylated homocysteine, O-sulfate, O-phosphate and O-carboxylate esters of tyrosine, 3-sulfotyrosine, 3-carboxy-tyrosine, 3-phospho-tyrosine, 4-methane sulfonic acid ester of tyrosine, 4-methane phosphonic acid ester of tyrosine, 3,5-diiodotyrosine, 3-nitro-tyrosine, ε-alkyl lysine, and delta-alkyl ornithine. Any of these α-amino acids may be substituted with a methyl group at the alpha position, a halogen at any aromatic residue on the α-amino side chain, or an appropriate protective group at the O, N, or S atoms of the side chain residues. Appropriate protective groups are disclosed in "Protective Groups In Organic Synthesis," T. W. Greene and P. G. M. Wuts, J. Wiley & Sons, NY, N.Y., 1991.

The term "substitute" refers to the replacement of a hydrogen atom in a compound with a substituent group. In the present invention, those hydrogen atoms which form a part of a hydrogen bonding moiety which is capable of forming a hydrogen bond with the carbonyl oxygen of Arg-341 of ICE or the carbonyl oxygen of Ser-339 of ICE are excluded from substitution. These excluded hydrogen atoms include those which comprise an —NH— group which is alpha to a —CO— group and are depicted as —NH— rather than an X group or some other designation in the following diagrams: (a) through (t), (v) through (z).

The term "straight chain" refers to a contiguous unbranching string of covalently bound atoms. The straight chain may be substituted, but these substituents are not a part of the straight chain.

The term "$K_i$" refers to a numerical measure of the effectiveness of a compound in inhibiting the activity of a target enzyme such as ICE. Lower values of $K_i$ reflect higher effectiveness. The $K_i$ value is a derived by fitting experimentally determined rate data to standard enzyme kinetic equations (see I. H. Segel, *Enzyme Kinetics*, Wiley-Interscience, 1975).

The term "patient" as used in this application refers to any mammal, especially humans.

The term "pharmaceutically effective amount" refers to an amount effective in treating or ameliorating an IL-1-, apoptosis-, IGIF- or IFN-γ-mediated disease in a patient. The term "prophylactically effective amount" refers to an amount effective in preventing or substantially lessening IL-1-, apoptosis-, IGIF or IFN-γ mediated diseases in a patient.

The term "pharmaceutically acceptable carrier or adjuvant" refers to a non-toxic carrier or adjuvant that may be administered to a patient, together with a compound of this invention, and which does not destroy the pharmacological activity thereof.

The term "pharmaceutically acceptable derivative" means any pharmaceutically acceptable salt, ester, or salt of such ester, of a compound of this invention or any other compound which, upon administration to a recipient, is capable of providing (directly or indirectly) a compound of this invention or an anti-ICE active metabolite or residue thereof.

Pharmaceutically acceptable salts of the compounds of this invention include, for example, those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N—($C_{1-4}$ alkyl)$_4^+$ salts.

This invention also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

The ICE inhibitors of this invention may contain one or more "asymmetric" carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration. Although specific compounds and scaffolds exemplified in this application may be depicted in a particular stereochemical configuration, compounds and scaffolds having either the opposite stereochemistry at any given chiral center or mixtures thereof are also envisioned.

The ICE inhibitors of this invention may comprise ring structures which may optionally be substituted at carbon, nitrogen or other atoms by various substituents. Such ring structures may be singly or multiply substituted. Preferably, the ring structures contain between 0 and 3 substituents. When multiply substituted, each substituent may be picked independently of any other substituent as long as the combination of substituents results in the formation of a stable compound.

Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

Substituents may be represented in various forms. These various forms are known to the skilled practitioner and may be used interchangeably. For example, a methyl substituent on a phenyl ring may be represented in any of the following forms:

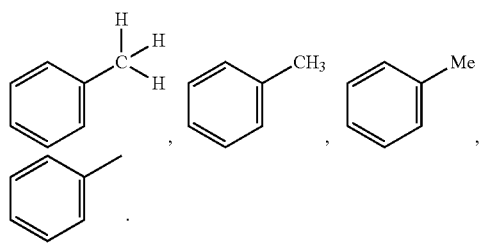

Various forms of substituents such as methyl are used herein interchangeably.

DETAILED DESCRIPTION OF THE INVENTION

In order that the invention herein described may be more fully understood, the following detailed description is set forth.

The ICE inhibitors of one embodiment (A) of this invention are those of formula α:

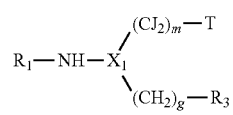

wherein:
$X_1$ is —CH;
g is 0 or 1;
each J is independently selected from the group consisting of —H, —OH, and —F, provided that when a first and second J are bound to a C and said first J is —OH, said second J is —H;
m is 0, 1, or 2;
T is —OH, —CO—CO$_2$H, —CO$_2$H, or any bioisosteric replacement for —CO$_2$H;
$R_1$ is selected from the group consisting of the following formulae, in which any ring may optionally be singly or multiply substituted at any carbon by $Q_1$, at any nitrogen by $R_5$, or at any atom by =O, —OH, —CO$_2$H, or halogen; any saturated ring may optionally be unsaturated at one or two bonds; and wherein $R_1$ (e) and $R_1$ (y) are optionally benzo-fused;

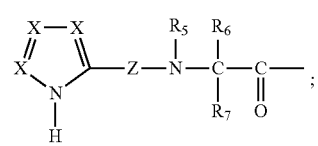

(a)

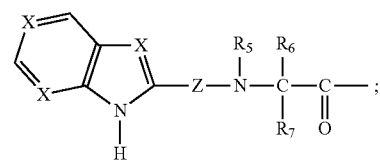

(b)

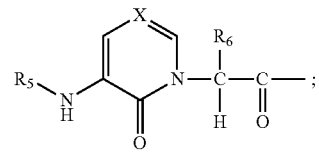

(c)

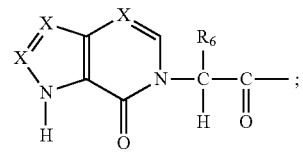

(d)

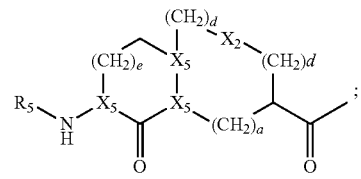

(e)

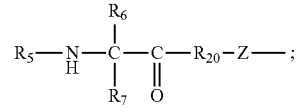

(f)

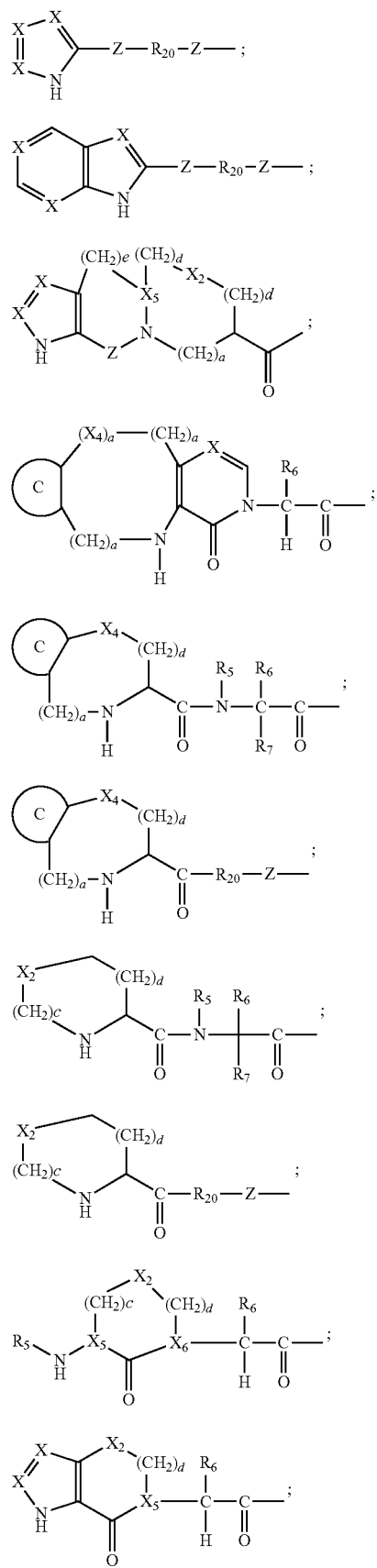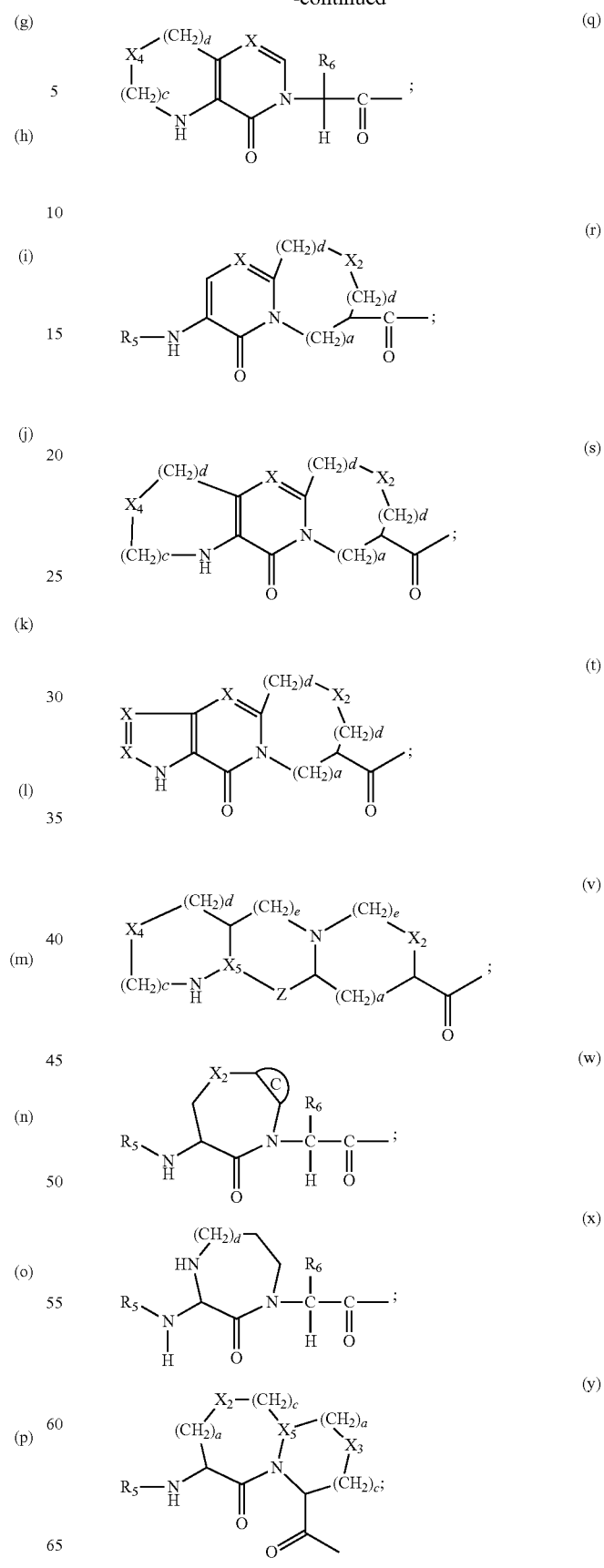

$R_{20}$ is selected from the group consisting of:

(aa1) 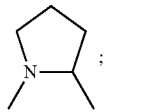

(aa2) 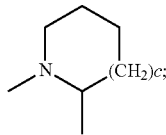

(aa3) 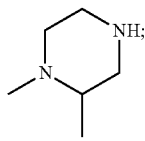

(aa4) 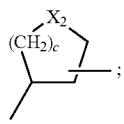

(aa5) 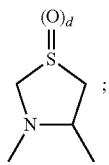

(bb) 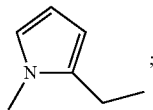

(cc) 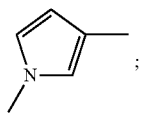

(dd) 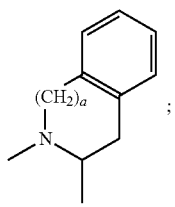

(ee) 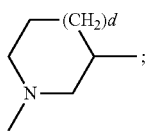

(ff) 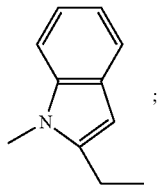

(gg) 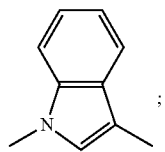

(gga) 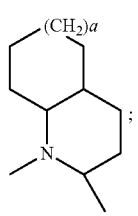

(ggb) 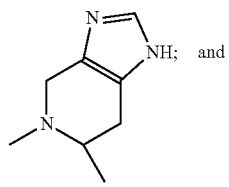

(ggc) 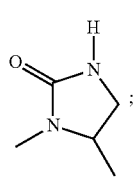

wherein each ring C is independently chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_3$ is:
—CN,
—CH=CH—$R_9$,
—CH=N—O—$R_9$,
—(CH$_2$)$_{1-3}$-$T_1$-$R_9$,
—CJ$_2$-$R_9$,
—CO—$R_{13}$, or

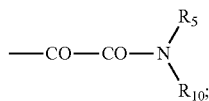

each $R_4$ is independently selected from the group consisting of:
—H,
—Ar$_1$,
—$R_9$,
-$T_1$-$R_9$, and
—(CH$_2$)$_{1,2,3}$-$T_1$-$R_9$;

each $T_1$ is independently selected from the group consisting of:
CH=CH—,
—O—,
—S—,
—SO—,
—SO$_2$—,
—NR$_{10}$—,
—NR$_{10}$—CO—,
—CO—, —O—CO—,
—CO—O—,
—CO—NR$_{10}$—,
—O—CO—NR$_{10}$—, —NR$_{10}$—CO—O—,
—NR$_{10}$—CO—NR$_{10}$—,
—SO$_2$—NR$_{10}$—,
—NR$_{10}$—SO$_2$—, and
—NR$_{10}$—SO$_2$—NR$_{10}$—;

each R$_5$ is independently selected from the group consisting of:
—H, —Ar$_1$,
—CO—Ar$_1$,
—SO$_2$—Ar$_1$,
—CO—NH$_2$,
—SO$_2$—NH$_2$,
—R$_9$,
—CO—R$_9$,
—CO—O—R$_9$,
—SO$_2$—R$_9$,

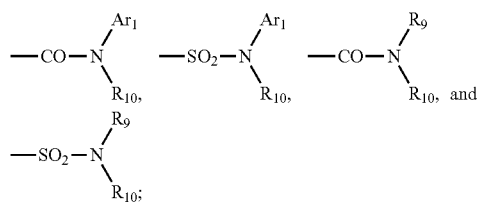

R$_6$ and R$_7$ taken together form a saturated 4-8 member carbocyclic ring or heterocyclic ring containing —O—, —S—, or —NH—; or R$_7$ is —H and R$_6$ is
—H
Ar$_1$,
—R$_9$,
—(CH$_2$)$_{1,2,3}$-T$_1$-R$_9$, or
an α-amino acid side chain residue;

each R$_9$ is a C$_{1-6}$ straight or branched alkyl group optionally singly or multiply substituted with —OH, —F, or =O and optionally substituted with one or two Ar$_1$ groups;

each R$_{10}$ is independently selected from the group consisting of —H or a C$_{1-6}$ straight or branched alkyl group;

each R$_{13}$ is independently selected from the group consisting of —Ar$_2$, —R$_4$ and

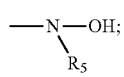

each Ar$_1$ is a cyclic group independently selected from the set consisting of an aryl group which contains 6, 10, 12, or 14 carbon atoms and between 1 and 3 rings, a cycloalkyl group which contains between 3 and 15 carbon atoms and between 1 and 3 rings, said cycloalkyl group being optionally benzo-fused, and a heterocycle group containing between 5 and 15 ring atoms and between 1 and 3 rings, said heterocycle group containing at least one heteroatom group selected from —O—, —S—, —SO—, —SO$_2$—, =N—, and —NH—, said heterocycle group optionally containing one or more double bonds, said heterocycle group optionally comprising one or more aromatic rings, and said cyclic group optionally being singly or multiply substituted with —NH$_2$, —CO$_2$H, —Cl, —F, —Br, —I, —NO$_2$, —CN, =O, —OH, -perfluoro C$_{1-3}$ alkyl,

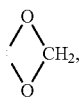

or -Q$_1$;

each Ar$_2$ is independently selected from the following group, in which any ring may optionally be singly or multiply substituted by -Q$_1$ and -Q$_2$:

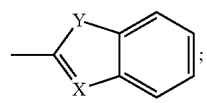

(hh)

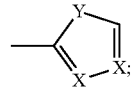

(ii)

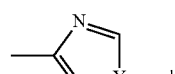

(jj)

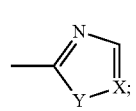

(kk)

each Q$_1$ is independently selected from the group consisting of:
—Ar$_1$
—O—Ar$_1$
—R$_9$,
-T$_1$-R$_9$, and
—(CH$_2$)$_{1,2,3}$-T$_1$-R$_9$;

each Q$_2$ is independently selected from the group consisting of —OH, —NH$_2$, —CO$_2$H, —Cl, —F, —Br, —I, —NO$_2$, —CN, —CF$_3$, and

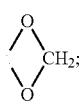

provided that when —Ar$_1$ is substituted with a Q$_1$ group which comprises one or more additional —Ar$_1$ groups, said additional —Ar$_1$ groups are not substituted with Q$_1$;

each X is independently selected from the group consisting of =N—, and =CH—;

each X$_2$ is independently selected from the group consisting of —O—, —CH$_2$—, —NH—, —S—, —SO—, and —SO$_2$—;

each X$_3$ is independently selected from the group consisting of —CH$_2$—, —S—, —SO—, and —SO$_2$—;

each X$_4$ is independently selected from the group consisting of —CH$_2$— and —NH—;

each $X_5$ is independently selected from the group consisting of

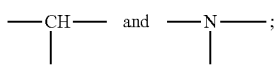

$X_6$ is —CH— or —N—;
each Y is independently selected from the group consisting of —O—, —S—, and —NH;
each Z is independently CO or $SO_2$;
each a is independently 0 or 1;
each c is independently 1 or 2;
each d is independently 0, 1, or 2; and
each e is independently 0, 1, 2, or 3;
provided that when
$R_1$ is (f),
$R_6$ is an α-amino acid side chain residue, and
$R_7$ is —H,
then (aa1) and (aa2) must be substituted with $Q_1$;
also provided that when
$R_1$ is (o),
g is 0,
J is —H,
m is 1,
$R_6$ is an α-amino acid side chain residue,
$R_7$ is —H,
$X_2$ is —$CH_2$—,
$X_5$ is

$X_6$ is

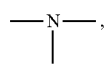

and
$R_3$ is

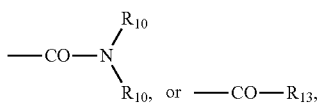

when
$R_{13}$ is:
—$CH_2$—O—CO—$Ar_1$,
—$CH_2$—S—CO—$Ar_1$,
—$CH_2$—O—$Ar_1$,
—$CH_2$—S—$Ar_1$, or
—$R_4$ when —$R_4$ is —H;
then the ring of the $R_1$(o) group must be substituted with $Q_1$ or benzofused; and
provided that when
$R_1$ is (w),
g is 0,
J is —H,
m is 1,
T is —$CO_2H$, $X_2$ is 0,
$R_5$ is benzyloxycarbonyl, and
ring C is benzo,
then $R_3$ cannot be —CO—$R_{13}$ when:
$R_{13}$ is —$CH_2$—O—$Ar_1$ and
$Ar_1$ is 1-phenyl-3-trifluoromethyl-pyrazole-5-yl wherein the phenyl is optionally substituted with a chlorine atom;
or when
$R_{13}$ is —$CH_2$—O—CO—$Ar_1$, wherein
$Ar_1$ is 2,6-dichlorophenyl.
Preferred compounds of embodiment A employ formula α, wherein $R_1$ is (w):

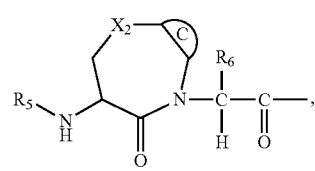

(w)

wherein the other substituents are as described above.
Other preferred compounds of embodiment A employ formula α, wherein $R_1$ is (y):

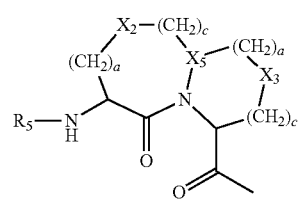

(y)

wherein the other substituents are as described above.
More preferred compounds of embodiment A employ formula α, wherein:
$X_1$ is —CH;
g is 0;
J is —H;
m is 0 or 1 and T is —CO—$CO_2H$, or any bioisosteric replacement for —$CO_2H$, or
m is 1 and T is —$CO_2H$;
$R_1$ is selected from the group consisting of the following formulae, in which any ring may optionally be singly or multiply substituted at any carbon by $Q_1$, at any nitrogen by $R_5$, or at any atom by =O, —OH, —$CO_2H$, or halogen, and wherein (e) is optionally benzofused:

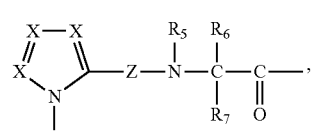

(a)

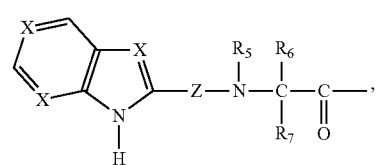

(b)

-continued (c) 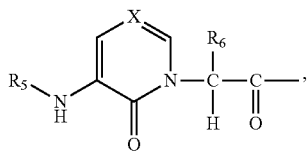

(e) 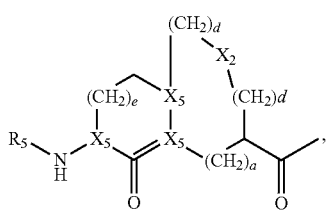

(f) 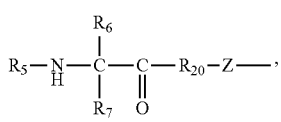

(g) 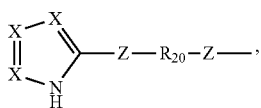

(h) 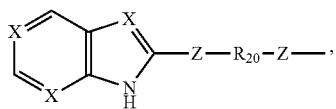

(o) 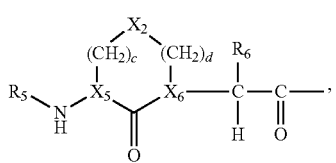

(r) 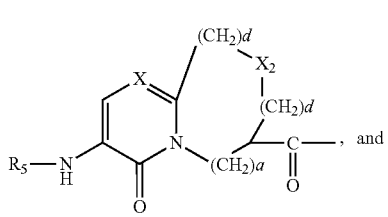, and (w) 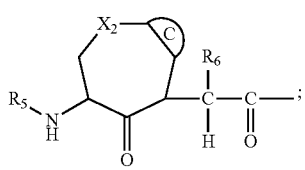;

-continued $R_{20}$ is:

(aa1) 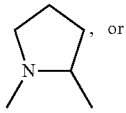, or (aa2) 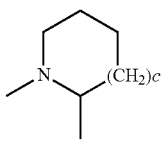

and c is 1;

ring C is benzo optionally substituted with —$C_{1-3}$ alkyl, —O—$C_{1-3}$ alkyl, —Cl, —F or —$CF_3$;

when $R_1$ is (a) or (b), $R_5$ is preferably —H, and when $R_1$ is (c), (e), (f), (o), (r), (w), (x) or (y), $R_5$ is preferably:
—CO—$Ar_1$,
—$SO_2$—$Ar_1$,
—CO—$NH_2$,
—CO—NH—$Ar_1$,
—CO—$R_9$,
—CO—O—$R_9$,
—$SO_2$—$R_9$, or
—CO—NH—$R_9$, $R_7$ is —H and $R_6$ is:
—H,
—$R_9$, or
—$Ar_1$;

$R_9$ is a $C_{1-6}$ straight or branched alkyl group optionally substituted with =O and optionally substituted with —$Ar_1$;

$R_{10}$ is —H or a —$C_{1-3}$ straight or branched alkyl group;

$Ar_1$ is phenyl, naphthyl, pyridyl, benzothiazolyl, thienyl, benzothienyl, benzoxazolyl, 2-indanyl, or indolyl optionally substituted with —O—$C_{1-3}$ alkyl, —NH—$C_{1-3}$ alkyl, —N—($C_{1-3}$ alkyl)$_2$, —Cl, —F, —$CF_3$, —$C_{1-3}$ alkyl, or

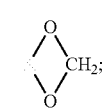

$Q_1$ is $R_9$ or —$(CH_2)_{0,1,2}$-$T_1$-$(CH_2)_{0,1,2}$—$Ar_1$, wherein $T_1$ is —O— or —S—;

each X is independently selected from the group consisting of =N—, and =CH—;

each $X_2$ is independently selected from the group consisting of —O—, —$CH_2$—, —NH—, —S—, —SO—, and —$SO_2$—;

each $X_5$ is independently selected from the group consisting of

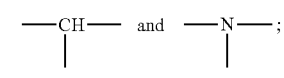

$X_6$ is

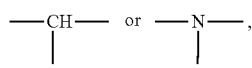

provided that when:
$R_1$ is (o),
$X_2$ is —$CH_2$—,
$X_5$ is

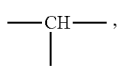

and
$X_6$ is

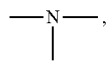

then the ring of the $R_1$(o) group must be substituted with $Q_1$ or benzofused; and
Z is C=O.

Most preferably, compounds of this more preferred embodiment are those wherein the $R_1$ group is:

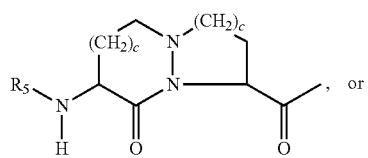
(e1)

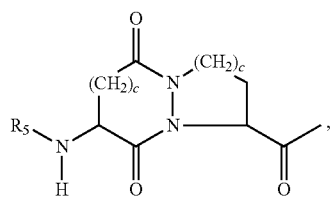
(e2)

and c is 2; or

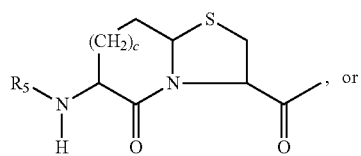
(e4)

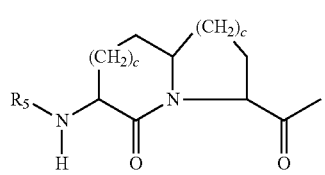
(e7)

which is optionally benzofused,
and c is 1 or 2;
provided that when $R_1$ is (e4),
g is 0,
J is —H,
m is 1,
T is —$CO_2H$,
$R_5$ is benzyloxycarbonyl, and
c is 1,
then $R_3$ cannot be —CO—$R_{13}$ when
$R_{13}$ is —$CH_2$—O—$Ar_1$ and
$Ar_1$ is 1-phenyl-3-trifluoromethyl-pyrazole-5-yl, wherein the phenyl is optionally substituted with a chlorine atom; or when
$R_{13}$ is —$CH_2$—O—CO—$Ar_1$, wherein
$Ar_1$ is 2,6-dichlorophenyl,
and when the 2-position of the scaffold ring is substituted with para-fluoro-phenyl; and
also provided that when
$R_1$ is (e7),
g is 0,
J is —H,
m is 1,
T is —$CO_2H$ or —CO—NH—OH,
$R_5$ is a protective group for the N atom of an amino acid side chain residue, and
each c is 1,
then $R_3$ cannot be —CO—$R_{13}$ when
$R_{13}$ is:
—$CH_2$—O—CO—$Ar_1$,
—$CH_2$—S—CO—$Ar_1$,
—$CH_2$—O—$Ar_1$, or
—$CH_2$—S—$Ar_1$.

The most preferred compounds of this embodiment are those wherein:
$R_1$ is:

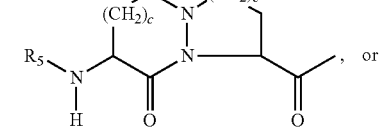
(e1)

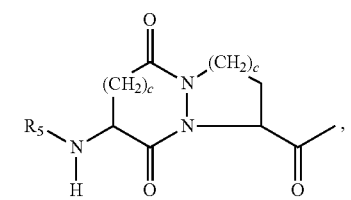
(e2)

and c is 2;
m is 1;
T is —$CO_2H$; and
$R_3$ is —CO—$R_{13}$.

Other most preferred compounds of this embodiment are those wherein:

R$_1$ is:

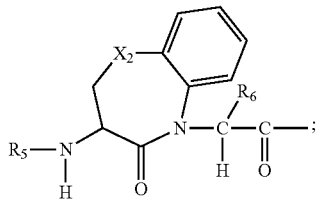
(w1)

wherein
X$_2$ is:
—O—,
—S—,
—SO$_2$—, or
—NH—;
optionally substituted with R$_5$ or Q$_1$ at X$_2$ when X$_2$ is —NH—; and
ring C is benzo substituted with —C$_{1-3}$ alkyl, —O—C$_{1-3}$ alkyl, —Cl, —F or —CF$_3$.

The ICE inhibitors of another embodiment (B) of this invention are those of formula (I):

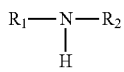
(I)

wherein:
R$_1$ is selected from the group consisting of the following formulae:

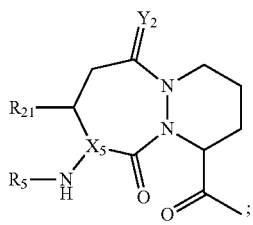
(e10)

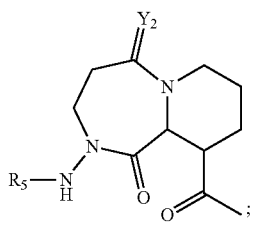
(e11)

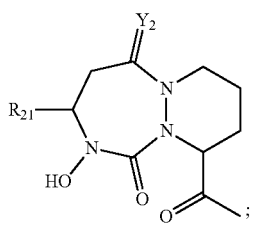
(e12)

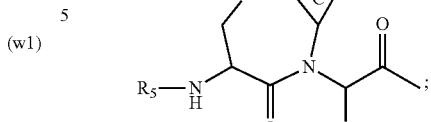
(w2)

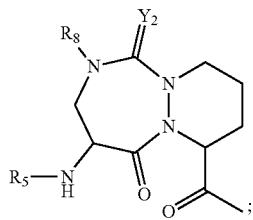
(y1)

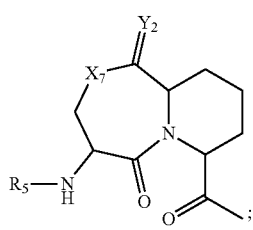
(y2)

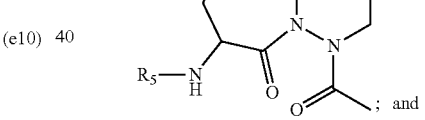
(z)

; and ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

R$_2$ is:

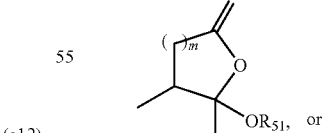
(a)

or

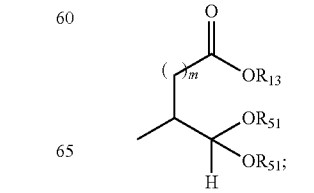
(b)

m is 1 or 2;

$R_5$ is selected from the group consisting of:
— $C(O)$—$R_{10}$,
— $C(O)O$—$R_9$,

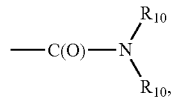

— $S(O)_2$—$R_9$,
— $C(O)$—$CH_2$—$O$—$R_9$,
— $C(O)C(O)$—$R_{10}$,
— $R_9$,
— H, and
— $C(O)C(O)$—$OR_{10}$;

$X_5$ is

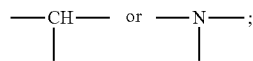

$Y_2$ is $H_2$ or O;
$X_7$ is —$N(R_8)$— or —O—;
$R_6$ is selected from the group consisting of —H and —$CH_3$;
$R_8$ is selected from the group consisting of:
— $C(O)$—$R_{10}$,
— $C(O)O$—$R_9$,
— $C(O)$—$N(H)$—$R_{10}$,
— $S(O)_2$—$R_9$,
— $S(O)_2$—$NH$—$R_{10}$,
— $C(O)$—$CH_2$—$OR_{10}$,
— $C(O)C(O)$—$R_{10}$;
— $C(O)$—$CH_2N(R_{10})(R_{10})$,
— $C(O)$—$CH_2C(O)$—$O$—$R_9$,
— $C(O)$—$CH_2C(O)$—$R_9$,
— H, and
— $C(O)$—$C(O)$—$OR_{10}$;

each $R_9$ is independently selected from the group consisting of —$Ar_3$ and a —$C_{1-6}$ straight or branched alkyl group optionally substituted with $Ar_3$, wherein the —$C_{1-6}$ alkyl group is optionally unsaturated;

each $R_{10}$ is independently selected from the group consisting of —H, —$Ar_3$, a $C_{3-6}$ cycloalkyl group, and a —$C_{1-6}$ straight or branched alkyl group optionally substituted with $Ar_3$, wherein the —$C_{1-6}$ alkyl group is optionally unsaturated;

$R_{13}$ is selected from the group consisting of H, $Ar_3$, and a $C_{1-6}$ straight or branched alkyl group optionally substituted with $Ar_3$, —$CONH_2$, —$OR_5$, —OH, —$OR_9$, or —$CO_2H$;

each $R_{51}$ is independently selected from the group consisting of $R_9$, —$C(O)$—$R_9$, —$C(O)$—$N(H)$—$R_9$, or each $R_{51}$ taken together forms a saturated 4-8 member carbocyclic ring or heterocyclic ring containing —O—, —S—, or —NH—;

each $R_{21}$ is independently selected from the group consisting of —H or a —$C_{1-6}$ straight or branched alkyl group;

each $Ar_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, $SO_2$, =N—, and —NH—, said heterocycle group optionally containing one or more double bonds, said hetero-cycle group optionally comprising one or more aromatic rings, and said cyclic group optionally being singly or multiply substituted by -$Q_1$;

each $Q_1$ is independently selected from the group consisting of —$NH_2$, —$CO_2H$, —Cl, —F, —Br, —I, —$NO_2$, —CN, =O, —OH, -perfluoro $C_{1-3}$ alkyl, $R_5$, —$OR_5$, —$NHR_5$, $OR_9$, —$NHR_9$, $R_9$, —$C(O)$—$R_{10}$, and

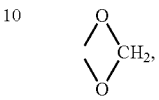

provided that when —$Ar_3$ is substituted with a $Q_1$ group which comprises one or more additional —$Ar_3$ groups, said additional —$Ar_3$ groups are not substituted with another —$Ar_3$.

Preferably, $R_5$ is selected from the group consisting of:
— $C(O)$—$R_{10}$,
— $C(O)O$—$R_9$, and
— $C(O)$—$NH$—$R_{10}$.

Alternatively, $R_5$ is selected from the group consisting of:
— $S(O)_2$—$R_9$,
— $S(O)_2$—$NH$—$R_{10}$,
— $C(O)$—$C(O)$—$R_{10}$,
— $R_9$, and
— $C(O)$—$C(O)$—$OR_{10}$.

More preferably:

m is 1;

$R_{13}$ is H or a —$C_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

$R_{21}$ is —H or —$CH_3$;

$R_{51}$ is a $C_{1-6}$ straight or branched alkyl group optionally substituted with $Ar_3$, wherein $Ar_3$ is phenyl, optionally substituted by -$Q_1$;

$Ar_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;

each $Q_1$ is independently selected from the group consisting of —$NH_2$, —Cl, —F, —Br, —OH, —$R_9$, —NH—$R_5$ wherein $R_5$ is —$C(O)$—$R_{10}$ or —$S(O)_2$—$R_9$, —$OR_5$ wherein $R_5$ is —$C(O)$—$R_{10}$, —$OR_9$, —$NHR_9$, and

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

The ICE inhibitors of another embodiment (C) of this invention are those of formula (II):

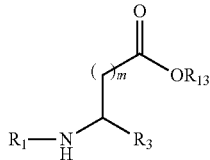
(II)

wherein:

m is 1 or 2;

$R_1$ is selected from the group consisting of the following formulae:

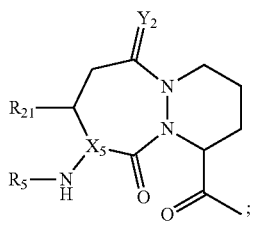
(e10)

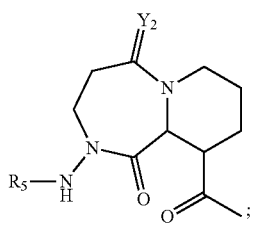
(e11)

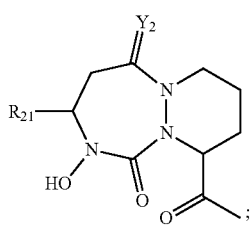
(e12)

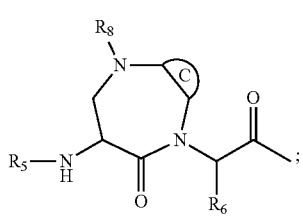
(w2)

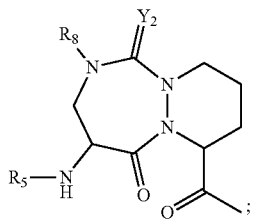
(y1)

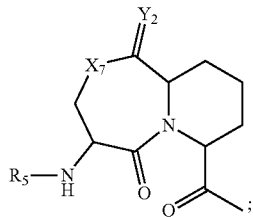
(y2)

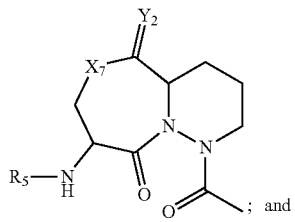
(z)

ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_3$ is selected from the group consisting of:
—CN,
—C(O)—H,
—C(O)—CH$_2$-T$_1$-R$_{11}$,
—C(O)—CH$_2$—F,
—C=N—O—R$_9$, and
—CO—Ar$_2$;

$R_5$ is selected from the group consisting of:
—C(O)—R$_{10}$,
—C(O)O—R$_9$,

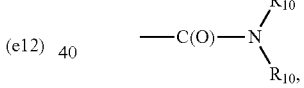

—S(O)$_2$—R$_9$,
—C(O)—CH$_2$—O—R$_9$,
—C(O)C(O)—R$_{10}$,
—R$_9$,
—H, and
—C(O)C(O)—OR$_{10}$, $X_5$ is

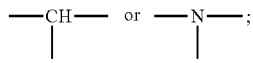

$Y_2$ is H$_2$ or O;
$X_7$ is —N(R$_8$)— or —O—;
each $T_1$ is independently selected from the group consisting of —O—, —S—, —S(O)—, and —S(O)$_2$—;
$R_6$ is selected from the group consisting of —H and —CH$_3$;
$R_8$ is selected from the group consisting of:
—C(O)—R$_{10}$,
—C(O)O—R$_9$,
—C(O)—NH—R$_{10}$,
—S(O)$_2$—R$_9$,
—S(O)$_2$—NH—R$_{10}$, —C(O)—CH₂—OR₁₀,
—C(O)C(O)—R₁₀,
—C(O)—CH₂—N(R₁₀)(R₁₀),
—C(O)—CH₂C(O)—O—R₉,
—C(O)—CH₂C(O)—R₉,
—H, and
—C(O)—C(O)—OR₁₀;

each R₉ is independently selected from the group consisting of —Ar₃ and a —C₁₋₆ straight or branched alkyl group optionally substituted with Ar₃, wherein the —C₁₋₆ alkyl group is optionally unsaturated;

each R₁₀ is independently selected from the group consisting of —H, —Ar₃, a C₃₋₆ cycloalkyl group, and a —C₁₋₆ straight or branched alkyl group optionally substituted with Ar₃, wherein the —C₁₋₆ alkyl group is optionally unsaturated;

each R₁₁ is independently selected from the group consisting of:
—Ar₄,
—(CH₂)₁₋₃—Ar₄,
—H, and
—C(O)—Ar₄;

R₁₃ is selected from the group consisting of H, Ar₃, and a C₁₋₆ straight or branched alkyl group optionally substituted with Ar₃, —CONH₂, —OR₅, —OH, —OR₉, or —CO₂H; —OR₁₃ is optionally —N(H)—OH;

each R₂₁ is independently selected from the group consisting of —H or a —C₁₋₆ straight or branched alkyl group;

Ar₂ is independently selected from the following group, in which any ring may optionally be singly or multiply substituted by -Q₁:

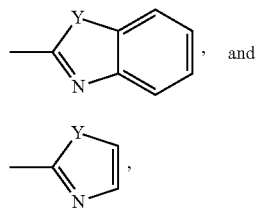

(hh)

, and (ii)

wherein each Y is independently selected from the group consisting of O and S;

each Ar₃ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO₂, =N—, and —NH—, —N(R₅)—, and —N(R₉)— said heterocycle group optionally containing one or more double bonds, said heterocycle group optionally comprising one or more aromatic rings, and said cyclic group optionally being singly or multiply substituted by -Q₁;

each Ar₄ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, SO₂, =N—, —NH—, —N(R₅)—, and —N(R₉)— said heterocycle group optionally containing one or more double bonds, said heterocycle group optionally comprising one or more aromatic rings, and said cyclic group optionally being singly or multiply substituted by -Q₁;

each Q₁ is independently selected from the group consisting of —NH₂, —CO₂H, —Cl, —F, —Br, —I, —NO₂, —CN, =O, —OH, -perfluoro C₁₋₃ alkyl, R₅, —OR₅, —NHR₅, OR₉, —NHR₉, R₉, —C(O)—R₁₀, and

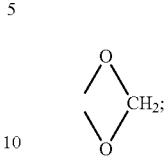

provided that when —Ar₃ is substituted with a Q₁ group which comprises one or more additional —Ar₃ with another —Ar₃.

Preferred compounds of this embodiment include, but are not limited to:

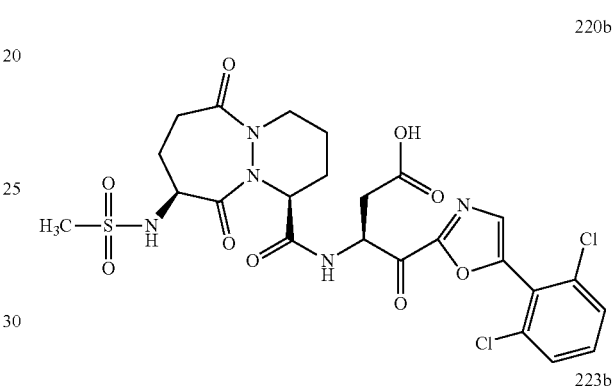

220b

223b

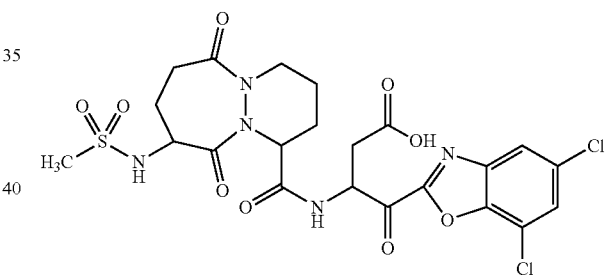

223e

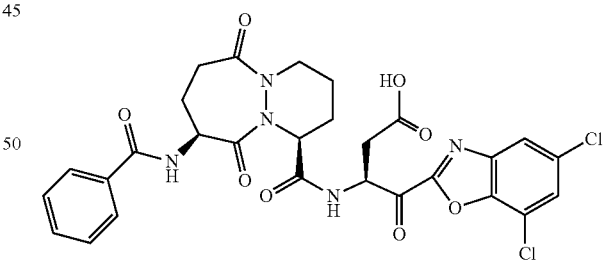

226e

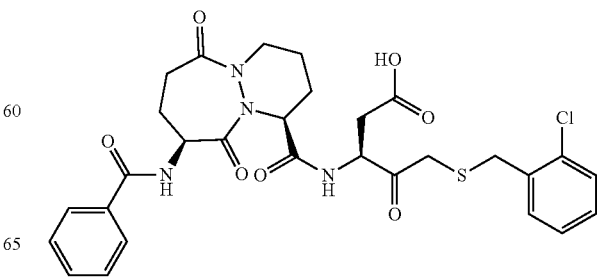

227e
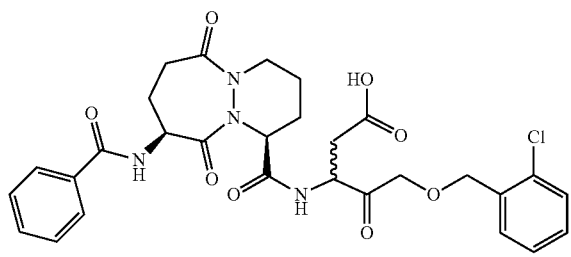
307a
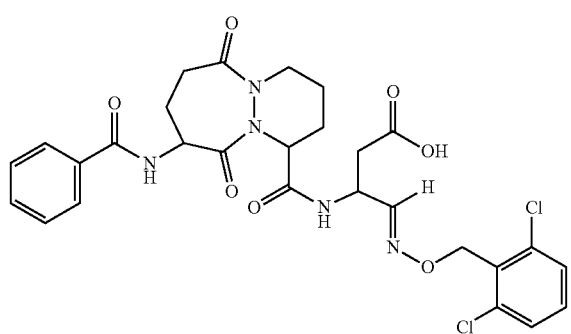
307b
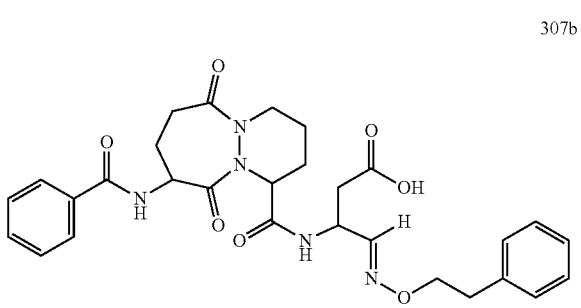
429
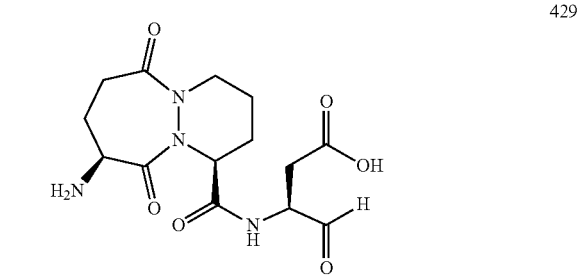
820b
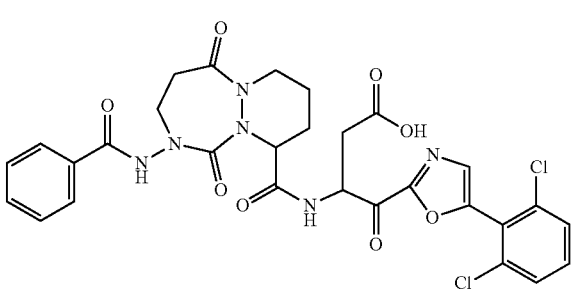
823b
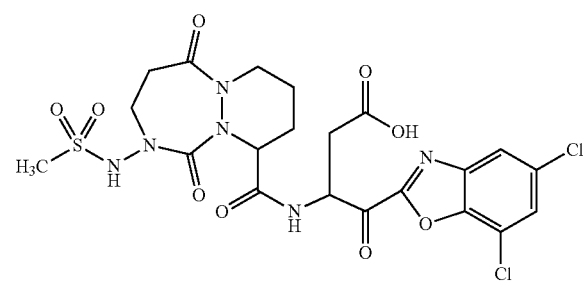
823e
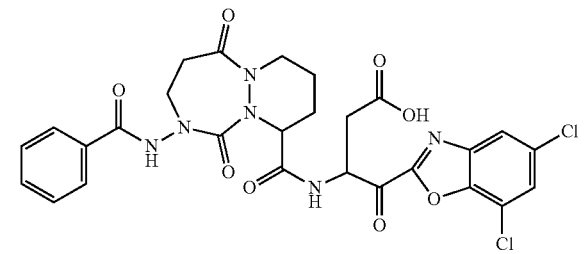
826e
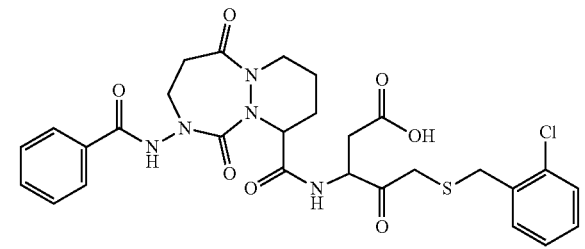
827e
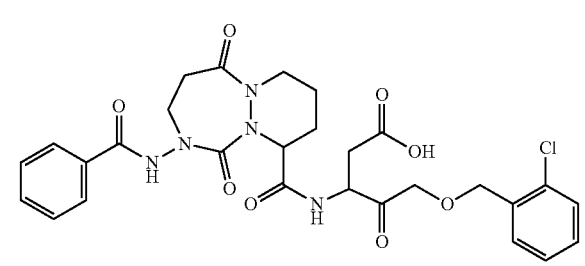
907a
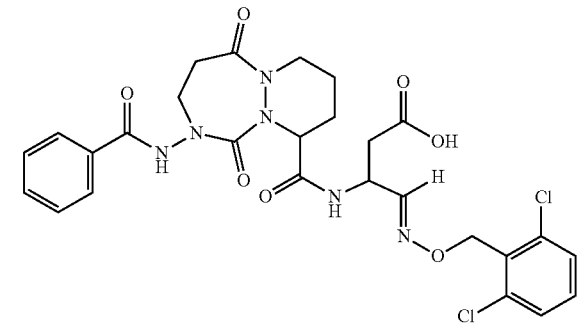

907b

1029

Preferred compounds of embodiment C employ formula (II), wherein $R_1$ is (e11) and the other substituents are as defined above.

Other preferred compounds of embodiment C employ formula (II), wherein $R_1$ is (e12) and the other substituents are as defined above.

Other preferred compounds of embodiment C employ formula (II) wherein $R_1$ is (y1) and the other substituents are as defined above.

Other preferred compounds of embodiment C employ formula (II) wherein $R_1$ is (y2) and the other substituents are as defined above.

Other preferred compounds of embodiment C of employ formula (II) wherein $R_1$ is (z) and the other substituents are as defined above.

Other preferred compound of embodiment C employ formula (II) wherein $R_1$ is (w2) and the other substituents are as defined above.

More preferably, $R_1$ is (w2) and
m is 1;
ring C is benzo, pyrido, or thieno;
$R_3$ is selected from the group consisting of —C(O)—H, —C(O)—$Ar_2$, and —C(O)$CH_2$-$T_1$-$R_{11}$;
$R_5$ is selected from the group consisting of:
—C(O)—$R_{10}$, wherein $R_{10}$ is —$Ar_3$; —C(O)O—$R_9$, wherein $R_9$ is —$CH_2$—$Ar_3$; —C(O)C(O)—$R_{10}$, wherein $R_{10}$ is —$CH_2Ar_3$;
—$R_9$, wherein $R_9$ is a $C_{1-2}$ alkyl group substituted with —$Ar_3$; and
—C(O)C(O)—$OR_{10}$, wherein $R_{10}$ is —$CH_2Ar_3$;
$T_1$ is O or S;
$R_6$ is H;
$R_8$ is selected from the group consisting —C(O)—$R_{10}$, —C(O)—$CH_2$—$OR_{10}$, and —C(O)$CH_2$—N($R_{10}$)($R_{10}$), wherein $R_{10}$ is H, $CH_3$, or —$CH_2CH_3$;
$R_{11}$ is selected from the group consisting of —$Ar_4$, —$(CH_2)_{1-3}$—$Ar_4$, and —C(O)—$Ar_4$;
$R_{13}$ is H or a —$C_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

$Ar_2$ is (hh);

Y is O;

$Ar_3$ is phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl;

$Ar_4$ is phenyl, tetrazolyl, naphthyl, pyridinyl, oxazolyl, pyrimidinyl, or indolyl;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$NHR_9$, and

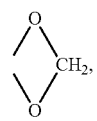

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Preferred compounds of this embodiment include, but are not limited to:

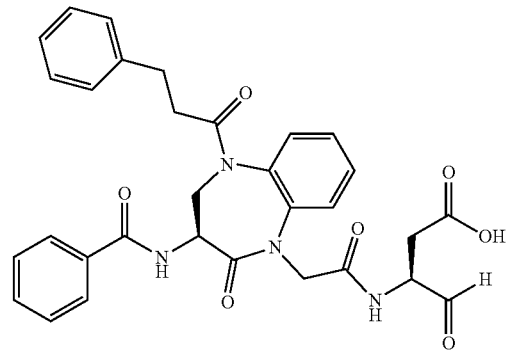

605a

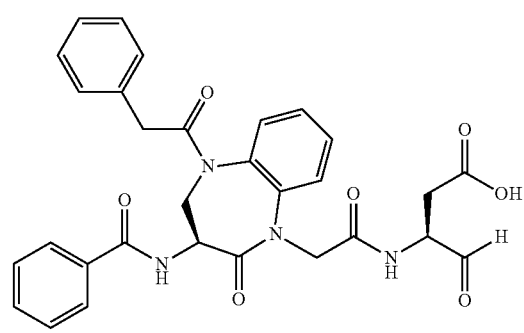

605b

37
-continued
605c
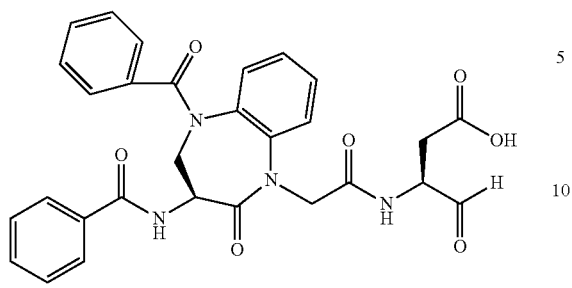
605d
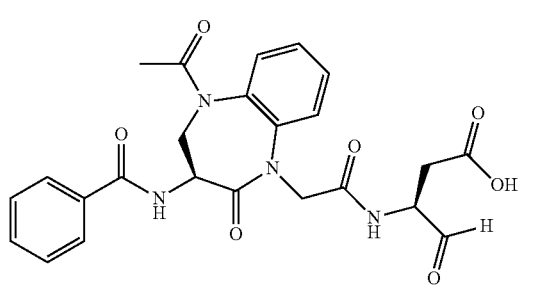
605e
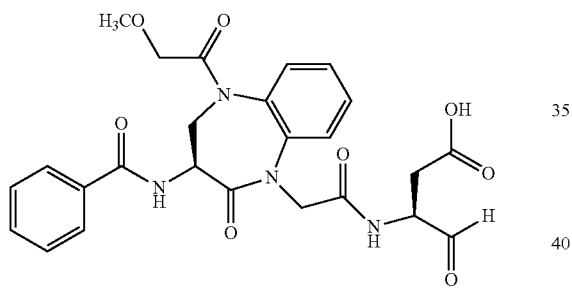
605f

605g
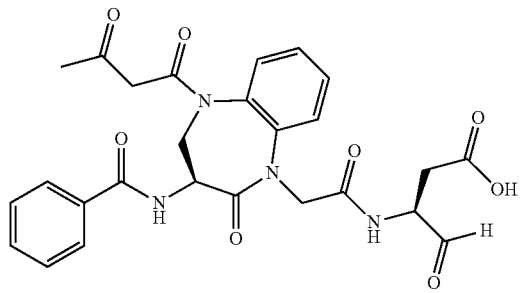
38
-continued
605h
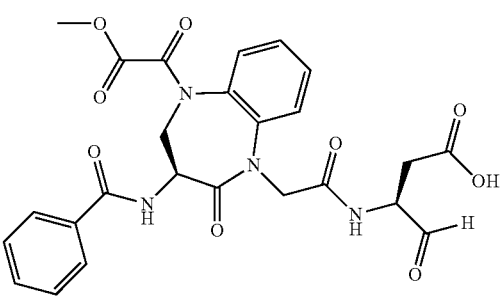
605i
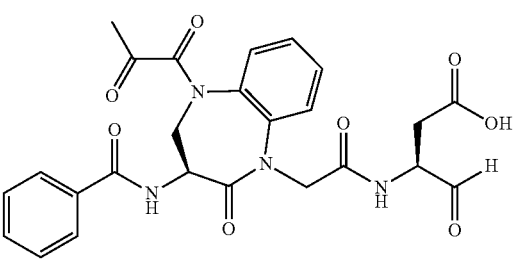
605j
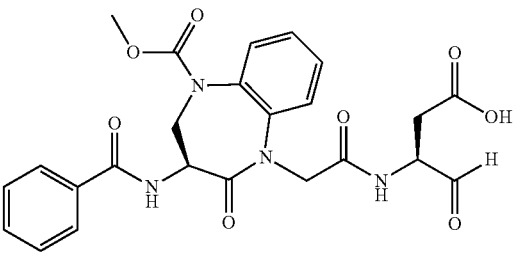
605m
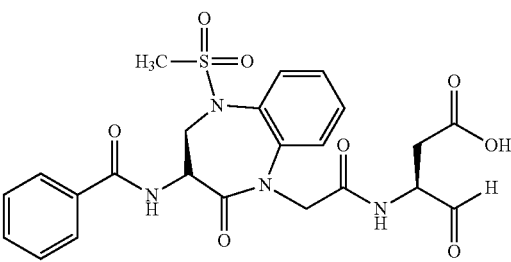
605n
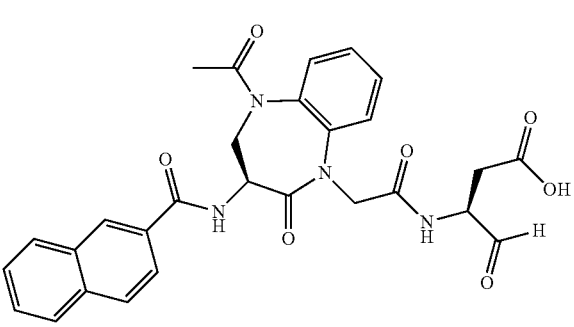

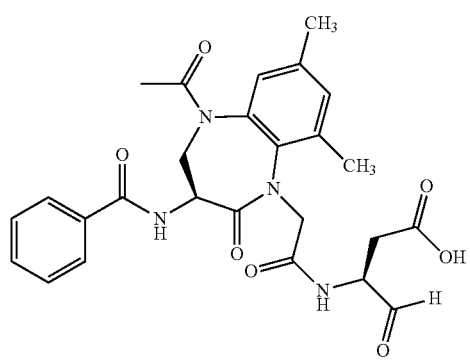
605o
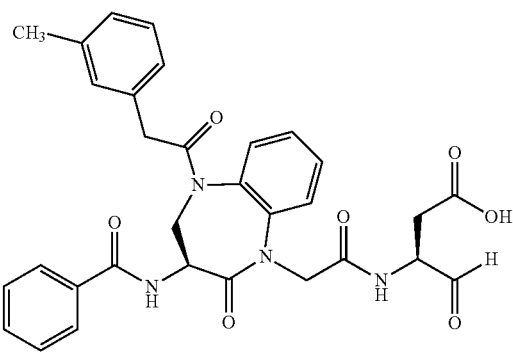
605t
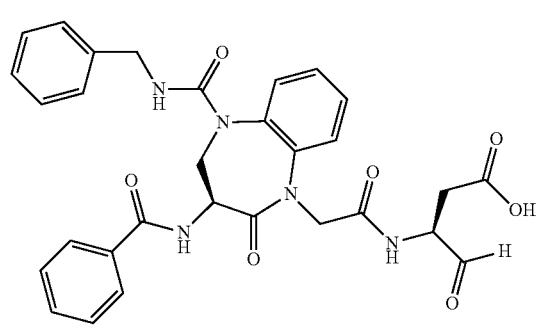
605p
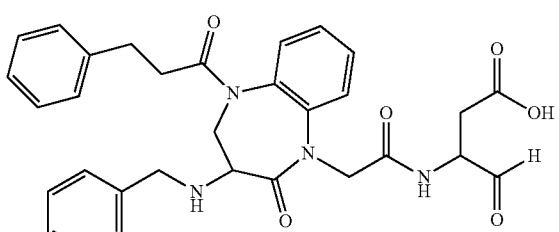
605v
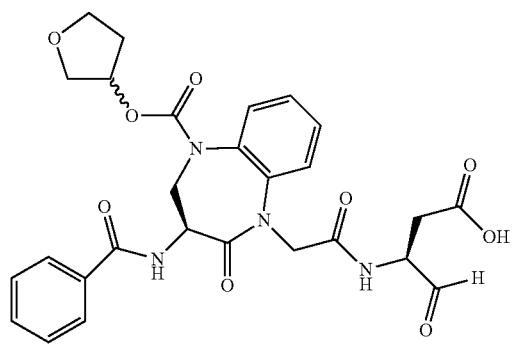
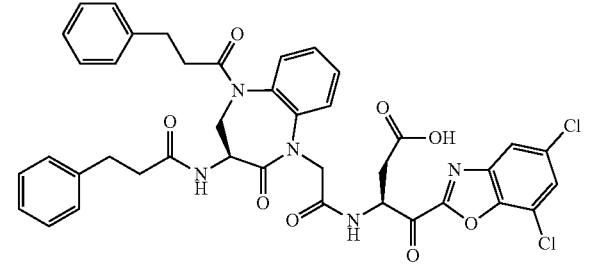
609a
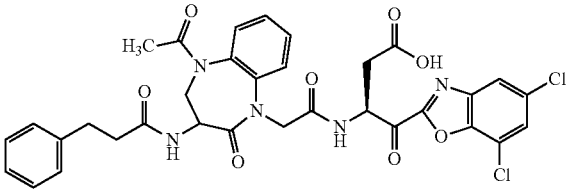
609b
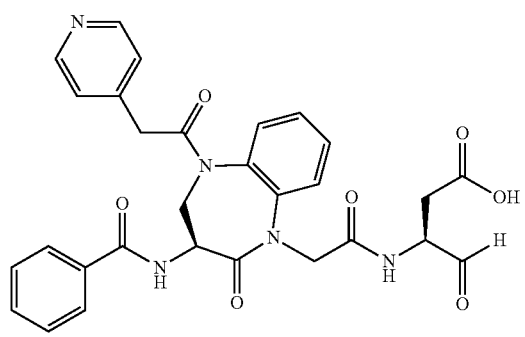
605s
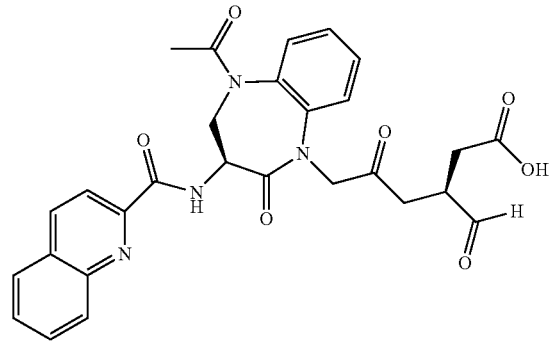
619

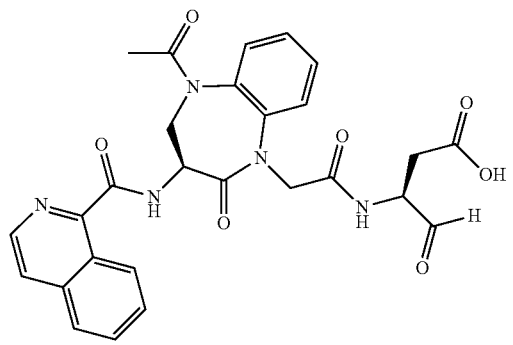
620
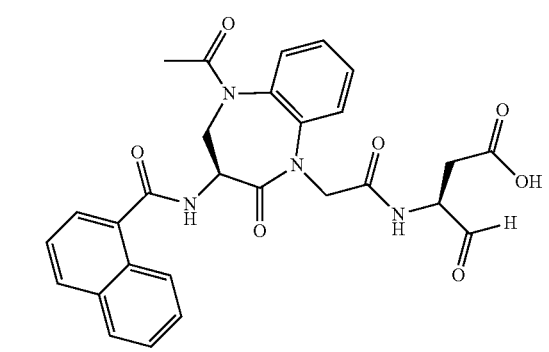
621
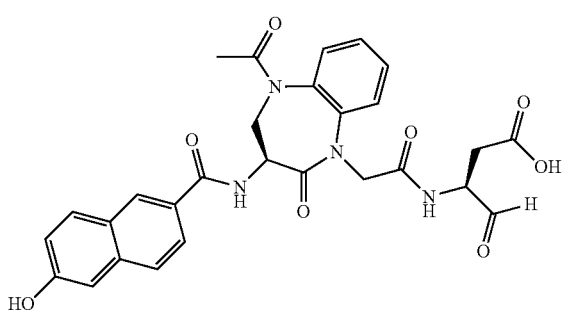
622
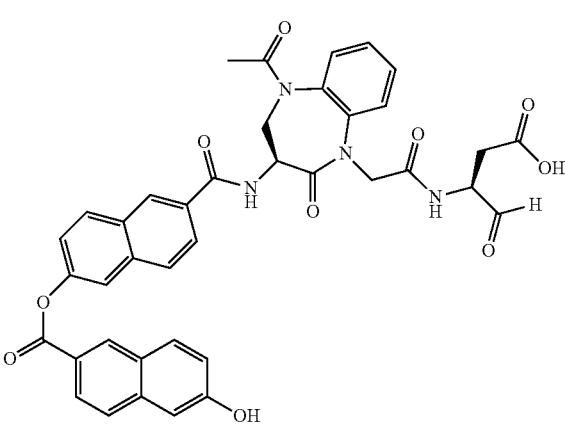
623
624
625
626
627
628

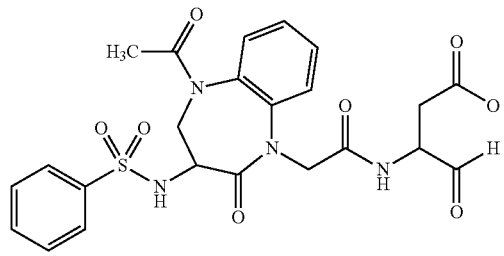

629


630


631


632


633

634

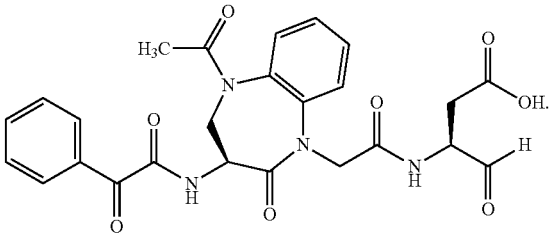

635

Other preferred compounds of embodiment C employ formula (II) wherein $R_1$ is (e10), $X_5$ is CH, and the other substituents are as defined above.

More preferred compounds of embodiment C employ formula (II) wherein $R_1$ is (e10), $X_5$ is CH, $R_3$ is CO—$Ar_2$, and the other substituents are as defined above.

Other more preferred compounds of embodiment C employ formula (II) wherein $R_1$ is (e10), $X_5$ is CH, $R_3$ is —C(O)—CH$_2$—T$_1$-R$_{11}$, $R_{11}$ is —(CH$_2$)$_{1-3}$—Ar$_4$, and the other substituents are as defined above.

Other more preferred compounds of embodiment C employ formula (II) wherein $R_1$ is (e10) and $X_5$ is CH and $R_3$ is —C(O)—CH$_2$-T$_1$-R$_{11}$;

$T_1$ is O; and $R_{11}$ is —C(O)—Ar$_4$, and the other substituents are as defined above.

More preferably, in these more preferred compounds, $R_5$ is selected from the group consisting of:

—C(O)—R$_{10}$,

—C(O)O—R$_9$, and

—C(O)—NH—R$_{10}$.

Alternatively, in these more preferred compounds, $R_5$ is selected from the group consisting of:

—S(O)$_2$—R$_9$,

—S(O)$_2$—NR—R$_{10}$,

—C(O)—C(O)—R$_{10}$,

—R$_9$, and

—C(O)—C(O)—OR$_{10}$.

Most preferably, in these more preferred compounds, m is 1;

$T_1$ is O or S;

$R_{13}$ is H or a —C$_{1-4}$ straight or branched alkyl group optionally substituted with —Ar$_3$, —OH, —OR$_9$, or —CO$_2$H, wherein the R$_9$ is a —C$_{1-4}$ branched or straight alkyl group, wherein Ar$_3$ is morpholinyl or phenyl, wherein the phenyl is optionally substituted with Q$_1$;

$R_{21}$ is —H or —CH$_3$;

$R_{51}$ is a C$_{1-6}$ straight or branched alkyl group optionally substituted with Ar$_3$, wherein Ar$_3$ is phenyl, optionally substituted by -Q$_1$;

Ar$_2$ is (hh);

Y is O, and

Ar$_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;

Ar$_4$ is phenyl, tetrazolyl, pyridinyl, oxazolyl, naphthyl, pyrimidinyl, or thienyl;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$NHR_9$, and

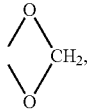

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other more preferred compounds of embodiment C employ formula (II) wherein $R_1$ is (e10), $X_5$ is CH, $R_3$ is —C(O)—H, and the other substituents are as defined above.

More preferably, in these more preferred compounds, $R_5$ is selected from the group consisting of:
- —C(O)—$R_{10}$,
- —C(O)O—$R_9$, and
- —C(O)—NH—$R_{10}$.

Alternatively, in these more preferred compounds, $R_5$ is selected from the group consisting of:
- —$S(O)_2$—$R_9$,
- —$S(O)_2$—NH—$R_{10}$,
- —C(O)—C(O)—$R_{10}$,
- —$R_9$, and
- —C(O)—C(O)—$OR_{10}$.

Most preferably, in these more preferred compounds,
m is 1;
$T_1$ is O or S;
$R_{13}$ is H or a —$C_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;
$R_{21}$ is —H or —$CH_3$;
$R_{51}$ is a $C_{1-6}$ straight or branched alkyl group optionally substituted with $Ar_3$, wherein $Ar_3$ is phenyl, optionally substituted by -$Q_1$;
$Ar_2$ is (hh);
Y is O, and
$Ar_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;
$Ar_4$ is phenyl, tetrazolyl, pyridinyl, oxazolyl, naphthyl, pyrimidinyl, or thienyl;
each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$NHR_9$, and

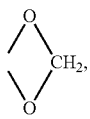

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other more preferred compounds of embodiment C employ formula (II) wherein $R_1$ is (e10) and $X_5$ is CH, $R_3$ is —CO—$CH_2$-$T_1$-$R_{11}$, and $R_{11}$ is —$Ar_4$, and the other substituents are as defined above.

More preferably, in these more preferred compounds, $R_5$ is selected from the group consisting of:
- —C(O)—$R_{10}$,
- —C(O)O—$R_9$, and
- —C(O)—NH—$R_{10}$.

Alternatively, in these more preferred compounds, $R_5$ is selected from the group consisting of:
- —$S(O)_2$—$R_9$,
- —$S(O)_2$—NH—$R_{10}$,
- —C(O)—C(O)—$R_{10}$,
- —$R_9$, and
- —C(O)—C(O)—$OR_{10}$.

Most preferably, in these more preferred compounds,
m is 1;
$T_1$ is O or S;
$R_{13}$ is H or a —$C_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;
$R_{21}$ is —H or —$CH_3$;
$R_{51}$ is a $C_{1-6}$ straight or branched alkyl group optionally substituted with $Ar_3$, wherein $Ar_3$ is phenyl, optionally substituted by -$Q_1$;
$Ar_2$ is (hh);
Y is O, and
$Ar_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;
$Ar_4$ is phenyl, tetrazolyl, pyridinyl, oxazolyl, naphthyl, pyrimidinyl, or thienyl;
each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$NHR_9$, and

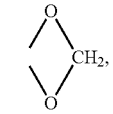

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other preferred compounds of embodiment C employ formula (II) wherein $R_1$ is (e10), $X_5$ is N, and the other substituents are as defined above.

More preferred compounds of embodiment C, employ formula (II) wherein $R_1$ is (e10), $X_5$ is N, $R_3$ is CO—$Ar_2$, and the other substituents are as defined above.

Other more preferred compounds of embodiment C, employ formula (II) wherein $R_1$ is (e10), $X_5$ is N, $R_3$ is —C(O)—$CH_2$-$T_1$-$R_{11}$, $R_{11}$ is —$(CH_2)_{1-3}$—$Ar_4$, and the other substituents are as defined above.

Other more preferred compounds of embodiment C, employ formula (II) wherein $R_1$ is (e10) and $X_5$ is N and:
$R_3$ is —C(O)—$CH_2$-$T_1$-$R_{11}$;
$T_1$ is O; and
$R_{11}$ is —C(O)—$Ar_4$, and the other substituents are as defined above.

More preferably, in these more preferred compounds, $R_5$ is selected from the group consisting of:
—C(O)—$R_{10}$,
—C(O)O—$R_9$, and
—C(O)—NH—$R_{10}$.

Alternatively, in these more preferred compounds, $R_5$ is selected from the group consisting of:
—S(O)$_2$—$R_9$,
—S(O)$_2$—NH—$R_{10}$,
—C(O)—C(O)—$R_{10}$,
—$R_9$, and
—C(O)—C(O)—$OR_{10}$.

Most preferably, in these more preferred compounds, $R_5$ is selected from the group consisting of:
—S(O)$_2$—$R_9$,
—S(O)$_2$—NH—$R_{10}$,
—C(O)—C(O)—$R_{10}$,
—$R_9$, and
—C(O)—C(O)—$OR_{10}$.
m is 1;
$T_1$ is O or S;
$R_{13}$ is H or a —$C_{1-4}$ straight or branched alkyl group optionally substituted with —$Ar_3$, —OH, —$CR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;
$R_{21}$ is —H or —$CH_3$;
$R_{51}$ is a $C_{1-6}$ straight or branched alkyl group optionally substituted with $Ar_3$, wherein $Ar_3$ is phenyl, optionally substituted by -$Q_1$;
$Ar_2$ is (hh);
Y is O, and
$Ar_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;
$Ar_4$ is phenyl, tetrazolyl, pyridinyl, oxazolyl, naphthyl, pyrimidinyl, or thienyl;
each $Q_1$ is independently selected from the group consisting of —$NH_2$, —Cl, —F, —Br, —OH, —$R_9$, —NH—$R_5$ wherein $R_5$ is —C(O)—$R_{10}$ or —S(O)$_2$—$R_9$, —$OR_5$ wherein $R_5$ is —C(O)—$R_{10}$, —$OR_9$, —$NHR_9$, and

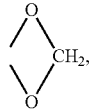

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other more preferred compounds of embodiment C, employ formula (II) wherein $R_1$ is (e10), $X_5$ is N, $R_3$ is —C(O)—H, and the other substituents are as defined above.

More preferably, in these more preferred compounds, $R_5$ is selected from the group consisting of:
—C(O)—$R_{10}$,
—C(O)O—$R_9$, and
—C(O)—NH—$R_{10}$.

Alternatively, in these more preferred compounds, $R_5$ is selected from the group consisting of:
—S(O)$_2$—$R_9$,
—S(O)$_2$—NH—$R_{10}$,
—C(O)—C(O)—$R_{10}$,
—$R_9$, and
—C(O)—C(O)—$OR_{10}$.

Most preferably, in these more preferred compounds,
m is 1;
$T_1$ is O or S;
$R_{13}$ is H or a —$C_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;
$R_{21}$ is —H or —$CH_3$;
$R_{51}$ is a $C_{1-6}$ straight or branched alkyl group optionally substituted with $Ar_3$, wherein $Ar_3$ is phenyl, optionally substituted by -$Q_1$;
$Ar_2$ is (hh);
Y is O, and
$Ar_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;
$Ar_4$ is phenyl, tetrazolyl, pyridinyl, oxazolyl, naphthyl, pyrimidinyl, or thienyl;
each $Q_1$ is independently selected from the group consisting of —$NH_2$, —Cl, —F, —Br, —OH, —$R_9$, —NH—$R_5$ wherein $R_5$ is —C(O)—$R_{10}$ or —S(O)$_2$—$R_9$, —$OR_5$ wherein $R_5$ is —C(O)—$R_{10}$, —$OR_9$, —$NHR_9$, and

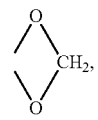

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other more preferred compounds of embodiment C, employ formula (II) wherein $R_1$ is (e10), $X_5$ is N, $R_3$ is —CO—$CH_2$-$T_1$-$R_{11}$, $R_{11}$ is —$Ar_4$, and the other substituents are as defined above.

More preferably, in these more preferred compounds, $R_5$ is selected from the group consisting of:
—C(O)—$R_{10}$,
—C(O)O—$R_9$, and
—C(O)—NH—$R_{10}$.

Alternatively, in these more preferred compounds, $R_5$ is selected from the group consisting of:
—S(O)$_2$—$R_9$,
—S(O)$_2$—NH—$R_{10}$,
—C(O)—C(O)—$R_{10}$,
—$R_9$, and
—C(O)—C(O)—O$R_{10}$.

Most preferably, in these more preferred compounds
m is 1;
$T_1$ is O or S;
$R_{13}$ is H or a —$C_{1-4}$ straight or branched alkyl group optionally substituted with —Ar$_3$, —OH, —OR$_9$, or —CO$_2$H, wherein the $R_9$ is a —$C_{1-4}$ branched or straight alkyl group, wherein Ar$_3$ is morpholinyl or phenyl, wherein the phenyl is optionally substituted with $Q_1$;
$R_{21}$ is —H or —CH$_3$;
$R_{51}$ is a $C_{1-6}$ straight or branched alkyl group optionally substituted with Ar$_3$, wherein Ar$_3$ is phenyl, optionally substituted by -$Q_1$;
Ar$_2$ is (hh);
Y is O, and
Ar$_3$ is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl;
Ar$_4$ is phenyl, tetrazolyl, pyridinyl, oxazolyl, naphthyl, pyrimidinyl, or thienyl;
each $Q_1$ is independently selected from the group consisting of —NH$_2$, —Cl, —F, —Br, —OH, —$R_9$, —NH—$R_5$ wherein $R_5$ is —C(O)—$R_{10}$ or —S(O)$_2$—$R_9$, —OR$_5$ wherein $R_5$ is —C(O)—$R_{10}$, —OR$_9$, —NHR$_9$, and

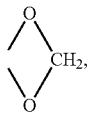

wherein each $R_9$ and $R_{10}$ are independently a —$C_{1-6}$ straight or branched alkyl group optionally substituted with Ar$_3$ wherein Ar$_3$ is phenyl;
provided that when —Ar$_3$ is substituted with a $Q_1$ group which comprises one or more additional —Ar$_3$ groups, said additional —Ar$_3$ groups are not substituted with another —Ar$_3$.

Preferred compounds of embodiment B include, but are not limited to:

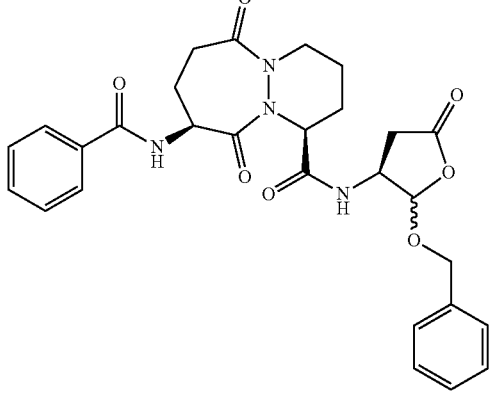

213e

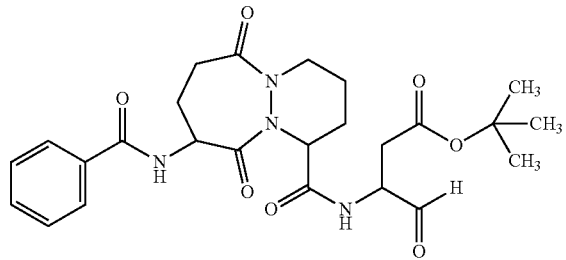

302

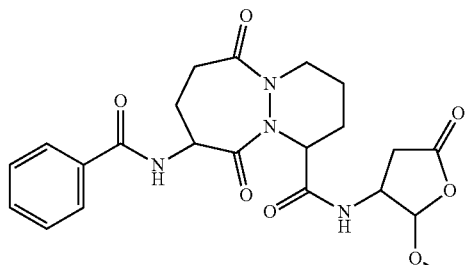

304a

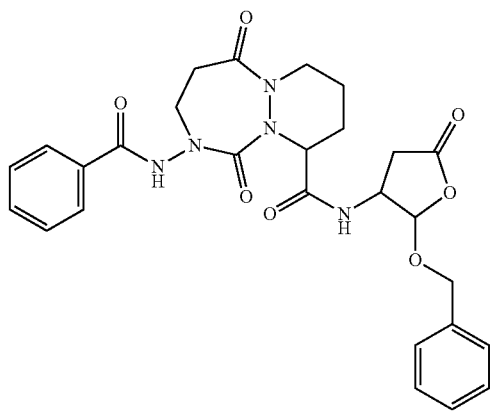

813e

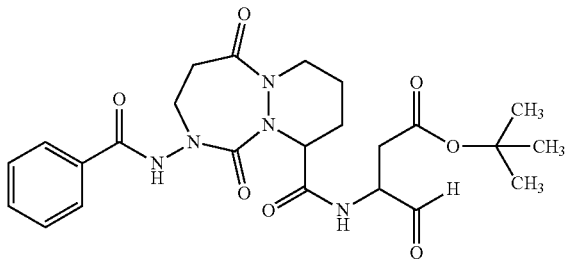

902

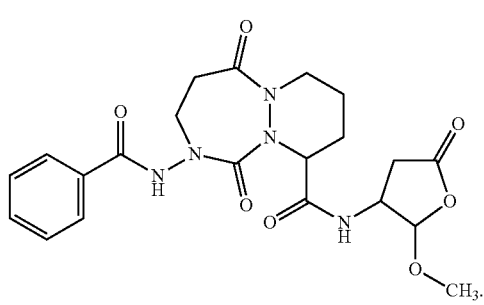

904a

Preferred compounds of embodiment C include, but are not limited to:
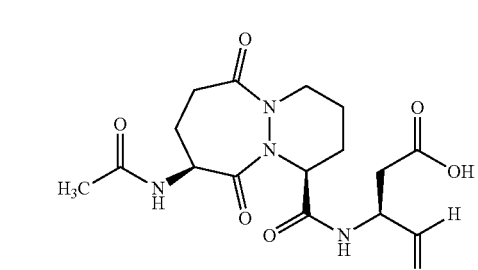
214c
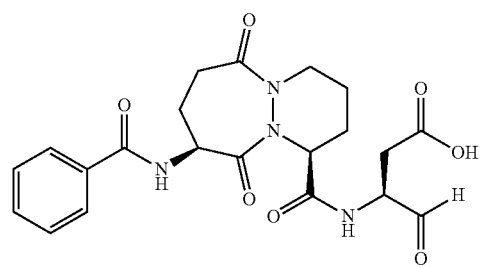
214e
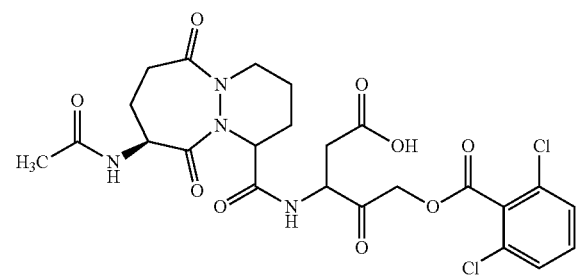
217c
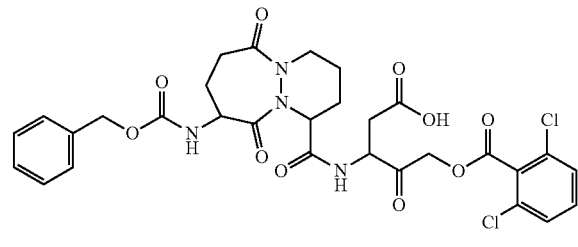
217d
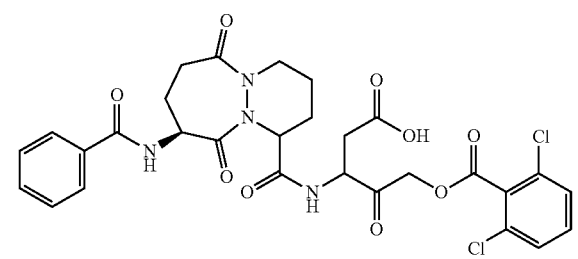
217e
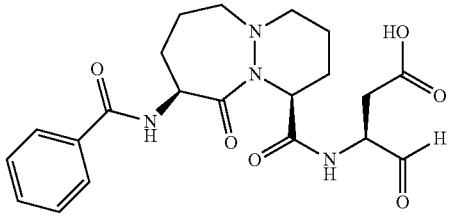
246
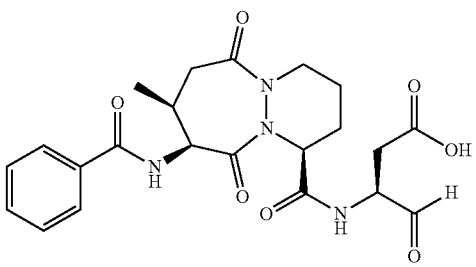
257
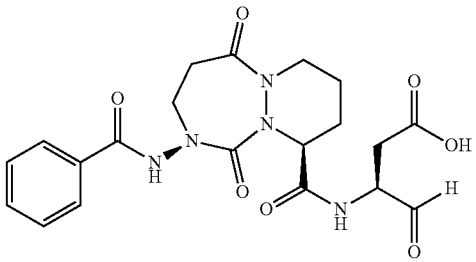
265
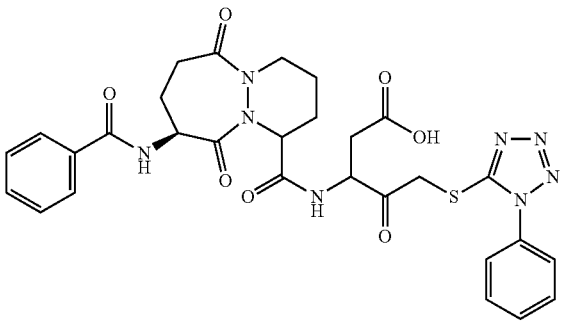
280
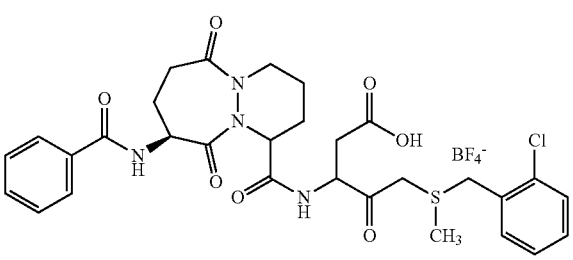
281

282
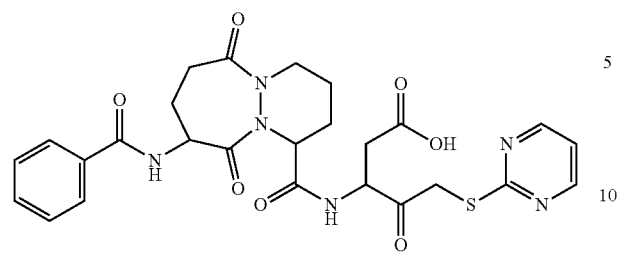
283
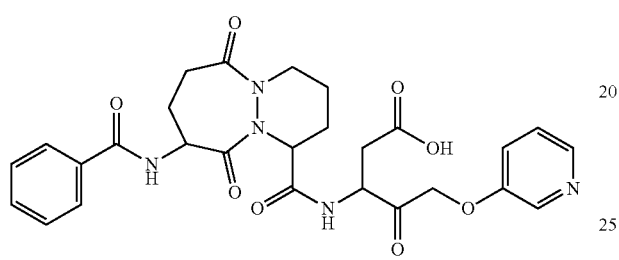
284
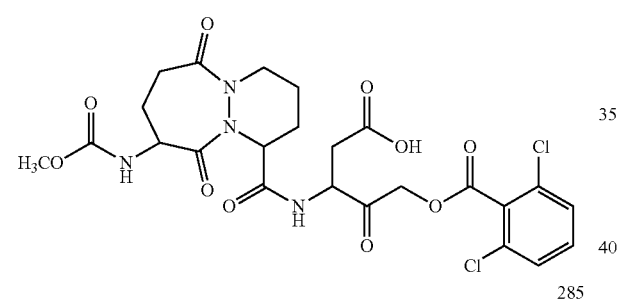
285
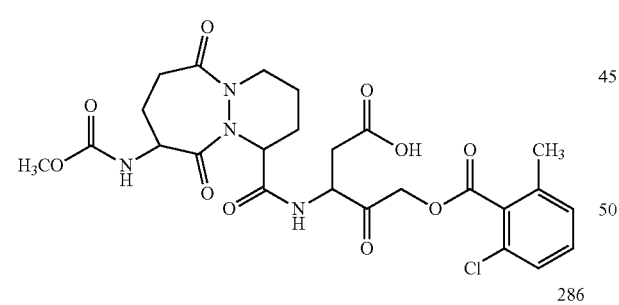
286
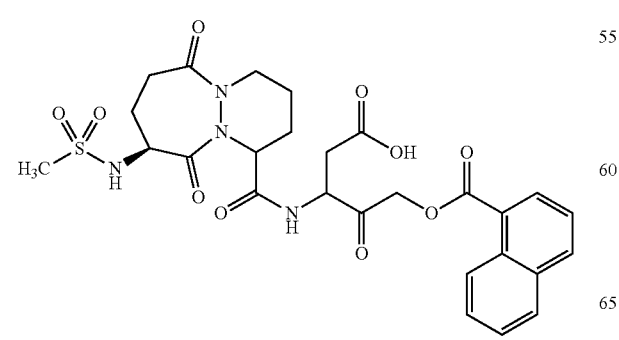
287
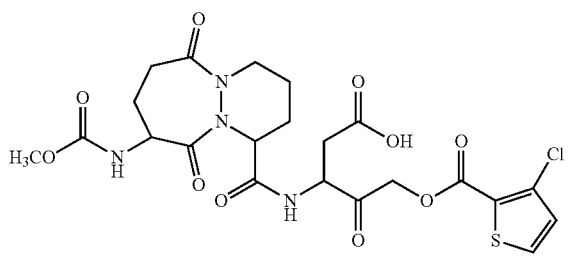
404
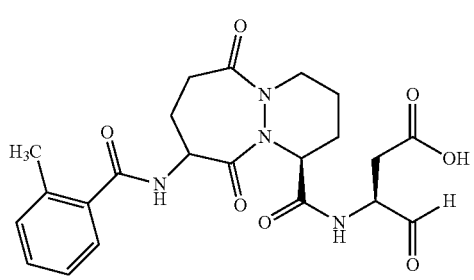
405
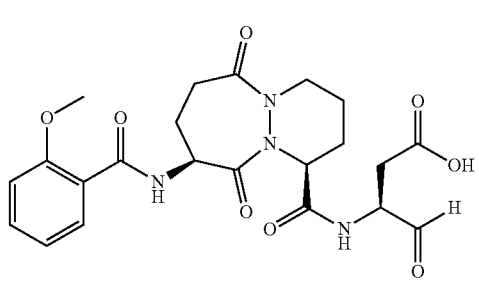
406
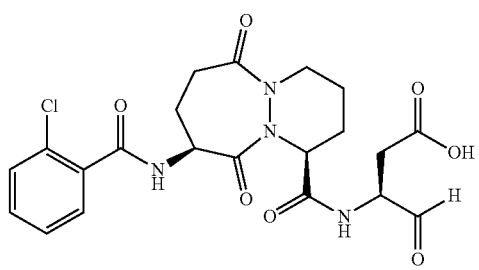
407
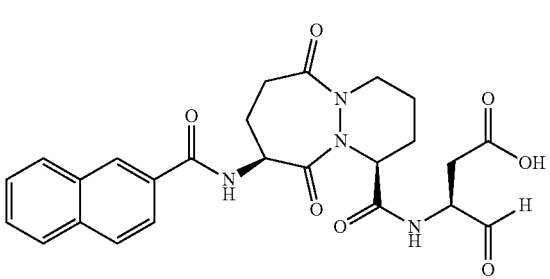

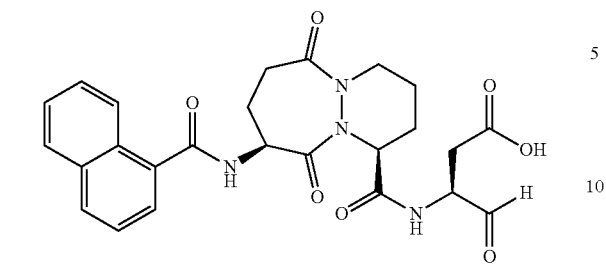
408
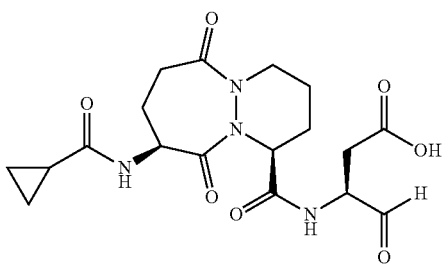
413
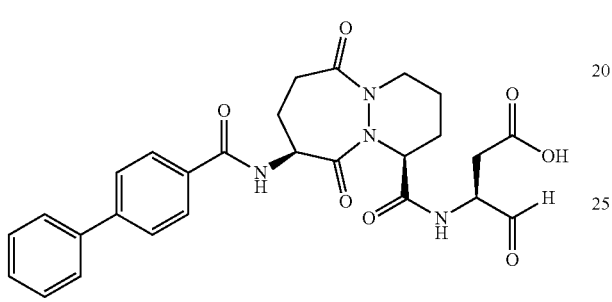
409
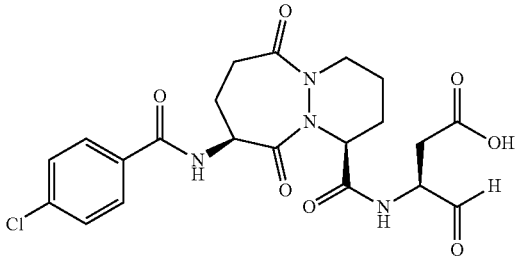
415
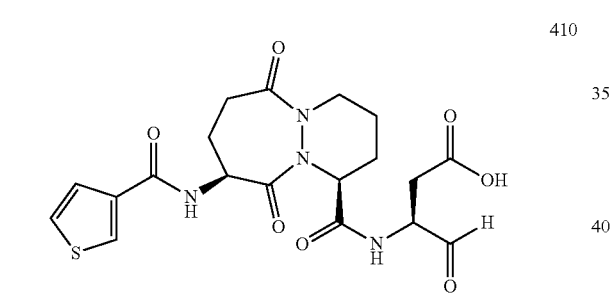
410
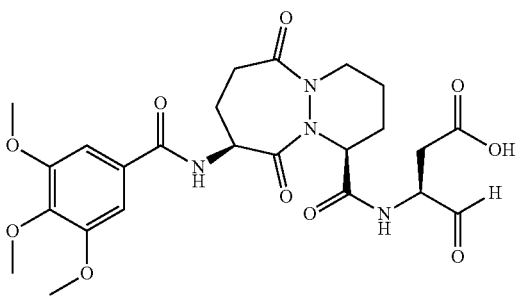
416
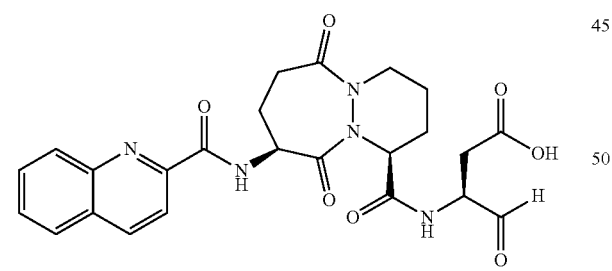
411
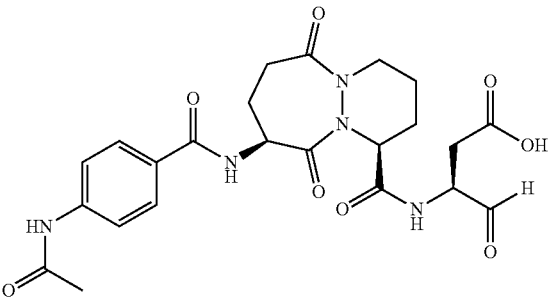
417
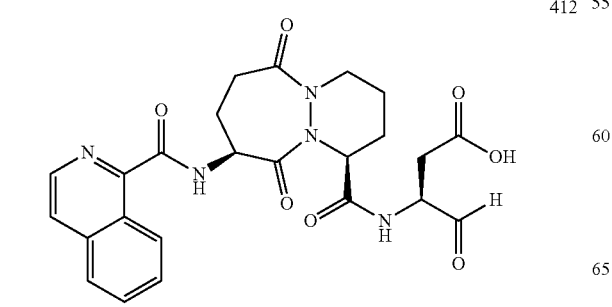
412
418

419
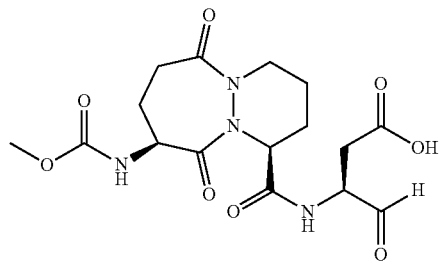
420
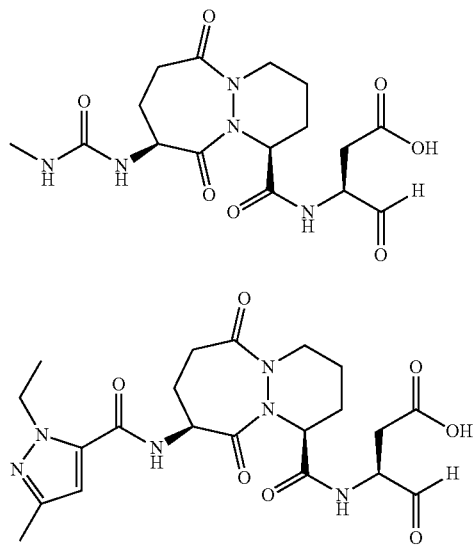
422
423
424
425
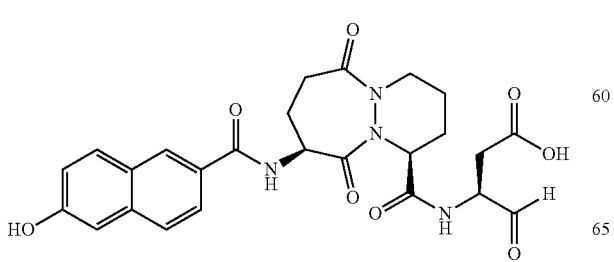
426
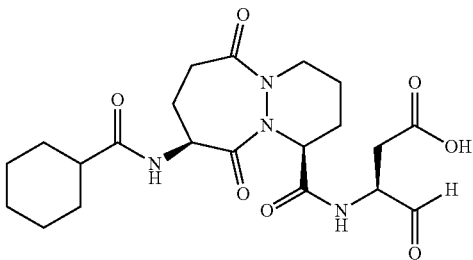
430
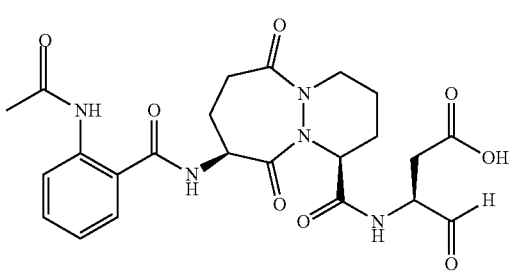
431
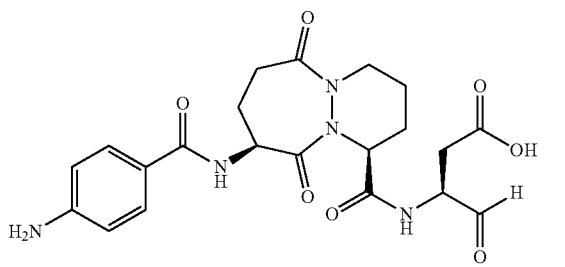
432
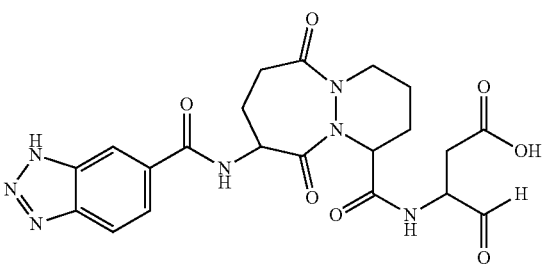
433
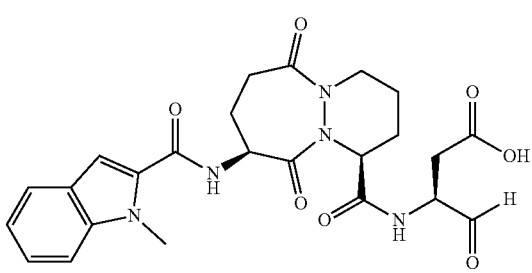

434
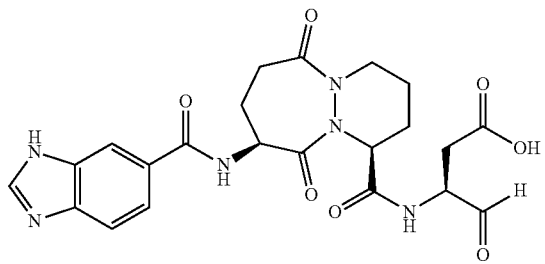
435
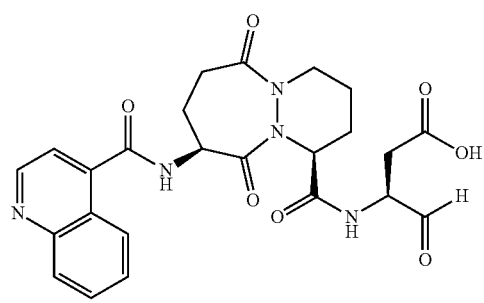
436
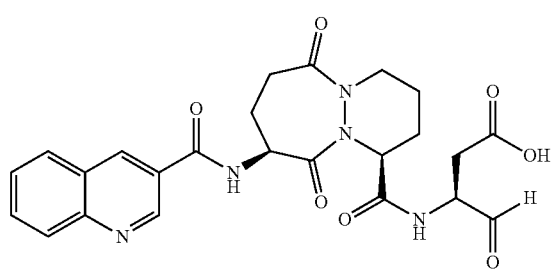
437
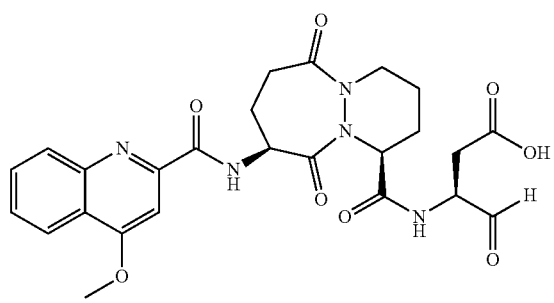
438
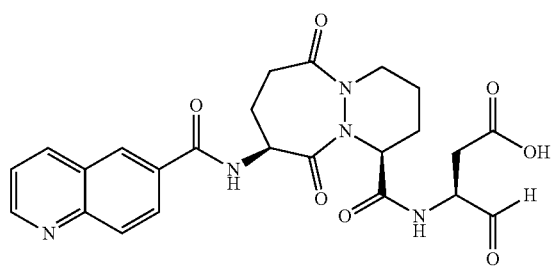
439
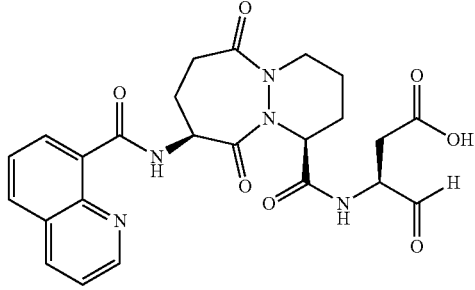
440
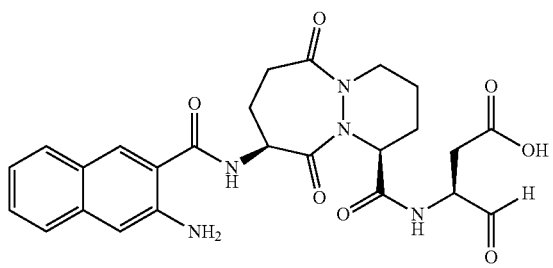
441
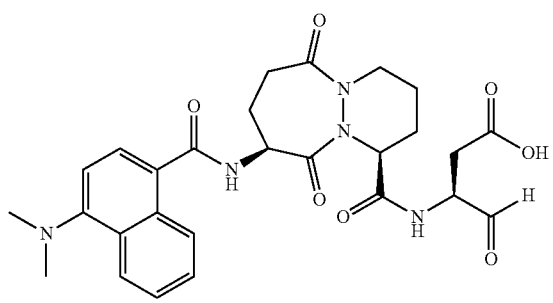
442
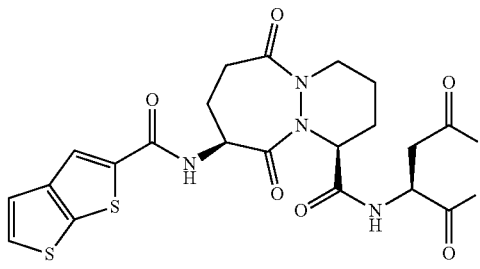
443
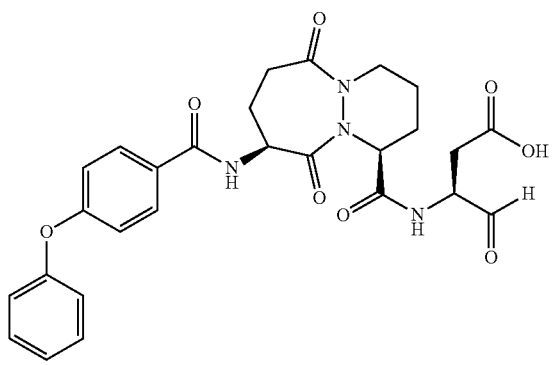

444
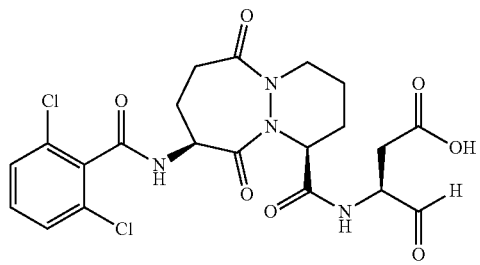
445
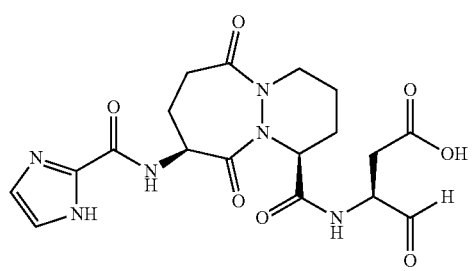
446
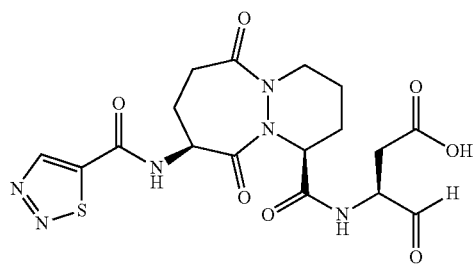
447
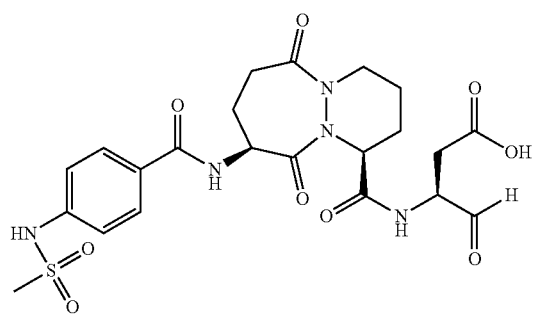
448
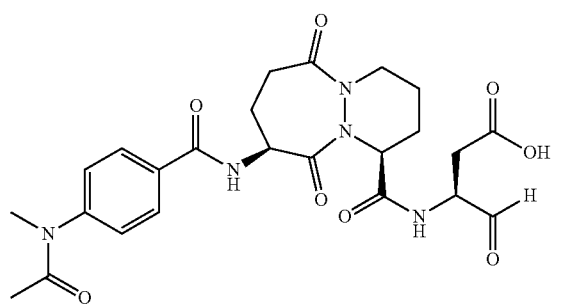
449
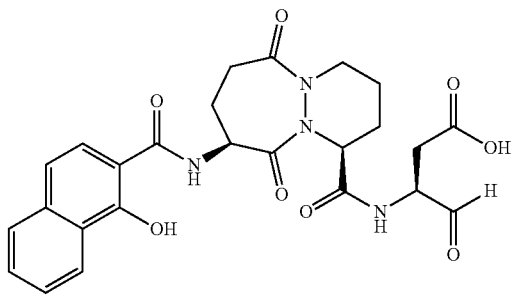
450
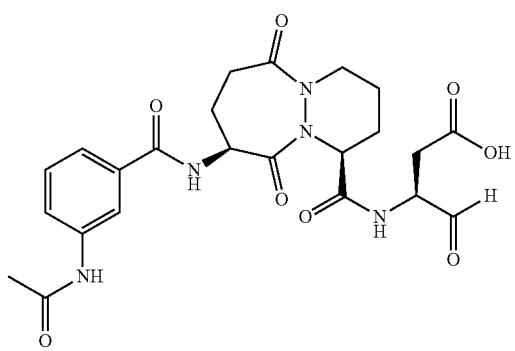
451
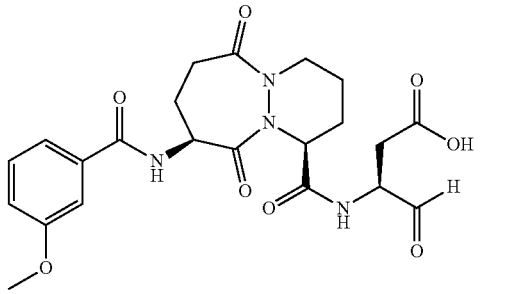
452
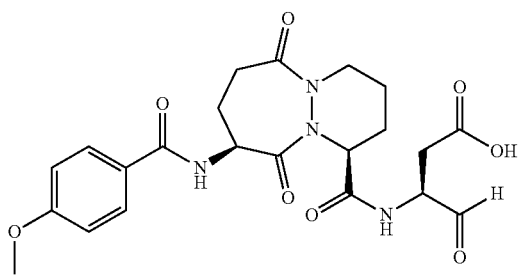
453
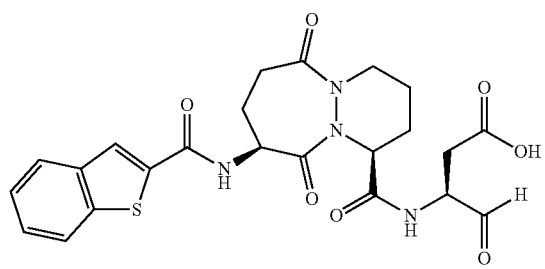

454
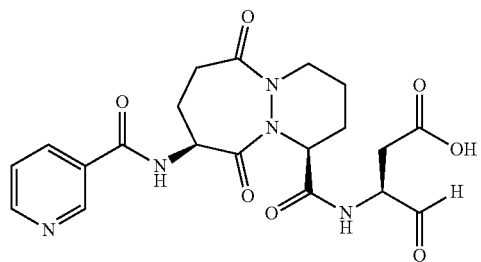
455
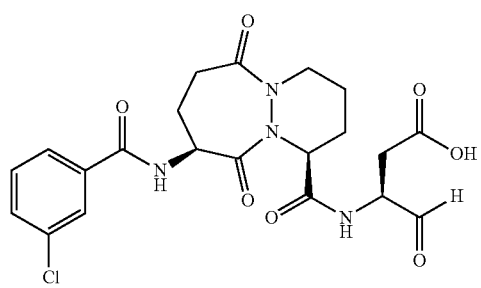
456
457
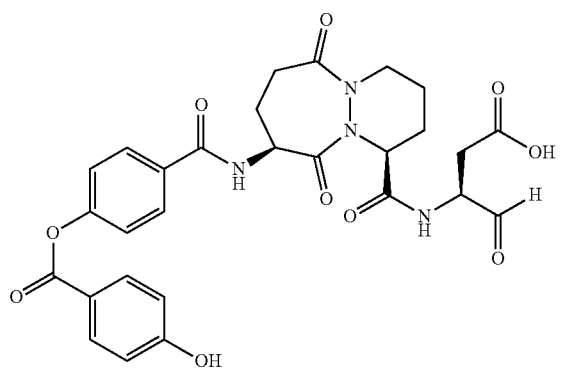
458
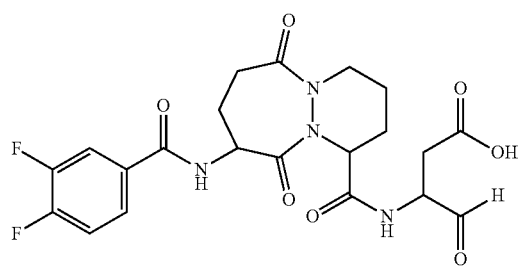
459
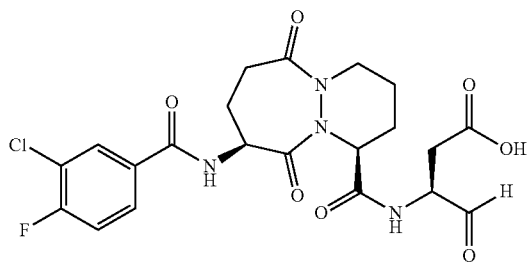
460
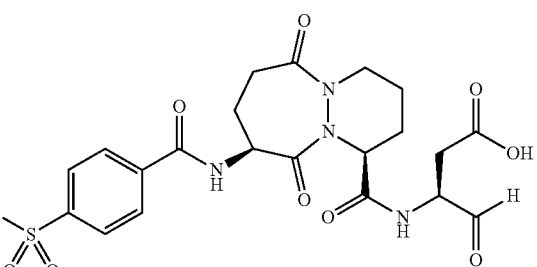
461
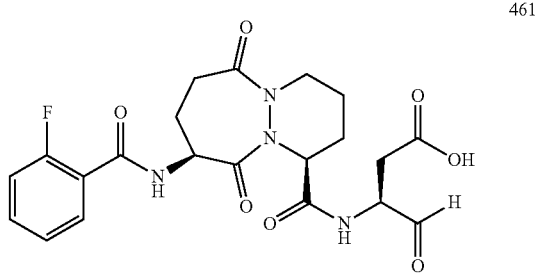
462
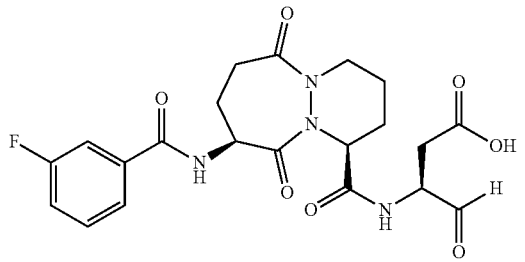
463
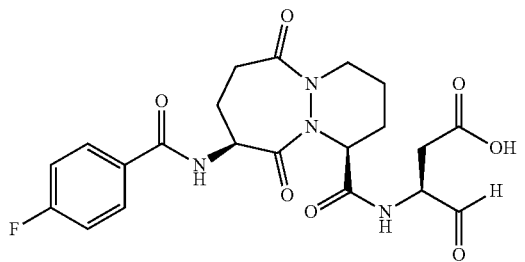

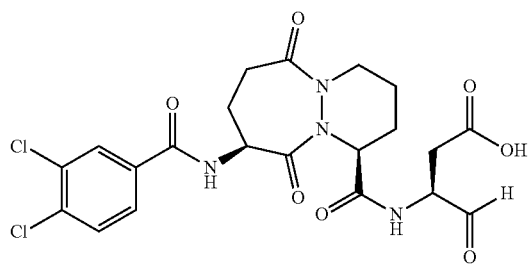
464
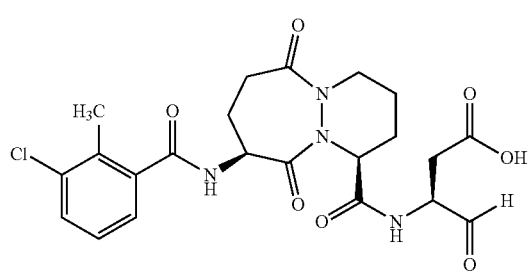
465
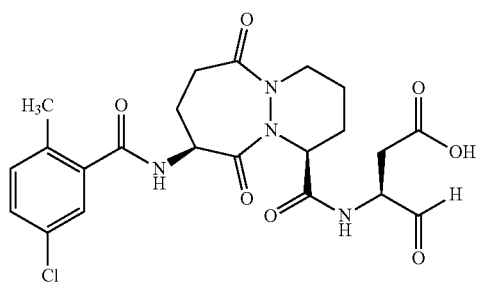
466
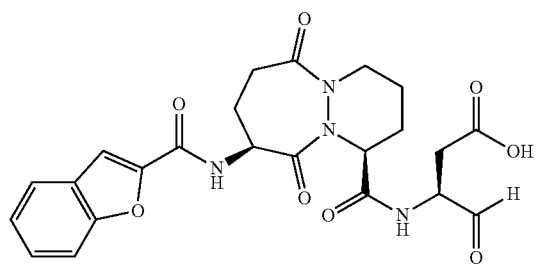
467
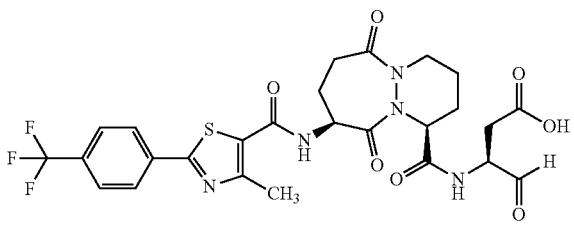
468
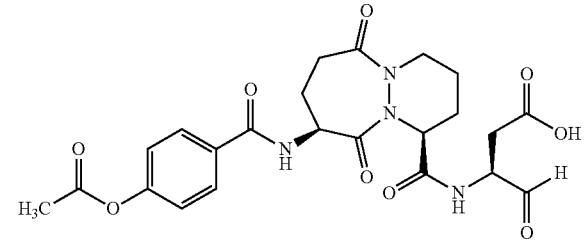
469
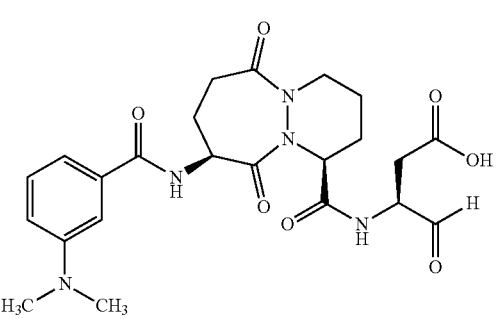
470
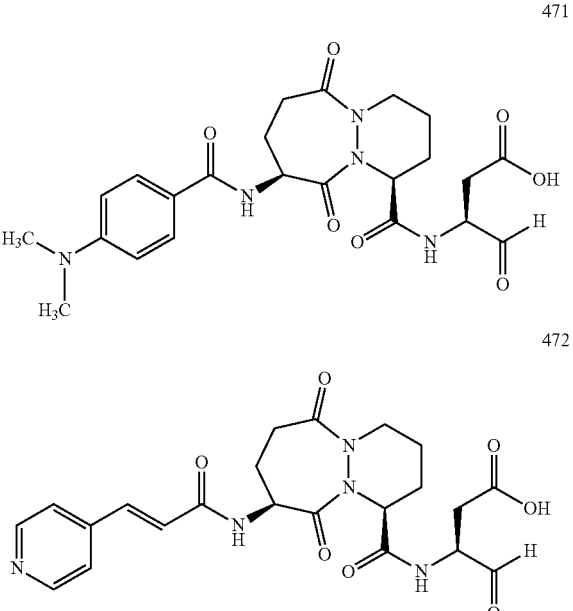
471
472
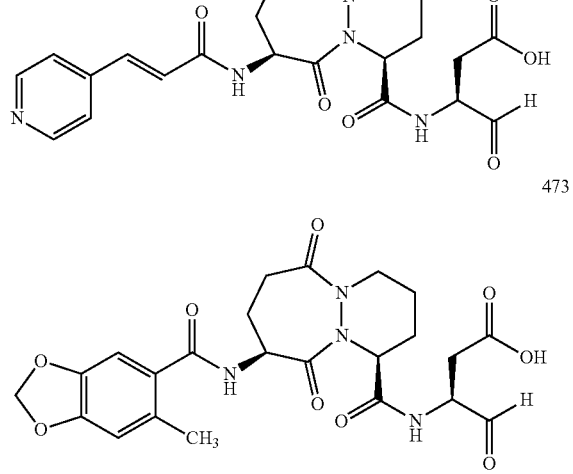
473

-continued
474
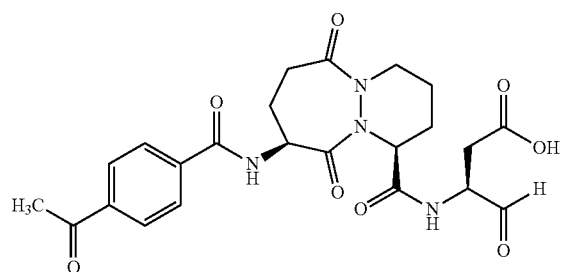
475
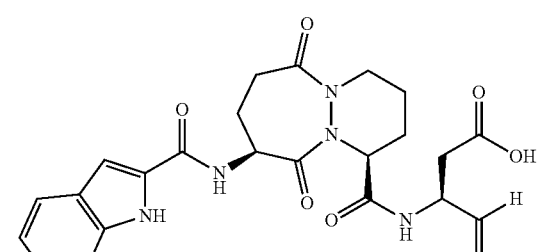
476
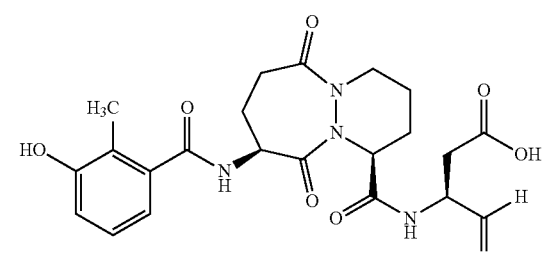
477
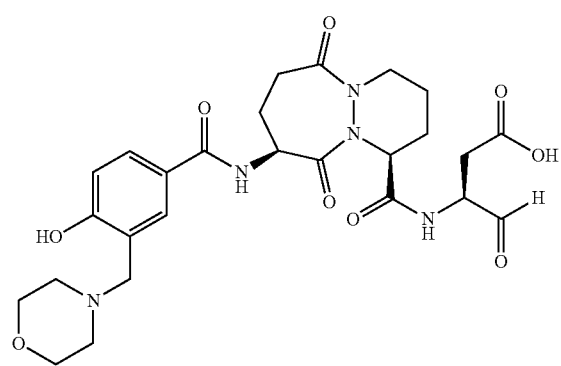
478
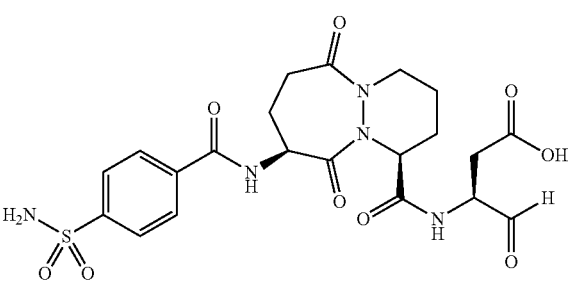
479
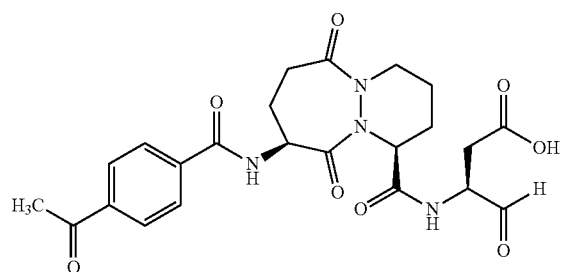
480
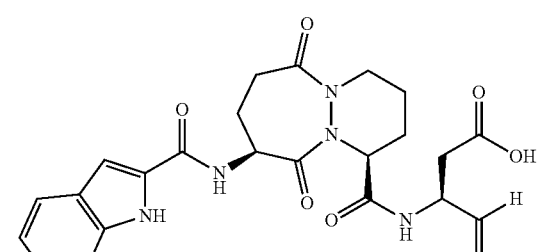
481
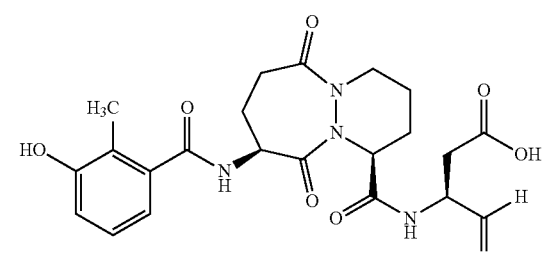
481s
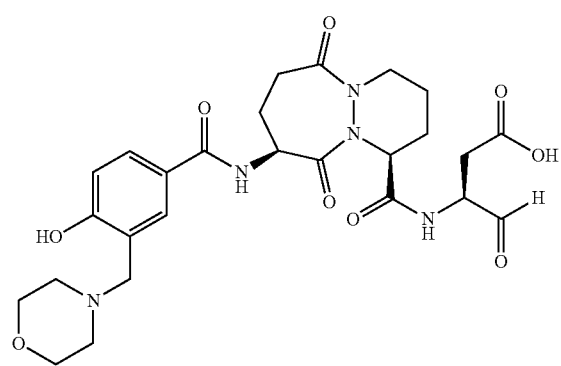
482
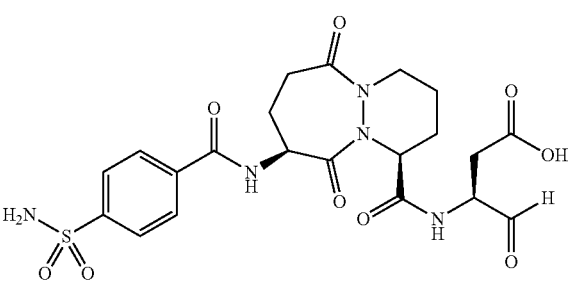

482s 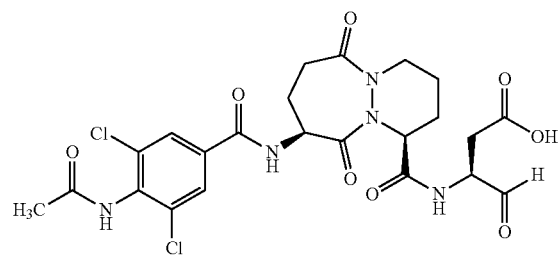
483 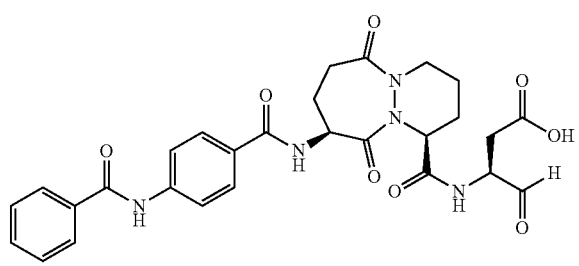
484 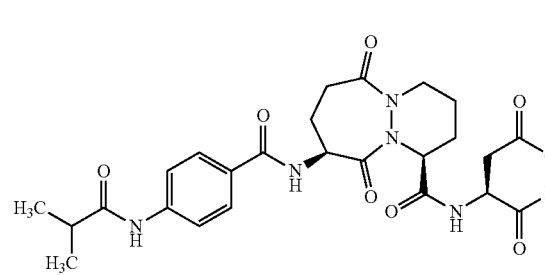
485 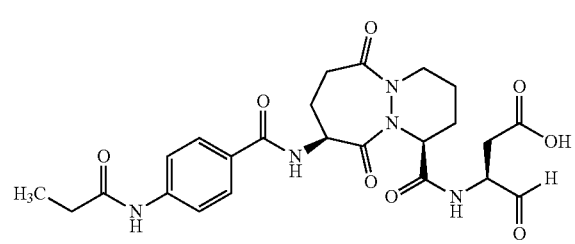
486 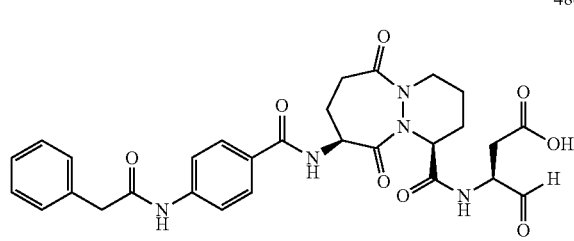
487 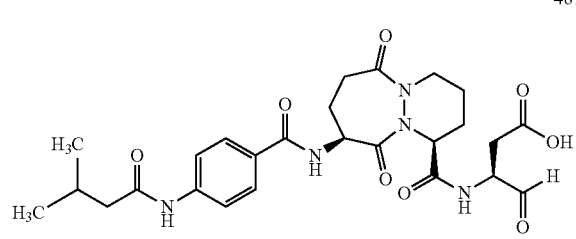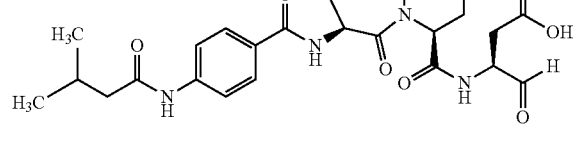
488 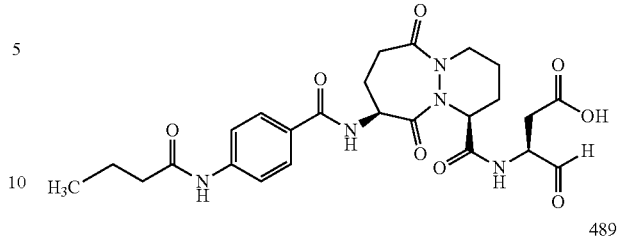
489 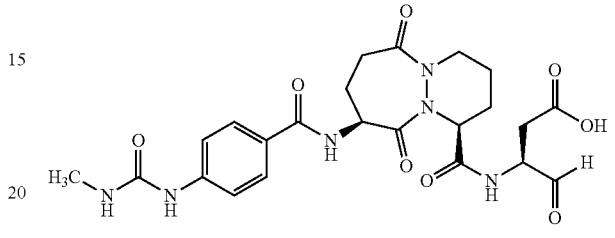
490 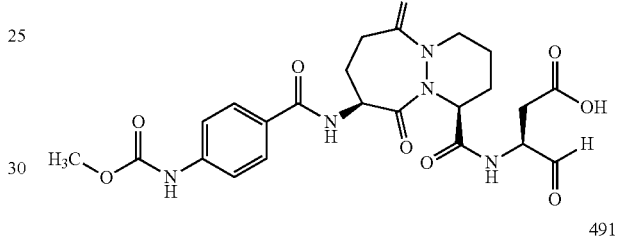
491 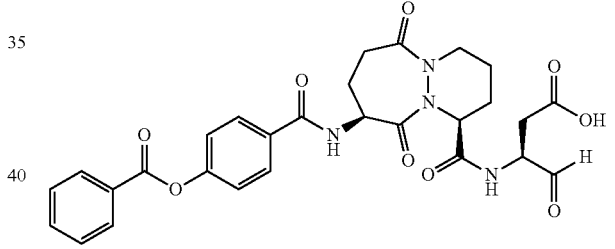
493 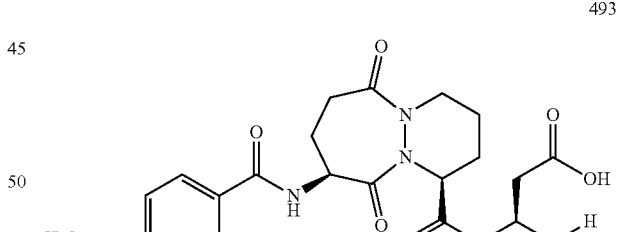
494 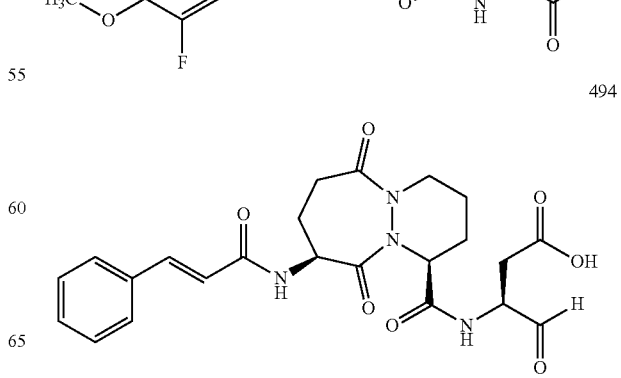

495
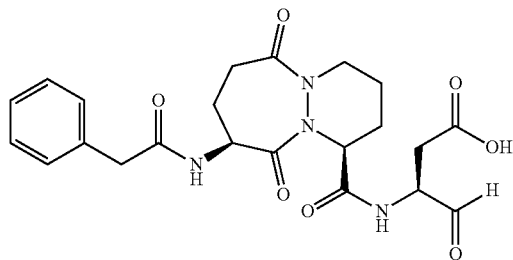
496
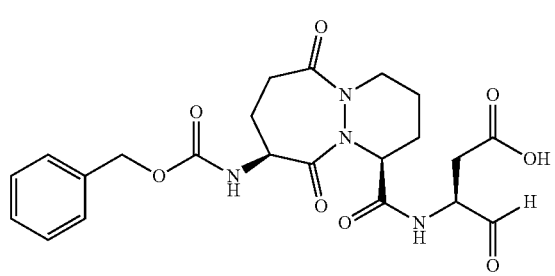
497
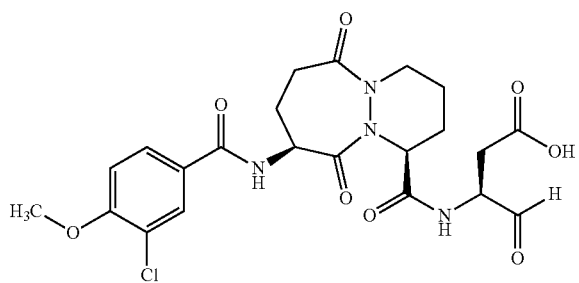
498
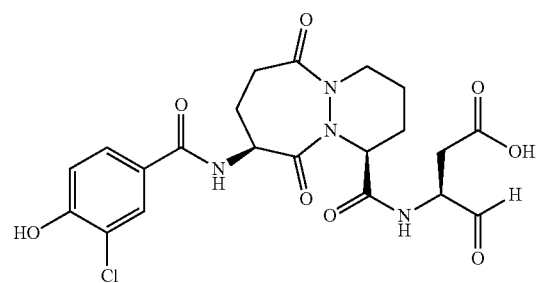
499
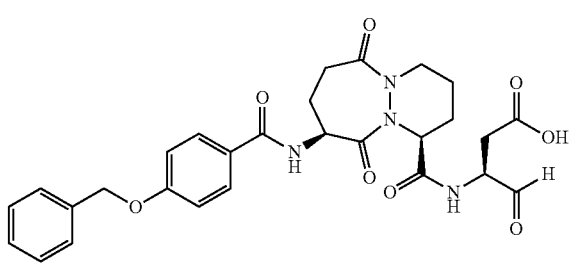
814c
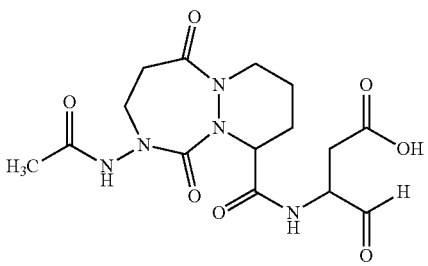
817c
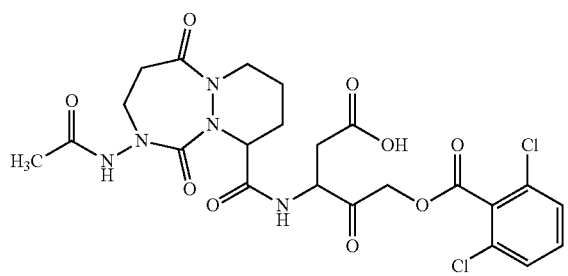
817d
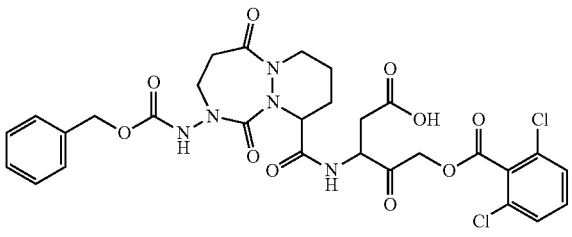
817e
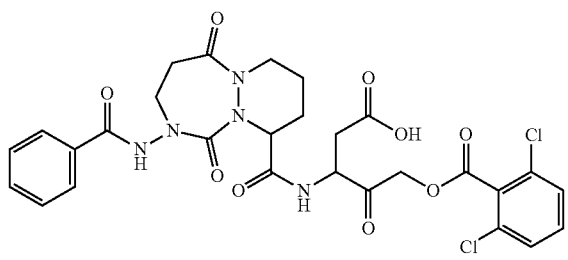
880
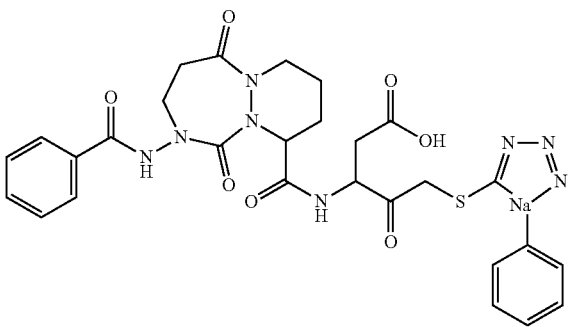

881
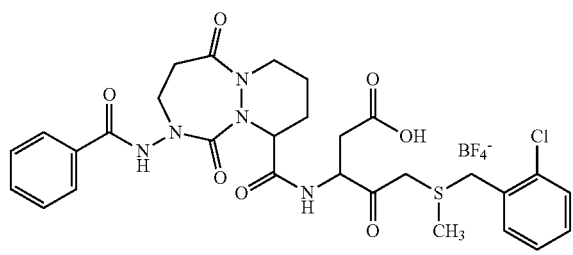
882
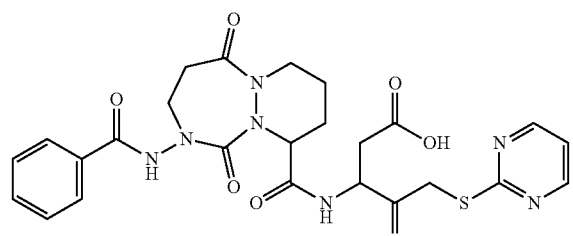
883
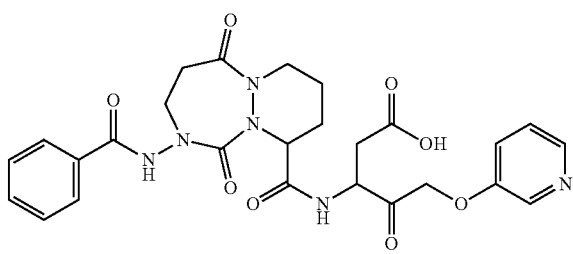
884
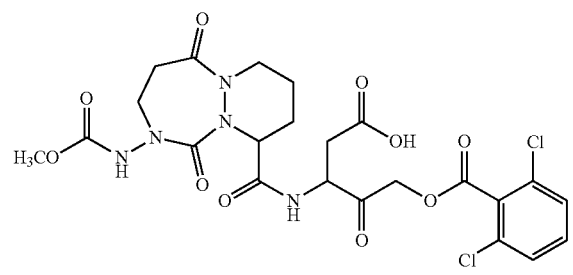
885
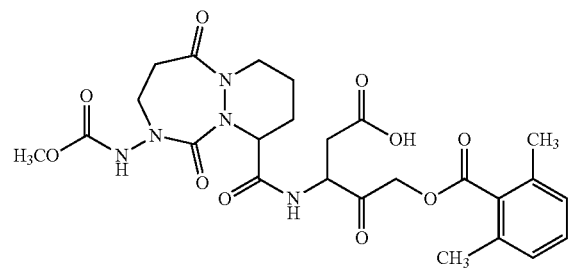
886
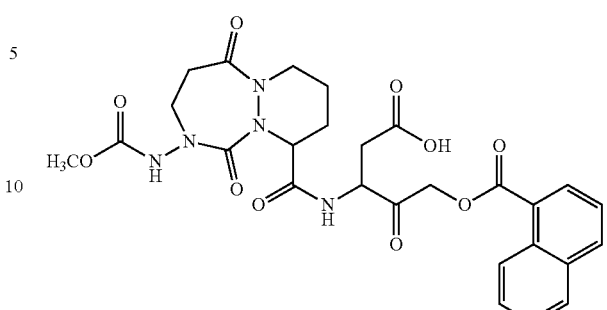
887
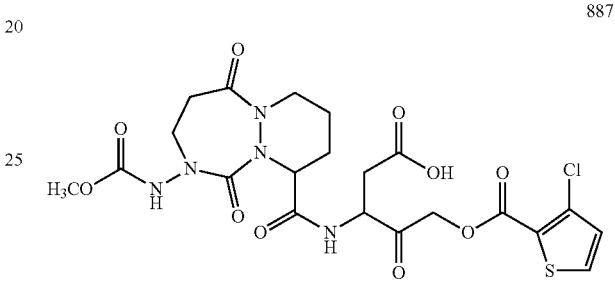
1004
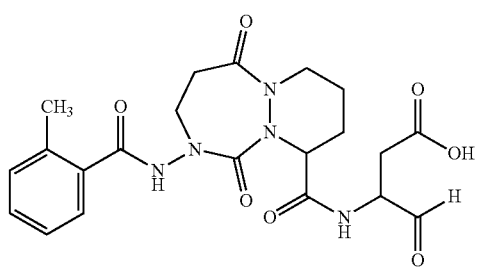
1005
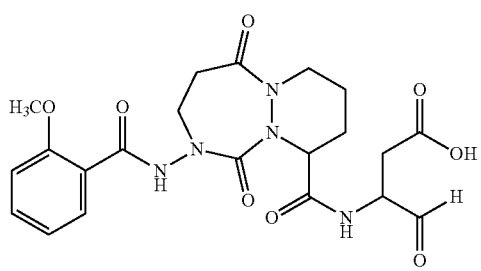
1006
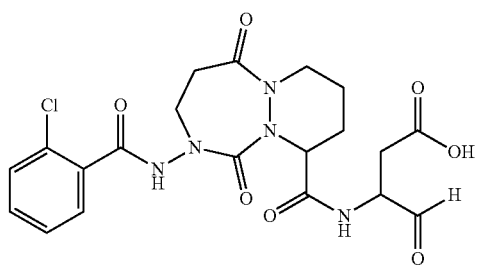

-continued
1007
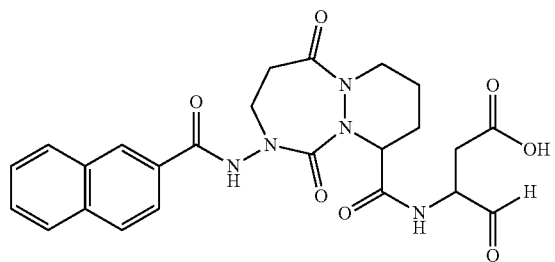
1008
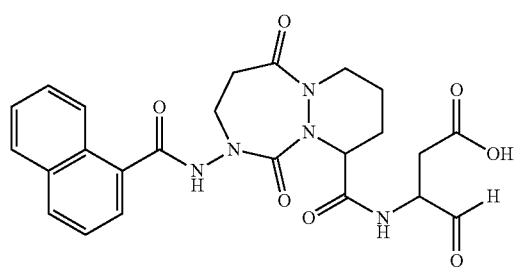
1009
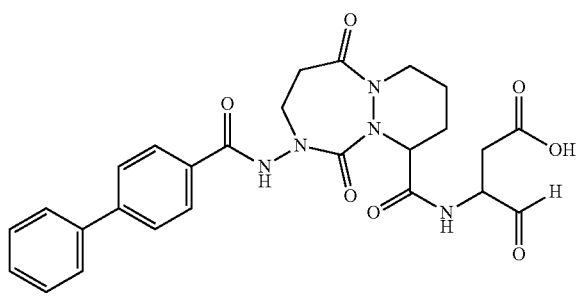
1010
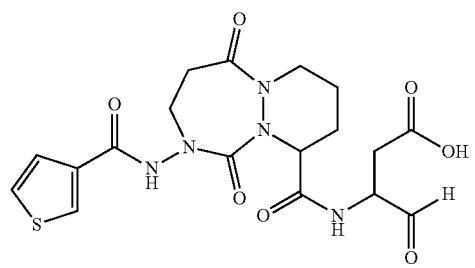
1011
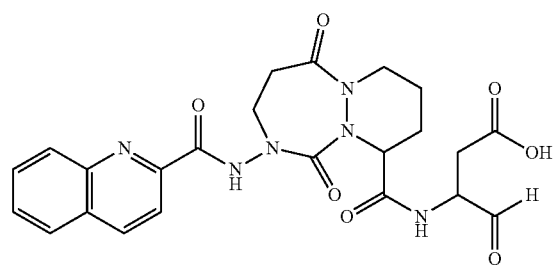
-continued
1012
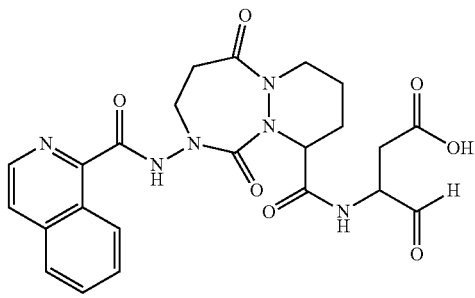
1013
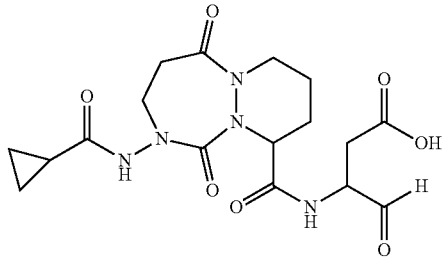
1015
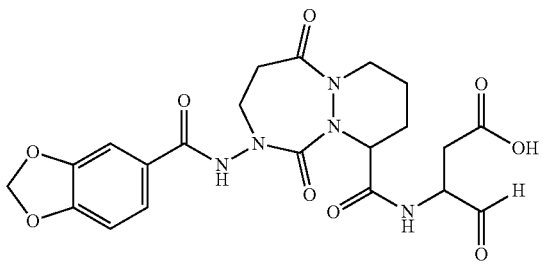
1016
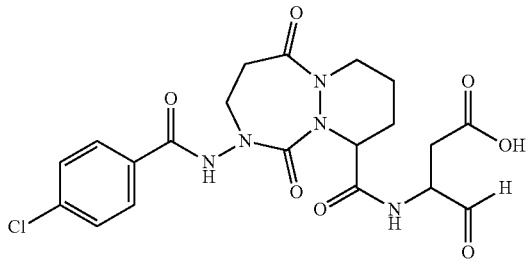
1017
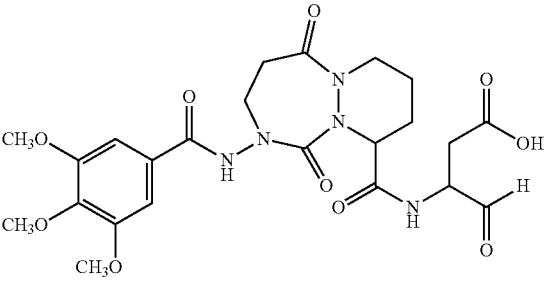

1018
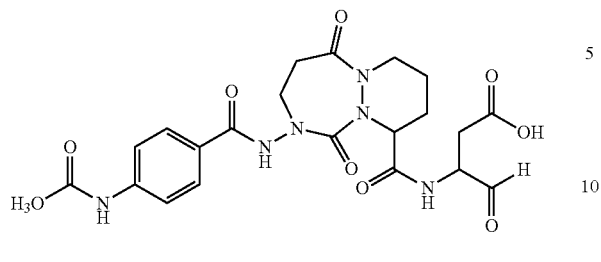
1019
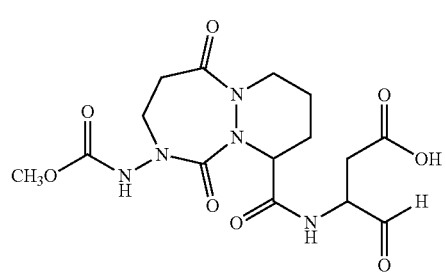
1020
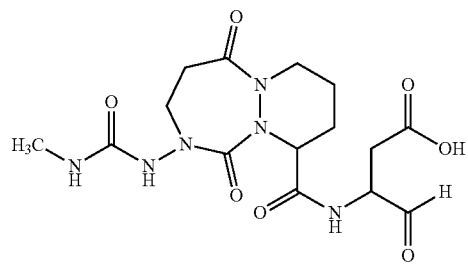
1022
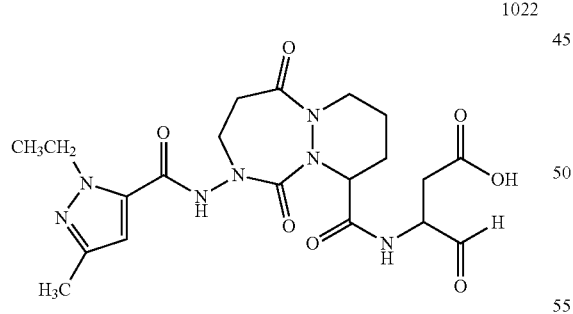
1023
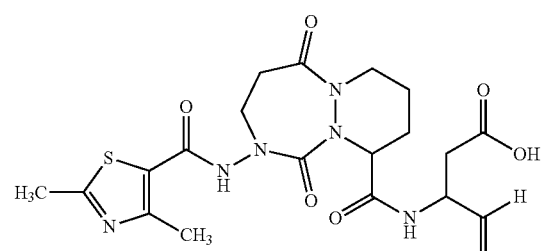
1024
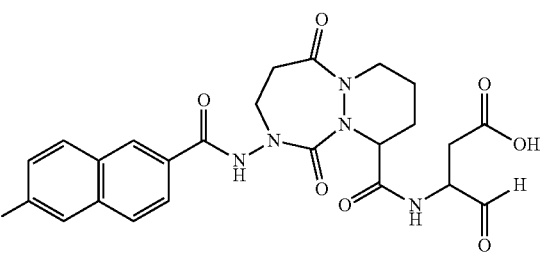
1025
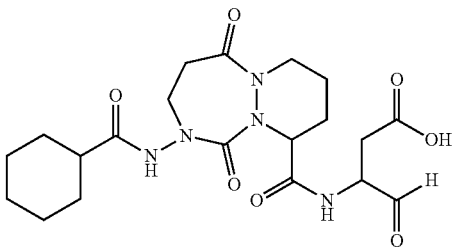
1026
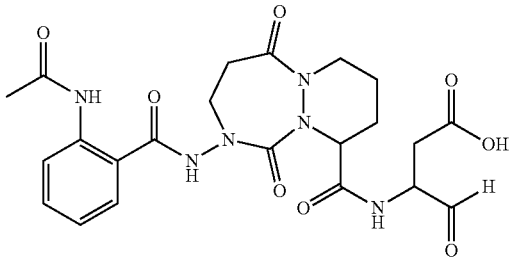
1030
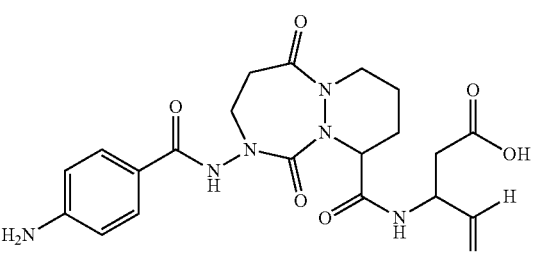
1031

1032
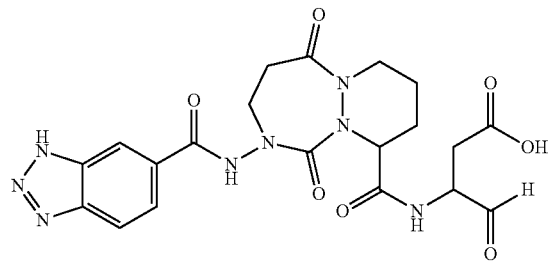
1037
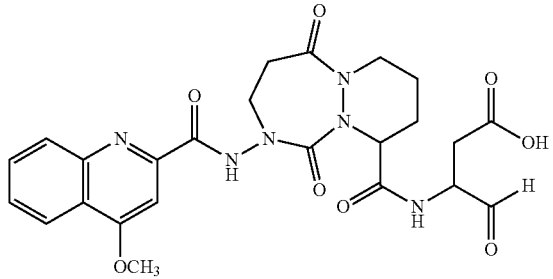
1033
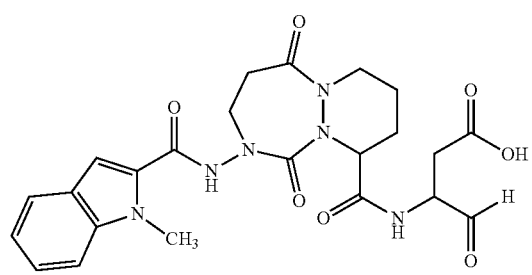
1038
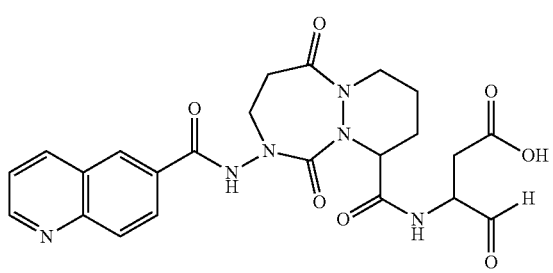
1034
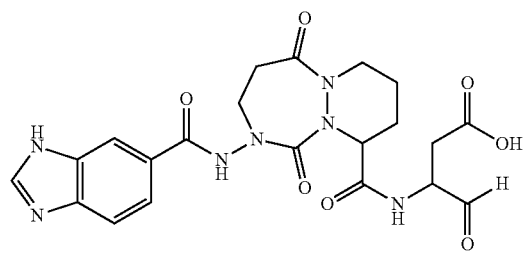
1039
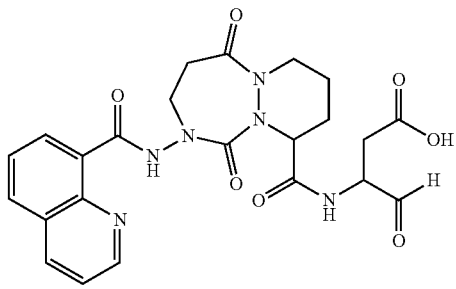
1035
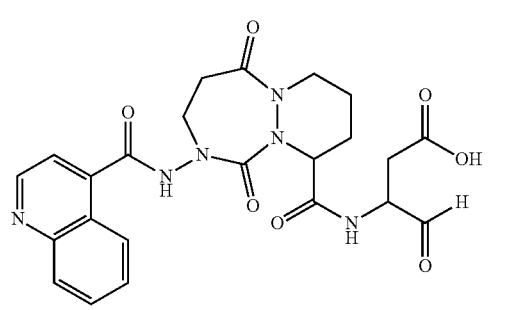
1040
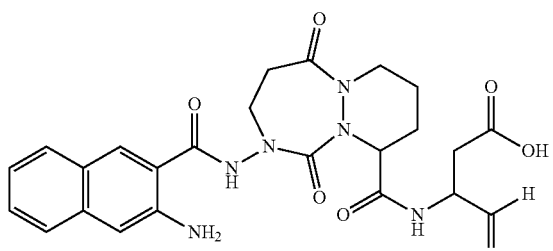
1036
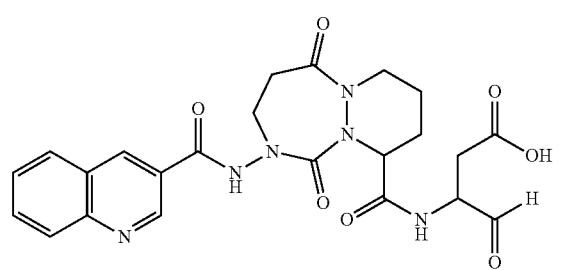
1041
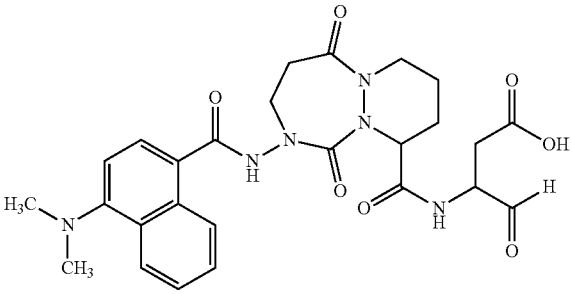

1042
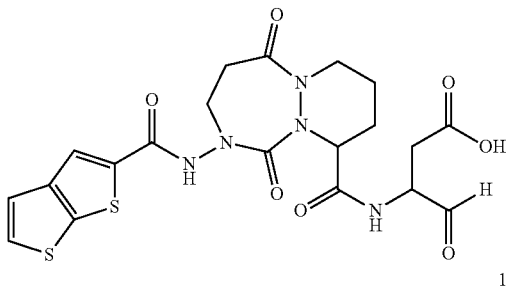
1043
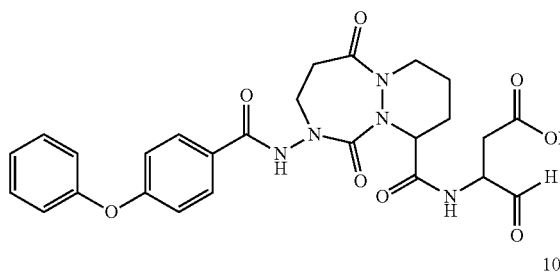
1044
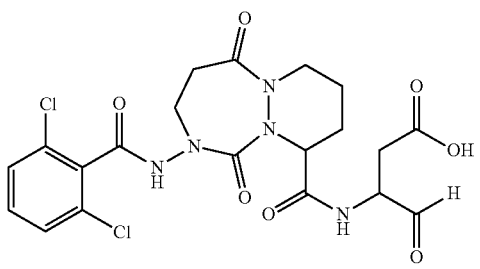
1045
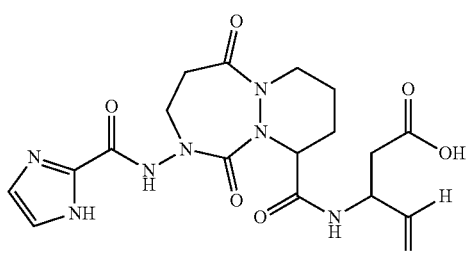
1046
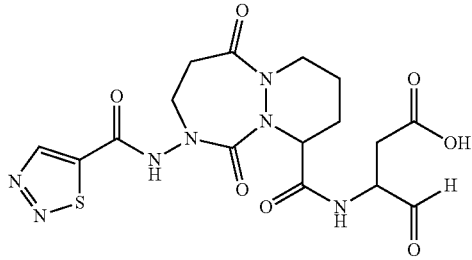
1047
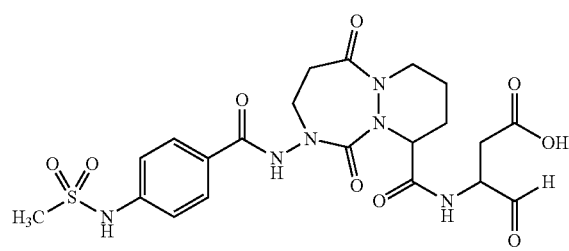
1048
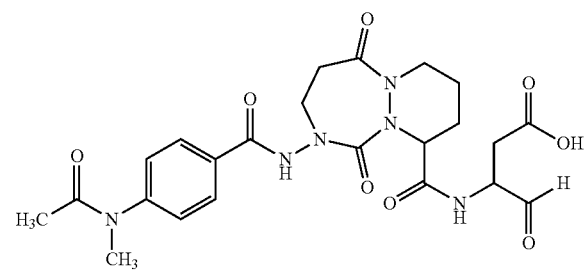
1049
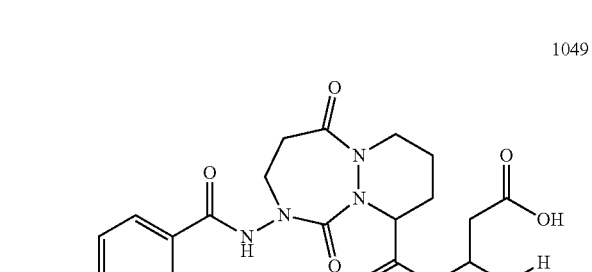
1050
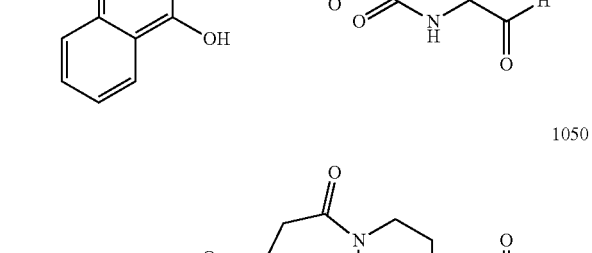
1051
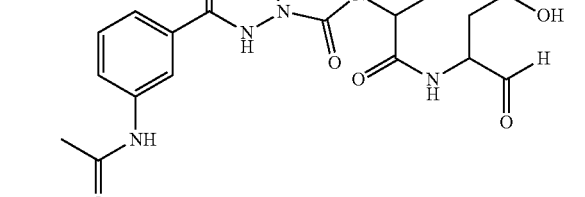
1052
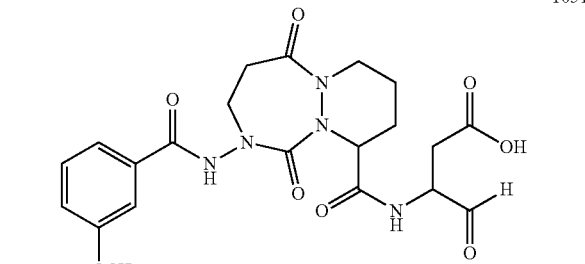

1053
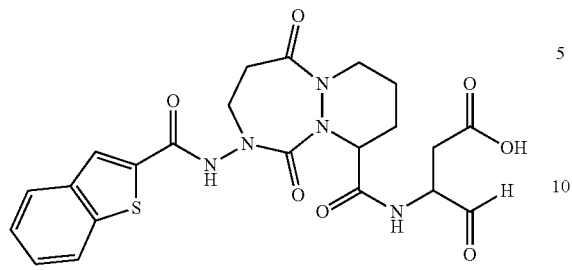
1054
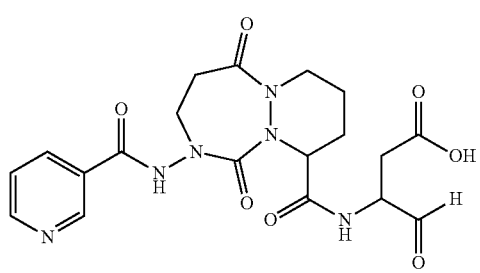
1055
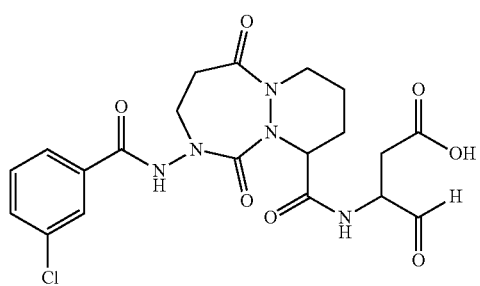
1056
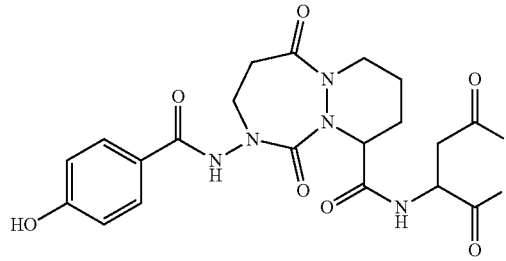
1057
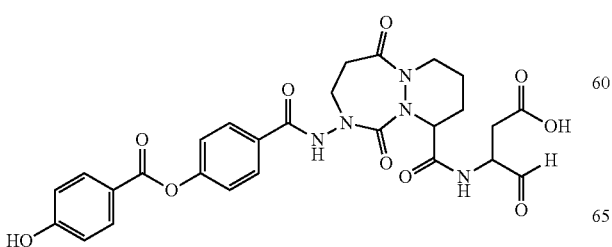
1058
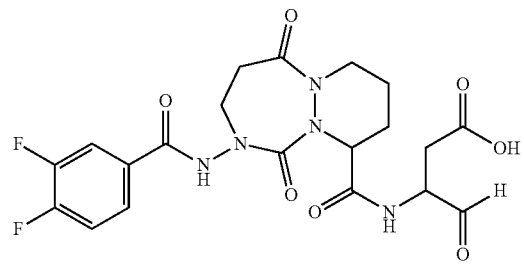
1059
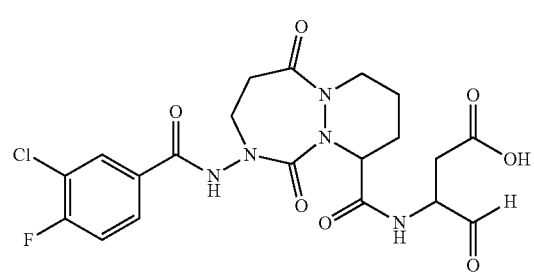
1060
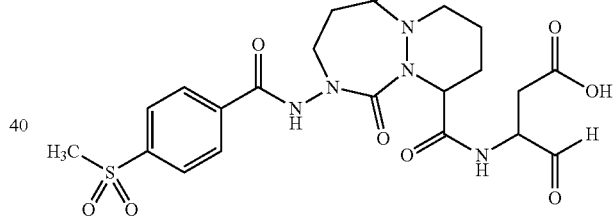
1061
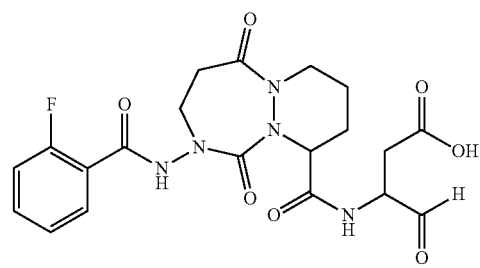
1062
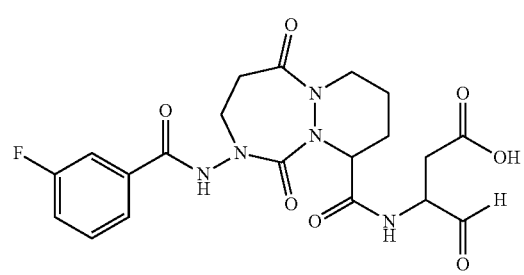

1063
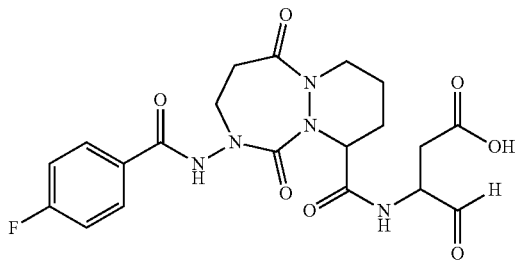
1064
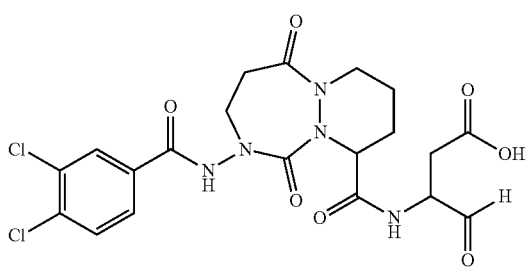
1065
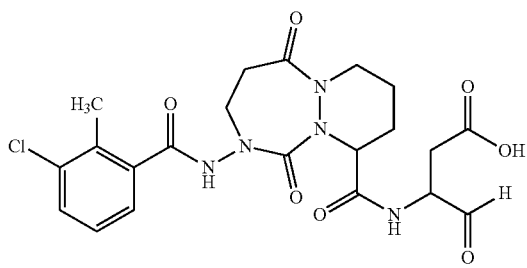
1066
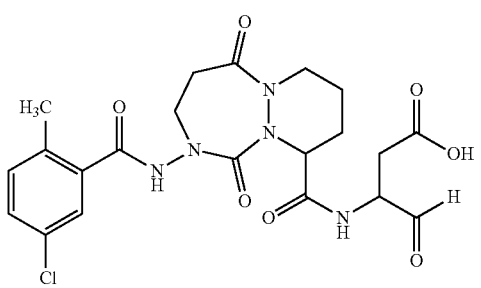
1067
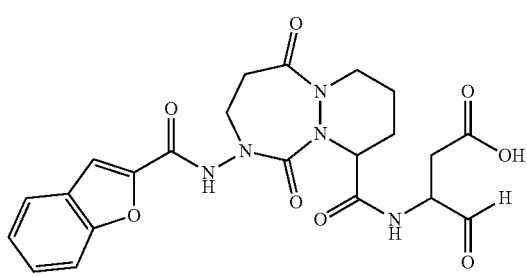
1068
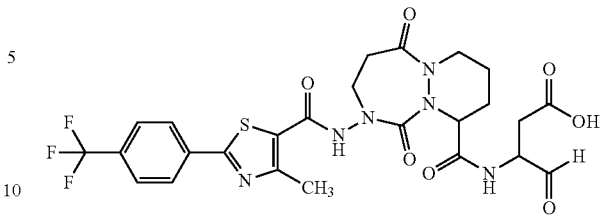
1069
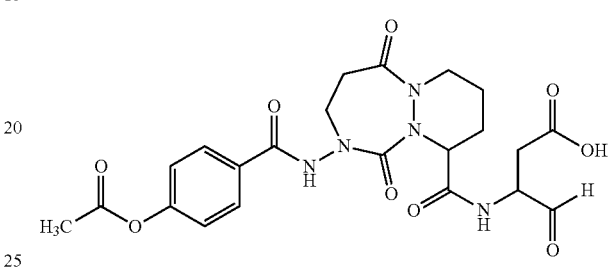
1070
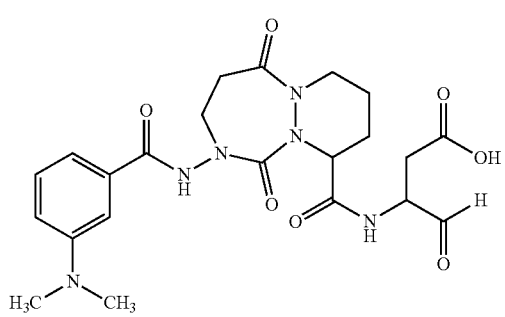
1071
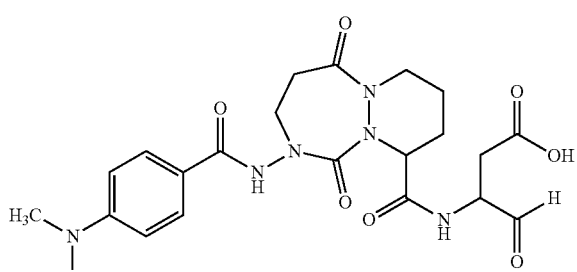
1073
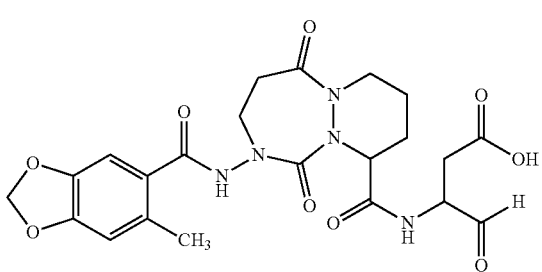

1074
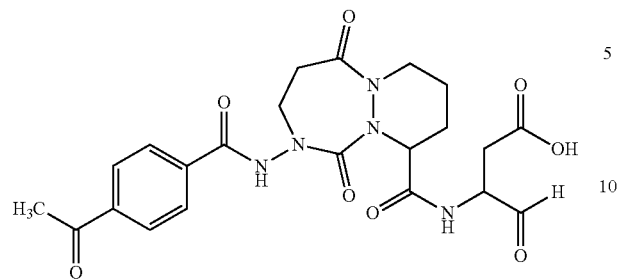
1075
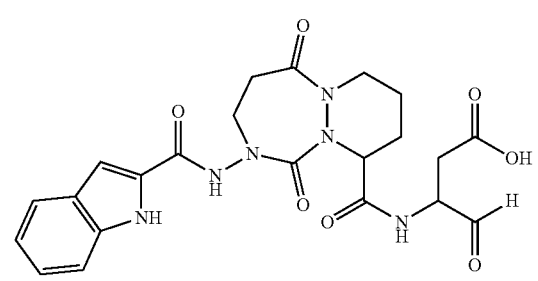
1076
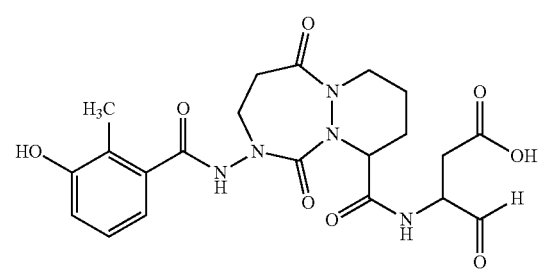
1077
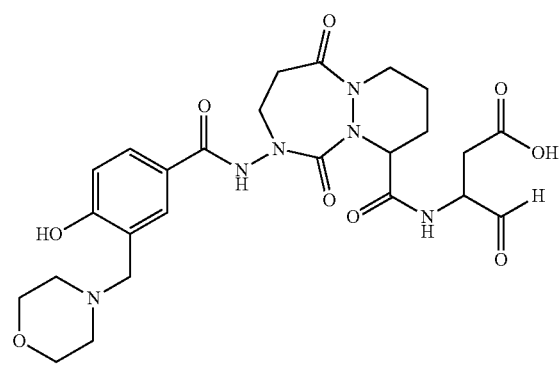
1078
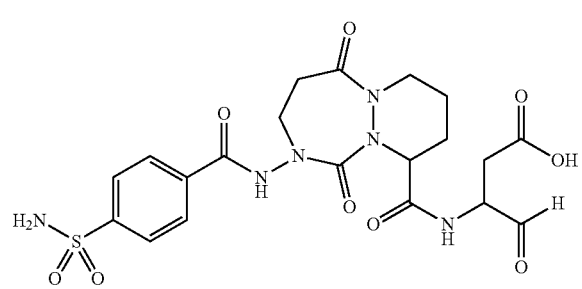
1079
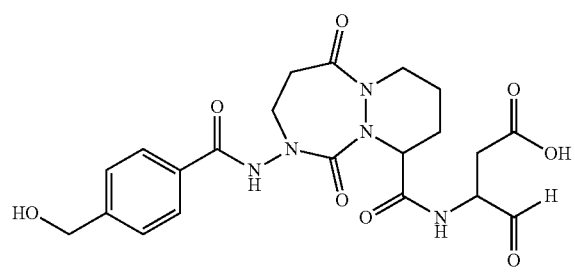
1080
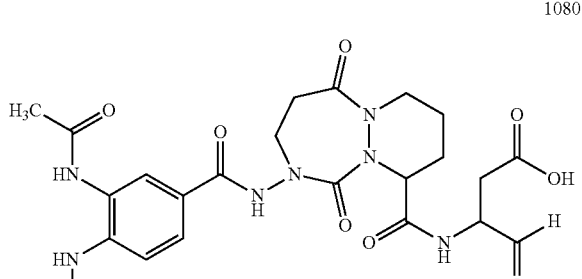
1081
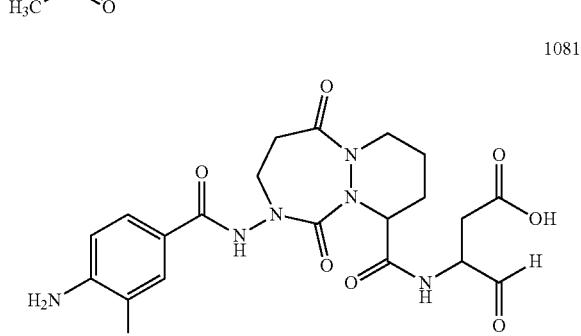
1081s
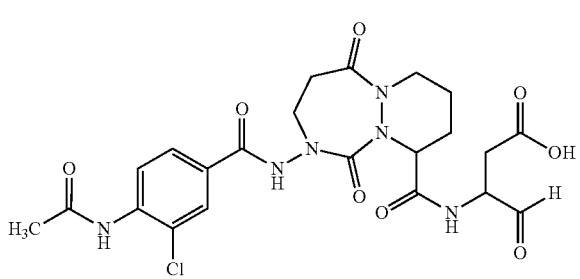
1082
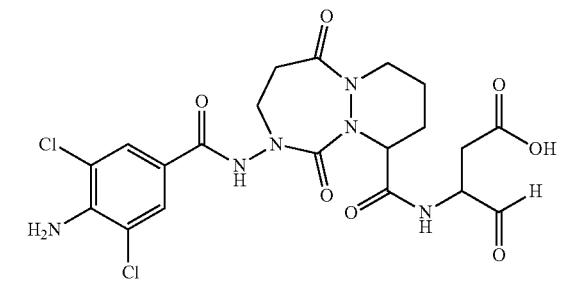

-continued
1083
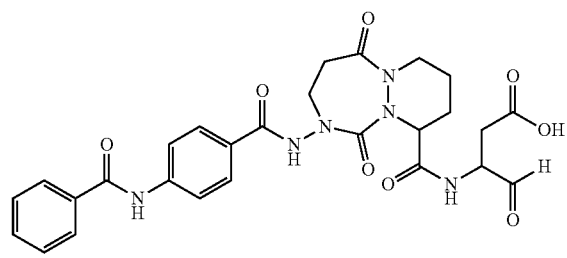
1082s
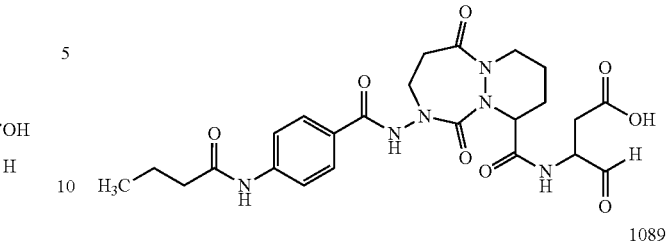
1084
1085
1086
1087
-continued
1088
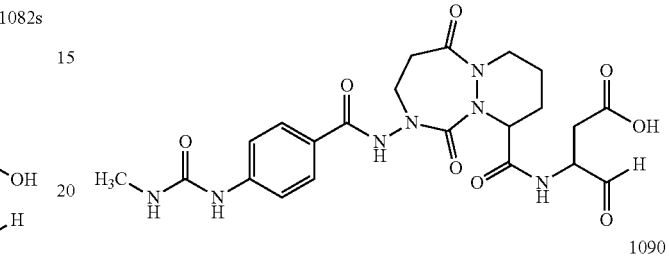
1089
1090
1091
1093
1094

1095
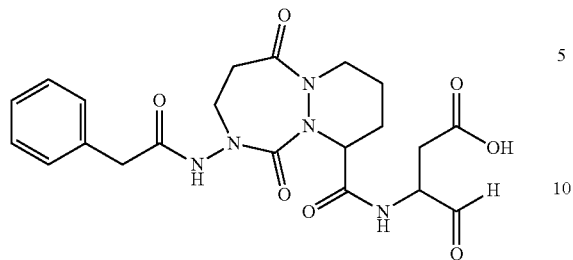
1096
1097
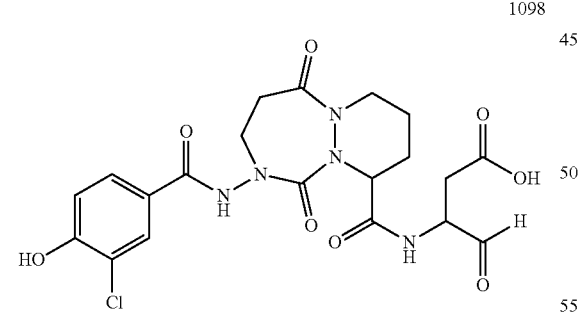
1098
1099
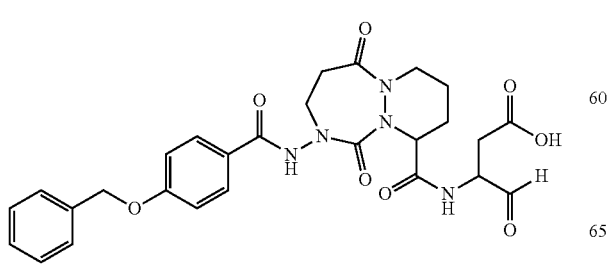
421
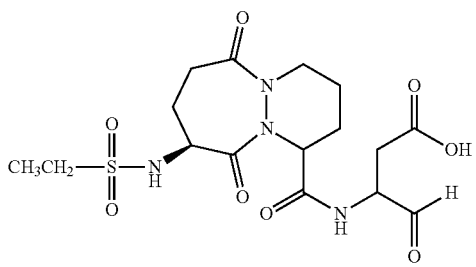
427
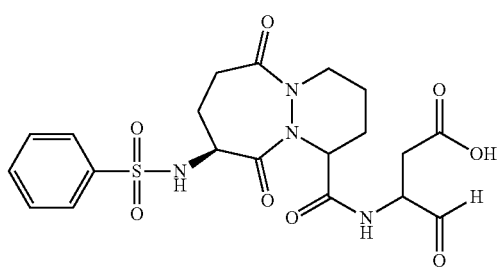
428
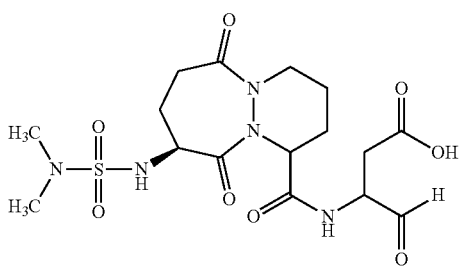
1021
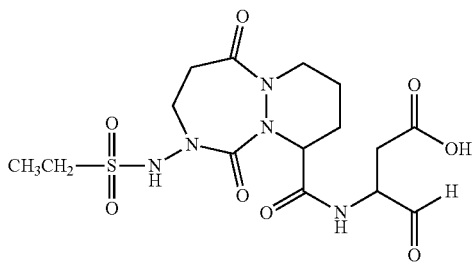
1027

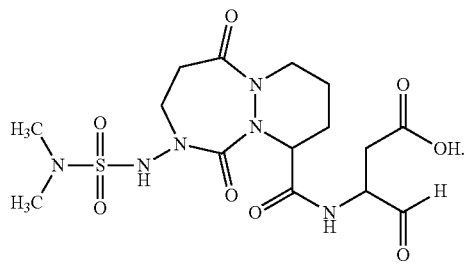
1028
Specific compounds of this invention also include, but are not limited to, those compounds whose structures comprise scaffolds 1-22:
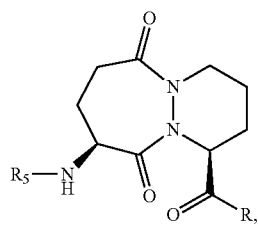
1
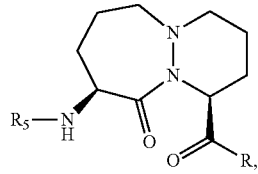
2
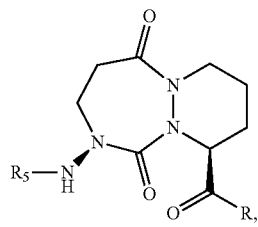
3
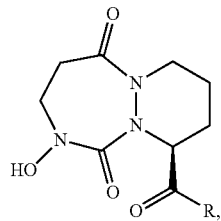
4
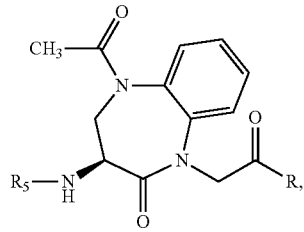
5
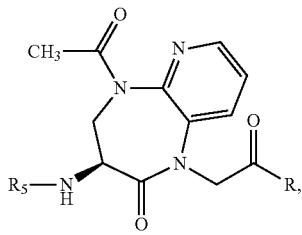
6
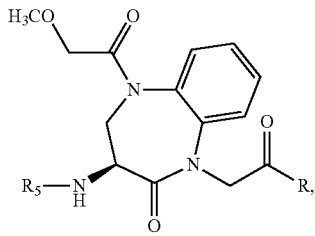
7
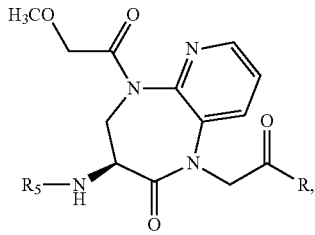
8
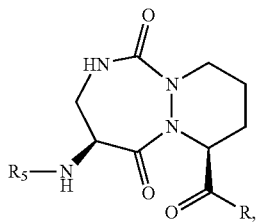
9
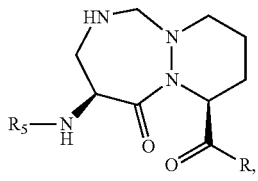
10
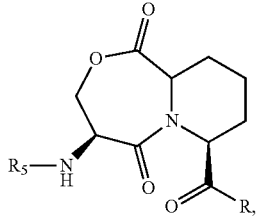
11
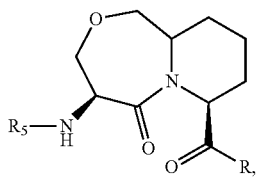
12

12
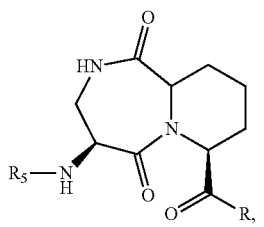
13
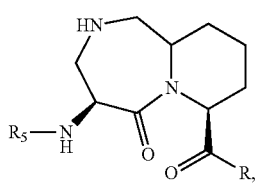
14
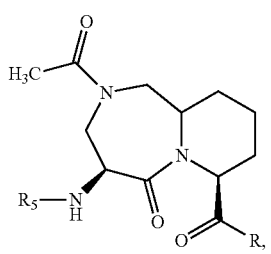
15
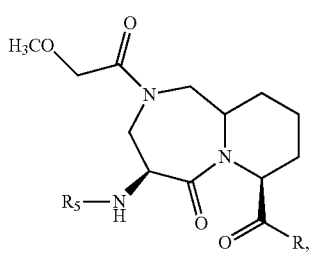
16
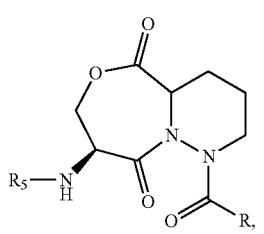
17
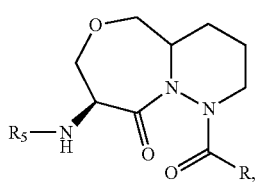
18
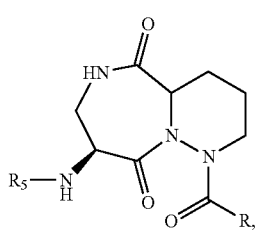
19
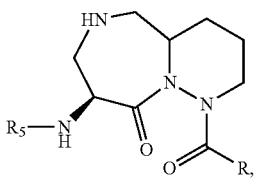
20
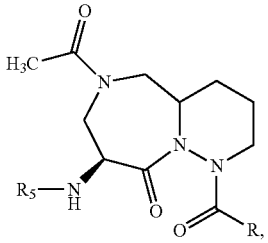
21
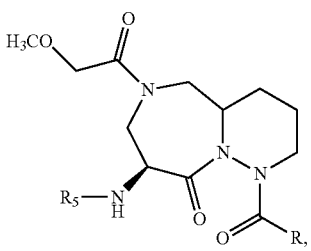
22
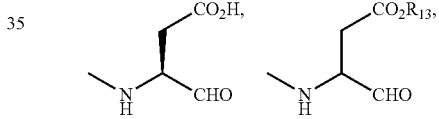
wherein:
R is
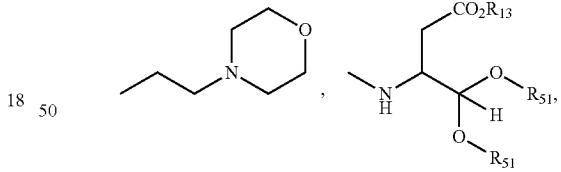
wherein
$R_{13}$ is —CH$_3$, —CH$_2$CH$_3$, —CH$_2$CH$_2$CH$_3$, —CH(CH$_3$)(CH$_3$), —CH$_2$CH$_2$CH$_2$CH$_3$, —CH$_2$—CH(CH$_3$)CH$_3$, —C(CH$_3$)$_3$, —CH$_2$Ph, or
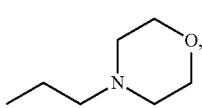
wherein
$R_{13}$ is —CH$_3$, —CH$_2$CH$_3$, —CH$_2$CH$_2$CH$_3$, —CH(CH$_3$)(CH$_3$), —CH$_2$CH$_2$CH$_2$CH$_3$, —CH$_2$—CH(CH$_3$)CH$_3$, —C(CH$_3$)$_3$, —CH$_2$Ph, or
and
each $R_{51}$ is —CH$_3$, —CH$_2$CH$_3$, —CH$_2$CH$_2$CH$_3$, —CH(CH$_3$)(CH$_3$), —CH$_2$CH$_2$CH$_2$CH$_3$, —CH$_2$—CH(CH$_3$)CH$_3$, —C(CH$_3$)$_3$, —CH$_2$Ph, or taken together form a ethylenedioxy acetal or a propylenedioxy acetal; or

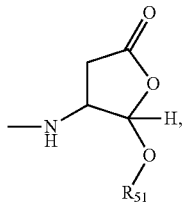

wherein

R$_{51}$ is —CH$_3$, —CH$_2$CH$_3$, —CH$_2$CH$_2$CH$_3$, —CH(CH$_3$)(CH$_3$), —CH$_2$CH$_2$CH$_2$CH$_3$, —CH$_2$—CH(CH$_3$)CH$_3$, —C(CH$_3$)$_3$, —CH$_2$Ph, —C(O)—CH$_3$ or —C(O)-Ph;

R$_5$ in each of the above compounds is the same as any one of the R$_5$ moieties shown for any one of compounds 139, 214c, 214e, 404-413, 415-491, 493-501.

Specific compounds of this invention also include, but are not limited to, compounds comprising scaffolds 1-28, wherein R, R$_{51}$, and R$_5$ are as defined above, and in which the —C(O)— of the R$_5$ moiety of any one of compounds 214c, 214e, 404-413, 415-418, 422-426, 430-456, 458-466, 468, 470-471, 473-491, 493, 495, 497-501 is replaced with —CH$_2$—, —C(O)C(O)—, or —CH$_2$C(O)C(O)—.

The ICE inhibitors of another embodiment (D) of this invention are those of formula (I):

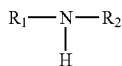 (I)

wherein:

R$_1$ is selected from the group consisting of the following formulae:

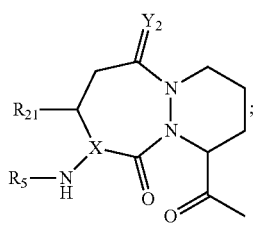 (e10)

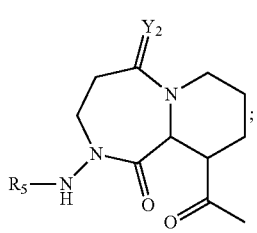 (e11)

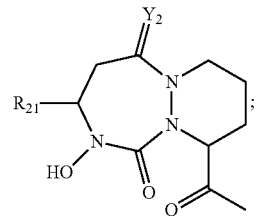 (e12)

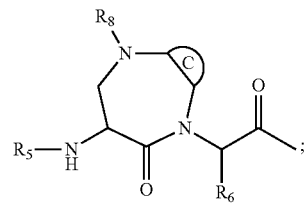 (w2)

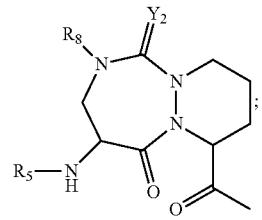 (y1)

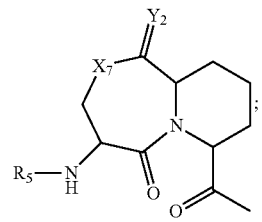 (y2)

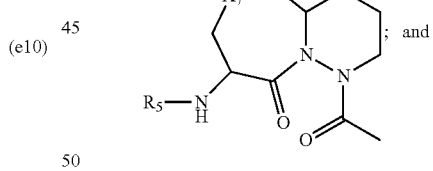 (z)

ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

R$_2$ is:

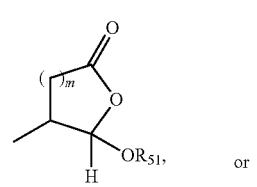 (a)

-continued

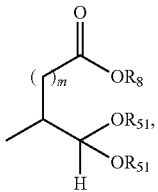
(b)

m is 1 or 2;

each $R_5$ is independently selected from the group consisting of:
—C(O)—$R_{10}$,
—C(O)O—$R_9$,
—C(O)—N($R_{10}$)($R_{10}$)
—S(O)$_2$—$R_9$,
—S(O)$_2$—NH—$R_{10}$,
—C(O)—CH$_2$—O—$R_9$,
—C(O)C(O)—$R_{10}$,
—$R_9$,
—H,
—C(O)C(O)—O$R_{10}$, and
—C(O)C(O)—N($R_9$)($R_{10}$);

$X_5$ is

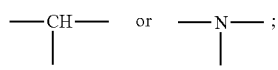

$Y_2$ is H$_2$ or O;
$X_7$ is —N($R_8$)— or —O—;
$R_6$ is selected from the group consisting of —H and —CH$_3$;
$R_8$ is selected from the group consisting of:
—C(O)—$R_{10}$,
—C(O)O—$R_9$,
—C(O)—N(H)—$R_{10}$,
—S(O)$_2$—$R_9$,
—S(O)$_2$—NH—$R_{10}$,
—C(O)—CH$_2$—O$R_{10}$,
—C(O)C(O)—$R_{10}$;
—C(O)—CH$_2$N($R_{10}$)($R_{10}$),
—C(O)—CH$_2$C(O)—O—$R_9$,
—C(O)—CH$_2$C(O)—$R_9$,
—H, and
—C(O)—C(O)—O$R_{10}$;

each $R_9$ is independently selected from the group consisting of —Ar$_3$ and a —C$_{1-6}$ straight or branched alkyl group optionally substituted with Ar$_3$, wherein the —C$_{1-6}$ alkyl group is optionally unsaturated;

each $R_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally unsaturated;

$R_{13}$ is selected from the group consisting of H, Ar$_3$, and a C$_{1-6}$ straight or branched alkyl group optionally substituted with Ar$_3$, —CONH$_2$, —OR$_5$, —OH, —OR$_9$, or —CO$_2$H;

each $R_{51}$ is independently selected from the group consisting of $R_9$, —C(O)—$R_9$, —C(O)—N(H)—$R_9$, or each $R_{51}$ taken together forms a saturated 4-8 member carbocyclic ring or heterocyclic ring containing —O—, —S—, or —NH—;

each $R_{21}$ is independently selected from the group consisting of —H or a —C$_{1-6}$ straight or branched alkyl group;

each Ar$_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, said heterocycle group optionally containing one or more double bonds, said heterocycle group optionally comprising one or more aromatic rings, and said cyclic group optionally being singly or multiply substituted by -Q$_1$;

each Q$_1$ is independently selected from the group consisting of —NH$_2$, —CO$_2$H, —Cl, —F, —Br, —I, —NO$_2$, —CN, =O, —OH, -perfluoro C$_{1-3}$ alkyl, R$_5$, —OR$_5$, —NHR$_5$, OR$_9$, —N(R$_9$)(R$_{10}$), R$_9$, —C(O)—R$_{10}$, and

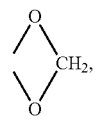

provided that when —Ar$_3$ is substituted with a Q$_1$ group which comprises one or more additional —Ar$_3$ groups, said additional —Ar$_3$ groups are not substituted with another —Ar$_3$.

Preferably, R$_5$ is selected from the group consisting of:
—C(O)—R$_{10}$,
—C(O)O—R$_9$, and
—C(O)—NH—R$_{10}$.

Alternatively, R$_5$ is selected from the group consisting of:
—S(O)$_2$—R$_9$,
—S(O)$_2$—NH—R$_{10}$,
—C(O)—C(O)—R$_{10}$,
—R$_9$, and
—C(O)—C(O)—OR$_{10}$.

More preferably:
m is 1;
R$_{13}$ is H or a —C$_{1-4}$ straight or branched alkyl group optionally substituted with —Ar$_3$, —OH, —OR$_9$, or —CO$_2$H, wherein the R$_9$ is a —C$_{1-4}$ branched or straight alkyl group, wherein Ar$_3$ is morpholinyl or phenyl, wherein the phenyl is optionally substituted with Q$_1$;
R$_{21}$ is —H or —CH$_3$;
R$_{51}$ is a C$_{1-6}$ straight or branched alkyl group optionally substituted with Ar$_3$, wherein Ar$_3$ is phenyl, optionally substituted by -Q$_1$;

each Ar$_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by -Q$_1$;

each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —N(R$_9$)(R$_{10}$), and

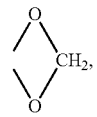

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

The ICE inhibitors of another embodiment (E) of this invention are those of formula (II):

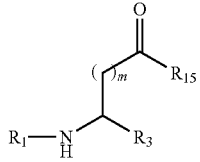

(II)

wherein:

m is 1 or 2;

$R_1$ is selected from the group consisting of the following formulae:

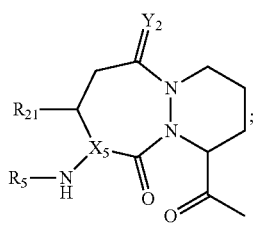

(e10)

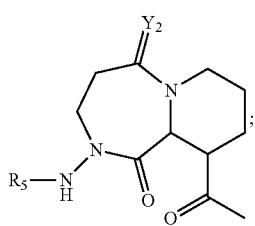

(e11)

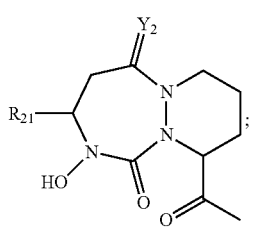

(e12)

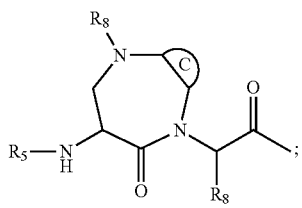

(w2)

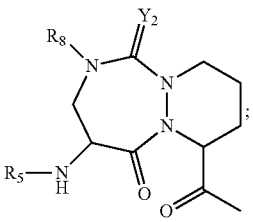

(y1)

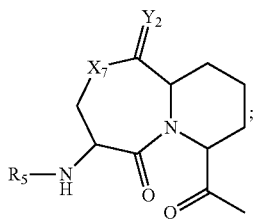

(y2)

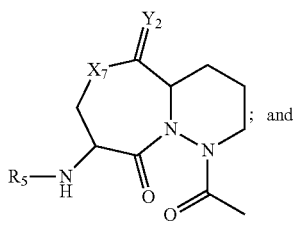

(z)

and ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_3$ is selected from the group consisting of:
—CN,
—C(O)—H,
—C(O)—$CH_2$-$T_1$-$R_{11}$,
—C(O)—$CH_2$—F,
—C—N—O—$R_9$, and
—CO—$Ar_2$;

each $R_5$ is independently selected from the group consisting of:
—C(O)—$R_{10}$,
—C(O)O—$R_9$,
—C(O)—N($R_{10}$)($R_{10}$)
S(O)$_2$—$R_9$,
—S(O)$_2$—NH—$R_{10}$,
—C(O)—$CH_2$—O—$R_9$,
—C(O)C(O)—$R_{10}$,
—$R_9$,
—H,
—C(O)C(O)—O$R_{10}$, and
—C(O)C(O)—N($R_9$)($R_{10}$);

$X_5$ is

—CH— or —N—;

$Y_2$ is $H_2$ or O;

$X_7$ is —N($R_8$)— or —O—;

each $T_1$ is independently selected from the group consisting of —O—, —S—, —S(O)—, and —S(O)$_2$—;

$R_6$ is selected from the group consisting of —H and —$CH_3$;

$R_8$ is selected from the group consisting of:
—C(O)—$R_{10}$,
—C(O)O—$R_9$,
—C(O)—NH—$R_{10}$,
—S(O)$_2$—$R_9$,
—S(O)$_2$—NH—$R_{10}$,
—C(O)—$CH_2$—$OR_{10}$,
—C(O)C(O)—$R_{10}$,
—C(O)—$CH_2$—N($R_{10}$)($R_{10}$),
—C(O)—$CH_2$C(O)—O—$R_9$,
—C(O)—$CH_2$C(O)—$R_9$,
—H, and
—C(O)—C(O)—$OR_{10}$;

each $R_9$ is independently selected from the group consisting of —$Ar_3$ and a —$C_{1-6}$ straight or branched alkyl group optionally substituted with $Ar_3$, wherein the —$C_{1-6}$ alkyl group is optionally unsaturated;

each $R_{10}$ is independently selected from the group consisting of —H, —$Ar_3$, a $C_{3-6}$ cycloalkyl group, and a —$C_{1-6}$ straight or branched alkyl group optionally substituted with $Ar_3$, wherein the —$C_{1-6}$ alkyl group is optionally unsaturated;

each $R_{11}$ is independently selected from the group consisting of:
—$Ar_4$,
—$(CH_2)_{1-3}$—$Ar_4$,
—H, and
—C(O)—$Ar_4$;

$R_{15}$ is selected from the group consisting of —OH, —$OAr_3$, —N(H)—OH, and a —$OC_{1-6}$ straight or branched alkyl group optionally substituted with —$Ar_3$, —$CONH_2$, —$OR_5$, —OH, —$OR_9$, or —$CO_2H$;

each $R_{21}$ is independently selected from the group consisting of —H or a —$C_{1-6}$ straight or branched alkyl group;

$Ar_2$ is independently selected from the following group, in which any ring may optionally be singly or multiply substituted by -$Q_1$:

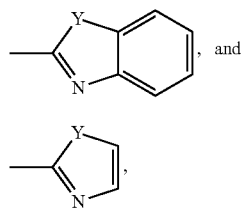

wherein each Y is independently selected from the group consisting of O and S;

each $Ar_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, $SO_2$, =N—, and —NH—, —N($R_5$)—, and —N($R_9$)— said heterocycle group optionally containing one or more double bonds, said heterocycle group optionally comprising one or more aromatic rings, and said cyclic group optionally being singly or multiply substituted by -$Q_1$;

each $Ar_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, $SO_2$, =N—, —NH—, —N($R_5$)—, and —N($R_9$)— said heterocycle group optionally containing one or more double bonds, said heterocycle group optionally comprising one or more aromatic rings, and said cyclic group optionally being singly or multiply substituted by -$Q_1$;

each $Q_1$ is independently selected from the group consisting of —$NH_2$, —$CO_2H$, —Cl, —F, —Br, —I, —$NO_2$, —CN, =O, —OH, -perfluoro $C_{1-3}$ alkyl, $R_5$, —$OR_5$, —$NHR_5$, $OR_9$, —N($R_9$)($R_{10}$), $R_9$, —C(O)—$R_{10}$, and

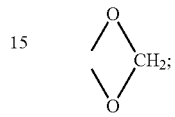

provided that when —$Ar_3$ is substituted with a $Q_1$ group which comprises one or more additional —$Ar_3$ groups, said additional —$Ar_3$ groups are not substituted with another —$Ar_3$.

Preferred compounds of embodiment E employ formula (II), wherein $R_1$ is (e11) and the other substituents are as defined above.

Other preferred compounds of embodiment E employ formula (II), wherein $R_1$ is (e12) and the other substituents are as defined above.

Other preferred compounds of embodiment E employ formula (II) wherein $R_1$ is (y1) and the other substituents are as defined above.

Other preferred compounds of embodiment E employ formula (II) wherein $R_1$ is (y2) and the other substituents are as defined above.

Other preferred compounds of embodiment E of employ formula (II) wherein $R_1$ is (z) and the other substituents are as defined above.

Other preferred compound of embodiment E employ formula (II) wherein $R_1$ is (w2) and the other substituents are as defined above.

More preferably, $R_1$ is (w2) and m is 1;

ring C is benzo, pyrido, or thieno;

$R_3$ is selected from the group consisting of —C(O)—H, —C(O)—$Ar_2$, and —C(O)$CH_2$-$T_1$-$R_{11}$;

$R_5$ is selected from the group consisting of:
—C(O)—$R_{10}$, wherein $R_{10}$ is —$Ar_3$;
—C(O)O—$R_9$, wherein $R_9$ is —$CH_2$—$Ar_3$;
—C(O)C(O)—$R_{10}$, wherein $R_{10}$ is —$Ar_3$;
—$R_9$, wherein $R_9$ is a $C_{1-2}$ alkyl group substituted with —$Ar_3$; and
—C(O)C(O)—$OR_{10}$, wherein $R_{10}$ is —$CH_2Ar_3$;

$T_1$ is O or S;

$R_6$ is H;

$R_8$ is selected from the group consisting —C(O)—$R_{10}$, —C(O)—$CH_2$—$OR_{10}$, and —C(O)$CH_2$—N($R_{10}$)($R_{10}$), wherein $R_{10}$ is H, $CH_3$, or —$CH_2CH_3$;

$R_{11}$ is selected from the group consisting of —$Ar_4$, —$(CH_2)_{1-3}$—$Ar_4$, and —C(O)—$Ar_4$;

$R_{15}$ is —OH or —$OC_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein Ar$_3$ is morpholinyl or phenyl, wherein the phenyl is optionally substituted with Q$_1$;

Ar$_2$ is (hh);

Y is O;

each Ar$_3$ cyclic group is independently selected from the set consisting of phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl, and said cyclic group optionally being singly or multiply substituted by -Q$_1$;

each Ar$_4$ cyclic group is independently selected from the set consisting of phenyl, tetrazolyl, naphthyl, pyridinyl, oxazolyl, pyrimidinyl, or indolyl, said cyclic group optionally being singly or multiply substituted by -Q$_1$;

each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —N(R$_9$)(R$_{10}$), and

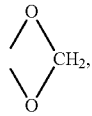

wherein each R$_9$ and R$_{10}$ are independently a —C$_{1-6}$ straight or branched alkyl group optionally substituted with Ar$_3$ wherein Ar$_3$ is phenyl;

provided that when —Ar$_3$ is substituted with a Q$_1$ group which comprises one or more additional —Ar$_3$ groups, said additional —Ar$_3$ groups are not substituted with another —Ar$_3$.

Other preferred compounds of embodiment E employ formula (II) wherein R$_1$ is (e10), X$_5$ is CH, and the other substituents are as defined above.

More preferred compounds of embodiment E employ formula (II) wherein R$_1$ is (e10), X$_5$ is CH, R$_3$ is CO—Ar$_2$, and the other substituents are as defined above.

Other more preferred compounds of embodiment E employ formula (II) wherein R$_1$ is (e10), X$_5$ is CH, R$_3$ is —C(O)—CH$_2$-T$_1$-R$_{11}$, R$_{11}$ is —(CH$_2$)$_{1-3}$—Ar$_4$, and the other substituents are as defined above.

Other more preferred compounds of embodiment E employ formula (II) wherein R$_1$ is (e10) and X$_5$ is CH and R$_3$ is —C(O)—CH$_2$-T$_1$-R$_{11}$, T$_1$ is O, R$_{11}$ is —C(O)—Ar$_4$, and the other substituents are as defined above.

More preferably, in these more preferred compounds, R$_5$ is selected from the group consisting of:
—C(O)—R$_{10}$,
—C(O)O—R$_9$, and
—C(O)—NH—R$_{10}$.

Alternatively, in these more preferred compounds, R$_5$ is selected from the group consisting of:
—S(O)$_2$—R$_9$,
—S(O)$_2$—NH—R$_{10}$,
—C(O)—C(O)—R$_{10}$,
—R$_9$, and
—C(O)—C(O)—OR$_{10}$.

Most preferably, in these more preferred compounds,
m is 1;
T$_1$ is O or S;
R$_{15}$ is —OH or —OC$_{1-4}$ straight or branched alkyl group optionally substituted with —Ar$_3$, —OH, —OR$_9$, or —CO$_2$H, wherein the R$_9$ is a —C$_{1-4}$ branched or straight alkyl group, wherein Ar$_3$ is morpholinyl or phenyl, wherein the phenyl is optionally substituted with Q$_1$;

R$_{21}$ is —H or —CH$_3$;

Ar$_2$ is (hh);

Y is O, and each Ar$_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by -Q$_1$;

each Ar$_4$ cyclic group is independently selected from the set consisting of phenyl, tetrazolyl, pyridinyl, oxazolyl, naphthyl, pyrimidinyl, or thienyl, said cyclic group being singly or multiply substituted by -Q$_1$;

each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —N(R$_9$)(R$_{10}$), and

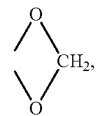

wherein each R$_9$ and R$_{10}$ are independently a —C$_{1-6}$ straight or branched alkyl group optionally substituted with Ar$_3$ wherein Ar$_3$ is phenyl;

provided that when —Ar$_3$ is substituted with a Q$_1$ group which comprises one or more additional —Ar$_3$ groups, said additional —Ar$_3$ groups are not substituted with another —Ar$_3$.

Other more preferred compounds of embodiment E employ formula (II) wherein R$_1$ is (e10), X$_5$ is CH, R$_3$ is —C(O)—H, and the other substituents are as defined above.

More preferably, in these more preferred compounds, R$_5$ is selected from the group consisting of:
—C(O)—R$_{10}$,
—C(O)O—R$_9$, and
—C(O)—NH—R$_{10}$.

Alternatively, in these more preferred compounds, R$_5$ is selected from the group consisting of:
—S(O)$_2$—R$_9$,
—S(O)$_2$—NH—R$_{10}$,
—C(O)—C(O)—R$_{10}$,
—R$_9$, and
—C(O)—C(O)—OR$_{10}$.

Most preferably, in these more preferred compounds,
m is 1;
R$_{15}$ is —OH or —OC$_{1-4}$ straight or branched alkyl group optionally substituted with —Ar$_3$, —OH, —OR$_9$, or —CO$_2$H, wherein the R$_9$ is a —C$_{1-4}$ branched or straight alkyl group, wherein Ar$_3$ is morpholinyl or phenyl, wherein the phenyl is optionally substituted with Q$_1$;

R$_{21}$ is —H or —CH$_3$;

each Ar$_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, said cyclic group optionally being singly or multiply substituted by -Q$_1$;

each $Q_1$ is independently selected from the group consisting of $-NH_2$, $-Cl$, $-F$, $-Br$, $-OH$, $-R_9$, $-NH-R_5$ wherein $R_5$ is $-C(O)-R_{10}$ or $-S(O)_2-R_9$, $-OR_5$ wherein $R_5$ is $-C(O)-R_{10}$, $-OR_9$, $-N(R_9)(R_{10})$, and

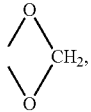

wherein each $R_9$ and $R_{10}$ are independently a $-C_{1-6}$ straight or branched alkyl group optionally substituted with $Ar_3$ wherein $Ar_3$ is phenyl;

provided that when $-Ar_3$ is substituted with a $Q_1$ group which comprises one or more additional $-Ar_3$ groups, said additional $-Ar_3$ groups are not substituted with another $-Ar_3$, Other more preferred compounds of embodiment E employ formula (II) wherein $R_1$ is (e10) and $X_5$ is CH, $R_3$ is $-CO-CH_2-T_1-R_{11}$, and $R_{11}$ is $-Ar_4$, and the other substituents are as defined above.

More preferably, in these more preferred compounds, $R_5$ is selected from the group consisting of:
- $-C(O)-R_{10}$,
- $-C(O)O-R_9$, and
- $-C(O)-NH-R_{10}$.

Alternatively, in these more preferred compounds, $R_5$ is selected from the group consisting of:
- $-S(O)_2-R_9$,
- $-S(O)_2-NH-R_{10}$,
- $-C(O)-C(O)-R_{10}$,
- $-R_9$, and
- $-C(O)-C(O)-OR_{10}$.

Most preferably, in these more preferred compounds,
m is 1;
$T_1$ is O or S;
$R_{15}$ is $-OH$ or a $-OC_{1-4}$ straight or branched alkyl group optionally substituted with $-Ar_3$, $-OH$, $-OR_9$, or $-CO_2H$, wherein the $R_9$ is a $-C_{1-4}$ branched or straight alkyl group, wherein $Ar_3$ is morpholinyl or phenyl, wherein the phenyl is optionally substituted with $Q_1$;
$R_{21}$ is $-H$ or $-CH_3$;
each $Ar_3$ cyclic group is phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by -$Q_1$;
each $Ar_4$ cyclic group is independently selected from the set consisting of phenyl, tetrazolyl, pyridinyl, oxazolyl, naphthyl, pyrimidinyl, or thienyl, said cyclic group optionally being singly or multiply substituted by -$Q_1$;
each $Q_1$ is independently selected from the group consisting of $-NH_2$, $-Cl$, $-F$, $-Br$, $-OH$, $-R_9$, $-NH-R_5$ wherein $R_5$ is $-C(O)-R_{10}$ or $-S(O)_2-R_9$, $-OR_5$ wherein $R_5$ is $-C(O)-R_{10}$, $-OR_9$, $-N(R_9)(R_{10})$, and

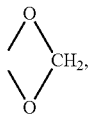

wherein each $R_9$ and $R_{10}$ are independently a $-C_{1-6}$ straight or branched alkyl group optionally substituted with $Ar_3$ wherein $Ar_3$ is phenyl;

provided that when $-Ar_3$ is substituted with a $Q_1$ group which comprises one or more additional $-Ar_3$ groups, said additional $-Ar_3$ groups are not substituted with another $-Ar_3$.

Other preferred compounds of embodiment E employ formula (II) wherein $R_1$ is (e10), $X_5$ is N, and the other substituents are as defined above.

More preferred compounds of embodiment E, employ formula (II) wherein $R_1$ is (e10), $X_5$ is N, $R_3$ is CO—$Ar_2$, and the other substituents are as defined above.

Other more preferred compounds of embodiment E, employ formula (II) wherein $R_1$ is (e10), $X_5$ is N, $R_3$ is $-C(O)-CH_2-T_1-R_{11}$, $R_{11}$ is $-(CH_2)_{1-3}-Ar_4$, and the other substituents are as defined above.

Other more preferred compounds of embodiment E, employ formula (II) wherein $R_1$ is (e10) and $X_5$ is N and:
$R_3$ is $-C(O)-CH_2-T_1-R_{11}$;
$T_1$ is O; and
$R_{11}$ is $-C(O)-Ar_4$, and the other substituents are as defined above.

More preferably, in these more preferred compounds, $R_5$ is selected from the group consisting of:
- $-C(O)-R_{10}$,
- $-C(O)O-R_9$, and
- $-C(O)-NH-R_{10}$.

Alternatively, in these more preferred compounds, $R_5$ is selected from the group consisting of:
- $-S(O)_2-R_9$,
- $-S(O)_2-NH-R_{10}$,
- $-C(O)-C(O)-R_{10}$,
- $-R_9$, and
- $-C(O)-C(O)-OR_{10}$.

Most preferably, in these more preferred compounds,
m is 1;
$T_1$ is O or S;
$R_{15}$ is $-OH$ or a $-OC_{1-4}$ straight or branched alkyl group optionally substituted with $-Ar_3$, $-OH$, $-OR_9$, or $-CO_2H$, wherein the $R_9$ is a $-C_{1-4}$ branched or straight alkyl group, wherein $Ar_3$ is morpholinyl or phenyl, wherein the phenyl is optionally substituted with $Q_1$;
$R_{21}$ is $-H$ or $-CH_3$;
$Ar_2$ is (hh);
Y is O, and
each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by -$Q_1$;
each $Ar_4$ cyclic group is independently selected from the set consisting of phenyl, tetrazolyl, pyridinyl, oxazolyl, naphthyl, pyrimidinyl, or thienyl, optionally being singly or multiply substituted by -$Q_1$;

each $Q_1$ is independently selected from the group consisting of —$NH_2$, —Cl, —F, —Br, —OH, —$R_9$, —NH—$R_5$ wherein $R_5$ is —C(O)—$R_{10}$ or —S(O)$_2$—$R_9$, —$OR_5$ wherein $R_5$ is —C(O)—$R_{10}$, —$OR_9$, —N($R_9$)($R_{10}$), and

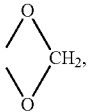

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other more preferred compounds of embodiment E, employ formula (II) wherein $R_1$ is (e10), $X_5$ is N, $R_3$ is —C(O)—H, and the other substituents are as defined above.

More preferably, in these more preferred compounds, $R_5$ is selected from the group consisting of:
—C(O)—$R_{10}$,
—C(O)O—$R_9$, and
—C(O)—NH—$R_{10}$.

Alternatively, in these more preferred compounds, $R_5$ is selected from the group consisting of:
—S(O)$_2$—$R_9$,
—S(O)$_2$—NH—$R_{10}$,
—C(O)—C(O)—$R_{10}$,
—$R_9$, and
—C(O)—C(O)—$OR_{10}$.

Most preferably, in these more preferred compounds,
m is 1;
$R_{15}$ is —OH or —$OC_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;
$R_{21}$ is —H or —$CH_3$;
each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by -$Q_1$;
each $Q_1$ is independently selected from the group consisting of —$NH_2$, —Cl, —F, —Br, —OH, —$R_9$, —NH—$R_5$ wherein $R_5$ is —C(O)—$R_{10}$ or —S(O)$_2$—$R_9$, —$OR_5$ wherein $R_5$ is —C(O)—$R_{10}$, —$OR_9$, —N($R_9$)($R_{10}$), and

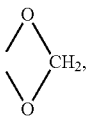

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other more preferred compounds of embodiment E, employ formula (II) wherein $R_1$ is (e10), $X_5$ is N, $R_3$ is —CO—$CH_2$-$T_1$-$R_{11}$, $R_{11}$ is —$Ar_4$, and the other substituents are as defined above.

More preferably, in these more preferred compounds, $R_5$ is selected from the group consisting of:
—C(O)—$R_{10}$,
—C(O)O—$R_9$, and
—C(O)—NH—$R_{10}$.

Alternatively, in these more preferred compounds, $R_5$ is selected from the group consisting of:
—S(O)$_2$—$R_9$,
—S(O)$_2$—NH—$R_{10}$,
—C(O)—C(O)—$R_{10}$,
—$R_9$, and
—C(O)—C(O)—$OR_{10}$.

Most preferably, in these more preferred compounds
m is 1;
$T_1$ is O or S;
$R_{15}$ is —OH or —$OC_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;
$R_{21}$ is —H or —$CH_3$;
each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by -$Q_1$;
each $Ar_4$ cyclic group is independently selected from the set consisting of phenyl, tetrazolyl, pyridinyl, oxazolyl, naphthyl, pyrimidinyl, or thienyl, said cyclic group being singly or multiply substituted by -$Q_1$;
each $Q_1$ is independently selected from the group consisting of —$NH_2$, —Cl, —F, —Br, —OH, —$R_9$, —NH—$R_5$ wherein $R_5$ is —C(O)—$R_{10}$ or —S(O)$_2$—$R_9$, —$OR_5$ wherein $R_5$ is —C(O)—$R_{10}$, —$OR_9$, —N($R_9$)($R_{10}$), and

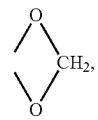

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

The ICE inhibitors of another embodiment (F) of this invention are those of formula (III):

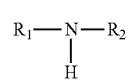

wherein:

R₁ is selected from the group consisting of the following formulae:

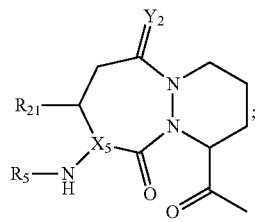
(e10)

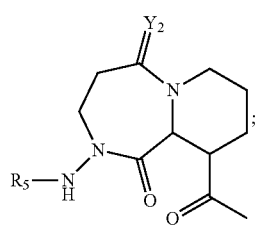
(e11)

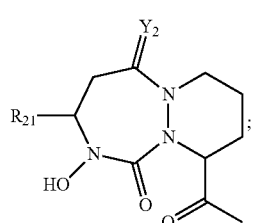
(e12)

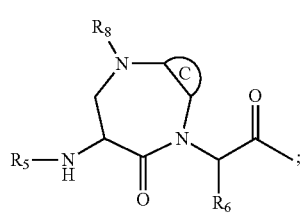
(w2)

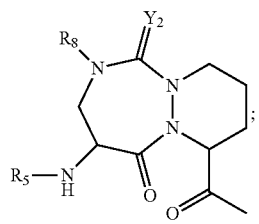
(y1)

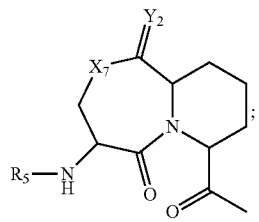
(y2)

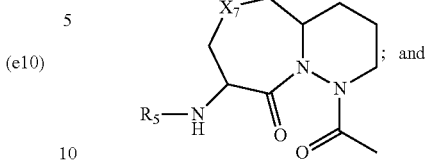
(z)

ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

R₂ is:

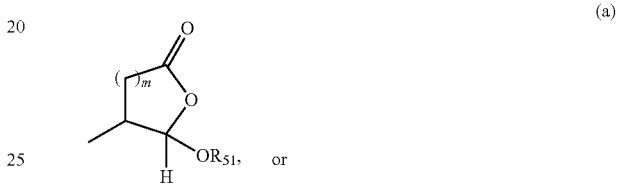
(a)

(b)

m is 1 or 2;

each $R_5$ is independently selected from the group consisting of:
— C(O)—$R_{10}$,
— C(O)O—$R_9$,
— C(O)—N($R_{10}$)($R_{10}$)
— S(O)₂—$R_9$,
— S(O)₂—NH—$R_{10}$,
— C(O)—CH₂—O—$R_9$,
— C(O)C(O)—$R_{10}$,
— $R_9$,
— H,
— C(O)C(O)—O$R_{10}$, and
— C(O)C(O)—N($R_9$)($R_{10}$);

$X_5$ is CH or N;
$Y_2$ is H₂ or O;
$X_7$ is —N($R_8$)— or —O—;
$R_6$ is selected from the group consisting of —H and —CH₃;
$R_8$ is selected from the group consisting of:
— C(O)—$R_{10}$,
— C(O)O—$R_9$,
— C(O)—N(H)—$R_{10}$,
— S(O)₂—$R_9$,
— S(O)₂—NH—$R_{10}$,
— C(O)—CH₂—O$R_{10}$,
— C(O)C(O)—$R_{10}$;
— C(O)—CH₂N($R_{10}$)($R_{10}$),
— C(O)—CH₂C(O)—O—$R_9$,
— C(O)—CH₂C(O)—$R_9$,
— H, and
— C(O)—C(O)—O$R_{10}$;

each $R_9$ is independently selected from the group consisting of —$Ar_3$ and a —$C_{1-6}$ straight or branched alkyl group optionally substituted with $Ar_3$, wherein the —$C_{1-6}$ alkyl group is optionally unsaturated;

each $R_{10}$ is independently selected from the group consisting of —H, —$Ar_3$, a $C_{3-6}$ cycloalkyl group, and a —$C_{1-6}$ straight or branched alkyl group optionally substituted with $Ar_3$, wherein the —$C_{1-6}$ alkyl group is optionally unsaturated;

$R_{13}$ is selected from the group consisting of H, $Ar_3$, and a $C_{1-6}$ straight or branched alkyl group optionally substituted with $Ar_3$, —$CONH_2$, —$OR_5$, —OH, —$OR_9$, or —$CO_2H$;

each $R_{21}$ is independently selected from the group consisting of —H or a —$C_{1-6}$ straight or branched alkyl group;

each $R_{51}$ is independently selected from the group consisting of $R_9$, —C(O)—$R_9$, —C(O)—N(H)—$R_9$, or each $R_{51}$ taken together forms a saturated 4-8 member carbocyclic ring or heterocyclic ring containing —O—, —S—, or —NH—;

each $Ar_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, $SO_2$, =N—, and —NH—, said heterocycle group optionally containing one or more double bonds, said heterocycle group optionally comprising one or more aromatic rings, and said cyclic group optionally being singly or multiply substituted by -$Q_1$;

each $Q_1$ is independently selected from the group consisting of —$NH_2$, —$CO_2H$, —Cl, —F, —Br, —I, —$NO_2$, —CN, =O, —OH, -perfluoro $C_{1-3}$ alkyl, $R_5$, —$OR_5$, —$NHR_5$, $OR_9$, —$N(R_9)(R_{10})$, $R_9$, —C(O)—$R_{10}$, and

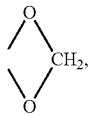

provided that when —$Ar_3$ is substituted with a $Q_1$ group which comprises one or more additional —$Ar_3$ groups, said additional —$Ar_3$ groups are not substituted with another —$Ar_3$.

Preferred compounds of embodiment F employ formula (III), wherein $R_1$ is (w2) and the other substituents are as defined above.

Preferably, when $R_1$ is (w2):
m is 1;
ring C is benzo, pyrido, or thieno;
$R_5$ is selected from the group consisting of:
—C(O)—$R_{10}$, wherein $R_{10}$ is —$Ar_3$;
—C(O)O—$R_9$, wherein $R_9$ is —$CH_2$—$Ar_3$;
—C(O)C(O)—$R_{10}$, wherein $R_{10}$ is —$Ar_3$;
—$R_9$, wherein $R_9$ is a $C_{1-2}$ alkyl group substituted with —$Ar_3$; and
—C(O)C(O)—$OR_{10}$, wherein $R_{10}$ is —$CH_2Ar_3$;
$R_6$ is H;
$R_8$ is selected from the group consisting —C(O)—$R_{10}$, —C(O)—$CH_2$—$OR_{10}$, and —$C(O)CH_2$—$N(R_{10})(R_{10})$, wherein $R_{10}$ is H, $CH_3$, or —$CH_2CH_3$;
$R_{13}$ is H or a $C_{1-4}$ straight or branched alkyl group optionally substituted with $Ar_3$, —OH, —$OR_9$, —$CO_2H$, wherein the $R_9$ is a $C_{1-4}$ branched or straight chain alkyl group; wherein $Ar_3$ is morpholinyl or phenyl, wherein the phenyl is optionally substituted with $Q_1$;

$Ar_3$ is phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$NHR_9$, and

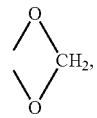

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other preferred compounds of embodiment F employ formula (III), wherein $R_1$ is (e11) and the other substituents are as defined above.

Other preferred compounds of embodiment F employ formula (III), wherein $R_1$ is (e12) and the other substituents are as defined above.

Other preferred compounds of embodiment F employ formula (III), wherein $R_1$ is (y1) and the other substituents are as defined above.

Alternatively, $R_5$ is —C(O)—C(O)—$OR_{10}$.

More preferably when $R_1$ is (e11), (e12), (y1), (y2), (z), (e10-A), and (e10-B):
m is 1;
$R_{21}$ is —H or —$CH_3$;
$R_{51}$ is a $C_{1-6}$ straight or branched alkyl group optionally substituted with $Ar_3$, wherein the $Ar_3$ cyclic group is phenyl, said cyclic group optionally being multiply or singly substituted by -$Q_1$;

each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, or indolyl, and said cyclic group optionally being singly or multiply substituted by -$Q_1$;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is C(O)—$R_{10}$, —$OR_9$, —$N(R_9)(R_{10})$, and

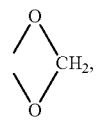

wherein each $R_9$ and $R_{10}$ are independently a —$C_{1-6}$ straight or branched alkyl group optionally substituted with $Ar_3$, wherein the $Ar_3$ cyclic group is phenyl, and said cyclic group optionally being singly or multiply substituted by -$Q_1$;

provided that when —$Ar_3$ is substituted with a -$Q_1$ group which comprises one or more additional —$Ar_3$ groups, said additional —$Ar_3$ groups are not substituted with another —$Ar_3$.

More preferably, in these more preferred compounds, the $Ar_3$ cyclic group is selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, benzofuranyl, and indolyl, and said cyclic group optionally being singly or multiply substituted by -$Q_1$.

Compounds in a preferred form of this embodiment F are those wherein:

$R_5$ is —C(O)—$R_{10}$, wherein:

$R_{10}$ is $Ar_3$, wherein the $Ar_3$ cyclic group is phenyl, said cyclic group optionally being singly or multiply substituted by:
—F,
—Cl,
—N(H)—$R_5$, wherein —$R_5$ is —H or —C(O)—$R_{10}$, wherein
$R_{10}$ is a —$C_{1-6}$ straight or branched alkyl group optionally substituted with $Ar_3$, wherein the $Ar_3$ cyclic group is phenyl, said cyclic group optionally being singly or multiply substituted by -$Q_1$,
—N($R_9$)($R_{10}$), wherein $R_9$ and $R_{10}$ are independently a —$C_{1-4}$ straight or branched alkyl group, or
—O—$R_5$, wherein $R_5$ is H or a —$C_{1-4}$ straight or branched alkyl group.

More preferably the $Ar_3$ cyclic group is phenyl optionally being singly or multiply substituted at the 3- or 5-position by —Cl or at the 4-position by —NH—$R_5$, —N($R_9$)($R_{10}$), or —O—$R_5$.

Other preferred compounds of embodiment F include those wherein $R_5$ is —C(O)—$R_{10}$, wherein $R_{10}$ is $Ar_3$ and the $Ar_3$ cyclic group is selected from the group consisting of indolyl, benzimidazolyl, thienyl, and benzo[b]thiophenyl, and said cyclic group optionally being singly or multiply substituted by -$Q_1$;

Other preferred compounds of embodiment F include those wherein $R_5$ is —C(O)—$R_{10}$, wherein $R_{10}$ is $Ar_3$ and the $Ar_3$ cyclic group is selected from quinolyl and isoquinolyl, and said cyclic group optionally being singly or multiply substituted by -$Q_1$.

Other preferred compounds of embodiment F are those wherein $R_5$ is —C(O)—$R_{10}$, wherein $R_{10}$ is $Ar_3$, wherein the $Ar_3$ cyclic group is phenyl, substituted by

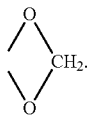

In another form of embodiment F the compounds are as described above, further provided that when:
m is 1;
$R_1$ is (e10);
$X_5$ is CH;
$R_{15}$ is —OH;
$R_{21}$ is —H; and
$Y_2$ is O and $R_3$ is —C(O)—H, then $R_5$ cannot be:
—C(O)—$R_{10}$, wherein $R_{10}$ is —$Ar_3$ and the $Ar_3$ cyclic group is phenyl, unsubstituted by -$Q_1$, 4-(carboxymethoxy)phenyl, 2-fluorophenyl, 2-pyridyl, N-(4-methylpiperazino)methylphenyl, or
—C(O)—$OR_9$, wherein $R_9$ is —$CH_2$—$Ar_3$, and the $Ar_3$ cyclic group is phenyl, unsubstituted by -$Q_1$; and when $Y_2$ is O, $R_3$ is —C(O)—$CH_2$-$T_1$-$R_{11}$, $T_1$ is O, and $R_{11}$ is $Ar_4$, wherein the $Ar_4$ cyclic group is 5-(1-(4-chlorophenyl)-3-trifluoromethyl)pyrazolyl), then $R_5$ cannot be:
—C(O)—$R_{10}$, wherein $R_{10}$ is —$Ar_3$ and the $Ar_3$ cyclic group is 4-(dimethylaminomethyl)phenyl, phenyl, 4-(carboxymethylthio)phenyl, 4-(carboxyethylthio)phenyl, 4-(carboxyethyl)phenyl, 4-(carboxypropyl)phenyl, 2-fluorophenyl, 2-pyridyl, N-(4-methylpiperazino)methylphenyl, or
—C(O)—$OR_9$, wherein $R_9$ is —$CH_2$—$Ar_3$ and the $Ar_3$ cyclic group is phenyl;

and when $R_{11}$ is $Ar_4$, wherein the $Ar_4$ cyclic group is 5-(1-phenyl-3-trifluoromethyl)pyrazolyl), then $R_5$ cannot be:
—C(O)—$OR_9$, wherein $R_9$ is —$CH_2$—$Ar_3$, and the $Ar_3$ cyclic group is phenyl;

and when $R_H$ is $Ar_4$, wherein the $Ar_4$ cyclic group is 5-(1-(2-pyridyl)-3-trifluoromethyl)pyrazolyl), then $R_5$ cannot be:
—C(O)—$R_{10}$, wherein $R_{10}$ is —$Ar_3$ and the $Ar_3$ cyclic group is 4-(dimethylaminomethyl)phenyl, or
—C(O)—$OR_9$, wherein $R_9$ is —$CH_2$—$Ar_3$, and the $Ar_3$ cyclic group is phenyl, unsubstituted by -$Q_1$; and when $Y_2$ is O, $R_3$ is —C(O)—$CH_2$-$T_1$-$R_{11}$, $T_1$ is O, and $R_{11}$ is —C(O)—$Ar_4$, wherein the $Ar_4$ cyclic group is 2,5-dichlorophenyl, then $R_5$ cannot be:
—C(O)—$R_{10}$, wherein $R_{10}$ is —$Ar_3$ and the $Ar_3$ cyclic group is 4-(dimethylaminomethyl)phenyl, 4-(N-morpholinomethyl)phenyl, 4-(N-methylpiperazino)methyl)phenyl, 4-(N-(2-methyl)imidazolylmethyl)phenyl, 5-benzimidazolyl, 5-benztriazolyl, N-carboethoxy-5-benztriazolyl, N-carboethoxy-5-benzimidazolyl, or
—C(O)—$OR_9$, wherein $R_9$ is —$CH_2$—$Ar_3$ and the $Ar_3$ cyclic group is phenyl, unsubstituted by -$Q_{11}$; and when $Y_2$ is $H_2$, $R_3$ is —C(O)—$CH_2$-$T_1$-$R_{11}$, $T_1$ is O, and $R_{11}$ is —C(O)—$Ar_4$, wherein the $Ar_4$ cyclic group is 2,5-dichlorophenyl, then $R_5$ cannot be:
—C(O)—$OR_9$, wherein $R_9$ is —$CH_2$—$Ar_3$ and the $Ar_3$ cyclic group is phenyl.

In another form of embodiment F, preferred compounds are those wherein $R_{21}$ is —H.

Alternatively, preferred compounds are those wherein $R_{21}$ is —$CH_3$.

Preferred compounds of embodiment F employ formula (III), wherein $R_1$ is (w2) and the other substituents are as defined above.

More preferably, $R_1$ is (w2) and
m is 1;
ring C is benzo, pyrido, or thieno;
$R_3$ is selected from the group consisting of —C(O)—H, —C(O)—$Ar_2$, and —C(O)$CH_2$-$T_1$-$R_{11}$;
$R_5$ is selected from the group consisting of:
—C(O)—$R_{10}$, wherein $R_{10}$ is —$Ar_3$;
—C(O)O—$R_9$, wherein $R_9$ is —$CH_2$—$Ar_3$;
—C(O)C(O)—$R_{10}$, wherein $R_{10}$ is —$Ar_3$;
—$R_9$, wherein $R_9$ is a $C_{1-2}$ alkyl group substituted with —$Ar_3$; and
—C(O)C(O)—$OR_{10}$, wherein $R_{10}$ is —$CH_2Ar_3$;
$T_1$ is O or S;
$R_6$ is H;
$R_8$ is selected from the group consisting —C(O)—$R_{10}$, —C(O)—$CH_2$—$OR_{10}$, and —C(O)$CH_2$—N($R_{10}$)($R_{10}$), wherein $R_{10}$ is H, $CH_3$, or —$CH_2CH_3$;
$R_{11}$ is selected from the group consisting of —$Ar_4$, —$(CH_2)_{1-3}$—$Ar_4$, and —C(O)—$Ar_4$;
$R_{15}$ is —OH or —$OC_{1-4}$ straight or branched alkyl group optionally substituted with —$Ar_3$, —OH, —$OR_9$, or —$CO_2H$, wherein the $R_9$ is a —$C_{1-4}$ branched or straight alkyl group, wherein $Ar_3$ is morpholinyl or phenyl, wherein the phenyl is optionally substituted with $Q_1$;

Ar$_2$ is (hh);

Y is O;

each Ar$_3$ cyclic group is independently selected from the set consisting of phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl, and said cyclic group optionally being singly or multiply substituted by -Q$_1$;

each Ar$_4$ cyclic group is independently selected from the set consisting of phenyl, tetrazolyl, naphthyl, pyridinyl, oxazolyl, pyrimidinyl, or indolyl, said cyclic group optionally being singly or multiply substituted by -Q$_1$;

each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —N(R$_9$)(R$_{10}$), and

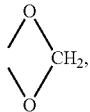

wherein each R$_9$ and R$_{10}$ are independently a —C$_{1-6}$ straight or branched alkyl group optionally substituted with Ar$_3$ wherein Ar$_3$ is phenyl;

provided that when —Ar$_3$ is substituted with a Q$_1$ group which comprises one or more additional —Ar$_3$ groups, said additional —Ar$_3$ groups are not substituted with another —Ar$_3$.

Other preferred compounds of embodiment F employ formula (III), wherein R$_1$ is (e11) and the other substituents are as defined above.

Other preferred compounds of embodiment F employ formula (III), wherein R$_1$ is (e12) and the other substituents are as defined above.

Other preferred compounds of embodiment F employ formula (III) wherein R$_1$ is (y1) and the other substituents are as defined above.

Other preferred compounds of embodiment F employ formula (III) wherein R$_1$ is (y2) and the other substituents are as defined above.

Other preferred compounds of embodiment F of employ formula (III) wherein R$_1$ is (z) and the other substituents are as defined above.

Other preferred compounds of embodiment F employ formula (III) wherein R$_1$ is (e10), X$_5$ is CH, and the other substituents are as defined above.

Other preferred compounds of embodiment F employ formula (III) wherein R$_1$ is (e10), X$_5$ is N, and the other substituents are as defined above.

More preferably, in these more preferred compounds, R$_5$ is selected from the group consisting of:

—C(O)—R$_{10}$,
—C(O)O—R$_9$, and
—C(O)—NH—R$_{10}$.

Alternatively, in these more preferred compounds, R$_5$ is selected from the group consisting of:

—S(O)$_2$—R$_9$,
—S(O)$_2$—NH—R$_{10}$,
—C(O)—C(O)—R$_{10}$,
—R$_9$,
—C(O)—C(O)—OR$_{10}$, and
—C(O)C(O)—N(R$_9$)(R$_{10}$).

Most preferably, in these more preferred compounds, m is 1;

R$_{13}$ is H or a —C$_{1-4}$ straight or branched alkyl group optionally substituted with —Ar$_3$, —OH, —OR$_9$, or —CO$_2$H, wherein the R$_9$ is a —C$_{1-4}$ branched or straight alkyl group, wherein Ar$_3$ is morpholinyl or phenyl, wherein the phenyl is optionally substituted with Q$_1$;

R$_{21}$ is —H or —CH$_3$;

R$_{51}$ is a C$_{1-6}$ straight or branched alkyl group optionally substituted with Ar$_3$, wherein Ar$_3$ is phenyl, optionally substituted by -Q$_1$;

each Ar$_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by -Q$_1$;

each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —N(R$_9$)(R$_{10}$), and

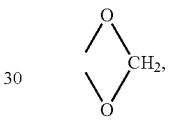

wherein each R$_9$ and R$_{10}$ are independently a —C$_{1-6}$ straight or branched alkyl group optionally substituted with Ar$_3$ wherein Ar$_3$ is phenyl;

provided that when —Ar$_3$ is substituted with a Q$_1$ group which comprises one or more additional —Ar$_3$ groups, said additional —Ar$_3$ groups are not substituted with another —Ar$_3$.

Preferred compounds of embodiment (F) include; but are not limited to:

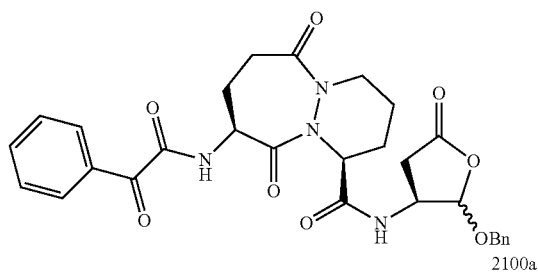

2001

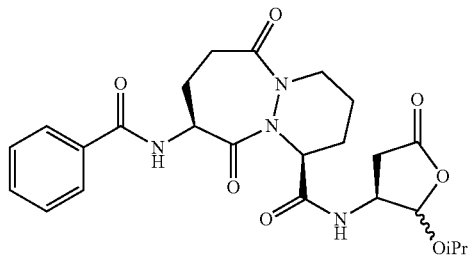

2100a

-continued

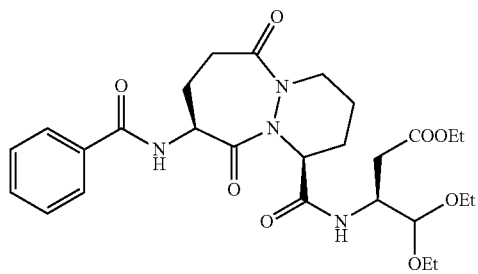
2100b

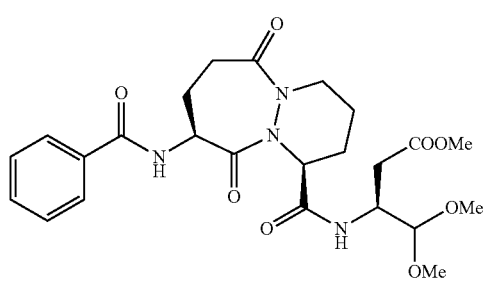
2100c

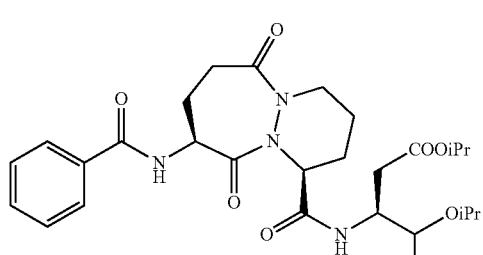
2100d

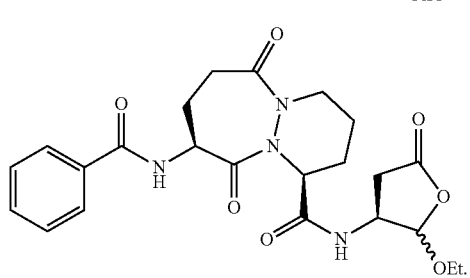
2100e

The ICE inhibitors of another embodiment (G) of this invention are those of formula (IV):

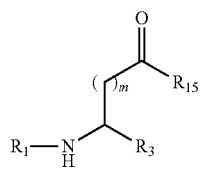

(IV)

wherein:
m is 1 or 2;
$R_1$ is selected from the group consisting of the following formulae:

Other preferred compounds of embodiment F employ formula (III), wherein $R_1$ is (y2) and the other substituents are as defined above.

Other preferred compounds of embodiment F employ formula (III), wherein $R_1$ is (z) and the other substituents are as defined above.

Other preferred compounds of embodiment F employ formula (III), wherein $R_1$ is (e10) and $X_5$ is CH (also referred to herein as e10-B), and the other substituents are as defined above.

Other preferred compounds of embodiment F employ formula (III), wherein $R_1$ is (e10) and $X_5$ is N, (also referred to herein as e10-A) and the other substituents are as defined above.

Preferably, when $R_1$ is (e11), (e12), (y1), (y2), (z), (e10-A), and (e10-B), $R_5$ is selected from the group consisting of:
—C(O)—$R_{10}$,
—C(O)O—$R_9$, and
—C(O)—NH—$R_{10}$.

Alternatively, when $R_1$ is (e11), (e12), (y1), (y2), (z), (e10-A), and (e10-B), $R_5$ is selected from the group consisting of:
—S(O)$_2$—$R_9$,
—S(O)$_2$—NH—$R_{10}$,
—C(O)—C(O)—$R_{10}$,
—$R_9$,
—C(O)—C(O)—O$R_{10}$, and
—C(O)C(O)—N($R_9$)($R_{10}$).

More preferably, $R_5$ is R—C(O)—C(O)—$R_{10}$

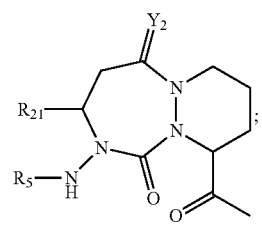
(e10-A)

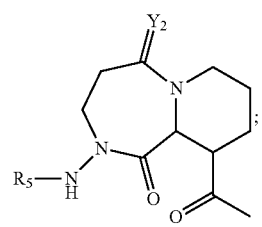
(e11)

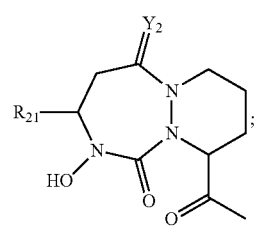
(e12)

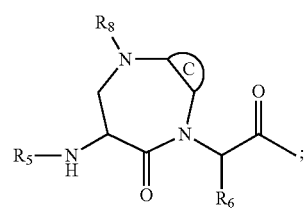
(w2)

-continued

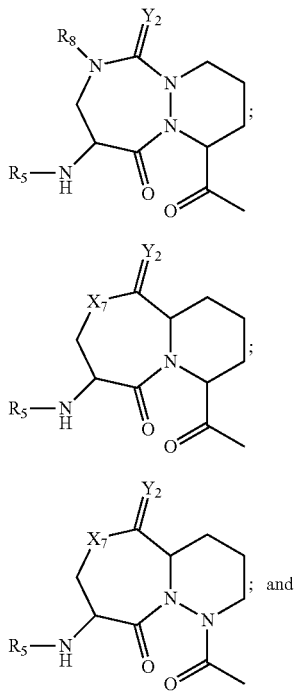

ring C is chosen from the group consisting of benzo, pyrido, thieno, pyrrolo, furano, thiazolo, isothiazolo, oxazolo, isoxazolo, pyrimido, imidazolo, cyclopentyl, and cyclohexyl;

$R_3$ is selected from the group consisting of:
—CN,
—C(O)—H,
—C(O)—CH$_2$-T$_1$-R$_{11}$,
—C(O)—CH$_2$—F,
—C=N—O—R$_9$, and
—CO—Ar$_2$;

each $R_5$ is independently selected from the group consisting of:
—C(O)—R$_{10}$,
—C(O)O—R$_9$,
—C(O)—N(R$_{10}$)(R$_{10}$)
—S(O)$_2$—R$_9$,
—S(O)$_2$—NH—R$_{10}$,
—C(O)—CH$_2$—O—R$_9$,
—C(O)C(O)—R$_{10}$,
—R$_9$,
—H,
—C(O)C(O)—OR$_{10}$, and
—C(O)C(O)—N(R$_9$)(R$_{10}$);

$Y_2$ is H$_2$ or O;
$X_7$ is —N(R$_8$)— or —O—;
each $T_1$ is independently selected from the group consisting of —O—, —S—, —S(O)—, and —S(O)$_2$—;
$R_6$ is selected from the group consisting of —H and —CH$_3$;
$R_8$ is selected from the group consisting of:
—C(O)—R$_{10}$,
—C(O)O—R$_9$,
—C(O)—NH—R$_{10}$,
—S(O)$_2$—R$_9$,
—S(O)$_2$—NH—R$_{10}$,
—C(O)—CH$_2$—OR$_{10}$,
—C(O)C(O)—R$_{10}$,
—C(O)—CH$_2$—N(R$_{10}$)(R$_{10}$),
—C(O)—CH$_2$C(O)—O—R$_9$,
—C(O)—CH$_2$C(O)—R$_9$,
—H, and
—C(O)—C(O)—OR$_{10}$;

each $R_9$ is independently selected from the group consisting of —Ar$_3$ and a —C$_{1-6}$ straight or branched alkyl group optionally substituted with Ar$_3$, wherein the —C$_{1-6}$ alkyl group is optionally unsaturated;

each $R_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally unsaturated;

each $R_{11}$ is independently selected from the group consisting of:
—Ar$_4$,
—(CH$_2$)$_{1-3}$—Ar$_4$,
—H, and
—C(O)—Ar$_4$;

$R_{15}$ is selected from the group consisting of —OH, —OAr$_3$, —N(H)—OH, and —OC$_{1-6}$, wherein C$_{1-6}$ is a straight or branched alkyl group optionally substituted with Ar$_9$, —CONH$_2$, —OR$_5$, —OH, —OR$_9$, or —CO$_2$H;

each $R_{21}$ is independently selected from the group consisting of —H or a —C$_{1-6}$ straight or branched alkyl group;

Ar$_2$ is independently selected from the following group, in which any ring may optionally be singly or multiply substituted by -Q$_1$ or phenyl, optionally substituted by Q$_1$:

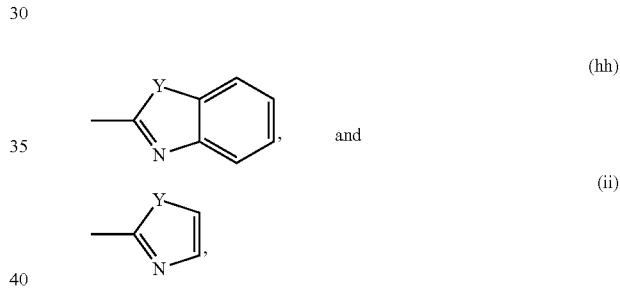

wherein each Y is independently selected from the group consisting of O and S;

each Ar$_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by -Q$_1$;

each Ar$_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, SO$_2$, =N—, —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by -Q$_1$;

each Q$_1$ is independently selected from the group consisting of —NH$_2$, —CO$_2$H, —Cl, —F, —Br, —I, —NO$_2$, —CN, =O, —OH, -perfluoro $C_{1-3}$ alkyl, $R_5$, —$OR_5$, —$NHR_5$, $OR_9$, —$N(R_9)(R_{10})$, $R_9$, —C(O)—$R_{10}$, and

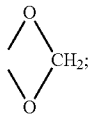

provided that when —$Ar_3$ is substituted with a $Q_1$ group which comprises one or more additional —$Ar_3$ groups, said additional —$Ar_3$ groups are not substituted with another —$Ar_3$;

Preferred compounds of embodiment G employ formula (IV), wherein $R_1$ is (w2) and the other substituents are as defined above.

Preferably, when $R_1$ is (w2):

m is 1;

ring C is benzo, pyrido, or thieno;

$R_5$ is selected from the group consisting of:
—C(O)—$R_{10}$, wherein $R_{10}$ is —$Ar_3$;
—C(O)O—$R_9$, wherein $R_9$ is —$CH_2$—$Ar_3$;
—C(O)C(O)—$R_{10}$, wherein $R_{10}$ is —$Ar_3$;
—$R_9$, wherein $R_9$ is a $C_{1-2}$ alkyl group substituted with —$Ar_3$; and
—C(O)C(O)—$OR_{10}$, wherein $R_{10}$ is —$CH_2Ar_3$;

$R_6$ is H;

$R_8$ is selected from the group consisting —C(O)—$R_{10}$, —C(O)—$CH_2$—$OR_{10}$, and —C(O)$CH_2$—$N(R_{10})(R_{10})$, wherein $R_{10}$ is H, $CH_3$, or —$CH_2CH_3$;

$R_{13}$ is H or a $C_{1-4}$ straight or branched alkyl group optionally substituted with $Ar_3$, —OH, —$OR_9$, $OC_2H$, wherein the $R_9$ is a $C_{1-4}$ branched or straight chain alkyl group; wherein $Ar_3$ is morpholinyl or phenyl, wherein the phenyl is optionally substituted with $Q_1$;

$Ar_3$ is phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$NHR_9$, and

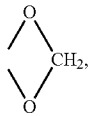

wherein each $R_9$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Other preferred compounds of embodiment G employ formula (IV) wherein $R_1$ is (e10-A) and the other substituents are as defined above.

Other preferred compounds of embodiment G employ formula (IV) wherein $R_1$ is (e11) and the other substituents are as defined above.

Other preferred compounds of embodiment G employ formula (IV) wherein $R_1$ is (e12) and the other substituents are as defined above.

Other preferred compounds of embodiment G employ formula (IV) wherein $R_1$ is (y1) and the other substituents are as defined above.

Other preferred compounds of embodiment G employ formula (IV) wherein $R_1$ is (y2) and the other substituents are as defined above.

Other preferred compounds of embodiment G employ formula (IV) wherein $R_1$ is (z) and the other substituents are as defined above.

More preferred compounds of embodiment G are those wherein $R_3$ is —CO—$Ar_2$.

Most preferably, when $R_3$ is —CO—$Ar_2$, Y is O.

Other more preferred compounds are those wherein $R_3$ is —C(O)—$CH_2$-$T_1$-$R_{11}$ and $R_{11}$ is —$(CH_2)_{1-3}$—$Ar_4$.

Most preferably, when $R_3$ is —C(O)—$CH_2$-$T_1$-$R_{11}$ and $R_{11}$ is —$(CH_2)_{1-3}$—$Ar_4$, $T_1$ is O.

Other more preferred compounds are those wherein:

$R_3$ is —C(O)—$CH_2$-$T_1$-$R_{11}$;

$T_1$ is O; and $R_{11}$ is —C(O)—$Ar_4$.

Other more preferred compounds are those wherein $R_3$ is —C(O)—H.

Other more preferred compounds are those wherein $R_3$ is —CO—$CH_2$-$T_1$-$R_{11}$ and $R_{11}$ is —$Ar_4$.

More preferably, when $R_3$ is —CO—$CH_2$-$T_1$-$R_{11}$ and $R_{11}$ is —$Ar_4$, $T_1$ is O or S.

More preferably, when $R_1$, is (e11), (e12), (y1), (y2), (z), (e10-A), and (e10-B), $R_5$ is selected from the group consisting of:
—C(O)—$R_{10}$,
—C(O)O—$R_9$, and
—C(O)—NH—$R_{10}$.

Alternatively, when $R_1$, is (e11), (e12), (y1), (y2), (z), (e10-A), and (e10-B), $R_5$ is selected from the group consisting of:
—$S(O)_2$—$R_9$,
—$S(O)_2$—NH—$R_{10}$,
—C(O)—C(O)—$R_{10}$,
—$R_9$,
—C(O)—C(O)—$OR_{10}$, and
—C(O)—C(O)—$N(R_9)(R_{10})$ More preferably, $R_5$ is —C(O)—C(O)—$R_{10}$.

Alternatively, $R_5$ is —C(O)—C(O)—$OR_{10}$.

Most preferably, when $R_1$ is (e11), (e12), (y1), (y2), (z), (e10-A), and (e10-B):

m is 1;

$R_{21}$ is —H or —$CH_3$;

$R_{51}$ is a $C_{1-6}$ straight or branched alkyl group optionally substituted with $Ar_3$, wherein the $Ar_3$ cyclic group is phenyl, said cyclic group optionally being multiply or singly substituted by -$Q_1$;

each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, or indolyl, and said cyclic group optionally being singly or multiply substituted by -$Q_1$;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$N(R_9)(R_{10})$, and

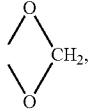

wherein each $R_9$ and $R_{10}$ are independently a —$C_{1-6}$ straight or branched alkyl group optionally substituted with $Ar_3$, wherein the $Ar_3$ cyclic group is phenyl, and said cyclic group optionally being singly or multiply substituted by -$Q_1$;

provided that when —$Ar_3$ is substituted with a -$Q_1$ group which comprises one or more additional —$Ar_3$ groups, said additional —$Ar_3$ groups are not substituted with another —$Ar_3$.

More preferably, in these more preferred compounds, the $Ar_3$ cyclic group is selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, benzofuranyl, and indolyl, and said cyclic group optionally being singly or multiply substituted by -$Q_1$.

Compounds in a preferred form of embodiment G are those wherein $R_{21}$ is H and the other substituents are as defined above.

Compounds in another preferred form of embodiment G are those wherein $R_{21}$ is $CH_3$ and the other substituents are as defined above.

The ICE inhibitors of another embodiment (H) of this invention are those of formula (V):

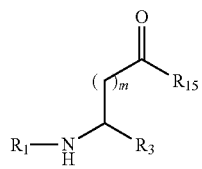

(V)

wherein:
m is 1 or 2;
$R_1$ is:

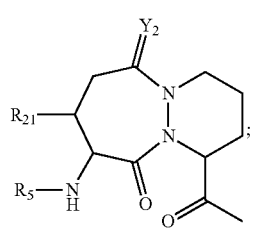

(e10-B)

$R_3$ is selected from the group consisting of:
—CN,
—C(O)—H,
—C(O)—$CH_2$-$T_1$-$R_{11}$,
—C(O)—$CH_2$—F,
—C=N—O—$R_9$, and
—CO—$Ar_2$;

each $R_5$ is independently selected from the group consisting of:
—C(O)—$R_{10}$,
—C(O)O—$R_9$,
—C(O)—$N(R_{10})(R_{10})$
—$S(O)_2$—$R_9$,
—$S(O)_2$—NH—$R_{10}$,
—C(O)—$CH_2$—O—$R_9$,
—C(O)C(O)—$R_{10}$,
—$R_9$,
—H, and
—C(O)C(O)—$N(R_9)(R_{10})$, and
—C(O)C(O)—$OR_{10}$;
$Y_2$ is $H_2$ or O;
each $T_1$ is independently selected from the group consisting of —O—, —S—, —S(O)—, and —$S(O)_2$—;
$R_8$ is selected from the group consisting of:
—C(O)—$R_{10}$,
—C(O)O—$R_9$,
—C(O)—NH—$R_{10}$,
—$S(O)_2$—$R_9$,
—$S(O)_2$—NH—$R_{10}$,
—C(O)—$CH_2$—$OR_{10}$,
—C(O)C(O)—$R_{10}$,
—C(O)—$CH_2$—$N(R_{10})(R_{10})$,
—C(O)—$CH_2$C(O)—O—$R_9$,
—C(O)—$CH_2$C(O)—$R_9$,
—H, and
—C(O)—C(O)—$OR_{10}$;

each $R_9$ is independently selected from the group consisting of —$Ar_3$ and a —$C_{1-6}$ straight or branched alkyl group optionally substituted with $Ar_3$, wherein the —$C_{1-6}$ alkyl group is optionally unsaturated;

each $R_{10}$ is independently selected from the group consisting of —H, —$Ar_3$, a $C_{3-6}$ cycloalkyl group, and a —$C_{1-6}$ straight or branched alkyl group optionally substituted with $Ar_3$, wherein the —$C_{1-6}$ alkyl group is optionally unsaturated;

each $R_{11}$ is independently selected from the group consisting of:
—$Ar_4$,
—$(CH_2)_{1-3}$—$Ar_4$,
—H, and
—C(O)—$Ar_4$;

$R_{15}$ is selected from the group consisting of —OH, —$OAr_3$, —N(H)—OH, and —$OC_{1-6}$, wherein $C_{1-6}$ is a straight or branched alkyl group optionally substituted with $Ar_3$, —$CONH_2$, —$OR_5$, —OH, —$OR_9$, or —$CO_2H$;

$R_{21}$ is —$CH_3$;

$Ar_2$ is independently selected from the following group, in which any ring may optionally be singly or multiply substituted by -$Q_1$ or phenyl, optionally substituted by $Q_1$:

(hh)

(ii)

wherein each Y is independently selected from the group consisting of O and S;

each $Ar_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, $SO_2$, —N—, and —NH—, —N($R_5$)—, and —N($R_9$)— said heterocycle group optionally containing one or more double bonds, said heterocycle group optionally comprising one or more aromatic rings, and said cyclic group optionally being singly or multiply substituted by -$Q_1$;

each $Ar_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, $SO_2$, =N—, —NH—, —N($R_5$)—, and —N($R_9$)— said heterocycle group optionally containing one or more double bonds, said heterocycle group optionally comprising one or more aromatic rings, and said cyclic group optionally being singly or multiply substituted by -$Q_1$;

each $Q_1$ is independently selected from the group consisting of —$NH_2$, —$CO_2H$, —Cl, —F, —Br, —I, —$NO_2$, —CN, =O, —OH, -perfluoro $C_{1-3}$ alkyl, $R_5$, —$OR_5$, —$NHR_5$, $OR_9$, —N($R_9$)($R_{10}$), $R_9$, —$R_{10}$, —C(O)—$R_{10}$, and

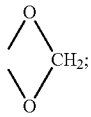

provided that when —$Ar_3$ is substituted with a $Q_1$ group which comprises one or more additional —$Ar_3$ groups, said additional —$Ar_3$ groups are not substituted with another —$Ar_3$;

Compounds of another form of embodiment (I) (form 1) are those of formula (V):

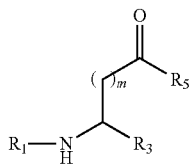

(V)

wherein:
m is 1 or 2;
$R_1$ is:

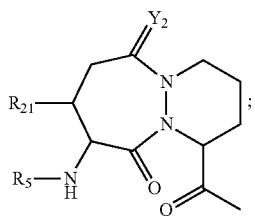

(e10-B)

$R_3$ is selected from the group consisting of:
—CN,
—C(O)—H,
—C(O)—$CH_2$-$T_1$-$R_{11}$,
—C(O)—$CH_2$—F,
—C=N—O—$R_9$, and
—CO—$Ar_2$;
each $R_5$ is —C(O)C(O)—$OR_{10}$;
$Y_2$ is $H_2$ or O;
each $T_1$ is independently selected from the group consisting of —O—, —S—, —S(O)—, and —S(O)$_2$—;
$R_8$ is selected from the group consisting of:
—C(O)—$R_{10}$,
—C(O)O—$R_9$,
—C(O)—NH—$R_{10}$,
—S(O)$_2$—$R_9$,
—S(O)$_2$—NH—$R_{10}$,
—C(O)—$CH_2$—$OR_{10}$,
—C(O)C(O)—$R_{10}$,
—C(O)—$CH_2$—N($R_{10}$)($R_{10}$),
—C(O)—$CH_2$C(O)—O—$R_9$,
—C(O)—$CH_2$C(O)—$R_9$,
—H, and
—C(O)—C(O)—$OR_{10}$;
each $R_9$ is independently selected from the group consisting of —$Ar_3$ and a —$C_{1-6}$ straight or branched alkyl group optionally substituted with $Ar_3$, wherein the —$C_{1-6}$ alkyl group is optionally unsaturated;
each $R_{10}$ is independently selected from the group consisting of —H, —$Ar_3$, a $C_{3-6}$ cycloalkyl group, and a —$C_{1-6}$ straight or branched alkyl group optionally substituted with $Ar_3$, wherein the —$C_{1-6}$ alkyl group is optionally unsaturated;
each $R_{11}$ is independently selected from the group consisting of:
—$Ar_4$,
—($CH_2$)$_{1-3}$—$Ar_4$,
—H, and
—C(O)—$Ar_4$;
$R_{15}$ is selected from the group consisting of —OH, —$OAr_3$, —N(H)—OH, and —$OC_{1-6}$, wherein $C_{1-6}$ is a straight or branched alkyl group optionally substituted with $Ar_3$, —$CONH_2$, —$OR_5$, —OH, —$OR_9$, or —$CO_2H$;
each $R_{21}$ is independently selected from the group consisting of —H or a —$C_{1-6}$ straight or branched alkyl group;
$Ar_2$ is independently selected from the following group, in which any ring may optionally be singly or multiply substituted by -$Q_1$ or phenyl, optionally substituted by $Q_1$:

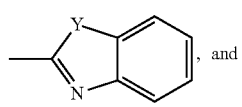
(hh)

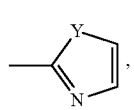
(ii)

wherein each Y is independently selected from the group consisting of O and S;
each $Ar_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by -Q$_1$;

each Ar$_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, SO$_2$, =N—, —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by -Q$_1$;

each Q$_1$ is independently selected from the group consisting of —NH$_2$, —CO$_2$H, —Cl, —F, —Br, —I, —NO$_2$, —CN, =O, —OH, -perfluoro C$_{1-3}$ alkyl, R$_5$, —OR$_5$, —NHR$_5$, OR$_9$, —N(R$_9$)(R$_{10}$), R$_9$, —C(O)—R$_{10}$, and

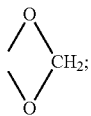

provided that when —Ar$_3$ is substituted with a Q$_1$ group which comprises one or more additional —Ar$_3$ groups, said additional —Ar$_3$ groups are not substituted with another —Ar$_3$;

Alternatively, compounds of this form of embodiment I (form 2) are those wherein R$_{21}$ is —CH$_3$.

Compounds of another form of embodiment (J) (form 1) are those of formula (V):

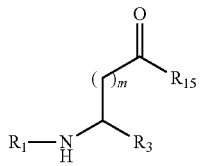

(V)

wherein:
m is 1 or 2;
R$_1$ is:

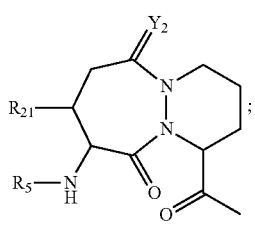

(e10-B)

R$_3$ is selected from the group consisting of:
—CN,
—C(O)—H,
—C(O)—CH$_2$-T$_1$-R$_{11}$,
—C(O)—CH$_2$—F,
—C=N—O—R$_9$, and
—CO—Ar$_2$;

each R$_5$ is independently selected from the group consisting of:
—C(O)—R$_{10}$,
—C(O)O—R$_9$,
—C(O)—N(R$_{10}$)(R$_{10}$)
—S(O)$_2$—R$_9$,
—S(O)$_2$—NH—R$_{10}$,
—C(O)—CH$_2$—O—R$_9$,
—C(O)C(O)—R$_{10}$,
—R$_9$,
—H,
—C(O)C(O)—OR$_{10}$, and
—C(O)C(O)—N(R$_9$)(R$_{10}$)

Y$_2$ is H$_2$ or O;

each T$_1$ is independently selected from the group consisting of —O—, —S—, —S(O)—, and —S(O)$_2$—;

R$_8$ is selected from the group consisting of:
—C(O)—R$_{10}$,
—C(O)O—R$_9$,
—C(O)—NH—R$_{10}$,
—S(O)$_2$—R$_9$,
—S(O)$_2$—NH—R$_{10}$,
—C(O)—CH$_2$—OR$_{10}$,
—C(O)C(O)—R$_{10}$,
—C(O)—CH$_2$—N(R$_{10}$)(R$_{10}$),
—C(O)—CH$_2$C(O)—O—R$_9$,
—C(O)—CH$_2$C(O)—R$_9$,
—H,
—C(O)—C(O)—OR$_{10}$, and
—C(O)—C(O)—N(R$_9$)(R$_{10}$);

each R$_9$ is independently selected from the group consisting of —Ar$_3$ and a —C$_{1-6}$ straight or branched alkyl group optionally substituted with Ar$_3$, wherein the —C$_{1-6}$ alkyl group is optionally unsaturated;

each R$_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally unsaturated;

each R$_{11}$ is independently selected from the group consisting of:
—Ar$_4$,
—(CH$_2$)$_{1-3}$—Ar$_4$,
—H, and
—C(O)—Ar$_4$;

R$_{15}$ is selected from the group consisting of —OH, —OAr$_3$, —N(H)—OH, and —OC$_{1-6}$, wherein C$_{1-6}$ is a straight or branched alkyl group optionally substituted with Ar$_3$, —CONH$_2$, —OR$_5$, —OH, —OR$_9$, or —CO$_2$H;

each R$_{21}$ is independently selected from the group consisting of —H or a —C$_{1-6}$ straight or branched alkyl group;

Ar$_2$ is independently selected from the following group, in which any ring may optionally be singly or multiply substituted by -Q$_1$ or phenyl, optionally substituted by Q$_1$:

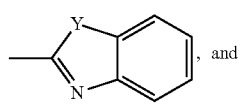

(hh)

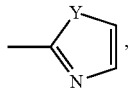

wherein each Y is independently selected from the group consisting of O and S;

each $Ar_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, $SO_2$, =N—, and —NH—, —$N(R_5)$—, and —$N(R_9)$— said heterocycle group optionally containing one or more double bonds, said heterocycle group optionally comprising one or more aromatic rings, and said cyclic group optionally being singly or multiply substituted by -$Q_1$;

each $Ar_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, $SO_2$, =N—, —NH—, —$N(R_5)$—, and —$N(R_9)$— said heterocycle group optionally containing one or more double bonds, said heterocycle group optionally comprising one or more aromatic rings, and said cyclic group optionally being singly or multiply substituted by -$Q_1$;

each $Q_1$ is independently selected from the group consisting of —$NH_2$, —$CO_2H$, —Cl, —F, —Br, —I, —$NO_2$, —CN, =O, —OH, -perfluoro $C_{1-3}$ alkyl, $R_5$, —$OR_5$, —$NHR_5$, $OR_9$, —$N(R_9)(R_{10})$, $R_9$, —C(O)—$R_{10}$, and

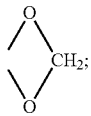

provided that when —$Ar_3$ is substituted with a $Q_1$ group which comprises one or more additional —$Ar_3$ groups, said additional —$Ar_3$ groups are not substituted with another —$Ar_3$;

provided that when:

m is 1;

$R_1$ is (e10);

$X_5$ is CH;

$R_{15}$ is —OH;

$R_{21}$ is —H; and $Y_2$ is O and $R_3$ is —C(O)—H, then $R_5$ cannot be:

—C(O)—$R_{10}$, wherein $R_{10}$ is —$Ar_3$ and the $Ar_3$ cyclic group is phenyl, unsubstituted by -$Q_1$, 4-(carboxymethoxy)phenyl, 2-fluorophenyl, 2-pyridyl, N-(4-methylpiperazino)methylphenyl, or —C(O)—$OR_9$, wherein $R_9$ is —$CH_2$—$Ar_3$, and the $Ar_3$ cyclic group is phenyl, unsubstituted by -$Q_1$; and when $Y_2$ is O, $R_3$ is —C(O)—$CH_2$-$T_1$-$R_{11}$, $T_1$ is O, and $R_{11}$ is $Ar_4$, wherein the $Ar_4$ cyclic group is 5-(1-(4-chlorophenyl)-3-trifluoromethyl)pyrazolyl), then $R_5$ cannot be:

—C(O)—$R_{10}$, wherein $R_{10}$ is —$Ar_3$ and the $Ar_3$ cyclic group is 4-(dimethylaminomethyl)phenyl, phenyl, 4-(carboxymethylthio)phenyl, 4-(carboxyethylthio)phenyl, 4-(carboxyethyl)phenyl, 4-(carboxypropyl)phenyl, 2-fluorophenyl, 2-pyridyl, N-(4-methylpiperazino)methylphenyl, or —C(O)—$OR_9$, wherein $R_9$ is —$CH_2$—$Ar_3$ and the $Ar_3$ cyclic group is phenyl;

and when $R_{11}$ is $Ar_4$, wherein the $Ar_4$ cyclic group is 5-(1-phenyl-3-trifluoromethyl)pyrazolyl), then $R_5$ cannot be:

—C(O)—$OR_9$, wherein $R_9$ is —$CH_2$—$Ar_3$, and the $Ar_3$ cyclic group is phenyl;

and when $R_{11}$ is $Ar_4$, wherein the $Ar_4$ cyclic group is 5-(1-(2-pyridyl)-3-trifluoromethyl)pyrazolyl), then $R_5$ cannot be:

—C(O)—$R_{10}$, wherein $R_{10}$ is —$Ar_3$ and the $Ar_3$ cyclic group is 4-(dimethylaminomethyl)phenyl, or —C(O)—$OR_9$, wherein $R_9$ is —$CH_2$—$Ar_3$, and the $Ar_3$ cyclic group is phenyl, unsubstituted by -$Q_{11}$; and when $Y_2$ is O, $R_3$ is —C(O)—$CH_2$-$T_1$-$R_{11}$, $T_1$ is O, and $R_{11}$ is —C(O)—$Ar_4$, wherein the $Ar_4$ cyclic group is 2,5-dichlorophenyl, then $R_5$ cannot be:

—C(O)—$R_{10}$, wherein $R_{10}$ is —$Ar_3$ and the $Ar_3$ cyclic group is 4-(dimethylaminomethyl)phenyl, 4-(N-morpholinomethyl)phenyl, 4-(N-methylpiperazino)methyl)phenyl, 4-(N-(2-methyl)imidazolylmethyl)phenyl, 5-benzimidazolyl, 5-benztriazolyl, N-carboethoxy-5-benztriazolyl, N-carboethoxy-5-benzimidazolyl, or —C(O)—$OR_9$, wherein $R_9$ is —$CH_2$—$Ar_3$, and the $Ar_3$ cyclic group is phenyl, unsubstituted by -$Q_{11}$; and when $Y_2$ is $H_2$, $R_3$ is —C(O)—$CH_2$-$T_1$-$R_{11}$, $T_1$ is O, and $R_{11}$ is —C(O)—$Ar_4$, wherein the $Ar_4$ cyclic group is 2,5-dichlorophenyl, then $R_5$ cannot be:

—C(O)—$OR_9$, wherein $R_9$ is —$CH_2$—$Ar_3$ and the $Ar_3$ cyclic group is phenyl.

Compounds of another form of embodiment J (form 2) are those wherein $R_{21}$ is —$CH_3$.

Compounds of another form of embodiment J (form 3) are those wherein $R_5$ is —C(O)—C(O)—$OR_{10}$.

Compounds of another form of embodiment J (form 4) are those wherein $R_5$ is —C(O)—C(O)—$OR_{10}$ and $R_{21}$ is —$CH_3$.

Preferred compounds of embodiments H, I, and J employ formula (V), wherein $R_3$ is —CO—$Ar_2$.

More preferably, when $R_3$ is —CO—$Ar_2$Y is O.

Preferred compounds of embodiments H, I, and J employ formula (V), wherein $R_3$ is —C(O)—$CH_2$-$T_1$-$R_{11}$ and $R_{11}$ is —$(CH_2)_{1-3}$—$Ar_4$.

More preferably, when $R_3$ is —C(O)—$CH_2$-$T_1$-$R_{11}$ and $R_{11}$ is —$(CH_2)_{1-3}$—$Ar_4$, $T_1$ is O.

Preferred compounds of embodiments H, I, and J employ formula (V), wherein $R_3$ is —C(O)—$CH_2$-$T_1$-$R_{11}$, $T_1$ is O, and $R_{11}$ is —C(O)—$Ar_4$.

Preferred compounds of embodiments H, I, and J employ formula (V), wherein $R_3$ is —C(O)—H.

Preferred compounds of embodiments H, I, and J employ formula (V), wherein $R_3$ is —CO—$CH_2$-$T_1$-$R_{11}$ and $R_{11}$ is —$Ar_4$.

More preferably, when $R_3$ is —CO—$CH_2$-$T_1$-$R_{11}$ and $R_{11}$ is —$Ar_4$, $T_1$ is O or S.

More preferred compounds of embodiments H and J (forms 1 and 2) are those wherein $R_5$ is selected from the group consisting of:

—C(O)—$R_{10}$,

—C(O)O—$R_9$, and

—C(O)—NH—$R_{10}$.

Alternatively, more preferred compounds of embodiments H and J (forms 1 and 2) are those wherein $R_5$ is selected from the group consisting of:

—$S(O)_2$—$R_9$,

—$S(O)_2$—NH—$R_{10}$,

—C(O)—C(O)—$R_{10}$,

—$R_9$,
—$C(O)$—$C(O)$—$OR_{10}$, and
—$C(O)$—$C(O)$—$N(R_9)(R_{10})$.

Most preferably, $R_5$ is —$C(O)$—$C(O)$—$R_{10}$.

Alternatively, $R_5$ is —$C(O)$—$C(O)$—$OR_{10}$.

More preferred compounds of embodiments H, I (form 2), and J (forms 2 and 4) are those wherein:

m is 1;

$Y_2$ is O;

$R_{15}$ is —OH or —$OC_{1-4}$ straight or branched alkyl group optionally substituted with $Ar_3$, —OH, —$OR_9$, —$CO_2H$, wherein the $R_9$ is a $O_{1-4}$ branched or straight chain alkyl group; wherein $Ar_3$ is morpholinyl or phenyl, wherein the phenyl is optionally substituted with $Q_1$;

$Ar_2$ is (hh);

Y is O, and each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, and indolyl, and said cyclic group optionally being singly or multiply substituted by -$Q_1$;

each $Ar_4$ cyclic group is independently selected from the group consisting of phenyl, tetrazolyl, pyridyl, oxazolyl, naphthyl, pyrimidinyl, and thienyl, and said cyclic group optionally being singly or multiply substituted by -$Q_1$;

each $Q_1$ is independently selected from the group consisting of —$NH_2$, —Cl, —F, —Br, —OH, —$R_9$, —NH—$R_5$ wherein $R_5$ is —$C(O)$—$R_{10}$ or —$S(O)_2$—$R_9$, —$OR_5$ wherein $R_5$ is —$C(O)$—$R_{10}$, —$OR_9$, —$N(R_9)(R_{10})$, and

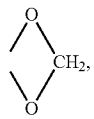

wherein each $R_9$ and $R_{10}$ are independently a —$C_{1-6}$ straight or branched alkyl group optionally substituted with $Ar_3$ wherein the $Ar_3$ cyclic group is phenyl, and said cyclic group optionally being singly or multiply substituted by -$Q_1$;

provided that when —$Ar_3$ is substituted with a $Q_1$ group which comprises one or more additional —$Ar_3$ groups, said additional —$Ar_3$ groups are not substituted with another —$Ar_3$.

More preferred compounds of embodiments I (form 1), and J (form 3) are those wherein:

m is 1;

$R_{21}$ is —H or —$CH_3$;

$R_{51}$ is a $C_{1-6}$ straight or branched alkyl group optionally substituted with $Ar_3$, wherein the $Ar_3$ cyclic group is phenyl, said cyclic group optionally being multiply or singly substituted by -$Q_1$;

each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl, benzofuranyl, or indolyl, and said cyclic group optionally being singly or multiply substituted by -$Q_1$;

each $Q_1$ is independently selected from the group consisting of —$NH_2$, —Cl, —F, —Br, —OH, —$R_9$, —NH—$R_5$ wherein $R_5$ is —$C(O)$—$R_{10}$ or —$S(O)_2$—$R_9$, —$OR_5$ wherein $R_5$ is —$C(O)$—$R_{10}$, —$OR_9$, —$N(R_9)(R_{10})$, and

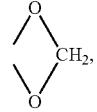

wherein each $R_9$ and $R_{10}$ are independently a —$C_{1-6}$ straight or branched alkyl group optionally substituted with $Ar_3$, wherein the $Ar_3$ cyclic group is phenyl, and said cyclic group optionally being singly or multiply substituted by -$Q_1$;

provided that when —$Ar_3$ is substituted with a -$Q_1$ group which comprises one or more additional —$Ar_3$ groups, said additional —$Ar_3$ groups are not substituted with another —$Ar_3$.

Preferably, in these more preferred compounds the $Ar_3$ cyclic group is selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, benzofuranyl, and indolyl, and said cyclic group optionally being singly or multiply substituted by -$Q_1$.

Preferred compounds of embodiments H, and J (forms 1 and 1) are those wherein:

$R_3$ is —$C(O)$—$CH_2$-$T_1$-$R_{11}$;

$T_1$ is O; and $R_{11}$ is —$C(O)$—$Ar_4$, wherein the $Ar_4$ cyclic group is selected from the set consisting of tetrazolyl, pyridyl, oxazolyl, pyrimidinyl, and thienyl, and said cyclic group optionally being singly or multiply substituted by -$Q_1$.

Preferred compounds of embodiments H, I, and J employ formula (V), wherein $R_3$ is —$CO$—$CH_2$-$T_1$-$R_{11}$, $R_{11}$ is —$Ar_4$, wherein the $Ar_4$ cyclic group is pyridyl, and said cyclic group optionally being singly or multiply substituted by -$Q_1$.

Preferred compounds of embodiment J (form 1) are those wherein:

$R_3$ is —$C(O)$—H, and $R_5$ is —$C(O)$—$R_{10}$, wherein:

$R_{10}$ is $Ar_3$, wherein the $Ar_3$ cyclic group is phenyl optionally being singly or multiply substituted by:

—F,

—Cl,

—$N(H)$—$R_5$, wherein —$R_5$ is —H or —$C(O)$—$R_{10}$, wherein $R_{10}$ is a —$C_{1-6}$ straight or branched alkyl group optionally substituted with $Ar_3$, wherein $Ar_3$ is phenyl, —$N(R_9)(R_{10})$, wherein $R_9$ and $R_{10}$ are independently a —$C_{1-4}$ straight or branched alkyl group, or —O—$R_5$, wherein $R_5$ is H or a —$C_{1-4}$ straight or branched alkyl group.

More preferably, $Ar_3$ is phenyl being optionally singly or multiply substituted at the 3- or 5-position by —Cl or at the 4-position by —NH—$R_5$, —$N(R_9)(R_{10})$, or —O—$R_5$.

Other more preferred compounds of embodiment J (form 1) are those wherein:

$R_3$ is —$C(O)$—H;

$R_5$ is —$C(O)$—$R_{10}$, wherein $R_{10}$ is $Ar_3$ and the $Ar_3$ cyclic group is selected from the group consisting of is indolyl, benzimidazolyl, thienyl, and benzo[b]thiophenyl, and said cyclic group optionally being singly or multiply substituted by -$Q_1$;

Other more preferred compounds of embodiment J (form 1) are those wherein:

$R_3$ is —C(O)—H;
$R_5$ is —C(O)—$R_{10}$, wherein $R_{10}$ is $Ar_3$ and the $Ar_3$ cyclic group is selected from quinolyl and isoquinolyl, and said cyclic group optionally being singly or multiply substituted by -$Q_1$.

Other more preferred compounds of embodiment J (form 1) are those wherein:

$R_3$ is —C(O)—H;
$R_5$ is —C(O)—$R_{10}$, wherein $R_{10}$ is $Ar_3$ and the $Ar_3$ cyclic group is phenyl, substituted by

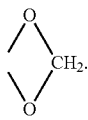

Preferred compounds of embodiment (J) include, but are not limited to:

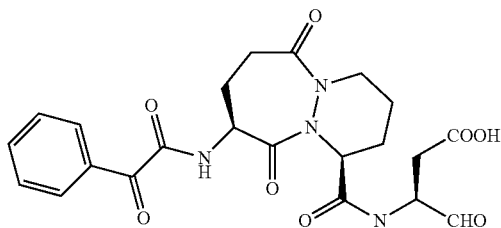
2002

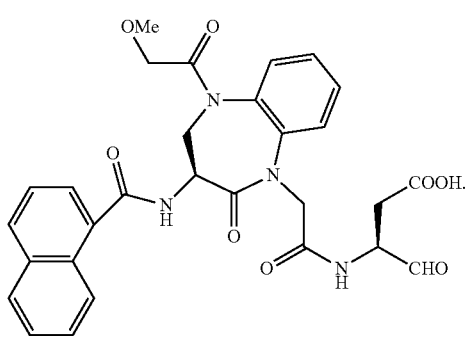
2201

The ICE inhibitors of another embodiment (K) of this invention are those of formula:

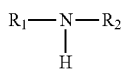
(VI)

wherein:
$R_1$ is:

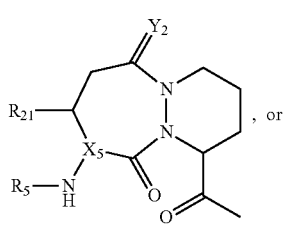
(e10)

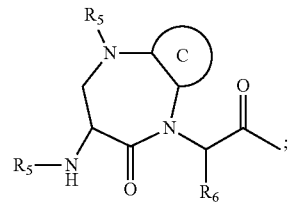
(w2)

C is a ring chosen from the set consisting of benzo, pyrido, thieno, pyrrolo, furano, thiazolo, isothiazolo, oxazolo, isoxazolo, pyrimido, imidazolo, cyclopentyl, and cyclohexyl; the ring optionally being singly or multiply substituted by -$Q_1$;

$R_2$ is:

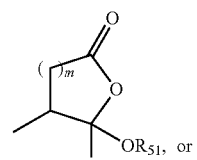
(a)

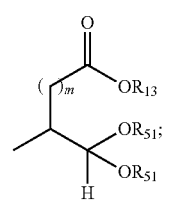
(b)

m is 1 or 2;
each $R_5$ is independently selected from the group consisting of:
—C(O)—$R_{10}$,
—C(O)O—$R_9$,
—C(O)—N($R_{10}$)($R_{10}$),
—S(O)$_2$—$R_9$,
—S(O)$_2$—NH—$R_{10}$,
—C(O)—CH$_2$—O$R_9$,
—C(O)C(O)—$R_{10}$,
—$R_9$,
—H,
—C(O)C(O)—O$R_{10}$, and
—C(O)C(O)—N($R_9$)($R_{10}$);
$X_5$ is CH or N;
$Y_2$ is H$_2$ or O;
$R_6$ is selected from the group consisting of —H and —CH$_3$;
$R_8$ is selected from the group consisting of:
—C(O)—$R_{10}$,
—C(O)O—$R_9$,
—C(O)—N(H)—$R_{10}$,
—S(O)$_2$—$R_9$,
—S(O)$_2$—NH—$R_{10}$,
—C(O)—CH$_2$—O$R_{10}$,
—C(O)C(O)—$R_{10}$;
—C(O)—CH$_2$N($R_{10}$)($R_{10}$),
—C(O)—CH$_2$C(O)—O—$R_9$,
—C(O)—CH$_2$C(O)—$R_9$,
—H, and
—C(O)—C(O)—O$R_{10}$;

each $R_9$ is independently selected from the group consisting of —$Ar_3$ and a —$C_{1-6}$ straight or branched alkyl group optionally substituted with $Ar_3$, wherein the —$C_{1-6}$ alkyl group is optionally unsaturated;

each $R_{10}$ is independently selected from the group consisting of —H, —$Ar_3$, a —$C_{3-6}$ cycloalkyl group, and a —$C_{1-6}$ straight or branched alkyl group optionally substituted with $Ar_3$, wherein the —$C_{1-6}$ alkyl group is optionally unsaturated;

$R_{13}$ is selected from the group consisting of H, $Ar_3$, and a —$C_{1-6}$ straight or branched alkyl group optionally substituted with $Ar_3$, —$CONH_2$, —$OR_5$, —OH, —$OR_9$, or —$CO_2H$;

each $R_{51}$ is independently selected from the group consisting of $R_9$, —C(O)—$R_9$, —C(O)—N(H)—$R_9$, or each $R_{51}$ taken together forms a saturated 4-8 member carbocyclic ring or heterocyclic ring containing —O—, —S—, or —NH—;

each $R_{21}$ is independently selected from the group consisting of —H or a —$C_{1-6}$ straight or branched alkyl group;

each $Ar_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, $SO_2$, =N—, and —NH—, said heterocycle group optionally containing one or more double bonds, said heterocycle group optionally comprising one or more aromatic rings, and said cyclic group optionally being singly or multiply substituted by -$Q_1$;

each $Q_1$ is independently selected from the group consisting of —$NH_2$, —$CO_2H$, —Cl, —F, —Br, —I, —$NO_2$, —CN, =O, —OH, -perfluoro $C_{1-3}$ alkyl, $R_5$, —$OR_5$, —$NHR_5$, —$OR_9$, —$N(R_9)(R_{10})$, —$R_9$, —C(O)—$R_{10}$, and

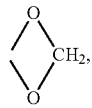

provided that when —$Ar_3$ is substituted with a $Q_1$ group which comprises one or more additional —$Ar_3$ groups, said additional —$Ar_3$ groups are not substituted with another —$Ar_3$.

Preferred compounds of this embodiment are those wherein:

m is 1;

C is a ring chosen from the set consisting of benzo, pyrido, or thieno the ring optionally being singly or multiply substituted by halogen, —$NH_2$, —NH—$R_5$, —NH—$R_9$, —$OR_{10}$, or —$R_9$, wherein $R_9$ is a straight or branched $C_{1-4}$ alkyl group and $R_{10}$ is H or a straight or branched $C_{1-4}$ alkyl group;

$R_6$ is H;

$R_{13}$ is H or a $C_{1-4}$ straight or branched alkyl group optionally substituted with $Ar_3$, —OH, —$OR_9$, —$CO_2H$, wherein the $R_9$ is a $C_{1-4}$ branched or straight chain alkyl group; wherein $Ar_3$ is morpholinyl or phenyl, wherein the phenyl is optionally substituted with $Q_1$;

$R_{21}$ is —H or —$CH_3$;

$R_{51}$ is a $C_{1-6}$ straight or branched alkyl group optionally substituted with $Ar_3$, wherein $Ar_3$ is phenyl, optionally substituted by -$Q_1$;

each $Ar_3$ cyclic group is independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl, and said cyclic group optionally being singly or multiply substituted by -$Q_1$;

each $Q_1$ is independently selected from the group consisting of —$NH_2$, —Cl, —F, —Br, —OH, —$R_9$, —NH—$R_5$ wherein $R_5$ is —C(O)—$R_{10}$ or —$S(O)_2$—$R_9$, —$OR_5$ wherein $R_5$ is —C(O)—$R_{10}$, —$OR_9$, —$NHR_9$, and

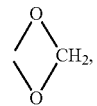

wherein each $R_8$ and $R_{10}$ are independently a —$C_{1-6}$ straight or branched alkyl group optionally substituted with $Ar_3$ wherein $Ar_3$ is phenyl;

provided that when —$Ar_3$ is substituted with a $Q_1$ group which comprises one or more additional —$Ar_3$ groups, said additional —$Ar_3$ groups are not substituted with another —$Ar_3$.

Preferably, in this preferred embodiment, $R_1$ is (w2) and the other substituents are as defined above.

Compounds of this preferred embodiment include, but are not limited to:

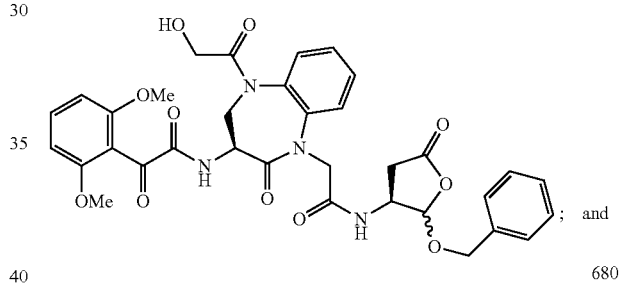

677

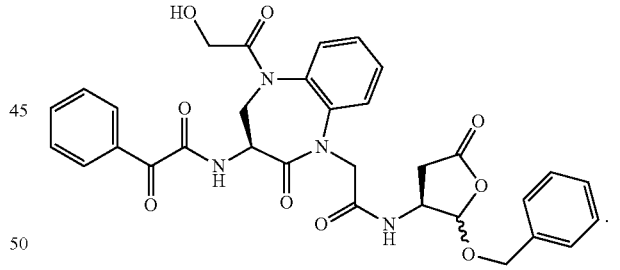

680

More preferably, $R_8$ is selected from the group consisting of:
—C(O)—$R_{10}$,
—C(O)O—$R_9$,
—C(O)—$CH_2$—$OR_{10}$, and
—C(O)—$CH_2C(O)$—$R_9$.

Most preferably, $R_8$ is —C(O)—$CH_2$—$OR_{10}$ and $R_{10}$ is —H or —$CH_3$.

Alternatively, in this preferred embodiment, $R_1$ is (e10) and $X_5$ is CH and the other substituents are as defined above.

Alternatively, in this preferred embodiment, $R_1$ is (e10) and $X_5$ is N and the other substituents are as defined above.

Preferably, in any of the above compounds of embodiment (K), $R_5$ is —C(O)—$R_{10}$ or —C(O)—C(O)—$R_{10}$ and the other substituents are as defined above.

More preferably, R$_{10}$ is —Ar$_3$ and the other substituents are as defined above.

More preferably, in these more preferred compounds:

R$_5$ is —C(O)—R$_{10}$ and R$_{10}$ is Ar$_3$, wherein the Ar$_3$ cyclic group is phenyl optionally being singly or multiply substituted by:

—R$_9$, wherein R$_9$ is a C$_{1-4}$ straight or branched alkyl group;

—F,

—Cl,

—N(H)—R$_5$, wherein —R$_5$ is —H or —C(O)—R$_{10}$, wherein R$_{10}$ is a —C$_{1-6}$ straight or branched alkyl group optionally substituted with Ar$_3$, wherein Ar$_3$ is phenyl, —N(R$_9$)(R$_{10}$), wherein R$_9$ and R$_{10}$ are independently a —C$_{1-4}$ straight or branched alkyl group, or —O—R$_5$, wherein R$_5$ is H or a —C$_{1-4}$ straight or branched alkyl group.

Preferred compounds of this more preferred embodiment include, but are not limited to:

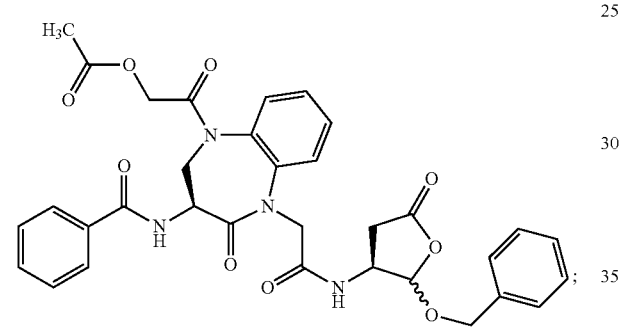

682

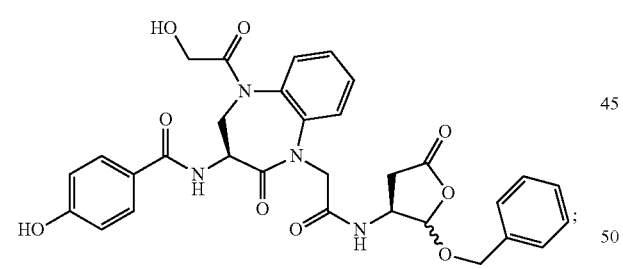

690b

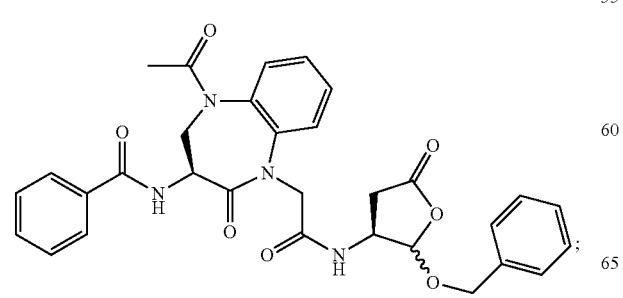

693

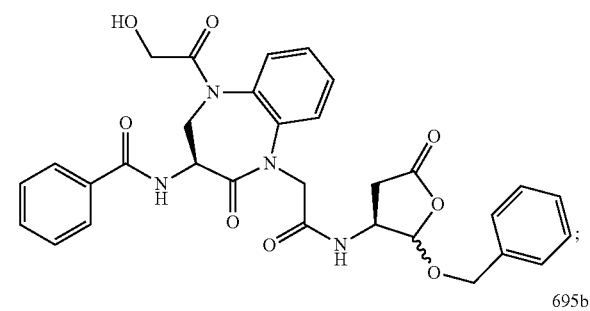

695a

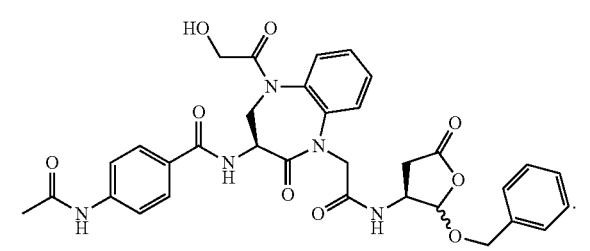

695b

Most preferably, Ar$_3$ is phenyl being singly or multiply substituted at the 3- or 5-position by —Cl or at the 4-position by —NH—R$_5$, —N(R$_9$)(R$_{10}$), or —O—R$_5$.

Preferred compounds of this most preferred embodiment include, but are not limited to:

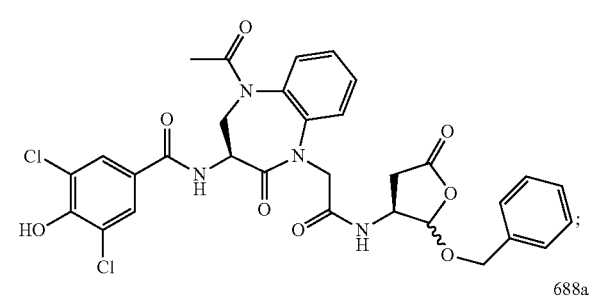

655

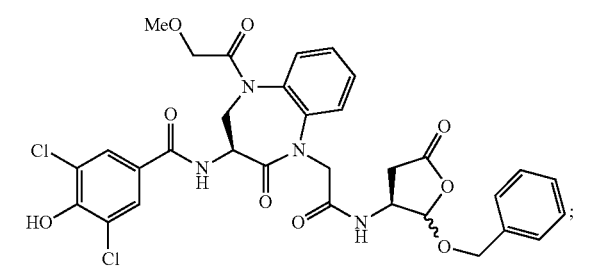

688a

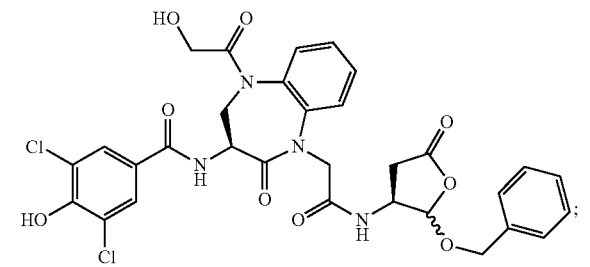

692a

-continued

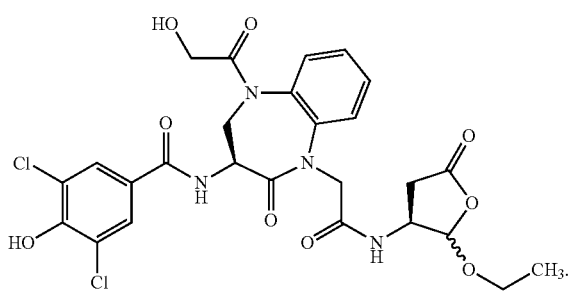
692b

Other preferred compounds of this most preferred embodiment include, but are not limited to:

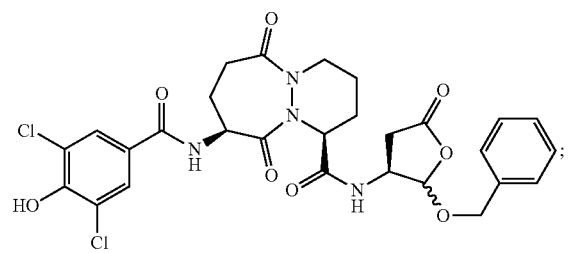
213k

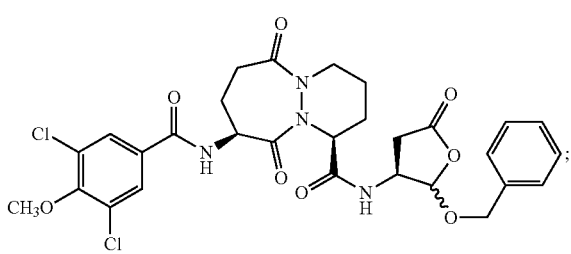
213m

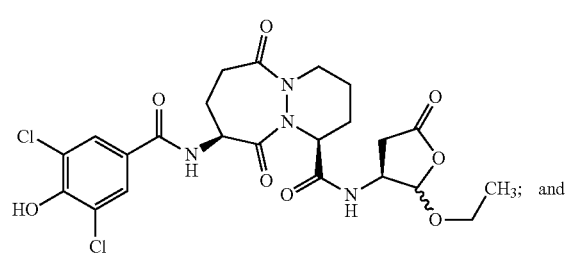
550k

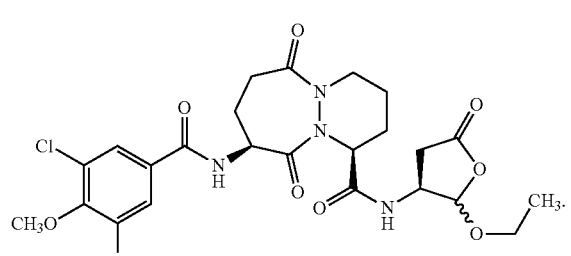
550m

Alternatively, $Ar_3$ is phenyl being singly or multiply substituted at the 3- or 5-position by —$R_9$, wherein $R_9$ is a $C_{1-4}$ straight or branched alkyl group; and at the 4-position by —O—$R_5$.

Preferred compounds of this most preferred embodiment include, but are not limited to:

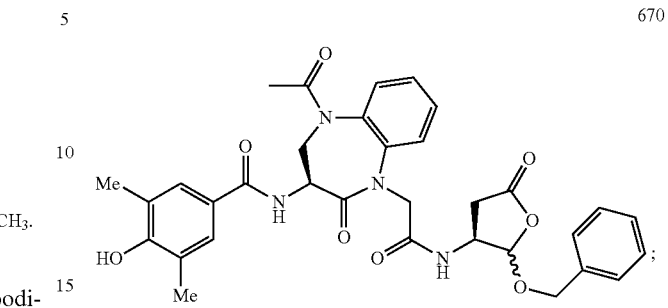
670

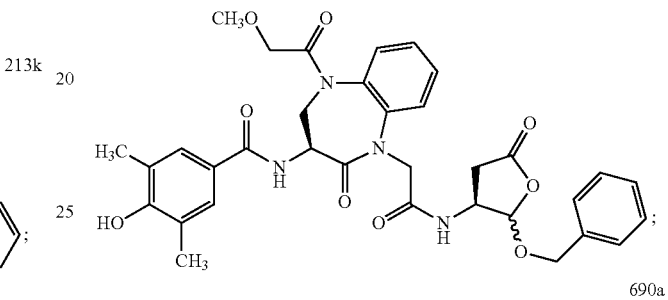
688b

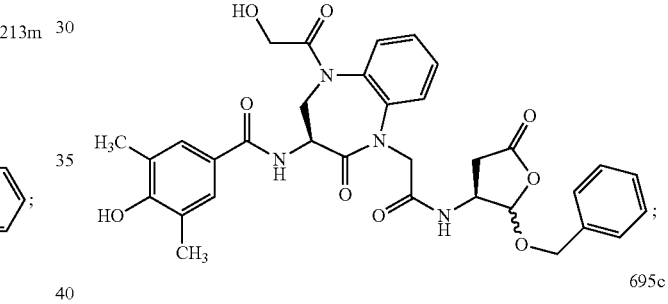
690a

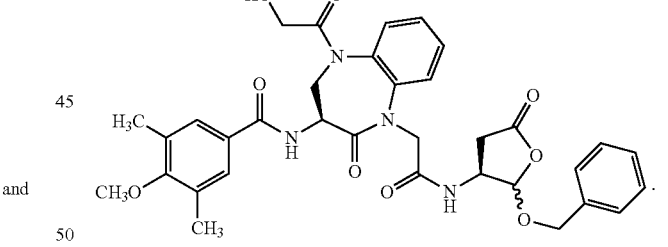
695c

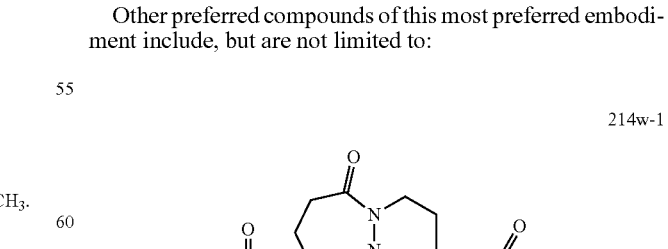

Other preferred compounds of this most preferred embodiment include, but are not limited to:

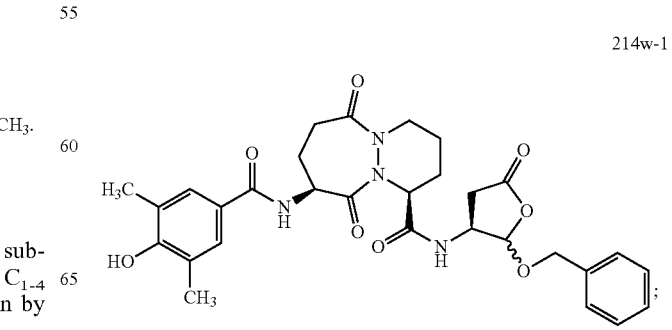
214w-1

-continued

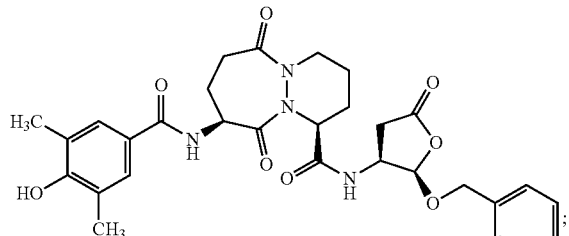
214w-2

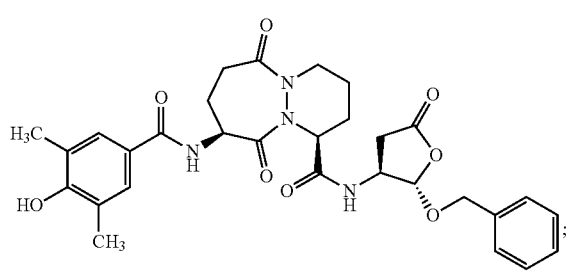
214w-3

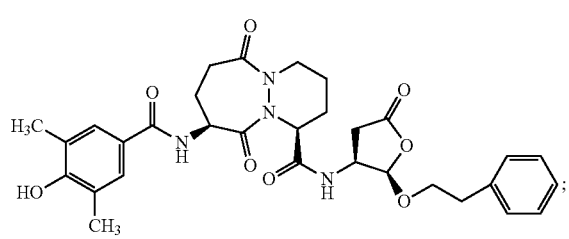
214w-4

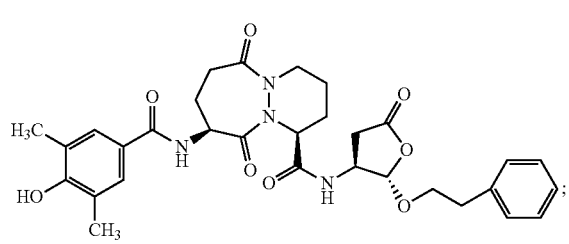
214w-5

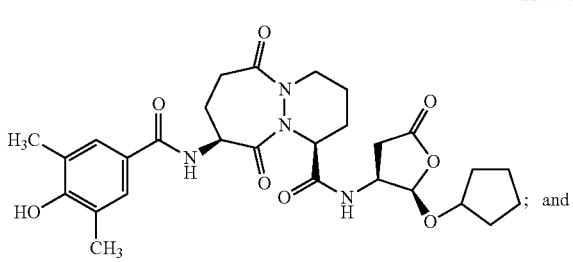
214w-6
; and

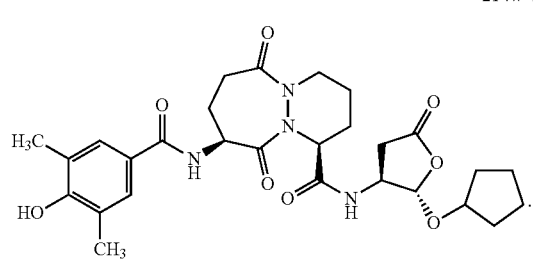
214w-7

Alternatively, in this more preferred embodiment, $R_5$ is —C(O)—$R_{10}$, wherein $R_{10}$ is $Ar_3$ and the $Ar_3$ cyclic group is selected from the group consisting of is indolyl, benzimidazolyl, thienyl, quinolyl, isoquinolyl and benzo[b]thiophenyl, and said cyclic group optionally being singly or multiply substituted by -$Q_1$.

Most preferably, the $Ar_3$ cyclic group is isoquinolyl.

Preferred compounds of this most preferred embodiment include, but are not limited to:

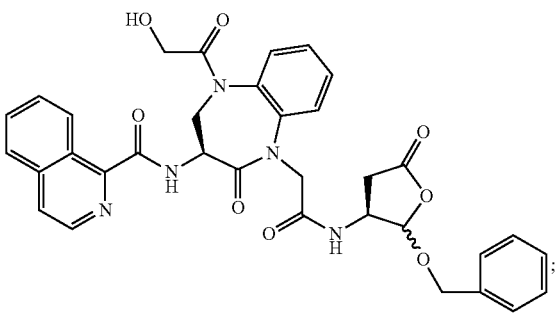
696a

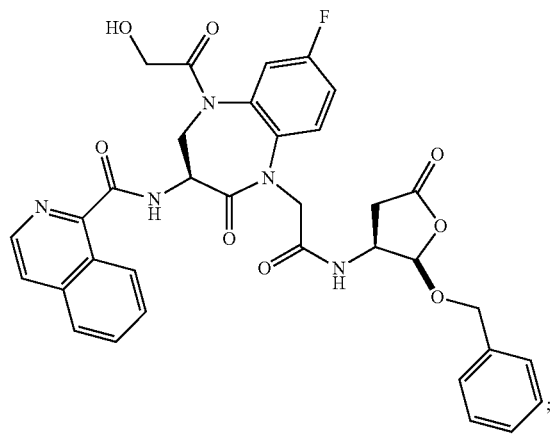
696a-1

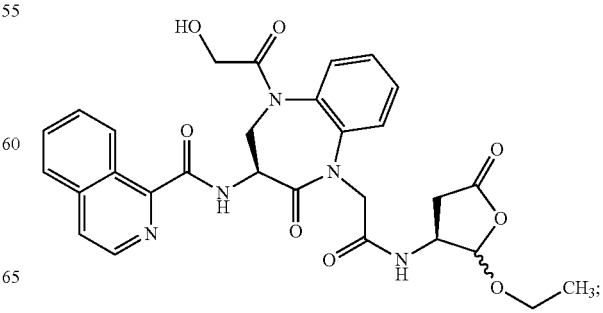
696b

145
-continued
696c
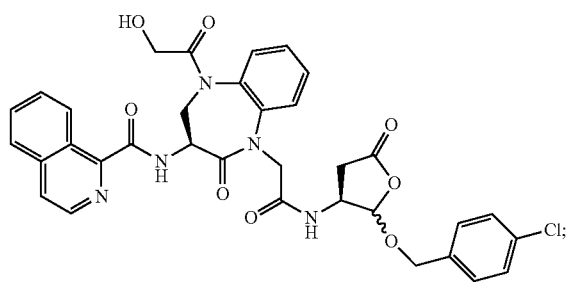
696d
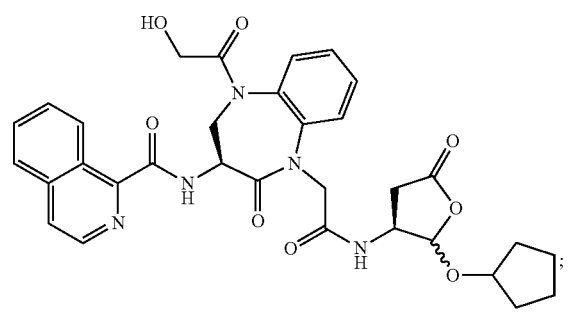
696e
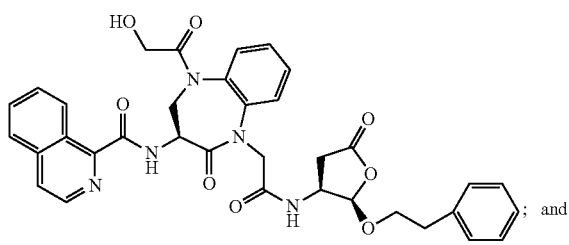
699a
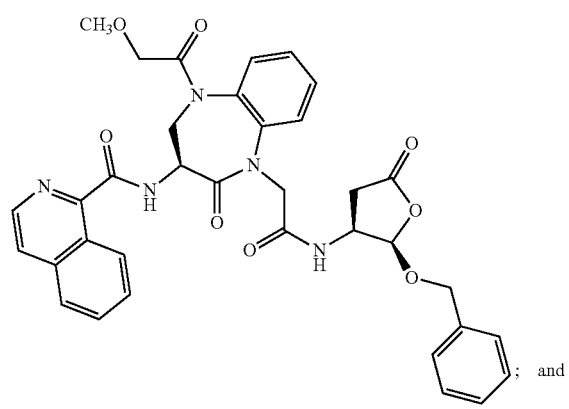
; and
146
-continued
699a-1
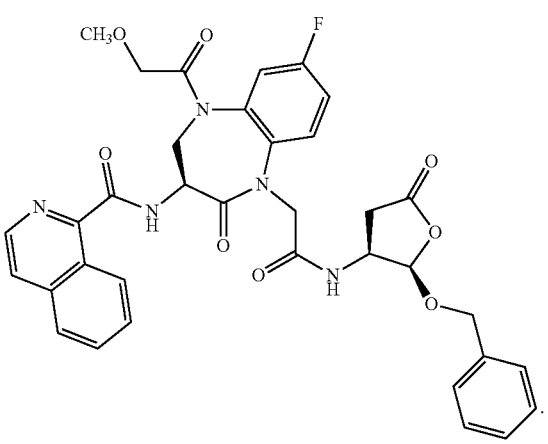
Other preferred compounds of this most preferred embodiment include, but are not limited to:
213y
412a 412b
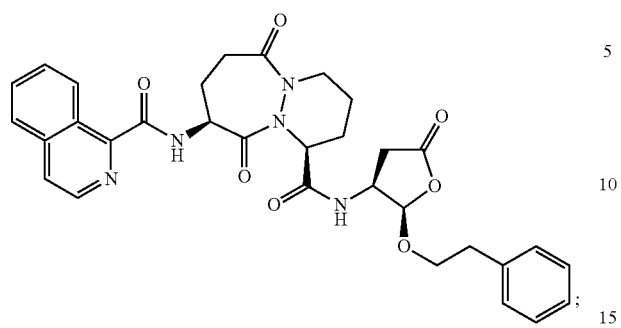
412c
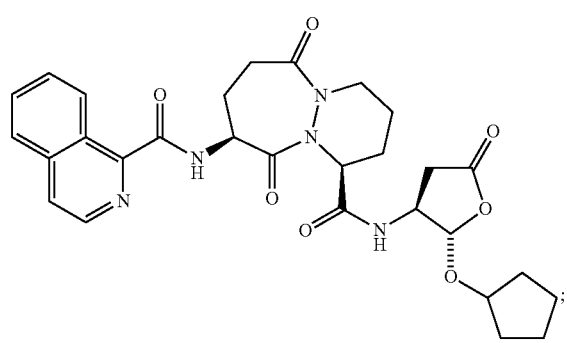
412d
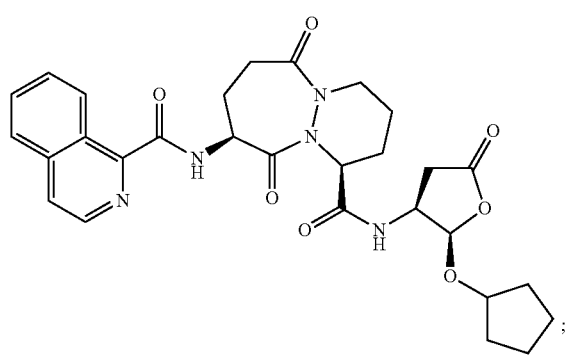
412e
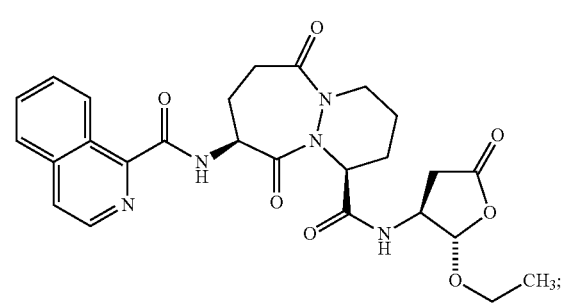
412f
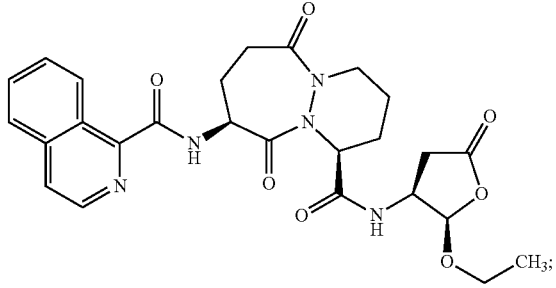
412g
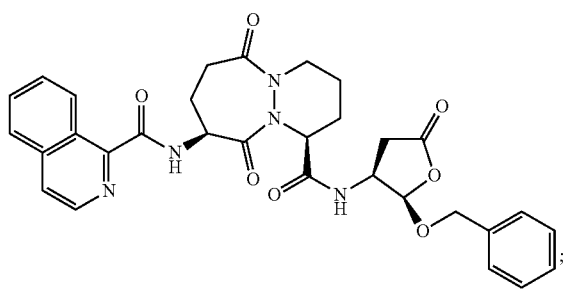
412h
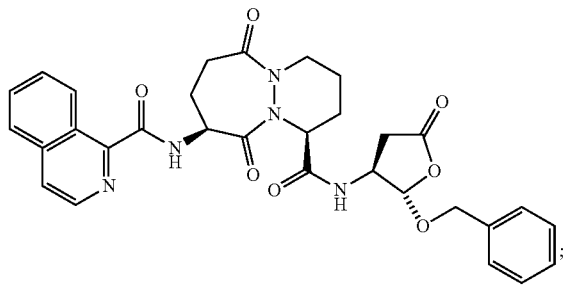
550q
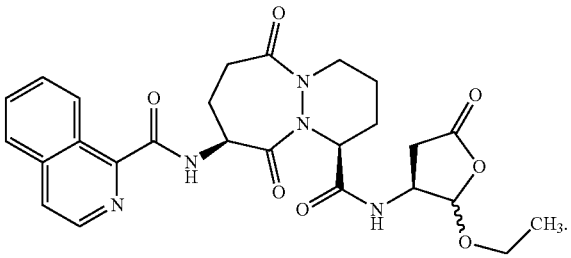
Alternatively, in this more preferred embodiment, $R_5$ is —C(O)—$R_{10}$, wherein $R_{10}$ is $Ar_3$ and the $Ar_3$ cyclic group is phenyl, substituted by
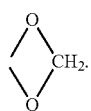

Preferred compounds of this more preferred embodiment include, but are not limited to:
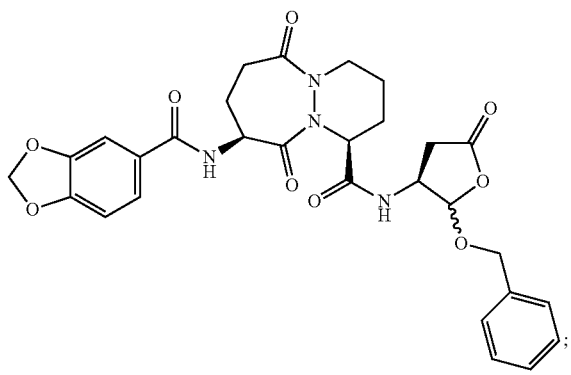
213n
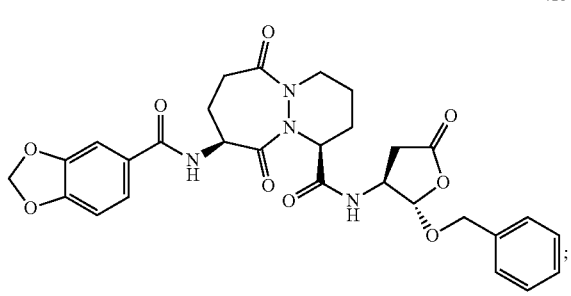
415a
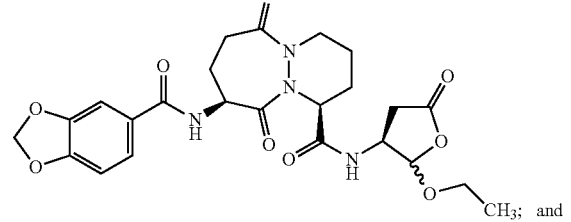
415b
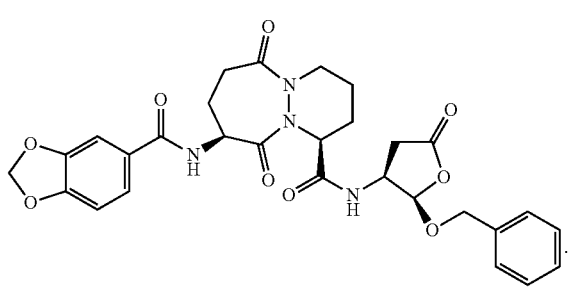
415c
Other compounds of embodiment (K) include, but are not limited to:
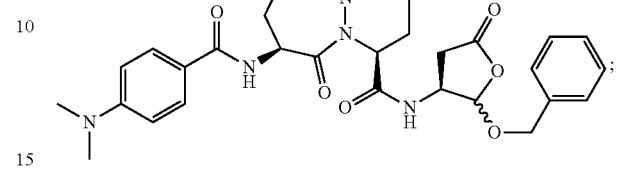
213f
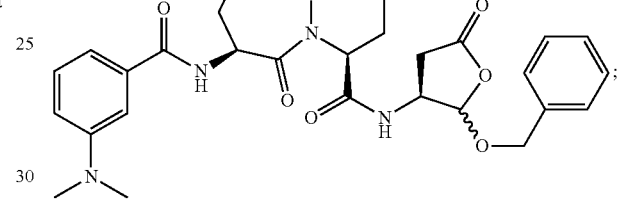
213g
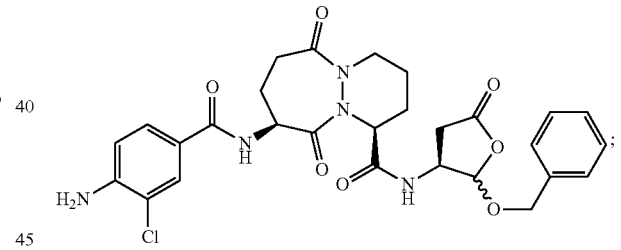
213h
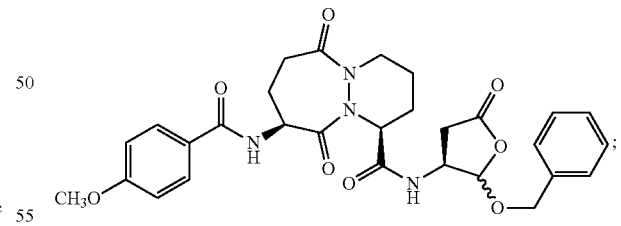
213i
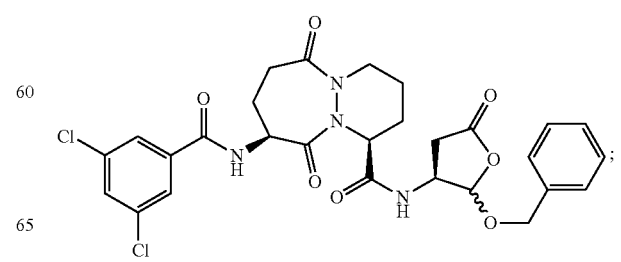
213j 151
-continued
213l
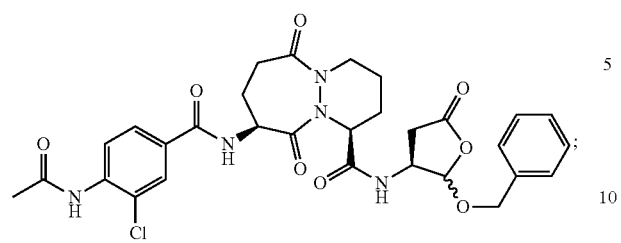
213o
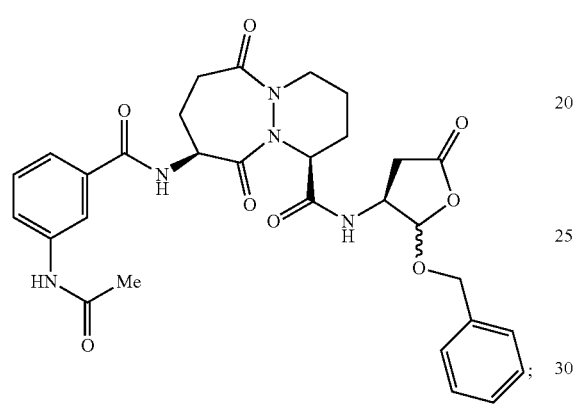
213p
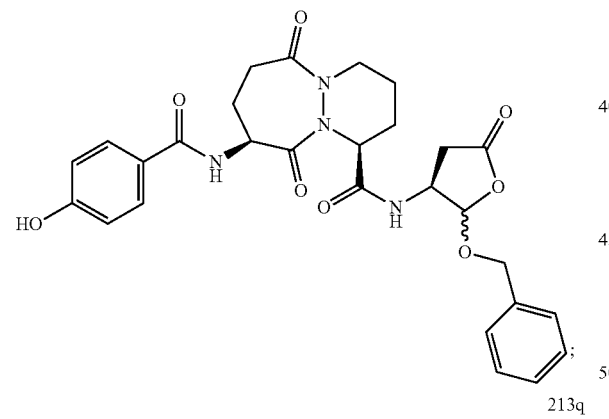
213q
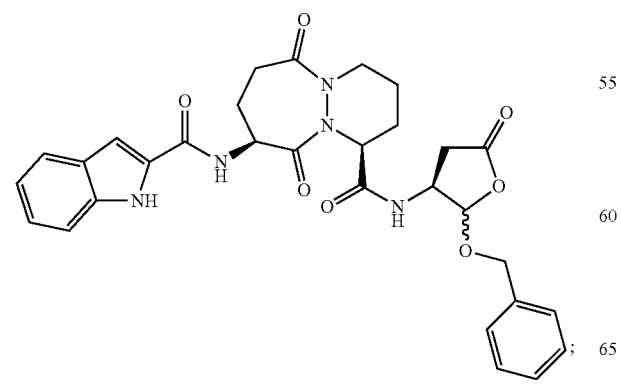
152
-continued
213r
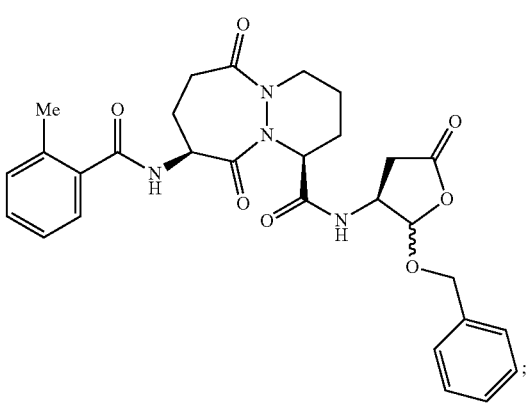
213s
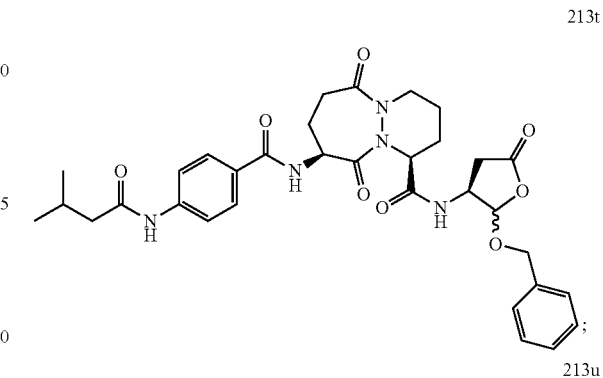
213t
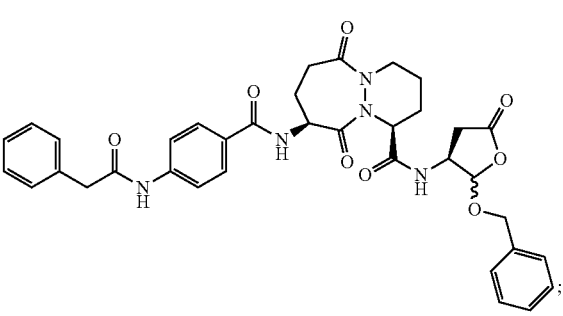
213u
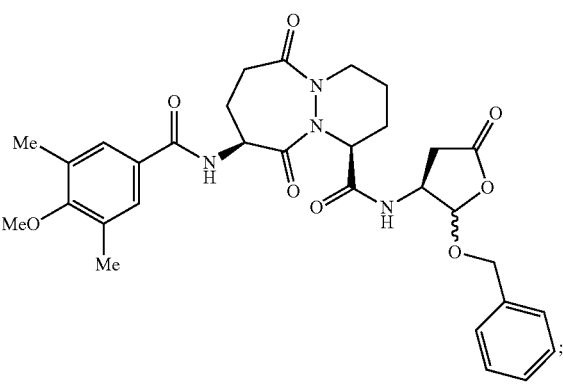

213v
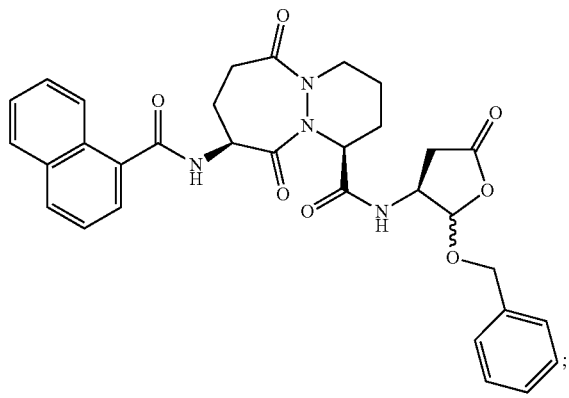
264a
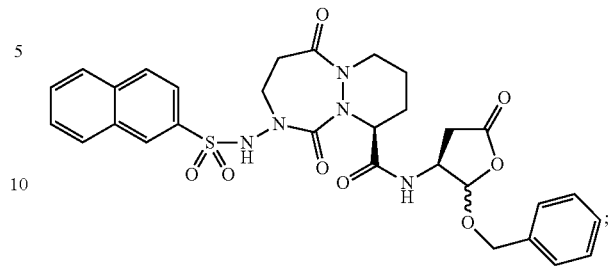
213w
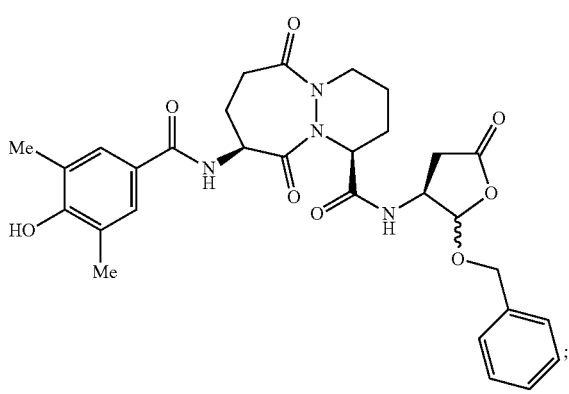
264c
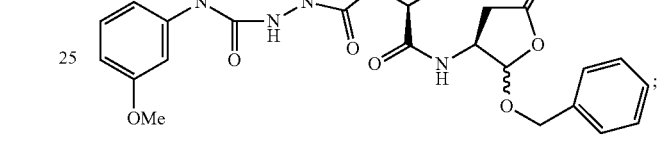
264d
213x
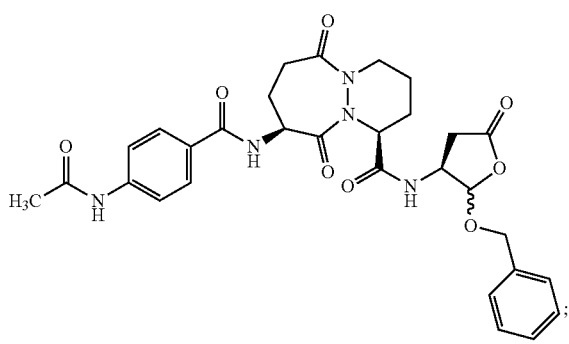
264e
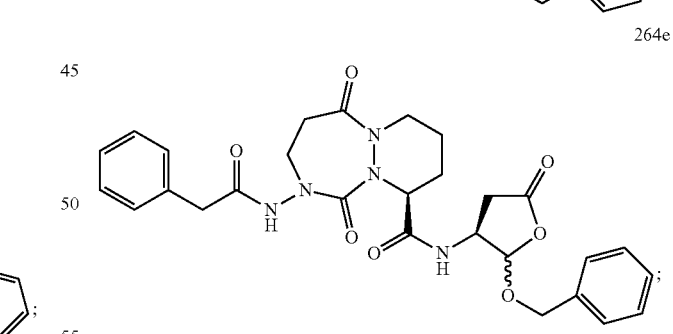
245b
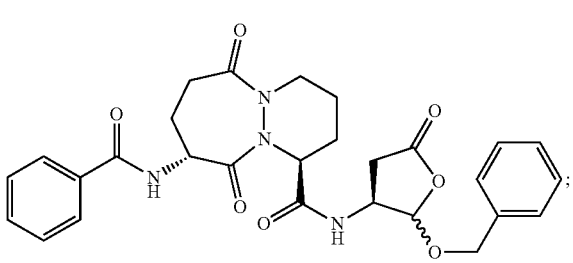
264f
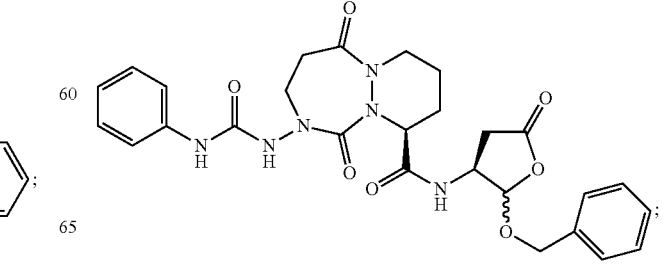

264g
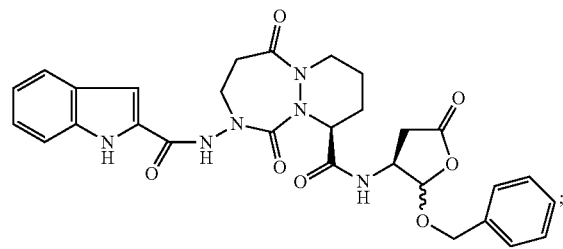
264l
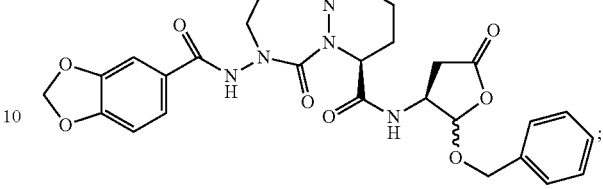
264h
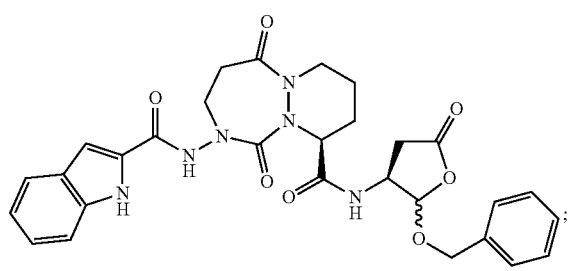
528
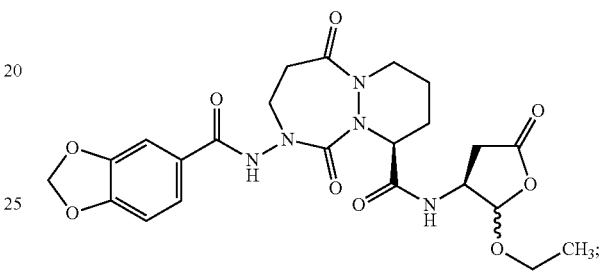
264i
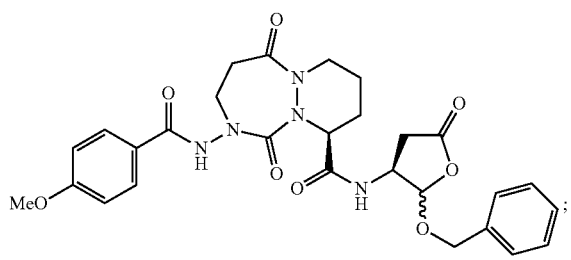
550f
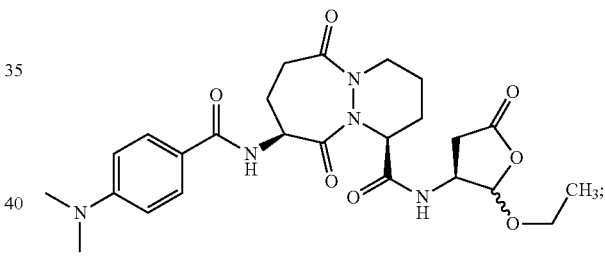
264j
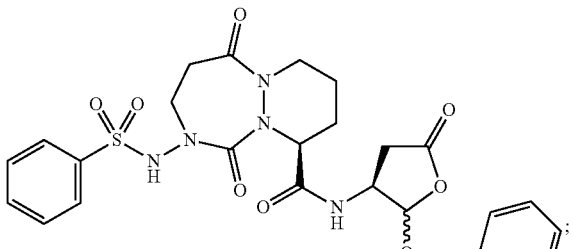
550g
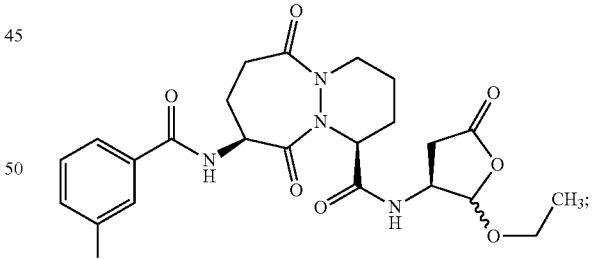
264k
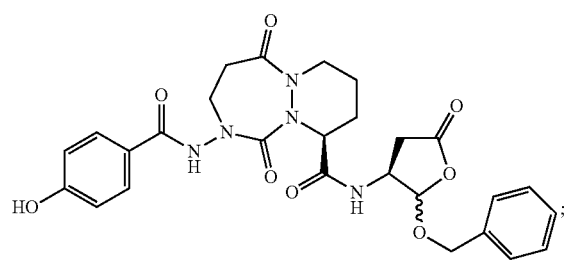
550h
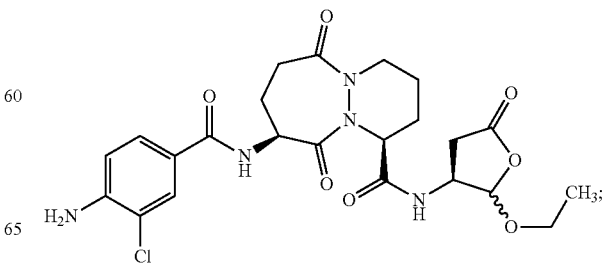

550i
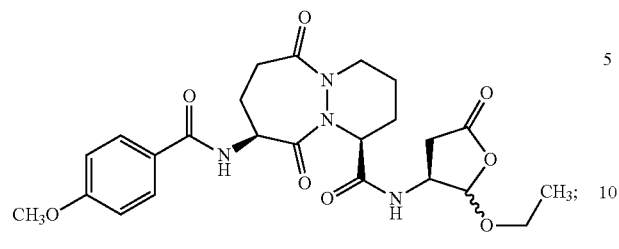
550p
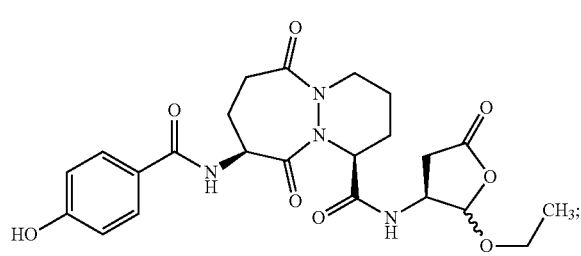
550j
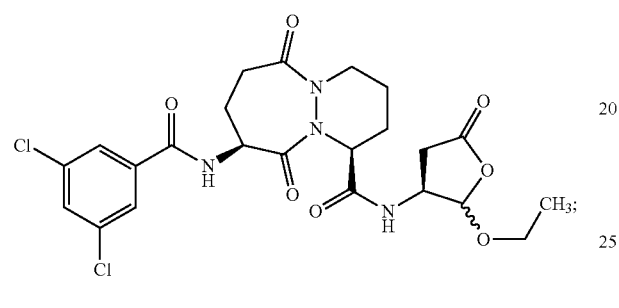
2100f
550l
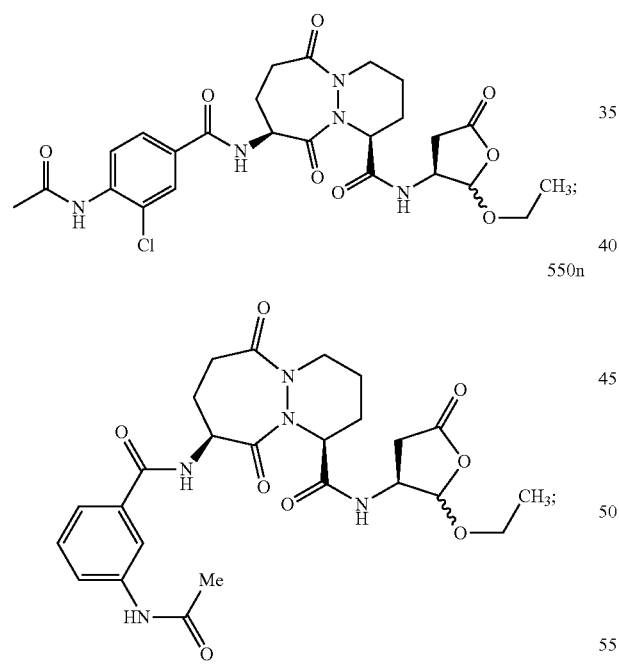
2100g
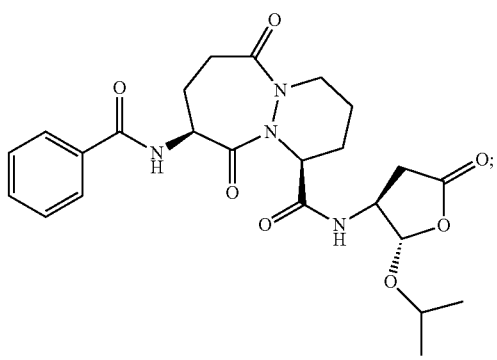
550n
2100h
550o
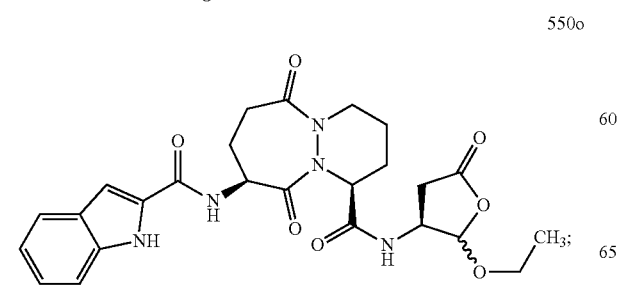
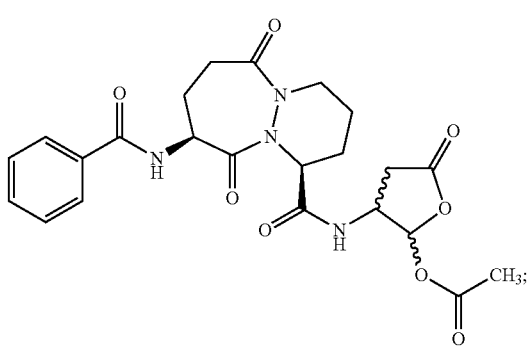

2100k

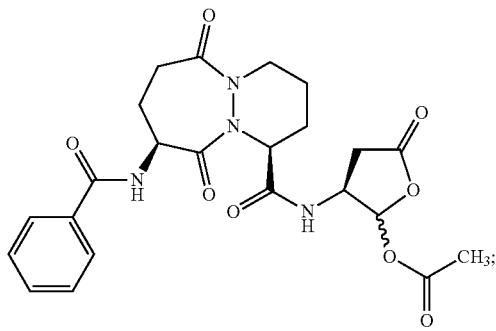

2100o

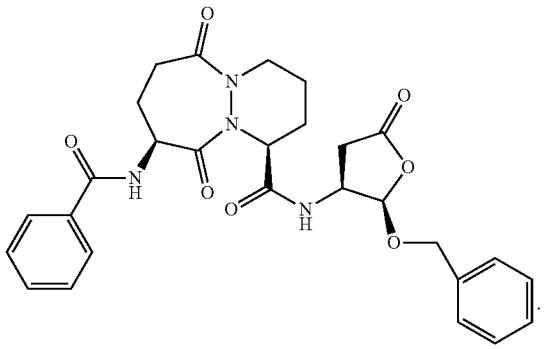

The ICE inhibitors of another embodiment (L) of this invention are those of formula:

(VII)

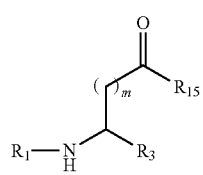

2100l

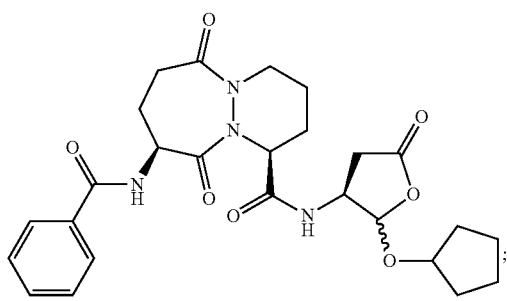

wherein:
m is 1 or 2;
$R_1$ is selected from the group consisting of the following formulae:

2100m

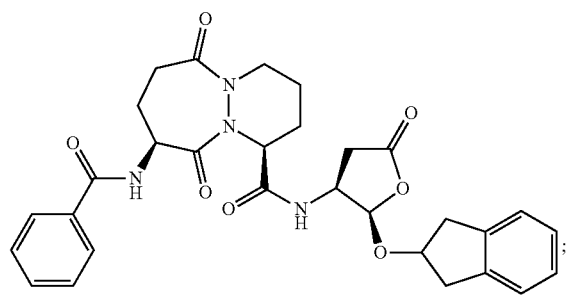

(w2)

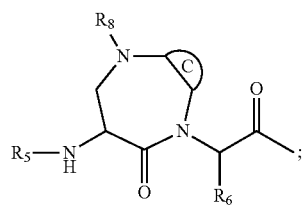

C is a ring chosen from the set consisting of benzo, pyrido, thieno, pyrrolo, furano, thiazolo, isothiazolo, oxazolo, isoxazolo, pyrimido, imidazolo, cyclopentyl, and cyclohexyl, the ring optionally being singly or multiply substituted by -$Q_1$;

$R_3$ is selected from the group consisting of:
—CN,
—C(O)—H,
—C(O)—$CH_2$-$T_1$-$R_{11}$,
—C(O)—$CH_2$—F,
—C=N—O—$R_9$, and
—CO—$Ar_2$;

each $R_5$ is independently selected from the group consisting of:
—C(O)—$R_{10}$,
—C(O)O—$R_9$,
—C(O)—N($R_{10}$)($R_{10}$)
—S(O)$_2$—$R_9$,
—S(O)$_2$—NH—$R_{10}$,
—C(O)—$CH_2$—O—$R_9$,
—C(O)C(O)—$R_{10}$,
—$R_9$, 2100n

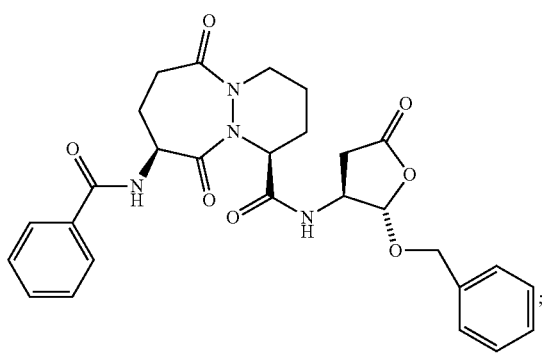

—H,
—C(O)C(O)—OR$_{10}$, and
—C(O)C(O)—N(R$_9$)(R$_{10}$);

each T$_1$ is independently selected from the group consisting of —O—, —S—, —S(O)—, and —S(O)$_2$—;

R$_6$ is selected from the group consisting of —H and —CH$_3$;

R$_8$ is selected from the group consisting of:
—C(O)—R$_{10}$,
—C(O)O—R$_9$,
—C(O)—NH—R$_{10}$,
—S(O)$_2$—R$_9$,
—S(O)$_2$—NH—R$_{10}$,
—C(O)—CH$_2$—OR$_{10}$,
—C(O)C(O)—R$_{10}$,
—C(O)—CH$_2$—N(R$_{10}$)(R$_{10}$),
—C(O)—CH$_2$C(O)—O—R$_9$,
—C(O)—CH$_2$C(O)—R$_9$,
—H, and
—C(O)—C(O)—OR$_{10}$;

each R$_9$ is independently selected from the group consisting of —Ar$_3$ and a —C$_{1-6}$ straight or branched alkyl group optionally substituted with Ar$_3$, wherein the —C$_{1-6}$ alkyl group is optionally unsaturated;

each R$_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally unsaturated;

each R$_{11}$ is independently selected from the group consisting of:
—Ar$_4$,
—(CH$_2$)$_{1-3}$—Ar$_4$,
—H, and
—C(O)—Ar$_4$;

R$_{15}$ is selected from the group consisting of —OH, —OAr$_3$, —N(H)—OH, and —OC$_{1-6}$, wherein C$_{1-6}$ is a straight or branched alkyl group optionally substituted with Ar$_3$, —CONH$_2$, —OR$_5$, —OH, —OR$_9$, or —CO$_2$H;

Ar$_2$ is independently selected from the following group, in which any ring may optionally be singly or multiply substituted by -Q$_1$ or phenyl, optionally substituted by Q$_1$:

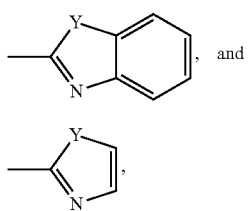

(hh)

, and (ii)

wherein each Y is independently selected from the group consisting of O and S;

each Ar$_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by -Q$_1$;

each Ar$_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, SO$_2$, =N—, —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by -Q$_1$;

each Q$_1$ is independently selected from the group consisting of —NH$_2$, —CO$_2$H, —Cl, —F, —Br, —I, —NO$_2$, —CN, =O, —OH, -perfluoro C$_{1-3}$ alkyl, R$_5$, —OR$_5$, —NHR$_5$, —OR$_9$, —N(R$_9$)(R$_{10}$), —R$_9$, —C(O)—R$_{10}$, and

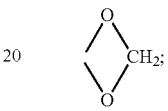

provided that when —Ar$_3$ is substituted with a Q$_1$ group which comprises one or more additional —Ar$_3$ groups, said additional —Ar$_3$ groups are not substituted with another —Ar$_3$.

Preferably, m is 1;

C is a ring chosen from the set consisting of benzo, pyrido, and thieno, the ring optionally being singly or multiply substituted by halogen, —NH$_2$, —NH—R$_5$, or —NH—R$_9$, —OR$_{10}$, or —R$_9$, wherein R$_9$ is a straight or branched —C$_{1-4}$ alkyl group, and R$_{10}$ is —H or a straight or branched —C$_{1-4}$ alkyl group;

T$_1$ is O or S;

R$_6$ is H;

R$_{11}$ is selected from the group consisting of —Ar$_4$, —(CH$_2$)$_{1-3}$—Ar$_4$, and —C(O)—Ar$_4$;

Ar$_2$ is (hh);

Y is O;

each Ar$_3$ cyclic group is independently selected from the set consisting of phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl, and said cyclic group optionally being singly or multiply substituted by -Q$_1$;

each Ar$_4$ cyclic group is independently selected from the set consisting of phenyl, tetrazolyl, naphthyl, pyridinyl, oxazolyl, pyrimidinyl, or indolyl, and said cyclic group optionally being singly or multiply substituted by -Q$_1$;

each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is —C(O)—R$_{10}$, —OR$_9$, —NHR$_9$, and

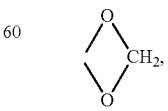

wherein each R$_9$ and R$_{10}$ are independently a —C$_{1-6}$ straight or branched alkyl group optionally substituted with —Ar$_3$ wherein Ar$_3$ is phenyl;

provided that when —Ar$_3$ is substituted with a Q$_1$ group which comprises one or more additional —Ar$_3$ groups, said additional —Ar$_3$ groups are not substituted with another —Ar$_3$.
Preferred compounds of this preferred embodiment include, but are not limited to:
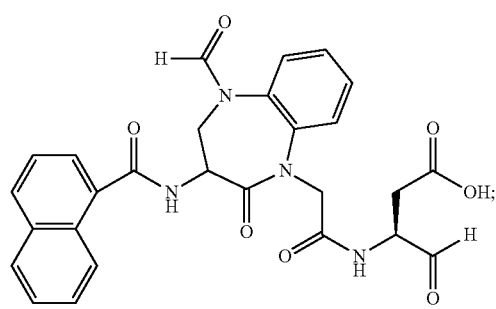
653
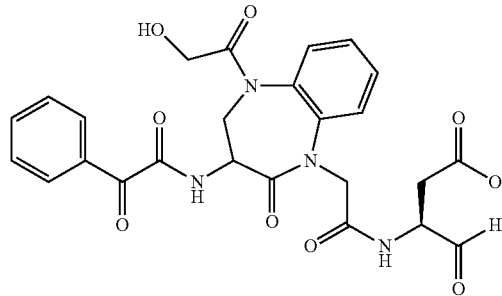
681
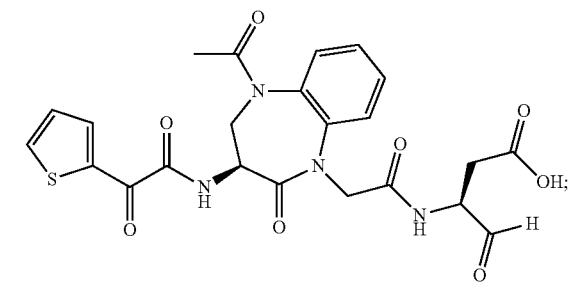
701
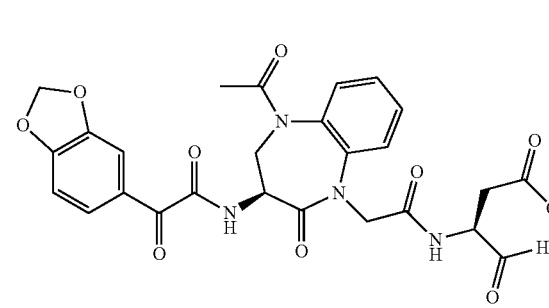
702
-continued
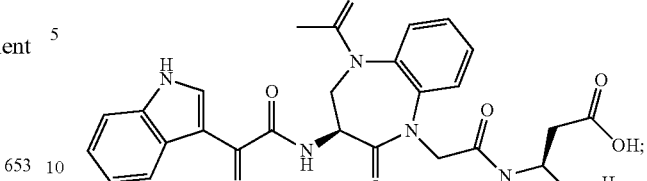
703
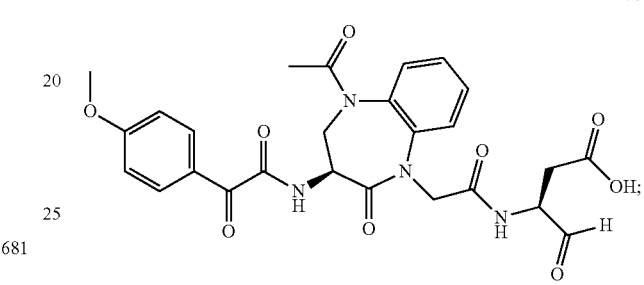
704
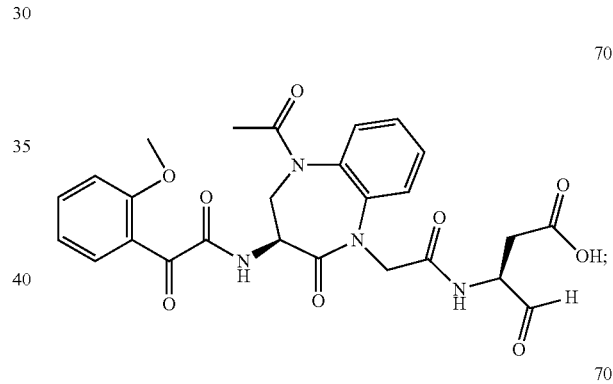
705
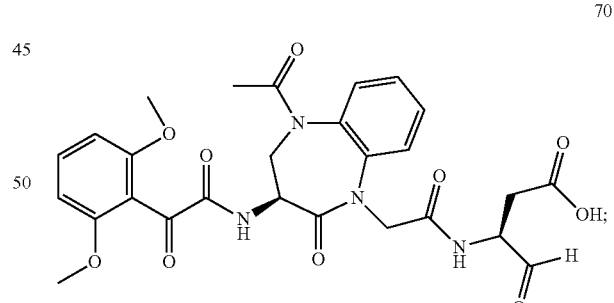
706
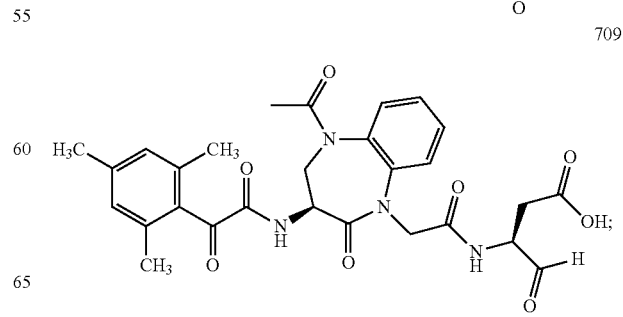
709

-continued

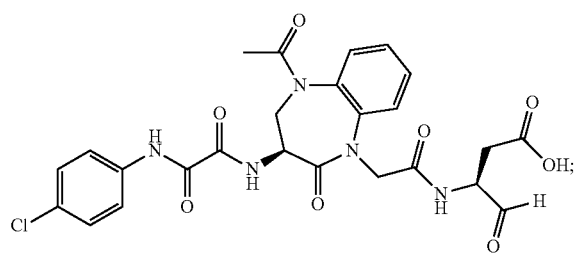

710

711

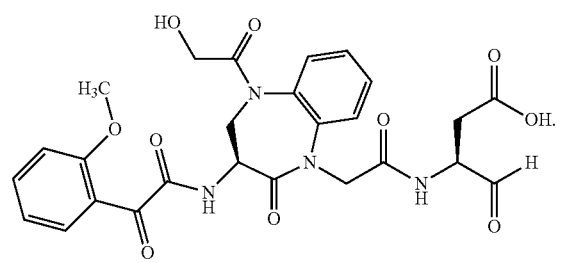

921

More preferably, $R_3$ is —C(O)—$Ar_2$ and the other substituents are as described above.

Alternatively, $R_3$ is —C(O)CH$_2$-T$_1$-R$_{11}$;

Alternatively, $R_3$ is —C(O)—H.

Preferably, in any of the above compounds of embodiment (L), $R_8$ is selected from the group consisting of:
- —C(O)—$R_{10}$,
- —C(O)O—$R_9$,
- —C(O)—CH$_2$—OR$_{10}$, and
- —C(O)—CH$_2$C(O)—$R_9$.

More preferably, $R_8$ is —C(O)—CH$_2$—OR$_{10}$ and $R_{10}$ is —H or —CH$_3$.

Alternatively, ICE inhibitors of embodiment (L) of this invention are those of formula:

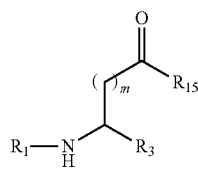

(V)

wherein:
m is 1;
$R_1$ is:

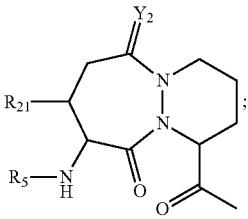

(e10-B)

$R_3$ is selected from the group consisting of:
- —CN,
- —C(O)—H,
- —C(O)—CH$_2$-T$_1$-R$_{11}$,
- —C(O)—CH$_2$—F,
- —C=N—O—R$_9$, and
- —CO—Ar$_2$;

each $R_5$ is independently selected from the group consisting of:
- —C(O)—R$_{10}$,
- —C(O)O—R$_9$,
- —C(O)—N(R$_{10}$)(R$_{10}$)
- S(O)$_2$—R$_9$,
- —S(O)$_2$—NH—R$_{10}$,
- —C(O)—CH$_2$—O—R$_9$,
- —C(O)C(O)—R$_{10}$,
- —R$_9$,
- —H,
- —C(O)C(O)—OR$_{10}$, and
- —C(O)C(O)—N(R$_9$)(R$_{10}$);

$Y_2$ is H$_2$ or O;

each $T_1$ is independently selected from the group consisting of —O— or —S—;

each $R_9$ is independently selected from the group consisting of —Ar$_3$ and a —C$_{1-6}$ straight or branched alkyl group optionally substituted with Ar$_3$, wherein the —C$_{1-6}$ alkyl group is optionally unsaturated;

each $R_{10}$ is independently selected from the group consisting of —H, —Ar$_3$, a C$_{3-6}$ cycloalkyl group, and a —C$_{1-6}$ straight or branched alkyl group optionally substituted with Ar$_3$, wherein the —C$_{1-6}$ alkyl group is optionally unsaturated;

each $R_{11}$ is independently selected from the group consisting of:
- —Ar$_4$,
- —(CH$_2$)$_{1-3}$—Ar$_4$,
- —H, and
- —C(O)—Ar$_4$;

$R_{15}$ is selected from the group consisting of —OH, —OAr$_3$, —N(H)—OH, and —OC$_{1-6}$, wherein C$_{1-6}$ is a straight or branched alkyl group optionally substituted with —Ar$_3$, —CONH$_2$, —OR$_5$, —OH, —OR$_9$, or —CO$_2$H;

$R_{21}$ is —H or —CH$_3$;

$Ar_2$ is:

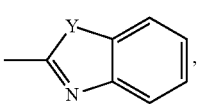

(hh)

wherein Y is O;

each $Ar_3$ is a cyclic group independently selected from the set consisting of phenyl, naphthyl, thienyl, quinolinyl, isoquinolinyl, pyrazolyl, thiazolyl, isoxazolyl, benzotriazolyl, benzimidazolyl, thienothienyl, imidazolyl, thiadiazolyl, benzo[b]thiophenyl, pyridyl benzofuranyl, and indolyl, and said cyclic group optionally being singly or multiply substituted by -$Q_1$;

each $Ar_4$ is a cyclic group independently selected from the set consisting of phenyl, tetrazolyl, pyridinyl, oxazolyl, naphthyl, pyrimidinyl, and thienyl, and said cyclic group optionally being singly or multiply substituted by -$Q_1$;

each $Q_1$ is independently selected from the group consisting of —$NH_2$, —Cl, —F, —Br, —OH, —$R_9$, —NH—$R_5$ wherein $R_5$ is —C(O)—$R_{10}$ or —S(O)$_2$—$R_9$, —O$R_5$ wherein $R_5$ is —C(O)—$R_{10}$, —O$R_9$, —NH$R_9$, and

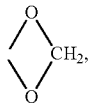

provided that when —$Ar_3$ is substituted with a $Q_1$ group which comprises one or more additional —$Ar_3$ groups, said additional —$Ar_3$ groups are not substituted with another —$Ar_3$;

provided that when:

m is 1;

$R_{15}$ is —OH;

$R_{21}$ is —H; and $Y_2$ is O and $R_3$ is —C(O)—H, then $R_5$ cannot be:

—C(O)—$R_{10}$, wherein $R_{10}$ is —$Ar_3$ and the $Ar_3$ cyclic group is phenyl, unsubstituted by -$Q_1$, 4-(carboxymethoxy) phenyl, 2-fluorophenyl, 2-pyridyl, N-(4-methylpiperazino) methylphenyl, or —C(O)—O$R_9$, wherein $R_9$ is —$CH_2$—$Ar_3$, and the $Ar_3$ cyclic group is phenyl, unsubstituted by -$Q_1$; and when $Y_2$ is O, $R_3$ is —C(O)—$CH_2$-$T_1$-$R_{11}$, $T_1$ is O, and $R_{11}$ is $Ar_4$, wherein the $Ar_4$ cyclic group is 5-(1-(4-chlorophenyl)-3-trifluoromethyl)pyrazolyl), then $R_5$ cannot be:

—H;

—C(O)—$R_{10}$, wherein $R_{10}$ is —$Ar_3$ and the $Ar_3$ cyclic group is 4-(dimethylaminomethyl)phenyl, phenyl, 4-(carboxymethylthio)phenyl, 4-(carboxyethylthio)phenyl, 4-(carboxyethyl)phenyl, 4-(carboxypropyl)phenyl, 2-fluorophenyl, 2-pyridyl, N-(4-methylpiperazino)methylphenyl, or —C(O)—O$R_9$, wherein $R_9$ is isobutyl or —$CH_2$—$Ar_3$ and the $Ar_3$ cyclic group is phenyl;

and when $R_{11}$ is $Ar_4$, wherein the $Ar_4$ cyclic group is 5-(1-phenyl-3-trifluoromethyl)pyrazolyl or 5-(1-(4-chloro-2-pyridinyl)-3-trifluoromethyl)pyrazolyl), then $R_5$ cannot be:

—C(O)—O$R_9$, wherein $R_9$ is —$CH_2$—$Ar_3$, and the $Ar_3$ cyclic group is phenyl;

and when $R_{11}$ is $Ar_4$, wherein the $Ar_4$ cyclic group is 5-(1-(2-pyridyl)-3-trifluoromethyl)pyrazolyl), then $R_5$ cannot be:

—C(O)—$R_{10}$, wherein $R_{10}$ is —$Ar_3$ and the $Ar_3$ cyclic group is 4-(dimethylaminomethyl)phenyl, or C(O)—O$R_9$, wherein $R_9$ is —$CH_2$—$Ar_3$, and the $Ar_3$ cyclic group is phenyl, unsubstituted by -$Q_1$; and when $Y_2$ is O, $R_3$ is —C(O)—$CH_2$-$T_1$-$R_{11}$, $T_1$ is O, and $R_{11}$ is —C(O)—$Ar_4$, wherein the $Ar_4$ cyclic group is 2,5-dichlorophenyl, then $R_5$ cannot be:

—C(O)—$R_{10}$, wherein $R_{10}$ is —$Ar_3$ and the $Ar_3$ cyclic group is 4-(dimethylaminomethyl)phenyl, 4-(N-morpholinomethyl)phenyl, 4-(N-methylpiperazino)methylphenyl, 4-(N-(2-methyl)imidazolylmethyl)phenyl, 5-benzimidazolyl, 5-benztriazolyl, N-carboethoxy-5-benztriazolyl, N-carboethoxy-5-benzimidazolyl, or —C(O)—O$R_9$, wherein $R_9$ is —$CH_2$—$Ar_3$, and the $Ar_3$ cyclic group is phenyl, unsubstituted by -$Q_{11}$; and when $Y_2$ is $H_2$, $R_3$ is —C(O)—$CH_2$-$T_1$-$R_{11}$, $T_1$ is O, and $R_{11}$ is —C(O)—$Ar_4$, wherein the $Ar_4$ cyclic group is 2,5-dichlorophenyl, then $R_5$ cannot be:

—C(O)—O$R_9$, wherein $R_9$ is —$CH_2$—$Ar_3$ and the $Ar_3$ cyclic group is phenyl.

Preferably, in any of the above compounds of embodiment (L), $R_3$ is —C(O)—H and $R_5$ is —C(O)—$R_{10}$ or —C(O)—C(O)—$R_{10}$ and the other substituents are as defined above.

More preferably $R_{10}$ is —$Ar_3$ and the other substituents are as defined above.

More preferably in these more preferred compounds:

$R_5$ is —C(O)—$R_{10}$ and $R_{10}$ is $Ar_3$, wherein the $Ar_3$ cyclic group is phenyl optionally being singly or multiply substituted by:

—$R_9$, wherein $R_9$ is a $C_{1-4}$ straight or branched alkyl group;

—F,

—Cl,

—N(H)—$R_5$, wherein —$R_5$ is —H or —C(O)—$R_{10}$, wherein $R_{10}$ is a —$C_{1-6}$ straight or branched alkyl group optionally substituted with $Ar_3$, wherein $Ar_3$ is phenyl, —N($R_9$)($R_{10}$), wherein $R_9$ and $R_{10}$ are independently a —$C_{1-4}$ straight or branched alkyl group, or —O—$R_5$, wherein $R_5$ is H or a —$C_{1-4}$ straight or branched alkyl group.

Preferred compounds of this preferred embodiment include, but are not limited to:

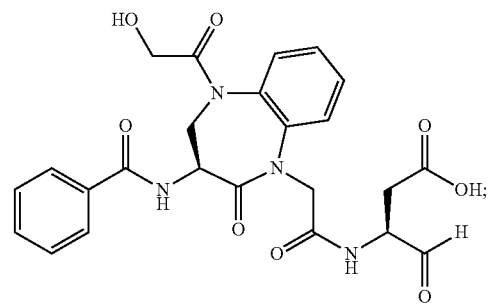

668

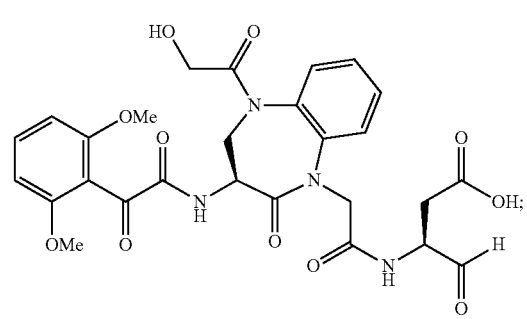

678

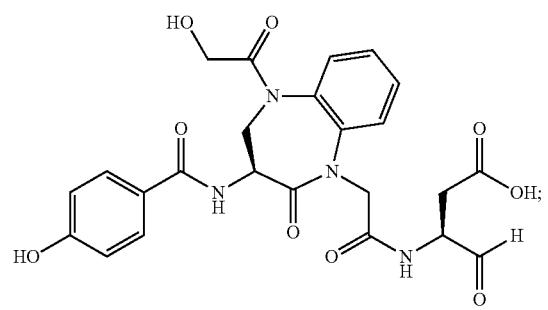
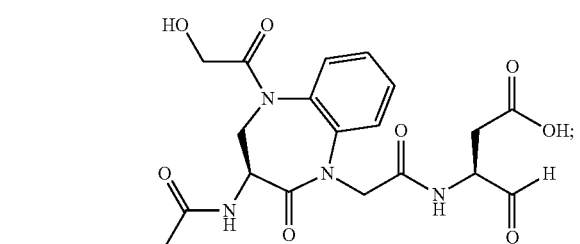
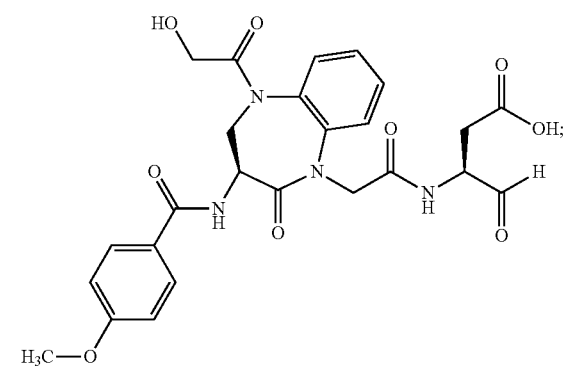
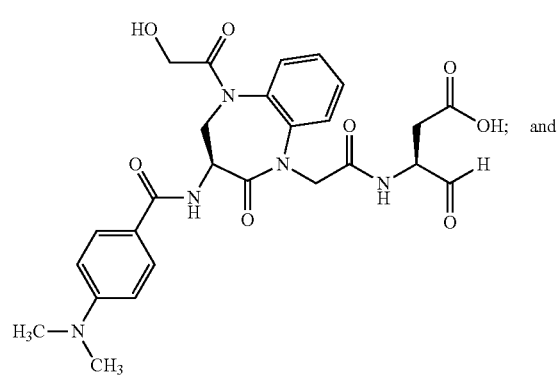
Most preferably, $Ar_3$ is phenyl being singly or multiply substituted at the 3- or 5-position by —Cl or at the 4-position by —NH—$R_5$, —N($R_9$)($R_{10}$), or —O—$R_5$.
Preferred compounds of this most preferred embodiment include, but are not limited to:

686
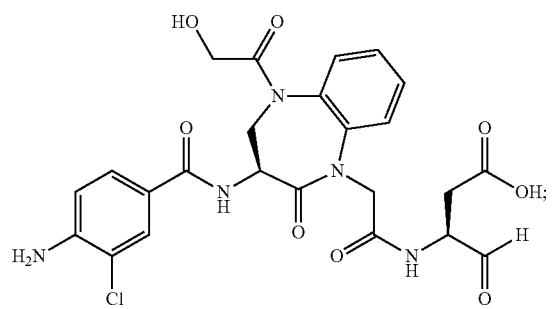
918
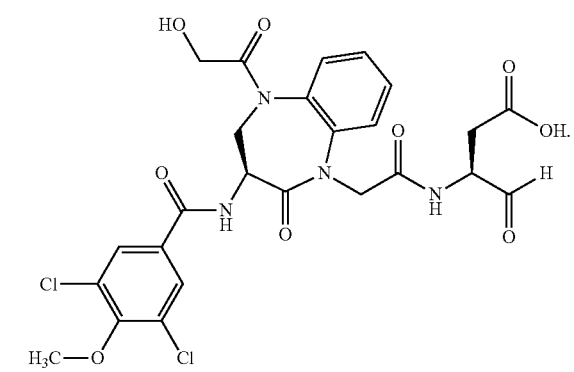
689a
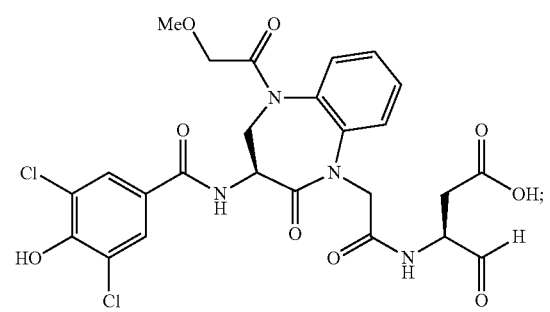
Other preferred compounds of this most preferred embodiment include, but are not limited to:
214k
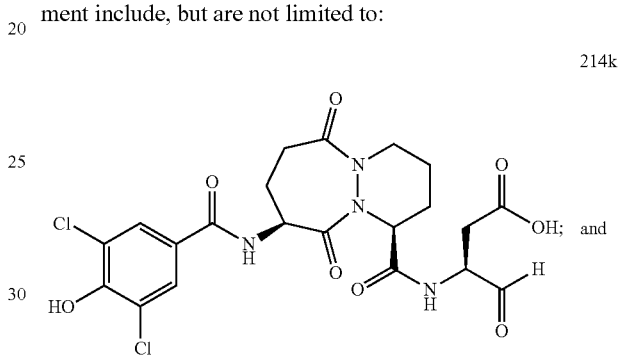
914
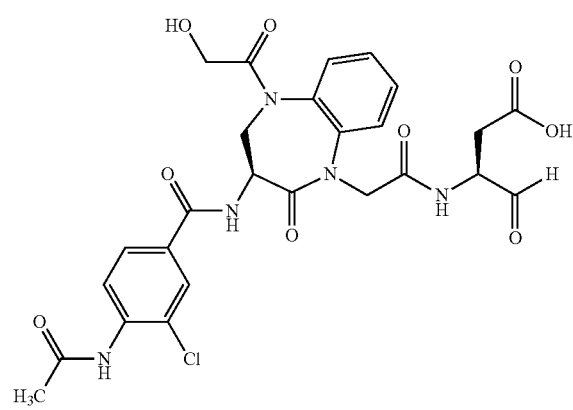
214m
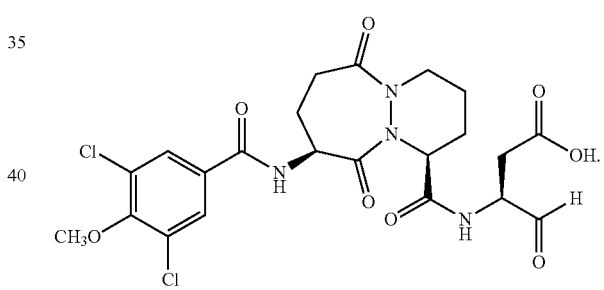
Alternatively, $Ar_3$ is phenyl being singly or multiply substituted at the 3- or 5-position by $—R_9$, wherein $R_9$ is a $C_{1-4}$ straight or branched alkyl group; and at the 4-position by $—O—R_5$.
Preferred compounds of this most preferred embodiment include, but are not limited to:
915
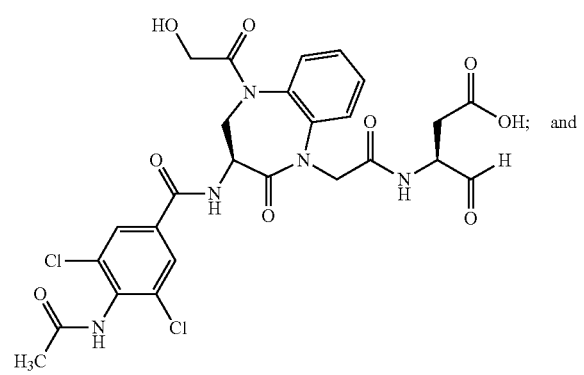
671
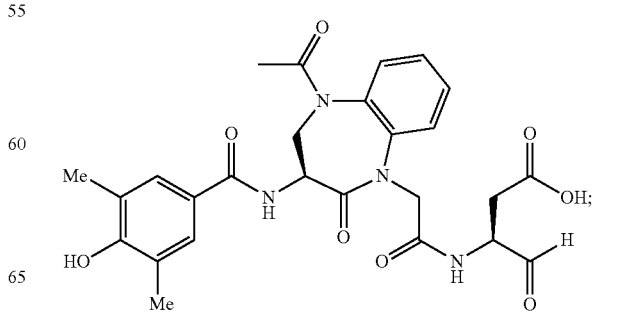

684

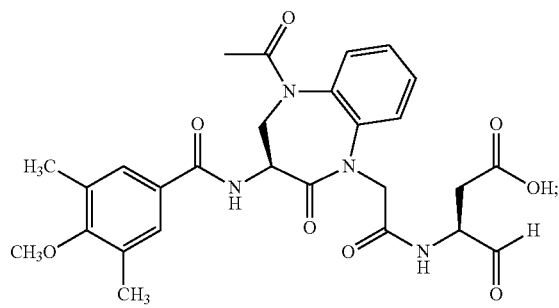

917

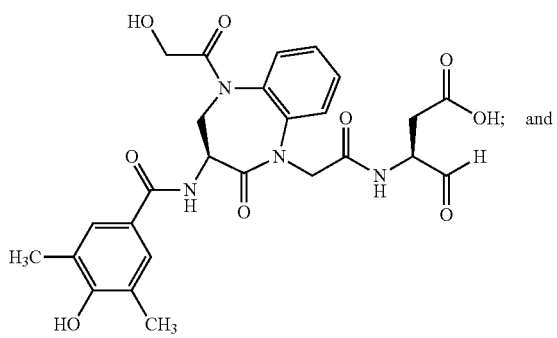

689b

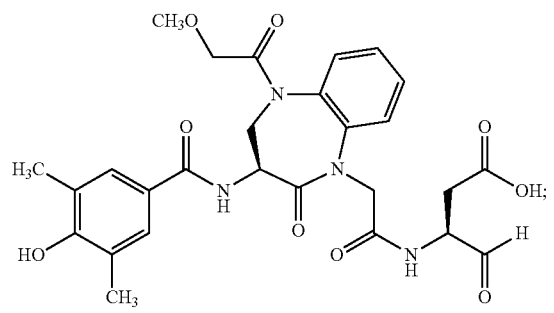

922

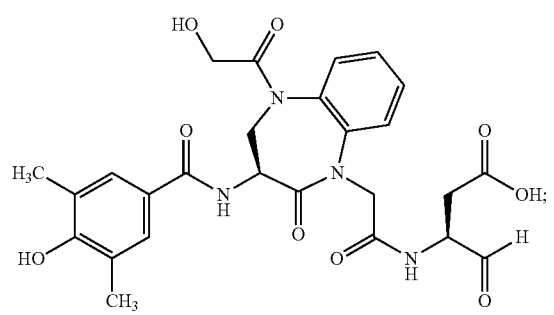

691a

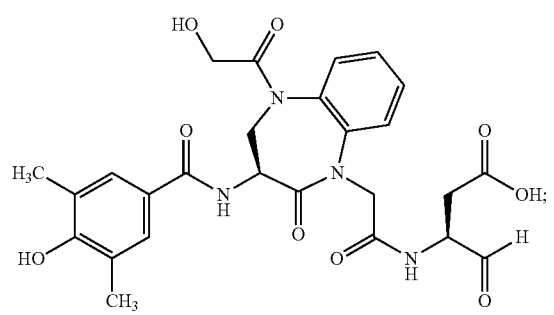

Another preferred compound of this most preferred embodiment includes, but is not limited to:

214w

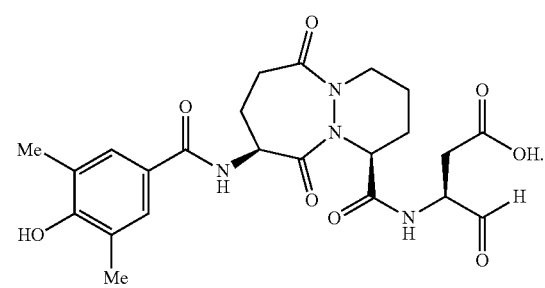

694

Alternatively, in this more preferred embodiment:

$R_5$ is —C(O)—$R_{10}$, wherein $R_{10}$ is $Ar_3$ and the $Ar_3$ cyclic group is selected from the group consisting of is indolyl, benzimidazolyl, thienyl, quinolyl, isoquinolyl and benzo[b]thiophenyl, and said cyclic group optionally being singly or multiply substituted by -$Q_1$.

Preferred compounds of this more preferred embodiment include, but are not limited to:

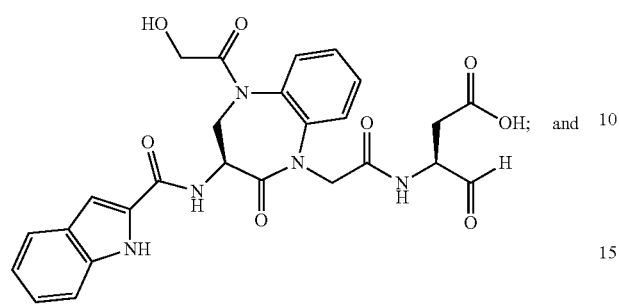

919

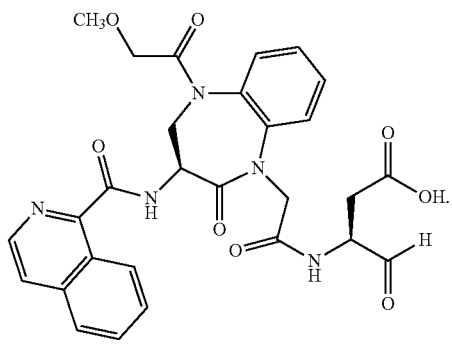

699

Another preferred compound of this most preferred embodiment includes, but is not limited to:

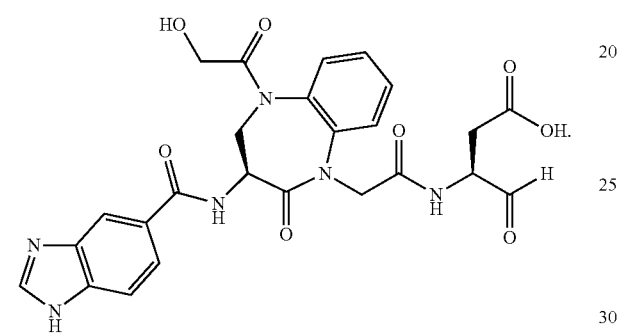

920

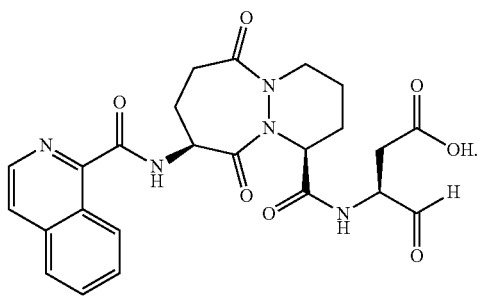

412

Most preferably, the Ar₃ cyclic group is isoquinolyl, and said cyclic group optionally being singly or multiply substituted by -Q₁.

A preferred compound of this most preferred embodiment includes, but is not limited to:

Alternatively, in this more preferred embodiment R₅ is —C(O)—R₁₀, wherein R₁₀ is —Ar₃ and the Ar₃ cyclic group is phenyl, substituted by

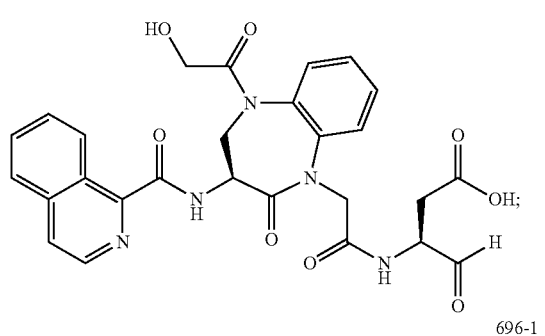

696

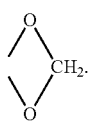

A preferred compound of this more preferred embodiment includes, but is not limited to:

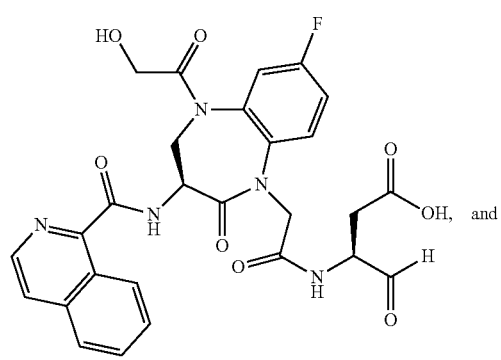

696-1

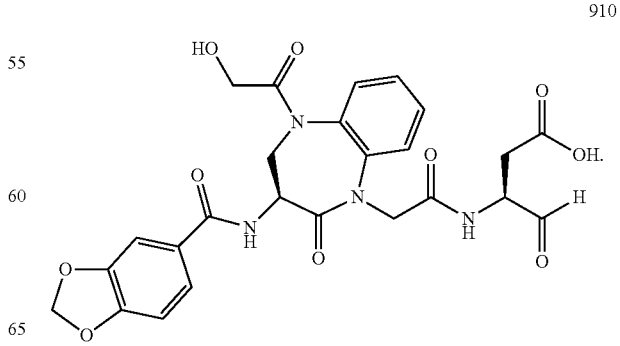

910

A preferred compound of this more preferred embodiment includes, but is not limited to:
415
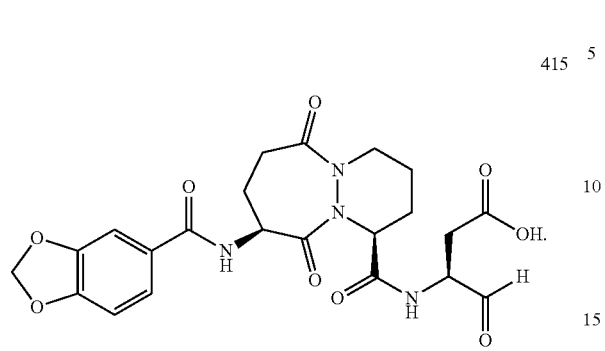
Other compounds of embodiment (L) include, but are not limited to:
214f
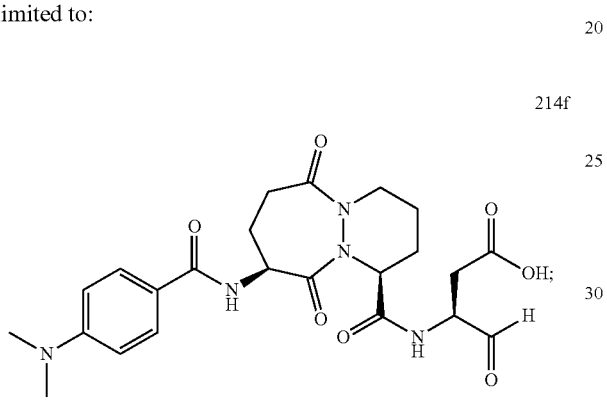
214g
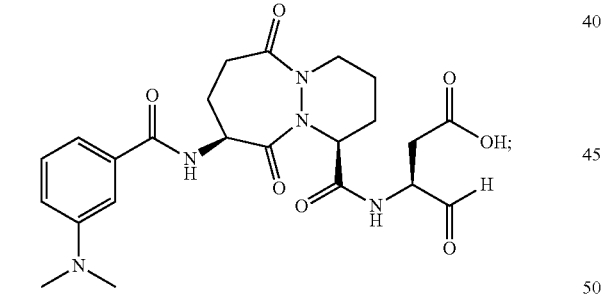
214h
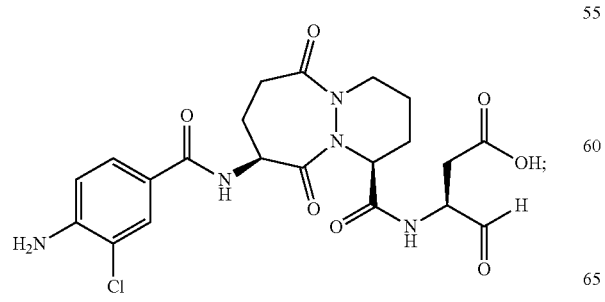
214i
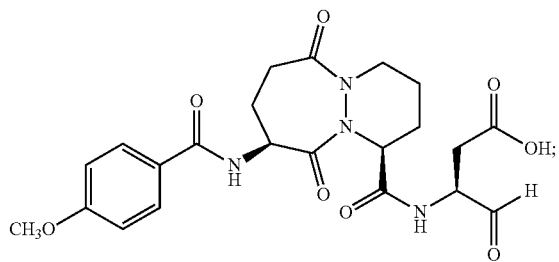
214j
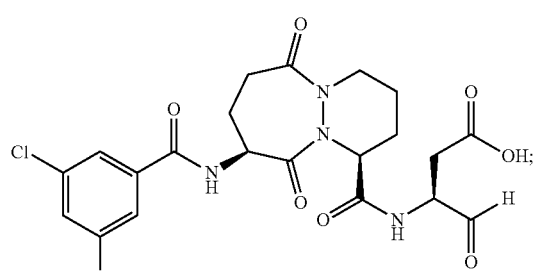
214l
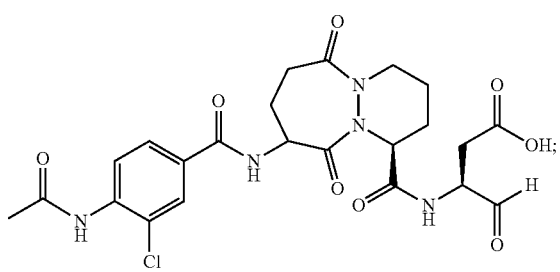
246b
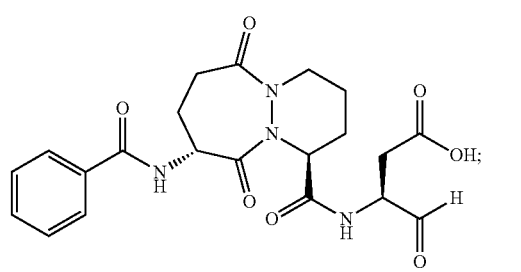
265a
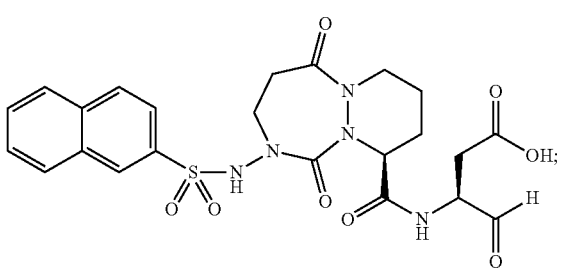

265c
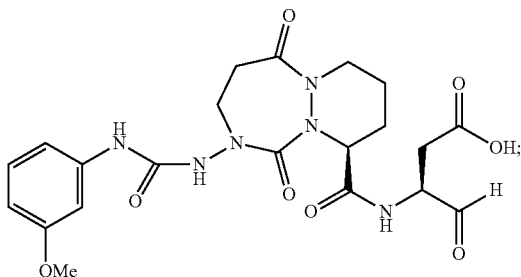
265d
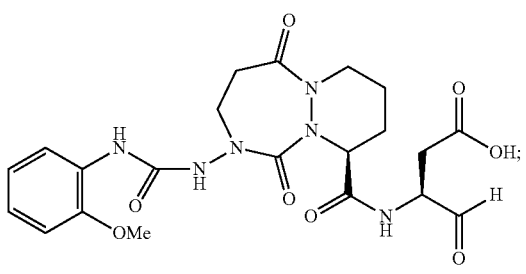
265f
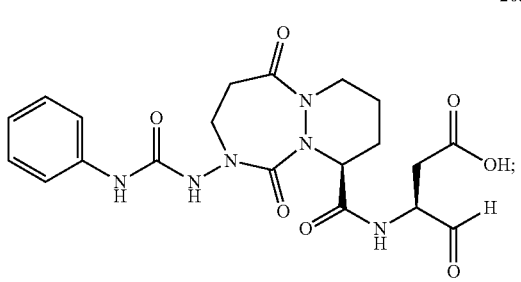
280b
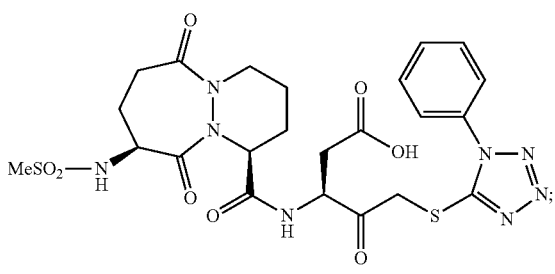
280c
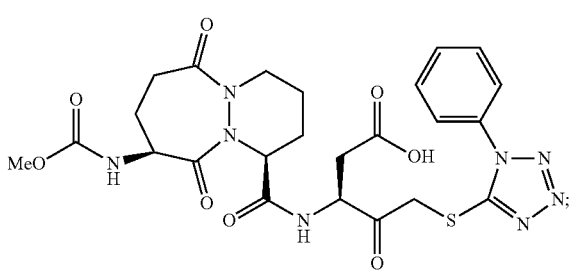
280d
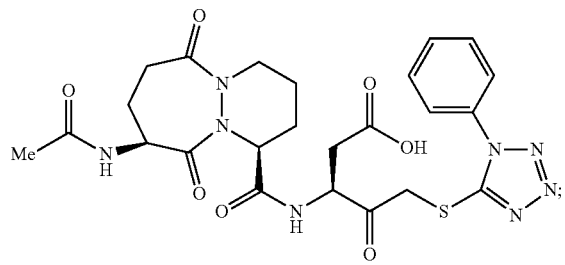
283b
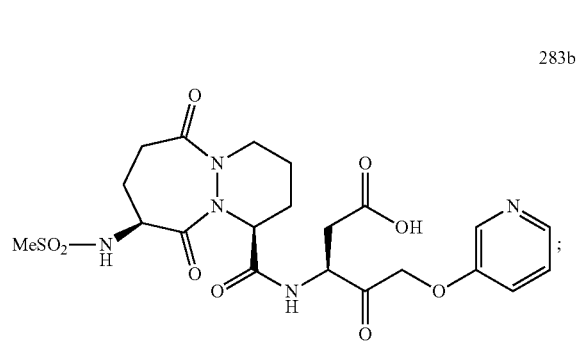
283c
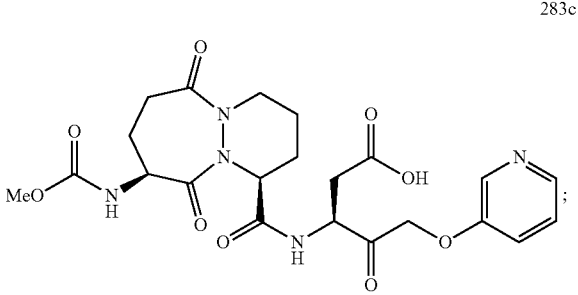
283d
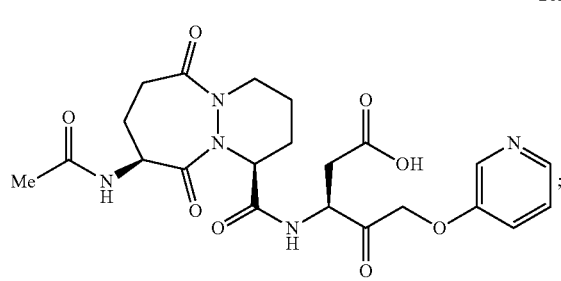
284
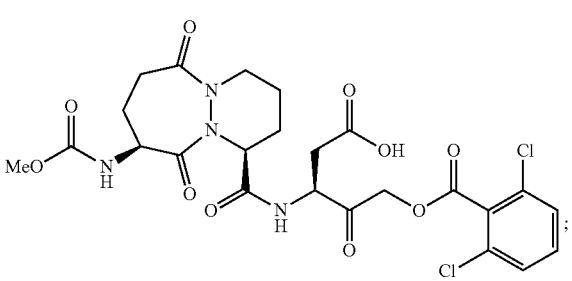

285
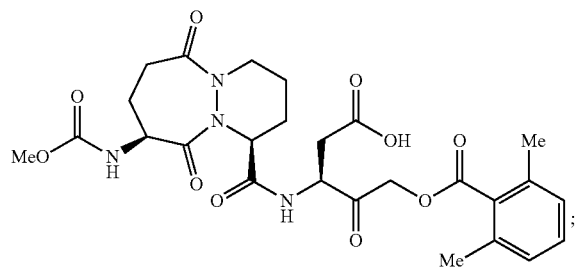
286
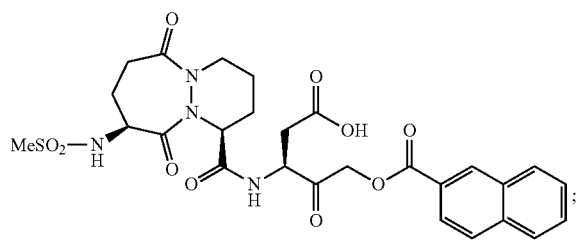
308c
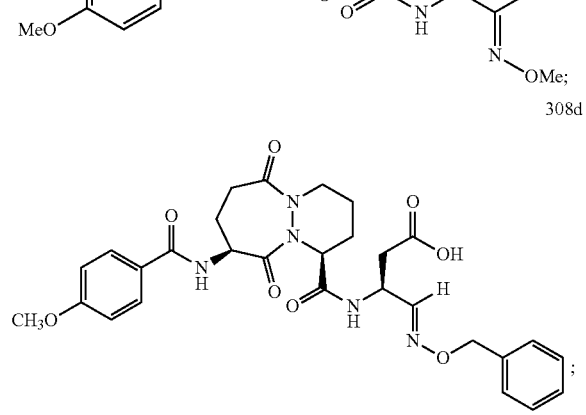
308d
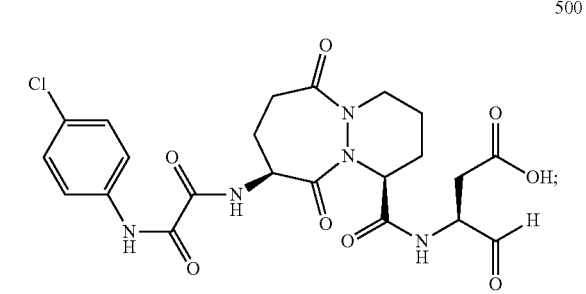
500
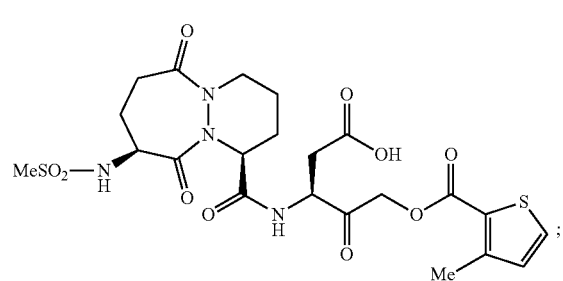
501
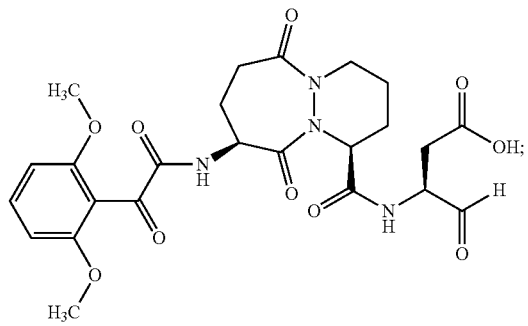
505b
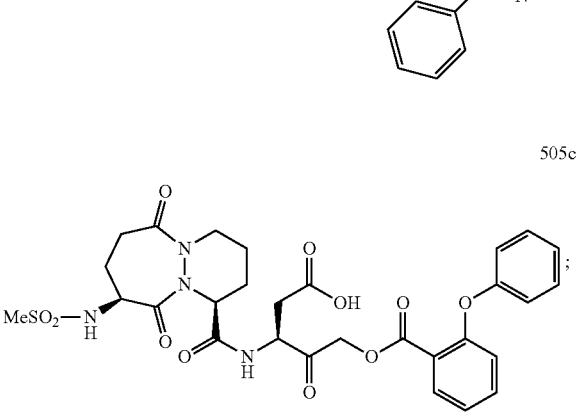
505c
505d
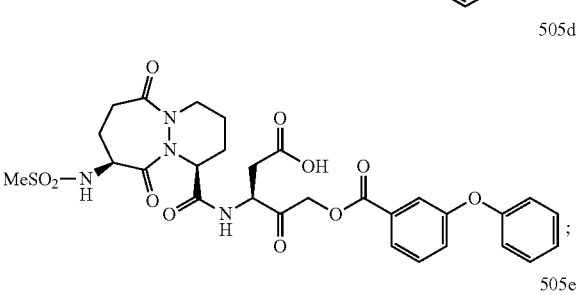
505e 183
-continued
505f
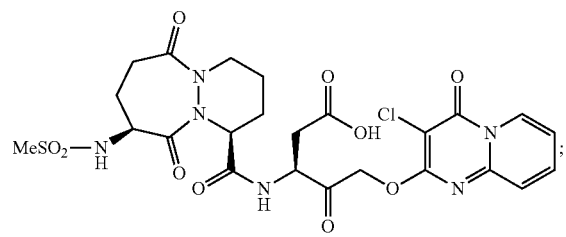
510a
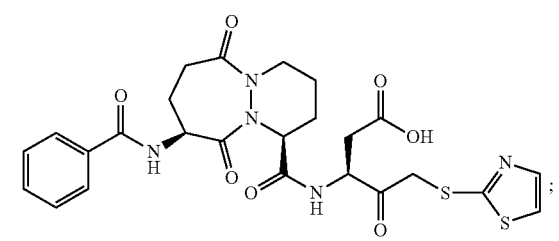
510b
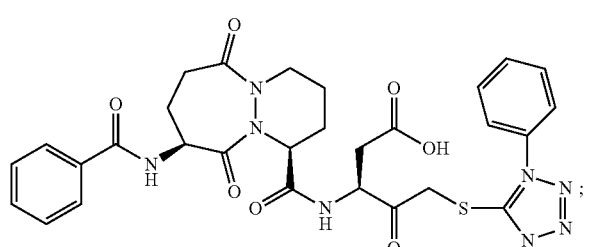
510c
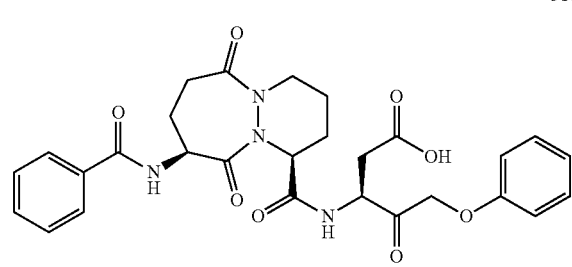
510d
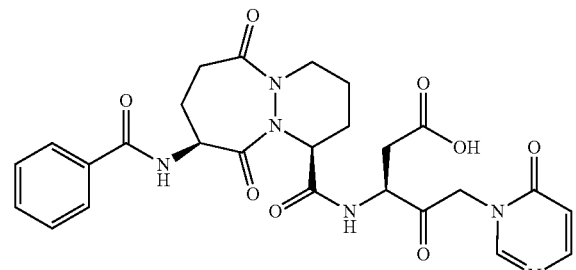
184
-continued
511c
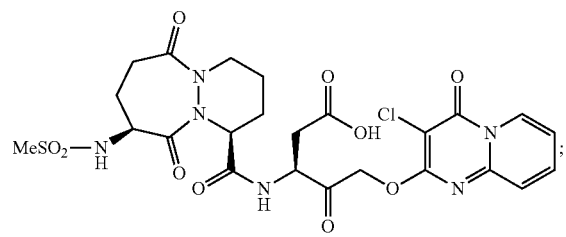
640
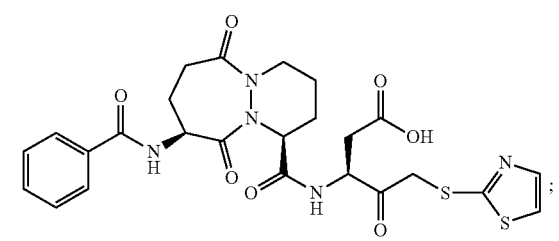
642
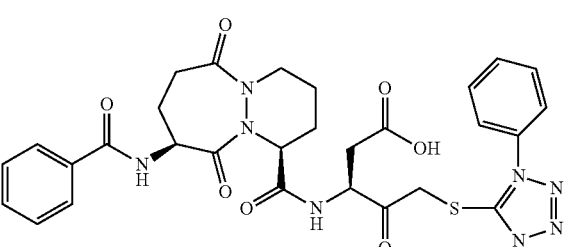
645
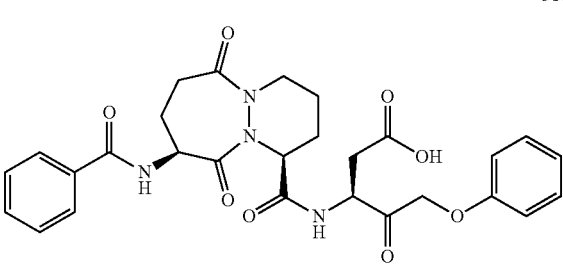
650
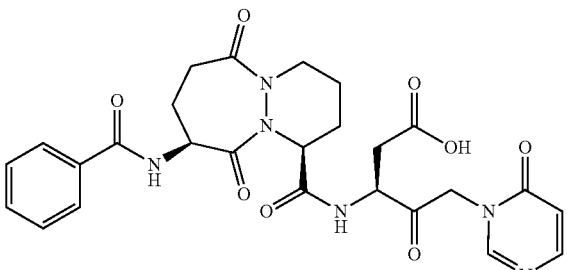

-continued
683
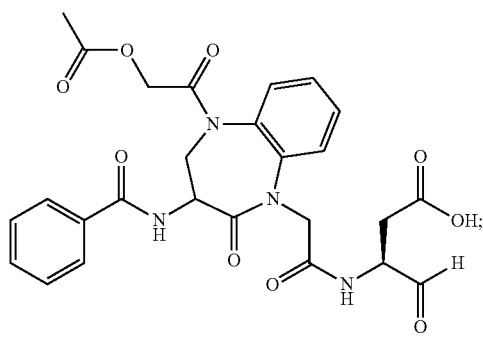
700
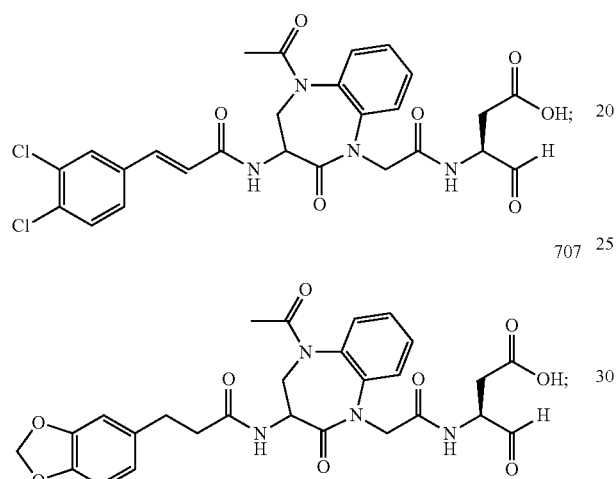
707
708
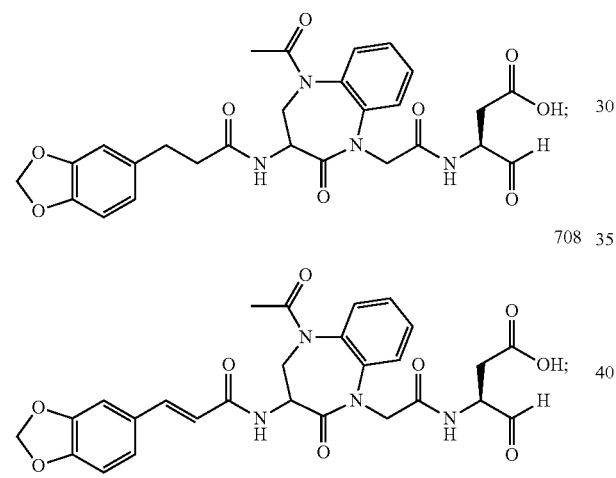
1018
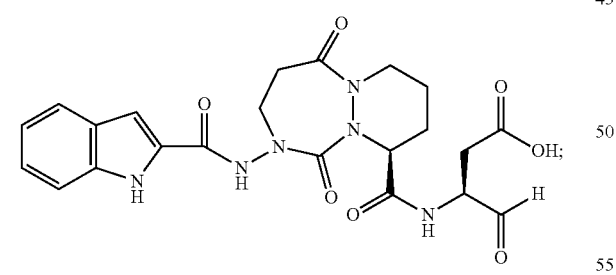
1052
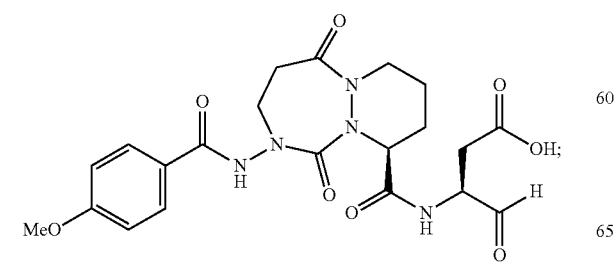
-continued
1053
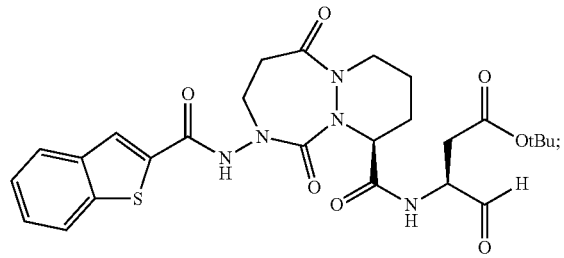
1056
1075
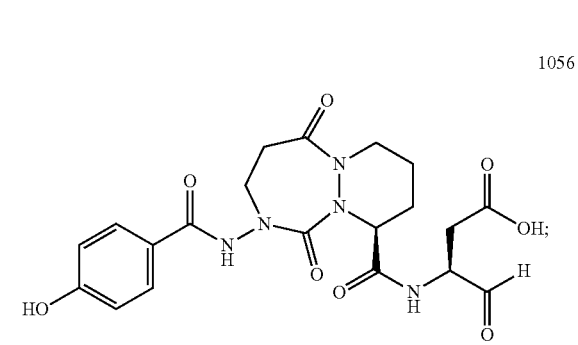
1095
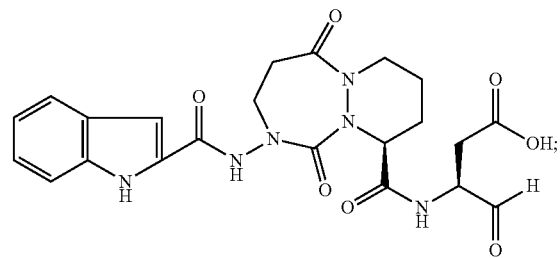
1105
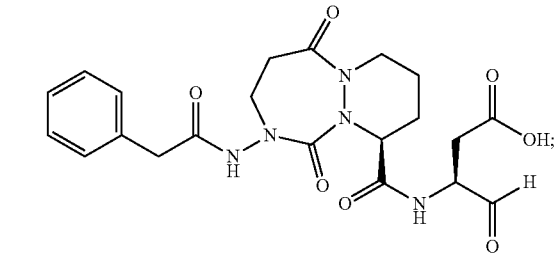

1106
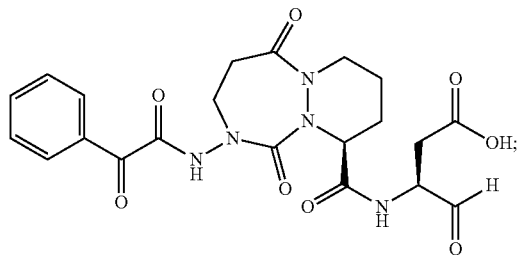
1107
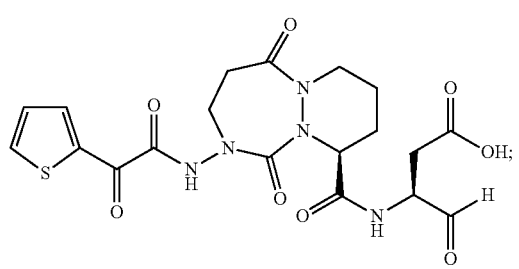
1108
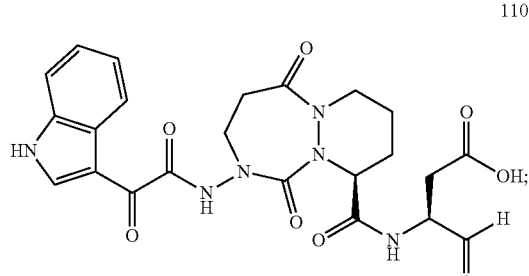
1109
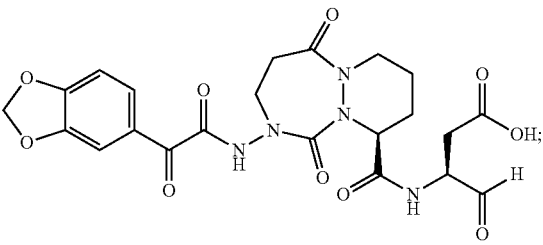
1110
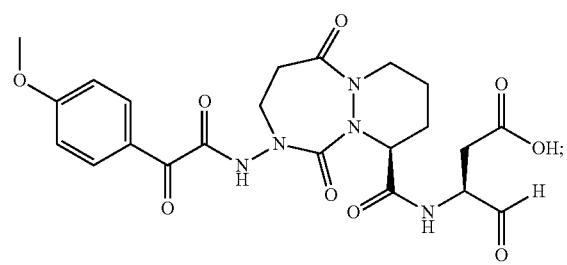
1111
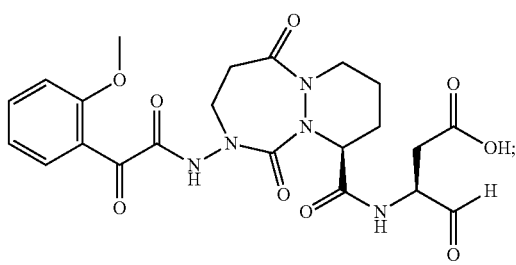
1112
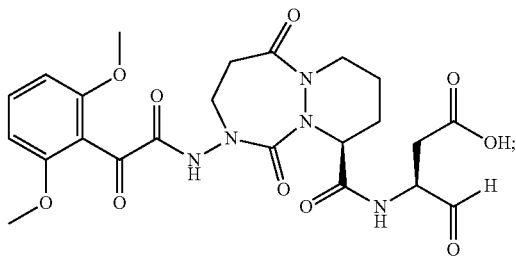
1113
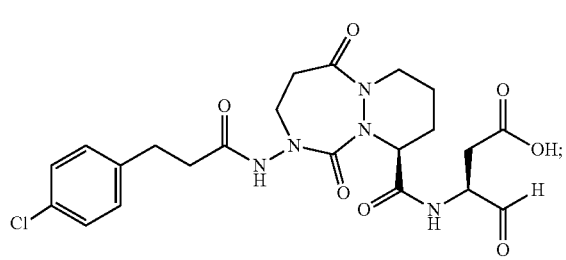
1114
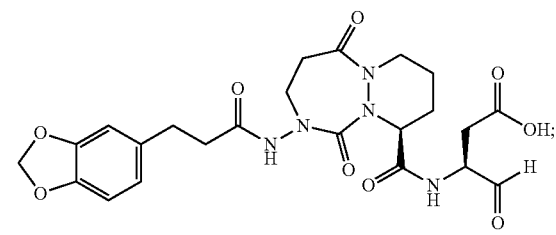
1115
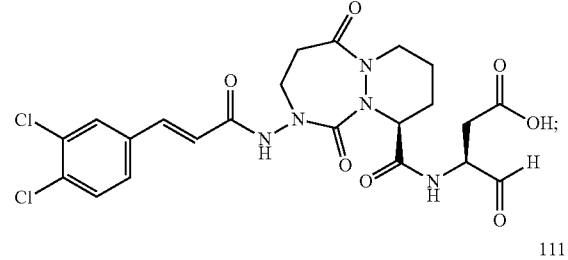
1116
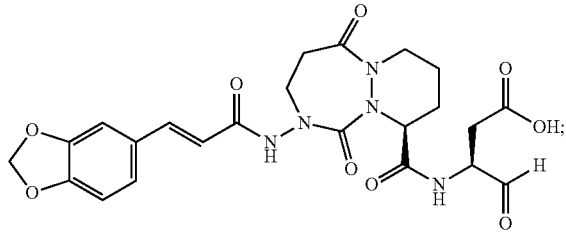

1117
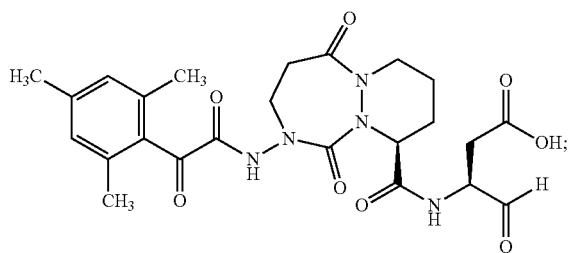
1118
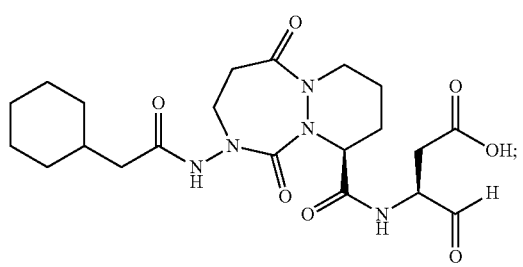
1119
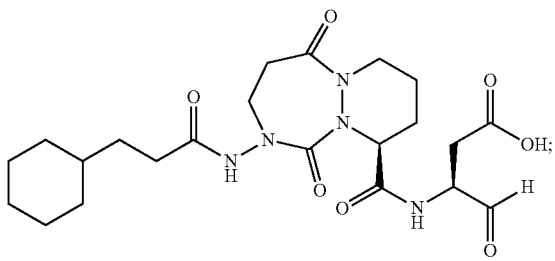
1120
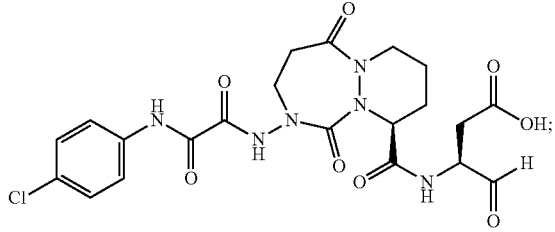
1121
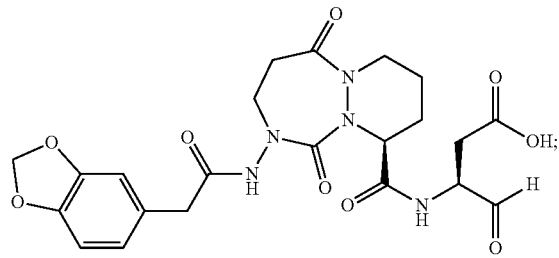
1122
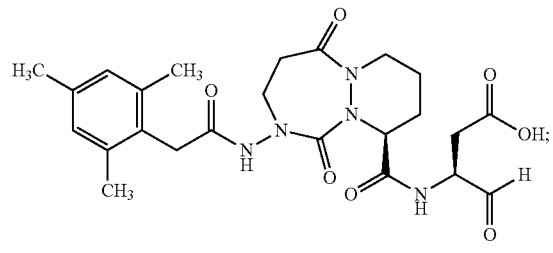
1123
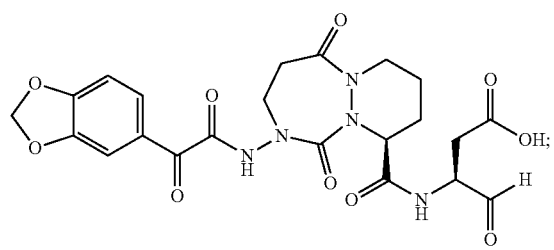
1124
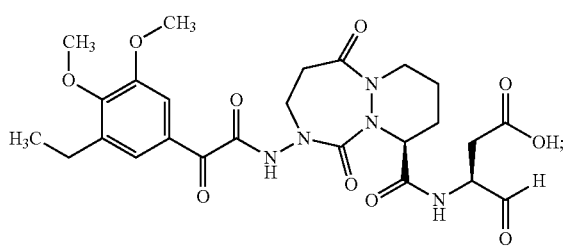
1125
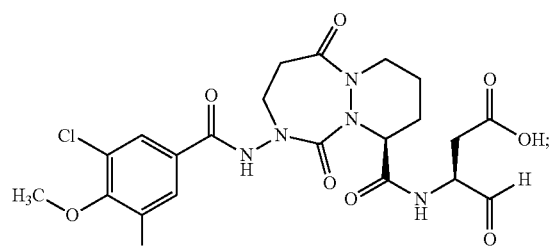
2100i
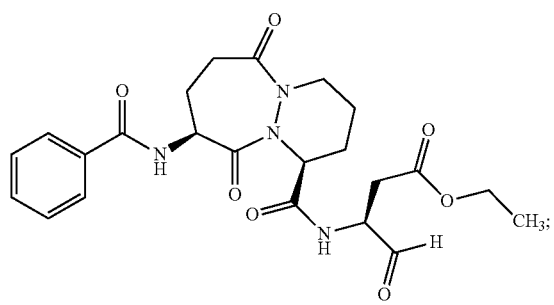

-continued
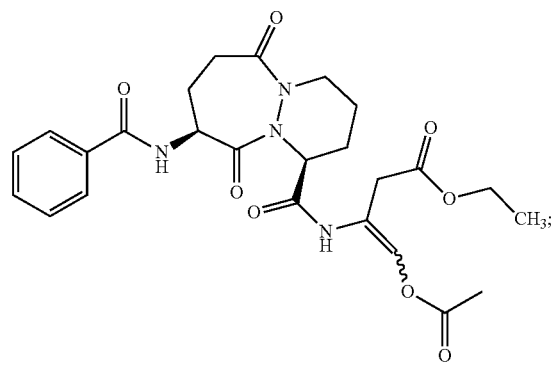
2100j
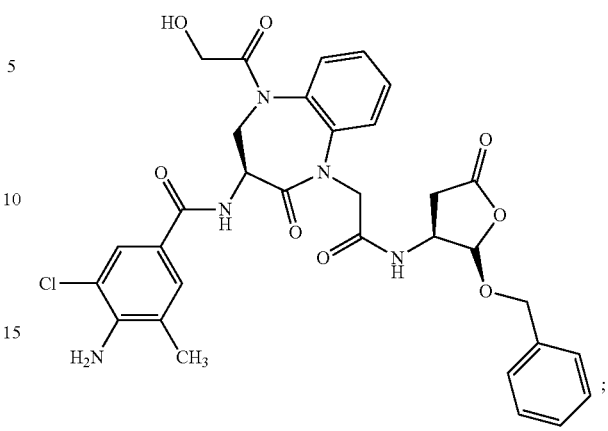
697a
Other compounds of embodiment (K) include, but are not limited to:
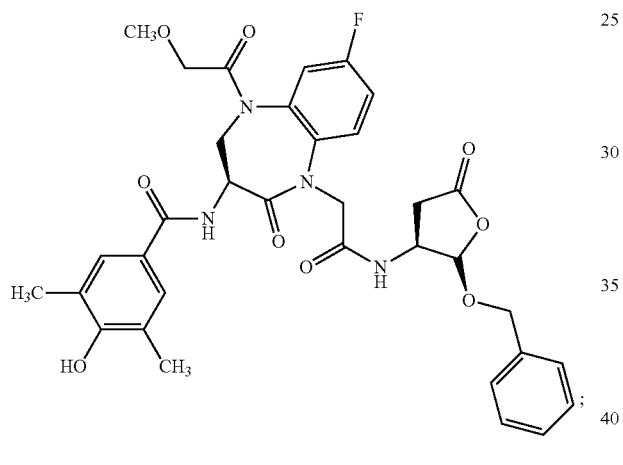
688b-1
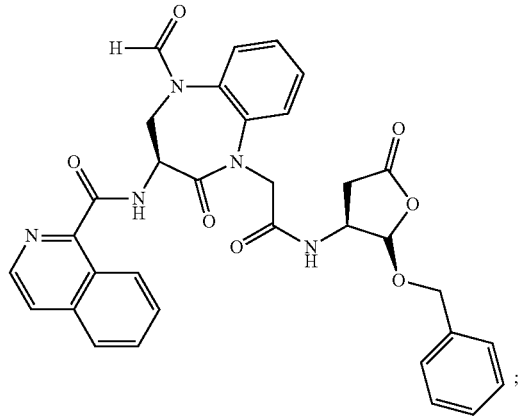
698a
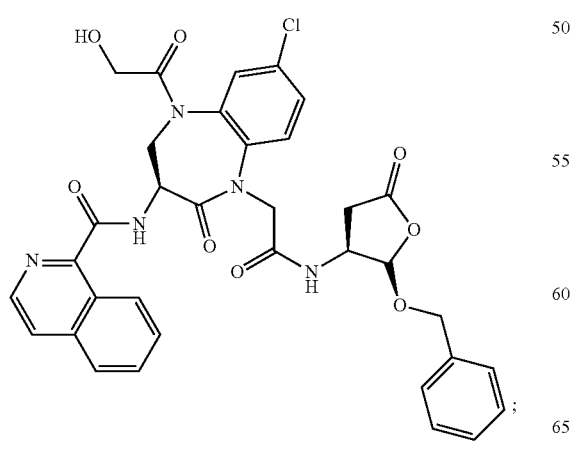
696a-2
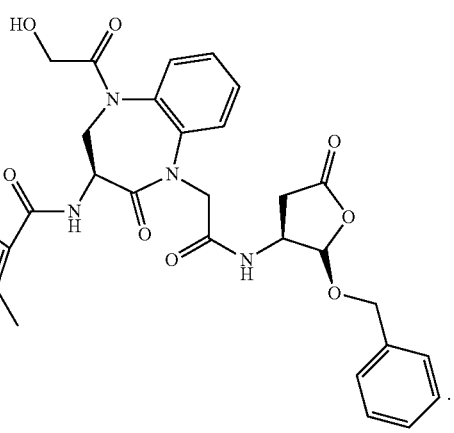
800

Other compounds of embodiment (L) include, but are not limited to:
684a
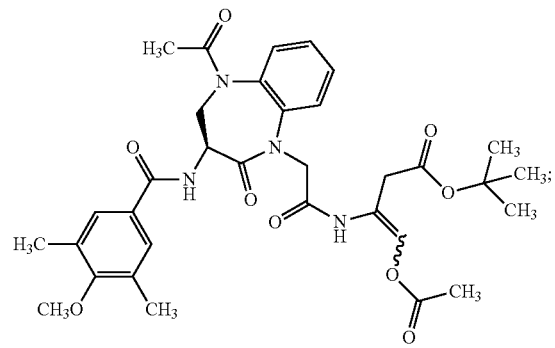
688c
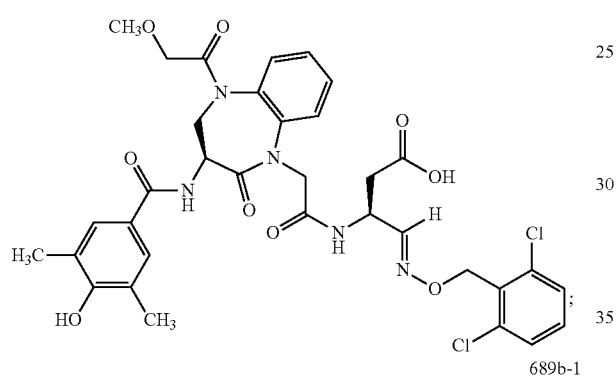
689b-1
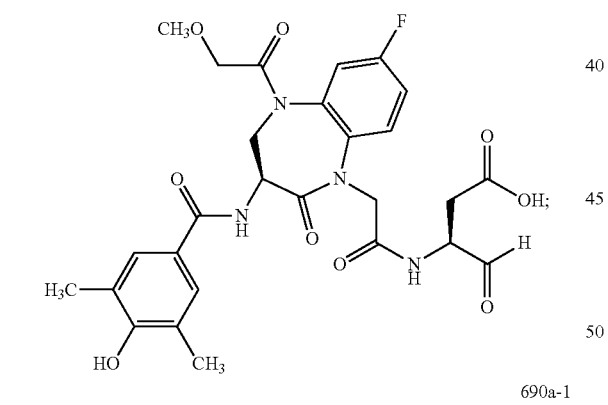
690a-1
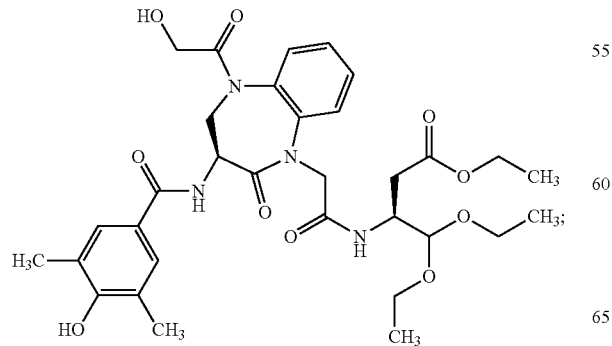
696-2
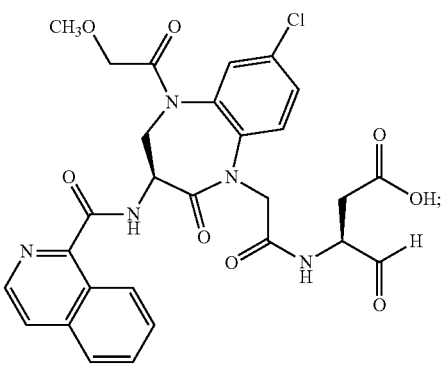
697
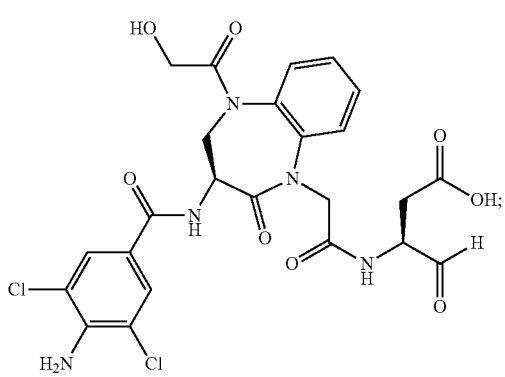
698
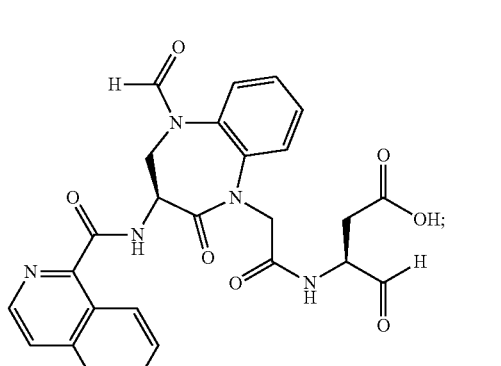
699a-2
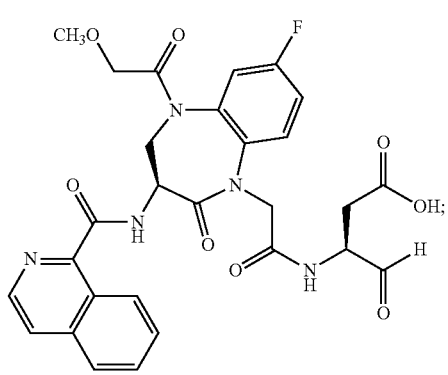

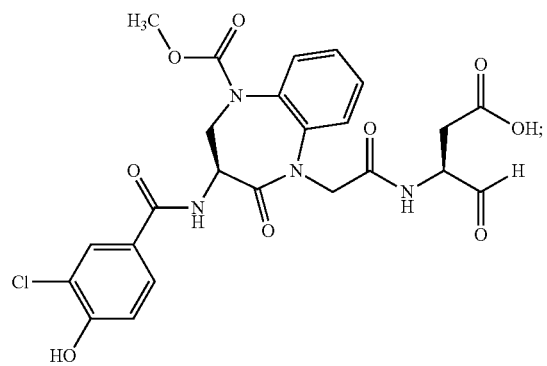
720
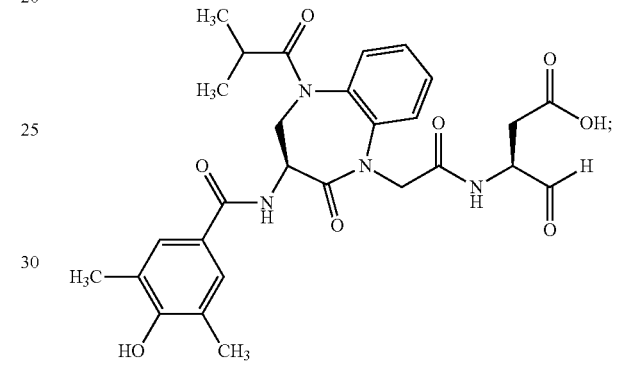
724
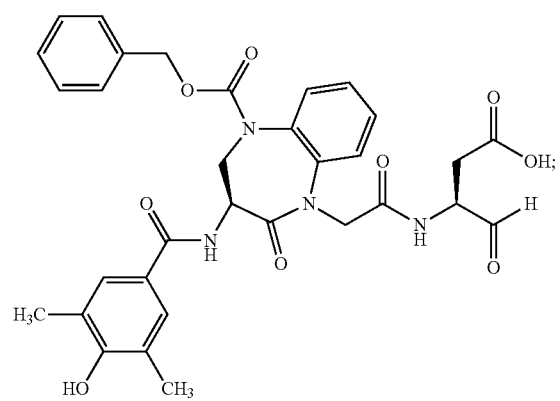
721
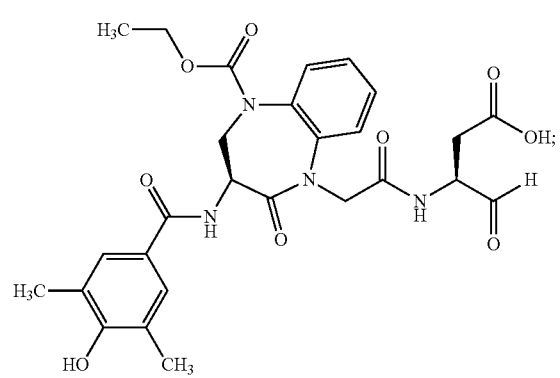
722
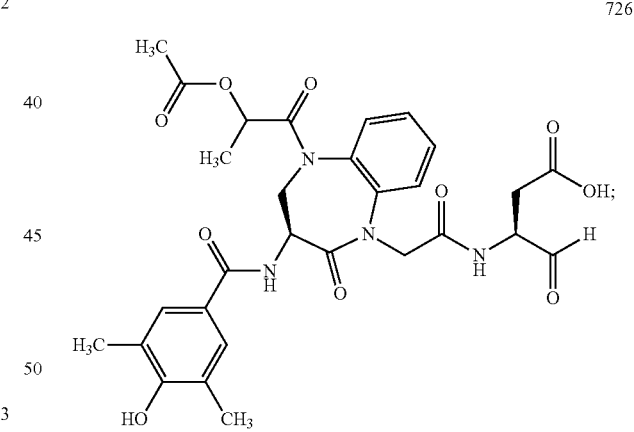
725
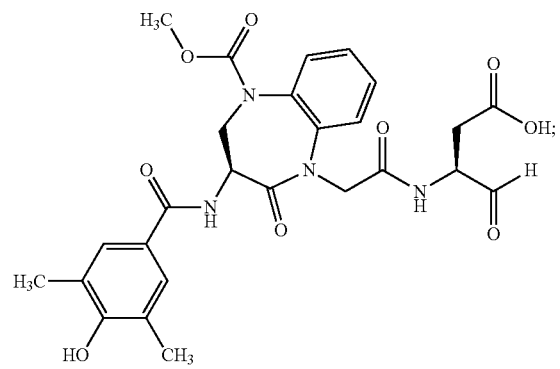
723
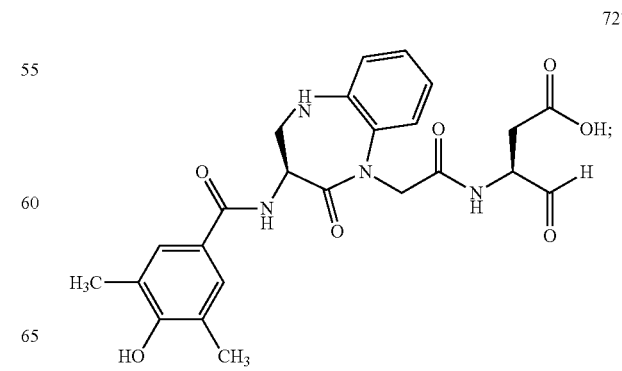
726
727

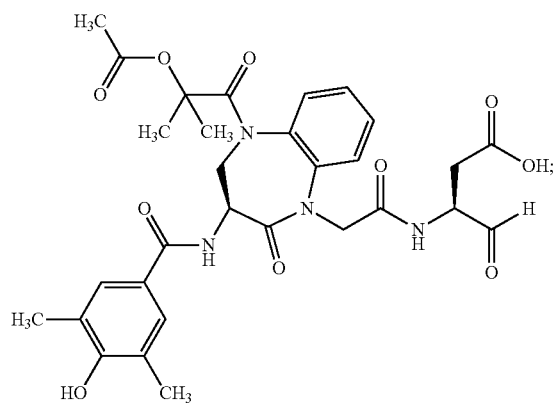
728
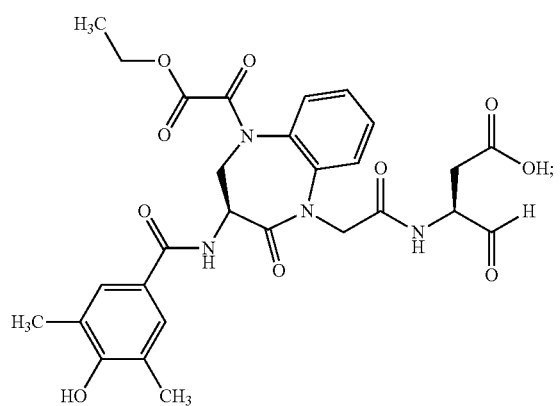
729
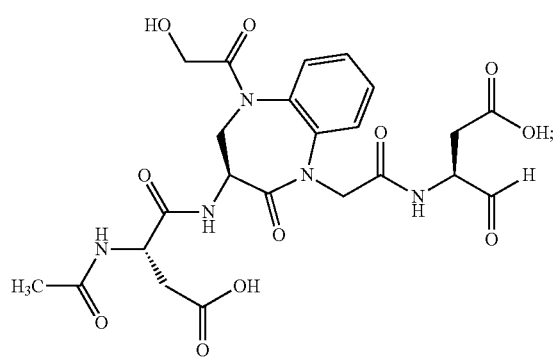
730
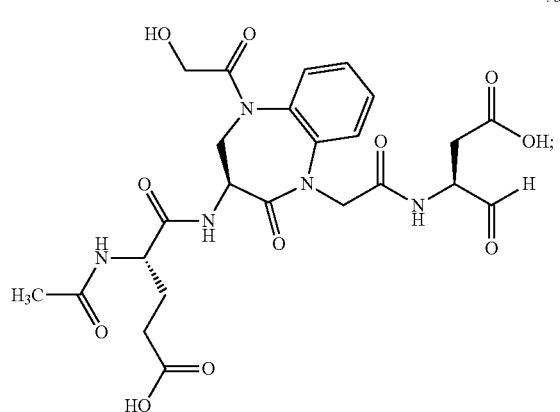
731
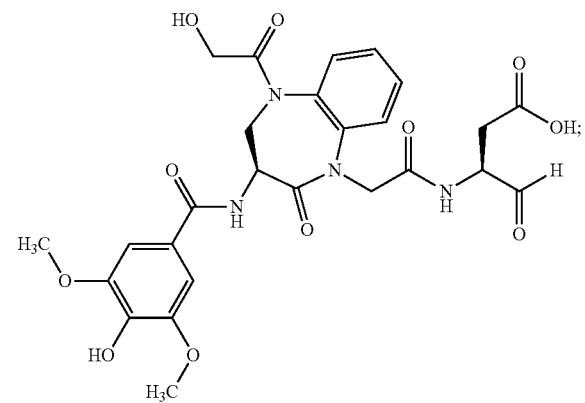
732
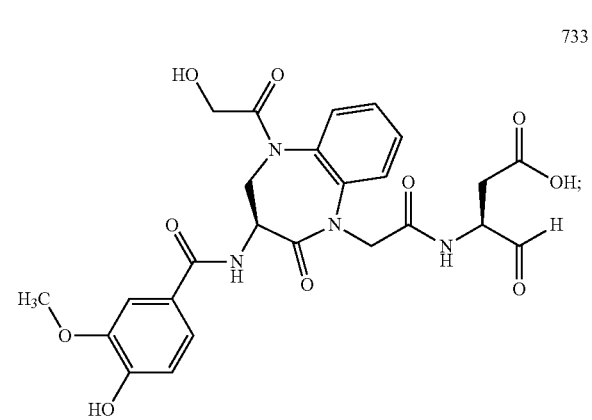
733
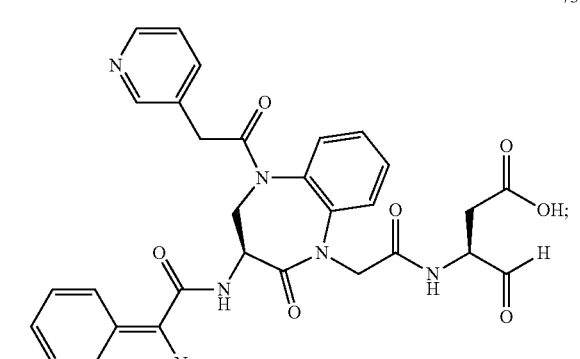
734
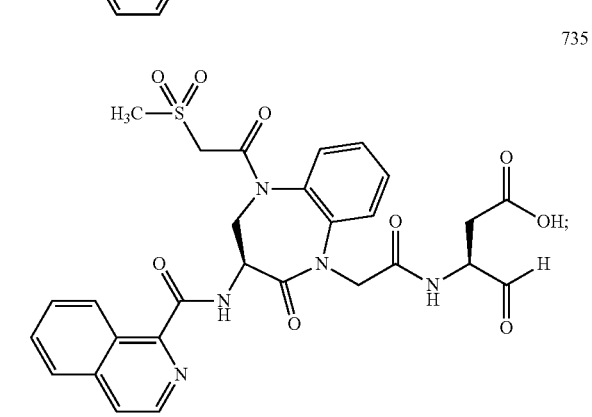
735

736 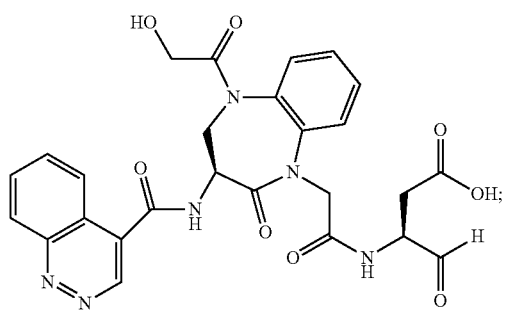
737 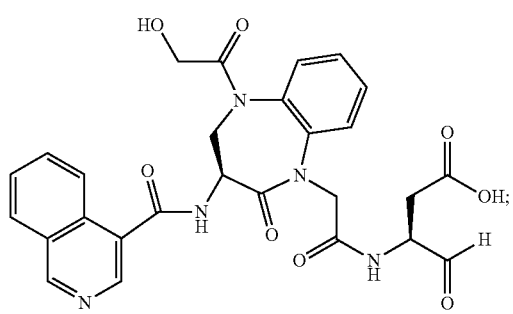
738 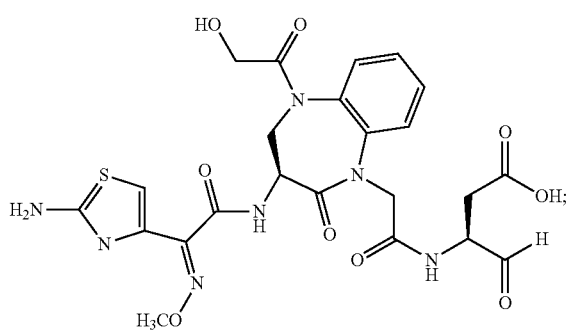
739 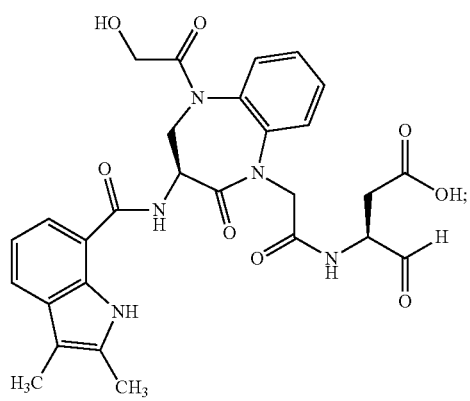
740 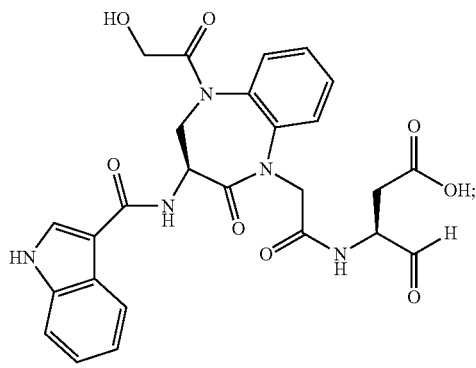
741 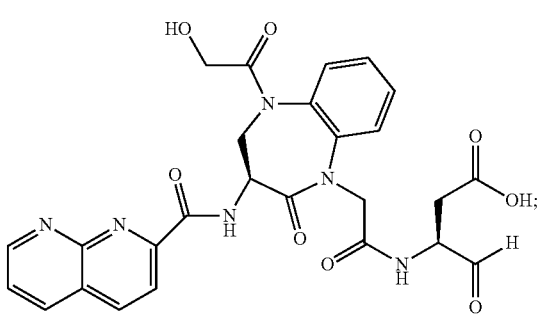
742 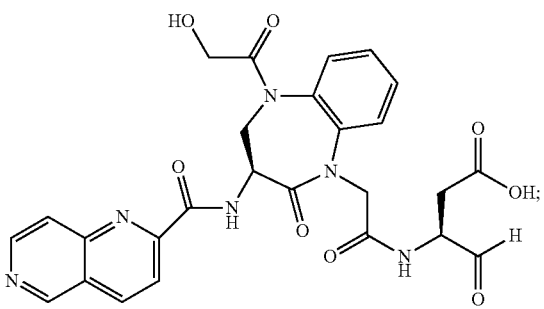
743 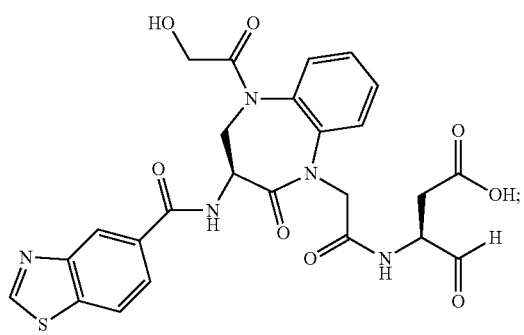

201
-continued
744
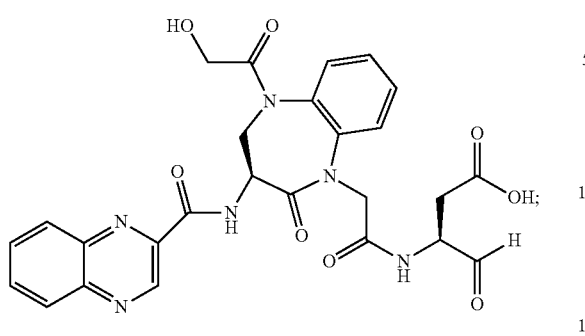
745
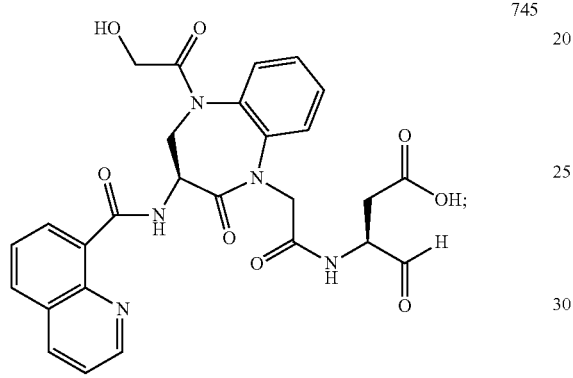
746
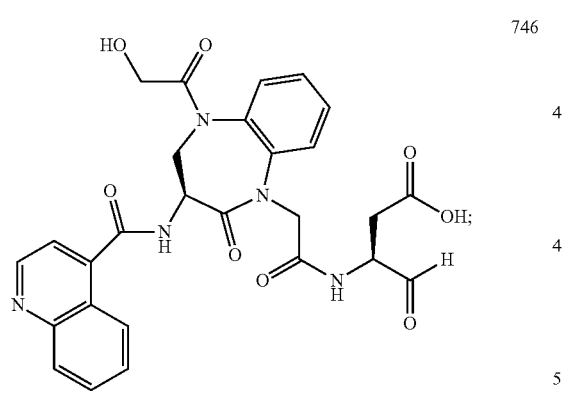
747
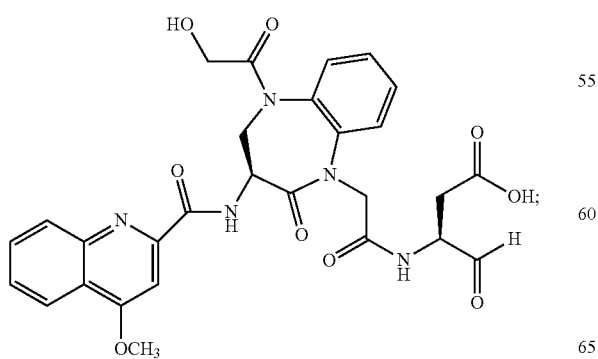
202
-continued
748
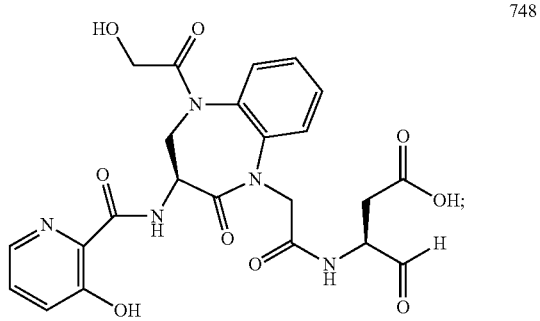
749
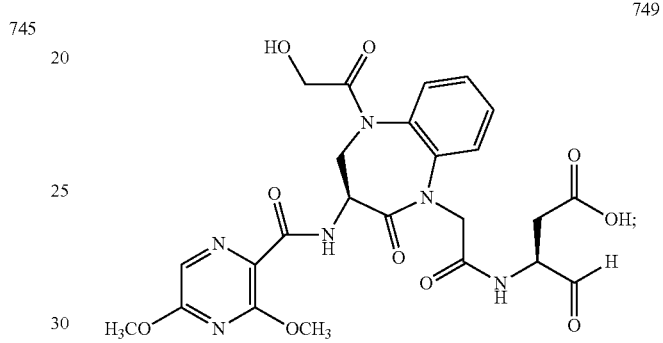
750
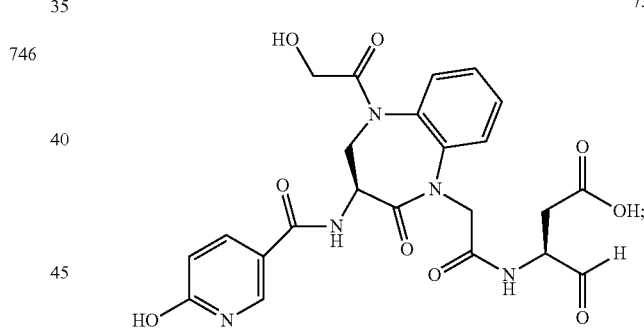
751
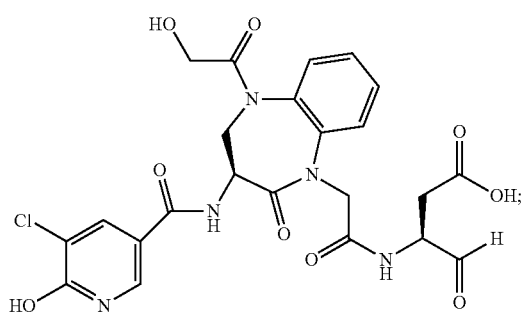

752
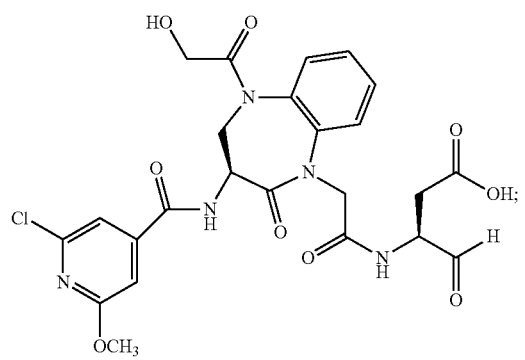
753
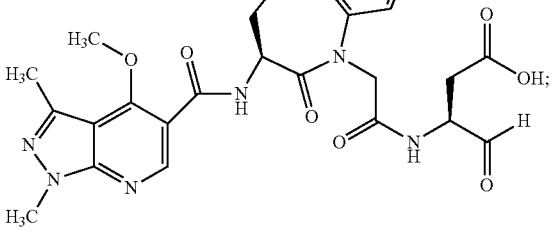
754
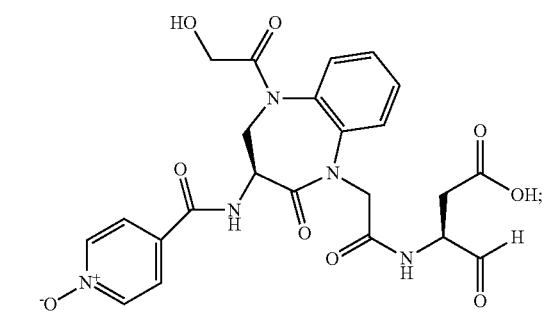
755
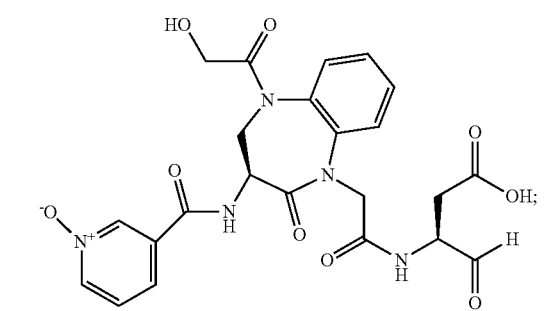
756
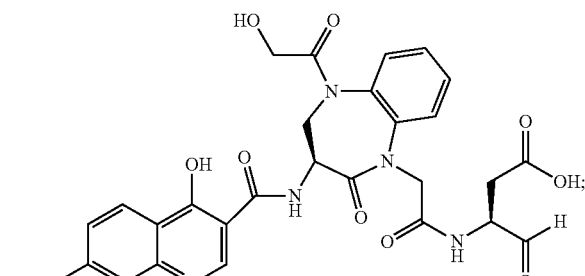
757
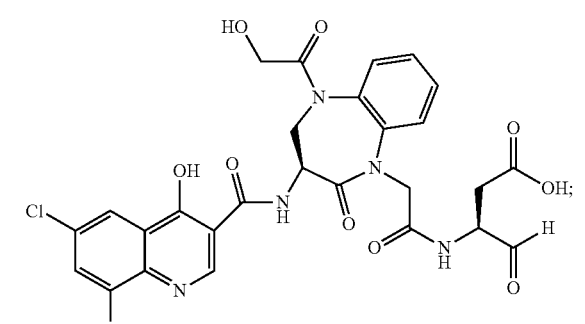
758
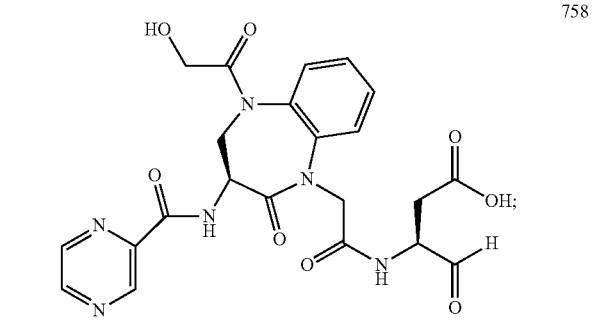
759
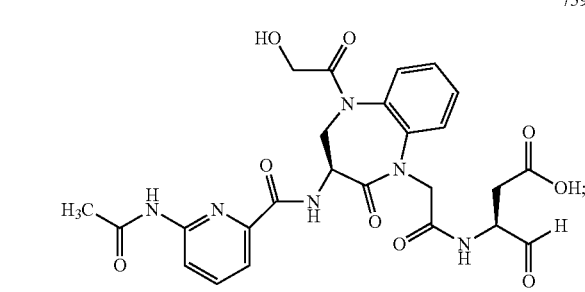
760
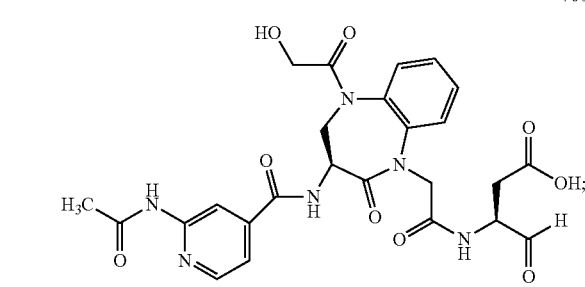

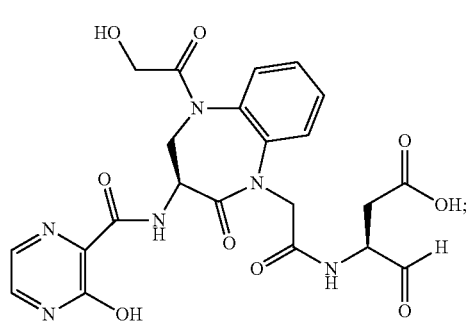
761

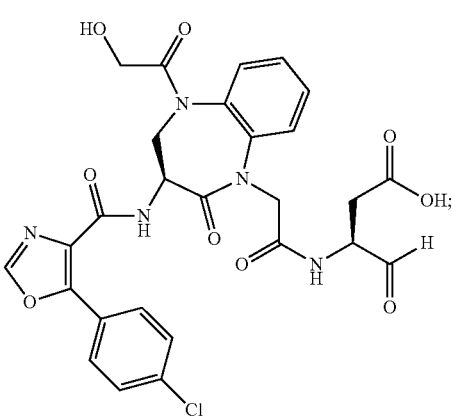
765

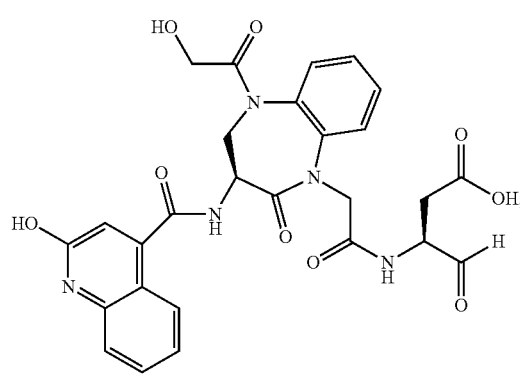
762

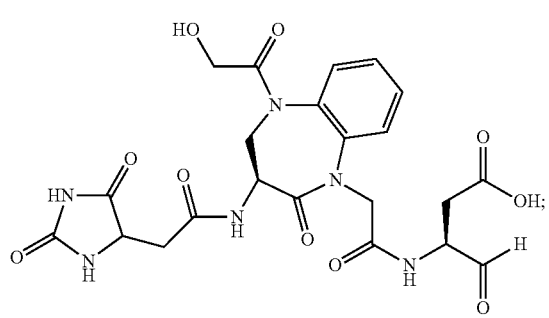
766

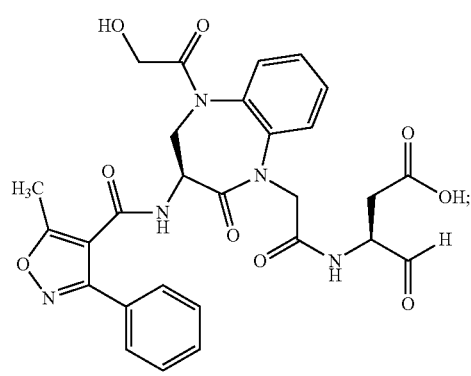
763

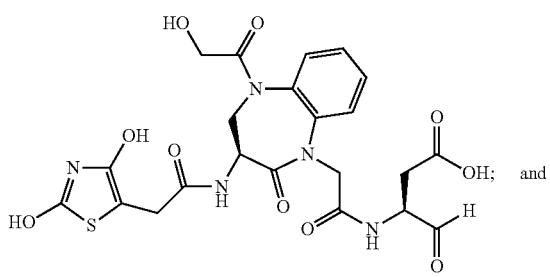
767

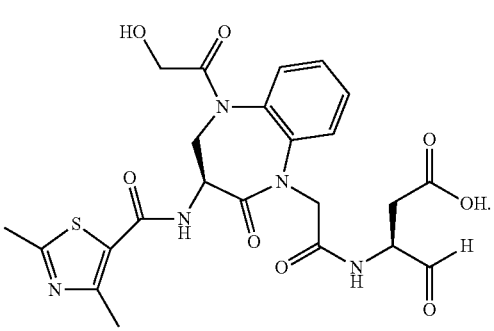
and

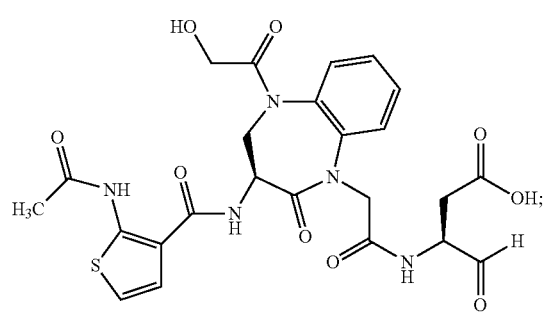
764

801

The most preferred compounds of embodiments (K) and (L) are those wherein the $Ar_3$ cyclic group is isoquinolyl.

Compounds of this invention are described in co-pending U.S. application Ser. Nos. 08/575,641 and 08/598,332 the disclosures of which are herein incorporated by reference.

The compounds of this invention have a molecular weight of less than or equal to about 700 Daltons, and more preferably between about 400 and 600 Daltons. These preferred compounds may be readily absorbed by the bloodstream of patients upon oral administration. This oral availability makes such compounds excellent agents for orally-administered treatment and prevention regimens against IL-1-, apoptosis-, IGIF- or IFN-γ mediated diseases.

It should be understood that the compounds of this invention may exist in various equilibrium forms, depending on conditions including choice of solvent, pH, and others known to the practitioner skilled in the art. All such forms of these compounds are expressly included in the present invention. In particular, many of the compounds of this invention, especially those which contain aldehyde or ketone groups in $R_3$ and carboxylic acid groups in T, may take hemi-ketal (or hemi-acetal) or hydrated forms. For example, compounds of embodiment (A) may take the forms depicted below:

contain ketone or aldehyde groups, especially where they occur in the $R_3$ group of the compounds of this invention. Other examples of pro-drug forms include the hemi-ketal, hemi-acetal, acyloxy ketal, acyloxy acetal, ketal, and acetal forms that are described in EQ1 and EQ2.

ICE and TX Cleave and Thereby Activate Pro-IGIF

The ICE protease was identified previously by virtue of its ability to process inactive pro-IL-1β to mature active IL-1β, a pro-inflammatory molecule, in vitro and in vivo. Here we show that ICE and its close homologue TX (Caspase-4, C. Faucheu et al., *EMBO*, 14, p. 1914 (1995)) can proteolytically

EQ1

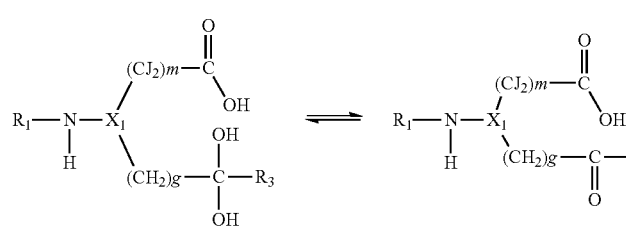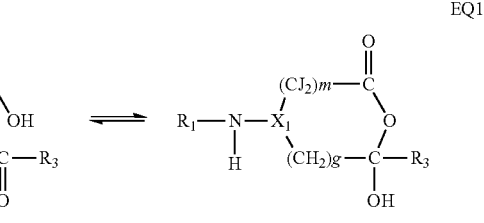

Hydrated Form

Hemi-ketal or
Hemi-acetal Form

Depending on the choice of solvent and other conditions known to the practitioner skilled in the art, compounds of this invention may also take acyloxy ketal, acyloxy acetal, ketal or acetal form:

cleave inactive pro-IGIF. This processing step is required to convert pro-IGIF to its active mature form, IGIF. Cleavage of pro-IGIF by ICE, and presumably by TX, also facilitates the export of IGIF out of cells.

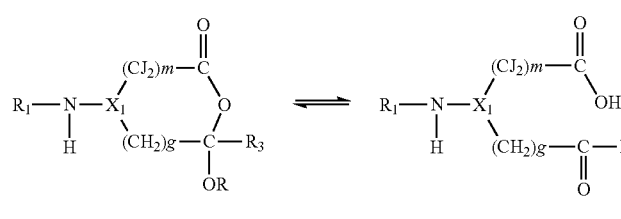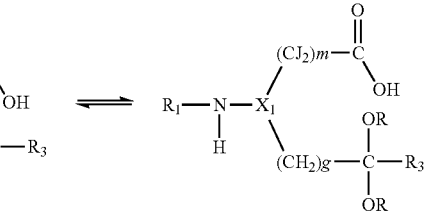

Acyloxy Ketal or
Acyloxy Acetal Form

Ketal or Acetal Form

In addition, it should be understood that the equilibrium forms of the compounds of this invention may include tautomeric forms. All such forms of these compounds are expressly included in the present invention.

It should be understood that the compounds of this invention may be modified by appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. In addition, the compounds may be altered to pro-drug form such that the desired compound is created in the body of the patient as the result of the action of metabolic or other biochemical processes on the pro-drug. Such pro-drug forms typically demonstrate little or no activity in in vitro assays. Some examples of pro-drug forms include ketal, acetal, oxime, imine, and hydrazone forms of compounds which We first used transient co-expression of plasmids transfected into Cos cells to determine whether any known members of the ICE/CED-3 protease family can process pro-IGIF to IGIF in cultured cells (Example 23) (FIG. 1A).

FIG. 1A demonstrates that ICE cleaves pro-IGIF in Cos cells co-transfected with plasmids that express pro-IGIF in the presence of active ICE. Cos cells were transfected with an expression plasmid for pro-IGIF alone (lane 2) or in combination with the indicated expression plasmids encoding wild type or inactive mutants of ICE/CED-3 family of proteases (lanes 3-12). Cell lysates were prepared and analyzed for the presence of IGIF protein by immunoblotting with an anti-IGIF antiserum. Lane 1 contained lysates from mock transfected cells.

Co-expression of pro-IGIF with ICE or TX resulted in the cleavage of pro-IGIF into a polypeptide similar in size to the naturally-occurring 18-kDa mature IGIF. This processing event is blocked by single point mutations that alter the catalytic cysteine residues and thus inactivate ICE and TX (Y. Gu et al., *EMBO*, 14, p. 1923 (1995)).

Co-expression with CPP32 (Caspase-3), a protease involved in programmed cell death (T. Fernandes-Alnemri et al., *J. Biol. Chem.,* 269, p. 30761 (1994); D. W. Nicholson et al., *Nature,* 376, p. 37 (1995)), resulted in the cleavage of pro-IGIF into a smaller polypeptide, while co-expression with CMH-1 (Caspase-7), a close homolog of CPP32 (J. A. Lippke et al., *J. Biol. Chem.,* 271, p. 1825 (1996)), failed to cleave pro-IGIF to any significant extent. Thus, ICE and TX appear to be capable of cleaving pro-IGIF into a polypeptide similar in size to the naturally-occurring 18-kDa IGIF.

We next examined the ability of these cysteine proteases to cleave pro-IGIF in vitro using a purified, recombinant $(His)_6$-tagged pro-IGIF as a substrate (Example 23).

Figure 1B:
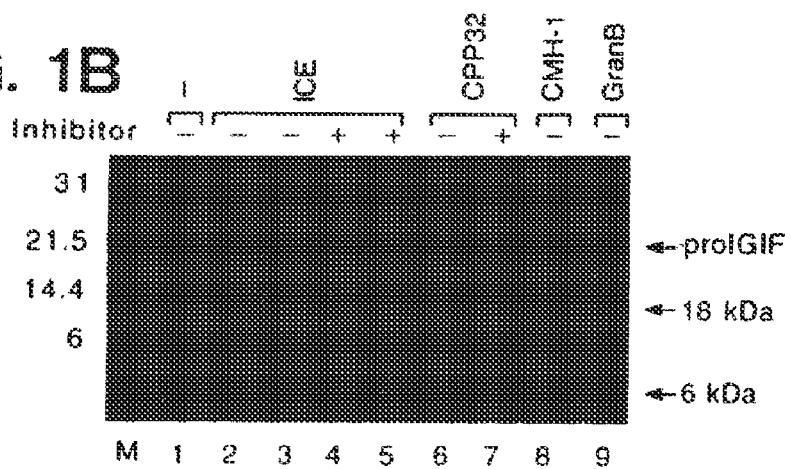
FIG. 1B ICE cleaves pro-IGIF at the authentic processing site in vitro as shown by Coomassie blue staining of proteolytic reaction products separated by SDS-PAGE (Example 23). The proteases and inhibitors used were: lane 1, buffer control; lane 2, 0.1 nM ICE; lane 3, 1 nM ICE; lanes 4 and 5, 1 nM ICE with 10 nM Cbz-Val-Ala-Asp-[(2,6-dichlorobenzoyl)oxy]methyl ketone and 100 nM Ac-Tyr-Val-Ala-Asp-aldehyde (SEQ ID NO: 2), respectively; lanes 6 and 7, 15 nM CPP32 with and without 400 nM Ac-Asp-Glu-Val-Asp-aldehyde (SEQ ID NO: 3) (D. W. Nicholson et al., Nature, 376, p. 37 (1995)), respectively; lane 8, 100 nM CMH-1; lane 9, 10 units/ml granzyme B; and M, molecular weight markers in kDa.

FIG. 1B demonstrates that pro-IGIF is cleaved in vitro by ICE. Purified recombinant $(His)_6$-tagged pro-IGIF (2 µg) was incubated with the indicated cysteine protease in the presence or absence of ICE or CPP32 inhibitors as described in Example 23. The cleavage products were analyzed by SDS-PAGE and Coomassie Blue staining.

ICE cleaved the 24 kDa pro-IGIF into two polypeptides of approximately 18-kDa and 6-kDa. N-terminal amino acid sequencing of the ICE cleavage products indicated that the 18-kDa polypeptide contains the same N-terminal amino acid residues (Asn-Phe-Gly-Arg-Leu, SEQ ID NO: 4) as the naturally occurring IGIF. This shows that ICE cleaves pro-IGIF at the authentic processing site (Asp35-Asn36) (H. Okamura et al., Infection and Immunity, 63, p. 3966 (1995); H. Okamura et al., *Nature,* 378, p. 88 (1995)). N-terminal amino acid sequencing of the CPP32 cleavage products indicated that CPP32 cleaved pro-IGIF at Asp69-Ile70.

The cleavage by ICE of pro-IGIF is highly specific with a catalytic efficiency $(k_{cat}/K_M)$ of $1.4 \times 10^7$ $M^{-1}s^{-1}$ ($K_M$=0.6±0.1 µM; $k_{cat}$=8.6±0.3 $s^{-1}$) and is inhibited by specific ICE inhibitors (Ac-Tyr-Val-Ala-Asp-aldehyde, SEQ ID NO: 2) and Cbz-Val-Ala-Asp-[(2,6-dichlorobenzoyl)oxy] methylketone, (N. A. Thornberry et al., *Nature,* 356, p. 768 (1992); R. E. Dolle et al., *J. Med. Chem.,* 37, p. 563 (1994)).

Figure 1C:
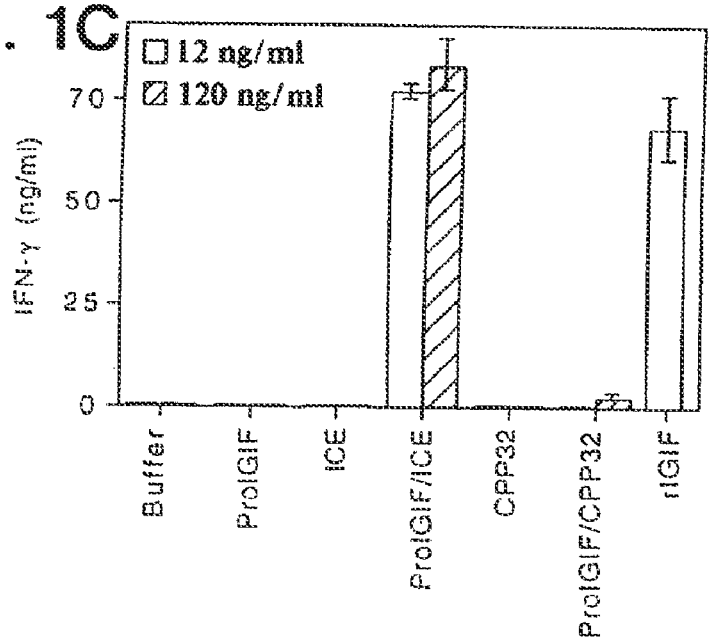
FIG. 1C ICE cleavage converts inactive pro-IGIF to active IGIF which induces IFN-γ production in Th1 helper cells. Uncleaved (Pro-IGIF), ICE-cleaved (Pro-IGIF/ICE), CPP32-cleaved (Pro-IGIF/CPP32), and recombinant mature IGIF (rIGIF) were incubated with A.E7 Th1 cells at 12 ng/ml (open bar) and 120 ng/ml (hatched bar) for eighteen hours and the levels of IFN-γ released into the culture medium assayed by ELISA (Example 23). A.E7 cells cultured with buffer, ICE alone (ICE) or CPP32 alone (CPP32) were assayed similarly for negative controls. The numbers represent the average of three determinations.

FIG. 1C demonstrates that ICE cleavage in vitro activates pro-IGIF. Uncleaved pro-IGIF, ICE- or CPP32-cleaved products of pro-IGIF, or recombinant mature IGIF (rIGIF) were each added to A.E7 cell cultures to a final concentration of 12 ng/ml or 120 ng/ml (see, Example 23). Eighteen hours later, IFN-γ in the cultural medium was quantified by ELISA. While the uncleaved pro-IGIF had no detectable IFN-γ inducing activity, ICE-cleaved pro-IGIF was active in inducing IFN-γ production in Th1 cells.

Like ICE, the ICE homolog TX also cleaved pro-IGIF into similarly sized polypeptides. However, its catalytic efficiency was about two orders of magnitude lower than that shown for ICE.

Consistent with the observations from the Cos cell experiments above, CPP32 cleaved pro-IGIF at a different site (Asp69-Ile7O) and the resulting polypeptides had little IFN-γ inducing activity (FIG. 1C). CMH-1 and granzyme B each failed to cleave pro-IGIF to any significant extent.

Together, these results demonstrate that, both in Cos cells and in vitro, ICE and TX are capable of processing the inactive pro-IGIF precursor at the authentic maturation site to generate a biologically active IGIF molecule.

Processing of Pro-IGIF by ICE Facilitates Its Export

IGIF is produced by activated Kupffer cells and macrophages in vivo and is exported out of the cells upon stimulation by endotoxin (H. Okamura et al., *Infection and Immunity,* 63, p. 3966 (1995); H. Okamura et al., *Nature,* 378, p. 88 (1995). We used the Cos cell co-expression system (Example 23) to examine whether the intracellular cleavage of pro-IGIF by ICE would facilitate the export of mature IGIF from the cell. Such is the case for pro-IL-1β when it is cleaved by ICE into active IL-1β (N. A. Thornberry et al., *Nature,* 356, p. 768 (1992)).

Figure 2A:
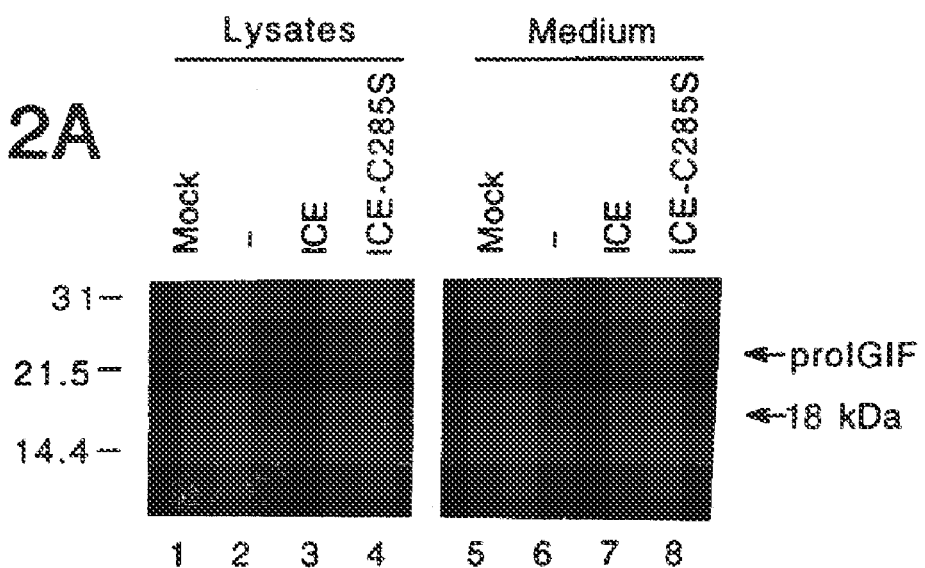
FIG. 2A Mature IGIF (18-kDa) is produced by Cos cells co-transfected with pro-IGIF and ICE-expressing plasmids. Cell lysates (left) and conditioned medium (right) from Cos cells transfected with a pro-IGIF expression plasmid in the absence (−) or presence of an expression plasmid encoding wild type (ICE) or inactive mutant (ICE-C285S) ICE. Transfected cells were metabolically labeled with $^{35}$S-methionine, proteins from cell lysates and conditioned medium immunoprecipitated with anti-IGIF antisera and separated by SDS-PAGE (Example 24). Mobilities of pro-IGIF and the 18-kDa mature IGIF are indicated on the right. Molecular weight markers in kDa are shown on the left.

In FIG. 2A, Cos cells transfected with an expression plasmid for pro-IGIF alone (lanes 2 and 6) or in combination with an expression plasmid encoding wild type (lanes 3 and 7) or inactive mutant ICE (lanes 4 and 8) were metabolically labeled with $^{35}$S-methionine (see, Example 24). Cell lysates (left) and conditioned medium (right) were immunoprecipitated with an anti-IGIF antiserum. The immunoprecipitated proteins were analyzed by SDS-PAGE and fluorography (FIG. 2A).

An 18-kDa polypeptide corresponding in size to mature IGIF was detected in the conditioned medium of Cos cells co-expressing pro-IGIF and ICE, while Cos cells co-expressing pro-IGIF and an inactive ICE mutant (ICE-C285S), or pro-IGIF alone (−) exported only very low levels of pro-IGIF and no detectable mature IGIF. We estimate that about 10% of the mature IGIF was exported from co-transfected cells, while greater than 99% of pro-IGIF was retained within the cells.

Figure 2B:
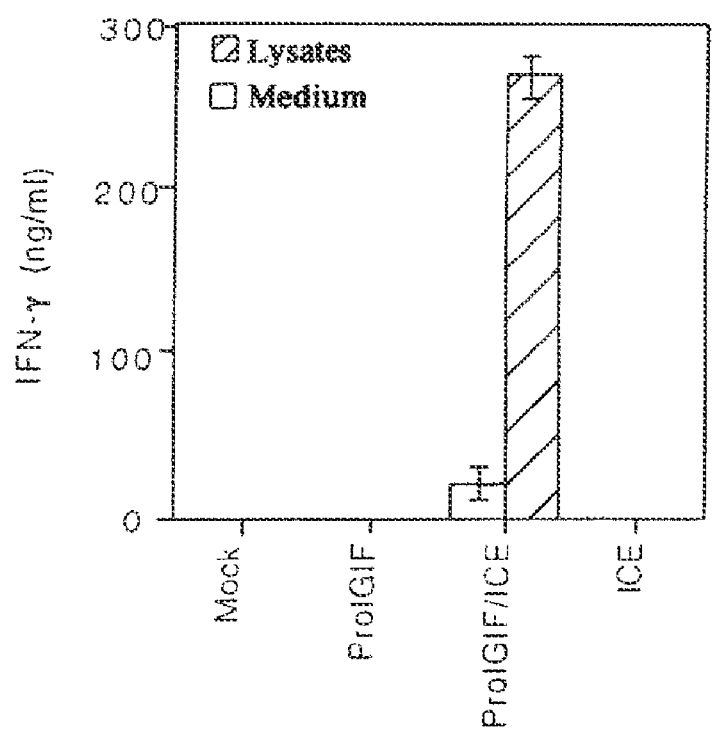
FIG. 2B IFN-γ inducing activity is detected in Cos cells co-transfected with pro-IGIF and ICE-expressing plasmids. Cell lysates (hatched bar) and conditioned medium (open bar) from Cos cells transfected with a pro-IGIF expression plasmid in the absence (Pro-IGIF) or presence (Pro-IGIF/ICE) of an expression plasmid encoding wild type (ICE) were assayed for IFN-γ levels (ng/ml) by ELISA. Cos cells transfected with buffer (Mock) or an ICE-expressing plasmid alone (ICE) served as negative controls (Example 24).

We also measured the presence of IFN-γ inducing activity in cell lysates and in the conditioned medium of the above transfected cells (see, Example 24). IFN-γ inducing activity was detected in both cell lysates and the conditioned medium of Cos cells co-expressing pro-IGIF and ICE, but not in cells expressing either pro-IGIF or ICE alone (FIG. 2B).

These results indicate that ICE cleavage of pro-IGIF facilitates the export of mature, active IGIF from cells.

Pro-IGIF is a Physiological Substrate of ICE In Vivo

To study the role of ICE in the proteolytic activation and export of IGIF under physiological conditions, we examined the processing of pro-IGIF and export of mature IGIF from lipopolysaccharide (LPS)-activated Kupffer cells harvested from *Propiobacterium acnes*-elicited wild type and ICE deficient (ICE−/−) mice (Example 25).

Figure 3A:
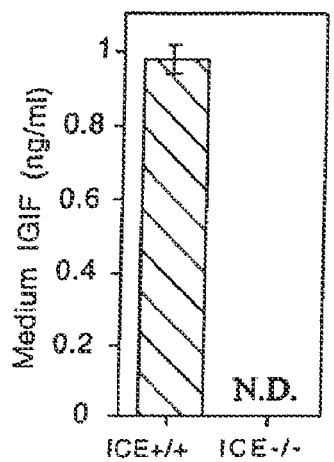
FIG. 3A Kupffer cells from mice lacking ICE are defective in the export of IGIF. Kupffer cells from wild type mice (ICE+/+) or ICE-deficient mice homozygous for an ICE mutation (ICE−/−) were isolated and primed with LPS for three hours. The levels of immunoreactive IGIF polypeptides in the conditioned media (ng/ml) of wild type cells were measured by ELISA (Example 25). N.D. (not detectable) indicates that the IGIF concentration was less than 0.1 ng/ml.

As shown in FIG. 3A, Kupffer cells from ICE−/− mice are defective in the export of IGIF. Kupffer cell lysates of wild type and ICE−/− mice contained similar amounts of IGIF as determined by ELISA. IGIF, however, could be detected only in the conditioned medium of wild type but not of the ICE−/− cells. Thus, ICE-deficient (ICE−/−) mice synthesize pro-IGIF, but fail to export it as extracellular pro- or mature IGIF.

Figure 3B:
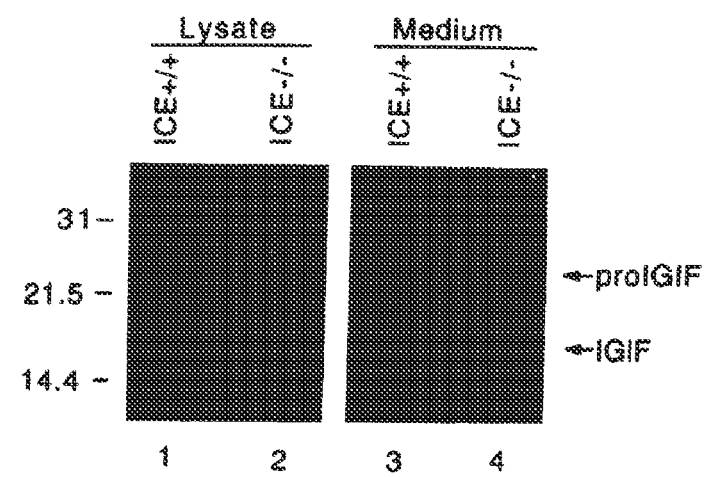
FIG. 3B Kupffer cells from mice lacking ICE are defective in the export of mature IGIF. Kupffer cells from wild type mice (ICE+/+) or ICE deficient mice homozygous for an ICE mutation (ICE−/−) were isolated and primed with LPS for three hours. Primed cells were metabolically labeled with $^{35}$S-methionine, proteins from cell lysates and conditioned medium immunoprecipitated with anti-IGIF antisera and separated by SDS-PAGE (Example 25). Mobilities of pro-IGIF and the 18-kDa mature IGIF are indicated on the right. Molecular mass markers in kDa are shown on the left.

To determine whether ICE-deficient (ICE−/−) mice process intracellular pro-IGIF but fail to export IGIF, Kupffer cells from wild type and ICE−/− mice were metabolically labeled with $^{35}$S-methionine and IGIF immunoprecipitation experiments were performed on cell lysates and conditioned media as described in Example 25. These experiments demonstrated that unprocessed pro-IGIF was present in both wild type and ICE−/− Kupffer cells. However, the 18-kDa mature IGIF was present only in the conditioned medium of wild type and not ICE−/− Kupffer cells (FIG. 3B). This shows that active ICE is required in cells for the export of processed IGIF out of the cell.

In addition, conditioned medium from wild type but not from ICE−/− Kupffer cells contained IFN-γ inducing activity that was not attributed to the action of IL-12 because it was insensitive to a neutralizing anti-IL-12 antibody. The absence of IGIF in the conditioned medium of ICE−/− Kupffer cells is consistent with the finding in Cos cells that the processing of pro-IGIF by ICE is required for the export of active IGIF.

Figure 3C:
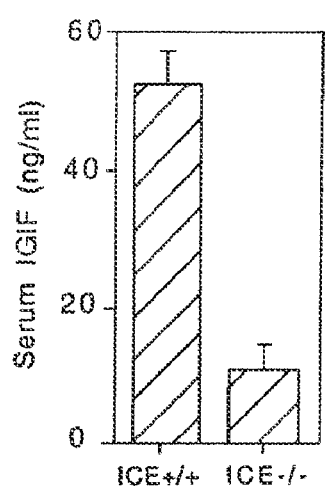
FIG. 3C Serum from ICE-deficient mice contains reduced levels of IGIF. Serum samples from wild type mice (ICE+/+) or ICE deficient mice homozygous for an ICE mutation (ICE−/−) were assayed for IGIF levels (ng/ml) by ELISA (Example 25).
Figure 3D:
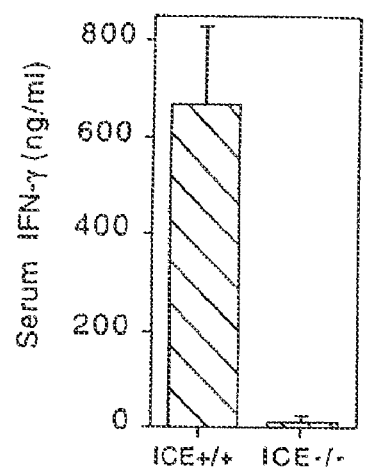
FIG. 3D Serum from ICE-deficient mice contains reduced levels of IFN-γ. Serum samples from wild type mice (ICE+/+) or ICE deficient mice homozygous for an ICE mutation (ICE−/−) were assayed for IFN-γ levels (ng/ml) by ELISA (Example 25).

FIGS. 3C and 3D show that, in vivo, ICE−/− mice have reduced serum levels of IGIF and IFN-γ, respectively. Wild type (ICE+/+) and ICE−/− mice (n=3) primed with heat-inactivated *P. acnes* were challenged with LPS (Example 26), and the levels of IGIF (FIG. 3C) and IFN-γ (FIG. 3D) in the sera of challenged mice were measured by ELISA three hours after LPS challenge (Example 25).

The sera of ICE−/− mice stimulated by *P. acnes* and LPS contained reduced levels of IGIF (FIG. 3C) and no detectable IFN-γ inducing activity in the presence of an anti-IL-12 antibody. The reduced serum levels of IGIF likely accounts for the significantly lower levels of IFN-γ in the sera of ICE−/− mice (FIG. 3D), because we have observed no significant difference in the production of IL-12 in ICE−/− mice under these conditions. Consistent with this interpretation is the finding that non-adherent splenocytes from wild type and ICE−/− mice produced similar amounts of IFN-γ when stimulated with recombinant active IGIF in vitro. Thus the impaired production of IFN-γ is not due to any apparent defect in the T cells of the ICE−/− mice.

Taken together, these results establish a critical role for ICE in processing the IGIF precursor and in the export of active IGIF both in vitro and in vivo.

Figure 4:
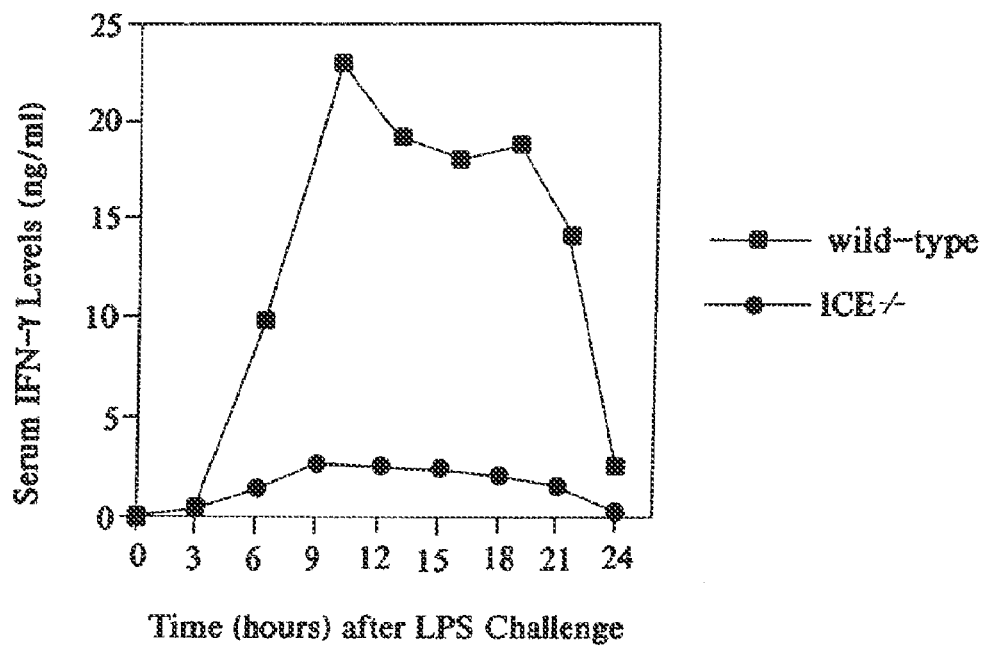
FIG. 4 Serum IFN-γ levels are significantly reduced in ICE-deficient mice after an acute challenge with LPS (Example 26). Serum samples from wild type mice (filled squares) or ICE-deficient mice (filled circles) were assayed for IFN-γ levels (ng/ml) by ELISA as a function of time (hours) after LPS challenge. Temperatures of the animals during the time course in degrees Celcius is shown for wild type mice (open squares) or ICE-deficient mice (open circles).

To examine in more detail the relationship between serum levels of IFN-γ and ICE activity in vivo, a time course after challenge of wild type and ICE-deficient mice with LPS was performed (Example 26) (FIG. 4).

FIG. 4 shows a time course increase of serum IFN-γ in wild type mice, with sustained levels of ≧17 ng/ml occurring from 9-18 hrs after LPS challenge. As predicted by the experiments discussed above, serum IFN-γ levels were significantly lower in ICE−/− mice, with a maximum of 2 ng/ml achieved over the same time period, which is approximately 15% of the level observed in wild type mice (FIG. 4).

Animals were also observed for clinical signs of sepsis and body temperature was measured at 4-hour intervals in wild type and ICE−/− mice challenged with 30 mg/kg or 100 mg/kg LPS (ICE−/− only). Results in FIG. 4 show that wild type mice experienced a significant decrease in body temperature (from 36° C. to 26° C.) within 12 hours of LPS challenge. Signs of clinical sepsis were evident and all animals expired within 24-28 hours.

In contrast, ICE−/− mice challenged with 30 mg/kg LPS experienced only a 3°-4° C. decrease in body temperature with minimal signs of distress and with no observed lethality. ICE−/− mice challenged with 100 mg/kg LPS experienced clinical symptoms, a decrease in body temperature, and mortality similar to wild type mice at the 30 mg/kg LPS dose.

The ICE Inhibitor Ac-YVAD-CHO (SEQ ID NO: 2) is an Equipotent Inhibitor of IL-18 and IFN-γ Production.

Since the processing and secretion of biologically active IGIF is mediated by ICE, we compared the activity of a reversible ICE inhibitor (Ac-YVAD-CHO, SEQ ID NO: 2) on IL-1β and IFN-γ production in a peripheral blood mononuclear cell (PBMC) assay (Examples 27).

Figure 5:
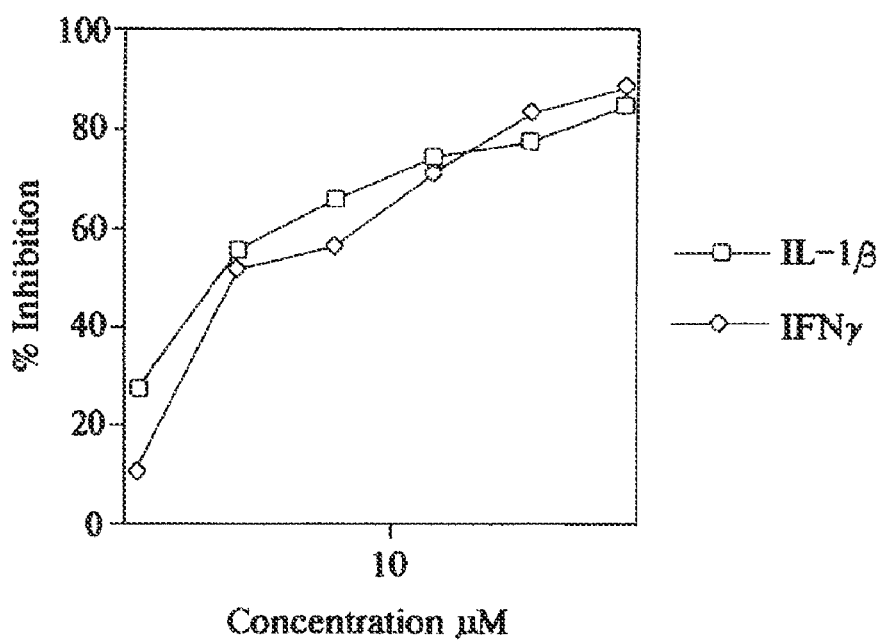
FIG. 5 The ICE inhibitor, AcYVAD-aldehyde (AcYVAD-CHO, SEQ ID NO: 2), inhibits LPS-stimulated IL-18 and IFN-γ synthesis by human peripheral blood mononuclear cells (PBMC). Percent (%) inhibition as a function of inhibitor concentration (μM) is shown for IL-1β (open squares) and IFN-γ (open diamonds) synthesis.

Results in FIG. 5 show a similar potency for the ability of the Ac-YVAD-CHO (SEQ ID NO: 2) ICE inhibitor to decrease IL-1β and IFN-γ production in human PBMCs, with an $IC_{50}$ of 2.5 μM for each. Similar results were obtained in studies with wild type mouse splenocytes.

These findings provide additional evidence that pro-IGIF is a physiological substrate for ICE and suggest that ICE inhibitors will be useful tools for controlling physiological levels of IGIF and IFN-γ.

In summary, we have found that ICE controls IGIF and IFN-γ levels in vivo and in vitro and that ICE inhibitors can decrease levels of IGIF and IFN-γ in human cells. These results have been described in co-pending U.S. application Ser. No. 08/712,878, the disclosure of which is herein incorporated by reference.

Compositions and Methods

The pharmaceutical compositions and methods of this invention will be useful for controlling IL-1, IGIF and IFN-γ levels in vivo. The methods and compositions of this invention will thus be useful for treating or reducing the advancement, severity of effects of IL-1, IGIF- and IFN-γ-mediated conditions.

The compounds of this invention are effective ligands for ICE. Accordingly, these compounds are capable of targeting and inhibiting events in IL-1-, apoptosis-, IGIF-, and IFN-γ-mediated diseases, and, thus, the ultimate activity of that protein in inflammatory diseases, autoimmune diseases, destructive bone, proliferative disorders, infectious diseases, and degenerative diseases. For example, the compounds of this invention inhibit the conversion of precursor IL-1β to mature IL-1β by inhibiting ICE. Because ICE is essential for the production of mature IL-1, inhibition of that enzyme effectively blocks initiation of IL-1-mediated physiological effects and symptoms, such as inflammation, by inhibiting the production of mature IL-1. Thus, by inhibiting IL-1β precursor activity, the compounds of this invention effectively function as IL-1 inhibitors.

Similarly, compounds of this invention inhibit the conversion of precursor IGIF to mature IGIF. Thus, by inhibiting IGIF production, the compounds of this invention effectively function as inhibitors of IFN-γ production.

Accordingly, one embodiment of this invention provides a method for decreasing IGIF production in a subject comprising the step of administering to the subject a pharmaceutical composition comprising a therapeutically effective amount of an ICE inhibitor and a pharmaceutically acceptable carrier.

Another embodiment of this invention provides a method for decreasing IFN-γ production in a subject comprising the step of administering to the subject a pharmaceutical composition comprising a therapeutically effective amount of an ICE inhibitor and a pharmaceutically acceptable carrier.

In another embodiment, the methods of this invention comprise the step of administering to a subject a pharmaceutical composition comprising an inhibitor of an ICE-related protease that is capable of cleaving pro-IGIF to active IGIF, and a pharmaceutically acceptable carrier. One such ICE-related protease is TX, as described above. This invention thus provides methods and pharmaceutical compositions for controlling IGIF and IFN-γ levels by administering a TX inhibitor.

Other ICE-related proteases capable of processing pro-IGIF into an active IGIF form may also be found. Thus it is envisioned that inhibitors of those enzymes may be identified by those of skill in the art and will also fall within the scope of this invention.

The compounds of this invention may be employed in a conventional manner for the treatment of diseases which are mediated by IL-1, apoptosis, IGIF or IFN-γ. Such methods of treatment, their dosage levels and requirements may be selected by those of ordinary skill in the art from available methods and techniques. For example, a compound of this invention may be combined with a pharmaceutically acceptable adjuvant for administration to a patient suffering from an IL-1-, apoptosis-, IGIF- or IFN-γ-mediated disease in a pharmaceutically acceptable manner and in an amount effective to lessen the severity of that disease.

Alternatively, the compounds of this invention may be used in compositions and methods for treating or protecting individuals against IL-1-, apoptosis-, IGIF- or IFN-γ-mediated diseases over extended periods of time. The compounds may be employed in such compositions either alone or together with other compounds of this invention in a manner consistent with the conventional utilization of ICE inhibitors in pharmaceutical compositions. For example, a compound of this invention may be combined with pharmaceutically acceptable adjuvants conventionally employed in vaccines and administered in prophylactically effective amounts to protect individuals over an extended period of time against IL-1-, apoptosis-, IGIF- or IFN-γ-mediated diseases.

The compounds of this invention may also be co-administered with other ICE inhibitors to increase the effect of therapy or prophylaxis against various IL-1-, apoptosis, IGIF- or IFN-γ-mediated diseases.

In addition, the compounds of this invention may be used in combination either conventional anti-inflammatory agents or with matrix metalloprotease inhibitors, lipoxygenase inhibitors and antagonists of cytokines other than IL-1β.

The compounds of this invention can also be administered in combination with immunomodulators (e.g., bropirimine, anti-human alpha interferon antibody, IL-2, GM-CSF, methionine enkephalin, interferon alpha, diethyldithiocarbamate, tumor necrosis factor, naltrexone and rEPO) or with prostaglandins, to prevent or combat IL-1-mediated disease symptoms such as inflammation.

When the compounds of this invention are administered in combination therapies with other agents, they may be administered sequentially or concurrently to the patient. Alternatively, pharmaceutical or prophylactic compositions according to this invention comprise a combination of an ICE inhibitor of this invention and another therapeutic or prophylactic agent.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as da-tocopherol polyethyleneglycol 1000 succinate, or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrines, or other solubilized derivatives may also be advantageously used to enhanve delivery of compounds of this invention.

The pharmaceutical compositions of this invention may be administered orally, parenterally, by inhalation spray, topically, rectally, nasally, buccally, vaginally or via an implanted reservoir. We prefer oral administration. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compounds or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as *Ph. Helv* or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxy-ethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-administered transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 1 and 50 mg/kg body weight per day of the active ingredient compound are useful in the prevention and treatment of IL-1-, apoptosis, IGIF and IFN-γ-mediated diseases, including inflammatory diseases, autoimmune diseases, destructive bone disorders, proliferative disorders, infectious diseases, degenerative diseases, necrotic diseases, osteoarthritis, acute pancreatitis, chronic pancreatitis, asthma, adult respiratory distress syndrome, glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, inflammatory bowel disease, Crohn's disease, psoriasis, graft vs. host disease, osteoporosis, multiple myeloma-related bone disorder, acute myelogenous leukemia, chronic myelogenous leukemia, metastatic melanoma, Kaposi's sarcoma, multiple myeloma sepsis, septic shock, Shigellosis, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke. Typically, the pharmaceutical compositions of this invention will be administered from about 1 to 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence or disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

The IL-1 mediated diseases which may be treated or prevented by the compounds of this invention include, but are not limited to, inflammatory diseases, autoimmune diseases, destructive bone disorders, proliferative disorders, infectious diseases, and degenerative diseases. The apoptosis-mediated diseases which may be treated or prevented by the compounds of this invention include degenerative diseases.

Inflammatory diseases which may be treated or prevented include, but are not limited to osteoarthritis, acute pancreatitis, chronic pancreatitis, asthma, and adult respiratory distress syndrome. Preferably the inflammatory disease is osteoarthritis or acute pancreatitis.

Autoimmune diseases which may be treated or prevented include, but are not limited to, glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, chronic active hepatitis, myasthenia gravis, multiple sclerosis, inflammatory bowel disease, Crohn's disease, psoriasis, and graft vs. host disease. Preferably the autoimmune disease is rheumatoid arthritis, inflammatory bowel disease, Crohn's disease, or psoriasis.

Destructive bone disorders which may be treated or prevented include, but are not limited to, osteoporosis and multiple myeloma-related bone disorder.

Proliferative diseases which may be treated or prevented include, but are not limited to, acute myelogenous leukemia, chronic myelogenous leukemia, metastatic melanoma, Kaposi's sarcoma, and multiple myeloma.

Infectious diseases which may be treated or prevented include, but are not limited to, sepsis, septic shock, and Shigellosis.

The IL-1-mediated degenerative or necrotic diseases which may be treated or prevented by the compounds of this invention include, but are not limited to, Alzheimer's disease, Parkinson's disease, cerebral ischemia, and myocardial ischemia. Preferably, the degenerative disease is Alzheimer's disease.

The apoptosis-mediated degenerative diseases which may be treated or prevented by the compounds of this invention include, but are not limited to, Alzheimer's disease, Parkinson's disease, cerebral ischemia, myocardial ischemia, spinal muscular atrophy, multiple sclerosis, AIDS-related encephalitis, HIV-related encephalitis, aging, alopecia, and neurological damage due to stroke.

The methods of this invention may be used for treating, or reducing the advancement, severity or effects of an IGIF- or IFN-γ-mediated inflammatory, autoimmune, infectious, proliferative, destructive bone, necrotic, and degenerative conditions, including diseases, disorders or effects, wherein the conditions are characterized by increased levels of IGIF or IFN-γ production.

Examples of such inflammatory conditions include, but are not limited to, osteoarthritis, acute pancreatitis, chronic pancreatitis, asthma, rheumatoid arthritis, inflammatory bowel disease, Crohn's disease, ulcerative collitis, cerebral ischemia, myocardial ischemia and adult respiratory distress syndrome.

Preferably, the inflammatory condition is rheumatoid arthritis, ulcerative collitis, Crohn's disease, hepatitis and adult respiratory distress syndrome.

Examples of such infectious conditions include, but are not limited to, infectious hepatitis, sepsis, septic shock and Shigellosis.

Examples of such autoimmune conditions include, but are not limited to, glomerulonephritis, systemic lupus erythematosus, scleroderma, chronic thyroiditis, Graves' disease, autoimmune gastritis, insulin-dependent diabetes mellitus (Type I), juvenile diabetes, autoimmune hemolytic anemia, autoimmune neutropenia, thrombocytopenia, myasthenia gravis, multiple sclerosis, psoriasis, lichenplanus, graft vs. host disease, acute dermatomyositis, eczema, primary cirrhosis, hepatitis, uveitis, Behcet's disease, acute dermatomyositis, atopic skin disease, pure red cell aplasia, aplastic anemia, amyotrophic lateral sclerosis and nephrotic syndrome.

Preferably the autoimmune condition is glomerulonephritis, insulin-dependent diabetes mellitus (Type I), juvenile diabetes, psoriasis, graft vs. host disease, including transplant rejection, and hepatitis.

Examples of such destructive bone disorders include, but are not limited to, osteoporosis and multiple myeloma-related bone disorder.

Examples of such proliferative conditions include, but are not limited to, acute myelogenous leukemia, chronic myelogenous leukemia, metastatic melanoma, Kaposi's sarcoma, and multiple myeloma.

Examples of such neurodegenerative conditions include, but are not limited to, Alzheimer's disease, Parkinson's disease and Huntington's disease.

Although this invention focuses on the use of the compounds disclosed herein for preventing and treating IL-1, apoptosis, IGIF- and IFN-γ-mediated diseases, the compounds of this invention can also be used as inhibitory agents for other cysteine proteases.

The compounds of this invention are also useful as commercial reagents which effectively bind to ICE or other cysteine proteases. As commercial reagents, the compounds of this invention, and their derivatives, may be used to block proteolysis of a target peptide in biochemical or cellular assays for ICE and ICE homologs or may be derivatized to bind to a stable resin as a tethered substrate for affinity chromatography applications. These and other uses which characterize commercial cystine protease inhibitors will be evident to those of ordinary skill in the art.

Process of Preparing N-Acylamino Compounds

The ICE inhibitors of this invention may be synthesized using conventional techniques. Advantageously, these compounds are conveniently synthesized from readily available starting materials.

The compounds of this invention are among the most readily synthesized ICE inhibitors known. Previously described ICE inhibitors often contain four or more chiral centers and numerous peptide linkages. The relative ease with which the compounds of this invention can be synthesized represents an advantage in the large scale production of these compounds.

For example, compounds of this invention may be prepared using the processes described herein. As can be appreciated by the skilled practitioner, these processes are not the only means by which the compounds described and claimed in this application may be synthesized. Further methods will be evident to those of ordinary skill in the art. Additionally, the various synthetic steps described herein may be performed in an alternate sequence or order to give the desired compounds.

This invention also provides a preferred method for preparing the compounds of this invention. Accordingly, in another embodiment (M) is provided a process for preparing an N-acylamino compound comprising the steps of:

a) mixing a carboxylic acid with an N-alloc-protected amino in the presence of an inert solvent, triphenylphoshine, a nucleophilic scavenger, and tetrakis-triphenyl phosphine palladium(0) at ambient temperature under an inert atmosphere; and b) adding to the step a) mixture, HOBT and EDC; and optionally comprising the further step of:

c) hydrolyzing the step b) mixture in the presence of a solution comprising an acid and H2O, wherein the step b) mixture is optionally concentrated, prior to hydrolyzing.

Preferably, the inert solvent is $CH_2Cl_2$, DMF, or a mixture of $CH_2Cl_2$ and DMF.

Preferably, the nucleophilic scavenger is dimedone, morpholine, trimethylsilyl dimethylamine, or dimethyl barbituric acid. More preferably, the nucleophilic scavenger is trimethylsilyl dimethylamine or dimethyl barbituric acid.

Preferably, the solution comprises trifluoroacetic acid in about 1-90% by weight. More preferably, the solution comprises trifluoroacetic acid in about 20-50% by weight.

Alternatively, the solution comprises hydrochloric acid in about 0.1-30% by weight. More preferably, the solution comprises hydrochloric acid in about 0.1-30% by weight.

More preferably, in the above process, the inert solvent is $CH_2Cl_2$, DMF, or a mixture of $CH_2Cl_2$ and DMF and the nucleophilic scavenger is dimedone, morpholine, trimethylsilyl dimethylamine, or dimethyl barbituric acid.

Most preferably, in the above process the inert solvent is $CH_2Cl_2$, DMF, or a mixture of $CH_2Cl_2$ and DMF and the nucleophilic scavenger is trimethylsilyl dimethylamine or dimethyl barbituric acid.

Preferably, the N-acyclamino compound is represented by formula (VIII):

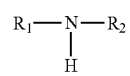

wherein:

R1 is as defined above in embodiment (A);

R2 is:

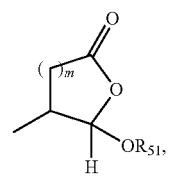

(a)

wherein $R_{51}$ is as defined above in embodiment (B);

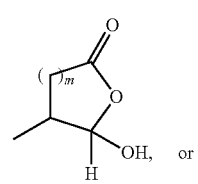

(b)

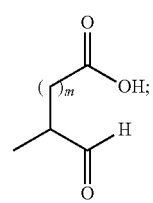

(c)

Preferably, the N-alloc-protected amine is:

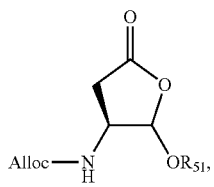

wherein $R_{51}$ is as defined above.

In preferred processes, the substituents are as defined in embodiment (A).

Alternatively, the N-acylamino compound is represented by formula (VIII), wherein $R_1$ is as defined above in embodiment (B) and $R_2$ is as defined above in embodiment (M).

Preferably in these alternative processes, the substituents are as defined above in embodiment (B).

Alternatively, the N-acylamino compound is represented by formula (VIII), wherein $R_1$ is as defined above in embodiment (C) and $R_2$ is as defined above in embodiment (M).

Preferably in these alternative processes, the substituents are as defined above in embodiment (C).

Alternatively, the N-acylamino compound is represented by formula (VIII), wherein $R_1$ is as defined above in embodiment (D) and $R_2$ is as defined above in embodiment (M).

Preferably in these alternative processes, the substituents are as defined above in embodiment (D).

Alternatively, the N-acylamino compound is represented by formula (VIII), wherein $R_1$ is as defined above in embodiment (E) and $R_2$ is as defined above in embodiment (M).

Preferably in these alternative processes, the substituents are as defined above in embodiment (E).

Alternatively, the N-acylamino compound is represented by formula (VIII), wherein $R_1$ is as defined above in embodiment (F) and $R_2$ is as defined above in embodiment (M).

Preferably in these alternative processes, the substituents are as defined above in embodiment (F).

Alternatively, the N-acylamino compound is represented by formula (VIII), wherein $R_1$ is as defined above in embodiment (G) and $R_2$ is as defined above in embodiment (G).

Preferably in these alternative processes, the substituents are as defined above in embodiment (G).

Alternatively, the N-acylamino compound is represented by formula (VIII), wherein $R_1$ is as defined above in embodiment (H) and $R_2$ is as defined above in embodiment (M).

Preferably in these alternative processes, the substituents are as defined above in embodiment (H).

Alternatively, the N-acylamino compound is represented by formula (VIII), wherein $R_1$ is as defined above in embodiment (I) and $R_2$ is as defined above in embodiment (M).

Preferably in these alternative processes, the substituents are as defined above in embodiment (I).

Alternatively, the N-acylamino compound is represented by formula (VIII), wherein $R_1$ is as defined above in embodiment (J) and $R_2$ is as defined above in embodiment (M).

Preferably in these alternative processes, the substituents are as defined above in embodiment (J).

Alternatively, the N-acylamino compound is represented by formula (VIII), wherein $R_1$ is as defined above in embodiment (K) and $R_2$ is as defined above in embodiment (M).

Preferably in these alternative processes, the substituents are as defined above in embodiment (K).

Alternatively, the N-acylamino compound is represented by formula (VIII), wherein $R_1$ is as defined above in embodiment (L) and $R_2$ is as defined above in embodiment (M).

Preferably in these alternative processes, the substituents are as defined above in embodiment (L).

In order that this invention be more fully understood, the following examples are set forth. These examples are for the purpose of illustration only and are not to be construed as limiting the scope of the invention in any way.

EXAMPLE 1

Inhibition of ICE

We obtained inhibition constants ($K_i$) and $IC_{50}$ values for compounds of this invention using the three methods described below:

1. Enzyme Assay with UV-Visible Substrate

This assay is run using an Succinyl-Tyr-Val-Ala-Asp-pNitroanilide (SEQ ID NO: 5) substrate. Synthesis of analogous substrates is described by L. A. Reiter (Int. J. Peptide Protein Res. 43, 87-96 (1994)). The assay mixture contains:
65 μl buffer (10 mM Tris, 1 mM DTT, 0.1% CHAPS @pH 8.1)
10 μl ICE (50 nM final concentration to give a rate of ~1 mOD/min)
5 μl DMSO/Inhibitor mixture
20 μl 400 μM Substrate (80 μM final concentration)
100 μl total reaction volume The visible ICE assay is run in a 96-well microtiter plate. Buffer, ICE and DMSO (if inhibitor is present) are added to the wells in the order listed. The components are left to incubate at room temperature for 15 minutes starting at the time that all components are present in all wells. The microtiter plate reader is set to incubate at 37° C. After the 15 minute incubation, substrate is added directly to the wells and the reaction is monitored by following the release of the chromophore (pNA) at 405-603 nm at 37° C. for 20 minutes. A linear fit of the data is performed and the rate is calculated in mOD/min. DMSO is only present during experiments involving inhibitors, buffer is used to make up the volume to 100 μl in the other experiments.

2. Enzyme Assay with Fluorescent Substrate

This assay is run essentially according to Thornberry et al. (Nature 356: 768-774 (1992)), using substrate 17 referenced in that article. The substrate is: Acetyl-Tyr-Val-Ala-Asp-amino-4-methylcoumarin (AMC) (SEQ ID NO: 6). The following components are mixed:
65 μl buffer (10 mM Tris, 1 mM DTT, 0.1% CHAPS @pH8.1)
10 μl ICE (2-10 nM final concentration)
5 μl DMSO/inhibitor solution
20 μl 150 μM Substrate (30 μM final)
100 μl total reaction volume The assay is run in a 96 well microtiter plate. Buffer and ICE are added to the wells. The components are left to incubate at 37° C. for 15 minutes in a temperature-controlled wellplate. After the 15 minute incubation, the reaction is started by adding substrate directly to the wells and the reaction is monitored @37° C. for 30 minutes by following the release of the AMC fluorophore using an excitation wavelength for 380 nm and an emission wavelength of 460 nm. A linear fit of the data for each well is performed and a rate is determined in fluorescence units per second.

For determination of enzyme inhibition constants ($K_i$) or the mode of inhibition (competitive, uncompetitive or non-competitive), the rate data determined in the enzyme assays at varying inhibitor concentrations are computer-fit to standard enzyme kinetic equations (see I. H. Segel, *Enzyme Kinetics*, Wiley-Interscience, 1975).

The determination of second order rate constants for irreversible inhibitors was performed by fitting the fluorescence vs time data to the progress equations of Morrison. Morrison, J. F., *Mol. Cell. Biophys.*, 2, pp. 347-368 (1985). Thornberry et al. have published a description of these methods for measurement of rate constants of irreversible inhibitors of ICE. Thornberry, N. A., et al. *Biochemistry*, 33, pp. 3923-3940 (1994). For compounds where no prior complex formation can be observed kinetically, the second order rate constants ($k_{inact}$) are derived directly from the slope of the linear plots of $k_{obs}$ vs. [I]. For compounds where prior complex formation to the enzyme can be detected, the hyperbolic plots of $k_{obs}$ vs. [I] are fit to the equation for saturation kinetics to first generate $K_i$ and k'. The second order rate constant $k_{inact}$ is then given by k'/$K_i$.

3. PBMC Cell Assay

IL-1β Assay with a Mixed Population of Human Peripheral Blood Mononuclear Cells (PBMC) or Enriched Adherent Mononuclear Cells Processing of pre-IL-1β by ICE can be measured in cell culture using a variety of cell sources. Human PBMC obtained from healthy donors provides a mixed population of lymphocyte subtypes and mononuclear cells that produce a spectrum of interleukins and cytokines in response to many classes of physiological stimulators. Adherent mononuclear cells from PBMC provides an enriched source of normal monocytes for selective studies of cytokine production by activated cells.

Experimental Procedure:

An initial dilution series of test compound in DMSO or ethanol is prepared, with a subsequent dilution into RPMI-10% FBS media (containing 2 mM L-glutamine, 10 mM HEPES, 50 U and 50 ug/ml pen/strep) respectively to yield drugs at 4× the final test concentration containing 0.4% DMSO or 0.4% ethanol. The final concentration of DMSO is 0.1% for all drug dilutions. A concentration titration which brackets the apparent $K_i$ for a test compound determined in an ICE inhibition assay is generally used for the primary compound screen.

Generally 5-6 compound dilutions are tested and the cellular component of the assay is performed in duplicate, with duplicate ELISA determinations on each cell culture supernatant.

PBMC Isolation and IL-1 Assay:

Buffy coat cells isolated from one pint human blood (yielding 40-45 ml final volume plasma plus cells) are diluted with media to 80 ml and LeukoPREP separation tubes (Becton Dickinson) are each overlaid with 10 ml of cell suspension. After 15 min centrifugation at 1500-1800×g, the plasma/media layer is aspirated and then the mononuclear cell layer is collected with a Pasteur pipette and transferred to a 15 ml conical centrifuge tube (Corning). Media is added to bring the volume to 15 ml, gently mix the cells by inversion and centrifuge at 300×g for 15 min. Resuspend the PBMC pellet in a small volume of media, count cells and adjust to $6 \times 10^6$ cells/ml.

For the cellular assay, 1.0 ml of the cell suspension is added to each well of a 24-well flat bottom tissue culture plate (Corning), 0.5 ml test compound dilution and 0.5 ml LPS solution (Sigma #L-3012; 20 ng/ml solution prepared in complete RPMI media; final LPS concentration 5 ng/ml). The 0.5 ml additions of test compound and LPS are usually sufficient to mix the contents of the wells. Three control mixtures are run per experiment, with either LPS alone, solvent vehicle control, and/or additional media to adjust the final culture volume to 2.0 ml. The cell cultures are incubated for 16-18 hr at 37° C. in the presence of 5% $CO_2$.

At the end of the incubation period, cells are harvested and transferred to 15 ml conical centrifuge tubes. After centrifugation for 10 min at 200×g, supernatants are harvested and transferred to 1.5 ml Eppendorf tubes. It may be noted that the cell pellet may be utilized for a biochemical evaluation of pre-IL-1β and/or mature IL-1β content in cytosol extracts by western blotting or ELISA with pre-IL-1β specific antisera.

Isolation of Adherent Mononuclear Cells:

PBMC are isolated and prepared as described above. Media (1.0 ml) is first added to wells followed by 0.5 ml of the PBMC suspension. After a one hour incubation, plates are gently shaken and nonadherent cells aspirated from each well. Wells are then gently washed three times with 1.0 ml of media and final resuspended in 1.0 ml media. The enrichment for adherent cells generally yields $2.5-3.0 \times 10^5$ cells per well. The addition of test compounds, LPS, cell incubation conditions and processing of supernatants proceeds as described above.

ELISA:

We have used Quantikine kits (R&D Systems) for measurement of mature IL-1β. Assays are performed according to the manufacturer's directions. Mature IL-1β levels of about 1-3 ng/ml in both PBMC and adherent mononuclear cell positive controls are observed. ELISA assays are performed on 1:5, 1:10 and 1:20 dilutions of supernatants from LPS-positive controls to select the optimal dilution for supernatants in the test panel.

The inhibitory potency of the compounds can be represented by an $IC_{50}$ value, which is the concentration of inhibitor at which 50% of mature IL-1β is detected in the supernatant as compared to the positive controls.

The skilled practitioner realizes that values obtained in cell assays, such as those described herein, can depend on multiple factors, such as cell type, cell source, growth conditions and the like.

EXAMPLE 2

Pharmacokinetic Studies In the Mouse

Peptidyl ICE inhibitors are cleared rapidly with clearance rates greater than 100μ/min/kg. Compounds with lower clearance rates have improved pharmacokinetic properties relative to peptidyl ICE inhibitors.

We obtained the rate of clearance in the mouse (μ/min/kg) for several compounds of this Invention using the method described below:

Sample Preparation and Dosing

Compounds were dissolved in sterile TRIS solution (0.02M or 0.05M) at a concentration of 2.5 mg/ml. Where necessary to ensure a complete solution, the sample was first dissolved in a minimum of dimethylacetamide (maximum of 5% of total solution volume) then diluted with the TRIS solution.

The drug solution was administered to CD-1 mice (Charles River Laboratories—26-31 g) via the tail vein at a dose volume of 10 ml/kg giving a drug dose of 25 mg/kg.

Mice were dosed in groups of 5 for each timepoint (generally from 2 minutes to 2 hours) then at the appropriate time the animals were anaesthetised with halothane and the blood collected into individual heparinized tubes by jugular severance. The blood samples were cooled to 0° C. then the plasma separated and stored at −20° C. until assayed.

Bioassay

Drug concentration in the plasma samples were determined by HPLC analysis with UV or MS (ESP) detection. Reverse phase chromatography was employed using a variety of bonded phases from C1 to C18 with eluents composed of aqueous buffer/acetonitrile mixtures run under isocratic conditions.

Quantitation was by external standard methods with calibration curves constructed by spiking plasma with drug solutions to give concentrations in the range of 0.5 to 50 µg/ml.

Prior to analysis the plasma samples were deproteinated by the addition of acetonitrile, methanol, trichloroacetic acid or perchloric acid followed by centrifugation at 10,000 g for 10 minutes. Sample volumes of 20 µl to 50 µl were injected for analysis.

Compound 214e

Dosing and Sampling

The drug was dissolved in sterile 0.02M Tris to give a 2.5 mg/ml solution which was administered to 11 groups of 5 male CD-1 mice via the tail vein at a dose of 25 mg/kg. At each of the following timepoints: 2, 5, 10, 15, 20, 30, 45, 60, 90 and 120 minutes a group of animals was anaesthetised and the blood collected into heparinized tubes. After separation the plasma was stored at −20° C. until assayed.

Assay

Aliquots of plasma (150 µl) were treated with 5% perchloric acid (5 µl) then mixed by vortexing and allowed to stand for 90 minutes prior to centrifugation. The resulting supernatant was separated and 20 µl was injected for HPLC analysis.

HPLC Conditions

| HPLC Conditions | | |
| --- | --- | --- |
| Column | 100 × 4.6 mm | Kromasil KR 100 5C4 |
| Mobile Phase | 0.1 m Tris pH 7.5 | 86% |
| | Acetonitrile | 14% |
| Flowrate | 1 ml/min | |
| Detection | UV at 210 nm | |
| Retention Time | 3.4 mins | |

The results of the analysis indicated a decrease in the mean plasma level of the drug from ~70 µg/ml at 2 minutes to <2 µg/ml at 90 and 120 minutes.

Compound 217e

Dosing and Sampling

The drug was dissolved in sterile 0.02M Tris to give a 2.5 mg/ml solution which was administered to 11 groups of 5 male CD-1 mice via the tail vein at a dose of 25 mg/kg. At each of the following timepoints: 2, 5, 10, 15, 20, 30, 45, 60, 90 and 120 minutes a group of animals was anaesthetised and the blood collected into heparinized tubes. After separation the plasma was stored at −20° C. until assayed.

Assay

Aliquots of plasma (100 µl) were diluted with acetonitrile (100 µl) then mixed by vortexing for 20 seconds before centrifugation for 10 minutes. The resulting supernatant was separated and 20 µl was injected for HPLC analysis.

HPLC Conditions

| HPLC Conditions | | |
| --- | --- | --- |
| Column | 150 × 4.6 mm | Zorbax SBC8 |
| Mobile Phase | 0.05M Phosphate buffer ph 7.1 | 72% |
| | Acetonitrile | 28% |
| Flowrate | 1.4 ml/min | |
| Detection | UV at 210 nm | |
| Retention Time | 3.0 and 3.6 mins (diasteromers) | |

The results of the analysis indicated a decrease in mean plasma concentrations from ~55 µg/ml at 2 minutes to <0.2 µg/ml at 60-120 minutes.

EXAMPLE 3

Peptidyl ICE inhibitors are cleared rapidly with clearance rates greater than 80 ml/min/kg. Compounds with lower clearance rates have improved pharmacokinetic properties relative to peptidyl ICE inhibitors.

We obtained the rate of clearance in the rat (ml/min/kg) for several compounds of this invention using the method described below:

In Vivo Rat Clearance Assay

Cannulations of the jugular and carotid vessels of rats under anesthesia were performed one day prior to the pharmacokinetic study. M. J. Free, R. A. Jaffee; 'Cannulation techniques for the collection blood and other bodily fluids'; in: *Animal Models; p.* 480-495; N. J. Alexander, Ed.; Academic Press; (1978). Drug (10 mg/mL) was administered via the jugular vein in a vehicle usually consisting of: propylene glycol/saline, containing 100 mM sodium bicarbonate in a 1:1 ratio. Animals were dosed with 10-20 mg drug/kg and blood samples were drawn at 0, 2, 5, 7, 10, 15, 20, 30, 60, and 90 minutes from an indwelling carotid catheter. The blood was centrifuged to plasma and stored at −20° C. until analysis. Pharmacokinetic analysis of data was performed by non-linear regression using standard software such as RStrip (MicroMath Software, UT) and/or Pcnonlin (SCI Software, NC) to obtain clearance values.

Analytical:

Rat plasma was extracted with an equal volume of acetonitrile (containing 0.1% TFA). Samples were then centrifuged at approximately 1,000×g and the supernatant analyzed by gradient HPLC. A typical assay procedure is described below.

200 µL of plasma was precipitated with 200 µL of 0.1% trifluoroacetic acid (TFA) in acetonitrile and 10 µL of a 50% aqueous zinc chloride solution, vortexed then centrifuged at ~1000×g and the supernatant collected and analyzed by HPLC.

HPLC Procedure:

| | |
| --- | --- |
| Column: | Zorbax SB-CN (4.6 × 150 mm) (5µ particle size) |

| | |
|---|---|
| Column temperature: | 50° C. |
| Flow rate: | 1.0 mL/min |
| Injection volume: | 75 µL. |
| Mobile phase: | A = 0.1% TFA in water and B = 100% acetonitrile |
| Gradient employed: | 100% A to 30% A in 15.5 min<br>0% A at 16 min<br>100% A at 19.2 min |
| Wavelength: | 214 nm |

A standard curve was run at 20, 10, 5, 2 and 1 µg/mL concentrations.

EXAMPLE 4

Whole Blood Assay for IL-1β Production

We obtained $IC_{50}$ values for several compounds of this invention using the method described below:

Purpose:

The whole blood assay is a simple method for measuring the production of IL-1b (or other cytokines) and the activity of potential inhibitors. The complexity of this assay system, with its full complement of lymphoid and inflammatory cell types, spectrum of plasma proteins and red blood cells is an ideal in vitro representation of human in vivo physiologic conditions.

Materials:

Pyrogen-free syringes (~30 cc)
Pyrogen-free sterile vacuum tubes containing lyophilized $Na_2EDTA$ (4.5 mg/10 ml tube)
Human whole blood sample (~30-50 cc)
1.5 ml eppendorf tubes
Test compound stock solutions (~25 mM in DMSO or other solvent)
Endotoxin-free sodium chloride solution (0.9%) and HBSS
Lipopolysaccharide (Sigma; Cat.# L-3012) stock solution at 1 mg/ml in HBSS
IL-1β ELISA Kit (R & D Systems; Cat # DLB50)
TNFα ELISA Kit (R & D Systems; Cat # DTA50)
Water Bath or Incubator Whole Blood Assay Experimental Procedure:

Set incubator or water bath at 30° C. Aliquot 0.25 ml of blood into 1.5 ml eppendorf tubes. Note: be sure to invert the whole blood sample tubes after every two aliquots. Differences in replicates may result if the cells sediment and are not uniformly suspended. Use of a positive displacement pipette will also minimize differences between replicate aliquots.

Prepare drug dilutions in sterile pyrogen-free saline by serial dilution. A dilution series which brackets the apparent $K_i$ for a test compound determined in an ICE inhibition assay is generally used for the primary compound screen. For extremely hydrophobic compounds, we have prepared compound dilutions in fresh plasma obtained from the same blood donor or in PBS-containing 5% DMSO to enhance solubility.

Add 25 µl test compound dilution or vehicle control and gently mix the sample. Then add 5.0 µl LPS solution (250 ng/ml stocked prepared fresh: 5.0 ng/ml final concentration LPS), and mix again. Incubate the tubes at 30° C. in a water bath for 16-18 hr with occasional mixing. Alternatively, the tubes can be placed in a rotator set at 4 rpm for the same incubation period. This assay should be set up in duplicate or triplicate with the following controls: negative control—no LPS; positive control—no test inhibitor; vehicle control—the highest concentration of DMSO or compound solvent used in the experiment. Additional saline is added to all control tubes to normalize volumes for both control and experimental whole blood test samples After the incubation period, whole blood samples are centrifuged for 10 minutes at ~2000 rpm in the microfuge, plasma is transferred to a fresh microfuge tube and centrifuged at 1000× g to pellet residual platelets if necessary. Plasma samples may be stored frozen at −70° C. prior to assay for cytokine levels by ELISA.

ELISA:

We have used R & D Systems (614 McKinley Place N.E. Minneapolis, Minn. 55413) Quantikine kits for measurement of IL-1β and TNF-α. The assays are performed according to the manufacturer's directions. We have observed IL-1β levels of ~1-5 ng/ml in positive controls among a range of individuals. A 1:200 dilution of plasma for all samples has been sufficient in our experiments for ELISA results to fall on the linear range of the ELISA standard curves. It may be necessary to optimize standard dilutions if you observe differences in the whole blood assay. Nerad, J. L. et al., *J. Leukocyte Biol.*, 52, pp. 687-692 (1992).

EXAMPLE 5

Inhibition of ICE Homologs

1. Isolation of ICE Homologs

Expression of TX in insect cells using a baculovirus expression system. We have subcloned Tx cDNA (Faucheu et al., supra 1995) into a modified pVL1393 transfer vector, co-transfected the resultant plasmid (pVL1393/TX) into insect cells with viral DNA and identified the recombinant baculovirus. After the generation of high titer recombinant virus stock, the medium was examined for TX activity using the visible ICE assay. Typically, infection of *Spodoptera frugiperda* (Sf9) insect cells at an MOI of 5 with recombinant virus stock resulted in a maximum expression after 48 hours of 4.7 µg/ml. ICE was used as a standard in the assay.

Amino terminal T7 tagged versions of ICE or TX were also expressed. Designed originally to assist the identification and purification of the recombinant proteins, the various constructs have also allowed examination of different levels of expression and of the relative levels of apoptosis experienced by the different homologs. Apoptosis in the infected Sf9 cells (examined using a Trypan Blue exclusion assay) was increased in the lines expressing ICE or TX relative to cells infected with the viral DNA alone.

Expression and purification of N-terminally $(His)_6$-tagged CPP32 in *E. coli*. A cDNA encoding a CPP32 (Fernandes-Alnemri et al, supra 1994) polypeptide starting at Ser (29) was PCR amplified with primers that add in frame XhoI sites to both the 5' and 3' ends of the cDNA and the resulting XhoI fragment ligated into a Xho I-cut pET-15b expression vector to create an in frame fusion with $(his)_6$ tag at the n-terminus of the fusion protein. The predicted recombinant protein starts with the amino acid sequence of MGSSHHHHHHSSG LVPRGSHMLE (SEQ ID NO: 7), where LVPRGS (SEQ ID NO: 8) represents a thrombin cleavage site, followed by CPP32 starting at Ser (29). *E. coli* BL21 (DE3) carrying the plasmid were grown to log phase at 30° C. and were then induced with 0.8 mM IPTG. Cells were harvested two hours after IPTG addition. Lysates were prepared and soluble proteins were purified by Ni-agarose chromatography. All of the expressed CPP32 protein was in the processed form. N-terminal sequencing analysis indicated that the processing occurred at the authentic site between Asp (175) and Ser (176). Approximately 50 μg of CPP32 protein from 200 ml culture. As determined by active site titration, the purified proteins were fully active. The protease preparation were also very active in vitro in cleaving Poly ADP ribose polymerase (PARP) as well as the synthetic DEVD-AMC (SEQ ID NO: 9) substrate (Nicholson et al, supra 1995).

2. Inhibition of ICE Homologs

The selectivity of a panel of reversible inhibitors for ICE homologs is depicted in Table 1. ICE enzyme assays were performed according to Wilson et al (supra 1994) using a YVAD-AMC (SEQ ID NO: 10) substrate (Thornberry et al, supra 1992). Assay of TX activity was performed using the ICE substrate under identical conditions to ICE. Assay of CPP32 was performed using a DEVD-AMC (SEQ ID NO: 9) substrate (Nicholson et al., supra 1995). In general, there is low selectivity between ICE and TX for a wide range of scaffolds. None of the synthetic ICE compounds tested are effective inhibitors of CPP32. Assay of the reversible compounds at the highest concentration (1 μM) revealed no inhibition.

TABLE 1

| Compound | $K_i$ ICE (nM) | $K_i$ TX (nM) | $K_i$ CPP32 (nM) |
|---|---|---|---|
| 214e | 7.5 | 7.0 ± 1.1 | >1000 |
| 135a | 90 | 55 ± 9 | >1000 |
| 125b | 60 | 57 ± 13 | >1000 |
| 137 | 40 | 40 ± 7 | >1000 |

Second-order rate constants for inactivation of ICE and ICE homologs with selected irreversible inhibitors are presented below (Table 2). The irreversible compounds studied are broad spectrum inhibitors of ICE and its homologs. Some selectivity, however, is observed with the irreversible compounds comparing inhibition of ICE and CPP32.

TABLE 2

| Compound | $k_{inact}$ (ICE) $M^{-1} s^{-1}$ | $k_{inact}$ (TX) $M^{-1} s^{-1}$ | $k_{inact}$ (CPP32) $M^{-1} s^{-1}$ |
|---|---|---|---|
| 138 | 120,000 | 150,000 | 550,000 |
| 217d | 475,000 | 250,000 | 150,000 |
| 108a | 100,000 | 25,000 | nd |

EXAMPLE 6

Inhibition of Apoptosis

Fas-Induced Apoptosis in U937 cells. Compounds were evaluated for their ability to block anti-Fas-induced apopotosis. In a preliminary experiment using RT-PCR, we detected mRNA encoding ICE, TX, ICH-1, CPP32 and CMH-1 in unstimulated U937 cells. We used this cell line for apoptosis studies. U937 cells were seeded in culture at $1 \times 10^5$ cells/ml and grown to $\sim 5 \times 10^6$ cells/ml. For apoptosis experiments, $2 \times 10^6$ cells were plated in 24-well tissue culture plates in 1 ml RPMI-1640-10% FBS and stimulated with 100 ng/ml anti-Fas antigen antibody (Medical and Biological Laboratories, Ltd.). After a 24 hr incubation at 37° C., the percentage of apoptotic cells was determined by FACS analysis using Apo-Tag reagents.

All compounds were tested initially at 20 μM and titrations were performed with active compounds to determine $IC_{50}$ values. Inhibition of apoptosis (>75% at 20 μM) was observed for 108a, 136, and 138. An $IC_{50}$ of 0.8 μM was determined for 217e compared to no inhibition of anti-Fas-induced apoptosis by 214e at 20 μM.

EXAMPLE 7

In Vivo Acute Assay for Efficacy as Anti-Inflammatory Agent

LPS-Induced IL-1β Production.

Figure 6:
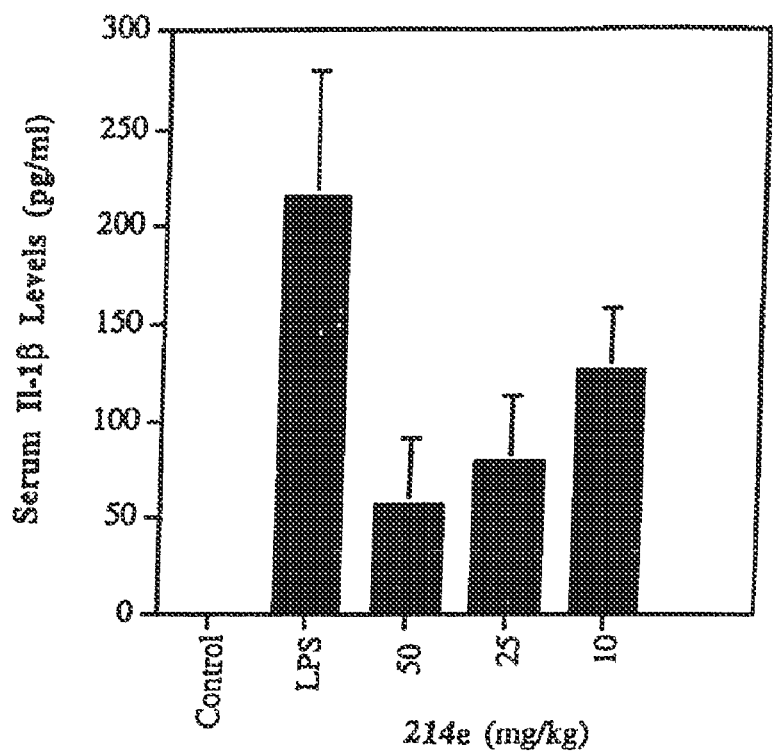
FIG. 6 Compound 214e inhibits IL-1β production in LPS-challenged mice. Serum samples from CD1 mice were assayed for IL-1β levels (pg/ml) by ELISA after LPS challenge. Compound 214e was administered by intraperitoneal (IP) injection one hour after LPS challenge. Blood was collected seven hours after LPS challenge (see Example 7).
Figure 7:
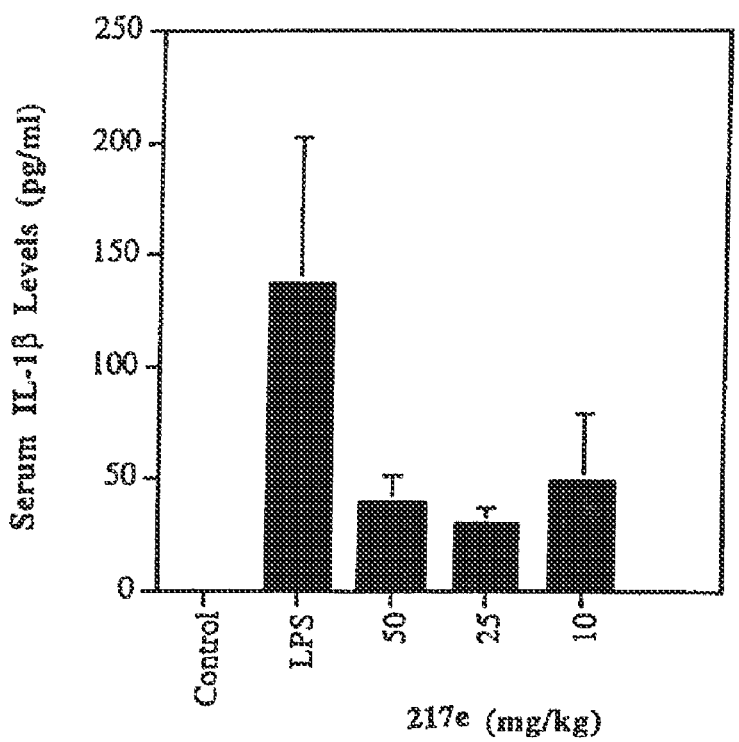
FIG. 7 Compound 217e inhibits IL-1β production in LPS-challenged mice. Serum samples from CD1 mice were assayed for IL-1β levels (pg/ml) by ELISA after LPS challenge. Compound 217e was administered by intraperitoneal (IP) injection one hour after LPS challenge. Blood was collected seven hours after LPS challenge (see Example 7).

Efficacy of 214e and 217e was evaluated in CD1 mice (n=6 per condition) challenged with LPS (20 mg/kg IP). The test compounds were prepared in olive oil:DMSO:ethanol (90:5:5) and administered by IP injection one hour after LPS. Blood was collected seven hours after LPS challenge. Serum IL-1β levels were measure by ELISA. Results in FIG. 6 show a dose dependent inhibition of IL-1β secretion by 214e, with an $ED_{50}$ of approximately 15 mg/kg. Similar results were obtained in a second experiment. A significant inhibition of IL-1β secretion was also observed in 217e treated mice (FIG. 7). However, a clear dose response was not apparent.

Figure 8:
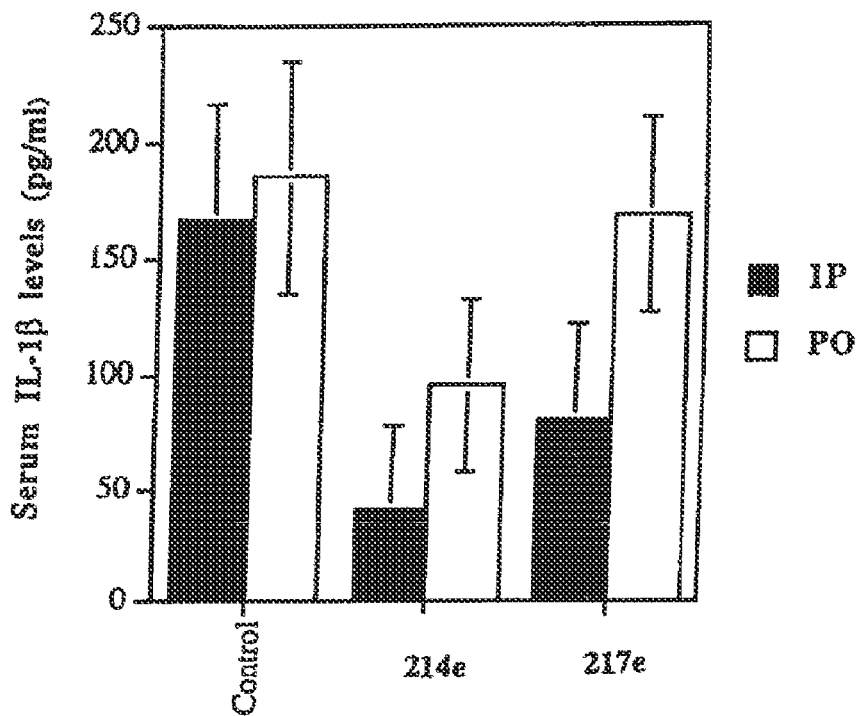
FIG. 8 Compound 214e, but not compound 217e, inhibits IL-1β production in LPS-challenged mice when administered by oral gavage. This assay measures oral absorption under similar conditions as those described for FIGS. 6 and 7. These results indicates that 214e is potentially orally active as an ICE inhibitor (see Example 7).

Compounds 214e and 217e (50 mg/kg) were also administered by oral gavage to assess absorption. Results in FIG. 8 show that 214e, but not 217e when administered orally inhibited IL-1β secretion, suggesting potential for oral efficacy of ICE inhibitors as anti-inflammatory agents.

Figure 9:
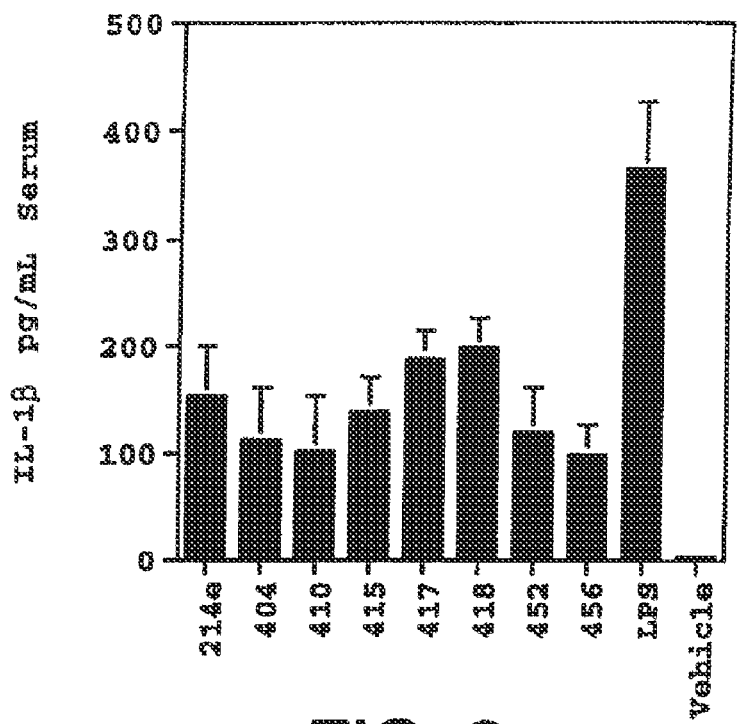
FIG. 9 Compound 214e and analogs of 214e also inhibit IL-1β production after IP administration. These results were obtained in the assay described for FIGS. 6 and 7 and Example 7.
Figure 10:
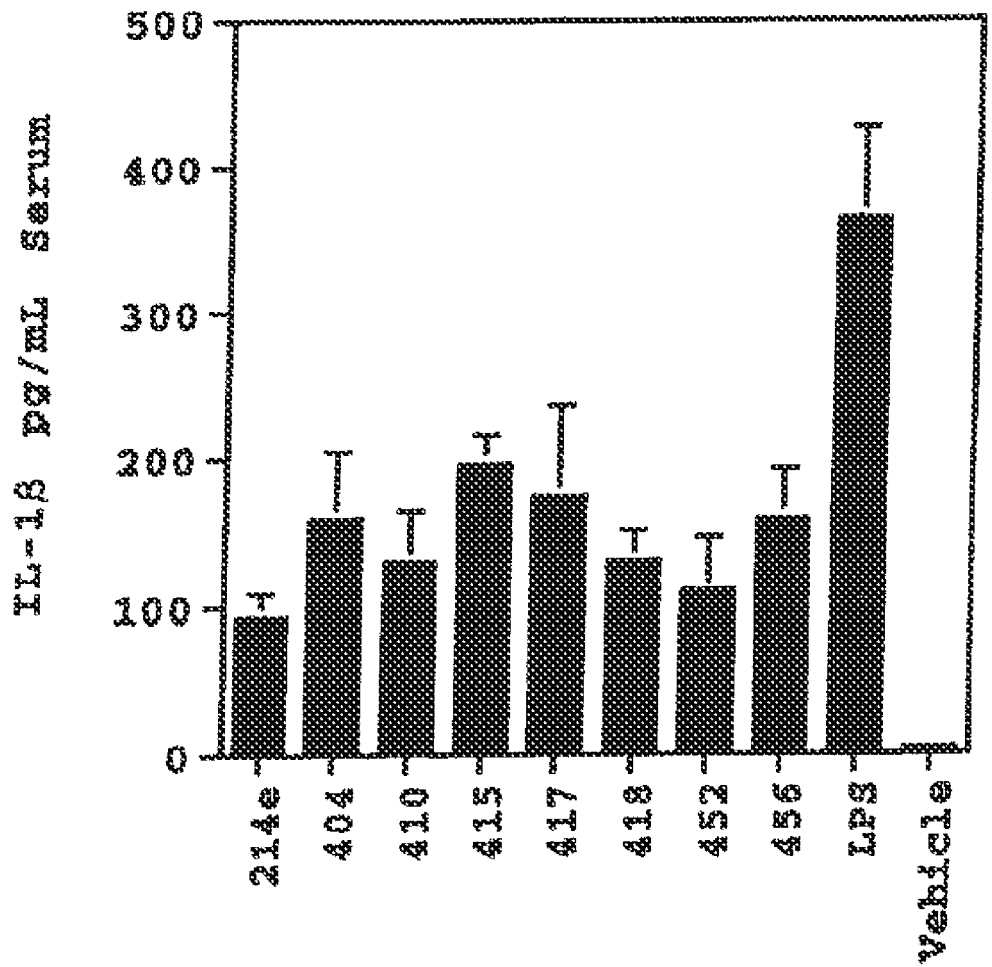
FIG. 10 Compound 214e, and analogs of 214e, also inhibit IL-1β production after oral (PO) administration. These results were obtained in the assay described for FIGS. 6 and 7 and Example 7.

The efficacy of analogs of 214e were also evaluated in LPS challenged mice after IP administration (FIG. 9) and PO administration (FIG. 10).

Table 3% Inhibition of IL-β Production by Analogs of 214e in LPS-Chellenged Mice after PO and IP Administration (50 mg/kg).

TABLE 3

| Compound | PO % Inhibition | IP % Inhibition |
|---|---|---|
| 214e | 75 | 78 |
| 265 | 27 | 30 |
| 416 | 52 | 39 |
| 434 | 80 | 74 |
| 438 | 13 | 40 |
| 442 | 10 | 0 |
| 2002 | — | 78 |

TABLE 4

Comparison of 214e Prodrugs for Efficacy in LPS Challenged Mice: Time Course Inhibition of IL-1β Production

| | Time of Compound Administration (relative to time of LPS challenge, PO, 50 mg/kg) | | | |
|---|---|---|---|---|
| Compound | −2 hr | −1 hr | 0 hr | +1 hr |
| 214e | | | | 55% |
| | 39* | —* | 80* | 75* |
| | 43* | 44* | 48* | 11* |
| | —* | —* | —* | 47* |
| 304a | 30 | 33 | 68 | 37 |
| 2100e | 49 | 54 | 94 | 66 |
| 2100a | 8 | 71 | 67 | 58 |
| 213e | 0 | 48 | 41 | 89 |
| 302 | 0 | 27 | 21 | 26 |
| 2100c | 0 | 0 | 85 | 40 |
| 2100d | 42 | 35 | 52 | 26 |
| 2100b | 0 | 0 | 47 | 26 |

TABLE 4-continued

Comparison of 214e Prodrugs for
Efficacy in LPS Challenged Mice:
Time Course Inhibition of IL-1β Production Time of Compound Administration
(relative to time of LPS challenge,
PO, 50 mg/kg)

| Compound | −2 hr | −1 hr | 0 hr | +1 hr |
|---|---|---|---|---|
| 2001 | ~63<br>64* | ~62<br>62* | ~57<br>58* | ~54<br>55* |

*Values obtained in subsequent assays

EXAMPLE 8

Measurement of Blood Levels of Prodrugs of 214e

Mice were administered a p.o. dose of compounds 302 and 304a (50 mg/kg) prepared in 0.5% carboxymethylcellulose. Blood samples were collected at 1 and 7 hours after dosing. Serum was extracted by precipitation with an equal volume of acetonitrile containing 2% formic acid followed by centrifugation. The supernatant was analyzed by liquid chromatography-mass spectrometry (ESI-MS) with a detection level of 0.03 to 3 μg/ml. Compounds 302 and 304a showed detectable blood levels when administered orally, 214e itself shows no blood levels above 0.10 μg/mL when administered orally. Compounds 302 and 304a are prodrugs of 214e and are metabolized to 214e in vivo (see FIG. 11).

EXAMPLE 9

We obtained the following data (see Tables 5 and 6) for compounds of this invention using the methods described in Examples 1-8. The structures of the compounds of Example 9 are shown in Example 10-17.

TABLE 5

| Compound | UV-Visible Ki (nM) | Cell PBMC avg. IC50 (nM) | Whole human blood IC50 (nM) | Clearance Mouse, i.v. ml/min/kg | Clearance Rat, i.v. ml/min/kg |
|---|---|---|---|---|---|
| 47b | 27 | 1800 | <600 | 338 | |
| 47a | 19 | 2600 | 5100 | 79 | 32 |
| 135a | 90 | 2800 | 5000 | >100 | |
| 135b | 320 | 1600 | 1700 | | |
| 125b | 60 | 800 | 4500 | | |
| 108b | 400 | 25000 | | >100 | |
| 137 | 40 | 1700 | 14000 | | |
| 139 | 350 | 2000 | | | |
| 213e | 130 | 900 | 600<br>400* | | |
| 214c | 1200 | 5000 | | | |
| 214e | 7.5 | 1600 | 1300 | 23 | 12 |
| 217c | | 1700 | 7000 | 70 | |
| 217e | | 175 | 2000 | >50 | |
| 220b | 600 | 2125 | | | |
| 223b | 99 | 5000 | | >100 | |
| 223e | 1.6 | 3000 | >20000 | 89 | |
| 226e | 15 | 1100 | 1800 | 109 | |
| 227e | 7 | 234 | 550 | | |
| 230e | | 325 | 300 | 67 | |
| 232e | 1100 | 4500 | | 22 | 26 |
| 235e | 510 | 4750 | | 36 | |
| 238e | 500 | 4250 | | | |
| 246 | 12 | 950 | 10000 | 31 | |
| 257 | 13 | 11000<br>6600* | | | |

TABLE 5-continued

| Compound | UV-Visible Ki (nM) | Cell PBMC avg. IC50 (nM) | Whole human blood IC50 (nM) | Clearance Mouse, i.v. ml/min/kg | Clearance Rat, i.v. ml/min/kg |
|---|---|---|---|---|---|
| 265 | 47 | 4300 | 1400 | 23 | 20 |
| 281 | 50 | 600<br>2500* | | | |
| 302 | 4500 | >20000 | >20000 | | |
| 304a | 200 | 1,400 | 2400<br>14000* | | |
| 307a | 55 | 14500 | 16000 | | |
| 307b | 165 | | 14000 | | |
| 404 | 2.9 | 1650<br>1800* | 1100 | 64 | 24 |
| 405 | 6.5 | 1700 | 2100 | | |
| 406 | 4 | 1650 | 2300 | | |
| 407 | 0.4 | 540 | 1700 | | |
| 408 | 0.5 | 1100 | 1000 | 41 | 23 |
| 409 | 3.7 | 2500 | | | |
| 410 | 17 | 2000 | 2800 | 32 | 20 |
| 411 | 0.9 | 540 | 1900 | | |
| 412 | 1.3 | 580<br>660* | 700<br>1000* | | 25 |
| 413 | 750 | 6200 | | | |
| 415 | 2.5 | 990<br>1000* | 450<br>3500* | 26 | 18 |
| 416 | 12 | 1200 | 3400 | | 47 |
| 417 | 8 | 2000 | 6000 | 33 | 22 |
| 418 | 2.2 | 1050<br>2200* | 7800<br>1800* | 13 | 5.9 |
| 419 | 280 | >8000 | | | |
| 420 | 1200 | 8000<br>>8000* | | | |
| 421 | 200 | 4300<br>4600* | | | |
| 422 | 50 | 2200 | 1200 | | |
| 423 | 10 | 2100<br>1800* | 1500 | | 45 |
| 424 | 45 | 2500 | 4000 | | |
| 425 | 0.8 | 650<br>700* | 650 | | |
| 426 | 90 | 4500<br>2500* | | | |
| 427 | 180 | 4500 | | | 36 |
| 428 | 280 | | | | |
| 429 | 7000 | | | | |
| 430 | 60 | >8000 | | | |
| 431 | 8 | >8000 | 8000 | | |
| 432 | 1.6 | 560 | 2000 | | |
| 433 | 2.9 | 1000<br>1100* | 1100 | | |
| 434 | 4.9 | 1600<br>1200* | 1800<br>1300* | | 20 |
| 435 | 8 | 4400 | | | |
| 436 | 7.5 | 2700 | | | |
| 437 | 12 | 1800 | 5000 | | |
| 438 | 28 | 1000 | 700<br>2900* | | 22 |
| 439 | 3.7 | 2800 | 3200<br>3400* | | |
| 440 | 2.3 | 5000 | 2000 | | |
| 441 | 1 | 2500 | 4500 | | |
| 442 | 3.2 | 900 | 2000 | | 54 |
| 443 | 3.6 | 2800 | 1500 | | |
| 444 | 15 | 3500 | 3500 | | |
| 445 | 135 | | 4000 | | |
| 446 | 62 | | 3000 | | |
| 447 | 5.8 | 2500 | 1500 | | |
| 448 | 130 | | 4000 | | |
| 449 | 12 | 1500 | 3200<br>13000* | | |
| 450 | 5 | 800 | 2200<br>1700* | 18 | 12 |
| 451 | 4 | 1800 | 1500<br>9000* | | |
| 452 | 4.5 | 600<br>800* | 650<br>1600* | | 27.3 |

TABLE 5-continued

| Compound | UV-Visible Ki (nM) | Cell PBMC avg. IC50 (nM) | Whole human blood IC50 (nM) | Clearance Mouse, i.v. ml/min/kg | Clearance Rat, i.v. ml/min/kg |
|---|---|---|---|---|---|
| 453 | 0.65 | 1300 | 1900 | | |
| | | | 1600* | | |
| 454 | 45 | 2500 | | | |
| 455 | 1.2 | 400 | 2800 | | 54 |
| | | | 2600* | | |
| 456 | 4.5 | 600 | 600 | | 12.7 |
| | | 1300* | 1400* | | |
| 457 | 6.2 | 2000 | 3500 | | |
| 458 | 20 | 2900 | | | |
| 459 | 5 | 1800 | | | |
| 460 | 115 | 400 | 2400 | | |
| 461 | 47 | | | | |
| 462 | 40 | | | | |
| 463 | 14 | 2400 | | | |
| | | 2800* | | | |
| 464 | 2.5 | 1000 | >1000 | | |
| | | | 2500* | | |
| 465 | 3 | 1000 | 800 | | |
| 466 | 0.8 | 1400 | 600 | | |
| 467 | 11 | 1900 | | | |
| 468 | 4.5 | 850 | 2500 | | |
| 470 | 5 | 500 | 360 | | 63 |
| | | | 500* | | |
| 471 | 1 | 750 | 400 | | 17 |
| 472 | 140 | | | | |
| 473 | 1 | 1000 | 400 | | |
| | | | 450* | | |
| 474 | 85 | | | | |
| 475 | 5.5 | 690 | 400 | 31 | 21 |
| | | 650* | 350* | | |
| 476 | 7 | 1600 | 2500 | | |
| 477 | 60 | | | | |
| 478 | 380 | | | | |
| 479 | 15 | 900 | 700 | | |
| | | | 2400* | | |
| 480 | 25 | 2300 | | | |
| 481 | 1.2 | 390 | 600 | | 34 |
| | | 930* | 500* | | |
| 482 | <0.2 | 340 | 380 | | |
| | | | 260* | | |
| 483 | 1.7 | 900 | 700 | | |
| 484 | 2 | 1550 | 5000 | | 15 |
| | | 1400* | | | |
| 485 | 2 | 900 | 900 | | |
| 486 | 2.3 | 480 | 500 | | 37 |
| | | 570* | | | |
| 487 | 2.4 | 650 | 500 | | 20 |
| | | 950* | 400* | | |
| 488 | 1.5 | 940 | 750 | | |
| 489 | 6 | 2260 | 15000 | | |
| | | 1700* | | | |
| 490 | 4.3 | 980 | 700 | | |
| | | 1000* | 1900* | | |
| 491 | 5 | 2500 | | | |
| 493 | 25 | 1200 | 800 | | |
| | | | 850* | | |
| 494 | 15 | 1350 | 7000 | | |
| | | 1500* | | | |
| 495 | 43 | | | | |
| 496 | 16 | 1550 | 6000 | | |
| | | 1600* | | | |
| 497 | 3.5 | 740 | 350 | | |
| | | | 700* | | |
| 498 | 1.5 | 560 | 500 | | |
| | | | 400* | | |
| 499 | 3.5 | 1200 | 9000 | | |
| | | 800* | | | |
| 605a | 90 | 2600 | >20000 | | |
| 605b | 45 | 10000 | | 97 | |
| 605c | 615 | 4500 | | 37 | |
| 605d | 95 | 5100 | 16000 | 33 | |
| | | | 5100* | | |
| 605e | 29 | 2250 | >10000 | | 24 |
| 605f | 475 | 12500 | | | |
| 605g | 165 | 22500 | | | |
| 605h | 460 | >25000 | | | |
| 605i | 680 | >20000 | | | |
| 605j | 110 | 8750 | | 71 | |
| 605m | 650 | 20000 | | | |
| 605n | 12 | 2100 | >20000 | 28 | |
| 605o | 72 | | 18000 | | |
| 605p | 125 | 3200 | >20000 | | |
| 605q | 1000 | | | | |
| 605s | 150 | 6000 | | | |
| 605t | 33 | | | | |
| 609a | 114 | >30000 | | | |
| 609b | 27 | >20000 | | | |
| 619 | 300 | | | | |
| 620 | 35 | 1000 | 19000 | | |
| 621 | 7.2 | 1300 | >20000 | | |
| 622 | 35 | 1300 | >20000 | | |
| 623 | 9 | | | | |
| 624 | 300 | | | | |
| 625 | 105 | | | | |
| 626 | 260 | | | | |
| 627 | 43 | 3250 | 8000 | | |
| 628 | 36 | 2750 | >20000 | | |
| 629 | 230 | | | | |
| 630 | 270 | | | | |
| 631 | 805 | | | | |
| 632 | 148 | | | | |
| 633 | 92 | 5750 | 20000 | | |
| 634 | 1400 | | | | |
| 635 | 55 | 1900 | 4000 | | |
| | | | 3400* | | |
| 605v | 1100 | >30000 | | | |
| 2201 | 9 | 2000 | 3500 | | 60 |
| | | | 3700* | | |
| 2100e | 250 | 800 | 600 | | |
| 2100a | 100 | 1100 | 850 | | |
| 2002 | 4 | 810 | 70 | | 32 |
| | | 860* | 1400* | | |
| 2100d | >100000 | >20000 | >20000 | | |
| 2100c | 7400 | >20000 | >20000 | | |
| 2100b | 8000 | >20000 | >20000 | | |
| 2001 | 135 | 1800 | 3500 | | |
| 1027 | 4000 | >20000 | >20000 | | 60 |
| 1015 | 40 | 2500 | 1700 | | 23 |

TABLE 6

| Compound | Fluorescent Assay $k_{inact}$ $M^{-1} s^{-1}$ | Cell PBMC avg. IC50 (nM) | Whole human blood IC50 (nM) | Clearance Mouse, i.v. ml/min/kg | Clearance Rat, i.v. ml/min/kg |
|---|---|---|---|---|---|
| 108a | $1 \times 10^5$ | 17500 | | | |
| 136 | $5.4 \times 10^5$ | 870 | 2800 | 93 | |
| 138 | $1.2 \times 10^5$ | 900 | 2900 | 116 | |
| 217d | $4.7 \times 10^5$ | 340 | 4000 | | |
| 280 | $4 \times 10^5$ | 650 | >1000 | | 187 |
| 283 | $1 \times 10^5$ | <200 | 450 | | 104 |
| 284 | $3.5 \times 10^5$ | 470 | 550 | 77 | 100 |
| 285 | $4.3 \times 10^5$ | 810 | 1000 | 130 | 50 |

* Values obtained upon reassay.

EXAMPLE 10

Compound 139 was synthesized by a method similar to the method used to synthesize 47a.

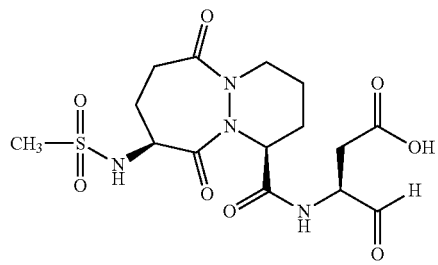
139

Compounds 136 and 138 were synthesized by a method similar to the method used to synthesize 57b.

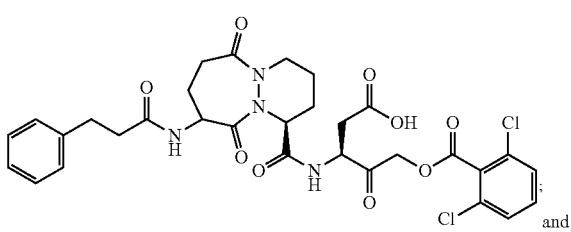
136

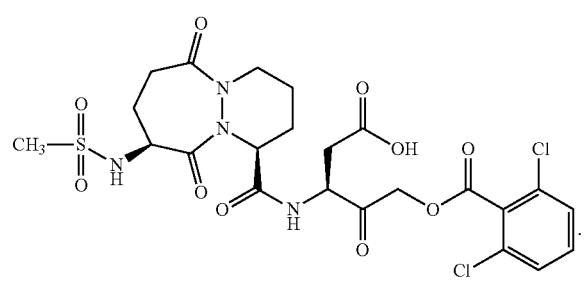
138

Compounds 135a, 135b, and 137 were synthesized by a method similar to the method used to synthesize 69a.

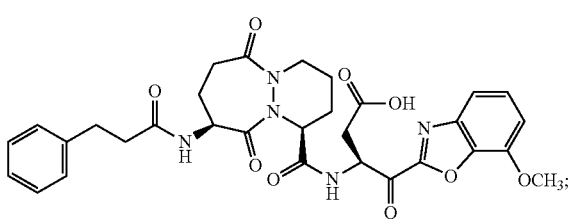
135a

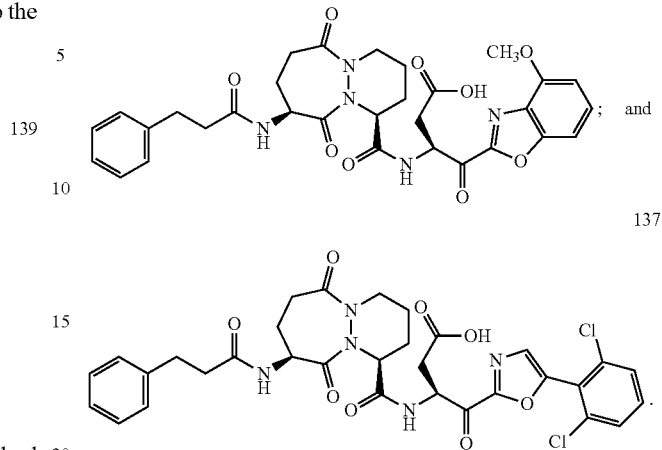

Compounds 813e, 814c, 814e, 817c, 817d, 817e, 820b, 823b, 823e, 826e, 827e, 830e, 832e, 835e, 838e, 846, 857, 865, 902, 904a, 907a, 907b, 1004-1013, 1015-1045, 1046-1068, 1070-1091, and 1093-1099 were synthesized by methods similar to those used to synthesize compound 264 and the corresponding compounds in Examples 10 and 11.

Compounds 47a, 47b, 108a, 108b, 125b, 213e, 214c, 217c, 217d, 217e, 220b, 223b, 223e, 226e, 227e, 230e, 232e, 235e, 238e, 246, 257, 264, 265, 280-287, 302, 304a, 307a, and 307b were synthesized as described below.

H. N-(N-Acetyl-tyrosinyl-valinyl-pipecolyl)-3-amino-4-oxobutanoic acid.

Step A. N-(N-tert-Butoxycarbonylpipecolyl)-4-amino-5-benzyloxy-2-oxotetrahydrofuran.

Reaction of N-tert-butoxycarbonylpipecolic acid (460 mg, 2.0 mmol) and N-allyloxycarbonyl-4-amino-5-benzyloxy-2-oxotetrahydrofuran (530 mg, 1.82 mmol) was carried out by a method analogous to that reported by Chapman (*Bioorg. & Med. Chem. Lett.* 2, pp. 613-618, (1992)) to give 654 mg of the title compound.

$^1$H NMR (500 MHz, CDCl$_3$ (existing as rotamers)) δ 7.35 (m, 5H), 6.88 (br. s, 1H), 4.9-4.45 (m, 4H), 3.95+(br. m, 2H), 3.06 (m, 1H), 2.9 (m, 1H), 2.7 (br. m, 1H), 2.45 (m, 1H), 2.2 (m, 1H), 1.7-1.5 (m, 3H), 1.45 (two s, 9H).

Step B. N-Pipecolyl-4-amino-5-benzyloxy-2-oxotetrahydrofuran.

N-(N-tert-Butoxycarbonylpipecolyl)-4-amino-5-benzyloxy-2-oxo-tetrahydrofuran (654 mg) was dissolved in 15 ml of 25% trifluoroacetic acid in dichloromethane and stirred at room temperature. The mixture was concentrated to give a gummy residue. The residue was dissolved in dichloromethane and washed with 10% sodium bicarbonate. The organic layer was dried over anhydrous sodium sulfate, filtered, and concentrated to give 422 mg of the title compound as a beige solid.

$^1$H NMR (500 MHz, CDCl$_3$) δ 7.38 (m, 5H), 7.15 (d, 1H), 5.55 (d, 1H), 4.95-4.8 (m, 1H), 4.78 (m, 1H), 4.65 (d, 1H), 4.45 (m, 1H), 3.2 (m, 0.5H), 3.05 (m, 0.5H), 2.95 (m, 0.5H), 2.85 (m, 0.5H), 2.65 (m, 1H), 2.55-2.38 (m, 1H), 1.95 (m, 1H), 1.8 (m, 1H), 1.6 (m, 2H), 1.38 (m, 2H).

Step C. N-(N-Acetyl-tyrosinyl-valinyl-pipecolyl)-4-amino-5-benzyloxy-2-oxo-tetrahydrofuran.

N-Acetyl-tyrosinyl-valine (464 mg, 1.44 mmol) and N-Pipecolyl-4-amino-5-benzyloxy-2-oxotetrahydrofuran (412 mg, 1.3 mmol) were dissolved in 5 ml each of dimethylformamide and dichloromethane and cooled to 0° C. To the cooled solution was added 1-hydroxybenzotriazole (HOBT; 210 mg, 1.56 mmol) followed by the addition of 1-(3-dimethylaminopropyl)-3-ethyl carbodiimide hydrochloride (EDC; 326 mg, 1.7 mmol). After stirring for 18 hours, the mixture was diluted with ethyl acetate and washed with water, 10% sodium hydrogen sulfate, 10% sodium bicarbonate, and water. The organic layer was concentrated to give a crude solid that was purified by flash chromatography ($SiO_2$) eluting with 94:6:1 (dichloromethane:isopropanol:pyridine) to give 370 mg of the title compound.

$^1$H NMR (500 MHz, $CD_3OD$ (existing as diastereomers as well as rotamers)) δ 7.35 (m, 5H), 7.05 (m, 2H), 6.68 (m, 2H), 5.65 & 5.25 (m, 1H), 4.9-3.95 (m, 8H), 3.4-2.6 (m, 4H), 2.5-2.1 (m, 1H), 1.98 (s, 1H), 1.9 (s, 1H), 1.85 (s, 1H), 1.8-1.6 (m, 2H), 1.55-1.3 (m, 4H), 0.95-0.85 (m, 6H).

Step D. N-(N-Acetyl-tyrosinyl-valinyl-pipecolyl)-3-amino-4-oxobutanoic acid.

To a solution of 100 mg of N-(N-Acetyl-tyrosinyl-valinyl-pipecolyl)-4-amino-5-benzyloxy-2-oxotetrahydrofuran in 10 ml of methanol was added 60 mg of $Pd(OH)_2$ on carbon and the mixture placed under an atmosphere of hydrogen via a balloon. The mixture was filtered through Celite and concentrated providing a white solid. This crude solid was dissolved in 2 ml of methanol and triturated with diethyl ether affording 26 mg of the title compound.

$^1$H NMR (500 MHz, $CD_3OD$ (existing as diastereomers as well as rotamers)) δ 7.1 (m, 2H), 6.7 (m, 2H), 5.2 (br. m, 1H), 4.8-3.6 (m, 6H), 3.2-2.5 (m, 4H), 2.5-2.1 (m, 1H), 1.95 (three s, 3H), 1.9-1.3 (m, 6H), 1.1-0.7 (m, 6H).

E. N-[N-Acetyl-tyrosinyl-valinyl-(4-benzyloxy)prolinyl]-3-amino-4-oxobutanoic acid.

Step A. N-(N-Allyloxycarbonyl-4-benzyloxyprolinyl)-3-amino-4-oxobutanoic acid tert-butyl ester semicarbazone.

The title compound was prepared by the reaction of N-allyloxycarbonyl-4-benzyloxyproline and 3-amino-4-oxobutanoic acid tert-butyl ester semicarbazone (T. L. Graybill et. al., Abstracts of papers, 206th National Meeting of the American Chemical Society, Abstract MEDI-235. Chicago, Ill. (1993)) under similar peptide coupling conditions as reported above (compound H; Step C).

$^1$H NMR (500 MHz, $CDCl_3$) δ 9.05 (br. s, 1H), 7.85 (br. m, 1H), 7.4-7.2 (m, 5H), 7.15 (br. s, 1H), 6.55 (br. s, 1H), 5.9 (m, 1H), 5.1-4.9 (br. m, 2H), 4.65-4.4 (m, 4H), 4.2 (br. m, 1H), 3.75-3.5 (m, 2H), 2.75-2.55 (m, 2H), 2.5 (br. m, 1H), 2.25 (br. m, 1H) 1.4 (s, 9H).

Step B. N-(N-Acetyl-tyrosinyl-valinyl-(4-benzyloxyprolinyl))-3-amino-4-oxobutanoic acid tert-butyl ester semicarbazone.

The title compound was prepared by reaction of N-acetyl-tyrosinyl-valine and N-(N-allyloxycarbonyl-4-benzyloxyprolinyl)-3-amino-4-oxobutanoic acid tert-butyl ester semicarbazone by reaction conditions reported for compound H, step A.

$^1$H NMR (500 MHz, $CD_3OD$) δ 7.35-7.2 (m, 6H), 7.0 (d, 2H), 6.65 (d, 2H), 4.85 (m, 1H), 4.6-4.45 (m, 4H), 4.3 (br. m, 1H), 4.15 (m, 1H), 3.7 (m, 1H), 2.95 (m, 1H), 2.75-2.6 (m, 3H), 2.35 (m, 1H), 2.1 (m, 1H), 1.9 (s, 3H), 1.4 (s, 9H), 0.95 (d, 3H), 0.90 (s, 3H).

Step C. N-(N-Acetyl-tyrosinyl-valinyl-(4-benzyloxyprolinyl))-3-amino-4-oxobutanoic acid.

N-(N-Acetyl-tyrosinyl-valinyl-(4-benzyloxyprolinyl))-3-amino-4-oxobutanoic acid tert-butyl ester semicarbazone (270 mg) was dissolved into 10 ml of 25% trifluoroacetic acid in dichloromethane and stirred at room temperature for 3 hours. The mixture was concentrated to give a solid residue. The residue was dissolved into a 10 ml mixture of methanol: acetic acid:37% formaldehyde (3:1:1) and stirred at room temperature for 1 hour. The mixture was concentrated and the resulting residue purified by flash chromatography ($SiO_2$) eluting with dichloromethane/methanol/formic acid (100:5: 0.5) to give 37 mg of the title compound.

$^1$H NMR (500 MHz, $CD_3OD$ (existing as a 1:1 mixture of diastereomers of the hemiacetal)) δ 7.4-7.25 (m, 5H), 7.0 (d, 2H), 6.65 (d, 2H), 4.65-4.05 (m, 7H), 3.75-3.4 (m, 2H), 3.05-2.3 (m, 5H), 2.2-1.95 (m, 2H), 1.90 (s, 3H), 1.0 (d, 3H), 0.95 (d, 3H).

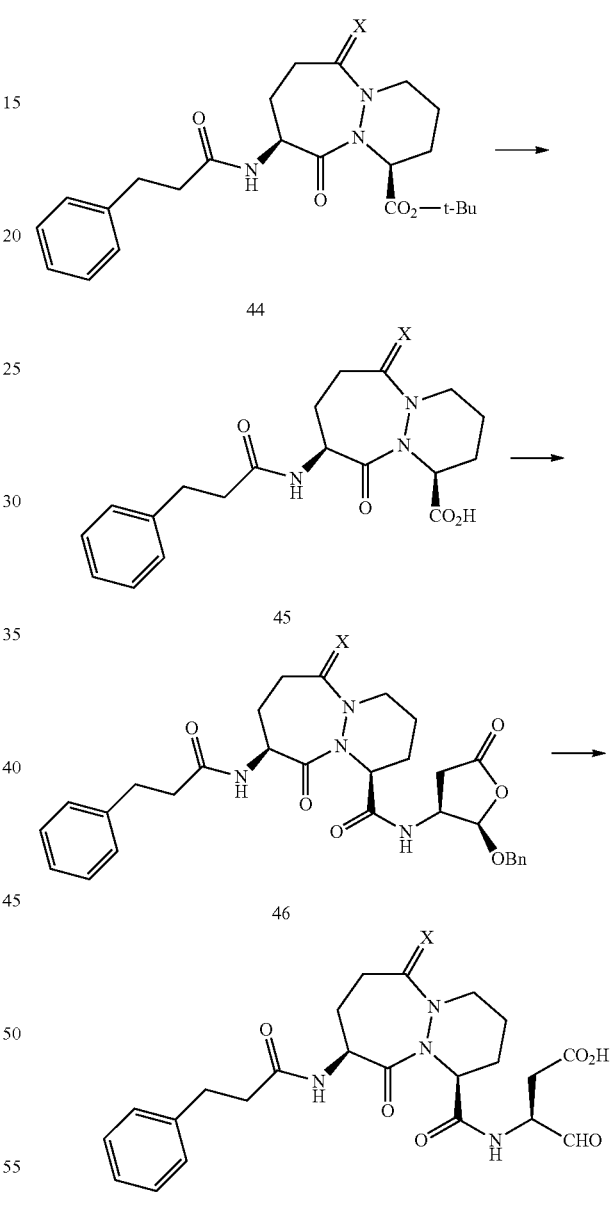

44

45

46

47

(a) X = O
(b) X = $H_2$ (1S,9S)t-Butyl 6,10-dioxo-octahydro-9-(3-phenylpropionylamino)-6H-pyridazino[1,2-a][1,2]diazepine-1-carboxylate (44a). To a solution of (1S,9S)t-butyl 9-amino-6,10-dioxo-octahydro-6H-pyridazino[1,2-a][1,2]diazepine-1-carboxylate (690 mg; 2.32 mmol; GB 2128984) in dioxane (16 ml) and water (4 ml) at 0° C. was added solid sodium bicarbonate (292 mg; 3.48 mmol) followed by dropwise addition of 3-phenylpropionyl chloride (470 mg; 2.78 mmol). The mixture was stirred at room temperature for 2 h then more sodium bicarbonate (200 mg; 2.38 mmol) and 3-phenylpropionyl chloride (100 mg; 0.6 mmol) were added. The mixture was stirred for a further 2 h at room temperature, diluted with ethyl acetate (50 ml), washed with saturated sodium bicarbonate (2×25 ml) then dried (MgSO$_4$) and concentrated. The residue was purified by flash chromatography (0-50% ethyl acetate/chloroform) and finally crystallized by trituration with ether to afford 860 mg (86%) of a white solid: rap. 137-138° C.; $[\alpha]_D^{23}$ −95.1° (c 0.549, CH$_2$Cl$_2$); IR (KBr) 3327, 1736, 1677, 1664, 1536, 1422, 1156; $^1$H NMR (CDCl$_3$) δ 7.24 (5H, m), 6.50 (1H, d, J=7.5), 5.24 (1H, m), 4.90 (1H, m), 4.60 (1H, m), 3.44 (1H, m), 2.93 (2H, m), 2.84 (1H, m), 2.64 (1H, m), 2.54 (2H, m), 2.26 (2H, m), 1.70 (4H, m), 1.70 (9H, s). MS (FAB, m/z): 430 (M$^+$+1), 374, 242, 105, 91.

(1S,9S)t-Butyl octahydro-10-oxo-9-(3-phenylpropionylamino)-6H-pyridazino-[1,2-a][1,2]diazepine-1-carboxylate (44b), was prepared from (1S,9S)t-butyl 9-amino-octahydro-10-oxo-6H-pyridazino[1,2-a][1,2]diazepine-1-carboxylate (Attwood et al., J. Chem. Soc. Perkin 1, pp. 1011-19 (1986)) as for 44a, to afford 810 mg (81%) of a colorless oil: $[\alpha]_D^{23}$ −33.5° (c 0.545, CH$_2$Cl$_2$); IR (film) 3334, 2935, 1737, 1728, 1659, 1642; $^1$H NMR (CDCl$_3$) δ 7.24 (5H, m), 6.75 (1H, d, J=6.7), 5.27 (1H, m), 4.92 (1H, m), 3.39 (1H, m), 3.03 (4H, m), 2.55 (3H, m), 2.33 (1H, m), 2.17 (1H, m), 1.80 (5H, m), 1.47 (9H, s), 1.39 (1H, m). MS (FAB, m/z): 416 (M$^+$+1), 360, 211, 143, 97.

(1S,9S)6,10-Dioxo-octahydro-9-(3-phenylpropionylamino)-6H-pyridazino[1,2-a][1,2]diazepine-1-carboxylic acid (45a). To a solution of (1S,9S)t-butyl 6,10-dioxo-octahydro-9-(3-phenylpropionylamino)-6H-pyridazino[1,2-a][1,2]diazepine-1-carboxylate (44a) (800 mg; 1.863 mmol) in dry dichloromethane (5 ml) at 0° C. was added trifluoroacetic acid (5 ml). The solution was stirred at room temperature for 3 h then concentrated. Dry ether (10 ml) was added to the residue then removed under vacuum. This process was repeated three times to afford a crystalline solid. The solid was triturated with ether and filtered to afford 590 mg (85%) of a white crystalline solid: mp. 196-197.5° C.; $[\alpha]_D^{23}$ −129.5° (c 0.2, CH$_3$OH); IR (KBr) 3237, 1729, 1688, 1660, 1633, 1574, 1432, 1285, 1205; $^1$H NMR (CD$_3$OD) δ 8.28 (1H, d, J=7.4), 7.22 (5H, m), 5.32 (1H, dd, J=5.9, 2.9), 4.75 (1H, m), 4.51 (1H, m), 3.50 (1H, m), 3.01 (1H, m), 2.91 (2H, m), 2.55 (2H, m), 2.29 (3H, m), 1.95 (2H, m), 1.71 (2H, m). Anal. Calcd for C$_{19}$H$_{23}$N$_3$O$_5$: C, 61.12; H, 6.21; N, 11.25. Found: C, 60.80; H, 6.28; N, 10.97. MS (FAB, m/z) 374 (M$^+$+1), 242, 105, 91.

(1S,9S) Octahydro-10-oxo-9-(3-phenylpropionylamino)-6H-pyridazino[1,2-a]-[1,2]diazepine-1-carboxylic acid (45b), was prepared from (1S,9S)t-butyl octahydro-10-oxo-9-(3-phenylpropionylamino)-6H-pyridazino[1,2-a][1,2]diazepine-1-carboxylate (44b) by the method described for compound 45a to afford 657 mg (96%) of 45b as a crystalline solid: mp. 198-202° C.; $[\alpha]_D^{23}$ −86.2° (c 0.5, CH$_3$OH); IR (KBr) 3294, 2939, 1729, 1645, 1620, 1574, 1453, 1214; $^1$H NMR (CD$_3$OD) δ 7.92 (1H, d, J=7.9), 7.20 (5H, m), 5.29 (1H, m), 4.90 (1H, m), 3.47 (1H, m), 3.08 (2H, m), 2.90 (2H, m), 2.55 (3H, m), 2.36 (1H, m), 1.81 (5H, m), 1.43 (2H, m). MS (FAB, m/z) 360 (M$^+$+1), 211,143,91.

[3S,2R,S,(1S,9S)]N-(2-Benzyloxy-5-oxotetrahydrofuran-3-yl)-6,10-dioxo-octahydro-9-(3-phenylpropionylamino)-6H-pyridazino[1,2-a][1,2]diazepine-1-carboxamide (46a). To a solution of (1S,9S)6,10-dioxo-octahydro-9-(3-phenylpropionylamino)-6H-pyridazino[1,2-a][1,2]diazepine-1-carboxylic acid (45a) (662 mg; 1.773 mmol) in dry dichloromethane (9 ml) and dry dimethyl formamide (3 ml) at room temperature was added bis(triphenylphosphine)palladium chloride (30 mg) and (3S,2R,S)-3-allyloxycarbonylamino-2-benzyloxy-5-oxotetrahydrofuran (Chapman, Bioorg. Med. Chem. Lett., 2, pp. 613-18 (1992)) (568 mg; 1.95 mmol) followed by dropwise addition of tri-n-butyltin hydride (1.19 g; 4.09 mmol). 1-Hydroxy-benzotriazole (479 mg; 3.546=1) was added to the mixture and the mixture was cooled to 0° C. before addition of 1-(3-dimethylaminopropyl)-3-ethylcarbodiimide hydrochloride (408 mg; 2.128 mmol). The mixture was stirred at room temperature for 3.25 h then diluted with ethyl acetate (50 ml), washed twice with dilute hydrochloric acid (20 ml), twice with saturated sodium bicarbonate (20 ml), once with brine then dried (MgSO$_4$) and concentrated. The resulting oil was purified by flash chromatography (0-100% ethyl acetate/chloroform) to afford 810 mg (81%) of 46a as a mixture of anomers: mp. 92-94° C.; IR (KBr) 3311, 1791, 1659, 1651, 1536; $^1$H NMR (CDCl$_3$) δ 7.49, 6.56 (1H, 2d, J=6.7, 7.8), 7.29 (10H, m), 6.37, 6.18 (1H, 2d, J=7.7, 7.6), 5.56, 5.34 (1H, d, s, J=5.2), 5.08-4.47 (6H), 3.18-2.80 (5H), 2.62-2.28 (5H), 2.04-1.53 (5H). MS (FAB, m/z), 563 (M$^+$+1), 328, 149, 91.

[3S,2R,S,(1S,9S)]N-(2-Benzyloxy-5-oxotetrahydrofuran-3-yl)-octahydro-10-oxo-9-(3-phenylpropionylamino)-6H-pyridazino[1,2-a][1,2]diazepine-1-carboxamide (46b), was prepared from 45b by the method described for 46a to yield 790 mg (96%) of a glass: m.p. 58-60° C.; IR (KBr) 3316, 2940, 1793, 1678, 1641, 1523, 1453, 1120; $^1$H NMR (CDCl$_3$) δ 7.28 (10H, m), 6.52, 6.42 (1H, 2d, J=7.2, 7.1), 5.53, 5.44 (1H, d, s, J=5.2), 5.35 (1H, m), 4.6-4.9, 4.34 (4H, m), 3.1-2.8 (6H, m), 2.6-2.1 (7H), 1.95-1.05 (5H). MS (FAB, m/z), 549 (M$^+$+1), 400, 310, 279, 91.

[3S(1S,9S)]3-(6,10-Dioxo-octahydro-9-(3-phenylpropionylamino)-6H-pyridazino[1,2-a][1,2]diazepine-1-carboxamido)-4-oxobutanoic acid (47a). A mixture of [3S,2R,S,(1S,9S)]N-(2-benzyloxy-5-oxotetrahydrofuran-3-yl)-6,10-dioxo-octahydro-9-(3-phenylpropionylamino)-6H-pyridazino[1,2-a][1,2]diazepine-1-carboxamide (46a) (205 mg; 0.364 mmol), 10% palladium on carbon (200 mg) and methanol (20 ml) was stirred under hydrogen at atmospheric pressure for 5 h. The mixture was filtered then concentrated to yield 154 mg (90%) of a glass: mp. 116-118° C.; $[\alpha]_D^{23}$ −140° (c 0.1, CH$_3$OH); IR (KBr) 3323 (br), 1783, 1731, 1658, 1539, 1455, 1425; $^1$H NMR (CD$_3$OD) δ 7.21 (5H, m), 5.17 (1H, m), 4.73 (1H, m), 4.50 (2H, m), 4.23 (1H, m), 3.38 (1H, m), 3.06 (1H, m), 2.91 (2H, m), 2.73-2.18 (6H, m) and 2.01-1.59 (5H, m). Anal. Calcd for C$_{23}$H$_{27}$N$_4$O$_7$+H$_2$O: C, 56.32; H, 6.16; N, 11.42. Found: C, 56.29; H, 6.11; N, 11.25. MS (FAB, m/z) 473 (M$^+$+1), 176, 149, 105, 91.

[3S(1S,9S)]3-(Octahydro-10-oxo-9-(3-phenylpropionylamino)-6H-pyridazino-[1,2-a][1,2]diazepine-1-carboxamido)-4-oxobutanoic acid (47b), was prepared from 46b by the method described for 47a. The residue was purified by flash chromatography (0-10% methanol/chloroform) to afford 65 mg (52%) of a glass; m.p. 8-90° C.; $[\alpha]_D^{23}$ −167.0° (c 0.1, methanol); IR (KBr) 3329, 2936, 1786, 1727, 1637; $^1$H NMR (CD$_3$OD) δ 7.23 (5H, m), 5.29 (1H, m), 4.83 (1H, m), 4.59 (1H, d, J=3.6), 4.29 (1H, m), 3.3-3.0 (3H, m), 2.91 (2H, m), 2.70-2.34 (5H, m), 2.19 (2H, m), 1.75 (4H, m), 1.36 (2H, m). Anal. Calcd for C$_{23}$H$_{30}$N$_4$O$_6$+0.5H$_2$O: C, 59.09; H, 6.68; N, 11.98. Found: C, 58.97; 6.68; N, 11.73. MS (FAB, m/z) 459 (M$^+$+1), 310, 149, 105, 91.

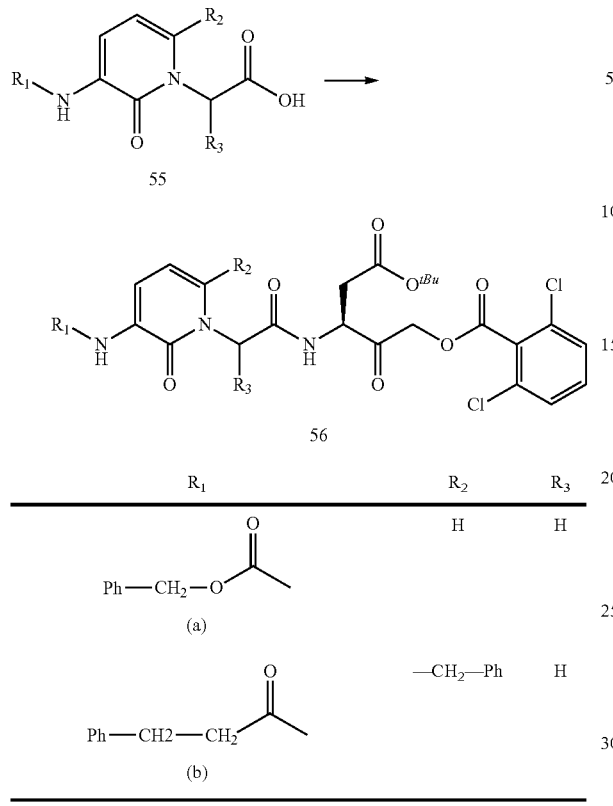

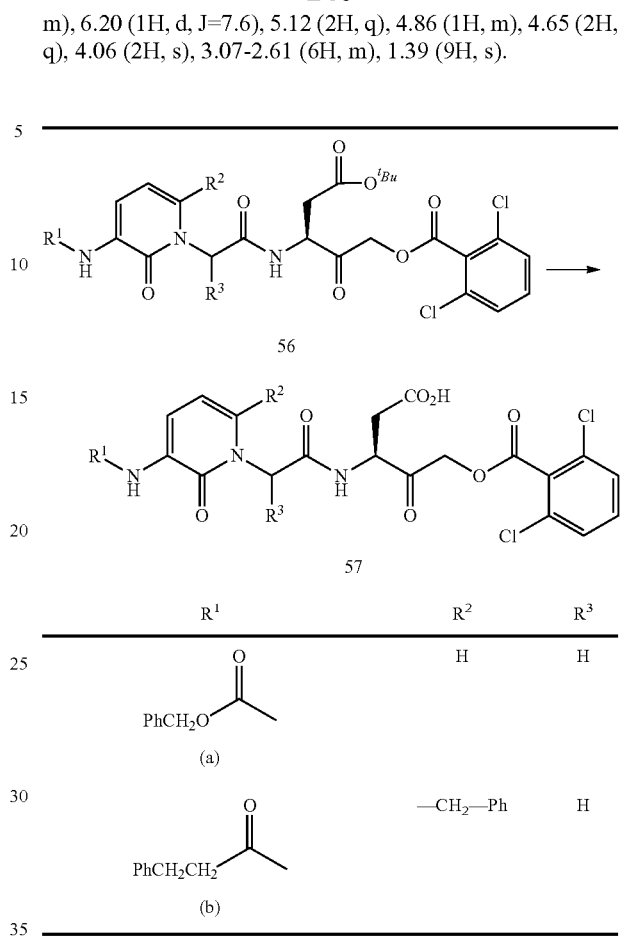

m), 6.20 (1H, d, J=7.6), 5.12 (2H, q), 4.86 (1H, m), 4.65 (2H, q), 4.06 (2H, s), 3.07-2.61 (6H, m), 1.39 (9H, s).

t-Butyl N-2-(3-benzyloxycarbonylamino-1,2-dihydro-2-oxo-1-pyridyl)acetyl-3-amino-5-(2,6-dichloro-benzoyloxy)-4-oxo-pentanoate (56a). The acetic acid (55a) (WO 93 21213) in THF (2 ml) was stirred at room temperature and treated with 1-hydroxybenzotriazole (60 mg, 0.448 mmol) and dimethylaminopropyl-3-ethylcarbodiimide hydrochloride (47 mg, 0.246 mmol). After 5 mins water (2 drops) was added and stirring continued for 20 minutes. Bis(triphenylphosphine) palladium II chloride (6 mg) was added followed by a solution of t-butyl 3-(allyloxycarbonylamino)-4-oxo-5-(2,6-dichlorobenzoyl-oxy)pentanoate (WO 93 16710) (103 mg, 0.224 mmol) in THF (1 ml). Tributyltin hydride (0.09 ml, 0.336 mmol) was added dropwise over 1 hour at room temperature. The mixture was stirred for a further 3 hours and poured onto ethyl acetate, washed with 1M HCl, aqueous NaHCO$_3$, brine, dried over MgSO$_4$ and concentrated in vacuo. The residue was triturated with pentane and the supernatant discarded. The remaining solid was purified by flash chromatography (50% ethyl acetate/hexane) to afford the title compound 92 mg (63%) as a colorless oil: $[\alpha]_D^{26}$ -29.6° (c 1.1, CH$_2$Cl$_2$); IR (film) 3377, 3365, 3332, 3312, 1733, 1691, 1650, 1599, 1515, 1366, 1261, 1153, 1068, 747; $^1$H NMR (CDCl$_3$) δ 8.09 (1H, d, J=6.8), 7.84 (1H, s), 7.58 (1H, d, J=8.3), 7.33 (8H, m), 7.02 (1H, dd, J=6.9, 1.7), 6.33 (1H, t, J=7.2), 5.20 (2H, s), 5.12 (2H, m), 4.89 (1H, dt), 4.65 (2H, m), 2.80 (2H, m), 1.38 (9H, s).

t-Butyl N-2-(6-benzyl-1,2-dihydro-2-oxo-3-(3-phenylpropionyl)amino-1-pyridyl)acetyl-3-amino-5-(2,6-dichlorobenzyloxy)-4-oxo-pentanoate (56b), was prepared by the method described for (56a) which afforded the title compound (66%) as a colorless oil: IR (film) 3364, 3313, 1738, 1688, 1648, 1600, 1566, 1514, 1433, 1369, 1254, 1152; $^1$H NMR (CDCl$_3$) δ 8.40 (1H, d, J 7.6), 8.30 (1H, s), 7.28 (13H, N-2(3-Benzyloxycarbonylamino-1,2-dihydro-2-oxo-1-pyridyl)acetyl-3-amino-5-(2,6-dichlorobenzoyloxy)-4-oxopentanoic acid (57a; Q). The ester 56a (210 mg, 0.356 mmol) in dichloromethane (0.5 ml) was cooled to 0° C. and treated with trifluoroacetic acid (0.5 ml), stirred and warmed to 20° C. over 30 minutes. The solution was evaporated to dryness under reduced pressure, redissolved in dichloromethane and concentrated (×3). The residue was triturated with ethyl acetate and diluted with ether to afford the title compound 162 mg (85%) as a colorless solid: m.p. 165-8° C. (decomposition); $[\alpha]_D^{23}$ -38.8° (c 0.1, CH$_3$OH); IR (KBr) 3332, 3275, 1723, 1658, 1649, 1597, 1581, 1562, 1526, 1432, 1385, 1258, 1218, 1206; $^1$H NMR (d$_6$-DMSO) δ 8.96 (1H, d, J=7.3), 8.34 (1H, s), 7.85 (1H, dd, J=7.3), 7.58 (3H, m), 7.35 (5H, m), 6.29 (1H, t, J=7.3), 5.26 (2H, m), 5.15 (2H, s), 4.69 (3H, m), 2.75 (2H, m). Anal. Calcd. C$_{27}$H$_{23}$N$_3$O$_9$Cl$_2$: C, 53.66; H, 3.84; N, 6.95. Found: C, 53.36; H, 3.90; N, 6.81. M.S. (+FAB); 604 (M$^+$+1), 285, 241, 195, 173, 149, 91.

N-2-(6-Benzyl-1,2-dihydro-2-oxo-3-(3-phenylpropionyl)amino-1-pyridyl)acetyl-3-amino-5-(2,6-dichloro-benzoyloxy)-4-oxo-pentanoic acid (57b; P), was prepared by the method described for 57a which afforded the title compound (78%) as colorless crystals: m.p. 116-120° C. (decomposition); $[\alpha]_D^{26}$ -41.1° (c 0.1, CH$_3$OH); IR (KBr) 3299, 1739, 1715, 1689, 1666, 1645, 1598, 1563, 1518, 1432, 1209, 1151; $^1$H NMR (d$_6$-DMSO) δ 9.24 (1H, s), 8.88 (1H, d, J=7.6), 8.18 (1H, d, J=7.7), 7.60 (3H, m), 7.26 (10H, m), 6.06 (1H, d, J=7.7), 5.23 (2H, ABq), 4.69 (3H, m), 3.93 (2H, s), 2.78 (6H, m). Anal. Calcd. for C$_{35}$H$_{31}$N$_3$O$_8$Cl$_2$.H$_2$O: C, 59.16; H, 4.68; N, 5.91. Found: C, 59.38; H, 4.53; N, 5.84. M.S. (+FAB); 694, (Cl=35, 37), (M$^+$+1); 692 (Cl=35, 35), (M$^+$+1).

241 242
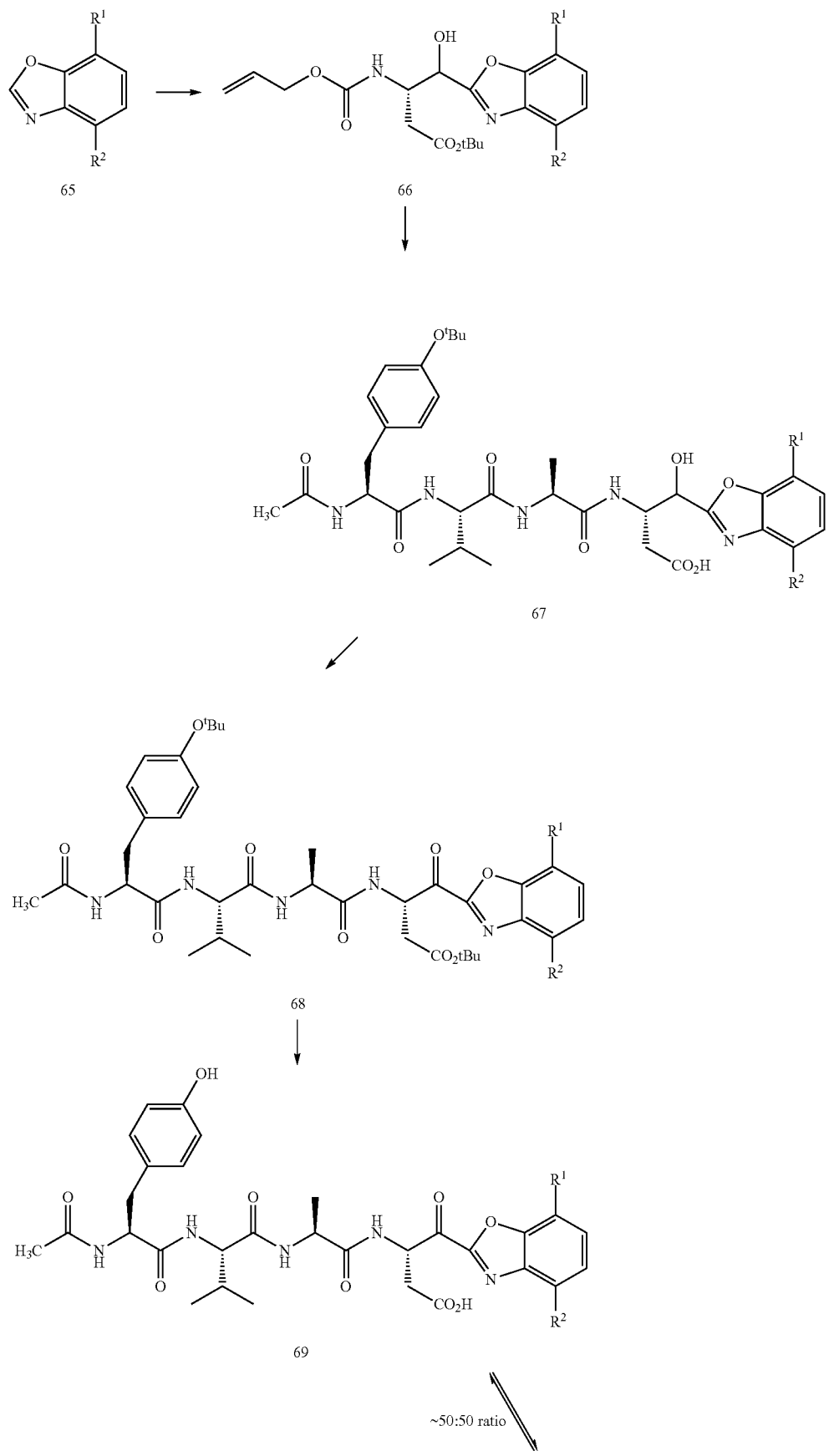

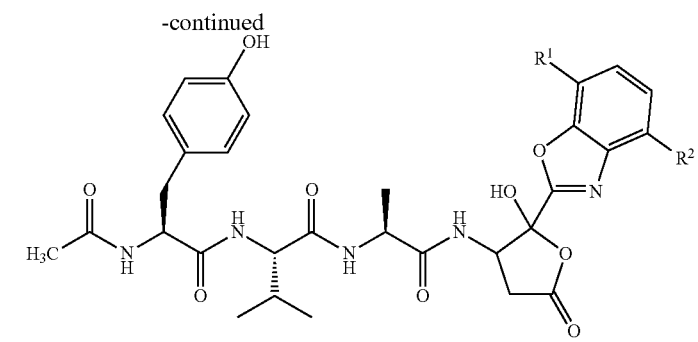

(a) $R^1 = OCH_3$, $R^2 = H$
(b) $R^1 = H$, $R^2 = OCH_3$

7-Methoxybenzoxazole (65a). A mixture of 2-nitro-6-methoxyphenol (2.62 g, 15.5 mmol) (EP 333176) and 10, Palladium on carbon (130 mg) in ethanol (50.0 ml) was stirred under an atmosphere of $H_2$ for 75 min. The mixture was filtered through Celite® then immediately treated with p-toluenesulphonic acid (32.0 mg) and triethylorthoformate (6.45 ml, 38.8 mmol) then heated under reflux under an atmosphere of $N_2$. After 20 h p-toluenesulphonic acid (30.0 mg) and triethylorthoformate (6.45 ml, 38.8 mmol) were added. After a total of 44 h heating, the reaction was allowed to cool and reduced in vacuo. The resulting residue was purified by flash chromatography (25:75 ethyl acetate/hexane) to give 1.97 g (85%) of the title compound as a yellow solid: m.p. 28-31° C.; IR (film) 1629, 1497, 1434, 1285, 1097; $^1$H NMR (CDCl$_3$) δ 8.09 (1H, s), 7.40 (1H, d, J=8.0), 7.28 (1H, t, J=8.0), 6.89 (1H, d, J=8.0), 4.02 (3H, s); $^{13}$C NMR (CDCl$_3$) δ 152.84, 145.82, 142.50, 139.99, 125.75, 113.42, 108.80, 56.97. Anal. Calcd. for $C_8H_7N_1O_2 \cdot 0.1H_2O$: C, 63.65; H, 4.81; N, 9.29. Found: C, 63.43, H, 4.88; N, 9.05. M.S. (+FAB); 150 (M$^+$+1).

4-Methoxybenzoxazole (65b). To a suspension of 4-hydroxybenzoxazole (2.00 g, 14.8 mmol) (Musser et al., J. Med. Chem., 30, pp. 62-67 (1987)) in acetone (80.0 ml) was added dried $K_2CO_3$ (2.25 g, 16.3 mmol) followed by iodomethane (1.38 ml, 22.2 mmol). The reaction was heated under reflux under $N_2$ for 4.5 h, then filtered and reduced in vacuo to afford the crude product. The resulting residue was purified by flash chromatography (25:75 ethyl acetate/hexane) to give 2.0 g (91%) of the title compound as a white crystalline solid: m.p. 72-74° C.; IR (KBr) 3089, 1619, 1610, 1503, 1496, 1322, 1275, 1090, 1071, 780, 741; $^1$H NMR (CDCl$_3$) δ 8.02 (1H, s), 7.32 (1H, t, J=8.0), 7.18 (1H, d, J=8.0), 6.81 (1H, d, J=8.0), 4.04 (3H, s). Anal. Calcd. for $C_8H_7NO_2$: C, 64.42; H, 4.73; N, 9.39. Found: C, 64.40; H, 4.84; N, 9.31; m/z (EI) 149 (M$^+$+1, 100%).

(3S,4R,S)t-Butyl N-(allyloxycarbonyl)-3-amino-4-hydroxy-4-(2-(7-methoxybenzoxazolyl))butanoate (66a). To a stirred solution of 7-methoxybenzoxazole 65a (548.6 mg, 3.68 mmol) in anhydrous THF (18.5 ml) at −78° C. under $N_2$ was added 1.56M n-butyl lithium in hexanes (2.47 ml, 3.86 mmol) dropwise, to produce a yellow colored solution. After stirring at −78° C. for 20 min, dry MgBr$_2$OEt$_2$ (1.045 g, 4.05 mmol) was added as a solid. The resulting heterogeneous mixture was warmed to −45° C. and stirred for 15 min. The reaction mixture was then recooled to −78° C. and a solution of (S)-Alloc-Asp(t-Bu)H (946.4 mg, 3.68 mmol) in THF (18.5 ml) was added dropwise. The reaction was stirred at −78° C. for 30 min, warmed to 0° C. and stirred for 1 h. The resulting homogeneous reaction was warmed to room temperature and stirred for 16 h. The reaction was quenched with 5% sodium bicarbonate (3.5 ml) then THF was removed in vacuo. The resulting aqueous residue was extracted with methylene chloride (×6). The combined extracts were washed with brine, dried (MgSO$_4$), filtered and reduced in vacuo to give 1.8 g of crude product. Flash chromatography (40:60 ethyl acetate/hexane) gave 1.21 g (81%) of the title compound, an oil, as a mixture of diastereoisomers at C-4: IR(CH$_2$Cl$_2$) 3425, 2983, 1725, 1504, 1290, 1157, 1101; $^1$H NMR (CDCl$_3$) δ 7.35-7.19 (2H, m), 6.89-6.81 (1H, m), 6.00-5.57 (2H, m), 5.32-5.05 (3H, m), 4.68-4.35 (3H, m), 4.01 (3H, s), 2.86-2.59 (2H, m), 1.45 (9H, s), 1.41 (9H, s); $^{13}$C NMR (CDCl$_3$) δ 171.18, 171.09, 165.80, 165.30, 156.71, 156.60, 145.65, 142.76, 142.71, 140.82, 140.72, 133.23, 125.81, 125.72, 118.41, 118.21, 113.07, 112.87, 108.95, 82.16, 70.28, 69.98, 66.52, 66.39, 57.03, 52.57, 52.29, 37.83, 36.86, 28.65. Anal. Calcd. for $C_{20}H_{26}N_2O_7 \cdot 0.6H_2O$: C, 57.57; H, 6.57; N, 6.72. Found: C, 57.49, H, 6.34; N, 6.60. M.S. (+FAB); 407 (M$^+$+1); 351, 307, 154.

(3S,4R,S)t-Butyl N-(allyloxycarbonyl)-3-amino-4-hydroxy-4-(2-(4-methoxybenzoxazolyl))butanoate (66b), was prepared according to the method described for 66a which afforded 1.29 g (26%, 68% based on recovered starting material) of the title compound as an oil and as a mixture of diastereoisomers at C-4: IR (CH$_2$Cl$_2$) 3400, 1725, 1625, 1505, 1369, 1354, 1281, 1263, 1226, 1158, 1092, 1048; $^1$H NMR (CDCl$_3$) δ 7.34-7.24 (1H, m), 7.16 (1H, d, J=8.2), 6.79 (1H, d, J=7.9), 6.00-5.50 (2H, m), 5.30-5.05 (3H, m), 4.70-4.35 (4H, m), 4.02 (3H, s), 2.90-2.45 (2H, m), 1.45-1.41 (9H, 2×s). Anal. Calcd. for $C_{20}H_{26}N_2O_7 \cdot 0.4H_2O$: C, 58.07; H, 6.53; N, 6.77. Found: C, 58.09; H, 6.41; N, 6.63. M.S. (+FAB); 407 (M$^+$+1, 88%); 351 (100).

(3S,4R,S)t-Butyl N-(N-acetyl-(S)—(O-tert-butyl-tyrosinyl)-(S)-valinyl-(S)-alaninyl)-3-amino-4-hydroxy-4-(2-(7-methoxybenzoxazolyl))butanoate (67a). To a stirred solution of the benzoxazole 66a (481.9 mg, 1.19 mmol) and Ac-Tyr ($^t$Bu)-Val-Ala-OH (586.3 mg, 1.30 mmol) in methylene chloride (3.5 ml) and DMF (3.5 ml) was added bis(triphenylphosphine) palladium (II) chloride (18.0 mg), followed by tributyltinhydride (0.80 ml, 2.96 mmol) dropwise. Hydroxybenzotriazole (320.4 mg, 2.37=01) was added and the mixture cooled to 0° C. 1-Ethyl-3-[3-(dimethylamino)propyl]carbodiimide hydrochloride (278.2 mg, 1.42 mmol) was added and the mixture was allowed to warm to room temperature and stirred for 16.5 h. The reaction was diluted with ethyl acetate and washed twice with 1M sodium hydrogensulphate, twice with saturated sodium bicarbonate, water, and brine. The organic layer was dried (MgSO$_4$), filtered and reduced in vacuo to yield 2.0 g of crude product. Flash chromatography (95:5 methylene chloride/methanol) gave 844.0 mg (94%) of the title compound as a white solid: m.p. 205° C.; IR (KBr)

3399, 3304, 2977, 1729, 1643, 1506, 1367, 1290, 1161; $^1$H NMR (d$_6$-DMSO) δ 8.24-7.78 (4H, m), 7.43-7.32 (2H, m), 7.23 (2H, d, J=8.5), 7.16-7.07 (1H, m), 6.93 (2H, d, J=8.5), 6.52, 6.40 (1H, 2xd, J=5.5, J=5.0), 5.03, 4.78-4.49, 4.45-4.16 (5H, brt, 2xm), 4.05, 4.04 (3H, 2xs), 3.08-2.35 (14H, m), 2.11-1.89 (1H, m), 1.83 (3H, s), 1.49-1.32, 1.15, 1.0-0.81 (27H, s, 2xm, J=7.0); $^{13}$C NMR (d$_6$-DMSO) δ 175.55, 175.18, 173.88, 173.75, 173.05, 169.23, 157.28, 148.55, 146.16, 143.21, 136.63, 133.55, 128.87, 127.17, 115.78, 111.92, 84.02, 81.50, 71.40, 61.15, 60.05, 57.79, 53.39, 51.62, 43.76, 40.52, 34.58, 32.52, 31.60, 26.35, 23.11, 22.71, 21.76. Anal. Calcd. for C$_{39}$H$_{55}$N$_5$O$_{10}$.0.5H$_2$O: C, 61.40; H, 7.40; N, 9.18. Found: C, 61.43; H, 7.31; N, 9.07. M.S. (+FAB); 754 (M$^+$+1); 698, 338, 267.

(3S,4R,S)t-Butyl N-(N-acetyl-(S)—(O-tert-butyl-tyrosinyl)-(S)-valinyl-(S)-alaninyl)-3-amino-4-hydroxy-4-(2-(4-methoxybenzoxazolyl))butanoate (67b), was prepared according to the method described for 67a which afforded 1.05 g (94%) of the title compound as a fine white powder: m.p. 210-213° C. (dec); IR (KBr) 3284, 2977, 1736, 1691, 1632, 1536, 1505, 1452, 1392, 1367, 1258, 1236, 1161, 1091; $^1$H NMR (d$_6$-DMSO) δ 8.20-7.75 (4H, m), 7.40-7.10 (4H, m), 7.00-6.80 (3H, m), 6.45, 6.34 (1H, 2xd, J=5.3, J=5.0), 5.00-4.10 (5H, m), 4.00, 3.99 (3H, 2xs), 3.00-2.25 (4H, m), 1.95 (1H, m), 1.78 (3H, s), 1.39-0.80 (27H, m). Anal. Calcd. for C$_{39}$H$_{55}$N$_5$O$_{10}$.0.5H$_2$O: C, 61.40; H, 7.40; N, 9.18. Found: C, 61.58; H, 7.38; N, 8.91. M.S. (+FAB); 754 (M$^+$+1, 30%); 72 (100).

(3S)t-Butyl N-(N-acetyl-(S)—(O-tert-butyl-tyrosinyl)-(S)-valinyl-(S)-alaninyl)-3-amino-4-(2-(7-methoxybenzoxazolyl))-4-oxobutanoate (68a). The Dess-Martin reagent (1.082 g, 2.55 mmol) (Ireland et al., *J. Org. Chem.*, 58, p. 2899 (1993); Dess et al., *J. Org. Chem.*, 48, pp. 4155-4156 (1983)) was added to a stirred suspension of the alcohol 67a (641.0 mg, 0.85 mmol) in methylene chloride (46.0 ml). The resulting mixture was stirred for 1 h before being partitioned between saturated sodium thiosulphate: saturated sodium bicarbonate (1:1, 86.0 ml) and ethyl acetate (86.0 ml). The resultant organic phase was washed in turn with saturated sodium thiosulphate: saturated sodium bicarbonate (1:1), saturated sodium bicarbonate, and brine. The organic phase was dried (MgSO$_4$), filtered and reduced in vacuo to give 660.0 mg of crude product. Flash chromatography (94:6 methylene chloride/methanol) gave 636.0 mg (100%) of the title compound as a white solid: m.p. 209° C.; [α]$_D^{24}$ −21.8° (c 0.16, methanol); IR (KBr) 3395, 3294, 2977, 1722, 1641, 1535, 1505, 1161; $^1$H NMR (CDCl$_3$) δ 8.43-8.16 (1H, m), 7.97-7.62 (2H, m), 7.49-7.14 (3H, m), 7.08-6.95 (3H, m), 6.89-6.73 (2H, m), 5.81-5.68 (1H, m), 5.16-4.86 (2H, m), 4.53 (1H, brt), 4.03 (3H, s), 3.16-2.84 (4H, m), 2.11-1.84 (4H, m), 1.46-1.14 (21H, m), 0.92-0.78 (6H, m); $^{13}$C NMR (CDCl$_3$) δ 186.28, 173.39, 171.90, 171.19, 171.03, 169.89, 156.43, 154.75, 146.32, 142.88, 140.98, 132.31, 130.54, 126.98, 124.73, 114.95, 111.42, 82.44, 78.71, 58.92, 57.20, 54.91, 53.47, 48.77, 39.43, 38.15, 32.79, 29.44, 28.60, 23.55, 20.27, 19.70, 19.34. M.S. (+FAB); 752 (M$^+$+1); 696, 336, 265.

(3S)t-Butyl N-(N-acetyl-(S)—(O)-tert-butyl-tyrosinyl)-(S)-valinyl-(S)-alaninyl)-3-amino-4-(2-(4-methoxybenzoxazolyl))-4-oxobutanoate (68b), was prepared according to the method described for the ketone 68a which afforded 420 mg (55%) of the title compound as a white solid: m.p. 211-213° C. (dec); [α]$_D^{24}$ −23.9° (c 0.82, methanol); IR (KBr) 3277, 3075, 1723, 1690, 1632, 1530, 1506, 1392, 1366, 1269, 1234, 1160, 1094; $^1$H NMR (CDCl$_3$) δ 8.15 (1H, brs), 7.7 (2H, brs), 7.46 (1H, t, J=8.3), 7.24 (2H, d, J=8.3), 7.10 (1H, brs), 7.03 (2H, d, J=8.3), 6.83 (3H, m), 5.74 (1H, q, J=6.9), 5.00 (2H, m), 4.51 (1H, t, J=7.0), 4.07 (3H, s), 3.20-2.95 (4H, m), 2.00 (4H, m), 1.42 (3H, d, J=6.8), 1.35 (9H, s), 1.23 (9H, s), 0.86 (6H, d, J=6.7). M.S. (+FAB); 752 (M$^+$+1, 7%); 72 (100).

(3S)N-(N-Acetyl-(S)-tyrosinyl-(S)-valinyl-(S)-alaninyl)-3-amino-4-(2-(7-methoxybenzoxazolyl))-4-oxobutanoate (69a; R). A solution of the ester 68a (600.0 mg, 0.80 mmol) in a 1:1 mixture of methylene chloride and trifluoroacetic acid (65.0 ml) was stirred for 1 h under a dry atmosphere of N$_2$. The solution was then reduced in vacuo, taken up in ether and reduced again. This process was repeated six times to afford the crude product as an off white solid. Flash chromatography (gradient 95:5 to 80:20 methylene chloride/methanol) gave 420.8 mg (83%) of the title compound as a hygroscopic white solid. The product existed as a mixture of three isomers in CD$_3$OD, consisting of the keto form (c 50%), and its acycloxy keto form (two isomers at C-4, c 50%): m.p. decomposes above 150° C.; [α]$_D^{24}$ −33.2° (c 0.17, methanol); IR (KBr) 3300, 1715, 1658, 1650, 1531, 1517, 1204; $^1$H NMR (CD$_3$OD) δ 7.46-7.19 (2H, m), 7.16-6.91 (3H, m), 6.70-6.59 (2H, m), 5.62-5.49 (1H, m), 5.00-4.72 (1H, obscurred m), 4.69-4.51 (1H, m), 4.49-4.08 (2H, m), 4.05-3.89 (3H, m), 3.16-2.47 (4H, m), 2.05-1.78 (4H, m), 1.41-1.11, 1.05-0.70 (9H, 2xm). Anal. Calcd. for C$_{31}$H$_{37}$N$_5$O$_{10}$.3H$_2$O: C, 53.67; H, 6.25; N, 10.10. Found: C, 53.76; H, 5.56; N, 10.28. M.S. (+FAB); 640 (M$^+$+1); 435, 147.

(3S)t-Butyl N-(N-acetyl-(S)-tyrosinyl-(S)-valinyl-(S)-alaninyl)-3-amino-4-(2-(4-methoxybenzoxazolyl))-4-oxobutanoate (69b; S), was prepared according to the method described for the acid 69a which afforded the hygroscopic title compound 252 mg (96%). The product existed as a mixture of three isomers in CD$_3$OD, consisting of the keto form, and its acycloxy ketal form (two isomers at C-4). The product existed as a single isomer in d-6 DMSO: m.p. 200-203° C. (dec.); [α]$_D^{24}$ −38.0° (c 0.23, methanol); IR (KBr) 3289, 2968, 1718, 1713, 1658, 1634, 1548, 1517, 1506, 1461, 1453, 1393, 1369, 1268, 1228, 1174, 1092; $^1$H NMR (d$_6$-DMSO) δ 9.20 (1H, brs), 8.71 (1H, d, J=6.2), 8.10 (2H, m), 7.83 (1H, d, J=8.7), 7.61 (1H, t, J=8.2), 7.46 (1H, d, J=8.2), 7.08 (3H, m), 6.65 (2H, d, J=8.3), 5.50 (1H, q, J=6.5), 4.50 (1H, m), 4.37 (1H, m), 4.20 (1H, m), 4.05 (3H, s), 3.09-2.77 (4H, m), 1.94 (1H, m), 1.79 (3H, s), 1.23 (3H, d, J=7.0), 0.82 (6H, m). Anal. Calcd. for C$_{31}$H$_{37}$N$_5$O$_{10}$.1.5H$_2$O: C, 55.85; H, 6.05; N, 10.51. Found: C, 55.21; H, 5.69; N, 10.13. M.S. (+FAB); 640 (M$^+$+1, 22%); 107 (100).

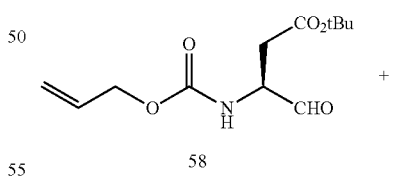

58

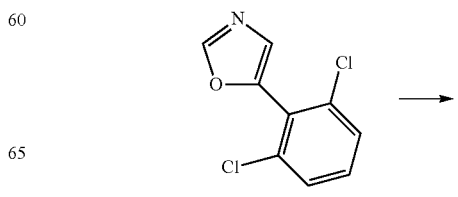

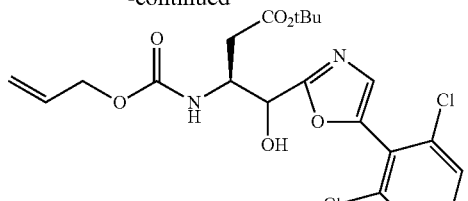

99

3(S)-(Allyloxycarbonyl)-amino-4-[(2,6-dichloro-phenyl)-oxazol-2-yl]-4(R,S)-hydroxy-butyric acid tert-butyl ester (99). A solution of 5-(2,6-Dichlorophenyl)oxazole (2.71 g, 12.7 mmol; prepared by a similar method described in Tet. Lett. 23, p. 2369 (1972)) in tetrahydrofuran (65 mL) was cooled to −78° C. under a nitrogen atmosphere. To this solution was added n-butyl lithium (1.5M solution in hexanes, 8.5 mL, 13.3 mmol) and stirred at −78° C. for 30 min. Magnesium bromide etherate (3.6 g, 13.9 mmol) was added and the solution was allowed to warm to −45° C. for 15 min. The reaction was cooled to −78° C. and aldehyde 58 (3.26 g, 12.7 mmol; Graybill et al., Int. J. Protein Res., 44, pp. 173-182 (1993)) in tetrahydrofuran (65 mL) was added dropwise. The reaction was stirred for 25 min., then allowed to warm to −40° C. and stirred for 3 h, and then at room temperature for 1 h. The reaction was quenched with 5% NaHCO$_3$ (12 mL) and stirred for 3 h. The tetrahydrofuran was removed in vacuo and the resulting residue was extracted with dichloromethane. The organic layer was washed with saturated sodium chloride solution and dried over magnesium sulfate, filtered, and concentrated to yield 6.14 g of the title compound. Purification gave 4.79 g (80%) of 99: $^1$H NMR (CDCl$_3$) δ 1.45 (s, 9H), 2.7-2.5 (m, 2H), 2.8 (dd, 1H), 4.2, 4.4 (2×d, 1H), 4.7-4.5 (m, 3H), 5.35-5.1 (m, 2H), 5.6, 5.7 (2×d, 1H), 6.0-5.8 (m, 1H), 7.2 (d, 1H), 7.3 (m, 1H), 7.4 (m, 2H).

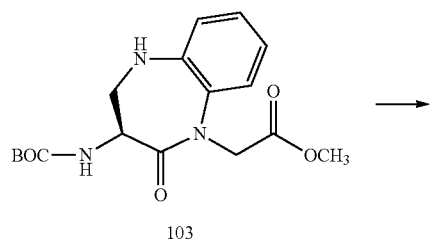

103

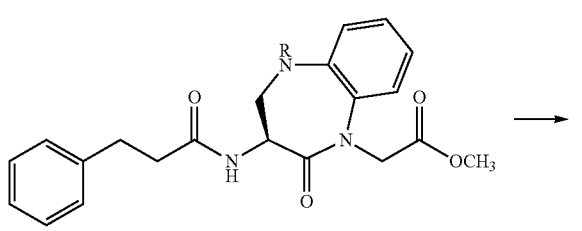

104

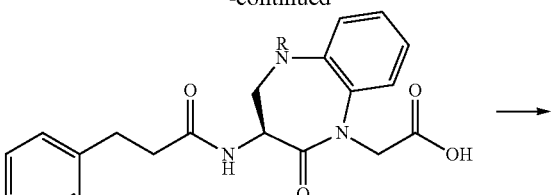

105

106 a R = H
b R = COCH$_2$CH$_2$Ph
c R = CH$_2$Ph

[2-oxo-3(S)-(3-phenylpropionylamino)-2,3,4,5-tetrahydro-benzo[b][1,4]diazepin-1-yl]acetic acid methyl ester (104a). Anhydrous hydrogen chloride was bubbled into a solution of (3(S)-tert-butoxycarbonylamino-2-oxo-2,3,4,5-tetrahydro-benzo[b][1,4]diazepin-1-yl)acetic acid methyl ester (103, 1 g, 2.86 mmol) in 25 ml of ethyl acetate for 2 minutes then stirred for 1 hour at room temperature. The reaction was evaporated to give 2-oxo-3(S)-amino-2,3,4,5-tetrahydrobenzo[b][1,4]diazepin-1-yl acetic acid methyl ester hydrochloride as a white solid.

The hydrochloride salt and hydrocinnamic acid (0.47 g, 3.15 mmol) were dissolved into 20 ml of dimethylformamide and cooled to 0° C. Diisopropylethylamine (1 ml, 5.72 mmol) was added to the solution followed by the addition of N-hydroxybenzotriazole and 1-(3-dimethylaminopropyl)-3-ethyl-carbodiimide hydrochloride. After stirring for 18 hours at room temperature, the mixture was diluted with 150 ml of ethyl acetate and washed with 10% sodium hydrogen sulfate, 10% sodium bicarbonate, and brine. The organic layer was dried over anhydrous sodium sulfate, filtered, and evaporated to a crude solid that was purified by flash chromatography eluting with 7:3 ethyl acetate/dichloromethane to afford 600 mg (55%) of the title compound as a white solid. $^1$H NMR (CDCl$_3$) δ 7.3-6.85 (9H, m), 6.55-6.0 (1H, d), 4.88-4.82 (1H, m), 4.72-4.65 (1H, d), 4.28-4.22 (1H, m), 3.95-3.9 (1H, m), 3.78 (3H, s), 3.65 (1H, br. s), 3.28-3.2 (1H, m), 2.95-2.84 (2H, m), 2.55-2.4 (2H, m).

(3(S)-(3-Phenylpropionylamino)-2-oxo-2,3,4,5-tetra-hydrobenzo[b][1,4]diazepin-1-yl)acetic acid (105a). (3(S)-(3-Phenylpropionylamino)-2-oxo-2,3,4,5-tetrahydro-benzo[b][1,4]diazepin-1-yl)acetic acid methyl ester (104a) was dissolved in 90% methanol. Lithium hydroxide hydrate was added to the reaction and the reaction was stirred at room temperature for 4 h. The reaction was evaporated in vacuo to give a white solid. This was dissolved in 20 ml of water and acidified to pH 5 and extracted with ethyl acetate to afford 304 mg (88%) of the title compound as a white solid. $^1$H NMR (CDCl$_3$) δ 7.5-6.9 (11H, m), 4.92-4.8 (1H, m), 4.7-4.58 (1H, d), 4.38-4.25 (1H, d), 3.88-3.78 (1H, m), 3.45-3.25 (1H, m), 3.05-2.85 (2H, m), 2.55-2.45 (2H, m).

4-Oxo-3(S)-{2-[2-oxo-3(S)-(3-phenylpropionylamino)-2,3,4,5-tetrahydro-benzo[b][1,4]diazepin-1-ylacetylamino}butyric acid (106a). N-[1-(2-Benzyloxy-5-oxotetrahydrofuran-3-ylcarbamoyl-methyl)-2-oxo-2,3,4,5-tetrahydro-1H-benzo[b][1,4]diazepin-3-yl]-3-phenylpropionamide was prepared from 105a by the procedure used to prepare compound H (step A) to afford 390 mg (93%) of the product as diastereomers. $^1$H NMR (CD$_3$OD) δ 7.58-7.22 (14H, m), 5.78-5.73 (0.5H, d), 5.64 (0.5H, s), 5.0-4.72 (4H, m), 4.54-4.42 (2H, m), 3.82-3.76 (0.5H, m), 3.68-3.62 (0.5H, m), 3.28-3.21 (0.5H, m), 3.19-3.12 (0.5H, m), 3.07-2.98 (2H, m), 2.78-2.48 (4H, m).

The resulting product was converted to 106a by the method described to prepare compound H (Step D) to afford the title compound as a white solid (17%): $^1$H NMR (CD$_3$OD) δ 7.54-6.98 (9H, m), 5.58-5.44 (1H, m), 4.8-4.2 (4H, m), 3.96-3.3 (2H, m), 3.30-3.05 (1H, m), 2.98-2.25 (5H, m).

[2-oxo-5-(3-phenylpropionyl)-3(S)-(3-phenylpropionylamino)-2,3,4,5-tetrahydrobenzo[b][1,4]diazepin-1-yl]acetic acid methyl ester (104b). Anhydrous hydrogen chloride was bubbled into a solution of (3(S)-tert-butoxycarbonylamino-2-oxo-2,3,4,5-tetrahydro-benzo[b][1,4]diazepin-1-yl)acetic acid methyl ester (103, 1 g, 2.86 mmol) in 25 ml of ethyl acetate for 2 minutes then stirred for 1 hour at room temperature. The reaction was evaporated to give 2-oxo-3(S)-amino-2,3,4,5-tetrahydrobenzo[b][1,4]diazepin-1-yl acetic acid methyl ester hydrochloride as a white solid.

The hydrochloride salt was suspended into 20 ml of dichloromethane and cooled to 0° C. Triethylamine (1.6 ml, 11.5 mmol) was added to the suspension followed by the dropwise addition of dihydrocinnamoyl chloride (0.9 ml, 6 mmol). The mixture was warmed to room temperature and stirred for 18 hours. The mixture was diluted with 25 ml of dichloromethane and washed twice with 50 ml of water and once with 50 ml of brine. The organic layer was dried over anhydrous sodium sulfate, filtered, and evaporated to give a viscous, yellow oil that was purified by flash chromatography eluting with 1:1 ethyl acetate/dichloromethane to afford 1.35 g (92%) of the title product as a white solid. $^1$H NMR (CDCl$_3$) δ 7.45-7.02 (14H, m), 6.37-6.32 (1H, d), 4.78-4.72 (1H, m), 4.52-4.3 (3H, m), 3.82-3.77 (1H, m), 3.74 (3H, s), 3.03-2.87 (4H, m), 2.58-2.45 (2H, m), 2.45-2.35 (1H, m), 2.25-2.16 (1H, m).

[2-oxo-5-(3-phenylpropionyl)-3-(3(S)-phenylpropionylamino)-2,3,4,5-tetrahydrobenzo[b][1,4]diazepin-1-yl]acetic acid (105b). [2-oxo-5-(3-phenylpropionyl)-3-(3-phenylpropionylamino)-2,3,4,5-tetrahydrobenzo[b][1,4]diazepin-1-yl]acetic acid methyl ester (104b; 680 mg, 1.32 mmol) was hydrolyzed by the procedure used to hydrolyze 105a to afford 645 mg (98%) of the title compound as a white solid. $^1$H NMR (CDCl$_3$) δ 7.58 (1H, br. s), 7.5-7.42 (1H, m), 7.35-6.95 (14H, m), 4.95-4.88 (1H, m), 4.64-4.55 (1H, d), 4.54-4.45 (1H, t), 4.15-4.05 (1H, d), 3.75 (1H, m), 3.05-2.75 (4H, m), 2.58-2.45 (2H, m), 2.45-2.28 (1H, m), 2.25-2.14 (1H, m).

2-oxo-3(S)-(2-[(2-oxo-5-(3-phenylpropionyl)-3(S)-(3-phenyl-propionyl-amino)-2,3,4,5-tetrahydrobenzo[b][1,4]diazepin-1-yl]acetylamino/butyric acid (106b). [2-oxo-5-(3-phenylpropionyl)-3-(3-phenylpropionylamino)-2,3,4,5-tetrahydrobenzo[b][1,4]diazepin-1-yl]acetic acid and 3-amino-4-oxobutyric acid tert-butylester semicarbazone were coupled by the procedure used in the preparation of compound K (step A) to give 350 mg (85%) of a white solid. $^1$H NMR (CDCl$_3$) δ 9.05 (1H, br. s), 7.58-7.55 (1H, d), 7.5-7.35 (1H, m), 7.35-6.95 (14H, m), 6.75-6.72 (1H, d), 6.25 (1H, br. s), 5.25 (1H, br. s), 4.95-4.88 (1H, m), 4.8-4.72 (1H, m), 4.55-4.4 (2H, m), 3.92-3.88 (1H, d), 3.73-3.68 (1H, m), 2.95-2.8 (4H, m), 2.8-2.72 (1H, m), 2.62-2.55 (1H, m), 2.55-2.45 (2H, m), 2.4-2.32 (1H, m), 2.2-2.12 (1H, m), 1.45 (9H, s).

4-oxo-3-(2-[2-oxo-5-(3-phenylpropionyl)-3-(3-phenylpropionyl-amino)-2,3,4,5-tetrahydrobenzo[b][1,4]diazepin-1-yl]-acetyl-amino/butyric acid tert-butyl ester semicarbazone was deprotected as described in the preparation of compound K (step C) to give 118 mg (47%) of the title compound as a white solid. $^1$H NMR (CD$_3$OD) δ 7.48-6.95 (14H, m), 4.65-4.15 (6H, m), 3.5-3.4 (1H, m), 2.85-2.72 (4H, m), 2.65-2.5 (1H, m), 2.5-2.34 (3H, m), 2.34-2.15 (2H, m).

[5-Benzyl-2-oxo-3(S)-(3-phenylpropionylamino)-2,3,4,5-tetrahydro-benzo[b][1,4]diazepin-1-yl]acetic acid methyl ester (104c). [2-oxo-3-(3-phenylpropionylamino)-2,3,4,5-tetrahydrobenzo-[b][1,4]diazepin-1-yl]acetic acid methyl ester (104a; 500 mg, 1.31 mmol), calcium carbonate (155 mg, 1.58 mmol), and benzyl bromide (170 μl, 1.44 mmol) were taken into 10 ml of dimethylformamide and heated to 80° C. for 8 hours. The mixture was diluted with 150 ml of ethyl acetate and washed 4 times with 50 ml of water. The organic layer was dried over anhydrous sodium sulfate, filtered, and evaporated to give a viscous, yellow oil that was purified by flash chromatography eluting with dichloromethane/ethyl acetate (8:2) to give 460 mg (75%) of the title compound as a white solid. $^1$H NMR (CDCl$_3$) δ 7.34-7.05 (14H, m), 6.32-6.28 (1H, d), 4.84-4.76 (1H, d), 4.76-4.70 (1H, m), 4.43-4.37 (1H, d), 4.26-4.18 (1H, d), 4.06-4.00 (1H, d), 3.79 (3H, s), 3.45-3.37 (1H, m), 3.02-2.95 (1H, m), 2.90-2.82 (2H, m), 2.5-2.34 (2H, m).

[5-Benzyl-2-oxo-3(S)-(3-phenylpropionylamino)-2,3,4,5-tetrahydro-benzo[b][1,4]diazepin-1-yl]acetic acid (105c) was prepared by the hydrolysis of the ester (102c) by the procedure reported in Example 105a to give 450 mg (98%) of the title compound as a white solid: $^1$H NMR (CD$_3$OD) δ 7.5-7.05 (14H, m), 6.4 (1H, br. s), 4.85-4.55 (2H, m), 4.5-4.21 (2H, m), 4.12-3.92 (1H, d), 3.45-3.3 (1H, m), 3.1-2.8 (3H, m), 2.55-2.28 (3H, m).

3(S)-{2-[5-Benzyl-2-oxo-3-(3(S)-phenylpropionylamino)-2,3,4,5-tetrahydrobenzo[b][1,4]diazepin-1-yl]-acetylamino}-4-oxobutyric acid (106c). [5-Benzyl-2-oxo-3(S)-(3-phenylpropionylamino)-2,3,4,5-tetrahydrobenzo[b][1,4]diazepin-1-yl]acetic acid and 3(S)-amino-4-oxobutyric acid tert-butylester semicarbazone were coupled by the procedure used in the preparation of compound K (step A) and to afford 260 mg (85%) of a white solid: $^1$H NMR (CD$_3$OD) δ 7.35-7.0 (15H, m), 4.94-4.88 (1H, m), 4.68-4.58 (1H, d), 4.57-4.52 (1H, m), 4.41-4.34 (1H, d), 4.3-4.23 (1H, d), 4.1-4.04 (1H, d), 3.18-3.11 (1H, m), 3.09-2.98 (1H, m), 2.78-2.72 (2H, t), 2.65-2.57 (1H, m), 2.42-2.33 (3H, m). 3(S)-{2-[5-Benzyl-2-oxo-3(S)-(3-phenylpropionylamino)-2,3,4,5-tetrahydrobenzo[b][1,4]diazepin-1-yl]-acetylamino}-4-oxobutyric acid tert-butyl ester semicarbazone was deprotected as described in the preparation of compound K (step C) to give 168 mg (81%) of the title compound as a white solid. $^1$H NMR (CD$_3$OD) δ 7.37-7.0 (14H, m), 4.75-4.62 (1H, m), 4.6-4.45 (2H, m), 4.4-4.21 (2H, m), 4.15-3.95 (2H, m), 3.15-3.0 (2H, m), 2.82-2.67 (2H, m), 2.65-2.52 (1H, m), 2.5-2.32 (3H, m).

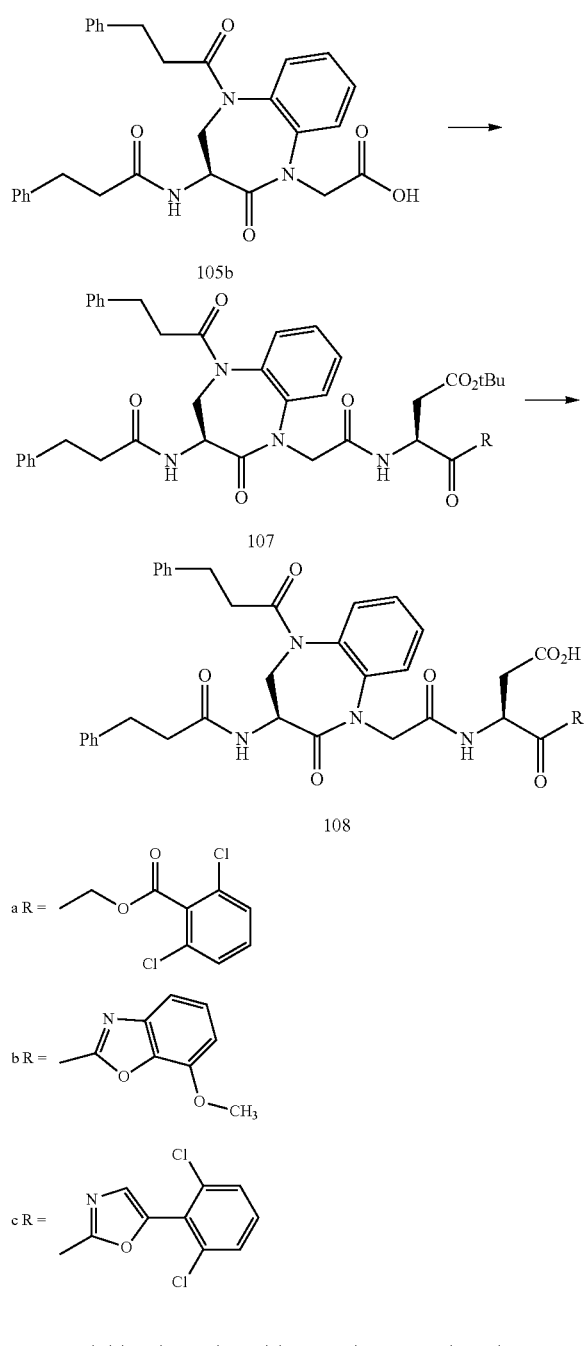

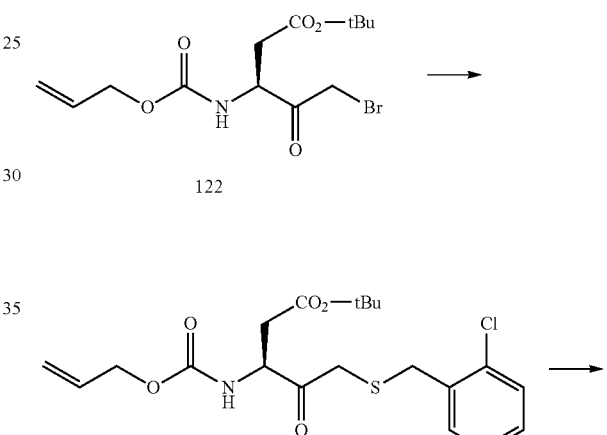

2,6-Dichlorobenzoic acid 4-carboxy-2-oxo-3(S)-{2-[2-oxo-5-(3-phenylpropionyl)-3(S)-(3-phenylpropionylamino)-2,3,4,5-tetrahydrobenzo[b][1,4]diazepin-1-yl]acetylamino}butyl ester (108a) was prepared from 107a by the method described for compound 57a which afforded 156 mg (68%) of the title compound as a white solid. $^1$H NMR (CD$_3$OD) δ 7.5-6.9 (17H, m), 5.16-5.02 (1H, dd), 4.88-4.71 (2H, m), 4.62-4.44 (2H, m), 4.42-4.28 (2H, m), 4.27-4.18 (1H, m), 3.47-3.41 (1H, m), 2.90-2.60 (5H, m), 2.46-2.4 (2H, m), 2.39-2.18 (2H, m).

4-(7-Methoxybenzoxazol-2-yl)-4-oxo-3(S)-{2-[2-oxo-5-(3-phenylpropionyl)-3(S)-(3-phenylpropionylamino)-2,3,4,5-tetrahydrobenzo[b][1,4]diazepin-1-yl]-acetylamino}butyric acid (108b) was prepared by the method described for compound 69a to give the title compound (50%) as a white solid. $^1$H NMR (CD$_3$OD) δ 7.41-6.88 (17H, m), 5.6-5.55 (0.5H, t), 5.48-5.43 (0.5H, t), 4.64-4.45 (2H, m), 4.45-4.30 (1H, m), 3.93 (1.5H, s), 3.90 (1.5H, s), 3.47-3.34 (1H, m), 3.10-2.85 (2H, m), 2.84-2.63 (5H, m), 2.6-2.4 (2H, m), 2.3-2.1 (2H, m).

2,6-Dichlorobenzoic acid 4-tert-butoxycarbonyl-2-oxo-3(S)-{2-[2-oxo-5-(3-phenylpropionyl)-3(S)-(3-phenylpropionylamino)-2,3,4,5-tetrahydro-benzo[b][1,4]diazepin-1-yl]acetyl-amino}butyl ester (107a). The resulting semicarbazone was prepared by the coupling of compound 105b and t-butyl 3-(allyloxycarbonylamino)-4-oxo-5-(2,6-dichlorobenzoyl-oxy)pentanoate (WO 93 16710) as described in compound 56a to give 256 mg (58%) of the title compound as a white solid. $^1$H NMR (CDCl$_3$) δ 7.45-7.04 (17H, m), 6.45-6.34 (2H, m), 5.28-5.21 (1H, m), 5.1-5.0 (1H, m), 4.95-4.90 (1H, m), 4.75-4.70 (1H, m), 4.55-4.44 (1H, m), 4.32-4.22 (1H, dd), 3.99-3.85 (1H, dd), 3.85-3.76 (1H, m), 3.06-2.83 (5H, m), 2.83-2.74 (1H, m), 2.6-2.44 (2H, m), 2.43-2.33 (1H, m), 2.24-2.15 (1H, m), 1.45 (9H, s).

a R = 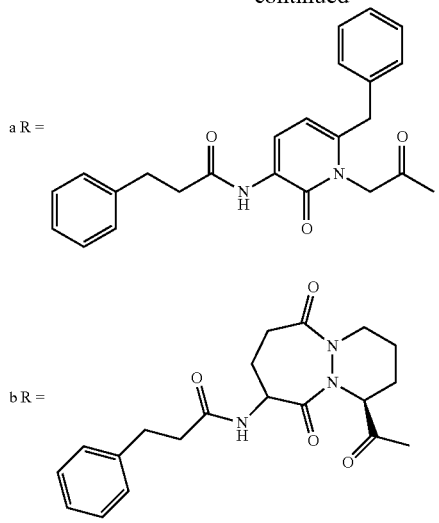

b R = t-Butyl (3S)N-(allyloxycarbonyl)-3-amino-5-(2-chlorophenylmethylthio)-4-oxo-pentanoate (123). Potassium fluoride (273 mg, 4.70 mmol) and then 2-chlorophenylmethyl thiol (373 mg, 2.35 mmol) were added to a stirred solution of (3S)t-butyl N-(allyloxycarbonyl)-3-amino-5-bromo-4-oxo-pentanoate (122; 749 mg, 2.14 mmol; WO 93 16710) in dimethylformamide (20 ml). The mixture was stirred for 3.5 h, quenched with water (50 ml) and extracted with ethyl acetate (2×50 ml). The combined organic extracts were washed with water (4×50 ml) then brine (50 ml). They were dried (MgSO$_4$) and concentrated to afford an oil which was purified by flash chromatography (10-35% ethyl acetate/hexane) to afford 832 mg (91%) of a colourless solid: mp. 45-6° C.; $[\alpha]_D^{20}$ −19.0° (c 1.0, CH$_2$Cl$_2$); IR (film) 3340, 2980, 2935, 1725, 1712, 1511, 1503, 1474, 1446, 1421, 1393, 1368, 1281, 1244, 1157, 1052, 1040, 995, 764, 739; $^1$H NMR (CDCl$_3$) δ 7.36 (2H, m), 7.21 (2H, m), 5.91 (2H, m), 5.27 (2H, m), 4.76 (1H, m), 4.59 (2H, d), 3.78 (2H, s), 3.36 (2H, m), 2.91 (1H, dd), 2.74 (1H, dd), 1.43 (9H, s). Anal. Calcd for C$_{20}$H$_{26}$ClNO$_5$S: C, 56.13; H, 6.12; N, 3.27; S, 7.49. Found: C, 56.08; H, 6.11; N, 3.26; S, 7.54. MS (C.I.) 430/28 (M$^+$+1, 3%), 374/2 (100).

t-Butyl (3S)3(2(6-benzyl-1,2-dihydro-2-oxo-3(3-phenyl-propionylamino)-1-pyridyl)acetylamino-5-(2-chlorophenyl-methylthio)-4-oxopentanoate (124a). 6-Benzyl-1,2-dihydro-2-oxo-3-(3-phenylpropionylamino)-pyridyl acetic acid (52b; 300 mg, 0.76 mmol) in THF (7 ml) was stirred with 1-hydroxybenzotriazole (205 mg, 1.52 mmol) and 1-(3-dimethylaminopropy-3-ethylcarbodiimide hydrochloride). After 3 min, water (12 drops) was added and the mixture stirred 10 min then treated with t-butyl (3S)N-(allyloxycarbonyl)-3-amino-5-(2-chlorophenylmethylthio)-4-oxopentanoate (123) (325 mg, 0.76 mmol), bis(triphenylphosphine) palladium II chloride (20 mg) and tributyltin hydride (0.6 ml, 2.28 mmol). The mixture was stirred for 5 h at room temperature, poured into ethyl acetate and washed with aqueous 1M HCl (×2), aqueous sodium bicarbonate, brine, dried (MgSO$_4$) and concentrated. The residue was triturated with pentane and the supernatant discarded. Chromatography (silica gel, 50% ethyl acetate/hexane) afforded a colourless foam (439 mg, 81%): $[\alpha]_D^{21}$ −18.3° (c 0.5, CH$_2$Cl$_2$); IR (KBr) 3356, 3311, 1722, 1689, 1646, 1599, 1567, 1513, 1367, 1154; $^1$H NMR (CDCl$_3$) δ 8.39 (1H, d), 8.23 (1H, s), 7.24 (14H, m), 6.16 (1H, d), 4.95 (1H, m), 4.63 (2H, m), 4.02 (2H, s), 3.74 (2H, s), 3.27 (2H, s), 2.85 (6H, m), 1.40 (9H, s). Anal. Calcd for C$_{39}$H$_{42}$ClN$_3$O$_6$S: C, 65.39; H, 5.91; N, 5.87. Found: C, 65.51; H, 5.99; N, 5.77.

t-Butyl[3S(1S,9S)]-3-(6,10-dioxo-1,2,3,4,7,8,9,10-octahydro)-9-(3-phenylpropionylamino)-6H-pyridazine[1,2-a][1,2]diazepine-1-carboxamido-5-(2-chlorophenylmethylthio)-4-oxopentanoate (124b) was prepared by a similar method as 124a from the thioether 123 and 3S(1S,9S)-3-(6,10-dioxo-1,2,3,4,7,8,9,10-octahydro)-9-(3-phenylpropionylamino)-6H-pyridazino[1,2-a][1,2]diazepine-1-carboxylic acid (45a) to afford 452 mg (50%) of colourless foam: mp 55-7° C.; $[\alpha]_D^{22}$ −94.0° (c 0.12, CH$_2$Cl$_2$); IR (KBr) 3288, 2934, 1741, 1722, 1686, 1666, 1644, 1523, 1433, 1260, 1225, 1146, 757; $^1$H NMR (CDCl$_3$) δ 7.35 (3H, m), 7.20 (7H, m), 6.46 (1H, d), 5.21 (1H, m), 4.97 (2H, m), 4.56 (1H, m), 3.75 (2H, s), 3.25 (3H, m), 2.93 (5H, m), 2.71 (1H, dd), 2.55 (2H, m), 2.30 (1H, m), 1.92 (3H, m), 1.66 (2H, m), 1.42 (9H, s). Anal. Calcd for C$_{35}$H$_{43}$ClN$_4$O$_7$S. 0.25H$_2$O: C, 59.73; H, 6.23; Cl, 5.04; N, 7.96; S, 4.56. Found: C, 59.73; H, 6.19; Cl, 5.10; N, 7.79; S, 4.58. MS (−FAB) 697 (M−1, 100).

(3S)3(2(6-Benzyl-1,2-dihydro-2-oxo-3-(3-phenylpropionylamino)-1-pyridyl)acetylamino-5-(2-chlorophenylmethylthio)-4-oxopentanoic acid (125a). t-Butyl-3(2(6-benzyl-1,2-dihydro-2-oxo-3-(3-phenylpropionylamino)-1-pyridyl)acetyl-amino-5-(2-chlorophenylmethylthio)-4-oxopentanoate (124a) (400 mg, 0.56 mmol) in dichloromethane (3 ml) at 0° C. was treated with trifluoroacetic acid (3 ml) and stirred at 0° C. for 1 h and room temperature for 0.5 h. The solution was concentrated then redissolved in dichloromethane and reconcentrated. This procedure was repeated three times. The residue was stirred in ether for 1 hr and filtered to yield a colourless solid (364 mg, 99%): mp. 165-7° C.; $[\alpha]_D^{22}$ −27.7° (c 0.2, CH$_2$Cl$_2$); IR (KBr) 3289, 1712, 1682, 1657, 1645, 1593, 1562, 1527, 1497, 1416, 1203, 1182; $^1$H NMR (CDCl$_3$) d 8.47 (1H, d), 8.21 (1H, s), 7.70 (1H, d), 7.22 (14H, m), 6.24 (1H, d), 5.03 (1H, m), 4.65 (2H, m), 4.06 (2H, s), 3.69 (2H, m), 3.23 (2H, m), 2.88 (6H, m).

[3S(1S,9S)]-3-(6,10-dioxo-1,2,3,4,7,8,9,10-octahydro)-9-(3-phenylpropionyl-amino)-6H-pyridazine[1,2-a][1,2]diazepine-1-carboxamido-5-(2-chlorophenyl-methylthio)-4-oxopentanoic acid (125b), was prepared by a similar method as 125a from the t-butyl ester 124b to afford 362 mg (93%) of colourless powder: mp 76-80° C.; $[\alpha]_D^{21}$ −134 (c 0.10, MeOH); IR (KBr) 3309, 2935, 1725, 1658, 1528, 1445, 1417, 1277, 1219, 1175; $^1$H NMR (D$_6$-DMSO) δ 8.80 (1H, d), 8.19 (1H, d), 7.31 (9H, m), 5.09 (1H, m), 4.74 (1H, m), 4.63 (1H, m), 4.35 (1H, m), 3.76 (2H, m), 3.28 (3H, m), 2.80 (5H, m), 2.52 (4H, m), 2.16 (2H, m), 1.90 (3H, m). Anal. Calcd for C$_{31}$H$_{35}$Cl$_2$N$_4$O$_7$S. 0.25H$_2$O: C, 57.49; H, 5.53; N, 8.65; S, 4.95. Found: C, 57.35; H, 5.43; N, 8.45; S, 4.88. MS (−FAB) 641 (M−1, 100).

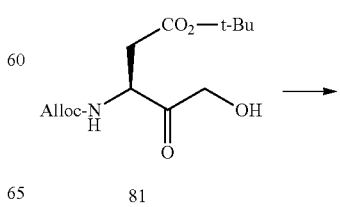

81

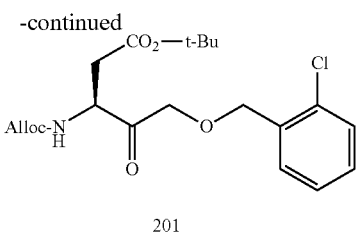

201

2-Chlorophenylmethyliodide. A mixture of 2-chlorophenylmethylbromide (4 g, 19.47 mmol) and NaI (14 g, 97.33 mmol) in acetone (40 ml) was stirred under reflux for 1 hour. The reaction mixture was cooled, filtered and concentrated in vacuo. The residue was triturated with hexane and filtered. The solution was concentrated in vacuo, and the resulting oil purified by flash chromatography (silica, hexane) to afford the title compound (4.67 g, 63%) as an oil: $^1$H NMR (CDCl$_3$) δ 7.34 (4H, m), 4.54 (2H, s).

(3S)t-Butyl N-(allyloxycarbonyl)-3-amino-5-(2-chlorophenylmethyloxy)-4-oxopentanoate (201). (3S)t-Butyl N-(allyloxycarbonyl)-3-amino-5-hydroxy-4-oxopentanoate (81, Chapman, et al., *Bioorg. & Med. Chem. Lett.*, 2, pp. 613-618 (1992) 0.144 g, 0.5 mmol) and 2-chlorophenylmethyliodide (0.569 g, 1.5 mmol) in CH$_2$Cl$_2$ (4 ml) were stirred vigorously with silver oxide (0.231 g, 1 mmol) and heated at 38° C. for 40 hours. The reaction mixture was cooled, filtered and the filtrate evaporated. The residue was purified by flash chromatography (silica, 0-20% ethylacetate in hexane) to afford the product as a colourless oil (0.138 g, 67%): [α]$_D^{24}$ +3.9° (c 1.3, CH$_2$Cl$_2$); $^1$H NMR (CDCl$_3$) δ 7.37 (4H, m), 5.88 (2H, m), 5.26 (2H, m), 4.69 (2H, s), 4.57 (3H, m), 4.50 (1H, d), 4.35 (1H, d), 3.03 (1H, dd), 2.76 (1H, dd), 1.42 (9H, s).

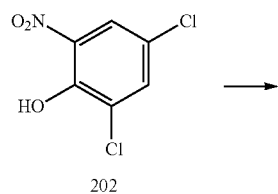

202

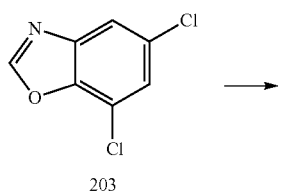

203

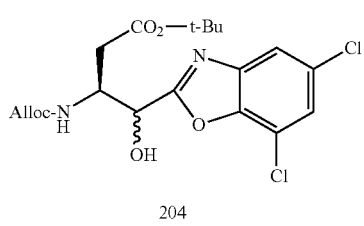

204

5,7-Dichlorobenzoxazole (203). A solution of 2,4-dichloro-6-nitrophenol (202, 40 g containing 20% moisture) in EtOAc (500 ml) was dried using MgSO$_4$, filtered and the filter cake washed with a little EtOAc. Platinum on carbon (5% sulphided—2 g) was added and the mixture hydrogenated until uptake of H$_2$ ceased. Triethyl orthoformate (160 ml) and p-toluene sulphonic acid (160 mg) were added and the mixture refluxed for 4 h. After cooling and removal of spent catalyst by filtration the solution was washed with sat. NaHCO$_3$ solution, water and brine, dried with MgSO$_4$ and evaporated to dryness. Trituration with hexane gave a solid which was collected by filtration, washed with hexane and dried to give the title compound (25.5 g, 88%) as a crystalline solid: mp 98-99° C.; IR (KBr) 3119, 1610, 1590, 1510, 1452, 1393, 1296, 1067, 850; $^1$H NMR (CDCl$_3$) δ 8.16 (1H, s), 7.69 (1H, d, J=1.9), 7.42 (1H, d, J=1.9); Anal. Calcd for C$_7$H$_3$Cl$_2$NO: C, 44.72; H, 1.61; N, 7.45; Cl, 37.70. Found: C, 44.84; H, 1.69; N, 7.31; Cl, 37.71.

(3S,4RS)t-Butyl N-(allyloxycarbonyl)-3-amino-4-hydroxy-4-(5,7-dichlorobenzoxazol-2-yl)butanoate (204). Magnesium bromide was prepared by reaction of Mg (7.45 g, 0.30 mole) in THF (516 ml) with I$_2$ (50 mg) and 1,2-dibromoethane (26.3 ml, 57.3 g, 0.30 mole) at reflux for 2 h and then cooling to −40° C. To the above was added rapidly via cannula a solution of 2-lithio-5,7-dichlorobenzoxazole at 70° C. (prepared from 5,7-dichlorobenzoxazole (203, 28.9 g, 0.154 mole) and butyl lithium (100 ml 1.52M in hexane) in THF (150 ml) at −70° C.). The mixture was stirred at −40° C. for 1 h and then cooled to −70° C. before adding a solution of (3S)t-butyl N-(allyloxycarbonyl)-3-amino-4-oxo-butanoate (Chapman, et al., *Bioorg. & Med. Chem. Lett.*, 2, pp. 613-618 (1992)) (20.3 g, 0.078 mole) in THF (160 ml) at less than −60° C. The reaction was allowed to warm to ambient temperature and was stirred for 16 h before quenching with ammonium chloride solution and extracting with 1:1 hexane:ethylacetate 600 ml. The organic solution was washed with water and brine, dried with MgSO$_4$ and evaporated to a syrup (52.9 g). Flash chromatography (SiO$_2$ 250 g—11 aliquots of 1:1 hexane:CH$_2$Cl$_2$×2, CH$_2$Cl$_2$, 5% EtOAc in CH$_2$Cl$_2$, 10% EtOAc in CH$_2$Cl$_2$, 20% EtOAc in CH$_2$Cl$_2$) gave impure product 24.6 g which on further chromatography (SiO$_2$ 1:1 hexane:ether) give the title compound as a golden-brown glass (22.7 g, 64%); IR (film) 3343, 2980, 1723, 1712, 1520, 1456, 1398, 1369, 1254, 1158, 993; $^1$H NMR (CDCl$_3$) δ 7.60 (1H, m), 7.37 (1H, m), 5.72 (1H, m), 5.64 (0.5H, d), 5.10 (2.5H, m), 4.7-4.3 (4H, m), 2.9-2.6 (2H, m), 1.46 and 1.42 (9H combined, 2×s). MS ES$^+$ Da/e 445 (M+1)$^+$ Cl 35 62%, 447 (M+1)$^+$ Cl 37 40%, 389 100%.

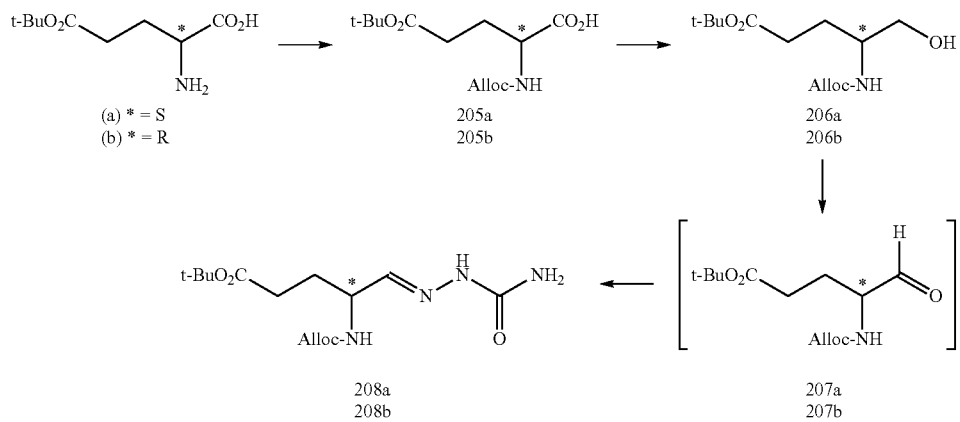

(2S)-N-Allyloxycarbonyl-5-(1,1-dimethylethyl) glutamate (205a). To a mixture of THF (200 ml) and water (100 ml) containing NaHCO$_3$ (16.6 g, 0.2 mol) was added glutaric acid t-butyl ester (10 g, 49.2 mmol) and then dropwise over 20 minutes allyl chloroformate (6.8 ml, 64 mmol). The mixture was stirred for 2 hours, extracted with EtOAc, washed with a sat. hydrogenocarbonate solution, water and a sat. salt solution, dried and evaporated to an oil 205a (9.5 g, 67.2%); $[\alpha]_D^{20}$ −6° (c 1.5, MeOH) $^1$H NMR (D$_6$-DMSO) δ 6.10 (1H, d), 5.96-5.88 (1H, m), 5.31-5.12 (2H, m), 4.45 (2H, m), 3.90-3.84 (1H, t), 2.18 (2H, m), 1.85-1.76 (2H, m), 1.36 (9H, s).

(2R)-N-Allyloxycarbonyl-5-(1,1-dimethylethyl) glutamate (205b), was prepared by an analogous method to 205a to afford a colourless oil (6.27 g, 88%): $[\alpha]_D^{20}$ +16° (c 0.095, MeOH); IR (KBr) 3678, 3332, 3088, 2980, 2937, 1724, 1530, 1453, 1393, 1370, 1331, 1255, 1155, 1056, 995, 935, 845, 778, 757, 636, 583; $^1$H NMR (CDCl$_3$) δ 9.24 (1H, broad s), 5.94-5.79 (1H, m), 5.58 (1H, d), 5.33-5.17 (2H, m), 4.55 (2H, d), 4.38-4.31 (1H, m), 2.41-1.95 (4H, m), 1.42 (9H, s); Anal. Calcd for C$_{13}$H$_{21}$NO$_6$: C, 54.35; H, 7.37; N, 4.88. Found: C, 54.4; H, 7.5; N, 4.8.

(4S)t-Butyl N-allyloxycarbonyl-4-amino-5-hydroxypentanoate (206a). To a solution of 205a (3.6 g, 12.5 mmol) in THF (100 ml) at 0° C. was added N-methyl morpholine (1.5 ml, 13 mmol) followed by isobutyl chloroformate, (1.1 ml, 13 mmol). After 15 minutes, this mixture was added to a suspension of NaBH$_4$ (0.95 g, 25 mmol) in THF (100 ml) and MeOH (25 ml) at −78° C. After 2 hours at −70° C., the mixture was quenched with acetic acid, diluted with EtOAc, washed with a sat. hydrogenocarbonate solution 3 times, water and a sat. solution of salt, dried and evaporated. Flash chromatography (2% MeOH in CH$_2$Cl$_2$) afforded 206a as a colourless oil (2.4 g, 70%): $[\alpha]_D^{20}$ −10° (c 3.88, CH$_2$Cl$_2$); $^1$H NMR (CDCl$_3$) δ 5.84 (1H, m), 5.34-5.17 (3H, m), 4.56-4.53 (2H, m), 3.68-3.59 (2H, m), 2.98 (1H, m), 2.40-2.30 (2H, t), 1.84-1.78 (2H, m), 1.43 (9H, s); Anal. Calcd for C$_{13}$H$_{23}$NO$_5$: C, 57.13; H, 8.48; N, 5.12. Found: C, 57.1; H, 8.6; N, 6.0

(4R)t-Butyl N-allyloxycarbonyl-4-amino-5-hydroxypentanoate (206b), was prepared by an analogous method to 206a which afforded the title compound as a light yellow oil (3.42 g, 57%): $[\alpha]_D^{20}$ +14 (c 0.166, MeOH); IR (KBr) 3341, 3083, 2976, 2936, 2880, 1724, 1533, 1454, 1419, 1369, 1332, 1251, 1156, 1062, 997, 933, 846, 777, 647; $^1$H NMR (CDCl$_3$) δ 5.98-5.81 (1H, m), 5.35-5.10 (3H, m), 4.55 (2H, d), 3.70-3.56 (3H, m), 2.50-2.47 (1H, broad s), 2.37-2.30 (2H, m), 1.89-1.74 (2H, m), 1.44 (9H, s); Anal. Calcd for C$_{13}$H$_{23}$NO$_5$: C, 57.13; H, 8.48; N, 5.12. Found: C, 56.9; H, 8.6; N, 5.6

(4S)t-Butyl N-Allyloxycarbonyl-4-amino-5-oxopentanoate (207a). To a solution of DMSO (1.51 g, 19.3 mmol) in CH$_2$Cl$_2$ (25 ml) at −70° C. was added oxalyl chloride (1.34 g, 19.3 mmol). After 10 minutes at −70° C., a solution of (206a) (2.4 g, 8.8 mmol) in CH$_2$Cl$_2$ (10 ml) was added dropwise and the mixture stirred for 15 minutes at −70° C. Diisopropylethylamine (3.4 g, 26.3 mmol) was added and the mixture stirred at −25° C. for 15 minutes then diluting with EtOAc (50 ml) washed with a solution of sodium hydrogen sulfate 2M, concentrated to give an oil which was used immediately without purification: $^1$H NMR (CDCl$_3$) δ 9.5 (1H, s), 6.0-5.5 (2H, m), 5.5-5.1 (2H, m), 4.5 (2H, m), 4.2 (1H, m), 2.4-2.10 (2H, m), 2.05 (2H, m), 1.36 (9H, s).

(4R)t-Butyl N-Allyloxycarbonyl-4-amino-5-oxopentanoate (207b), was prepared by an analogous method to 207a which afforded an oil (2.95 g, 96%) which was used without further purification in the next step: $[\alpha]_D^{20}$ +21° (c 0.942, MeOH); $^1$H NMR (CDCl$_3$) δ 9.58 (1H, s), 6.05-5.80 (1H, m), 5.57 (1H, broad s), 5.35-5.18 (2H, m), 4.56 (2H, d), 4.34-4.24 (1H, m), 2.38-2.16 (3H, m), 1.96-1.73 (1H, m), 1.43 (9H, s).

(4S)t-Butyl N-Allyloxycarbonyl-4-amino-5-oxopentanoate semicarbazone (208a). To a solution of 207a (2.39 g, 8.8 mmol), in MeOH (20 ml) was added sodium acetate (0.72 g, 8.8 mmol) and semicarbazide (0.98 g, 8.8 mmol) stirred overnight, concentrated and diluted with CH$_2$Cl$_2$ (100 ml), washed with water, dried and concentrated. Flash chromatography (2% MeOH in CH$_2$Cl$_2$) afforded 208a (2.10 g, 73%) as an oil: $[\alpha]_D^{20}$ −21 (c 2.55°, CH$_2$Cl$_2$); $^1$H NMR (CDCl$_3$) δ 9.98 (1H, s), 7.27 (1H, d), 5.8 (1H, m), 5.5 (1H, d), 5.35-5.19 (2H, m), 4.58 (2H, m), 4.14 (1H, m), 2.37 (2H, t), 2.09 (1H, m), 2.0-1.75 (2H, m); Anal. Calcd for C$_{14}$H$_{24}$N$_4$O$_5$: C, 51.21; H, 7.37; N, 17.06. Found: C, 50.2; H, 7.3; N, 16.1

(4R)t-Butyl N-Allyloxycarbonyl-4-amino-5-oxopentanoate semicarbazone (208b), was prepared by an analogous method to 208a which afforded a glassy oil (2.37 g, 66%): $[\alpha]_D^{20}$ +30 (c 0.26, CHCl$_3$); IR (KBr) 3476, 3360, 2979, 2923, 1700, 1586, 1527, 1427, 1394, 1369, 1338, 1253, 1156, 1060, 997, 929, 846, 775; $^1$H NMR (CDCl$_3$) δ 9.87 (1H, s), 7.09 (1H, d), 6.05-5.75 (3H, m), 5.58 (1H, d), 5.32-5.16 (2H, m), 4.54 (2H, d), 4.35 (1H, m), 2.32-2.26 (2H, m), 2.15-1.55 (2H, m), 1.41 (9H, s); Anal. Calcd for C$_{14}$H$_{24}$N$_4$O$_5$: C, 51.21; H, 7.37; N, 17.06. Found: C, 51.0; H, 7.5; N, 16.7.

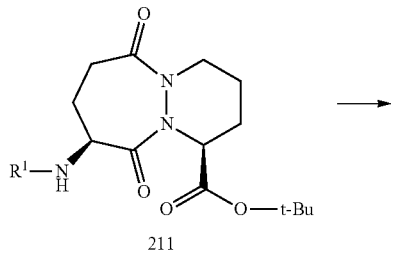

211

(b) R¹ = MeSO₂
(c) R¹ = MeCO
(d) R¹ = PhCH₂OCO
(e) R¹ = PhCO
(f) R¹ = Fmoc

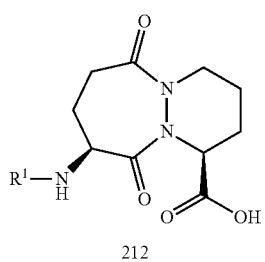

212

(b) R¹ = MeSO₂
(c) R¹ = MeCO
(d) R¹ = PhCH₂OCO
(e) R¹ = PhCO
(f) R¹ = Fmoc (1S,9S)t-Butyl 6,10-dioxo-9-methylsulphonylamino-1,2,3,4,7,8,9,10-octahydro-6H-pyridazino[1,2-a][1,2]diazepine-1-carboxylate (211b). A solution of t-butyl 9-amino-6,10-dioxo-1,2,3,4,7,8,9,10-octahydro-6H-pyridazino[1,2-a][1,2]diazepine-1-carboxylate (GB 2,128,984; 831 mg, 2.79 mmol) and diisopropylethylamine (1.22 ml, 6.99 mmol, 2.5 equiv) in CH₂Cl₂ (10 ml) under dry nitrogen was treated with methanesulphonyl chloride (237 µl, 3.07 mmol 1.1 equiv). The mixture was stirred for 1 h, diluted with EtOAc (75 ml) and washed with saturated NaHCO₃ (50 ml) and saturated aqueous sodium chloride (30 ml), dried (MgSO₄) and concentrated. Flash chromatography (10-35% EtOAc in CH₂Cl₂) afforded 211b (806 mg, 77%) as a colourless solid: mp 68-70° C.; $[\alpha]_D^{23}$ −109 (c 1.09, CH₂Cl₂); IR (KBr) 3270, 2980, 2939, 1735, 1677, 1458, 1447, 1418, 1396, 1370, 1328, 1272, 1252, 1232, 1222, 1156, 1131, 991; ¹H NMR (CDCl₃) δ 6.15 (1H, d), 5.31 (1H, m), 4.65-4.11 (2H, m), 3.47 (1H, m) 2.99 (3H, s), 2.89 (1H, m), 2.72-2.51 (2H, m), 2.34 (1H, m), 2.26 (1H, m), 2.05-1.62 (4H, m), 1.47 (9H, s); Anal. Calcd for C₁₅H₂₃N₃O₆S: C, 47.97; H, 6.71; N, 11.19; S, 8.54. Found: C, 48.28; H, 6.68; N, 10.86; S, 8.28. MS (+FAB) 376 (M⁺+1, 66%), 320 (100).

(1S,9S)t-Butyl 9-acetylamino-6,10-dioxo-1,2,3,4,7,8,9,10-octahydro-6H-pyridazino[1,2-a]-[1,2]diazepine-1-carboxylate (211c). Acetic anhydride (307 mg, 3.01 mmol) was added to a stirred mixture of t-butyl 9-amino-6,10-dioxo-1,2,3,4,7,8,9,10-octahydro-6H-pyridazino[1,2-a][1,2]diazepine-1-carboxylate (GB 2,128,984; 813.7 mg, 2.74 mmol), diisopropylethylamine (884 mg, 6.84 mmol) and CH₂Cl₂ (20 ml). The mixture was kept for 1 h then diluted with EtOAc, washed with NaHCO₃ solution then brine, dried (MgSO₄) and concentrated to yield a colourless oil. The product was purified by flash chromatography (0.5-8% MeOH/CH₂Cl₂) to afford 211c (804 mg, 71%) of colourless powder: mp 162-3° C.; $[\alpha]_D^{23}$ −109 (c 1.03, CH₂Cl₂); IR(KBr) 3358, 2974, 1733, 1693, 1668, 1528, 1462, 1431, 1406, 1371, 1278, 1271, 1250, 1233, 1217, 1154, 1124; δ ¹H NMR (CDCl₃) d 6.32 (1H, d), 5.29-5.25 (1H, m), 4.98-4.85 (1H, m), 4.68-4.58 (1H, m), 3.55-3.39 (1H, m), 2.91-2.66 (2H, m), 2.39-2.18 (2H, m), 2.03 (3H, s), 1.88-1.64 (4H, m), 1.47 (9H, s); Anal. Calcd for C₁₆H₂₅N₃O₅: C, 56.62; H, 7.43; N, 12.38. Found: C, 56.62; H, 7.43; N, 12.36; MS (+FAB) 340 (M⁺+1, 40%), 284 (100).

(1S,9S)t-Butyl 9-(benzyloxycarbonylamino)-6,10-dioxo-1,2,3,4,7,8,9,10-octahydro-6H-pyridazino[1,2-a][1,2]diazepine-1-carboxylate (211d). Benzyl chloroformate (1.07 g) was added dropwise to a stirred ice cold mixture of the (1S,9S)t-butyl 9-amino-6,10-dioxo-1,2,3,4,7,8,9,10-octahydro-6H-pyridazino[1,2-a][1,2]diazepine-1-carboxylate (GB 2,128,984; 1.55 g, 5.21 mmol), NaHCO₃ (0.66 g, 7.82 mmol), dioxan (32 ml) and water (8 ml). The mixture was kept at 5° C. for 15 min then for 2 h at room temperature. The mixture was diluted with EtOAc (50 ml), washed twice with sat. NaHCO₃ solution, dried (MgSO₄) and concentrated. The oily residue was purified by flash chromatography to afford 211d (1.98 g, 88%) of a colourless oil: $[\alpha]_D^{24}$ −56.4 (c 1.0, CH₂Cl₂); IR(thin film) 3325, 2979, 2946, 1728, 1677, 1528, 1456, 1422, 1370, 1340, 1272, 1245, 1156, 1122, 1056, 916, 734, 699; ¹H NMR (CDCl₃) δ 7.29 (5H, m), 5.81-5.72 (1H, m), 5.26-5.20 (1H, m), 5.05 (2H, s), 4.69-4.51 (2H, m), 3.48-3.36 (1H, m), 2.81-2.51 (2H, m), 2.34-2.19 (2H, m), 1.90-1.54 (4H, m), 1.41 (9H, s); Anal. Calcd for C₂₂H₂₉N₃O₆·H₂O: C, 58.79; H, 6.92; N, 9.35. Found: C, 59.10; H, 6.57; N, 9.25; MS (ES+) 454 (M⁺+Na, 87%), 432 (M⁺+1, 100).

(1S,9S)t-Butyl 9-benzoylamino-6,10-dioxo-1,2,3,4,7,8,9,10-octahydro-6H-pyridazino[1,2-a][1,2]-diazepine-1-carboxylate (211e). A solution of benzoyl chloride (1.61 g, 11.47 mmol) in CH₂Cl₂ (15 ml) was added dropwise to a stirred ice cold mixture of (1S,9S)t-butyl 9-amino-6,10-dioxo-1,2,3,4,7,8,9,10-octahydro-6H-pyridazino[1,2-a][1,2]diazepine-1-carboxylate (GB 2,128,984; 3.1 g, 10.43 mmol), dry CH₂Cl₂ (20 ml) and diisopropylethylamine (4.54 ml, 26.06 mmol). The mixture was kept cold for 1 h then left at room temperature for 0.5 h. The mixture was diluted with CH₂Cl₂, washed twice with brine, dried (MgSO₄) and concentrated. The residue was purified by flash chromatography (0-5% methanol in CH₂Cl₂) to afford 211e (4.0 g, 96%) of a colourless glass: mp 74-76° C.; $[\alpha]_D^{30}$ −75.0° (c 0.12, CH₂Cl₂). IR (KBr) 3350, 2979, 2938, 1736, 1677, 1662, 1536, 1422, 1276, 1250, 1155; ¹H NMR (CDCl₃) δ 8.72 (2H, m), 7.53-7.40 (3H, m), 7.07 (1H, d, J=7.2), 5.30 (1H, dd, J=3.0, 5.8), 5.12 (1H, m), 4.66 (1H, m), 3.51 (1H, m), 2.90 (2H, m), 2.38 (1H, dd, J 13.2, 6.8), 2.25 (1H, m), 1.9 (2H, m), 1.70 (1H, m). Anal. Calcd for C₂₁H₂₇N₃O₅ 0.5H₂O: C, 61.45; H, 6.88; N, 10.24. Found C, 61.69; H, 6.71; N, 10.18.

(1S,9S)t-Butyl 6,10-dioxo-9-(fluoren-9-ylmethyloxy-carbonylamino)-1,2,3,4,7,8,9,10-octahydro-6H-pyridazino[1,2-a][1,2]-diazepine-1-carboxylate (211f), was prepared in a similar manner to 211e, except 9-fluorenylmethylchloroformate was used instead of benzoylchloride to give a white glassy solid 211f (2.14 g, 89%): mp 190-192° C.; $[\alpha]_D^{25}$ −81.5° (c 0.1, CH₂Cl₂). IR (KBr) 3335, 2977, 1731, 1678, 1450, 1421, 1246, 1156, 742; ¹H NMR (CDCl₃) δ 7.60 (2H, m), 7.57 (2H, m), 7.50-7.26 (4H, m), 5.60 (1H, d, J=7.8), 5.28 (1H, m), 4.67 (2H, m), 4.38 (2H, m), 4.23 (1H, m), 3.59-3.41 (1H, m), 2.92-2.65 (2H, m), 2.41-2.21 (2H, m), 1.95-1.58 (4H, m), 1.47 (9H, s). MS (ES⁻, m/z) 520 (M⁺+1, 97%), 179 (100%).

(1S,9S)6,10-Dioxo-9-methysulphonylamino-1,2,3,4,7,8,9,10-octahydro-6H-pyridazino[1,2-a][1,2]diazepine-1-carboxylic acid (212b), was synthesized by the same method as compound 212e (635 mg, 85%) as a colourless powder: mp 209-12° C.; [α]$_D^{24}$ −132 (c 0.12, MeOH); IR (KBr) 3308, 2940, 1717, 1707, 1699, 1619, 1469, 1456, 1442, 1417, 1391, 1348, 1339, 1330, 1310, 1271, 1247, 1222, 1175, 1152, 1133, 993, 976; $^1$H NMR (CD$_3$OD) δ 5.35 (1H, m), 4.58-4.48 (1H, m), 4.46-4.36 (1H, m), 3.60-3.42 (1H, m), 3.01-2.87 (1H, m), 2.95 (3H, s), 2.55-2.39 (1H, m), 2.32-2.20 (2H, m), 2.09-1.89 (2H, m), 1.78-1.62 (2H, m); Anal. Calcd for C$_{11}$H$_{17}$N$_3$O$_6$S: C, 41.37; H, 5.37; N, 13.16; S, 10.04. Found: C, 41.59; H, 5.32; N, 12.75; S, 9.76; MS (ES−). Accurate Mass calculated for C$_{11}$H$_{18}$N$_3$O$_6$S (MH$^+$): 320.0916. Found: 320.0943.

(1S,9S)9-Acetylamino-6,10-dioxo-1,2,3,4,7,8,9,10-octahydro-6H-pyridazino[1,2-a][1,2]diazepine-1-carboxylic acid (212c), was prepared from 211e the same method as compound 212e as a white glassy solid (595 mg, 77%): mp >250° C.; [α]$_D^{24}$ −153 (c 0.10, MeOH); IR (KBr) 3280, 2942, 1742, 1697, 1675, 1650, 1616, 1548, 1470, 1443, 1281, 1249, 1202, 1187, 1171; $^1$H NMR (CD$_3$OD) δ 5.35-5.31 (1H, m), 4.81-4.71 (1H, m), 4.61-4.46 (1H, m), 3.59-3.44 (2H, m), 3.11-2.94 (1H, m), 2.58-2.39 (1H, m), 2.36-2.19 (2H, m), 2.11-1.83 (3H, m), 1.99 (3H, s), 1.78-1.56 (2H, m); Anal. Calcd for C$_{12}$H$_{17}$N$_3$O$_5$: C, 50.88; H, 6.05; N, 14.83. Found: C, 50.82; H, 6.02; N, 14.58; MS (ES−) 282 (M−1, 100%); Accurate Mass calculated for C$_{12}$H$_{18}$N$_3$O$_5$ (MH$^+$): 284.1246. Found: 284.1258.

(1S,9S)9-Benzyloxycarbonylamino-6,10-dioxo-1,2,3,4,7,8,9,10-octahydro-6H-pyridazino[1,2-a][1,2]diazepine-1-carboxylic acid (212d), was prepared from 211d by the same method as compound 212e as colourless crystals (170 mg, 97%): mp 60-100° C.; [α]$_D^{22}$ −103 (c 0.10, MeOH); IR (KBr) 3341, 2947, 1728, 1675, 1531, 1456, 1422, 1339, 1272, 1248, 1221, 1174, 1122, 1056, 982, 699; $^1$H NMR (CDCl$_3$) δ 7.35 (5H, s), 5.65 (1H, d), 5.48-5.40 (1H, m), 5.10 (2H, s), 4.76-4.57 (2H, m), 3.49-3.30 (2H, m), 2.92-2.59 (2H, m), 2.40-2.27 (2H, m), 1.97-1.67 (4H, m); MS (ES−) 374 (M−1, 100%). Accurate mass calculated for C$_{18}$H$_{22}$N$_3$O$_6$ (MH$^+$): 376.1509. Found: 376.1483. Accurate mass calculated for C$_{18}$H$_{21}$N$_3$O$_6$Na (MNa$^+$): 398.1328. Found: 398.1315.

(1S,9S)9-Benzoylamino-6,10-dioxo-1,2,3,4,7,8,9,10-octahydro-6H-pyridazino[1,2-a][1,2]-diazepine-1-carboxylic acid (212e). TFA (20 ml) was added to an ice cold stirred solution of the t-butyl ester 211e (4.15 g, 10.34 mmol) in dry CH$_2$Cl$_2$ (20 ml). The mixture was kept cold for 1.5 h then left for 2.5 h at rt, concentrated. TFA was removed by repeated concentrations of CH$_2$Cl$_2$\ether and ether solutions of the residue. Finally trituration of the residue with ether afforded 212e 3.05 g (85%) of a white glassy solid: mp 118-126° C.; [α]$_D^{24}$ −70.5° (c 0.1, CH$_2$Cl$_2$). IR (KBr) 3361, 2943, 1737, 1659, 1537, 1426, 1220, 1174; $^1$H NMR (CDCl$_3$) δ 7.80 (2H, m), 7.54-7.33 (4H, m), 8.83 (brs), 5.44 (1H, m), 5.26-5.13 (1H, m), 4.66 (1H, m), 3.59-3.41 (1H, m), 2.97, 2.76 (2H, 2m), 2.36 (2H, m), 1.98 (2H, m), 1.75 (2H, m). MS (ES$^-$, m/z) 344 (M−1, 100%).

(1S,9S)6,10-Dioxo-9(fluoren-9-ylmethyloxycarbonylamino)-1,2,3,4,7,8,9,10-octahydro-6H-pyridazino[1,2-a][1,2]-diazepine-1-carboxylic acid (212f), was prepared from 211f in 96% yield by the same method as for 212e: mp 120-126° C.; [α]$_D^{25}$ −72.5° (c 0.1, CH$_2$Cl$_2$). IR (KBr) 3406, 2950, 1725, 1670, 1526, 1449, 1421, 1272, 1248, 1223, 1175, 761, 741; $^1$H NMR (CDCl$_3$) δ 7.76 (2H, m), 7.62-7.26 (4H, m), 6.07, 5.76 (2H, brs, d, d, J=2.9), 5.46, 5.36 (1H, 2m), 4.79-4.54 (2H, m), 4.77 (2H, m), 4.21 (1H, m), 3.41 (1H, m), 2.89 (1H, m), 2.69 (1H, m), 2.35 (2H, m), 1.98, 1.73 (4H, 2m). MS (ES$^-$, m/z) 462 (M$^+$−1, 50%), 240 (100%).

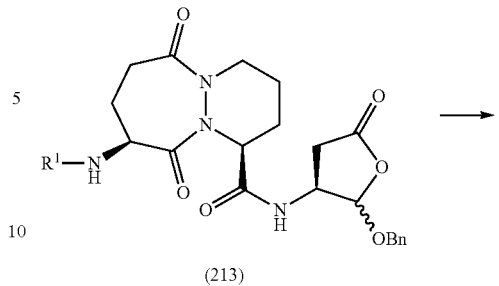

(213)

(c) R$^1$ = MeCO
(e) R$^1$ = PhCO

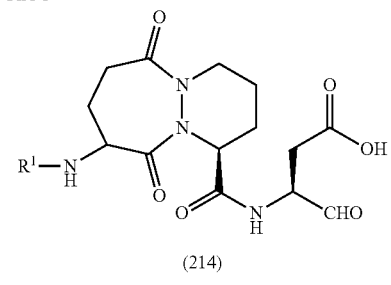

(214)

(c) R$^1$ = MeCO
(e) R$^1$ = PhCO

[2RS,3S(1S,9S)]N-(2-Benzyloxy-5-oxotetrahydrofuran-3-yl)-9-(acetylamino)-6,10-dioxo-1,2,3,4,7,8,9,10-octahydro-6H-pyridazino[1,2-a][1,2]diazepine-1-carboxamide (213c), was synthesized from 212c by the same method as compound 213e to afford a mixture of diastereomers (193 mg, 36%) as colourless crystals: IR (KBr) 3272, 1799, 1701, 1682, 1650, 1555, 1424, 1412, 1278, 1258, 1221, 1122, 937; $^1$H NMR (CDCl$_3$) δ 7.41-7.28 (5H, m), 6.52 (0.5H, d), 6.38 (0.5H, d), 6.22 (0.5H, d), 5.57 (0.5H, d), 5.36 (0.5H, s) 5.10-5.05 (1H, m), 5.00-4.45 (5.5H, m), 3.19-2.84 (3H, m), 2.72-2.56 (1H, m), 2.51-2.25 (2H, m), 2.02 (3H, s), 1.98-1.70 (3H, m), 1.66-1.56 (3H, m); Anal. Calcd for C$_{23}$H$_{28}$N$_4$O$_7$: C, 58.47; H, 5.97; N, 11.86. Found: C, 58.37; H, 6.09; N, 11.47. MS (ES−) 471 (M−1, 100%). Accurate mass calculated for C$_{23}$H$_{29}$N$_4$O$_7$ (MH$^+$): 473.2036. Found: 473.2012. Accurate mass calculated for C$_{23}$H$_{20}$O$_4$O$_7$Na (Mna$^+$): 495.1856. Found: 495.1853.

[1S,9S(2RS,3S)]9-Benzoylamino-6,10-dioxo-1,2,3,4,7,8,9,10-octahydro-N-(2-benzyloxy-5-oxotetrahydrofuran-3-yl)-6H-pyridazino[1,2-a][1,2]-diazepine-1-carboxamide (213e). Tributyltin hydride (2.2 ml, 8.18 mmol) was added dropwise to a solution of acid 212e (1.95 g, 5.6 mmol), (3S,2RS)3-allyloxycarbonylamino-2-benzyloxy-5-oxotetrahydrofuran (Chapman, Bioorg. & Med. Chem. Lett., 2, pp. 615-618 (1992); 1.80 g, 6.16 mmol) and (Ph$_3$P)$_2$PdCl$_2$ (50 mg) in dry CH$_2$Cl$_2$ (36 ml), with stirring, under dry nitrogen. After 5 min 1-hydroxybenzotriazole (1.51 g, 11.2 mmol 6.72 mmol) was added followed after cooling (ice/H$_2$O) by ethyldimethylaminopropyl carbodiimide hydrochloride (1.29 g, 6.72 mmol). After 5 mins the cooling bath was removed and the mixture was kept at room temperature for 4 h, diluted with EtOAc, washed with 1M HCl, brine, sat. aq. NaHCO$_3$ and brine, dried (MgSO$_4$) and concentrated. Flash chromatography (silica gel, 0-90% EtOAc in CH$_2$Cl$_2$) gave the product as a white solid (2.34 g, 78%): IR (KBr) 3499, 1792, 1658, 1536, 1421, 1279, 1257, 1123, 977, 699; $^1$H NMR (CDCl$_3$) δ 7.81 (2H, m), 7.54-7.34 (8H, m), 7.1, 6.97, 6.89, 6.48 (2H, m, d, J 7.7, d, J=7.5, d, J=7.6), 5.57, 5.28 (1H, d, J=5.2, s), 5.23-5.07

(2H, m), 4.93-4.42, 3.22-2.70, 2.51-2.26, 2.08-1.69, 1.22 (15H, 5m). Anal. Calcd for $C_{28}H_{30}N_4O_7 \cdot 0.5H_2O$: C, 61.87; H, 5.75; N, 10.32. Found C, 62.02; H, 5.65; N, 10.25.

[3S(1S,9S)]3-(9-Acetylamino-6,10-dioxo-1,2,3,4,7,8,9,10-octahydro-6H-pyridazino[1,2-a][1,2]diazepine-1-carboxamido)-4-oxobutanoic acid (214c), was synthesized from 213c by a method similar to the method used to synthesize 214e from 213e to provide colourless crystals (140 mg, 99%): mp 90-80° C.; $[\alpha]_D^{22}$ −114 (c 0.10, MeOH); IR (KBr) 3334, 3070, 2946, 1787, 1658, 1543, 1422, 1277, 1258; $^1$H NMR ($d^6$-DMSO) δ 8.66 (1H, m), 8.18 (1H, d), 6.76 (1H, s), 5.08 (1H, m), 4.68 (1H, m), 4.30 (1H, m), 2.92-2.70 (2H, m), 2.27-2.06 (3H, m), 1.95-1.72 (4H, m), 1.85 (3H, s), 1.58 (2H, m); MS (ES−) 381 (M−1, 100%); Accurate mass calculated for $C_{16}H_{23}N_4O_7$ (MH$^+$): 383.1567. Found: 383.1548.

[3S(1S,9S)]3-(9-Benzoylamino-6,10-dioxo-1,2,3,4,7,8,9,10-octahydro-6H-pyridazino[1,2-a][1,2]-diazepine-1-carboxamido)-4-oxobutanoic acid (214e). A mixture of 213e (2.29 g, 4.28 mmol), 10% palladium on carbon (1.8 g) and MeOH (160 ml) was stirred under $H_2$ at atmospheric pressure for 6.3 h. After filtering and concentrating the hydrogenation was repeated with fresh catalyst (1.8 g) for 5 h. After filtering and concentrating the residue was triturated with diethyl ether, filtered and washed well with ether to give 214e as a white solid (1.67 g, 88%): mp 143-147° C.; $[\alpha a]_D^{23}$ −125° (c 0.2, $CH_3OH$). IR (KBr) 3391, 1657, 1651, 1538, 1421, 1280, 1258; $^1$H NMR ($CD_3OD$) δ 7.90 (2H, m), 7.63-7.46 (3H, m), 5.25 (1H, m), 5.08-4.85 (1H, m), 4.68-4.53 (2H, m), 4.33-4.24 (1H, m), 3.62-3.44, 3.22-3.11, 2.75-2.21, 2.15-1.92, 1.73-1.66 (11H, 5m). Anal. Calcd for $C_{21}H_{24}N_4O_7 \cdot H_2O$: C, 54.54; H, 5.67; N, 12.11. Found C, 54.48; H, 5.63; N, 11.92.

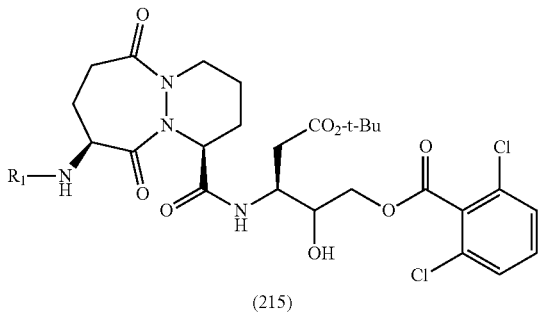

(215)

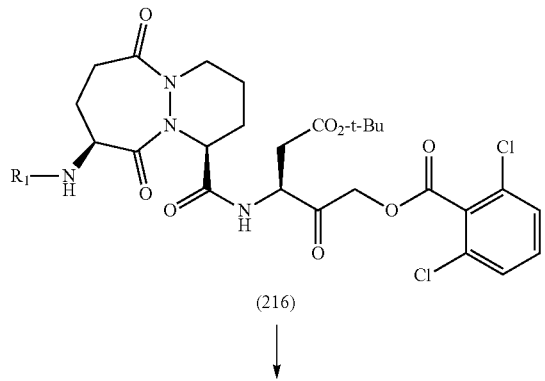

(216)

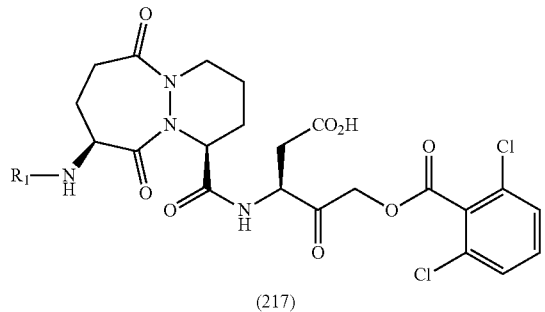

(217)

(c) $R_1$ = MeCO
(d) $R_1$ = PhCH$_2$OCO
(e) $R_1$ = PhCO

[3S,4RS(1S,9S)]t-Butyl 3-[(9-acetylamino-6,10-dioxo-1,2,3,4,7,8,9,10-octahydro-6H-pyridazino-(1,2-a][1,2]diazepine-1-carboxamido)-5-(2,6-dichlorobenzoyloxy)-4-hydroxypentanoate (215c), was synthesized from 214c by the same method as compound 215e, to afford a mixture of diastereomers as a white glassy solid (398 mg, 84%): IR (KBr) 3338, 2977, 1738, 1658, 1562, 1541, 1433, 1368, 1277, 1150; $^1$H NMR (CDCl$_3$) δ 7.36-7.32 (3H, m), 6.91 (1H, d), 6.30 (1H, d), 5.15-5.09 (1H, m) 5.01-4.88 (1H, m), 4.61-4.44 (2H, m), 4.37-4.08 (3H, m), 3.32-3.18 (1H, m), 3.04-2.89 (1H, m), 2.82-2.51 (4H, m), 2.39-2.29 (1H, m), 2.08-1.64 (4H, m) 2.02 (3H, s); Anal. Calcd for C$_{28}$H$_{34}$N$_4$Cl$_2$O$_9$: C, 52.26; H, 5.64; N, 8.71. Found: C, 52.44; H, 5.87; N, 8.16. MS (ES−) 645/3/1 (M−1, 26%), 189 (81), 134 (100). Accurate mass calculated for C$_{28}$H$_{37}$N$_4$Cl$_2$O$_9$ (MH$^+$): 643.1938. Found: 643.1924. Accurate mass calculated for C$_{28}$H$_{36}$N$_4$Cl$_2$O$_9$Na (MNa$^+$) 665.1757. Found: 665.1756.

[3S,4RS(1S,9S)]t-Butyl 3-(9-benzyloxycarbonylamino-6,10-dioxo-1,2,3,4,7,8,9,10-octahydro-6H-pyridazino[1,2-a][1,2]diazepine-1-carboxamido)-5-(2,6-dichlorobenzyloxy)-4-hydroxypentanoate (215d), was synthesized from 214d by the same method as compound 215e to afford a mixture of diastereomers (657 mg, 70%) as a glassy white solid: IR (KBr) 3420, 3361, 2975, 2931, 1716, 1658, 1529, 1434, 1367, 1348, 1250, 1157, 1083, 1055; $^1$H NMR (CDCl$_3$) δ 7.32 (8H, m), 7.14 (1H, d), 5.81 (1H, d), 5.15 (1H, m), 5.07 (2H, s), 4.74-4.65 (1H, m), 4.58-4.22 (4H, m), 4.15-4.06 (1H, m), 3.72 (1H, m), 3.32-3.21 (1H, m), 3.04-2.94 (1H, m), 2.69-2.52 (3H, m), 2.33-2.27 (1H, m), 1.95-1.59 (4H, m), 1.28 (9H, s); Anal. Calcd for C$_{34}$H$_{40}$N$_4$Cl$_2$O$_{10}$·0.5H$_2$O: C, 54.70; H, 5.54; N, 7.50. Found: C, 54.98; H, 5.59; N, 7.24. MS (ES−) 737/5/3 (M−1, 22%), 193/1/89 (100). Accurate mass calculated for C$_{34}$H$_{41}$N$_4$Cl$_2$O$_{10}$ (MH$^+$) 735.2120. Found: 735.2181.

[3S,4RS(1S,9S)]t-Butyl 3-(9-benzoylamino-6,10-dioxo-1,2,3,4,7,8,9,10-octahydro-6H-pyridazino[1,2-a][1,2]diazepine-1-carboxamido)-5-(2,6-dichlorobenzyloxy)-4-hydroxypentanoate (215e), Tributyltin hydride (4.6 ml; 11.4 mmol) was added dropwise to a stirred mixture of (3S,4RS) t-Butyl (N-allyloxycarbonyl)-3-amino-5-(2,6-dichlorobenzoyloxy)-4-hydroxypentanoate (prepared by a method similar to the method described in Revesz et al., *Tetrahedron. Lett.*, 35, pp. 9693-9696 (1994)) (2.64 g; 5.7 mmol), (Ph$_3$P)$_2$PdCl$_2$ (50 mg), CH$_2$Cl$_2$ (100 ml) and DMF (20 ml) at room temperature. The mixture was stirred for a further 10 min was then 1-hydroxybenzotriazole (1.54 g, 11.4 mmol) was added. The mixture was cooled to 0° C. then ethyldimethylaminopropyl carbodiimide hydrochloride (1.31 g; 6.84 mmol) added. The mixture was kept at this temperature for 15 min then at room temperature for 17 h. The mixture was diluted with EtOAc (300 ml), washed with 1M HCl (2×100 ml), sat. aq. NaHCO$_3$ (3×100 ml) and brine (2×100 ml), dried (MgSO$_4$) and concentrated. The residue was purified by flash chromatography (2-5% (MeOH/CH$_2$Cl$_2$) to afford 3.24 g (81%) of 215e as a glassy solid: mp 106-110° C.; IR (KBr) 3354, 1737, 1659, 1531, 1433, 1276, 1150; $^1$H NMR (CDCl$_3$) δ 7.80 (2H, dd, J=7.9 and 1.5), 7.75-7.26 (6H, m), 7.14-6.76 (2H, m), 5.30-5.02 (2H, m), 4.63-4.11 (5H, m), 3.44-3.26 (2H, m), 3.10-2.30 (5H, m), 2.10-1.60 (5H, m), 1.44 (9H, s); Anal. Calcd for C$_{33}$H$_{38}$Cl$_2$N$_4$O$_9$·0.75H$_2$O: C, 55.12; H, 5.54; N, 7.79; Cl, 9.86. Found: C, 55.04; H, 5.34; N, 7.80; Cl, 10.24. MS (ES+) 709/7/5 (M+1), 378 (59), 324 (64), 322 (100).

[3S(1S,9S)]t-Butyl 3-(9-acetylamino-6,10-dioxo-1,2,3,4,7,8,9,10-octahydro-6H-pyridazino[1,2-a][1,2]-diazepine-1-carboxamido)-5-(2,6-dichlorobenzoyloxy)-4-oxopentanoate (216c), was synthesized from 215c by the same method as compound 216e as a glassy white solid (300 mg, 83%): mp 80-125° C.; [α]$_D^{23}$ −89.1 (c 1.08, CH$_2$Cl$_2$); IR (KBr) 3356, 2979, 2935, 1740, 1659, 1532, 1434, 1369, 1276, 1260, 1151; $^1$H NMR (CDCl$_3$) δ 7.39-7.32 (3H, m), 7.13 (1H, d), 6.34 (1H, d), 5.22-5.17 (1H, m), 5.11 (1H, d), 5.04 (1H, d), 4.99-4.88 (2H, m), 4.64-4.52 (1H, m), 3.29-3.11 (1H, m), 3.05-2.67 (4H, m), 2.39-2.29 (1H, m), 2.02 (3H, s), 1.98-1.75 (4H, m), 1.46 (9H, s); Anal. Calcd for C$_{28}$H$_{34}$N$_4$Cl$_2$O$_9$: C, 52.42; H, 5.34; N, 8.73. Found: C, 52.53; H, 5.70; N, 7.85. MS (ES−) 643/41/39 (M−1, 100%). Accurate mass calculated for C$_{28}$H$_{35}$N$_4$Cl$_2$O$_9$ (MH$^+$): 641.1781. Found: 641.1735. Accurate mass calculated for C$_{28}$H$_{34}$N$_4$Cl$_2$O$_9$Na (Mna$^+$): 663.1601. Found: 663.1542.

[3S(1S,9S)]t-Butyl 3-(9-benzyloxycarbonylamino-6,10-dioxo-1,2,3,4,7,8,9,10-octahydro-6H-pyridazino[1,2-a][1,2]diazepine-1-carboxamido)-5-(2,6-dichlorobenzoyloxy)-4-oxopentanoate (216d), was synthesized from 215d by the same method as compound 216e to afford 216d as a white glassy solid (688 mg, 68%): mp 90-170° C.; [α]$_D^{25}$ −83.4 (c 1.01, CH$_2$Cl$_2$); IR (KBr) 3338, 2933, 1736, 1670, 1525, 1433, 1417, 1368, 1258, 1151, 1056, 1031; $^1$H NMR (CDCl$_3$) δ 7.33 (8H, m), 7.18 (1H, d), 5.65 (1H, d), 5.19 (1H, m), 5.09 (2H, s), 4.98-4.86 (1H, m), 4.82-4.49 (2H, d), 3.30-3.07 (1H, m), 3.05-2.59 (4H, m), 2.42-2.27 (1H, m), 2.18-1.59 (5H, m), 1.42 (9H, s); MS (ES−) 737/5/3 (M, 13%), 185 (100).

[3S(1S,9S)]t-Butyl 3-(9-benzoylamino-6,10-dioxo-1,2,3,4,7,8,9,10-octahydro-6H-pyridazino[1,2-a][1,2]diazepine-1-carboxamido)-5-(2,6-dichlorobenzoyloxy)-4-oxopentanoate (216e). Dess-Martin reagent (3.82 g; 9.0 mmol) was added to a stirred solution of the alcohol 215e (3.17 g; 4.5 mmol) in CH$_2$Cl$_2$ (100 ml). The mixture was stirred for 1 h, diluted with EtOAc (300 ml), then washed with a 1:1 mixture of sat. Na$_2$S$_2$O$_3$ and sat. NaHCO$_3$ (100 ml) followed by brine (100 ml). The mixture was dried (MgSO$_4$) then concentrated. The residue was purified by flash chromatography to afford 2.2 g (70%) of 216e as a colourless solid: mp 102-107° C.; [α]$_D^{32}$ −82.5 (c 0.1, CH$_2$Cl$_2$); IR (KBr) 3374, 2937, 1739, 1661, 1525, 1433, 1275, 1260, 1152; $^1$H NMR (CDCl$_3$) δ 7.85-7.78 (2H, m), 7.57-7.32 (6H, m), 7.09 (1H, d, J=7.9), 7.01 (1H, d, J 7.3), 5.25-5.16 (1H, m), 5.16-5.05 (1H, m), 5.15 (1H, d), 5.03 (1H, d), 4.99-4.90 (1H, m), 4.68-4.54 (1H, m), 3.31-3.17 (1H, m), 3.17-2.72 (4H, m), 2.45-2.35 (1H, m), 2.30-1.66 (5H, m), 1.44 (9H, s); Anal. Calcd for C$_{33}$H$_{36}$Cl$_2$N$_4$O$_9$·0.5H$_2$O: C, 55.62; H, 5.23; N, 7.86; Cl, 9.95. Found: C, 55.79; H, 5.15; N, 7.80; Cl 9.81. MS (ES+) 729/7/5 (M+Na), 707/5/3 (M+1), 163 (100%).

[3S(1S,9S)]3-(9-Acetylamino-6,10-dioxo-1,2,3,4,7,8,9,10-octahydro-6H-pyridazino[1,2-a][1,2]diazepine-1-carboxamido)-5-(2,6-dichlorobenzoyloxy)-4-oxopentanoic acid (217c), was synthesized from 216c by the same method as compound 217e as a glassy white solid (166 mg, 66%): mp 85-175° C.; [α]$_D^{25}$ −156 (c 0.13, MeOH); IR (KBr) 3373, 2929, 1742, 1659, 1562, 1533, 1433, 1412, 1274, 1266, 1223, 1197, 1145, 1138; $^1$H NMR (CD$_3$OD) δ 7.38 (3H, s), 5.14-5.03 (1H, m), 4.49-4.32 (2H, m), 3.50-3.27 (1H, m), 3.11-2.92 (1H, m), 2.84-2.62 (2H, m), 2.46-2.11 (2H, m), 2.05-1.46 (5H, m), 1.92 (3H, s); Anal. Calcd for C$_{24}$H$_{26}$N$_4$Cl$_2$O$_9$·H$_2$O: C, 47.77; H, 4.68; N, 9.29. Found: C, 47.75; N, 4.59; N, 9.07. MS (ES+) 627/5/3 (M+K, 21%), 611/9/7 (M+Na, 87), 589/7/5 (M$^+$+1, 71), 266 (100); Accurate mass calculated for C$_{24}$H$_{27}$N$_4$Cl$_2$O$_9$ (MH$^+$): 585.1155. Found: 585.1134.

[3S(1S,9S)]3-(9-Benzyloxycarbonylamino-6,10-dioxo-1,2,3,4,7,8,9,10-octahydro-6H-pyridazino[1,2-a][1,2]-diazepine-1-carboxamido)-5-(2,6-dichlorobenzoyloxy)-4-oxopentanoic acid (217d), was synthesized from 216d by the same method as compound 217e to afford 217d as a white glassy solid (310 mg, 96%): mp 85-110° C.; [α]$_D^{24}$ −85.9 (c 0.13, MeOH); IR (KBr) 3351, 2945, 1738, 1669, 1524, 1433, 1258, 1147, 1057; $^1$H NMR (CD$_3$OD) δ 7.56 (4H, m), 7.45 (5H, m), 5.32 (2H, m), 5.20 (2H, s), 4.76-4.48 (3H, m), 3.65-3.38 (3H, m), 3.27-3.09 (2H, m), 3.03-2.89 (2H, m), 2.65-2.24 (3H, m), 2.19-1.62 (5H, m); MS (ES−) 679/7/5 (M−1, 100%); Accurate mass calculated for C$_{30}$H$_{31}$N$_4$Cl$_2$O$_{10}$ (MH$^+$): 677.1417. Found: 677.1430.

[3S(1S,9S)]3-(9-Benzoylamino-6,10-dioxo-1,2,3,4,7,8,9,10-octahydro-6H-pyridazino[1,2-a][1,2]-diazepine-1-carboxamido)-5-(2,6-dichlorobenzoyloxy)-4-oxopentanoic acid (217e), TFA (25 ml) was added dropwise to an ice cold stirred solution of the ester 216e (2.11 g, 3.0 mmol). The mixture was stirred at 0° C. for 20 min then at room temperature for 1 h. The mixture was evaporated to dryness then coevaporated with ether three times. Addition of dry ether (50 ml) and filtration afforded 1.9 g (98%) of 217e as a colourless solid: mp 126-130° C.; [α]$_D^{30}$ −122.0 (c 0.1, MeOH); IR (KBr) 3322, 1740, 1658, 1651, 1532, 1433, 1277, 1150; $^1$H NMR (D$_6$-DMSO) δ 8.87 (1H, d, J=7.4), 8.61 (1H, d, J=7.8), 7.92-7.86 (2H, m), 7.65-7.43 (6H, m), 5.25-5.12 (3H, m), 4.94-4.60 (2H, m), 4.44-4.22 (1H, m), 3.43-3.10 (1H, m), 3.00-2.52 (3H, m), 2.45-2.10 (3H, m), 2.10-1.75 (2H, m), 1.75-1.50 (2H, m); Anal. Calcd for C$_{29}$H$_{28}$Cl$_2$N$_4$O$_9$·1H$_2$O: C, 52.34; H, 4.54; N, 8.42; Cl, 10.66. Found: C, 52.02; H, 4.36; N, 8.12; Cl, 10.36. MS (ES−) 649/7/5 (M−1), 411 (100%).

(4H, m), 2.38-2.28 (1H, m), 2.07-1.81 (4H, m); Anal. Calcd for C$_{28}$H$_{35}$N$_5$Cl$_2$O$_9$S·0.5H$_2$O: C, 48.21; H, 5.20; N, 10.03. Found: C, 48.35; H, 5.26; N, 9.48. MS (ES+) 714/2/0 (M+Na, 25%), 692/90/88 (M$^+$+1, 51), 636/4/2 (38), 246 (100). Accurate mass calculated for C$_{28}$H$_{36}$N$_5$Cl$_2$O$_9$S (MH$^+$): 688.1611. Found: 688.1615.

[3S(1S,9S)]t-Butyl 4-[5-(2,6-dichlorophenyl)-oxazol-2-yl]-3-(6,10-dioxo-9-methylsulphonylamino-1,2,3,4,7,8,9,10-octahydro-6H-pyridazino[1,2-a][1,2]diazepine-1-carboxamido)-4-oxobutanoate (219b), was prepared from 218b in an analogous way to compound 216e as an off-white powder (675 mg, 81%): mp 100-200° C.; [α]$_D^{24}$ −84.9 (c 1.01, CH$_2$Cl$_2$); IR (KBr) 3336, 2978, 2936, 1719, 1674, 1510, 1433, 1421, 1369, 1329, 1274, 1257, 1155, 991, 789; $^1$H NMR (CDCl$_3$) δ 7.47-7.38 (4H, m), 7.24 (1H, d), 5.61-5.53 (1H, m), 5.48 (1H, d), 5.38-5.30 (1H, m), 4.67-4.45 (2H, m), 3.48-3.18 (2H, m), 3.04-2.90 (2H, m), 2.97 (3H, s), 2.69-2.54 (1H, m), 2.42-2.32 (1H, m), 2.22-2.15 (1H, m), 2.07-1.93 (3H, m), 1.71-1.65 (2H, m), 1.38 (9H, s); Anal. Calcd for C$_{28}$H$_{33}$N$_3$Cl$_2$O$_9$S: C, 48.98; H, 4.84; N, 10.20; S, 4.67. Found: C, 48.73; H, 4.95; N, 9.65; S, 4.54. MS (ES+) 692/90/88 (M$^+$+1, 100%), 636/4/2 (71). Accurate mass calculated for C$_{28}$H$_{34}$N$_5$Cl$_2$O$_9$S (MH$^+$): 686.1454. Found: 686.1474.

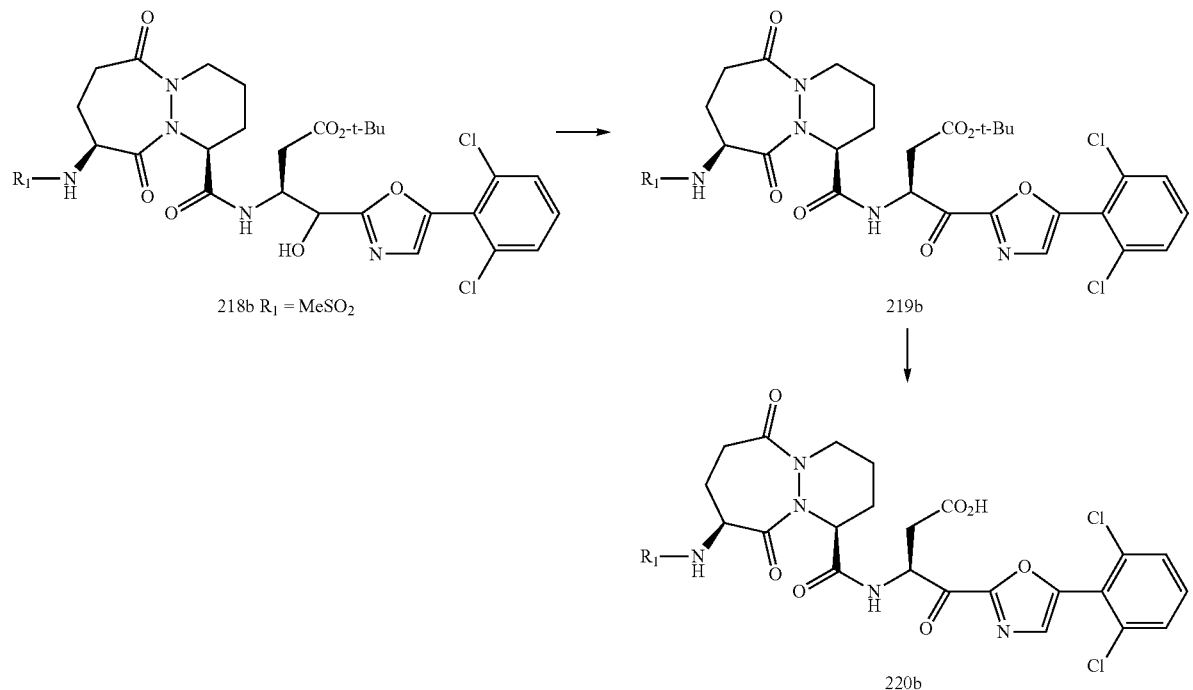

[3S,4RS(1S,9S)]t-Butyl 4-[5-(2,6-dichlorophenyl)-oxazol-2-yl]-3-(6,10-dioxo-9-methylsulphonylamino-1,2,3,4,7,8,9,10-octahydro-6H-pyridazino[1,2-a][1,2]diazepine-1-carboxamido)-4-hydroxybutanoate (218b), was prepared from the acid 212b and 99 in an analogous way to compound 215e to afford a mixture of diastereomers (865 mg, 80%) as a colourless solid: IR (KBr) 3298, 2974, 1723, 1659, 1544, 1518, 1430, 1394, 1370, 1328, 1273, 1256, 1156, 1134; $^1$H NMR (CDCl$_3$) δ 7.45-7.28 (4H, m), 7.26-7.15 (2H, m), 5.26-5.10 (2H, m), 4.80-4.67 (1H, m), 4.59-4.42 (2H, m), 3.32-3.17 (1H, m), 2.96 (3H, 2×s), 2.93-2.79 (1H, m), 2.71-2.53

[3S(1S,9S)]-4-[5-(2,6-Dichlorophenyl)oxazol-2-yl]-3-(6,10-dioxo-9-methylsulphonylamino-1,2,3,4,7,8,9,10-octahydro-6H-pyridazino[1,2-a][1,2]diazepine-1-carboxamido)-4-oxobutanoic acid (220b), was prepared from 219b in an analogous way to compound 217e as a pale cream powder (396 mg, 87%): mp 100-200° C.; [α]$_D^{27}$ −129 (c 0.12, MeOH); IR (KBr) 3310, 3153, 1713, 1667, 1557, 1510, 1432, 1421, 1329, 1273, 1258, 1221, 1193, 1153, 1134, 992, 789; $^1$H NMR (d$^6$DMSO) δ 7.88 (1H, s), 7.81-7.60 (4H, m), 5.49-5.28 (1H, m), 5.24-5.14 (1H, m), 4.46-4.22 (2H, m), 3.30-3.03 (2H, m), 2.97-2.76 (3H, m), 2.96 (3H, s), 2.46-2.24 (1H, m), 2.16-2.05 (1H, m), 2.03-1.78 (3H, m), 1.68-1.46 (2H, m);

MS (ES−) 632/30/28 (M−1, 68%), 149/7/5 (100). Accurate mass calculated for $C_{24}H_{26}N_5Cl_2O_9S$ (MH$^+$): 630.0828. Found: 630.0852.

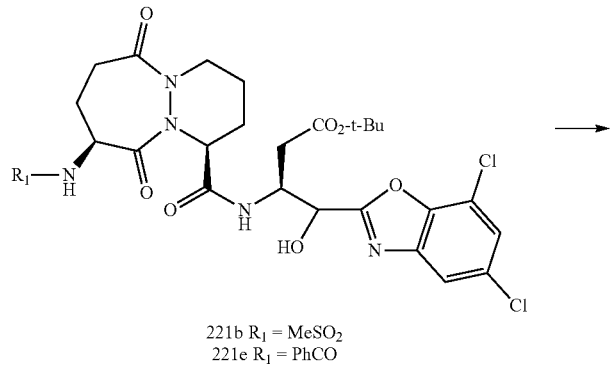

221b R$_1$ = MeSO$_2$
221e R$_1$ = PhCO

222b R$_1$ = MeSO$_2$
222e R$_1$ = PhCO

223b R$_1$ = MeSO$_2$
223e R$_1$ = PhCO

[3S,4RS(1S,9S)]t-Butyl 4-(5,7-dichlorobenzoxazol-2-yl)-3-(6,10-dioxo-9-methylsulphonylamino-1,2,3,4,7,8,9,10-octahydro-6H-pyridazino[1,2-a][1,2]diazepine-1-carboxamido)-4-hydroxybutanoate (221b), was prepared from the acid 212b and (3S,4RS)t-butyl N-(allyloxycarbonyl)-3-amino-4-hydroxy-4-(5,7-dichlorobenzoxazol-2-yl)butanoate (204) by an analogous method as that used for compound 215e to afford a mixture of diastereomers (460 mg, 70%) as a glass: IR (film) 3325, 1725, 1664, 1453, 1399, 1373, 1327, 1274, 1256, 1155; $^1$H NMR (CDCl$_3$) δ 7.57 (1H, m), 7.36 (2H, m), 6.06 (1H, t), 5.29 (2H, m), 4.79 (1H, m), 4.47 (1H, m), 3.23 (1H, m), 2.97 and 2.94 (3H combined, 2xs), 2.9-2.4 (4H, m), 2.30 (1H, m), 1.96 (4H, m), 1.41 and 1.37 (9H combined, 2xs). MS ES Da/e 660 (M−1)$^−$ Cl$^{35}$ 100%, 662 (M−1)$^−$ Cl$^{37}$.

[3S,4RS(1S,9S)]t-Butyl 3-(9-benzoylamino-6,10-dioxo-1,2,3,4,7,8,9,10-octahydro-6H-pyridazino[1,2-a][1,2]diazepine-1-carboxamido)-4-(5,7-dichlorobenzoxazol-2-yl)-4-hydroxybutanoate (221e), was prepared from the acid (212e) and (3S,4RS)t-butyl N-(allyloxycarbonyl)-3-amino-4-hydroxy-4-(5,7-dichlorobenzoxazol-2-yl)butanoate (204) by an analogous method as that used for compound 215e to afford a mixture of diastereomers (613 mg, 87%) as a glass: IR (film) 3328, 1729, 1660, 1534, 1454, 1422, 1399, 1276, 1254, 1155; $^1$H NMR (CDCl$_3$) δ 7.80 (2H, d), 7.60-7.35 (5H, m), 7.05 (2H, m), 5.13 (3H, m), 4.74 (1H, m), 4.51 (1H, m), 3.25 (1H, m), 3.1-2.6 (5H, m), 2.33 (1H, m), 2.1-1.5 (5H, m), 1.43 and 1.41 (9H combined, 2xs). MS ES$^+$ Da/e 688 (M+1)$^+$ Cl$^{35}$ 55%, 690 (M+1)$^+$ Cl$^{37}$ 35%, 328 100%.

[3S(1S,9S)]t-Butyl 4-(5,7-dichlorobenzoxazol-2-yl)-3-(6,10-dioxo-9-methylsulphonylamino-1,2,3,4,7,8,9,10-octahydro-6H-pyridazino[1,2-a][1,2]diazepine-1-carboxamido)-4-oxobutanoate (222b), was prepared from 221b by an analogous method as that used for compound 216e to afford a colourless glass (371 mg, 86%): $[\alpha]_D^{26}$ −81.0 (c 0.1, CH$_2$Cl$_2$); IR (KBr) 3324, 2979, 2936, 1726, 1664, 1394, 1370, 1328, 1155, 991; $^1$H NMR (CDCl$_3$) δ 7.78 (1H, d), 7.57 (2H, m), 5.87 (1H, d), 5.69 (1H, m), 5.47 (1H, m), 4.55 (2H, m), 3.24 (2H, m), 3.0 (5H, m+s), 2.59 (1H, m), 2.39 (1H, m), 2.2-1.7 (4H, m), 1.65 (1H, m), 1.40 (9H, s).

[3S(1S,9S)]t-Butyl 3-(9-benzoylamino-6,10-dioxo-1,2,3,4,7,8,9,10-octahydro-6H-pyridazino[1,2-a][1,2]diazepine-1-carboxamido)-4-(5,7-dichlorobenzoxazol-2-yl)-4-oxobutanoate (222e), was prepared from 221e by an analogous method as that used for compound 216e to afford a colourless glass (480 mg, 84%): $[\alpha]_D^{25}$ −86.4° (c 0.1 CH$_2$Cl$_2$); IR (KBr) 3337, 2978, 2938, 1728, 1657, 1534, 1456, 1422, 1395, 1370, 1277, 1250, 1154; $^1$H NMR (CDCl$_3$) δ 7.80 (3H, m), 7.50 (4H, m), 7.20 (1H, d), 7.02 (1H, d), 5.60 (1H, m), 5.28 (1H, m), 5.15 (1H, m), 4.11 (1H, m), 3.34 (2H, m), 2.96 (3H, m), 2.40 (1H, m), 2.20 (1H, m), 1.92 (2H, m), 1.67 (2H, m), 1.38 (9H, s). MS ES$^−$ Da/e 684 (M−1)$^−$ Cl$^{35}$ 47%, 686 (M−1)$^−$ Cl$^{37}$ 32%.

[3S(1S,9S)]-4-(5,7-Dichlorobenzoxazol-2-yl)-3-(6,10-dioxo-9-methylsulphonylamino-1,2,3,4,7,8,9,10-octahydro-6H-pyridazino[1,2-a][1,2]diazepine-1-carboxamido)-4-oxobutanoic acid (223b), was prepared from 222b by an analogous method as that used for compound 217e to afford an off-white solid (257 mg, 78%): $[\alpha]_D^{25}$ −105.7° (c 0.1, CH$_2$Cl$_2$); IR (KBr) 3321, 1723, 1663, 1407, 1325, 1151, 992; $^1$H NMR (D$_6$-DMSO) δ 8.96 (1H, d), 8.18 (1H, d), 7.96 (1H, d), 5.50 (1H, m), 5.15 (1H, m), 4.30 (2H, m), 3.06 (2H, m), 2.87 (5H, m+s), 2.29 (1H, m), 1.99 (4H, m), 1.56 (2H, m).

[3S(1S,9S)]3-(9-Benzoylamino-6,10-dioxo-1,2,3,4,7,8,9,10-octahydro-6H-pyridazino[1,2-a][1,2]diazepine-1-carboxamido)-4-(5,7-dichlorobenzoxazol-2-yl)-4-oxobutanoic acid (223e), was prepared from 222e by an analogous method as that used for compound 217e to afford a pale cream solid (311 mg, 78%): mp 167-180° C.; $[\alpha]_D^{23}$ −88.6° (c 0.1 CH$_2$Cl$_2$); IR (KBr) 3331, 1724, 1658, 1534, 1458, 1421, 1279, 1256, 991; $^1$H NMR (CDCl$_3$) δ 7.77 (4H, m), 7.4 (5H, m), 5.57 (1H, bs), 5.33 (1H, bs), 5.47 (1H, q), 4.56 (1H, bd), 3.60 (2H, m), 3.20 (3H, m), 2.76 (1H, m), 2.36 (1H, dd), 2.0 (3H, m), 1.66 (1H, m). MS ES Da/e 628 (M-1)$^-$ Cl$^{35}$ 7%, 630 (M-1)$^-$ Cl$^{37}$ 2.3%, 584 100%.

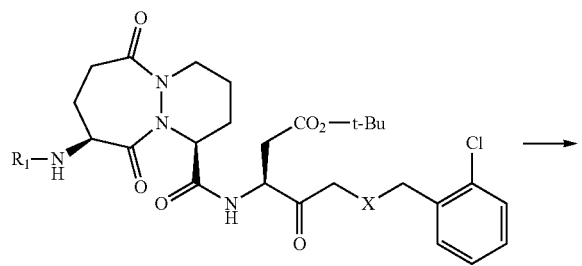

224e R$_1$ = PhCO, X = S
225e R$_1$ = PhCO, X = O

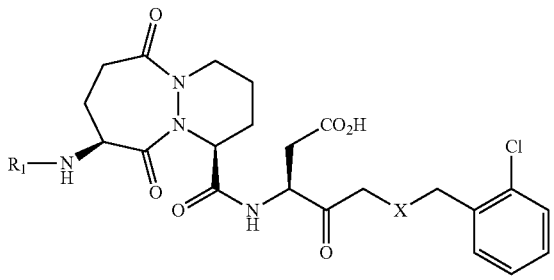

226e R$_1$ = PhCO, X = S
227e R$_1$ = PhCO, X = O

[3S(1S,9S)]t-Butyl 3-(9-benzoylamino-6,10-dioxo-1,2,3,4,7,8,9,10-octahydro-6H-pyridazino[1,2-a][1,2]-diazepine-1-carboxamido)-5-(2-chlorophenyl)methylthio-4-oxopentanoate (224e). 1-Hydroxybenzotriazole (0.23 g, 1.71 mmol) and ethyl dimethylaminopropyl carbodiimide hydrochloride was added to a stirred solution of the acid 212e (0.295 g, 0.853 mmol) in THF (5 ml). After 5 min water (0.5 ml) was added followed, after a further 7 min, by the addition of a solution of (3S)t-butyl-3-allyloxycarbonylamino-5-(2-chloro-phenyl)methylthio-4-oxopentanoate (123, 0.478 g, 1.02 mmol) and (PPh$_3$)$_2$PdCl$_2$ (20 mg) in THF (2 ml). Tributyltin hydride (0.65 ml, 2.33 mmol) was added dropwise during 20 min. The mixture was kept for 4.5 h then diluted with EtOAc, washed with 1M HCl, brine, sat. aq. NaHCO$_3$ and then brine again. The mixture was dried (MgSO$_4$) and concentrated. The residue was triturated several times with hexane, which was decanted and discarded, then purified by flash chromatography (10-100% EtOAc in CH$_2$Cl$_2$) to afford 0.2 g (35%) of a white glassy solid: mp 70-72° C.; $[\alpha]_D^{26}$ −82.5° (c 0.02, CH$_2$Cl$_2$). IR (KBr) 3404, 1726, 1660, 1534, 1524, 1422, 1277, 1254, 1154; $^1$H NMR (CDCl$_3$) δ 7.83-7.78 (2H, m), 7.7, 7.75-7.32, 7.26-7.20 (7H, 3m), 7.12 (1H, d, J=8.2), 7.01 (1H, d, J=7.3), 5.23-5.08 (2H, m), 5.03-4.94 (1H, m), 4.62 (1H, dt, J=14.5), 3.78 (2H, m), 3.38-3.29 (1H, m), 3.26 (2H, s), 3.06-2.82 (4H, m), 2.71 (1H, dd, J=17.2, 4.5), 2.39 (1H, dd, J=13.2, 6.5), 2.15-1.83, 1.73-1.63 (5H, m), 1.45 (9H, s). Anal. Calcd for C$_{33}$H$_{39}$ClN$_4$O$_7$S: C, 59.05; H, 5.86; N, 8.35. Found: C, 59.00; H, 5.80; N, 7.92.

[3RS,(1S,9S)]t-Butyl 3-(9-benzoylamino-6,10-dioxo-1,2,3,4,7,8,9,10-octahydro-6H-pyridazino[1,2-a][1,2]-diazepine-1-carboxamido)-5-(2-chlorophenylmethyloxy)-4-oxopentanoate (225e) was prepared from acid 212e and (3S) t-butyl N-(allyloxycarbonyl)-3-amino-5-(2-chlorophenylmethyloxy)-4-oxopentanoate (201) using a method similar to that used for compound 224e, to afford 40 mg (23%) of a glassy solid: $^1$H NMR (CDCl$_3$) δ 7.83-7.73 (2H, m), 7.67-7.10 (9H, m), 5.23-5.09 (2H, m), 4.59 (1H, m), 4.45-4.22 (2H, m), 3.7-3.19, 3.08-2.72, 2.71-2.47, 2.05-1.85, 1.72-1.61, 1.45-1.26 (20H, 6m).

[3S(1S,9S)]3-(9-Benzoylamino-6,10-dioxo-1,2,3,4,7,8,9,10-octahydro-6H-pyridazino[1,2-a][1,2]-diazepine-1-carboxamido)-5-(2-chlorophenyl)methylthio-4-oxopentanoic acid (226e), was prepared from 224e by an analogous method as that used for compound 217e which afforded 0.22 g (81%) of an off-white solid: mp 95-100° C.; $[\alpha]_D^{23}$ −95.6° (c 0.2, CH$_2$Cl$_2$). IR (KBr) 3393, 1720, 1658, 1529, 1422, 1279; $^1$H NMR (D$_6$-DMSO) 8.80 (1H, d, J=7.5), 7.89 (2H, m), 7.7 (1H, d, J=7.7), 7.56-7.28 (7H, m), 5.10 (1H, m), 4.87-4.73 (2H, m), 4.39 (1H, m), 3.77 (2H, m), 3.44, 3.35 (2H, +H$_2$O, 2m), 2.97-2.56, 2.2, 1.92, 1.61 (11H, 4m). Anal. Calcd for C$_{29}$H$_{31}$ClN$_4$O$_7$S 0.5H$_2$O: C, 55.02; H, 5.10; N, 8.85. Found: C, 55.00; H, 5.09; N, 8.71.

[3RS,(1S,9S)]3-Benzoylamino-6,10-dioxo-1,2,3,4,7,8,9,10-octahydro-6H-pyridazino[1,2-a][1,2]-diazepine-1-carboxamido)-5-(2-chlorophenylmethyloxy)-4-oxopentanoic acid (227e), was prepared from 225e by an analogous method as that used for compound 217e. The product was further purified by flash chromatography (0-5% MeOH/CH$_2$Cl$_2$) to afford 19 mg (81%) of a glassy solid: $^1$H NMR (CDCl$_3$) δ 7.79 (2H, m), 7.66-7.18 (9H, m), 5.30-5.10 (2H, m), 4.85 (1H, m), 4.65 (2H, m), 4.53 (1H, m), 4.28 (2H, m), 3.28, 3.01, 2.72, 2.33, 1.94, 1.60 (11H, 6m). MS (ES$^-$, m/z) 597 (M$^+$-1, 100%).

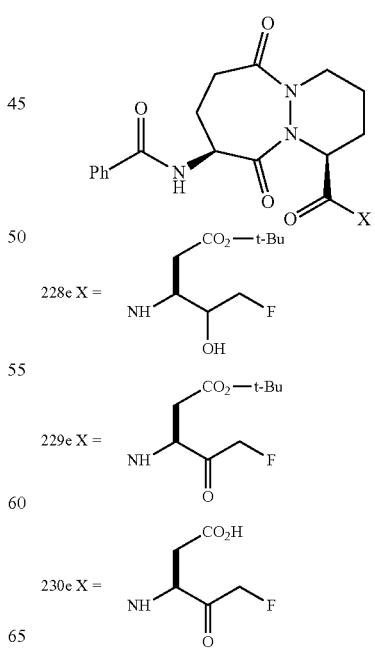

228e X =

229e X =

230e X =

[3RS,4RS(1S,9S)]t-Butyl 3-(9-benzoylamino-6,10-dioxo-1,2,3,4,7,8,9,10-octahydro-6H-pyridazino[1,2-a][1,2]-diazepine-1-carboxamido)-5-fluoro-4-(228e). 1-Hydroxybenzotriazole (0.23 g, 1.68 mmol) followed by ethyldimethylaminopropyl carbodiimide hydrochloride (0.21 g, 1.09 mmol) were added to a stirred solution of the acid 212e (0.29 g, 0.84 mmol) in $CH_2Cl_2$ (3 ml) at rt. The mixture was kept for 10 min then a solution of (3RS,4RS)t-butyl 3-amino-5-fluoro-4-hydroxypentanoate (Revesz, L. et al. *Tetrahedron Lett.*, 52, pp. 9693-9696 (1994); 0.29 g, 1.40 mmol) in $CH_2Cl_2$ (3 ml) was added followed by 4-dimethylaminopyridine (10 mg). The solution was stirred for 17 h, diluted with EtOAc, washed with 1M HCl, sat. aq. $NaHCO_3$ and brine again, dried ($MgSO_4$) and concentrated. The residue was purified by flash chromatography (50-100% EtOAc/$CH_2Cl_2$ and 5% MeOH/EtOAc) to afford 0.25 g (56%) of a white glassy solid: IR (KBr) 3343, 1726, 1658, 1536, 1426, 1279, 1257, 1157; $^1H$ NMR ($CDCl_3$) δ 7.84-7.79 (2H, m), 7.57-7.40 (3H, m), 7.05-6.92, 6.73 (2H, 2m), 5.17-5.04 (2H, m), 4.56, 4.35-4.21, 4.04 (5H, 3m), 3.36, 3.09-2.34, 2.00 (11H, 3m), 1.46 (9H, s). Anal. Calcd for $C_{26}H_{35}FN_4O_7$ 0.5$H_2O$: C, 57.45; H, 6.65; N, 10.31. Found: C, 57.64; H, 6.56; N, 10.15.

[3RS,4RS(1S,9S)]t-Butyl 3-(9-benzoylamino-6,10-dioxo-1,2,3,4,7,8,9,10-octahydro-6H-pyridazino[1,2-a][1,2]-diazepine-1-carboxamido)-5-fluoro-4-oxypentanoate (229e) was prepared from 228c by an analogous method to that used for compound 216e. After purification by flash chromatography (30-50% EtOAc/$CH_2Cl_2$) the product was obtained as a white glassy solid (0.194 g, 89%): IR (KBr) 3376, 1728, 1659, 1529, 1424, 1279, 1256, 1156.

[3RS,(1S,9S)]3-(9-Benzoylamino-6,10-dioxo-1,2,3,4,7,8,9,10-octahydro-6H-pyridazino[1,2-a][1,2]-diazepine-1-carboxamido)-5-fluoro-4-oxopentanoic acid (230e), was prepared from 229e by an analogous method to that used for compound 217e to afford 230e as a white glassy solid (100%): mp 105-125° C.; $[α]_D^{23}$ -91.4° (c 0.72, $CH_3OH$). IR (KBr) 3336, 1789, 1737, 1659, 1535, 1426, 1279, 1258, 1186; $^1H$ NMR ($CD_3OD$) δ 7.71-7.68 (2H, m), 7.37-7.23 (3H, m), 5.02, 4.88-4.63, 4.37-4.0 (6H, 3m), 3.30, 2.97, 2.68-2.60, 2.37-1.54 (11H, 4m). MS ($ES^-$, m/z) 475 ($M^+$-1, 100%).

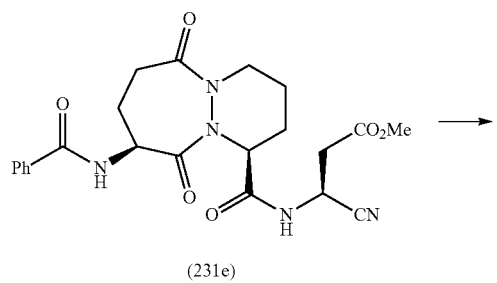

(231e)

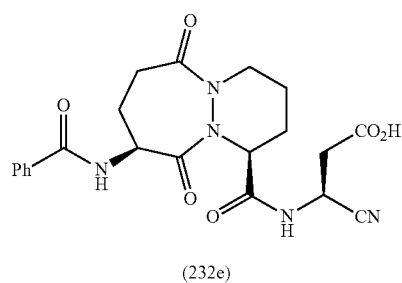

(232e)

[3S(1S,9S)]-Methyl 9-(benzoylamino)-3-[6,10-dioxo-1,2,3,4,7,8,9,10-octahydro-6H-pyridazino[1,2-a][1,2]diazepine-1-carboxamido]-3-cyanopropanoate (231e). N-Fluorenylmethyloxy-carbonyl-3-amino-3-cyanopropionic acid methyl ester (EP0547699A1, 385 mg, 1.1 mmol) was treated with 17 ml of diethylamine. After 1.5 h stirring at room temperature the solution was concentrated. The residue was chromatographed on silica gel (3% methanol in $CH_2Cl_2$) and gave the free amine as a pale yellow oil. To a solution of this oil and hydroxybenzotriazole (297 mg, 2.19 mmol) in DMF (5 ml), was added at 0° C. ethyldimethylaminopropyl carbodiimide (232 mg, 1.21 mmol, 1.1 equiv) followed by (1S,9S) 9-(benzoylamino)-(6,10-dioxo-1,2,3,4,7,8,9,10-octahydro-6H-pyridazino[1,2-a][1,2]diazepine-1-carboxylic acid (212e). After stirring at 0° C. for 5 min and then at room temperature overnight, the mixture was diluted with $CH_2Cl_2$ (50 ml) and the resulting solution washed successively with 1M HCl (2×30 ml), $H_2O$ (30 ml), 10% $NaHCO_3$ (2×30 ml) and sat. aq. NaCl, dried ($MgSO_4$) and concentrated. Purification by flash chromatography on silica gel (3% methanol in $CH_2Cl_2$) afforded the compound 231e (404 mg, 83%) as a solid: $[α]_D^{20}$ -121° (c 0.14, $CH_2Cl_2$); $^1H$ NMR ($CDCl_3$) δ 7.40-7.83 (5H, m), 7.38 (1H, d), 6.96 (1H, d), 5.27-5.07 (2H, m), 4.66-4.50 (1H, m), 3.79 (3H, s), 3.23-2.73 (6H, m), 2.47-2.33 (1H, m), 2.15-1.82 (4H, m); Anal. Calcd for $C_{22}H_{25}N_5O_6$: C, 58.0; H, 5.53; N, 15.38. Found: C, 57.6; H, 5.6; N, 15.0.

[3S(1S,9S)]9-(Benzoylamino)-3-[6,10-dioxo-1,2,3,4,7,8,9,10-octahydro-6H-pyridazino[1,2-a][1,2]diazepine-1-carboxamido]-3-cyanopropanoic acid (232e). A solution of methyl ester 231e (400 mg, 0.88 mmol) in methanol (30 ml) and water (30 ml) was cooled at 0° C. and treated with diisopropylethylamine. The solution was stirred at 0° C. for 10 min and then at room temperature overnight. The heterogeneous mixture was concentrated and the solid obtained was chromatographed on silica gel (5% methanol/1% formic acid in $CH_2Cl_2$) affording the free acid 232e (170 mg, 44%) as a white solid: mp 155° C. (dec); $[α]_D^{20}$ -117° (c 0.1, MeOH); IR (KBr) 3343, 3061, 2955, 1733, 1656, 1577, 1533, 1490, 1421, 1342, 1279, 1256, 1222, 1185, 708; $^1H$ NMR ($D^4$-MeOH) δ 7.88-7.28 (5H, m), 5.20-5.03 (1H, m), 4.98-4.84 (2H, m), 4.75-4.53 (1H, m), 4.51-4.34 (1H, m), 3.45-3.22 (1H, m), 3.14-2.94 (1H, m), 3.14-2.94 (1H, m), 2.88-2.61 (2H, m), 2.53-1.50 (8H, m); Anal. Calcd for $C_{21}H_{23}N_5O_6$·1.5$H_2O$: C, 53.84; H, 5.59; N, 14.95; 0, 25.61. Found: C, 54.3; H, 5.4; N, 14.3.

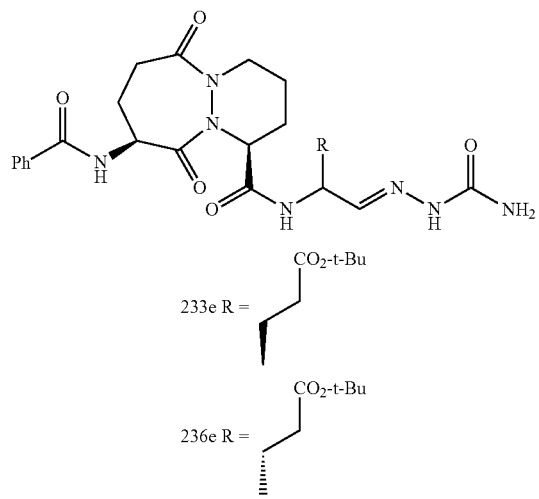
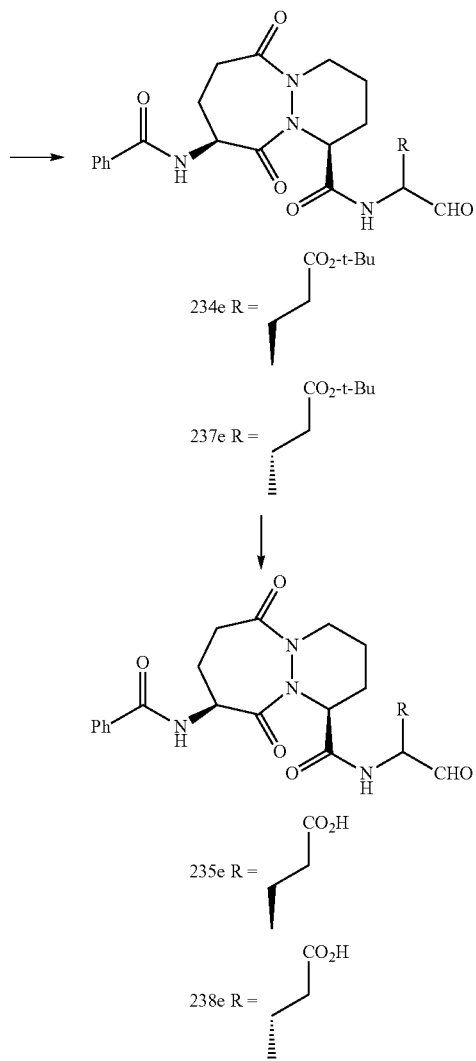

[4S,(1S,9S)]t-Butyl 4-[9-(benzoylamino)-6,10-dioxo-1,2,3,4,7,8,9,10-octahydro-6H-pyridazino[1,2-a][1,2]diazepine-1-carboxamido]-5-oxopentanoate semicarbazone (233e). A solution of (1S,9S)6,10-dioxo-1,2,3,4,7,8,9,10-octahydro-9-(benzoylamino)-6H-pyridazino[1,2-a][1,2]diazepine-1-carboxylic acid (212e) (345 mg, 1.0 mmol), (4S)t-butyl N-(allyloxycarbonyl)-4-amino-5-oxopentanoate semicarbazone (208a) (361 mg, 1.1 mmol, 1.1 equiv) and $(Ph_3P)_2PdCl_2$ (20 mg) in $CH_2Cl_2$ (5 ml), was treated dropwise with n-$Bu_3SnH$ (0.621 ml, 2.3=1, 2.1 equiv). The resulting orange brown solution was stirred at 25° C. for 10 min and then 1-hydroxybenzotriazole (297 mg, 2.2 mmol, 2 equiv) was added. The mixture was cooled to 0° C. and ethyldimethylaminopropyl carbodiimide (253 mg, 1.3 mmol, 1.2 equiv) added. After stirring at 0° C. for 10 min and then at room temperature overnight, the mixture was diluted with EtOAc (50 ml) and the resulting solution washed successively with 1M HCl (3×25 ml), 10% $NaHCO_3$ (3×25 ml) and sat. aq. NaCl, dried ($MgSO_4$) and concentrated. Flash chromatography on silica gel (2-10% methanol in $CH_2Cl_2$) afforded compound 233e (280 mg, 49%) as a tan solid: $[\alpha]_D^{20}$ −95 (c 0.09, MeOH); IR (KBr) 3477, 3333, 2968, 2932, 1633, 1580, 1535, 1423, 1378, 1335, 1259, 1156, 1085, 709; $^1H$ NMR ($CDCl_3$) δ 9.32 (1H, s), 7.83-7.39 (6H, m), 7.11-7.09 (1H, m), 6.30-5.30 (2H, brs), 5.17-5.05 (2H, m), 4.62-4.38 (2H, m), 3.30-3.15 (1H, m), 3.13-2.65 (2H, m), 2.46-2.19 (3H, m), 2.15-1.54 (8H, m), 1.42 (9H, s).

[4R,(1S,9S)]t-Butyl 4-[9-(benzoylamino)-6,10-dioxo-1,2,3,4,7,8,9,10-octahydro-6H-pyridazino[1,2-a][1,2]diazepine-1-carboxamido]-5-oxopentanoate semicarbazone (236e), was prepared by an analogous method to that used for 233e using (4R)t-butyl N-allyloxycarbonyl-4-amino-5-oxopentanoate semicarbazone (208b, 435 mg, 1.33 mmol). The product was obtained as a foam (542 mg, 71%): $[\alpha]_D^{20}$ −99 (c 0.19, $CHCl_3$); IR (KBr) 3473, 3331, 3065, 2932, 2872, 1660, 1580, 1533, 1488, 1423, 1370, 1337, 1278, 1254, 1223, 1155, 1080, 1024, 983, 925, 877, 846, 801, 770, 705; $^1H$ NMR ($CDCl_3$) δ 9.42 (1H, s), 7.81 (2H, d), 7.51-7.40 (4H, m), 7.06 (1H, d), 6.50-5.50 (2H, broad s), 5.25-5.00 (2H, m), 4.60-4.45 (2H, m), 3.15-2.85 (2H, m), 2.75-2.35 (1H, m), 2.30-1.23 (11H, m), 1.42 (9H, s).

[4S,(1S,9S)]t-Butyl 4-[9-(benzoylamino)-6,10-dioxo-1,2,3,4,7,8,9,10-octahydro-6H-pyridazino[1,2-a][1,2]diazepine-1-carboxamido]-5-oxopentanoate (234e). A solution of semicarbazone 233e (390 mg, 0.68 mmol) in methanol (10 ml) was cooled at 0° C. and then treated with a 38% aq. solution of formaldehyde (2 ml) and 1M HCl (2 ml). The reaction mixture was then stirred overnight at room temperature. The solution was concentrated to remove the methanol. The aq. solution was extracted with EtOAc (30 ml). The organic solution was successively washed with 10% NaHCO$_3$ (30 ml) and sat. aq. NaCl (30 ml), dried (MgSO$_4$) and concentrated. Purification by flash chromatography on silica gel (2-5% methanol in CH$_2$Cl$_2$) afforded 234e (179 mg, 51%) as a white foam: $[\alpha]_D^{20}$ −101° (c 0.064, MeOH); IR (KBr) 3346, 2976, 2934, 1730, 1657, 1535, 1456, 1425, 1278, 1255, 1156, 708; $^1$H NMR (CDCl$_3$) δ 9.56 (1H, s), 7.88-7.38

[4R,(1S,9S)]-4-[9-(Benzoylamino)-6,10-dioxo-1,2,3,4,7,8,9,10-octahydro-6H-pyridazino[1,2-a][1,2]diazepine-1-carboxamido]-5-oxopentanoic acid (238e), was prepared from 237e by an analogous route to 235e which afforded a beige foam (190 mg, 60%): $[\alpha]_D^{20}$ −78 (c 0.145, MeOH); IR (KBr) 3400, 3070, 2955, 2925, 2855, 1653, 1576, 1541, 1490, 1445, 1427, 1342, 1280, 1258, 1205, 1189, 1137, 1075, 1023, 983, 930, 878, 843, 801, 777, 722; $^1$H NMR (D$_6$-DMSO) δ 9.40 (1H, s), 8.72-8.60 (2H, m), 7.89 (2H, d), 7.56-7.44 (3H, m), 5.17 (1H, m), 4.90-4.83 (1H, m), 4.46-4.36 (1H, m), 4.20-4.15 (1H, m), 3.40-3.30 (1H, m), 2.98-2.90 (2H, m), 2.50-1.60 (10H, m).

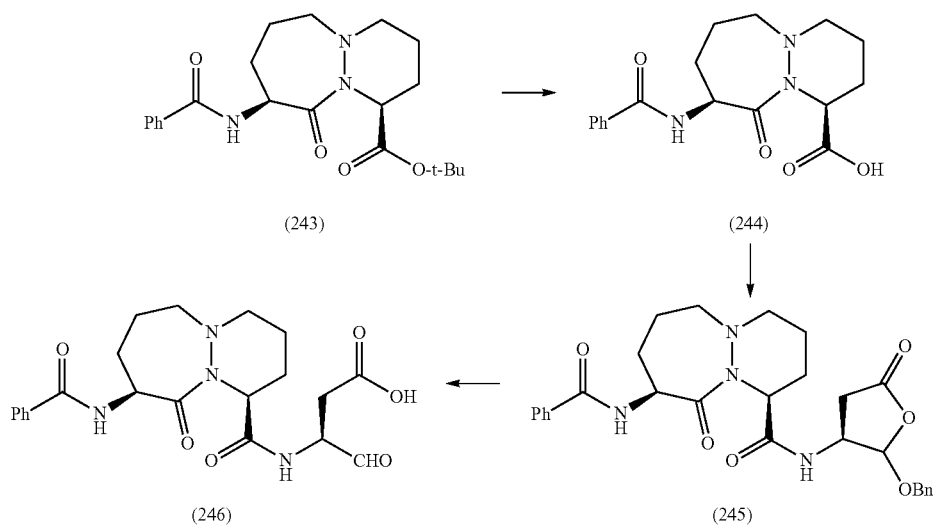

(5H, m), 7.01 and 6.92 (2H, 2d), 5.27-5.08 (2H, m), 4.69-4.46 (1H, m), 3.50-3.27 (2H, m), 3.15-2.73 (2H, m), 2.46-1.83 (10H, m), 1.45 (9H, s).

[4R,(1S,9S)]t-Butyl 4-[(9-(benzoylamino)-6,10-dioxo-1,2,3,4,7,8,9,10-octahydro-6H-pyridazino[1,2-a][1,2]diazepine-1-carboxamido]-5-oxopentanoate (237e), was prepared from 236e by an analogous method to 234e to afford a white foam (390 mg, 85%): $[\alpha]_D$ −113° (c 0.242, CHCl$_3$); IR (KBr) 3352, 3065, 2974, 1729, 1657, 1536, 1489, 1454, 1423, 1369, 1338, 1278, 1255, 1223, 1156, 1078, 1026, 981, 846, 709.

[4S,(1S,9S)]-4-[9-(Benzoylamino)-6,10-dioxo-1,2,3,4,7,8,9,10-octahydro-6H-pyridazino[1,2-a][1,2]diazepine-1-carboxamido]-5-oxopentanoic acid (235e). A solution of t-butyl ester 234e (179 mg, 0.35 mmol) in dry CH$_2$Cl$_2$ (3 ml) was cooled to 0° C. and treated with trifluoroacetic acid (2 ml). The resulting solution was stirred at 0° C. for 30 min and then at room temperature for 2 h. The solution was concentrated, the residue taken up in dry CH$_2$Cl$_2$ (5 ml) and the mixture again concentrated. This process was repeated once again with more CH$_2$Cl$_2$ (5 ml). The residue obtained was crystallized in diethyl ether. The precipitate was collected and purified on silica gel column (5% methanol in CH$_2$Cl$_2$) which afforded compound 235e as a white solid (111 mg, 70%): mp 142° C. (dec); $[\alpha]_D^{20}$ −85.5 (c 0.062, MeOH); IR (KBr) 3409, 3075, 2952, 1651, 1541, 1424, 1280, 1198, 1136, 717; $^1$H NMR (D$_6$-DMSO) δ 9.40 (1H, s), 8.62 (2H, m), 7.96-7.38 (5H, m), 5.19-5.02 (1H, m), 4.98-4.79 (1H, m), 4.48-4.19 (1H, m), 3.51-3.11 (2H, m), 3.04-2.90 (2H, m), 2.38-1.46 (10H, m).

(1S,9S)t-Butyl 9-benzoylamino-octahydro-10-oxo-6H-pyridazino[1,2-a][1,2]diazepine-1-carboxylate (243), was prepared from (1S,9S)t-butyl 9-amino-octahydro-10-oxo-6H-pyridazino[1,2-a][1,2]diazepine-1-carboxylate (Attwood, et al. *J. Chem. Soc., Perkin* 1, pp. 1011-19 (1986)), by the method described for 211e, to afford 2.03 g (86%) of a colourless foam: $[\alpha]_D^{25}$ −15.9° (c 0.5, CH$_2$Cl$_2$); IR (KBr) 3400, 2976, 2937, 1740, 1644, 1537, 1448, 1425, 1367, 1154; $^1$H NMR (CDCl$_3$) δ 7.88-7.82 (2H, m), 7.60-7.38 (4H, m), 5.48 (1H, m), 4.98 (1H, m), 3.45 (1H, m), 3.22-2.96 (2H, m), 2.64 (1H, m), 2.43-2.27 (2H, m), 1.95 (2H, m), 1.82-1.36 (4H, m), 1.50 (9H, s); Anal. Calcd for C$_{21}$H$_{29}$N$_3$O$_4$.0.25H$_2$O: C, 64.35; H, 7.59; N, 10.72. Found: C, 64.57; H, 7.43; N, 10.62. MS (ES+, m/z) 388 (100%, M$^+$+1).

(1S,9S)9-Benzoylamino-octahydro-10-oxo-6H-pyridazino[1,2-a][1,2]diazepine-1-carboxylic acid (244), was prepared from (1S,9S)t-butyl 9-benzoylamino-octahydro-10-oxo-6H-pyridazino[1,2-a][1,2]diazepine-1-carboxylate (243), by the method described for 212e, to afford 1.52 g (89%) of a white powder: mp. 166-169° C. (dec); $[\alpha]_D^{25}$ −56.4° (c 0.5, CH$_3$OH); IR (KBr) 3361, 2963, 2851, 1737, 1663, 1620, 1534, 1195, 1179; $^1$H NMR (D$_6$-DMSO) δ 12.93 (1H, brs), 8.44 (1H, d, J=8.4), 7.93 (2H, m), 7.54 (3H, m), 5.46 (1H, m), 4.87 (1H, m), 3.12 (2H, m), 2.64 (1H, m), 2.64 (1H, m), 2.27 (1H, m), 1.98-1.68 (7H, m), 1.40 (1H, m); Anal. Calcd for C$_{17}$H$_{21}$N$_3$O$_4$.0.25H$_2$O: C, 60.79; H, 6.45; N, 12.51. Found: C, 61.07; H, 6.35; N, 12.55. MS (ES$^+$, m/z) 332 (58%, M$^+$+1), 211 (100).

[3S,2RS(1S,9S)]N-(2-Benzyloxy-5-oxotetrahydrofuran-3-yl)-9-benzoylamino-octahydro-10-oxo-6H-pyridazino[1,2-a][1,2]diazepine-1-carboxamide (245), was prepared from (1S,9S)9-benzoylamino-octahydro-10-oxo-6H-pyridazino[1,2-a][1,2]-diazepine-1-carboxylic acid (244), by the method described for 213e, to afford 601 mg (76%) of a colourless foam: IR (KBr) 3401, 2945, 1794, 1685, 1638, 1521, 1451, 1120; $^1$H NMR (CDCl$_3$) δ 7.87-7.77 (2H, m), 7.57-7.14 (10H, m), 5.59-5.47 (2H, m), 4.97-4.32 (4H, m), 3.27-1.35 (14H, m); Anal. Calcd for C$_{28}$H$_{32}$N$_4$O$_6$.0.5H$_2$O: C, 63.50; H, 6.28; N, 10.58. Found: C, 63.48; H, 6.14; N, 10.52. MS (ES+, m/z) 521 (100%, M$^+$+1).

[3S(1S,9S)]3-(9-Benzoylamino-octahydro-10-oxo-6H-pyridazino[1,2-a][1,2]diazepine-1-carboxamide-4-oxobutanoic acid (246), was prepared from [3S,2RS(1S,9S)]N-(2-benzyloxy-5-oxotetrahydrofuran-3-yl)-9-benzoylamino-octahydro-10-oxo-6H-pyridazino[1,2-a][1,2]diazepine-1-carboxamide (245), by the method described for 214e, to afford 396 mg (84%) of a white powder: mp. 110-115° C.; $[α]_D^{26}$ −126° (c 0.2, CH$_3$OH); IR (KBr) 3345, 2943, 1787, 1730, 1635, 1578, 1528, 1488, 1450, 1429; $^1$H NMR (CD$_3$OD) δ 7.88 (2H, m), 7.48 (3H, m), 5.55 (1H, m), 4.91 (1H, m), 4.56 (1H, m), 4.29 (1H, m), 3.41-3.05 (3H, m), 2.76-2.41 (3H, m), 2.28-2.01 (3H, m), 1.86-1.65 (4H, m), 1.36 (1H, m); Anal. Calcd for C$_{21}$H$_{26}$N$_4$O$_6$.1.25H$_2$O: C, 55.68; H, 6.34; N, 12.37. Found: C, 55.68; H, 6.14; N, 12.16. MS (ES−, m/z) 429 (100%, M$^+$−1).

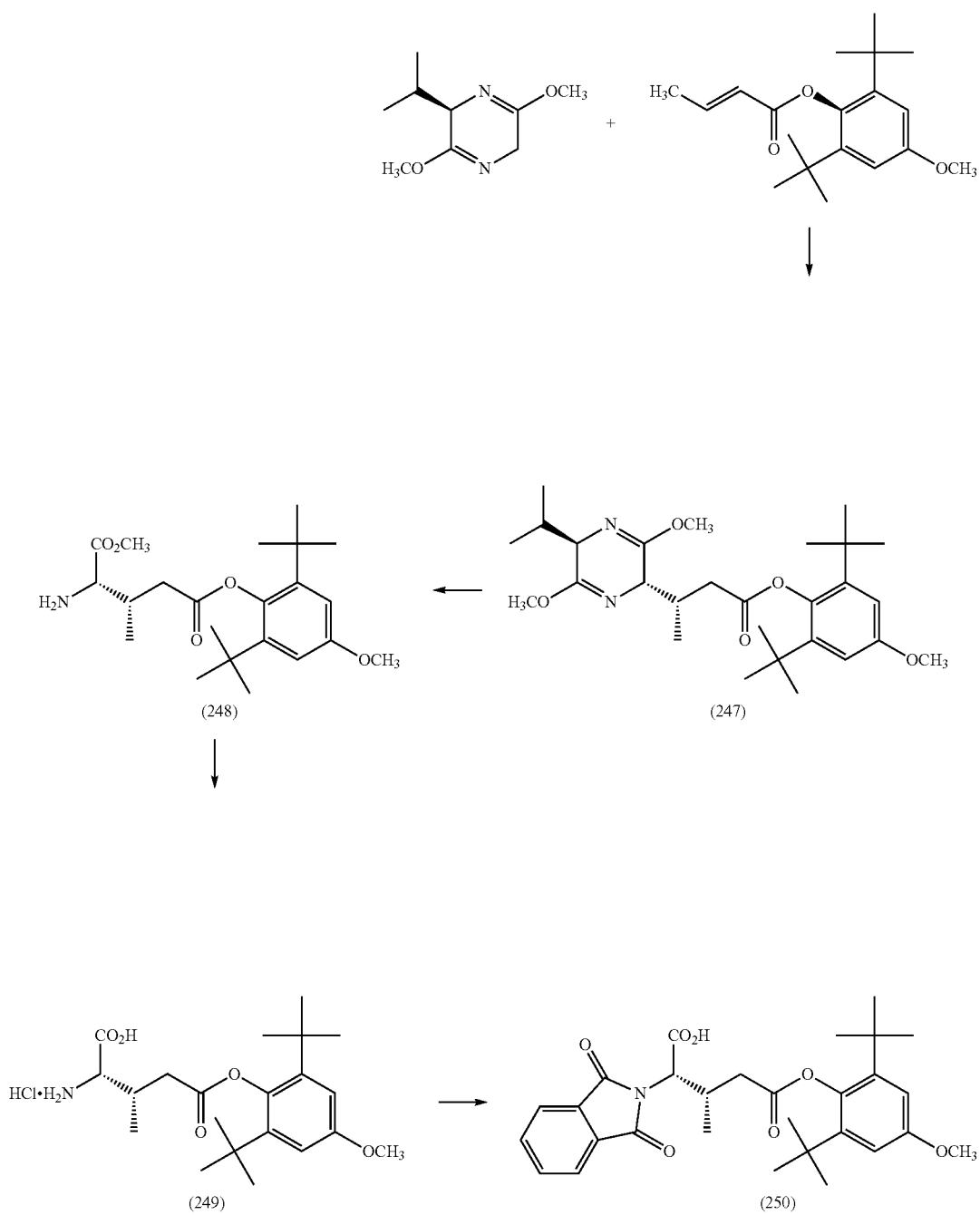

[(3S(2R,5S)]-2,6-Di-tert-butyl-4-methoxyphenyl-3-[5-(2,5-dihydro-3,6-dimethoxy-2-(1-methylethyl)pyrazinyl)]butanoate (247). n-Butyllithium (1.6M in hexane) (22.3 ml, 35.7 mmol) was added dropwise over 20 min to a solution of (2R)-(−)-2,5-dihydro-3,6-dimethoxy-2-(1-methylethyl)pyrazine (5.8 ml, 6.0 g, 32.4 mmol) in THF (250 ml) cooled to −75° C. at a rate such that the temperature was maintained below −72° C. The reaction mixture was stirred for 1 h at −75° C. and a solution of 2,6-di-t-butyl-4-methoxyphenyl-2-butenoate (Suzuck et al. Liebigs Ann. Chem. pp. 51-61 (1992)) (9.9 g, 32.5 mmol) in THF (60 ml) was added over 30 minutes maintaining the temperature below −72° C. during the addition. The reaction mixture was kept at −75° C. for 1.5 h and a solution of glacial acetic acid (6 ml) in THF (25 ml) was added at −75° C. and the solution warmed to room temperature. The solution was poured onto 10% NH$_4$Cl (300 ml) and extracted with diethyl ether (3×250 ml). The combined organic phases were washed with brine (2×200 ml), dried over Na$_2$SO$_4$ and evaporated to dryness under reduced pressure. The residual oil was purified by flash chromatography on silica gel (20% heptane in CH$_2$Cl$_2$) which afforded the title compound as a light yellow oil (13.5 g, 85%): [α]$_D^{20}$ −64° (c 0.22, MeOH); IR (KBr) 2962, 2873, 2840, 1757, 1697, 1593, 1460, 1433, 1366, 1306, 1269, 1236, 1187, 1157, 1126, 1063, 1038, 1011, 970, 924, 892, 867, 846, 831, 797, 773, 754; $^1$H NMR (CDCl$_3$) δ 6.85 (2H, s), 4.21 (1H, t, J=3.5), 3.98 (1H, t, J=3.5), 3.79 (3H, s), 3.71 (3H, s), 3.69 (3H, s), 3.15 (1H, dd, J 17.8, 7.9), 2.86-2.81 (1H, m), 2.58 (1H, dd, J=17.8, 5.9), 2.28-2.19 (1H, m), 1.33 (18H, s), 1.02 (3H, d, J=6.8), 0.70 (6H, dd, J=13, 6.8).

(2S,3S)-5-[2,6-Di-t-butyl-4-methoxyphenyl]1-methyl-3-methylglutamate (248). A solution of [3S(2R,5S)]-2,6-di-t-butyl-4-methoxyphenyl-3-[5-(2,5-dihydro-3,6-dimethoxy-2-(1-methylethyl)pyrazinyl)]butanoate (247) (22.4 g, 45.8 mmol) in acetonitrile (300 ml) and 0.25N HCl (366 ml, 2 equiv) was stirred at room temperature under nitrogen atmosphere for 4 days. The acetonitrile was evaporated under reduced pressure and diethylether (250 ml) was added to the aq. phase. The pH of the aq. phase was adjusted to pH8-9 with concentrated ammonia solution (32%) and the phases separated. The aq. phase was extracted with diethylether (2×250 ml). The combined organic phases were dried over Na$_2$SO$_4$ and evaporated to dryness under reduced pressure. The residual oil was purified by flash chromatography on silica gel (2% methanol in CH$_2$Cl$_2$) which afforded the required product as a light yellow oil (8.2 g, 45%): [α]$_D^{20}$ +20° (c 0.26, MeOH); IR(KBr) 3394, 3332, 3000, 2962, 2915, 2877, 2838, 1738, 1697, 1593, 1453, 1430, 1419, 1398, 1367, 1304, 1273, 1251, 1221, 1203, 1183, 1126, 1063, 1025, 996, 932, 891, 866, 847, 800, 772, 745; $^1$H NMR (CDCl$_3$) δ 6.85 (2H, s), 3.79 (3H, s), 3.74 (3H, s), 3.72-3.69 (1H, m), 3.05-2.85 (1H, m), 2.67-2.50 (2H, m), 1.32 (18H, s), 0.93 (3H, d, J=7); Anal. Calcd for C$_{22}$H$_{35}$NO$_5$: C, 67.15; H, 8.96; N, 3.56. Found: C, 67.20; H, 9.20; N, 3.70.

(2S,3S)-5-[2,6-Di-t-butyl-4-methoxyphenyl]3-methylglutamate (249). A solution of (2S,3S)-5-[2,6-di-t-butyl-4-methoxyphenyl]3-methylglutamate (248) (8.0 g, 20.3 mmol) in 5N HCl (200 ml) was heated at reflux for 2 h. The reaction mixture was evaporated to dryness under reduced pressure. The residue was dissolved in cyclohexane (×4) and evaporated to dryness (×4) which afforded a white solid (7.9 g, 93%): mp 230° C.; [α]$_D^{20}$ +22° (c 0.27, MeOH); IR (KBr) 3423, 2964, 1755, 1593, 1514, 1456, 1421, 1371, 1303, 1259, 1201, 1179, 1138, 1106, 1060, 966, 926, 861, 790, 710; $^1$H NMR (MeOD) δ 6.76 (2H, s), 4.02 (1H, d, J=3.7), 3.67 (3H, s), 3.05-2.85 (1H, m), 2.80-2.55 (2H, m), 1.22 (18H, s), 1.09 (3H, d, J=6.3); $^{13}$C NMR (MeOD) δ 174.5, 171.4, 158.6, 145.2, 143.1, 113.2, 58.3, 56.3, 39.8, 36.9, 32.5, 16.6; Anal. Calcd for C$_{21}$H$_{34}$ClNO$_5$: C, 60.64; H, 8.24; N, 3.37. Found: C, 60.80; H, 8.40; N, 3.40.

(2S,3S)-5-[2,6-Di-t-butyl-4-methoxyphenyl]3-methyl-2-phthalimido-1,5-pentanedioate (250). Diisopropylethylamine (4.1 ml, 3.04 g, 23.5 mmol, 1.25 equiv) and phthalic anhydride (3.5 g, 23.6 mmol, 1.25 equiv) were added to a solution of (2S,3S)-5-[2,6-di-t-butyl-4-methoxyphenyl]3-methylglutamate (249) (7.8 g, 18.6 mmol) in toluene (300 ml). and the resulting mixture was heated at reflux for 3 hours. After cooling to room temperature, the reaction mixture was evaporated to dryness and the resulting oil purified by flash chromatography on silica gel (2% methanol in CH$_2$Cl$_2$) which afforded the required product as a white foam (8.35 g, 87%): [α]$_D^{20}$ −20° (c 1.04, MeOH); IR (KBr) 3480, 2968, 2880, 1753, 1721, 1594, 1462, 1422, 1388, 1303, 1263, 1216, 1183, 1148, 1062, 1003, 933, 899, 755, 723; $^1$H NMR (CDCl$_3$) δ 7.92-7.87 (2H, m), 7.78-7.73 (2H, m), 6.84 (2H, s), 4.95 (1H, d), 3.78 (3H, s), 3.30-3.05 (2H, m), 2.85-2.65 (1H, m), 1.30 (18H, s), 1.13 (3H, d).

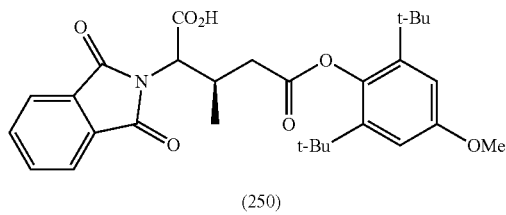

(250)

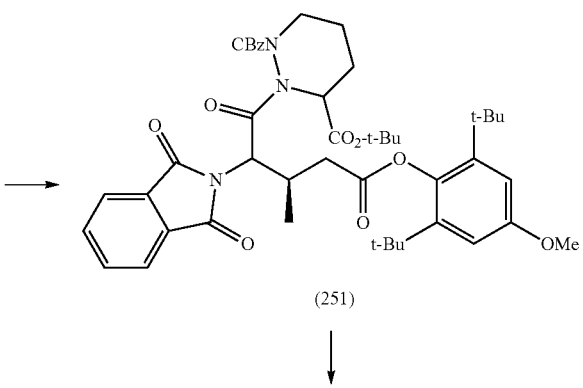

(251)

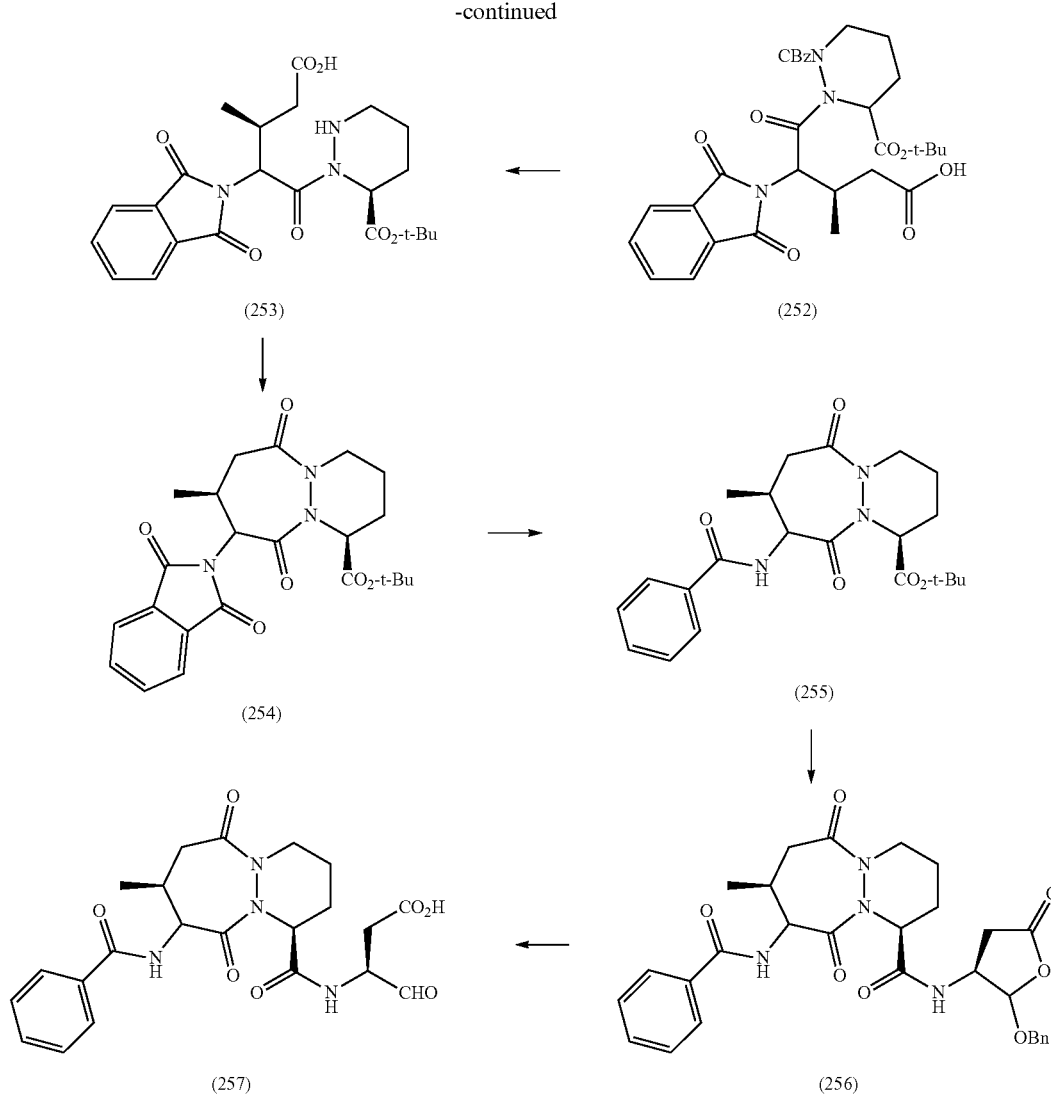

1-(2,6-di-t-Butyl-4-methoxy)-phenyl-5-(1-benzyloxycarbonyl-3-t-butoxycarbonyl-hexahydro-pyridazin-2-yl)-3-methyl-4-phthalimidopentan-1,5-dioate (251). A solution of the amino acid (250) (1.2 g, 2.35 mmol) in dry diethylether (10 ml) was treated with phosphorus pentachloride (0.52 g, 2.5 mmol) at room temperature for 2 h. The mixture was concentrated and treated several times with toluene and again evaporated to dryness. The resulting acid chloride was dissolved in dry THF (5 ml) and $CH_2Cl_2$ (5 ml) and cooled to 0° C. t-Butyl-1-(benzyloxycarbonyl)-hexahydro-3-pyridazine-carboxylate (0.753 g, 2.35 mmol, 1 equiv) and N-ethylmorpholine (3 ml) were added to the solution. The reaction mixture was stirred for 30 min at 0° C. and then overnight at room temperature. The mixture was evaporated and the resulting residue taken up with $CH_2Cl_2$ (30 ml). The solution was washed with 1M HCl, water, 10% $NaHCO_3$, dried ($MgSO_4$) and evaporated. The resulting white foam was purified on silica gel (0-2% methanol in $CH_2Cl_2$) which afforded the required compound 251 as a pale yellow glassy solid (740 mg, 39%): $[\alpha]_D^{20}$ −22 (c 0.42, MeOH); IR (KBr) 3441, 2966, 1725, 1693, 1386, 1255, 1221, 1186, 1154, 1123, 1063, 724; $^1$H NMR (CDCl$_3$) δ 7.94-7.89 (4H, m), 7.56-7.28 (5H, m), 6.84 (2H, 2s), 5.29-5.20 (2H, AB), 4.91-4.81 (1H, m), 4.05- 3.88 (1H, m), 3.78 (3H, s), 3.75-3.80 (1H, m), 3.28-2.95 (2H, m), 2.23-1.51 (6H, m), 1.45 (9H, s), 1.31 (9H, s), 1.28 (9H, s), 1.27 (3H, d).

(1S,8S,9S)t-Butyl 6,10-dioxo-8-methyl-1,2,3,4,7,8,9,10-octahydro-9-phthalimido-6H-pyridazino[1,2-a][1,2]diazepin-1-carboxylate (254). A solution of the protected acid (251) (715 mg, 0.893 mmol) in acetonitrile was treated with Cerium (IV) ammonium nitrate (1.8 g, 3.3 mmol, 3.7 equiv) in water (3 ml) for 4 h at room temperature. Mannitol (600 mg, 3.3 mmol, 3.7 equiv) was added and the mixture was stirred for 1 h. Diethylether (50 ml) and water (30 ml) were added to the mixture. After decantation, the aq. phase was extracted with diethylether (4×50 ml). The combined organic phase was washed with water, dried ($MgSO_4$) and concentrated. Chromatography on silica gel (10% methanol in $CH_2Cl_2$) afforded 5-(1-benzyloxycarbonyl-3-t-butoxycarbonyl-hexahydropyridazin-2-yl)carbonyl-3-methyl-4-phthalimidopentanoic acid (252) (360 mg, 64%): $[\alpha]_D^{20}$ −49.2 c 0.118, MeOH). This product was used without further purification (360 mg, 0.609 mmol), and was hydrogenated in methanol (30 ml) using 10% Pd/carbon (36 mg) for 3 h. The reaction mixture was filtered and the resulting solution concentrated to afford the amine (253) as a foam (270 mg, 96%)

$[\alpha]_D^{20}$ −56.1 (c 0.18 MeOH). The amine (253) was dissolved in dry THF (10 ml) and phosphorous pentachloride (305 mg, 1.47 mmol, 2.5 equiv) was added. The mixture was then cooled to −5° C. and N-ethylmorpholine was added under nitrogen. The reaction mixture was stirred overnight at room temperature. The mixture was concentrated and the residue taken up with $CH_2Cl_2$ (20 ml), cold $H_2O$ (20 ml), 1M HCl (20 ml). After decantation, the aq. phase was reextracted with $CH_2Cl_2$ (2×20 ml). The combined organic phase was washed with 10% $NaHCO_3$ and water, dried ($MgSO_4$) and concentrated. The resulting oil was purified on silica gel (1% methanol in $CH_2Cl_2$) affording the bicyclic compound (254) as a solid (65 mg, 25%): $[\alpha]_D^{20}$ −77 (c 0.208, MeOH); IR (KBr) 3471, 3434, 2975, 2928, 1767, 1723, 1443, 1389, 1284, 1243, 1151, 1112, 720; $^1$H NMR (CDCl$_3$) δ 7.94-7.69 (4H, m), 5.34-5.27 (1H, m), 4.89-4.66 (2H, m), 3.94-3.64 (2H, m), 3.02-2.84 (1H, m), 2.34-2.19 (2H, m), 1.94-1.61 (3H, m), 1.47 (9H, s), 1.14 (3H, d); Anal. Calcd for $C_{23}H_{27}N_3O_6$: C, 62.57; H, 6.17; N, 9.52. Found: C, 62.60; H, 6.40; N, 9.10.

(1S,8S,9S)t-Butyl-9-benzoylamino-6,10-dioxo-8-methyl-1,2,3,4,7,8,9,10-octahydro-6H-pyridazino[1,2-a][1,2]diazepine-1-carboxylate (255). A solution of the bicyclic compound (254) (70 mg, 0.16 mmol) in ethanol was treated with hydrazine hydrate (0.02 ml, 4 mmol, 2.5 equiv). After 5 h stirring at room temperature, the mixture was concentrated and the resulting residue taken up in toluene and reevaporated. The residue was treated with 2M acetic acid (2 ml) for 16 h. The resulting precipitate was filtered and washed with 2M acetic acid (10 ml). The filtrate was basified with solid $NaHCO_3$ and then extracted with EtOAc. The organic solution was washed with water, dried ($MgSO_4$) and concentrated. Purification by flash chromatography on silica gel (2% methanol in $CH_2Cl_2$) afforded the free amine as a foam (50 mg, 100%). The amine (50 mg, 0.16 mmol) was dissolved in dioxane (1 ml) and water (0.25 ml) and treated with $NaHCO_3$ (0.034 g, 0.04 mmol) followed by benzoylchloride (0.047 ml, 0.40 mmol, 2.8 equiv). The mixture was stirred overnight at room temperature, then diluted with EtOAc (15 ml). The organic solution was washed with 10% $NaHCO_3$ and sat. aq. NaCl, dried ($MgSO_4$) and concentrated. Purification by flash chromatography on silica gel (2% methanol in $CH_2Cl_2$) afforded the benzamide 255 as a foam (67 mg, 100%): $^1$H NMR (CDCl$_3$) δ 7.89-7.39 (5H, m), 6.79 (1H, d), 5.32-5.20 (1H, m), 4.98-4.82 (1H, m), 4.75-4.64 (1H, m), 3.84-3.65 (1H, m), 3.09-2.89 (1H, m), 2.45-2.18 (2H, m), 2.00-1.61 (4H, m), 1.48 (9H, s), 1.28 (3H, d).

[3S(1S,8S,9S)]3-(9-benzoylamino-6,10-dioxo-8-methyl-1,2,3,4,7,8,9,10-octahydro-6H-pyridazino[1,2-a][1,2]diazepine-1-carboxamido)-4-oxobutanoic acid (257). A solution of t-butyl ester 255 (67 mg, 0.16 mmol) in $CH_2Cl_2$ (1 ml) was treated at 0° C. with trifluoroacetic acid (1 ml). The resulting solution was stirred at 0° C. for 15 min and then at room temperature for 1 h. The solution was concentrated, the residue taken up in dry $CH_2Cl_2$ (2×2 ml) and the mixture again concentrated (×2). The residue was crystallized from diethylether. Filtration of the precipitate afforded the free acid of 255 as a grey solid (40 mg, 70%). A solution of acid (40 mg, 0.11 mmol), N-allyloxycarbonyl-4-amino-5-benzyloxy-2-oxotetrahydrofuran (Chapman, *Bioorg. & Med. Chem. Lett.*, 2, pp. 615-18 (1992); 39 mg, 0.13 mmol, 1.2 equiv) and $(Ph_3P)_2PdCl_2$ (3 mg) in a mixture of dry $CH_2Cl_2$ (1 ml) and dry DMF (0.2 ml) was treated dropwise with n-Bu$_3$SnH (0.089 ml, 0.33 mmol, 3 equiv). The resulting solution was stirred at 25° C. for 10 min and then 1-hydroxybenzotriazole (36 mg, 0.266 mmol, 2.4 equiv) was added. The mixture was cooled to 0° C. and ethyldimethylaminopropyl carbodiimide (31 mg, 0.16 mmol, 1.5 equiv) was added. After stirring at 0° C. for 10 min and then at room temperature overnight, the mixture was diluted with EtOAc (20 ml) and the resulting solution washed successively with 1M HCl (2×5 ml), 10% $NaHCO_3$ (2×5 ml) and sat. aq. NaCl (5 ml), dried ($MgSO_4$) and concentrated. Flash chromatography on silica gel (2% methanol in $CH_2Cl_2$) afforded a mixture of diastereoisomers (256) as a grey solid (50 mg, 82%). This product (256) was used without further purification (50 mg, 0.091 mmol) and was hydrogenated in methanol (5 ml) using 10% Pd/carbon (30 mg) for 24 h. The reaction mixture was filtered and the resulting solution concentrated. Flash chromatography on silica gel (2-20% methanol in $CH_2Cl_2$) afforded compound 257 (9 mg, 21%) as a white solid: $^1$H NMR (D$^4$-MeOH) δ 7.88-7.29 (5H, m), 5.18-4.99 (1H, m), 4.59-4.35 (3H, m), 4.26-4.11 (1H, m), 3.65-3.41 (2H, m), 3.18-2.91 (1H, m), 2.62-1.47 (8H, m), 1.29-1.00 (3H, 2d) (mixture of acetal and hemiacetal). MS (ES−) 457.

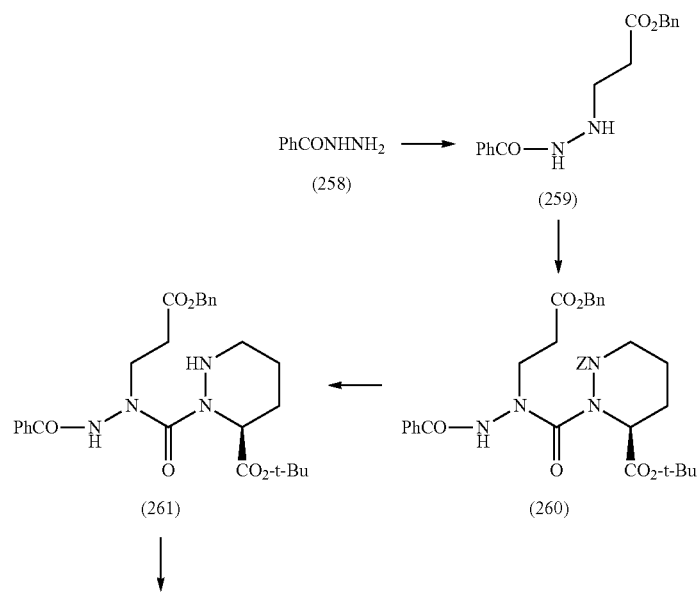

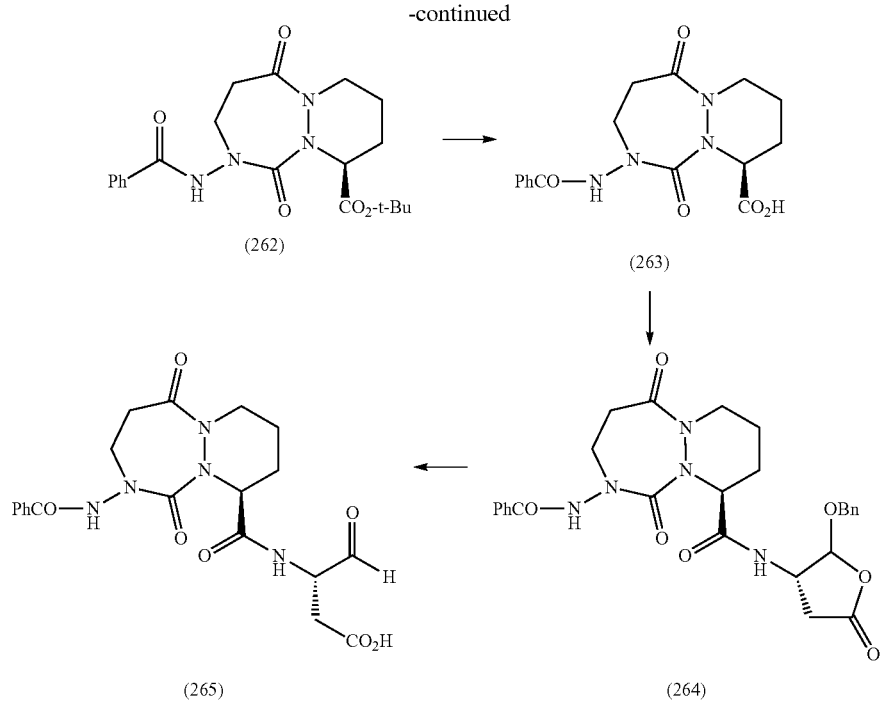

Benzyl 3-(N'-benzoylhydrazino)propanoate (259). Benzylacrylate (1.13 ml, 7.34 mmol) was added to a stirred suspension of benzoylhydrazine (285) (1.0 g, 7.34 mmol) in isopropanol (28 ml). The mixture was refluxed for 20 h, cooled to room temperature then concentrated. The residue was purified by flash chromatography (20% EtOAc in $CH_2Cl_2$) to afford 259 (1.098 g, 50%) as an oil which crystallized on standing: mp 65° C.; IR (KBr) 3283, 1723, 1644, 1316, 1201, 1156; $^1$H NMR (CDCl$_3$) δ 8.32-8.18 (1H, m), 7.81-7.70 (2H, m), 7.57-7.23 (8H, m), 5.36-4.92 (1H, brm), 5.11 (2H, s), 3.26 (2H, t, J=6.5), 2.59 (2H, t, J=6.5); $^{13}$C NMR (CDCl$_3$) δ 172.12, 167.27, 135.65, 132.54, 131.66, 128.45, 128.10, 128.06, 126.84, 66.31, 47.33, 33.31; Anal. Calcd for $C_{17}H_{18}N_2O_3$: C, 68.44; H, 6.08; N, 9.39. Found: C, 68.42; H, 6.10; N, 9.38. MS (ES+) 321 (M+Na, 38%), 299 (M$^+$+1, 100).

(3S)-1-Benzyl 3-t-butyl 2-(N'-benzoyl-N-(2-benzyloxycarbonylethyl)hydrazinocarbonyl)hexahydro-pyridazine-1,3-dicarboxylate (260). A solution of (3S)-1-benzyl 3-t-butyl hexahydropyridazine-1,3-dicarboxylate (Hassall et al. *J. Chem. Soc. Perkin* 1, pp. 1451-1454 (1979)) (925.3 mg, 2.89 mmol) and diisopropylethylamine (0.70 ml, 4.0 mmol) in a 1.93M toluene solution of phosgene (17.96 ml, 34.7 mmol) was stirred at room temperature for 45 min, then concentrated to leave a yellow solid. To this solid was added toluene (18 ml), hydrazide (259) (861.6 mg, 2.89 mmol) and diisopropylethylamine (0.70 ml, 4.0 mmol). The mixture was stirred at room temperature for 2.75 h, then concentrated. The resulting residue was taken up in EtOAc, washed twice with 1M HCl, brine, then dried (MgSO$_4$), filtered and concentrated to afford 2.15 g of crude material. Flash chromatography (40% EtOAc in hexane) afforded 1.65 g (89%) of the title compound as a white foam: mp 40° C.; $[α]_D^{24}$ -55.78° (c 0.40, $CH_2Cl_2$); IR (KBr) 3436, 2930, 1733, 1689, 1455, 1412' 1367, 1258, 1156, 697; $^1$H NMR (CDCl$_3$) δ 8.54-8.23 (0.5H, m), 7.97-7.09 (15.5H), 5.16-4.80 (4H, m), 4.66-4.32 (1H, m), 4.24-3.55 (3.3H, m), 3.50-3.26 (0.4H, m), 3.19-2.49 (2.3H, m), 2.11-1.43 (6H, m), 1.32-1.05 (7H, m); Anal. Calcd for $C_{35}H_{40}N_4O_8$·0.5$H_2O$: C, 64.31; H, 6.32; N, 8.57. Found: C, 64.18; H, 6.27; N, 8.56. MS (ES+) 662 (M+Na, 84%), 645 (M$^+$+1, 100), 384 (77).

(6S)-3-(N'benzoyl-N-(6-t-butoxycarbonylhexa-hydropyridazine-1-carbonyl)hydrazino)propanoic acid (261). A solution of 260 (1.59 g, 2.47 mmol) in MeOH (142 ml) was treated with 10% Palladium on carbon (230.0 mg) and stirred under an atmosphere of $H_2$ for 1.5 h. The mixture was filtered and the solvent evaporated to afford 1.04 g (100%) of a white foam. This was used in the next step without further purification: mp <40° C.; $[α]_D^{26}$ +1.6° (c 0.26, $CH_2Cl_2$); IR (KBr) 3422, 2977, 2986, 1728, 1677, 1486, 1445, 1396, 1369, 1309, 1228, 1155, 916, 716; $^1$H NMR (CDCl$_3$) δ 10.0-9.7 (1H, brm), 7.86 (2H, d, J=7.5), 7.62-7.38 (3H, m), 7.3-5.6 (2H, brm), 4.57 (1H, brd, J=4.0), 4.05-3.77 (2H, m), 3.00-2.82 (1H, m), 2.80-2.43 (3H, m), 2.20-2.03 (1H, m), 2.00-1.47 (1H, m), 1.62-1.14 (11H, m); $^{13}$C NMR (CDCl$_3$) δ 175.00, 171.17, 167.62, 160.68, 132.39, 131.77, 128.67, 127.38, 82.27, 54.38, 48.04, 46.35, 33.62, 28.02, 25.68, 21.61. MS (ES+) 443 (M+Na, 68%), 421 (M$^+$+1), 100), 365 (50), 131 (61).

(4S)t-Butyl 7-benzamido-6,10-dioxo-1,2,3,4,7,8,9,10-octahydro-6H-pyridazino[1,2-a][1,2,4]triazepine-4-carboxylate (262). To a solution of amino acid 261 (1.012 g, 2.41 mmol) in dry THF (26 ml) at 0° C. was added N-ethylmorpholine (597 µl, 4.69 mmol), followed by PCl$_5$ (651.3 mg, 3.12 mmol). The reaction was stirred at 0° C. for 2 h, then allowed to warm to rt and stirred for a further 15.5 h. The mixture was concentrated and the resulting residue taken up in EtOAc, washed twice with 1M HCl, sat. NaHCO$_3$, brine, then dried (MgSO$_4$), filtered and concentrated. Flash chromatography (20% EtOAc in $CH_2Cl_2$) gave 727.3 mg (75%) of the title compound as a white foam: $[α]_D^{26}$ +51.0° (c 0.20, $CH_2Cl_2$); IR (KBr) 3436, 2979, 1733, 1670, 1483, 1437, 1420, 1299, 1243, 1156; $^1$H NMR (CDCl$_3$) δ 8.70 (1H, s), 7.78 (2H, d, J=7.0), 7.57-7.32 (3H, m), 5.08 (1H, dd, J=2.5, 5.5), 4.59-4.43 (1H, m), 4.08-3.69 (3H, m), 3.07-2.84 (1H, m), 2.57-2.35 (1H, m), 2.34-2.14 (1H, m), 2.07-1.43 (3H, m), 1.48 (9H, s); $^{13}$C NMR (CDCl$_3$) δ 172.41, 169.04, 166.35, 158.35, 132.24, 132.03, 128.61, 127.31, 82.77, 55.41, 54.07, 41.57, 32.21, 28.04, 24.97, 20.37; Anal. Calcd for C$_{20}$H$_{26}$N$_4$O$_5$: C, 59.69; H, 6.51; N, 13.92. Found: C, 59.53; H, 6.53; N, 13.84. MS (ES+) 425 (M+Na, 71%), 403 (M$^+$+1, 100), 145 (41).

(4S)-7-Benzamido-6,10-dioxo-1,2,3,4,7,8,9,10-octahydro-6H-pyridazino[1,2-a][1,2,4]triazepine-4-carboxylic Acid (263). A solution of ester 262 (720.0 mg, 1.80 mmol) in a 1:1 mixture of CH$_2$Cl$_2$ and TFA (150 ml) was stirred for 1.3 h under a dry atmosphere. The solution was then reduced in vacuo, taken up in Et$_2$O and reduced again. This process was repeated six times to afford the crude product as an off-white solid. The product was purified by flash chromatography (5% MeOH in CH$_2$Cl$_2$) to afford 520.0 mg (83%) of the title compound as a white foam: $[α]_D^{25}$+59.5° (c 1.82, CH$_2$Cl$_2$); IR (KBr) 3435, 3266, 2956, 1732, 1664, 1524, 1486, 1440, 1302; $^1$H NMR (CDCl$_3$) δ 9.13 (1H, s), 7.77 (2H, d, J=7.5), 7.57-7.32 (3H, m), 5.27-5.16 (1H, m), 4.62-4.43 (1H, m), 4.09-2.70 (3H, m), 3.14-2.89 (1H, m), 2.59-2.43 (1H, m), 2.38-2.20 (1H, m), 2.14-1.89 (1H, m), 1.82-1.59 (2H, m); $^{13}$C NMR (CDCl$_3$) δ 173.65, 172.28, 166.44, 158.42, 132.44, 131.31, 128.61, 127.39, 54.83, 54.01, 42.11, 31.79, 24.42, 20.29; MS (ES−) 345 (M−H$^+$, 100%), 161 (45).

[2RS,3S(4S)]N-(2-Benzyloxy-5-oxotetrahydrofuran-3-yl)-6,10-dioxo-1,2,3,4,7,8,9,10-octahydro-6H-pyridazino[1,2-a][1,2,4]triazepine-4-carboxamide (264). To a solution of acid 263 (300.0 mg, 0.87 mmol) and (2RS,3S)-3-allyloxycarbonylamino-2-benzyloxy-5-oxotetrahydrofuran (Chapman, Bioorg. & Med. Chem. Lett. 2, pp. 615-18 (1992)) (277.6 mg, 0.95 mmol) in dry CH$_2$Cl$_2$ (2.5 ml) and dry DMF (2.5 ml) at rt was added bis(triphenylphosphine) palladium chloride (13.0 mg), followed by tri-n-butyltin hydride (466.0 µl, 1.73 mmol). The reaction was stirred for 5 min, then 1-hydroxybenzotriazole (234.1 mg, 1.73 mmol) was added and the mixture was cooled to 0° C. before addition of 1-(3-dimethylaminopropyl)-3-ethylcarbodiimide hydrochloride (204.5 mg, 1.04 mmol). The mixture was allowed to warm to rt and stirred for 16.5 h. The mixture was diluted with EtOAc, washed with 1M NaHSO$_4$ twice with sat. NaHCO$_3$, then H$_2$O and brine. The organic layer was dried (MgSO$_4$), filtered and concentrated. The residue was purified by flash chromatography (5% MeOH in CH$_2$Cl$_2$) to afford 358.3 mg (77%) of the title compound as a white solid: IR (KBr) 3435, 1791, 1665, 1526, 1421, 1285; $^1$H NMR (CDCl$_3$) δ 8.76 and 8.49 (1H, 2×s), 7.92-7.73 (2H, m), 7.62-7.24 (8.5H, m), 6.86 (0.5H, d, J=8.0), 5.53 and 5.33 (1H, d, J=5.5, s), 4.95-4.34 (5H, m), 4.04-3.54 (3H, m), 3.03-2.64 (2H, m), 2.49-2.14 (2H, m), 2.11-1.46 (4H, m); MS (ES+) 558 (M+Na, 100%), 536 (M$^+$+1, 78), 404 (58).

[3S(4S)]3-(7-Benzamido-6,10-dioxo-1,2,3,4,7,8,9,10-octahydro-6H-pyridazino[1,2-a][1,2,4]triazepine-4-carboxamido)-4-oxobutanoic acid (265). A mixture of 264 (350.0 mg, 0.65 mmol), 10% palladium on carbon (350 mg) and methanol (36 ml) was stirred under an atmosphere of H$_2$ for 6.5 h. The mixture was filtered and the solvent evaporated. Et$_2$O was added and the solvent removed again. This process was repeated four times to reveal 283 mg (97%) of the title compound, as a white crystalline solid: mp decarboxylates above 140° C.; $[α]_D^{26}$ +33.5 (c 0.18, MeOH), IR (KBr) 3428, 1663, 1528, 1487, 1437, 1288; $^1$H NMR (D$_6$-DMSO) δ 10.56 (1H, s), 8.71-8.57 (1H, m), 7.88-7.81 (2H, m), 7.65-7.46 (3H, m), 4.97-4.85 (1H, m), 4.38-4.0 (3H, m), 3.88-3.52 (3H, m), 2.91-2.71 (2H, m), 2.50-2.38 (1H, m), 2.35-2.21 (1H, m), 2.10-1.94 (1H, m), 1.93-1.49 (3H, m); $^{13}$C NMR (D$_6$-DMSO) δ 173.66, 172.49, 169.97, 169.89, 164.96, 157.62, 132.35, 131.85, 128.39, 127.32, 53.81, 52.69, 40.90, 33.17, 31.60, 24.40, 24.13, 19.24; MS (ES−).

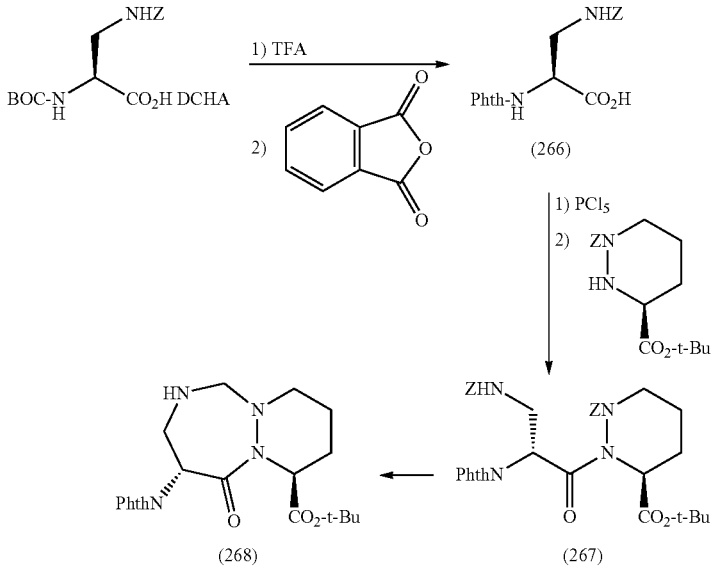

(2S)3-Benzyloxycarbonylamino-2-phthalimidopropionic acid (266). A solution of (2S)3-benzyloxycarbonylamino-2-tert-butoxycarbonylaminopropionic acid dicyclohexylamine salt (3 g, 5.8 mmol) in dichloromethane (200 ml) was washed four times with 1M HCl solution, dried (MgSO$_4$) and concentrated. The resulting oil was dissolved in dry dichloromethane (35 ml), cooled to 0° C. and treated with trifluoroacetic acid (35 ml). This solution was stirred at 0° C. for 1.5 h then evaporated to dryness. Dichloromethane (50 ml) was added to the residue then removed under vacuum. This process repeated six times to afford a white solid. The white solid was suspended in toluene (50 ml), treated with powdered phthalic anhydride (940 mg, 6.35 mmol) and refluxed for 18 h. The resulting solution was concentrated to afford an oil which was purified by flash chromatography (2-10% methanol/dichloromethane) to afford 266, 2.01 g (94%) as a white powder: IR (KBr) 3600-2500br, 1776, 1714, 1530, 1469, 1455, 1392, 1263, 1131, 722; $^1$H NMR (CDCl$_3$) δ 7.83 (2H, m), 7.72 (2H, m), 7.29 (5H, m), 5.41 (1H, m), 5.03 (2H, s), 3.90 (2H, m); MS (ES−), 367 (M−1).

[3S(2S)]t-Butyl 1-benzyloxycarbonyl-2-(3-benzyloxycarbonylamino-2-phthalimidopropionyl)pyridazine-3-carboxylate (267). A suspension of the acid 266 (1.32 g, 3.58 mmol) in dry ether (37 ml) was treated with phosphorus pentachloride (1.04 g, 5 mmol) and stirred at room temperature for 2 h. The solution was filtered to remove unreacted phosphorus pentachloride then evaporated to dryness.

The residue was treated with dry toluene (25 ml) then evaporated to dryness. This process was repeated several times. The resulting oil was dissolved in dry dichloromethane (25 ml), cooled to 0° C. and treated with a solution of (3S)t-butyl 1-benzyloxycarbonylpyridazine-3-carboxylate (1.15 g, 3.58 mmol) in dry dichloromethane (2 ml) followed by 5% aqueous sodium bicarbonate solution (25 ml). The mixture was stirred rapidly at room temperature for 20 h then diluted with ethyl acetate (100 ml) and acidified to pH2 with 1M HCl. The organic phase was washed twice with dilute HCl solution then brine, dried (MgSO$_4$) and concentrated. The resulting oil was purified by flash chromatography (2-20% ethyl acetate/dichloromethane then 10-20% methanol/dichloromethane) to afford (267), 1.25 g (52%) as a white powder: IR (KBr) 3367, 2955, 1722, 1517, 1455, 1387, 1369, 1251, 1153, 721; $^1$HÊNMR (CDCl$_3$) δ 7.81 (2H, m), 7.74 (2H, m), 7.63 (1H, brs), 7.31 (10H, m), 5.46-4.76 (5H, m), 4.07-3.54 (4H, m), 2.4 (1H, m), 2.0-1.6 (3H, m), 1.40 (9H, s); MS (ES$^+$), 671 (M+1), 693 (M+Na).

(1S,9S)t-Butyl 1,2,3,4,7,8,9,10-octahydro-10-oxo-9-phthalimido-6H-pyridazino[1,2-a][1,2,4]triazepine-1-carboxylate (268). A solution of ester 267 (50 mg, 0.074 mmol) in methanol (15 ml) was treated with 10% palladium on carbon (50 mg) and hydrogenated at room temperature and atmospheric pressure for 24 h. The mixture was evacuated thoroughly to remove hydrogen then treated with 37% aqueous formaldehyde (18 mg, 0.22 mmol) and stirred under nitrogen for 2 h. The mixture was filtered, evaporated to dryness and the product purified by flash chromatography (4-100% ethyl acetate/dichloromethane) to afford 268 14.5 mg (48%) as an oil: $^1$H NMR (CDCl$_3$) δ 7.85 (2H, m), 7.71 (2H, m), 5.78 (1H, dd, J=10, 5), 4.99 (1H, dd, J=6.1, 1.5), 4.07 (1H, d, J=10.6), 3.49 (1H, dd, J=14, 5), 3.39 (1H, d, J=10.3), 3.24 (1H, dd, J=14, 10.2), 3.17 (2H, m), 2.39 (1H, m), 1.84-1.46 (3H), 1.51 (9H, s); MS (ES$^+$), 415 (M+1), 437 (M+Na).

Compounds 280-283 were prepared from 212b by a method similar to the method used to prepare 226e. Compounds 284-287 were prepared by a method similar to the method used to prepare 217e.

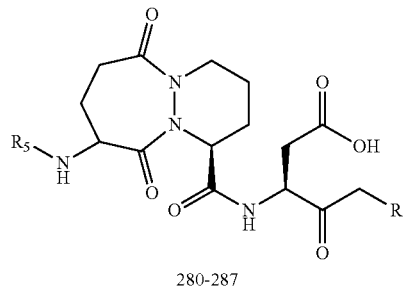

280-287

| compound | R$_5$ | R |
|---|---|---|
| 280 |  | 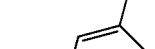 |
| 281 |  |  |
| 282 |  |  |
| 283 |  |  |
| 284 |  |  |
| 285 |  | 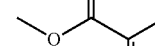 |
| 286 |  | 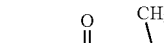 |

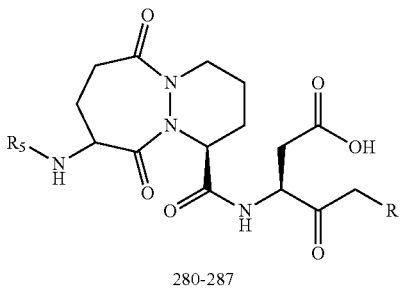

280-287

| compound | R5 | R |
|---|---|---|
| 287 | H3C-O-C(O)- | methyl 3-chlorothiophene-2-carboxylate group |

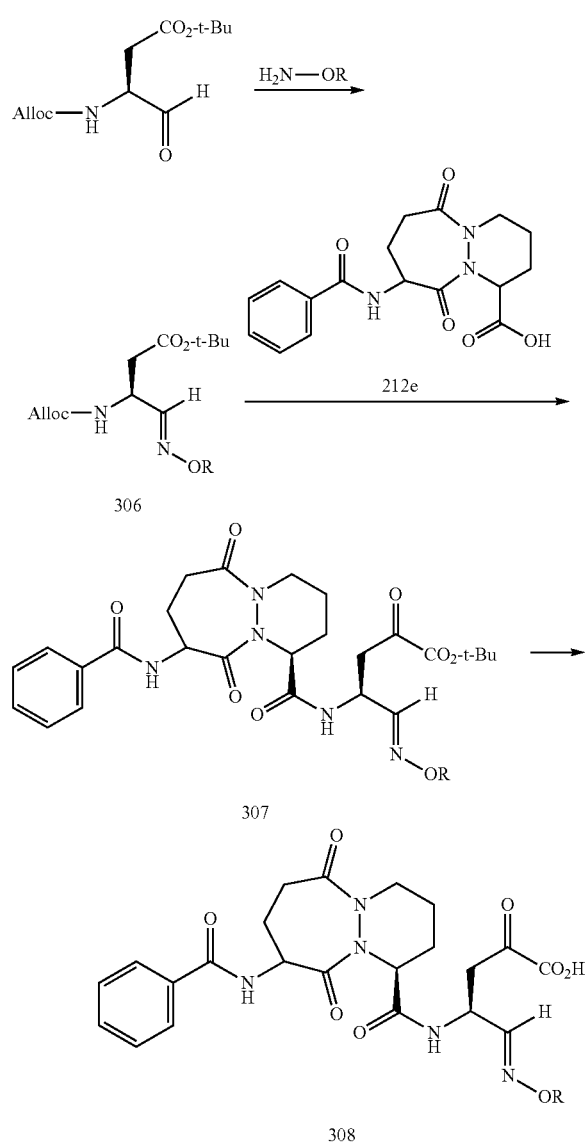

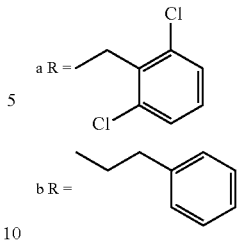

a R = 2,6-dichlorophenyl
b R = 2-phenylethyl (3S)3-Allyloxycarbonylamino-4-oxobutyric acid tert-butyl ester O-(2,6-dichlorophenylmethyl)oxime (306a) was prepared by a similar procedure as 208a except that 2,6-dichlorophenylmethoxyamine (prepared by a similar method as 306b) was used instead of semicarbazide to give 870 mg (quant.) as a clear oil.

(3S)3-Allyloxycarbonylamino-4-oxobutyric acid tert-butyl ester O-(2-(phenyl)ethyl)oxime (306b) was prepared by a similar procedure as 208a except that 2-(phenyl)ethoxyamine (U.S. Pat. No. 5,346,911) was used instead of semicarbazide to give 395 mg (quant.) as a clear oil.

[3S(1S,9S)3-(9-Benzoylamino-6,10-dioxo-1,2,3,4,7,8,9,10-octahydro-6H-pyridazino[1,2-a][1,2]diazapine-1-carboxamido)-amino]-4-oxobutanoicacid t-butyl ester, O-(2,6-dichlorophenylmethyl)oxime (307a) was prepared by a procedure similar to 233e except 306a was used instead of 207a to give 23 mg (23%) of 307a as a white solid.

[3S(1S,9S)3-(9-Benzoylamino-6,10-dioxo-1,2,3,4,7,8,9,10-octahydro-6H-pyridazino[1,2-a][1,2]diazapine-1-carboxamido)-amino]-4-oxobutanoic acid t-butyl ester, O-(2-(phenyl)ethyl)oxime (307b) was prepared by a procedure similar to 233e except 306b was used instead of 207a to give 43 mg (48%) of 307b as a white solid.

[3S(1S,9S)3-(9-Benzoylamino-6,10-dioxo-1,2,3,4,7,8,9,10-octahydro-6H-pyridazino[1,2-a][1,2]diazapine-1-carboxamido)-amino]-4-oxobutanoic acid, O-(2,6-dichlorophenylmethyl)oxime (308a) was prepared by from 307a a procedure similar to the preparation of 235e from 234e to give 15.2 mg (74%) as white solid: $^1$H NMR (CD$_3$OD) δ 0.9 (m), 1.3 (s), 1.7 (m), 1.8 (m), 2.0 (m), 2.1-2.2 (m), 2.3 (dd), 2.4-2.5 (m), 2.6 (m), 2.7-2.8 (m), 3.1 (m), 3.3 (m), 3.4-3.5 (m), 4.5 (m), 4.9 (m), 5.1 (m), 5.3 (d), 5.4 (s), 6.8 (d), 7.2-7.5 (m), 7.8 (dd), 8.4 (dd).

[3S(1S,9S)3-(9-Benzoylamino-6,10-dioxo-1,2,3,4,7,8,9,10-octahydro-6H-pyridazino[1,2-a][1,2]diazapine-1-carboxamido)-amino]-4-oxobutanoic acid, O-(2-(phenyl)ethyl)oxime (308b) was prepared by from 307b a procedure similar to the preparation of 235e from 234e to give 25.2 mg (68%) as white solid: $^1$H NMR (CD$_3$OD) δ 1.2 (m), 1.6-1.7 (m), 2.0-2.1 (m), 2.2 (m), 2.3 (m), 2.5 (m), 2.6-2.7 (dd), 2.9 (t), 3.0 (t), 3.1 (m), 3.3-3.5 (m), 4.2 (t), 4.25 (m), 4.5 (m), 5.2 (t), 5.3 (t), 6.7 (d), 7.1-7.2 (m), 7.35 (dd), 70.4 (m), 7.5 (m), 7.8 (dd), 8.3 (dd).

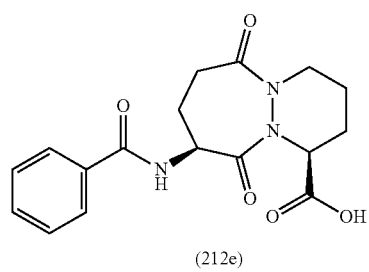

(212e)

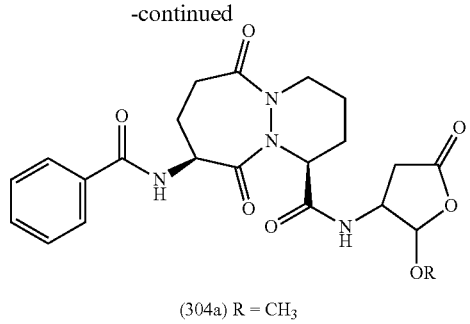

(304a) R = CH₃

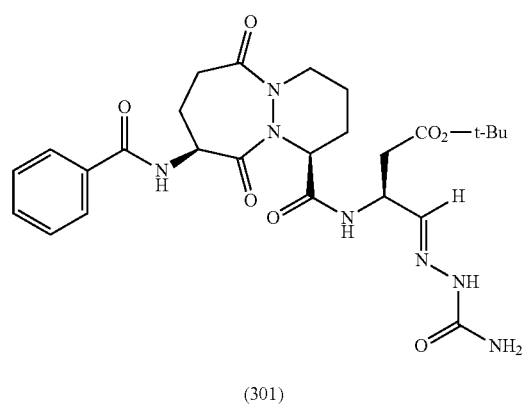

(301)

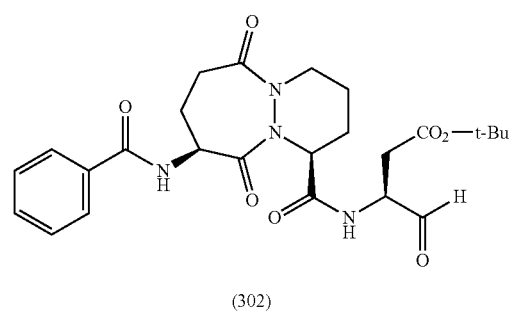

(302)

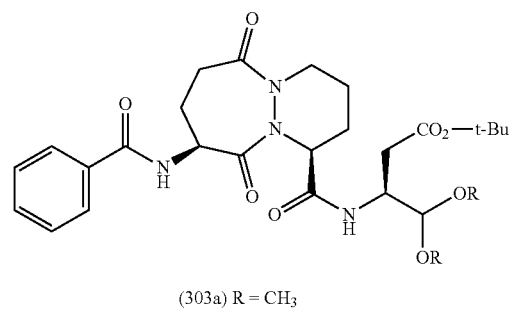

(303a) R = CH₃

[3S(1S,9S)3-(9-Benzoylamino-6,10-dioxo-1,2,3,4,7,8,9, 10-octahydro-6H-pyriazino-[1,2-a][1,2]diazapine-1-carboxamido)-amino]-4-oxobutanoic acid tert-butyl ester (302).

Step A: 301 was prepared by procedure similar to 605a (Step A), except 212e was used instead of 603a to give 540 mg (34%) to give a white solid.

Step B: 302. A solution of 301 (50.7 mg; 0.091 mmol) in 2.8 ml of MeOH/HOAc/37% aq. formaldehyde (5:1:1) was stirred at rt for 5.5 h. and the reaction was concentrated to 0.7 ml in vacuo. The residue was dissolved in 3 ml of CH₃CN and concentrated to 0.7 ml (3×), dissolved in toluene and concentrated to 0.7 ml in vacuo (2×), and concentrated to dryness. Chromatography (flash, SiO₂, 5% isopropanol/CH₂Cl₂) gave 302 (45.5 mg, 78%) as a white solid: $^1$H NMR (DMSO-d₅) δ 1.0-1.15 (m, 2H), 1.4 (s, 9H), 1.65 (m, 2H), 1.9-2.1 (m, 2H), 2.15-2.4 (m, 3H), 2.55 (m, 1H), 2.7-3.0 (m, 2H), 4.3-4.6 (m, 2H), 4.9 (m, 1H), 5.2 (m, 1H), 7.4-7.6 (m, 2H), 7.8-8.0 (m, 2H), 8.6 (m, 1H), 8.8 (m, 1H), 9.4 (s, 1H).

[1S,9S(2RS,3S)]9-Benzoylamino-6,10-dioxo-1,2,3,4,7,8, 9,10-octahydro-N-(2-methoxy-5-oxo-tetrahydro-furan-3-yl)-6H-pyridazino[1,2-a][1,2]diazapine-1-carboxamide. (304a).

Step A: A solution of 302 (90 mg; 0.18 mmol) in 10 ml of MeOH was treated with trimethylorthoformate (1 ml) and p-toluene sulfonic acid hydrate (5 mg; 0.026 mmol) and the reaction was stirred for 20 h. The reaction was treated with 3 ml of aq. sat. NaHCO₃ and concentrated in vacuo. The residue was taken up in EtOAc and washed with dilute aq. NaHCO₃, dried over MgSO₄ and concentrated in vacuo to give 80 mg of 303a.

Step B: 303a was dissolved in 2 ml of TFA and stirred at rt for 15 min. The reaction was dissolved in CH₂Cl₂ and concentrated in vacuo (3×). Chromatography (flash, SiO₂, 1% to 3% MeOH/CH₂Cl₂ gave 43 mg (64%) of 304a as a white solid: $^1$H NMR (CDCl₃) δ 1.55-1.8 (m, 2H), 1.9-2.15 (m, 4H), 2.25-2.5 (m, 2H), 2.7-3.3 (m, 4H), 3.45, 3.6 (s, s, 3H), 4.4, 4.75 (2m, 1H), 4.6 (m, 1H), 4.95, 5.4 (t, d, 1H), 5.1-5.2 (m, 1H), 6.45, 7.05 (2d, 1H), 6.95 (m, 1H), 7.45 (m, 2H), 7.5 (m, 1H), 7.85 (m, 2H).

EXAMPLE 11
Compounds 214e, 404-413, 415-445, 446-468, 470-491, and 493-499 were synthesized as described in Example 11 and Table 7.
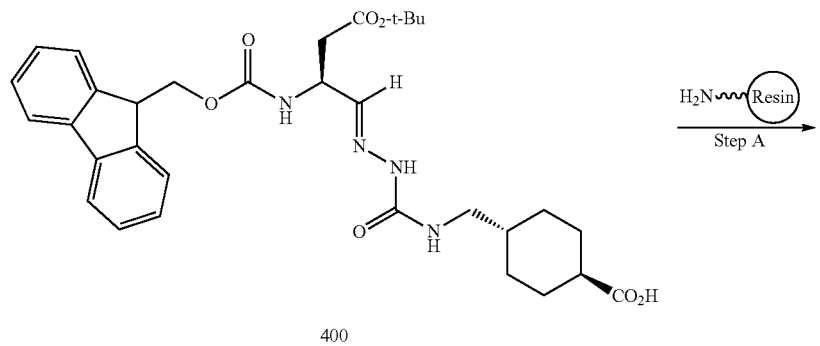
400
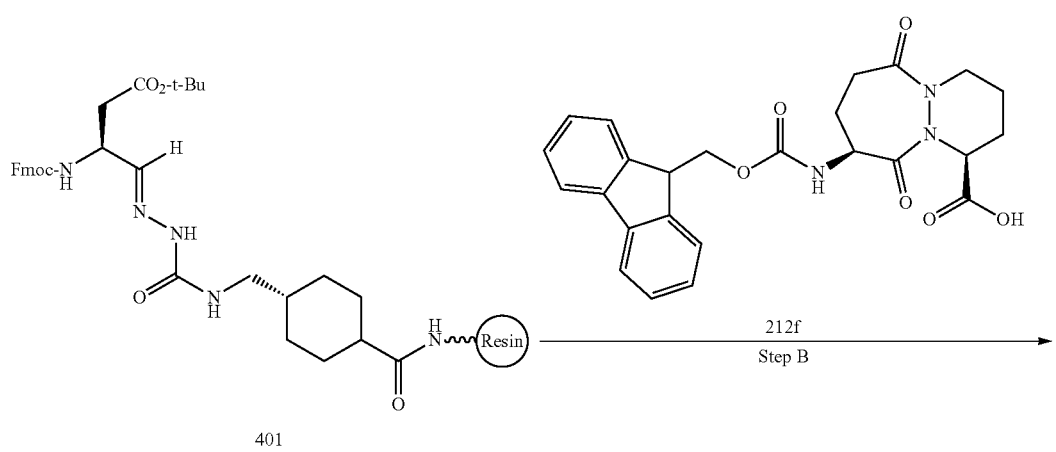
401
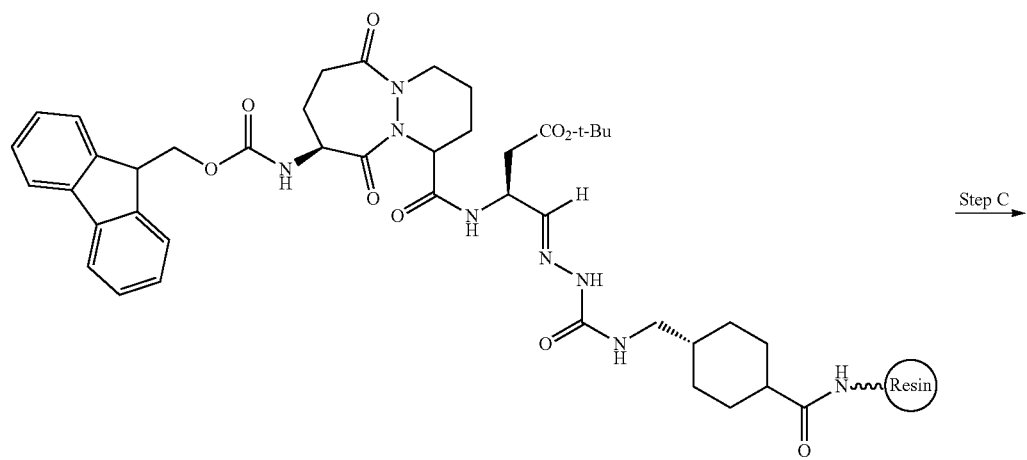
402

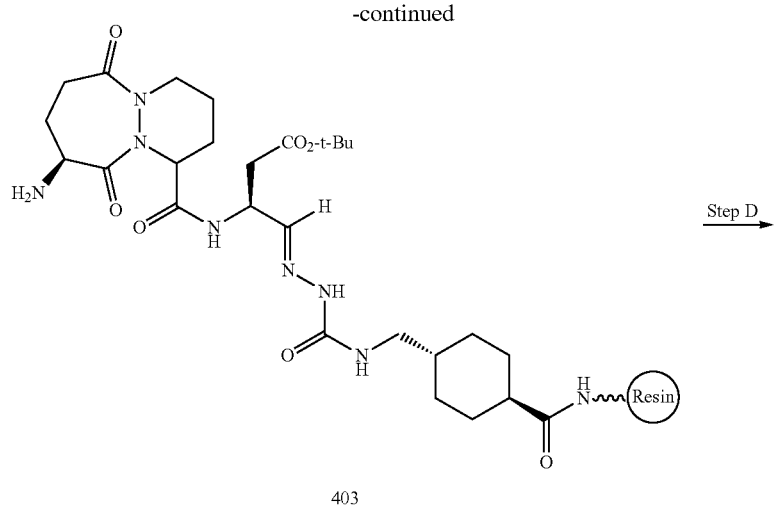

403

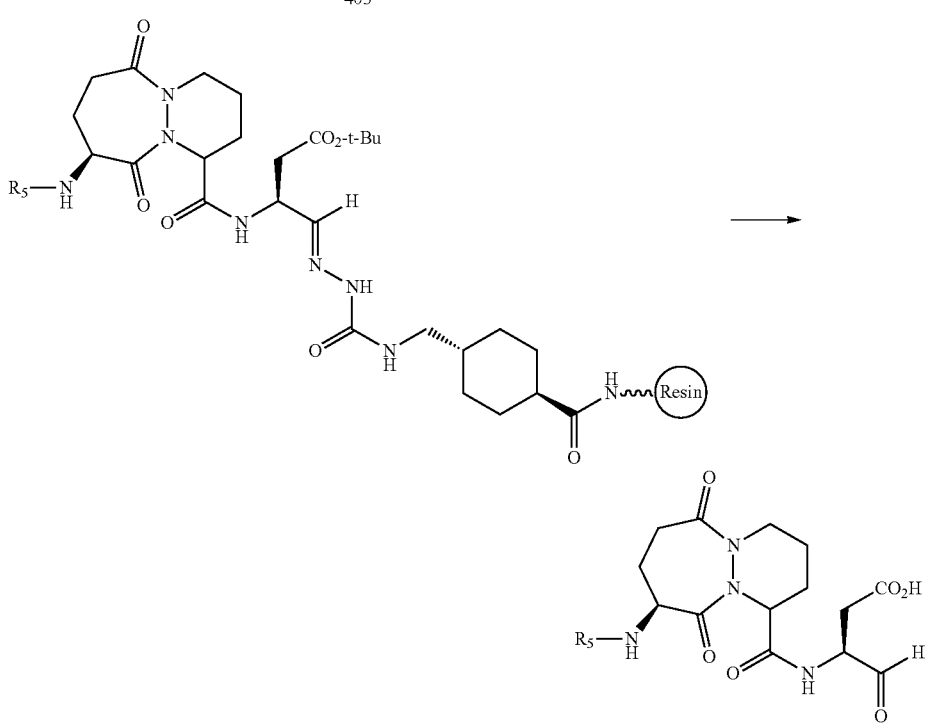

214e, 404-499

Step A. Synthesis of 401. TentaGel S® NH₂ resin (0.16 mmol/g, 10.0 g) was placed in a sintered glass funnel and washed with DMF (3×50 mL), 10% (v/v) DIEA in DMF (2×50 mL) and finally with DMF (4×50 mL). Sufficient DMF was added to the resin to obtain a slurry followed by 400 (1.42 g, 2.4 mmol, prepared from (3S)-3-(fluorenylmethyloxycarbonyl)-4-oxobutryic acid t-butyl ester according to A. M. Murphy et. al. *J. Am. Chem. Soc.*, 114, 3156-3157 (1992)), 1-hydroxybenzotriazole hydrate (HOBT.H₂O; 0.367 g, 2.4 mmol), O-benzotriazol-1-yl-N,N,N,N'-tetramethyluronium hexafluorophosphate (HBTU; 0.91 g, 2.4 mmol), and DIEA (0.55 mL, 3.2 mmol). The reaction mixture was agitated overnight at rt using a wrist arm shaker. The resin was isolated on a sintered glass funnel by suction filtration and washed with DMF (3×50 mL). Unreacted amine groups were then capped by reacting the resin with 20% (v/v) Ac₂O/DMF (2×25 mL) directly in the funnel (10 min/wash). The resin was washed with DMF (3×50 mL) and CH₂Cl₂ (3×50 mL) prior to drying overnight in vacuo to yield 401 (11.0 g, quantitative yield).

Step B. Synthesis of 402. Resin 401 (6.0 g, 0.16 mmol/g, 0.96 mmol) was swelled in a sintered glass funnel by washing with DMF (3×25 mL). The Fmoc protecting group was then cleaved with 25% (v/v) piperidine/DMF (25 mL) for 10 min (intermittent stirring) and then for 20 min with fresh piperidine reagent (25 ml). The resin was then washed with DMF (3×25 ml), followed by N-methypyrrolidone (2×25 mL).

After transferring the resin to a 100 mL flask, N-methypyrrolidone was added to obtain a slurry followed by 212f (0.725 g, 1.57 mmol), HOBT.H₂O (0.25 g, 1.6 mmol), HBTU (0.61 g, 1.6 mmol) and DIEA (0.84 mL, 4.8 mmol). The reaction mixture was agitated overnight at rt using a wrist arm shaker.

The resin work-up and capping with 20% (v/v) Ac$_2$O in DMF were performed as described for 401 to yield 402 (6.21 g, quantitative yield).

Step C. Synthesis of 403. This compound was prepared from resin 402 (0.24 g, 0.038 mmol) using an Advanced ChemTech 396 Multiple Peptide synthesizer. The automated cycles consisted of a resin wash with DMF (3×1 mL), deprotection with 25% (v/v) piperidine in DMF (1 mL) for 3 min followed by fresh reagent (1 mL) for 10 min to yield resin 403. The resin was washed with DMF (3×1 mL) and N-methypyrrolidone (3×1 mL).

Step D. Method 1. [3S(1S,9S)]-3-(6,10-Dioxo-1,2,3,4,7,8,9,10-octahydro-9-(thiophene-3-carbonylamino)-6H-pyridazine[1,2-a][1,2]diazepine-1-carboxamido)-4-oxobutanoic acid (409). Resin 403 was acylated with a solution of 0.4M thiophene-3-carboxylic acid and 0.4M HOBT in N-methypyrrolidone (1 mL), a solution of 0.4M HBTU in N-methylpyrrolidone (0.5 mL) and a solution of 1.6M DIEA in N-methypyrrolidone (0.35 mL) and the reaction was shaken for 2 hr at rt. The acylation step was repeated. Finally, the resin was washed with DMF (3×1 mL), CH$_2$Cl$_2$ (3×1 mL) and dried in vacuo. The aldehyde was cleaved from the resin and globally deprotected by treatment with 95% TFA/5% H$_2$O (v/v, 1.5 mL) for 30 min at rt. After washing the resin with cleavage reagent (1 mL), the combined filtrates were added to cold 1:1 Et$_2$O:pentane (12 mL) and the resulting precipitate was isolated by centrifugation and decantation. The resulting pellet was dissolved in 10% CH$_3$CN/90% H$_2$O/0.1% TFA (15 mL) and lyophilized to obtain crude 409 as a white powder. The compound was purified by semi-prep RP-HPLC with a Rainin Microsorb™ C18 column (5μ, 21.4×250 mm) eluting with a linear CH$_3$CN gradient (5%-45%) containing 0.1% TFA (v/v) over 45 min at 12 mL/min. Fractions containing the desired product were pooled and lyophilized to provide 409 (10.8 mg, 63%).

Step D. Method 1A. Synthesis of 418. Following a similar procedure as method 1, resin 403 was acylated with 4-(1-fluorenylmethoxycarbonylamino)benzoic acid and repeated. The Fmoc group was removed as described in Step C and the free amine was acetylated with 20% (v/v) Ac$_2$O in DMF (1 mL) and 1.6M DIEA in N-methylpyrrolidone (0.35 mL) for 2 hr at rt. The acetylation step was repeated. Cleavage of the aldehyde from the resin gave 418 (3.2 mg).

Step D. Method 1B. Synthesis of 447. Following a similar procedure as method 1A, resin 403 was acylated with 0.4M 4-(1-fluorenylmethoxycarbonylamino)benzoic acid. The acylation step was repeated once. The Fmoc group was removed as before and the free amine was reacted with 1M methanesulfonyl chloride in CH$_2$Cl$_2$ (0.5 mL) and 1M pyridine in CH$_2$Cl$_2$ (0.60 mL) for 4 hr at rt. Cleavage of the aldehyde from the resin gave 447 (10.0 mg).

Step D. Method 2. Synthesis of 214e. Following a similar procedure as method 1, resin 403 was acylated with 0.5M benzoyl chloride in N-methylpyrrolidone (1 mL) and 1.6M DIEA in N-methylpyrrolidone (0.35 mL) for 2 hr at rt. The acylation step was repeated. Cleavage of the aldehyde from the resin gave 214e (5.1 mg, 30%).

Step D. Method 3. Synthesis of 427. Following a similar procedure as method 1, resin 403 was reacted with 1.0M benzenesulfonyl chloride in CH$_2$Cl$_2$ (0.5 mL) and 1M pyridine in CH$_2$Cl$_2$ (0.60 mL) for 4 hr at rt. The reaction was repeated. Cleavage of the aldehyde from the resin gave 427 (7.2 mg, 40%).

Step D. Method 4. Synthesis of 420. Following a similar procedure as method 1, resin 403 was reacted with 0.5M methylisocyanate in N-methylpyrrolidone (1 mL) and 1.6M DIEA in N-methylpyrrolidone (0.35 mL) for 2 hr at rt. The reaction was repeated. Cleavage of the aldehyde from the resin gave 420 (8.3 mg, 55%).

Step D. Method 5. Synthesis of 445. Following a similar procedure at method 1, resin 403 was acylated with 0.27M imidazole-2-carboxylic acid (1 mL) in 2:1 DMF:H$_2$O (with 1 eq. DIEA) and 1M 1-(3-dimethylaminopropyl)-3-ethylcarbodiimide hydrochloride (EDC) in 2:1 N-methylpyrrolidone/H$_2$O (0.35 mL) for 3 hr at rt. Cleavage of the aldehyde from the resin gave 445 (9.5 mg).

Analytical HPLC Methods:

(1) Waters DeltaPak C18, 300 Å (5μ, 3.9×150 mm). Linear CH$_3$CN gradient (5%-45%) containing 0.1% TFA (v/v) over 14 min at 1 mL/min.

(2) Waters DeltaPak C18, 300 Å (5μ, 3.9×150 mm). Linear CH$_3$CN gradient (0%-25%) containing 0.1% TFA (v/v) over 14 min at 1 mL/min.

(3) Waters DeltaPak C18, 300 A (5μ, 3.9×150 mm). Isocratic elution with 0.1% TFA/water (v/v) at 1 mL/min.

(4) Waters DeltaPak C18, 300 A (5μ, 3.9×150 mm). Linear CH$_3$CN gradient (0%-30%) containing 0.1% TFA (v/v) over 14 min at 1 mL/min.

(5) Waters DeltaPak C18, 300 Å (5μ, 3.9×150 mm). Linear CH$_3$CN gradient (0%-35%) containing 0.1% TFA (v/v) over 14 min at 1 mL/min.

TABLE 7

| Cmpd. | Structure | MF | MW | HPLC RT min | MS (M+H)+ | Syn. Method |
|---|---|---|---|---|---|---|
| 214e | 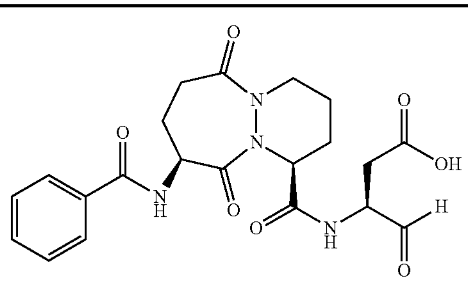 | C21H24N4O7 | 444.45 | 6.67 (2) 98% | 445 | 2 |

TABLE 7-continued

| Cmpd. | Structure | MF | MW | HPLC RT min | MS (M+H)+ | Syn. Method |
|---|---|---|---|---|---|---|
| 404 | 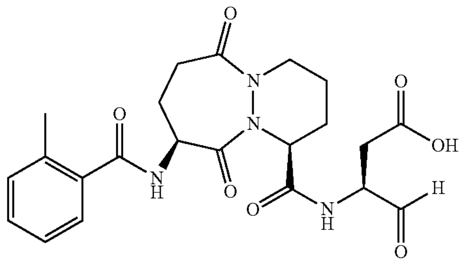 | C22H26N4O7 | 458.48 | 6.66 (2) 97% | 459 | 2 |
| 405 | 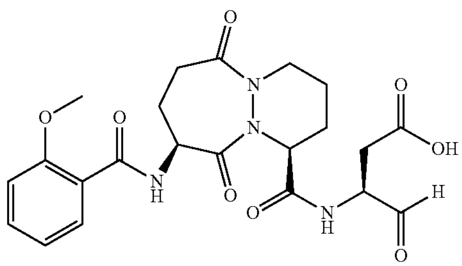 | C22H26N4O8 | 474.47 | 8.2 (1) 98% | 475 | 2 |
| 406 | 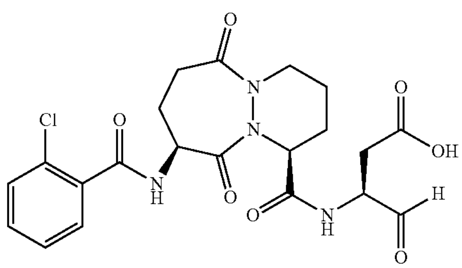 | C21H23ClN4O7 | 478.89 | 6.33 (1) 98% | 479 | 2 |
| 407 | 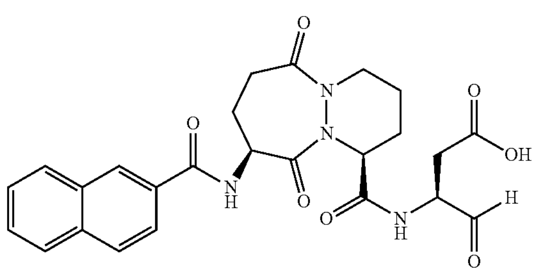 | C25H26N4O7 | 494.51 | 9.90 (1) 98% | 495 | 2 |
| 408 | 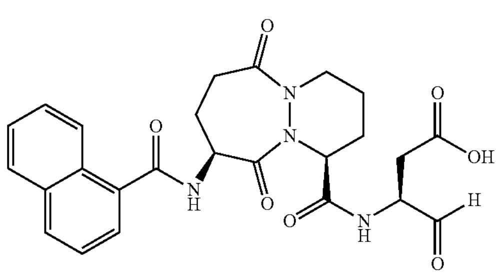 | C25H26N4O7 | 494.51 | 9.0 (1) 98% | 495 | 2 |

TABLE 7-continued

| Cmpd. | Structure | MF | MW | HPLC RT min | MS (M + H)+ | Syn. Method |
|---|---|---|---|---|---|---|
| 409 | 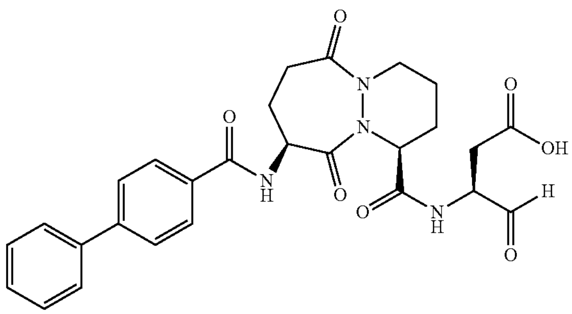 | C27H28N4O7 | 520.55 | 11.14 (1) 98% | 521 | 2 |
| 410 | 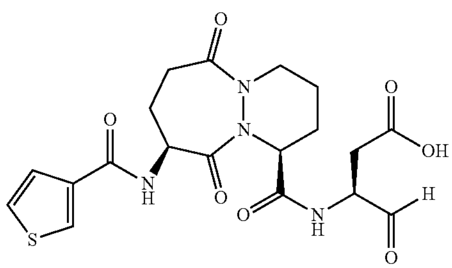 | C19H22N4O7S | 450.47 | 4.87 (1) 98% | 451 | 1 |
| 411 | 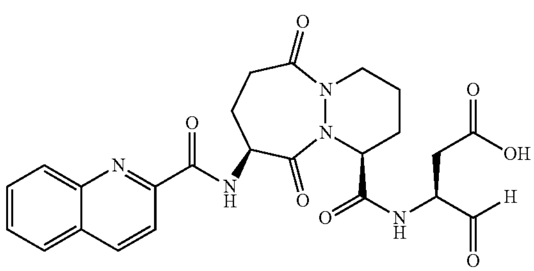 | C24H25N5O7 | 495.50 | 10.7 (1) 98% | 496 | 1 |
| 412 | 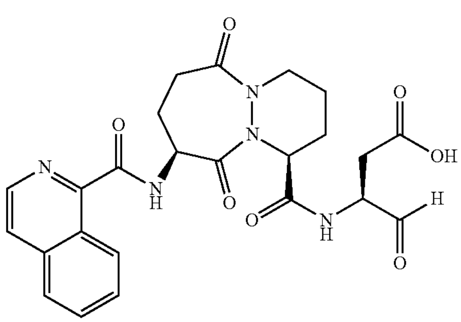 | C24H25N5O7 | 495.50 | 8.57 (1) 98% | 496 | 1 |
| 413 | 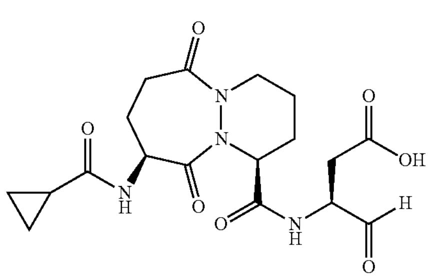 | C18H24N4O7 | 408.41 | 7.21 (2) 98% | 409 | 1 |

TABLE 7-continued

| Cmpd. | Structure | MF | MW | HPLC RT min | MS (M + H)+ | Syn. Method |
|---|---|---|---|---|---|---|
| 415 | 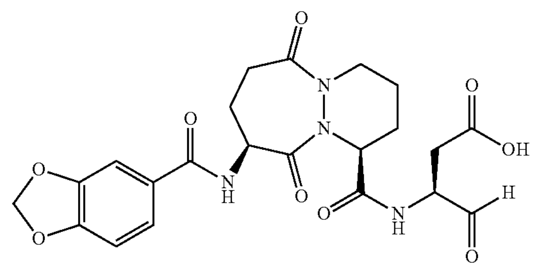 | C22H24N4O9 | 488.46 | 7.58 (1) 98% | 489 | 1 |
| 416 | 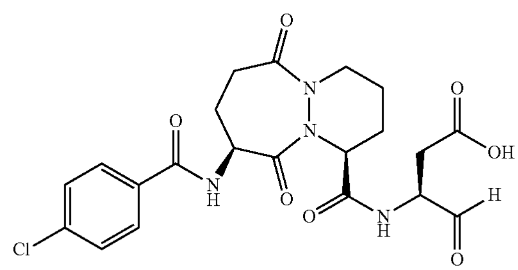 | C21H23ClN4O7 | 478.89 | 9.66 (1) 98% | 479 | 1 |
| 417 | 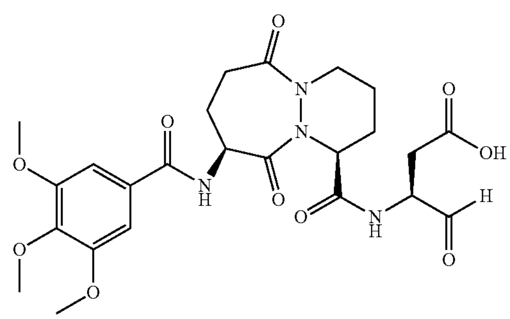 | C24H30N4O10 | 534.53 | 8.12 (1) 535 | 535 | 1 |
| 418 | 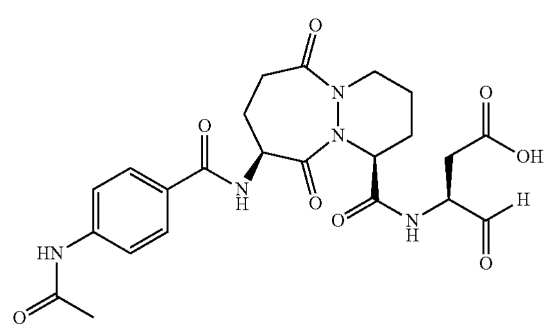 | C23H27N5O8 | 501.50 | 5.93 (1) 98% | 502 | 1A |
| 419 | 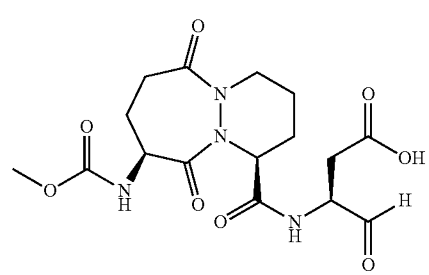 | C16H22N4O8 | 398.38 | 6.84 (2) 98% | 399 | 2 |

TABLE 7-continued

| Cmpd. | Structure | MF | MW | HPLC RT min | MS (M + H)+ | Syn. Method |
|---|---|---|---|---|---|---|
| 420 | 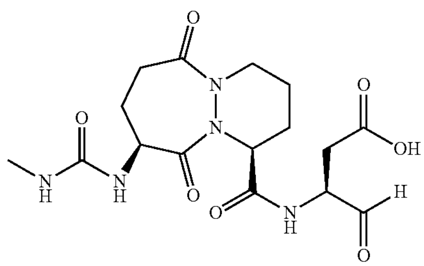 | C16H23N5O7 | 397.39 | 5.25 (2) 98% | 398 | 4 |
| 421 | 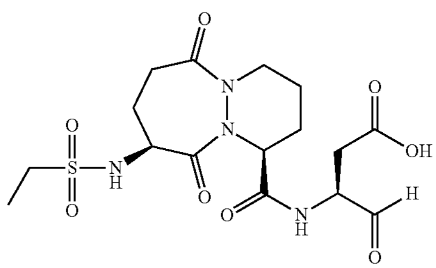 | C16H24N4O8S | 432.46 | 7.13 (2) 98% | 433 | 3 |
| 422 | 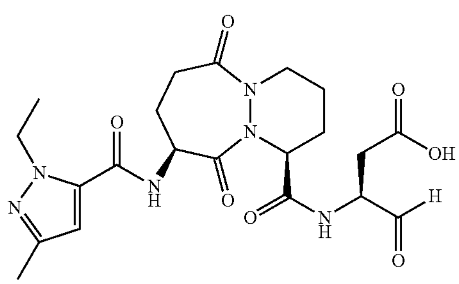 | C21H28N6O7 | 476.49 | 6.89 (1) 98% | 477 | 1 |
| 423 | 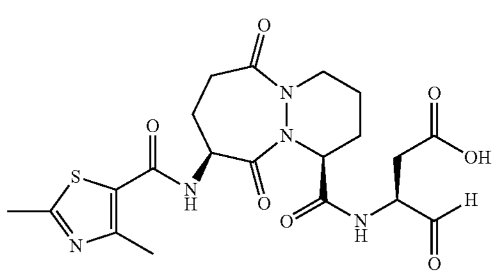 | C20H25N5O7S | 479.52 | 5.62 (1) 98% | 480 | 1 |
| 424 | 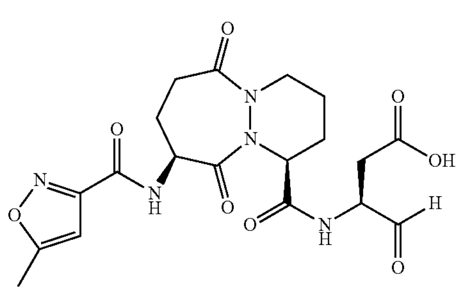 | C19H23N5O8 | 449.42 | 6.28 (1) 450 | 450 | 1 |

TABLE 7-continued

| Cmpd. | Structure | MF | MW | HPLC RT min | MS (M + H)+ | Syn. Method |
|---|---|---|---|---|---|---|
| 425 | 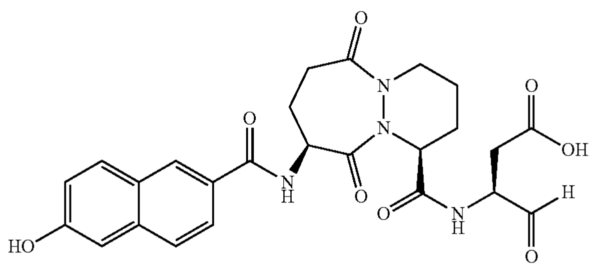 | C25H26N4O8 | 510.51 | 8.25 (1) 98% | 511 | 1 |
| 426 | 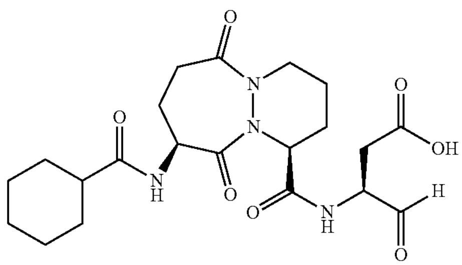 | C21H30N4O7 | 450.50 | 8.0 (1) 98% | 451 | 2 |
| 427 | 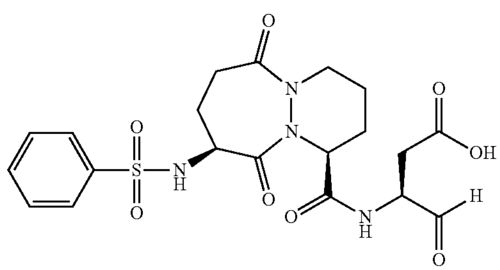 | C20H24N4O8S | 480.50 | 7.87 (1) 98% | 481 | 3 |
| 428 | 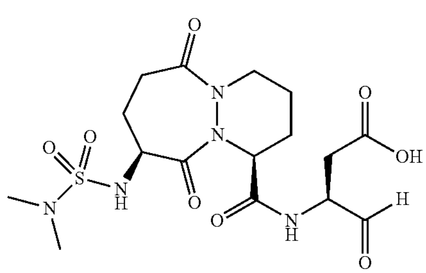 | C16H25N5O8S | 447.47 | 5.13 (1) 98% | 448 | 3 |
| 429 | 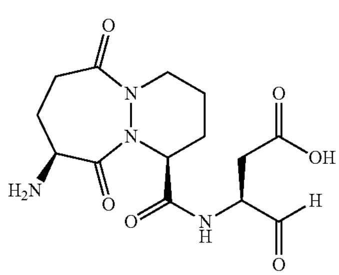 | C14H20N4O6 | 340.34 | 3.19 (3) 98% | 341 | |

TABLE 7-continued

| Cmpd. | Structure | MF | MW | HPLC RT min | MS (M + H)+ | Syn. Method |
|---|---|---|---|---|---|---|
| 430 | 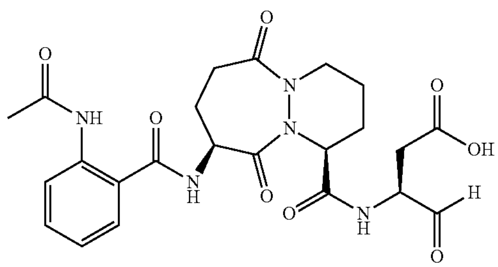 | C23H27N5O8 | 501.50 | 5.53 (1) 98% | 502 | 1A |
| 431 | 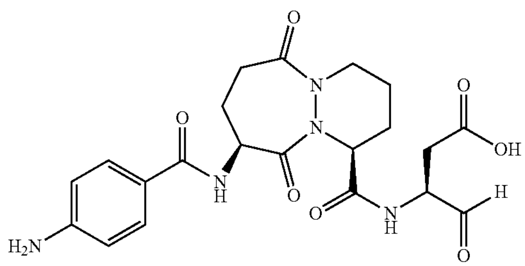 | C21H25N5O7 | 459.46 | 6.66 (2) 98% | 460 | 1 |
| 432 | 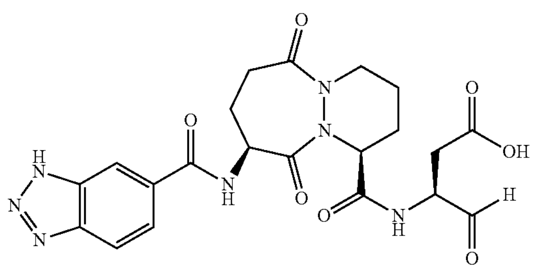 | C21H23N7O7 | 485.46 | 5.59 (1) 98% | 486 | 1 |
| 433 | 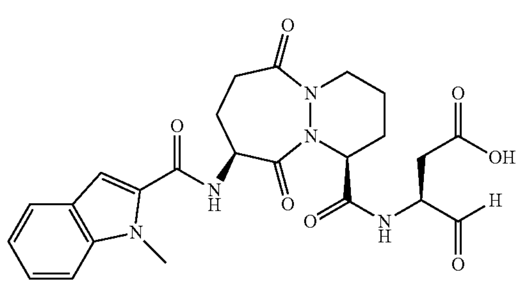 | C24H27N5O7 | 497.51 | 11.07 (1) 97% | 498 | 1 |
| 434 | 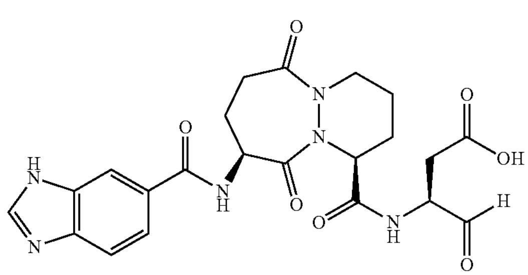 | C22H24N6O7 | 484.47 | 4.43 (1) 98% | 485 | 1 |

TABLE 7-continued

| Cmpd. | Structure | MF | MW | HPLC RT min | MS (M + H)+ | Syn. Method |
|---|---|---|---|---|---|---|
| 435 | 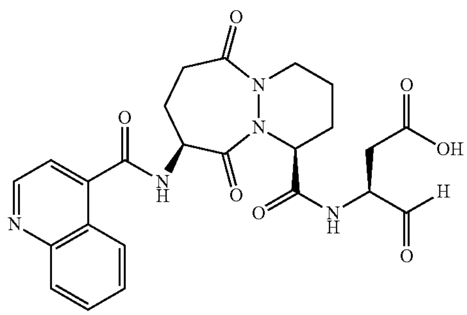 | C24H25N5O7 | 495.50 | 5.10 (1) 98% | 496 | 1 |
| 436 | 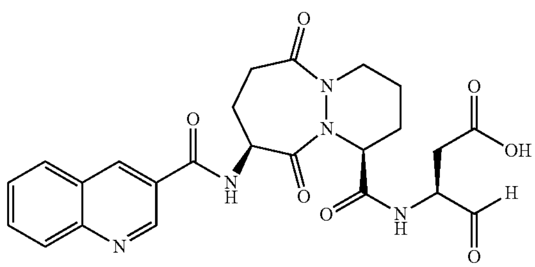 | C24H25N5O7 | 495.50 | 8.20 (4) 98% | 496 | 1 |
| 437 | 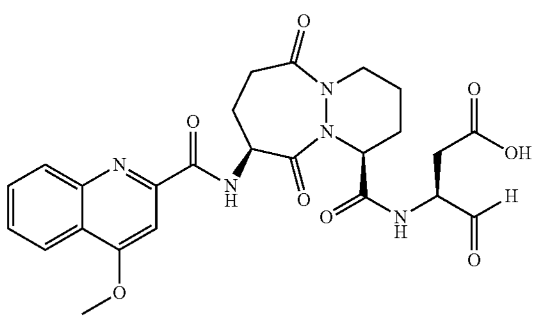 | C25H27N5O8 | 525.52 | 12.78 (5) 98% | 526 | 1 |
| 438 | 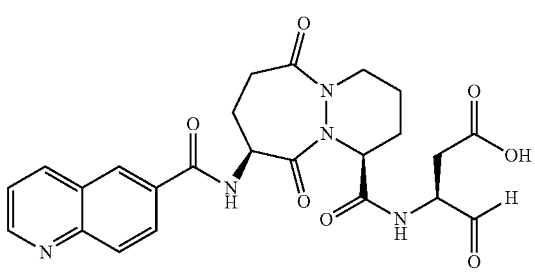 | C24H25N5O7 | 495.50 | 4.85 (1) 98% | 496 | 1 |
| 439 | 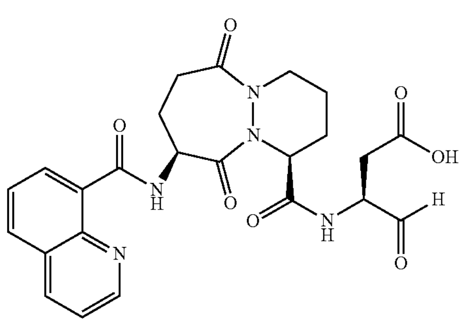 | C24H25N5O7 | 495.50 | 8.70 (5) 98% | 496 | 1 |

TABLE 7-continued

| Cmpd. | Structure | MF | MW | HPLC RT min | MS (M + H)+ | Syn. Method |
|---|---|---|---|---|---|---|
| 440 | 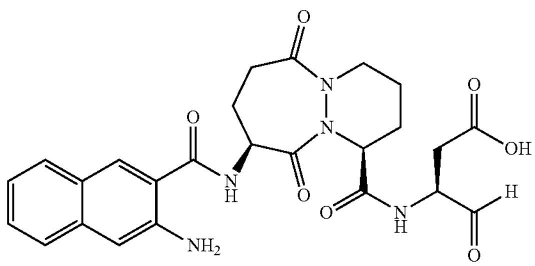 | C25H27N5O7 | 509.52 | 9.96 (5) 98% | 510 | 1 |
| 441 | 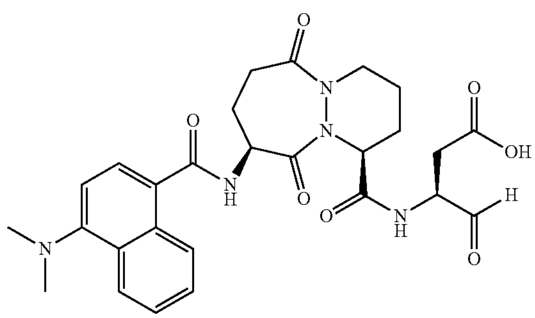 | C27H31N5O7 | 537.58 | 6.15 (1) 98% | 538 | 1 |
| 442 | 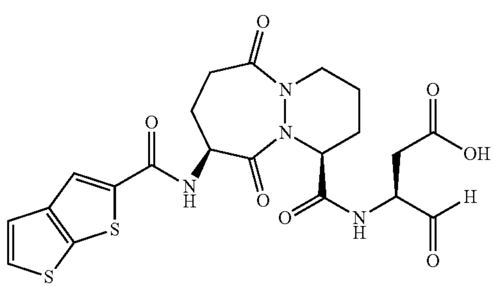 | C21H22N4O7S2 | 506.56 | 10.10 (1) 98% | 507 | 1 |
| 443 | 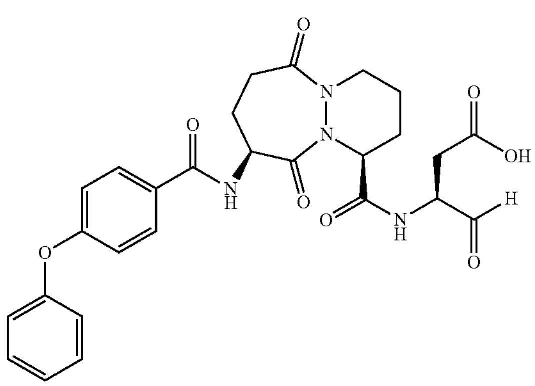 | C27H28N4O8 | 536.55 | 13.12 (1) 98% | 537 | 1 |
| 444 | 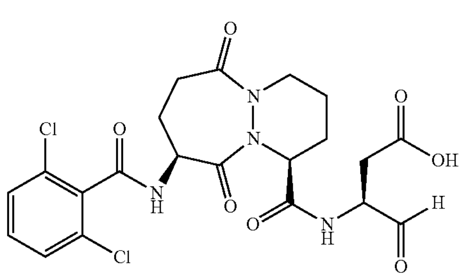 | C21H22Cl2N4O7 | 513.34 | 9.96 (5) 98% | 510 | 1 |

TABLE 7-continued

| Cmpd. | Structure | MF | MW | HPLC RT min | MS (M + H)+ | Syn. Method |
|---|---|---|---|---|---|---|
| 445 | 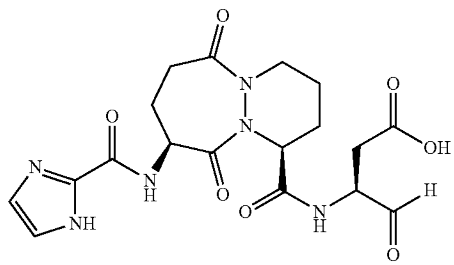 | C18H22N6O7 | 434.41 | 5.72 (1) 98% | 435 | 5 |
| 446 | 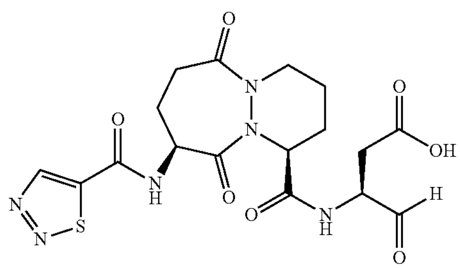 | C17H20N6O7S | 452.45 | 5.00 (1) 98% | 453 | 1 |
| 447 | 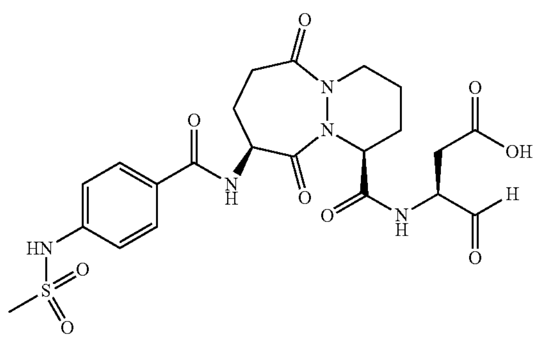 | C22H27N5O9S | 537.55 | 6.32 (1) 98% | 538 | 1B |
| 448 | 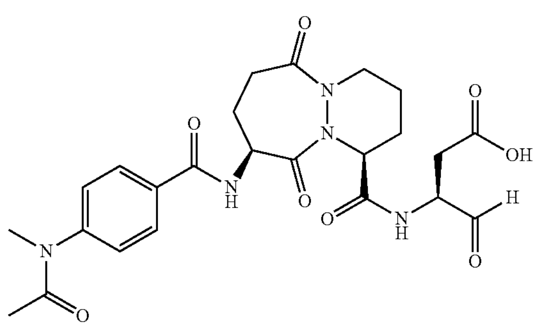 | C24H29N5O8 | 515.53 | 6.36 (1) 98% | 516 | 1A |
| 449 | 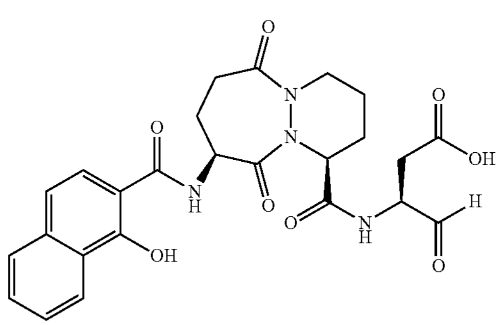 | C25H26N4O8 | 510.51 | 13.86 (1) 98% | 511 | 1 |

TABLE 7-continued

| Cmpd. | Structure | MF | MW | HPLC RT min | MS (M + H)+ | Syn. Method |
|---|---|---|---|---|---|---|
| 450 | 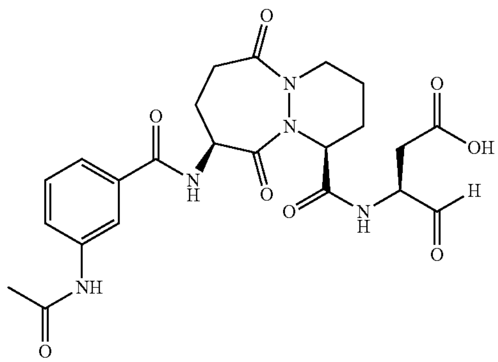 | C23H27N5O8 | 501.50 | 6.10 (1) 98% | 502 | 1A |
| 451 | 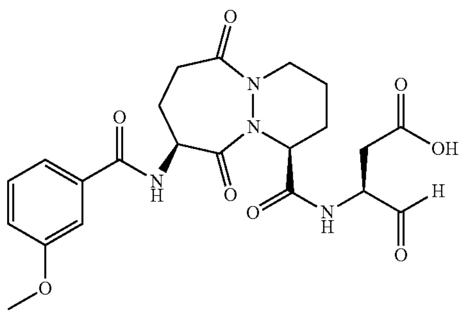 | C22H26N4O8 | 474.47 | 8.02 (1) 98% | 475 | 2 |
| 452 | 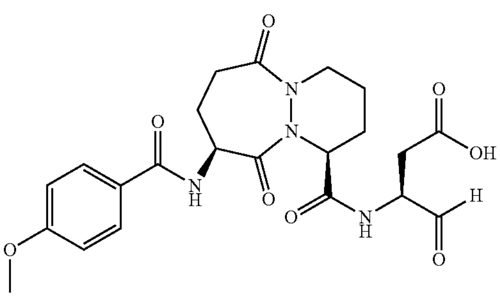 | C22H26N4O8 | 474.47 | 7.77 (1) 98% | 475 | 2 |
| 453 | 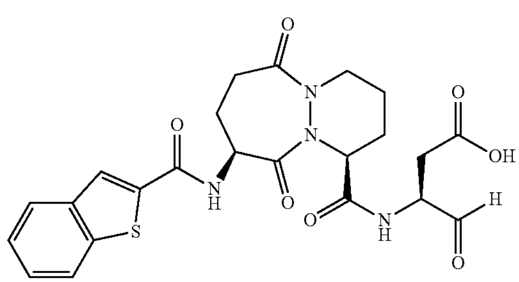 | C23H24N4O7S | 500.53 | 11.11 (1) 98% | 501 | 2 |
| 454 | 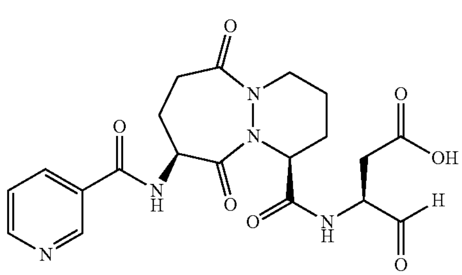 | C20H23N5O7 | 445.44 | 6.24 (2) 98% | 446 | 2 |

TABLE 7-continued

| Cmpd. | Structure | MF | MW | HPLC RT min | MS (M + H)+ | Syn. Method |
|---|---|---|---|---|---|---|
| 455 | 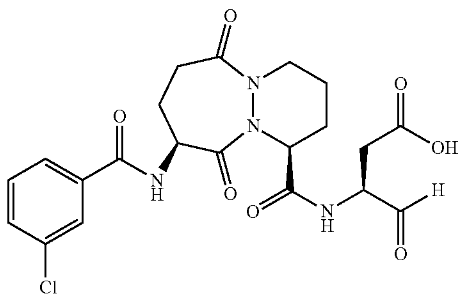 | C21H23ClN4O7 | 478.89 | 9.45 (1) 98% | 479 | 2 |
| 456 | 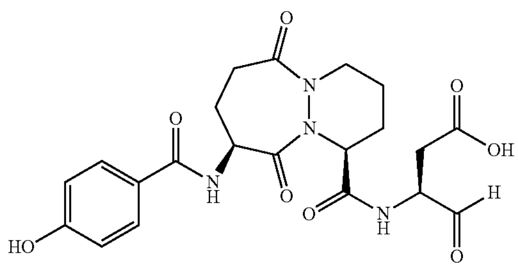 | C21H24N4O8 | 460.45 | 5.58 (1) 98% | (M + Na) 483 | 1 |
| 457 | 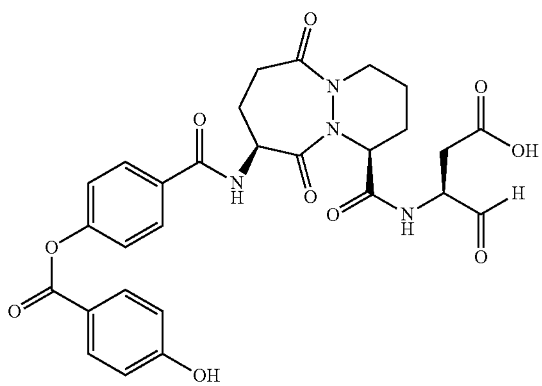 | C28H28N4O10 | 580.56 | 10.42 (1) 98% | (M + Na) 603 | 1 |
| 458 | 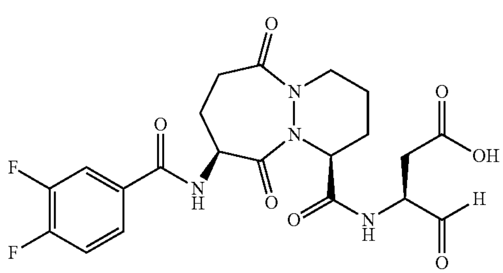 | C21H22F2N4O7 | 480.43 | 8.65 (1) 98% | 481.1 | 1 |
| 459 | 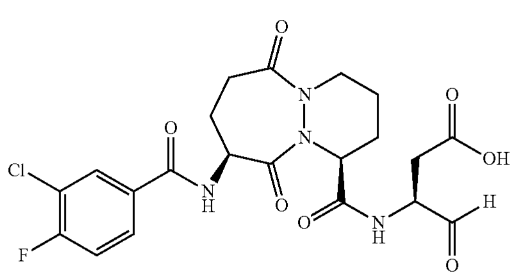 | C21H22ClFN4O7 | 496.88 | 10.11 (1) 98% | 498.3 | 1 |

TABLE 7-continued

| Cmpd. | Structure | MF | MW | HPLC RT min | MS (M+H)+ | Syn. Method |
|---|---|---|---|---|---|---|
| 460 | 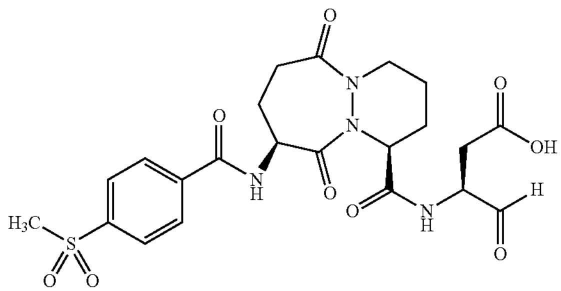 | C22H26N4O9S | 522.54 | 6.16 (1) 98% | 523.6 | 1 |
| 461 | 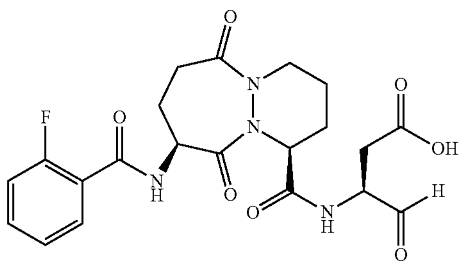 | C21H23FN4O7 | 462.44 | 7.41 (1) 98% | 463.3 | 1 |
| 462 | 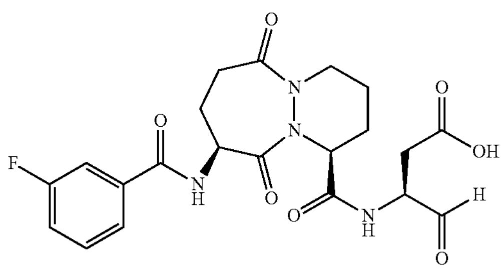 | C21H23FN4O7 | 462.44 | 7.71 (1) 98% | 463.3 | 1 |
| 463 | 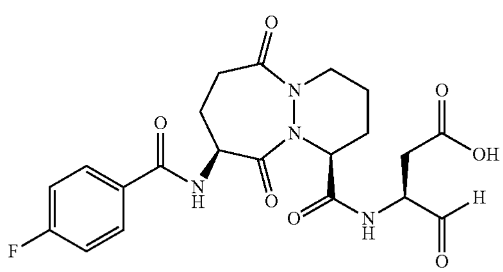 | C21H23FN4O7 | 462.44 | 7.64 (1) 98% | 464 | 1 |
| 464 | 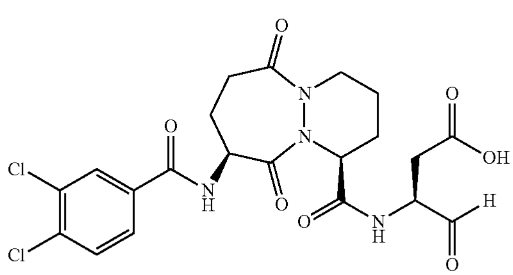 | C21H22Cl2N4O7 | 513.34 | 11.59 (1) 98% | 414.5 | 1 |

TABLE 7-continued
| Cmpd. | Structure | MF | MW | HPLC RT min | MS (M + H)+ | Syn. Method |
|---|---|---|---|---|---|---|
| 465 | 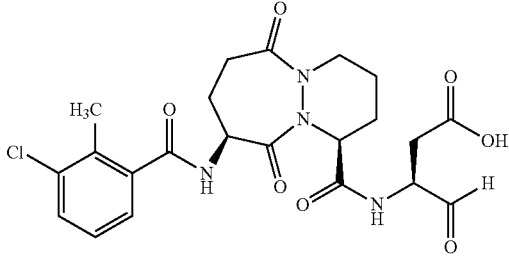 | C22H25ClN4O7 | 492.92 | 9.65 (1) 98% | 493.9 | 1 |
| 466 | 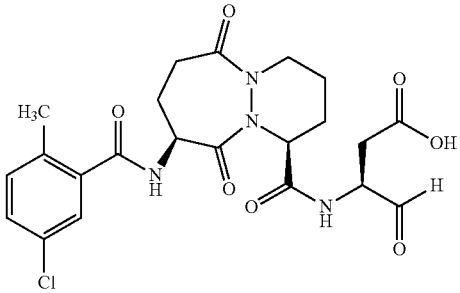 | C22H25ClN4O7 | 492.92 | 9.63 (1) 98% | 493.9 | 1 |
| 467 | 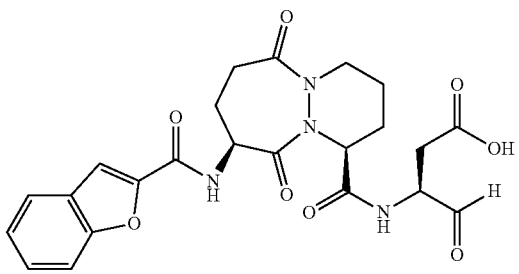 | C23H24N4O8 | 484.47 | 9.73 (1) 98% | 485.8 | 1 |
| 468 | 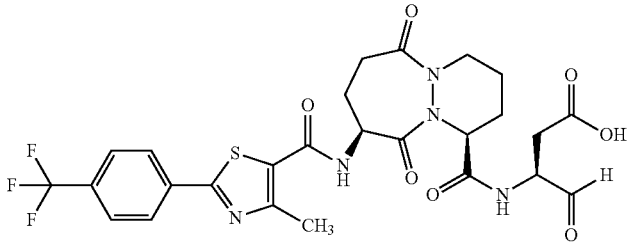 | C26H26F3N5O7S | 609.59 | 14.84 (1) 98% | 609.7 | 1 |
| 470 | 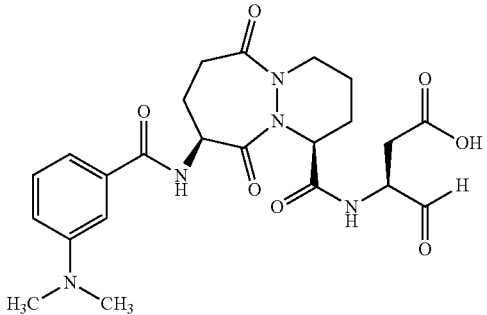 | C23H29N5O7 | 487.52 | 4.57 (1) 98% | 489.5 | 1 |

TABLE 7-continued

| Cmpd. | Structure | MF | MW | HPLC RT min | MS (M + H)+ | Syn. Method |
|---|---|---|---|---|---|---|
| 471 | 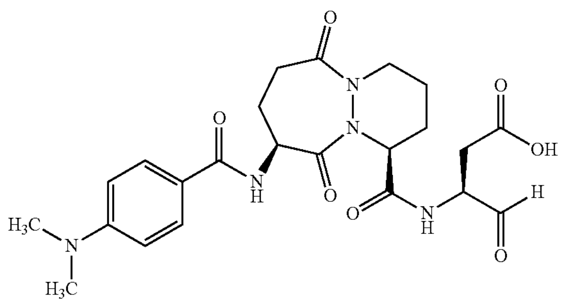 | C23H29N5O7 | 487.52 | 5.74 (1) 98% | 488.2 | 1 |
| 472 | 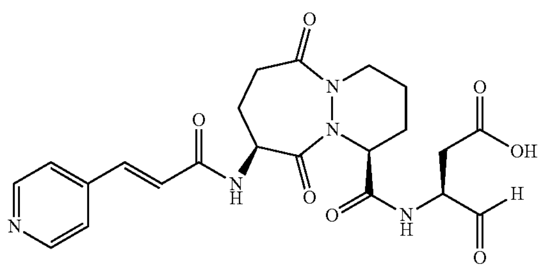 | C22H25N5O7 | 471.47 | 4.00 (1) 98% | 474 | 1 |
| 473 | 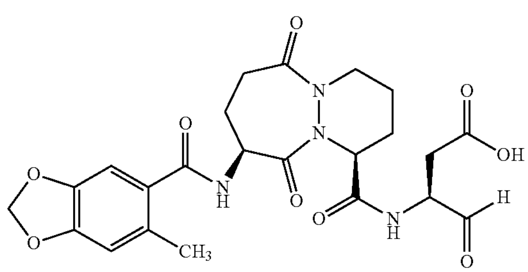 | C23H26N4O9 | 502.49 | 7.65 (1) 98% | 503.6 | 1 |
| 474 | 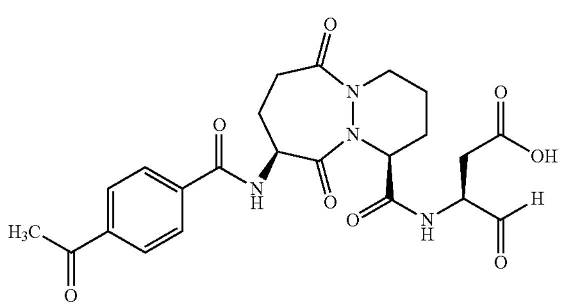 | C23H26N4O8 | 486.49 | 7.16 (1) 98% | 488.1 | 1 |
| 475 | 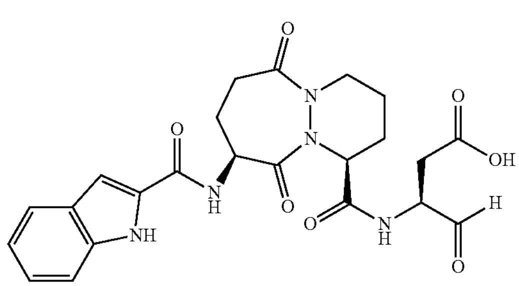 | C23H25N5O7 | 483.49 | 9.77 (1) 97% | 485.1 | 1 |

//

TABLE 7-continued

| Cmpd. | Structure | MF | MW | HPLC RT min | MS (M + H)+ | Syn. Method |
|---|---|---|---|---|---|---|
| 476 | 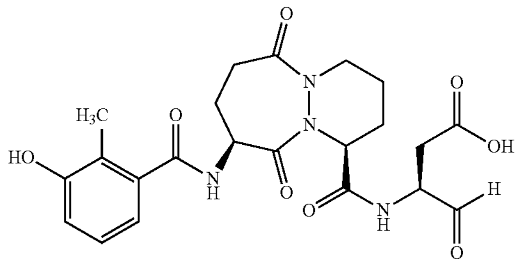 | C22H26N4O8 | 474.47 | 5.25 (1) 98% | 475.8 | 1 |
| 477 | 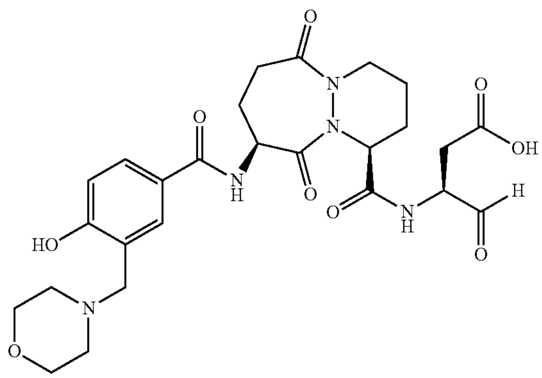 | C26H33N5O9 | 559.58 | 4.76 (1) 95% | 561.8 | 1 |
| 478 | 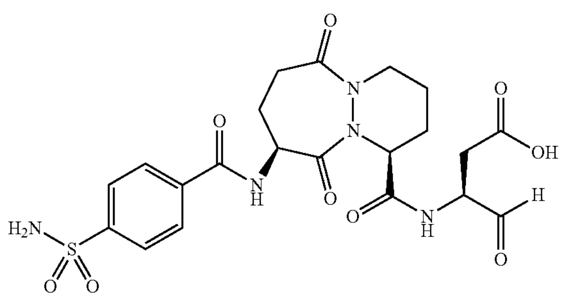 | C21H25N5O9S | 523.53 | 5.25 (1) 98% | 524.3 | 1 |
| 479 | 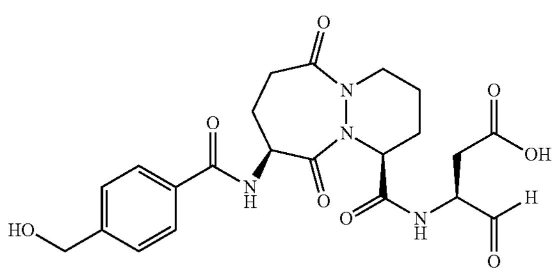 | C22H26N4O8 | 474.47 | 5.35 (1) 98% | 475.8 | 1 |
| 480 | 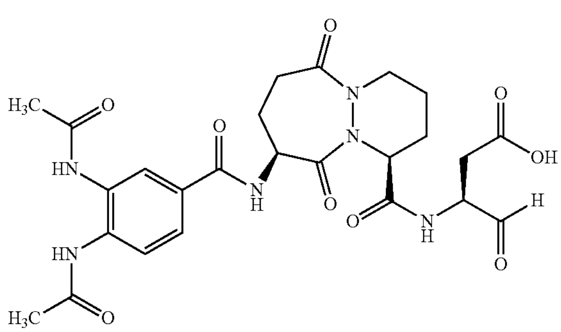 | C25H30N6O9 | 558.55 | 5.11 (1) 98% | 559.3 | 1A |

TABLE 7-continued

| Cmpd. | Structure | MF | MW | HPLC RT min | MS (M + H)+ | Syn. Method |
|---|---|---|---|---|---|---|
| 481 | 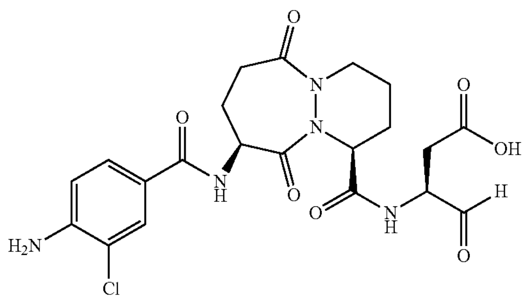 | C21H24ClN5O7 | 493.9 | 7.10 (1) 98% | 495.1 | 1 |
| 482 | 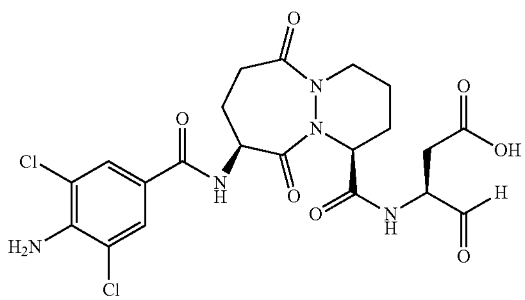 | C21H23Cl2N5O7 | 528.4 | 9.05 (1) 98% | 529.8 | 1 |
| 483 | 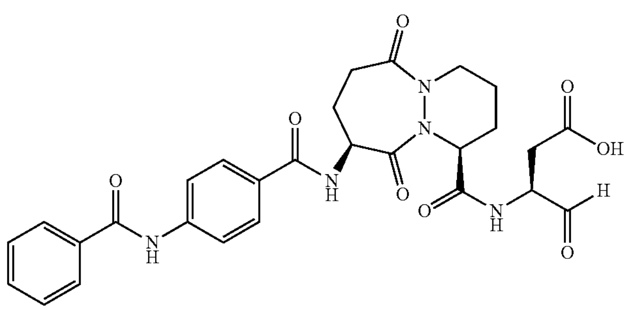 | C28H29N5O8 | 563.57 | 10.01 (1) 98% | 565.6 | 1, 2 |
| 484 | 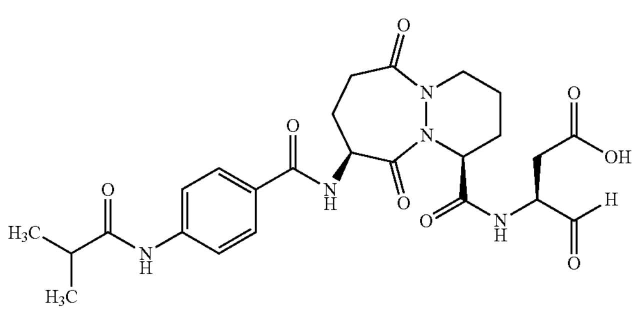 | C25H31N5O8 | 529.55 | 7.88 (1) 98% | 531 | 1, 2 |
| 485 | 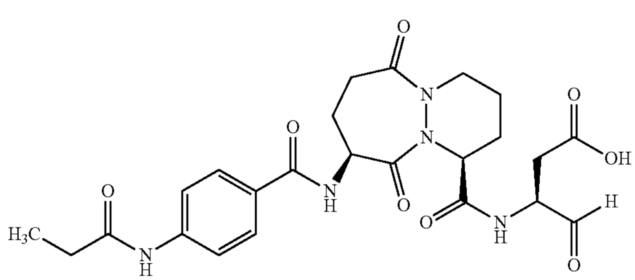 | C24H29N5O8 | 515.53 | 7.00 (1) 98% | 517.6 | 1, 2 |

TABLE 7-continued

| Cmpd. | Structure | MF | MW | HPLC RT min | MS (M + H)+ | Syn. Method |
|---|---|---|---|---|---|---|
| 486 | 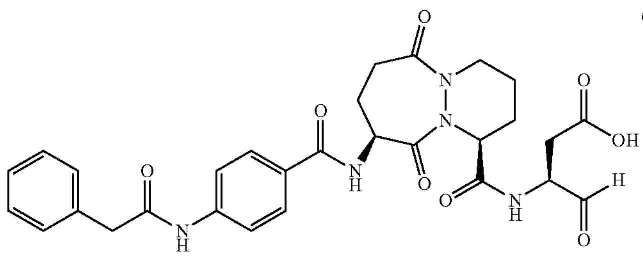 | C29H31N5O8 | 577.60 | 10.43 (1) 98% | 579.4 | 1, 2 |
| 487 | 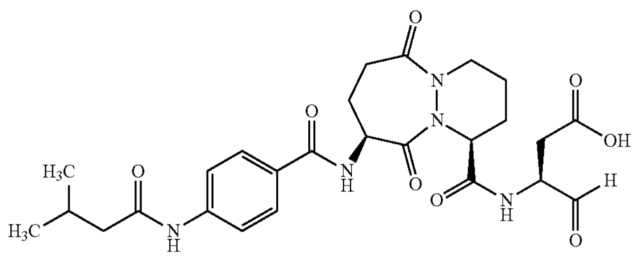 | C26H33N5O8 | 543.58 | 9.30 (1) 98% | 545.7 | 1, 2 |
| 488 | 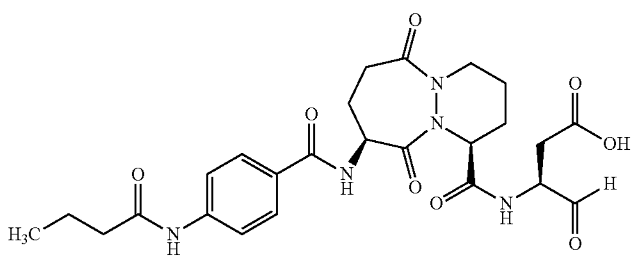 | C25H31N5O8 | 529.55 | 8.13 (1) 98% | 531.1 | 1, 2 |
| 489 | 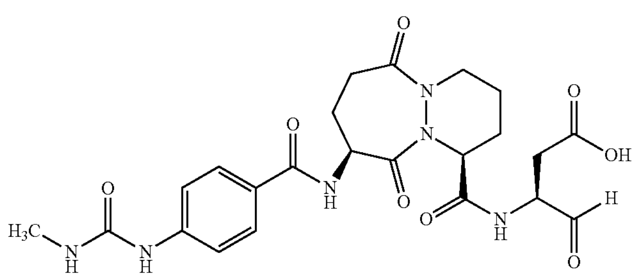 | C23H28N6O8 | 516.52 | 5.89 (1) 98% | 517.8 | 1, 4 |
| 490 | 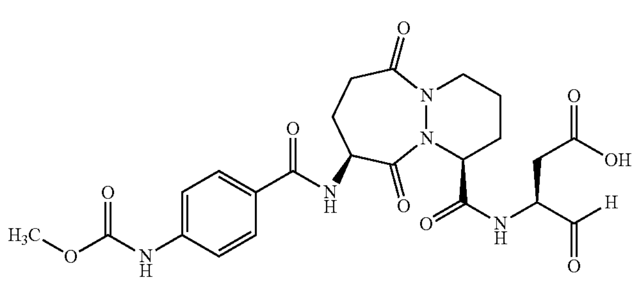 | C23H27N5O9 | 517.50 | 7.27 (1) 98% | (M + Na) 540.8 | 1, 2 |

TABLE 7-continued

| Cmpd. | Structure | MF | MW | HPLC RT min | MS (M+H)+ | Syn. Method |
|---|---|---|---|---|---|---|
| 491 | 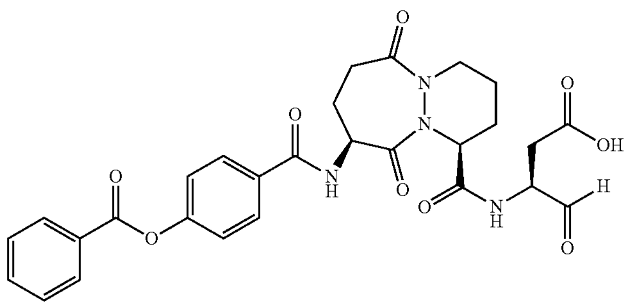 | C28H28N4O9 | 564.56 | 12.9 (1) 98% | 565.3 | 1 |
| 493 | 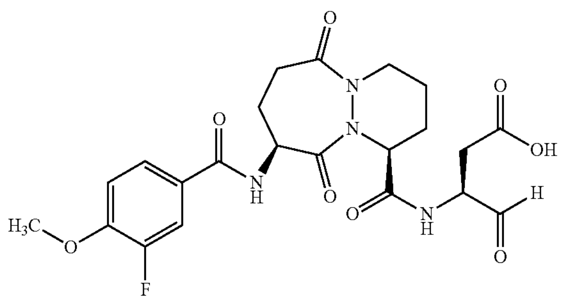 | C22H25FN4O8 | 492.46 | 8.31 (1) 98% | 493.9 | 1 |
| 494 | 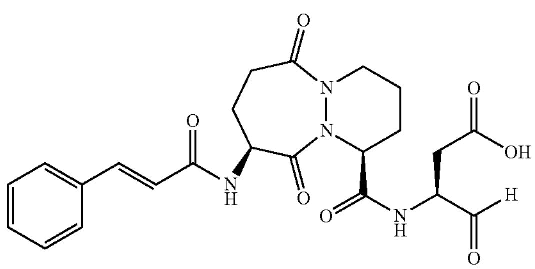 | C23H26N4O7 | 470.49 | 9.34 (1) 98% | 471.2 | 2 |
| 495 | 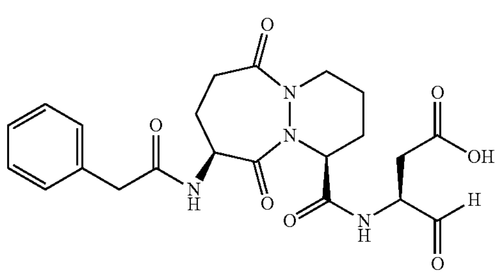 | C22H26N4O7 | 458.48 | 7.24 (1) 98% | 459.9 | 2 |
| 496 | 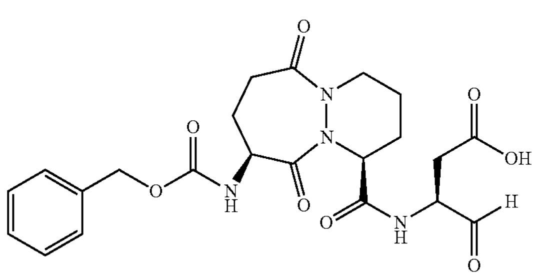 | C22H26N4O8 | 474.47 | 9.47 (1) 98% | 475.7 | 2 |

TABLE 7-continued
| Cmpd. | Structure | MF | MW | HPLC RT min | MS (M + H)+ | Syn. Method |
|---|---|---|---|---|---|---|
| 497 | 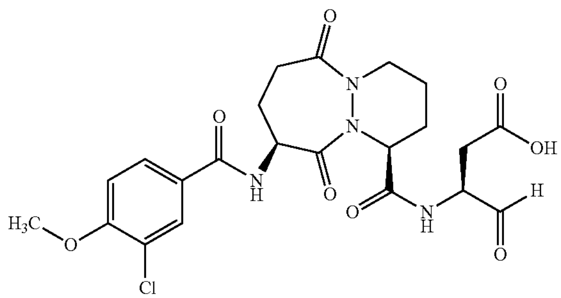 | C22H25ClN4O8 | 508.92 | 9.58 (1) 98% | 509.5 | 1 |
| 498 | 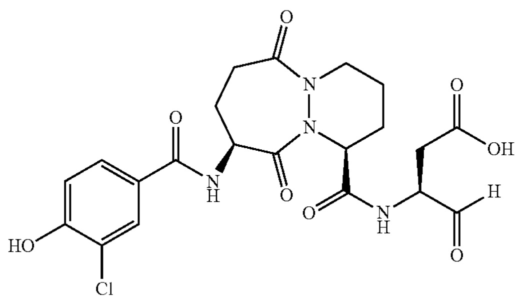 | C21H23ClN4O8 | 494.89 | 7.18 (1) 98% | 495.1 | 1 |
| 499 | 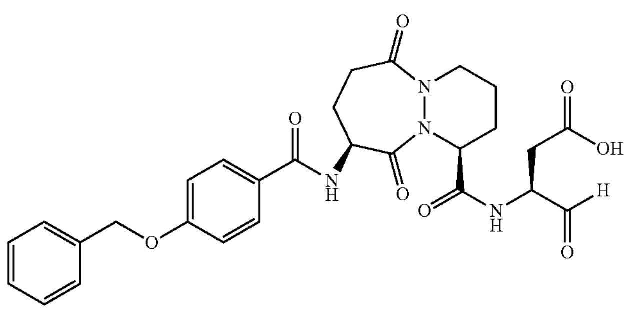 | C28H30N4O8 | 550.57 | 13.27 (1) 98% | 552 | 1 |
EXAMPLE 12
Compounds 605a-j, 605m-q, 605s, 605t, and 605v were synthesized as described below.
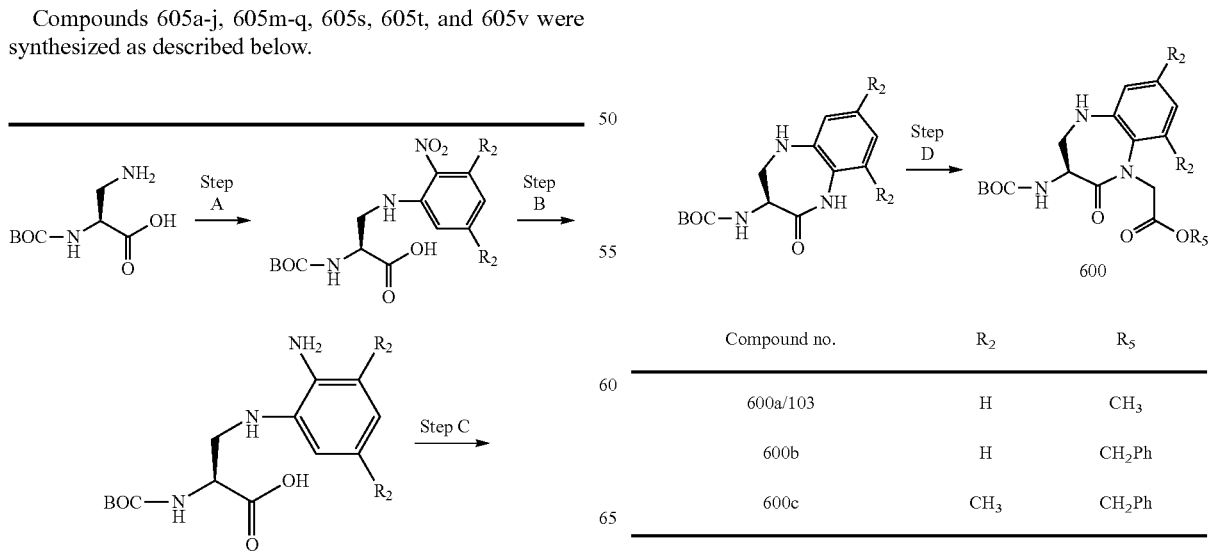
| Compound no. | R$_2$ | R$_5$ |
|---|---|---|
| 600a/103 | H | CH$_3$ |
| 600b | H | CH$_2$Ph |
| 600c | CH$_3$ | CH$_2$Ph |

(3S)-2-oxo-3-tert-butoxycarbonylamino-2,3,4,5-tetrahydro-1H-1,5-benzodiazepine-1-acetic acid methyl ester (600a/103).

Step A. (2S)-2-tert-Butoxycarbonylamino-3-(2-nitrophenyl-amino)-propionic acid. (2S)-2-tert-Butoxycarbonylamino-3-aminopropionic acid (10 g, 49 mmol), 2-fluoronitrobenzene (5.7 ml, 54 mmol), and NaHCO₃ (8.25 g, 98 mmol) was taken into 130 ml of DMF and heated at 80° C. for 18 h. The reaction was evaporated in vacuo to give a viscous orange residue that was dissolved in 300 ml of H₂O and extracted with Et₂O (3×150 ml). The aq. solution was acidified to pH 5 with 10% NaHSO₄ and extracted with EtOAc (3×250 ml). The combined extracts were dried over anhydrous Na₂SO₄, filtered, and evaporated to give 12.64 g (83%) of the title compound as an orange amorphous solid: ¹H NMR (CD₃OD) δ 8.15-8.10 (1H, d), 7.54-7.48 (1H, t), 7.13-7.08 (1H, d), 6.73-6.65 (1H, t), 4.45-4.35 (1H, m), 3.9-3.8 (1H, dd), 3.65-3.55 (1H, dd), 1.45 (9H, s).

Step B. (2S)-2-tert-Butoxycarbonylamino-3-(2-aminophenyl-amino)-propionic acid. A mixture of (2S)-2-tert-Butoxycarbonylamino-3-(2-nitrophenylamino)propionic acid (12.65 g, 40.5 mmol) and 0.5 g of 10% Pd/C in 100 ml of MeOH under hydrogen at 1 atmosphere was stirred for 4 h. The solution was filtered through Celite 545 and the filtrate evaporated in vacuo to afford the 11.95 g of the title compound in quantitative yield as a dark brown solid that was used without purification: ¹H NMR (CD₃OD) δ 6.75-6.70 (3H, m), 6.65-6.58 (1H, m), 4.35-4.3 1H, m), 3.6-3.38 (2H, m), 1.45 (9H, s).

Step C. (3S)-2-oxo-3-tert-Butoxycarbonylamino-1,3,4,5-tetrahydro-1H-1,5-benzodiazepine. 1-(3-Dimethylaminopropyl)-3-ethylcarbodiimide hydrochloride (8.54 g, 44.5 mmol) was added to a cooled (0° C.) solution of (2S)-2-tert-butoxycarbonylamino-3-(2-aminophenylamino)propionic acid (11.95 g, 40.5 mmol) in 100 ml of DMF and stirred for 18 h. The reaction was poured into 700 ml of EtOAc and washed four times with 100 ml of H₂O. The organic layer was dried over anhydrous Na₂SO₄, filtered, and evaporated to give a brown solid that was purified by flash chromatography eluting with 3:7 EtOAc/hexane to give 8 g (71%) of the title compound: ¹H NMR (CDCl₃) δ 7.78 (1H, s), 7.02-6.95 (1H, m), 6.88-6.82 (1H, m), 6.82-6.78 (1H, m), 6.75-6.70 (1H, m), 5.8-5.7 (1H, d), 4.55-4.45 (1H, m), 3.95 (1H, s), 3.9-3.82 (1H, m), 3.48-3.40 (1H, m), 1.45 (9H, s).

Step D. (3S)-2-oxo-3-tert-butoxycarbonylamino-2,3,4,5-tetrahydro-1H-1,5-benzodiazepine-1-acetic acid methyl ester (600a/103). A 1.0 M solution of lithium bis(trimethylsilyl)amide (3.4 ml, 3.4 mmol) in THF was added dropwise to a −78° C. solution of (3S)-2-oxo-3-tert-butoxycarbonylamino-2,3,4,5-tetrahydro-1H-1,5-benzodiazepine (0.94 g, 3.38 mmol) in 20 ml of anhydrous THF and stirred for 30 min. Methyl bromoacetate (0.44 ml, 4 mmol) was added dropwise to the reaction mixture then warmed to RT. The reaction was diluted with 100 ml of EtOAc and washed with 0.3N KHSO₄ (50 ml), H₂O (2×50 ml), and brine. The combined organics were dried over anhydrous Na₂SO₄, filtered, and evaporated to afforded a gum that was purified by flash chromatography eluting with 3:7 EtOAc/Hex. to give 0.98 g (83%) of the title compound as a white solid. ¹H NMR (CDCl₃) δ 7.15-7.07 (2H, m), 6.98-6.94 (1H, m), 6.88-6.84 (1H, d), 5.62-5.55 (1H, d), 4.71-4.65 (1H, d), 4.65-4.6 (1H, m), 4.33-4.27 (1H, d), 3.96-3.90 (1H, m), 3.78 (3H, s), 3.44-3.37 (1H, m), 1.4 (9H, s).

(3S)-2-oxo-3-tert-butoxycarbonylamino-2,3,4,5-tetrahydro-1H-1,5-benzodiazepine-1-acetic acid benzyl ester (600b). Prepared by a similar method described for the preparation of 600a/103 (Step D), except benzyl bromoacetate was used instead of methyl bromoacetate to give 600b in quantitative yield.

(3S)-2-oxo3-tert-butoxycarbonylamino-2,3,4,5-tetrahydro-7,9-dimethyl-1H-1,5-benzodiazepine-1-acetic acid benzyl ester (600c).

Step A. (2S)-2-tert-Butoxycarbonylamino-3-(2-nitro-3,5-dimethylphenylamino)-propionic acid. Prepared by a method similar as described for 600a/103 (Step A), except 2-fluoro-4,6-dimethyl-nitrobenzene was used instead of 2-fluoronitrobenzene to give the desired compound in 93% yield.

Step B. (2S)-2-tert-Butoxycarbonylamino-3-(2-amino-3,5-dimethylphenyl-amino)-propionic acid. (2S)-2-tert-Butoxycarbonylamino-3-(2-nitro-3,5-dimethylphenyl-amino) propionic acid was converted to the title compound in quantitive yield as described in the preparation of 600a/103 (Step B).

Step C. 2-Oxo-(3S)-3-tert-butoxycarbonylamino-2,3,4,5-tetrahydro-7,9-dimethyl-1H-1,5-benzodiazepine. A 0° C. solution of (2S)-2-tert-butoxycarbonylamino-3-(2-amino-3,5-dimethylphenyl-amino)-propionic acid (763 mg, 2.36 mmol) and N-methylmorpholine (483 mg, 4.78 mmol) in 60 ml of anhydrous THF was treated dropwise with isobutylchloroformate (352 mg, 2.5 mmol). The reaction was stirred for 2 h at 0° C., at RT for 1 h and poured over EtOAc. The mixture was washed with aq. 5% NaHSO₄, sat. aq. NaHCO₃, and sat. aq. NaCl, dried over NaSO₄, and concentrated in vacuo. Chromatography (flash, SiO₂, 10% to 25% to 50% EtOAc/CH₂Cl₂) gave 490 mg (68%) of the desired product.

Step D. (3S)-2-oxo-3-tert-butoxycarbonylamino-2,3,4,5-tetrahydro-7,9-dimethyl-1H-1,5-benzodiazepine-1-acetic acid benzyl ester (600c). (2S)-2-tert-Butoxycarbonylamino-3-(2-amino-3,5-dimethylphenyl-amino)-propionic acid was converted to 600c, 75% by a similar method for the preparation of 600b.

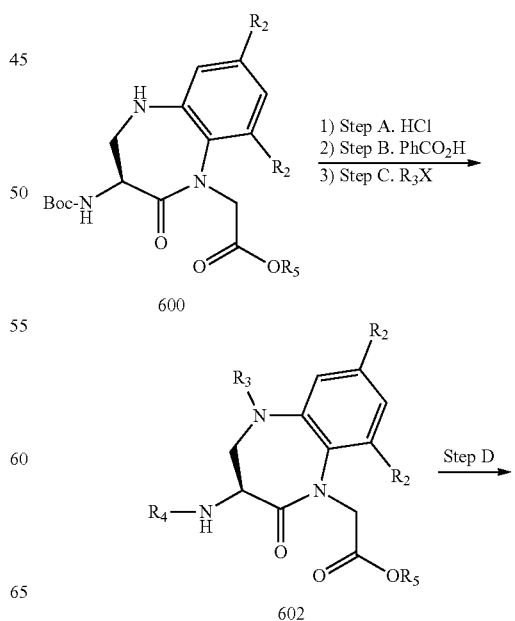

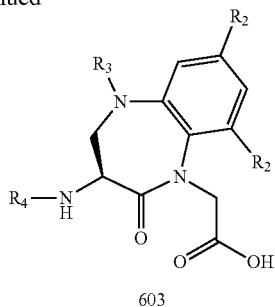

603

(3S)-2-oxo-3-benzoylamino-5-(3-phenylpropionyl)-2,3,4,5-tetrahydro-1H-1,5-benzo diazepine-1-acetic acid methyl ester (602a).

Step A. Anhydrous HCl was bubbled into a solution of (3S)-2-oxo-3-tert-butoxycarbonylamino-2,3,4,5-tetrahydro-1H-1,5-benzodiazepine-1-acetic acid methyl ester (600a/103, 4.0 g, 11.4 mmol) in 20 ml of $CH_2Cl_2$ for 20 min then stirred for 1 h at RT. The reaction was evaporated to give (3S)-2-oxo-3-amino-2,3,4,5-tetrahydro-1H-1,5-benzodiazepine-1-acetic acid methyl ester hydrochloride as a white solid.

Step B. The white solid was dissolved in 70 ml of DMF and benzoic acid (1.5 g, 12.3 mmol) was added. The reaction was cooled in a ice/$H_2O$ bath and treated with 1-(3-dimethylaminopropyl)-3-ethylcarbodiimide hydrochloride (2.4 g, 12.5 mmol), 1-hydroxybenzotriazole (1.7 g, 12.6 mmol) and diisopropylethylamine (3.0 g, 23.2 mmol). The reaction was stirred for 18 h at RT under nitrogen atmosphere and poured onto $H_2O$. The aq. mixture was extracted with EtOAc (2×). The combined organic layers were washed with aq. 0.5 N $NaHSO_4$, $H_2O$, sat. aq. $NaHCO_3$, $H_2O$ and sat. aq. NaCl, dried over $MgSO_4$ and concentrated in vacuo. Chromatography (flash, $SiO_2$, 10% to 30% EtOAc/$CH_2Cl_2$) gave 3.4 g (85%) of (3S)-2-oxo-3-(benzoylamino)-2,3,4,5-tetrahydro-1H-1,5-benzodiazepine-1-acetic acid methyl ester as a white solid.

Step C. Method A. (3S)-2-oxo-3-benzoylamino-5-(3-phenylpropionyl)-2,3,4,5-tetrahydro-1H-1,5-benzodiazepine-1-acetic acid methyl ester (602a). A solution of (3S)-2-oxo-3-(benzoylamino)-2,3,4,5-tetrahydro-1H-1,5-benzodiazepine-1-acetic acid methyl ester (200 mg, 0.57 mmol) in $CH_2Cl_2$ (10 ml) was treated with triethylamine (119 mg, 1.13 mmol) and 3-phenylpropionyl chloride (114 mg, 0.68 mmol). The reaction was stirred at RT for 30 min and diluted with $CH_2Cl_2$. The solution was washed with aq. 10% HCl sat.

aq. $NaHCO_3$ and sat. aq. NaCl, dried over $Na_2SO_4$ and concentrated in vacuo to give 240 mg (87%) of 602a as a white foam.

Step C. Method B. (3S)-2-oxo-3-benzoylamino-5-acetoacetyl-2,3,4,5-tetrahydro-1H-1,5-benzodiazepine-1-acetic acid benzyl ester (602g). A 0° C. solution of (3S)-2-oxo-3-(benzoylamino)-2,3,4,5-tetrahydro-1H-1,5-benzodiazepine-1-acetic acid benzyl ester (600b) (465 mg, 1.10 mmol) in $CH_2Cl_2$ (5 ml) was treated with acetoacetic acid in 1 ml of $CH_2Cl_2$ followed by slow addition of 1-(3-dimethylaminopropyl)-3-ethylcarbodiimide hydrochloride (431 mg, 2.2 mmol) in 2 ml of $CH_2Cl_2$ under $N_2$ atmosphere. After 15 min the reaction was poured onto EtOAc, washed with aq. 5% $NaHSO_4$, dried over $Na_2SO_4$ and concentrated in vacuo.

Chromatography (flash, $SiO_2$, 0% to 10% to 25% MeOH/$CH_2Cl_2$) gave 580 mg of (3S)-2-oxo-3-(benzoylamino)-5-acetoacetyl-2,3,4,5-tetrahydro-1H-1,5-benzodiazepine-1-acetic acid benzyl ester as a white solid.

Step C. Method C. (3S)-2-oxo-3-benzoylamino-5-methoxycarbonyl-2,3,4,5-tetrahydro-1H-1,5-benzo diazepine-1-acetic acid benzyl ester (602j). A vigorously-stirred, 0° C. solution of (3S)-2-oxo-3-(benzoylamino)-2,3,4,5-tetrahydro-1H-1,5-benzodiazepine-1-acetic acid benzyl ester (600b) (461 mg, 1.07 mmol) in THF (5 ml) and sat. aq. $NaHCO_3$ (2.5 ml) was treated with a THF solution (0.35 ml) of methyl chloroformate (151 mg, 1.6 mmol) and the reaction was stirred for 45 min at RT. The reaction was poured onto $CH_2Cl_2$ and washed with $H_2O$, dried over $Na_2SO_4$ and concentrated in vacuo. Chromatography (flash, $SiO_2$, 0% to 10% MeOH/$CH_2Cl_2$) gave 525 mg of 602j as a white solid.

Step C. Method D. (3S)-2-oxo-3-benzoylamino-5-benzylaminocarbonyl-2,3,4,5-tetrahydro-1H-1,5-benzodiazepine-1-acetic acid methyl ester (602p). A solution of 600a/103 (400 mg, 1.1 mmol) and benzylisocyanate (166 mg, 1.2 mmol) in 10 ml of $CH_2Cl_2$ and 10 ml of DMF and heated at 80° C. for 3 days. The reaction was cooled to RT poured onto $H_2O$ and extracted with EtOAc (2×). The combined organic layers were washed with $H_2O$ (4×) and sat. aq. NaCl, dried over $MgSO_4$ and concentrated in vacuo. Chromatography (flash, $SiO_2$, 50% to 80% EtOAc/hexane) gave 440 mg (80%) of 602p as a white solid.

Step C. Method E. (3S)2-oxo-3-benzylamino-5-(3-phenylpropionyl)-2,3,4,5-tetrahydro-1H-1,5-benzodiazepine-1-acetic acid methyl ester (602v). A solution of (3S)2-oxo-3-amino-5-(3-phenylpropionyl)-2,3,4,5-tetrahydro-1H-1,5-benzodiazepine-1-acetic acid methyl ester hydrochloride (560 mg, 1.34 mmol), benzaldehyde (146 mg, 1.34 mmol) and sodium acetate (220 mg, 2.68 mmol) in methanol (20 ml) was treated with 4 Å sieves (2 g) and $NaCNBH_3$ (168 mg, 2.68 mmol). The reaction was stirred for 2.5 h, acidified with 10% aq. HCl to pH 2 and washed with $Et_2O$ (2×75 ml). The organic layers were concentrated in vacuo to give an oil. Chromatography (flash, $SiO_2$, 0 to 35% EtOAc/$CH_2Cl_2$) gave 250 mg (40%) of 602v as a clear oil.

Step D. Method A. (3S)-2-Oxo-3-benzoylamino-5-(3-benzodiazepine-1-acetic acid (603a). (3S)-2-oxo-3-benzoylamino-5-(3-phenylpropionyl)-2,3,4,5-tetrahydro-1H-1,5-benzo diazepine-1-acetic acid methyl ester (602a; 1.25 g, 2.57 mmol) was dissolved in 11 ml of THF, MeOH and $H_2O$ (5:5:1) and treated with $LiOH \cdot H_2O$ (42 mg, 0.62 mmol) stirred at RT for 64 h. The reaction was concentrated in vacuo, diluted with $H_2O$ and acidified with aq. 1N HCl to give 230 mg of 603a as a white solid.

Step D. Method B. (3S)2-oxo-3-benzoylamino-5-acetyl-2,3,4,5-tetrahydro-1H-1,5-benzodiazepine-1-acetic acid (603d). A mixture of (3S)-2-oxo-3-(benzoylamino)-5-acetyl-2,3,4,5-tetrahydro-1H-1,5-benzodiazepine-1-acetic acid benzyl ester (602d; 510 mg, 1.08 mmol) and 5% Pd/C (250 mg) in MeOH (10 ml) stirred under $H_2$ (1 atm) for 0.5 h. The reaction was filtered and concentrated in vacuo 410 mg of 603d as a white solid.

The compounds of Table 8 were prepared as described in Table 9, using the methods of Example 12.

TABLE 8

| Compound no. | $R_2$ | $R_3$ | $R_4$ | $R_5$ |
|---|---|---|---|---|
| 602b | H | $PhCH_2C(O)$ | $PhC(O)$ | $CH_2Ph$ |
| 602c | H | $PhC(O)$ | $PhC(O)$ | $CH_2Ph$ |
| 602d | H | $CH_3C(O)$ | $PhC(O)$ | $CH_2Ph$ |
| 602e | H | $CH_3OCH_2C(O)$ | $PhC(O)$ | $CH_2Ph$ |
| 602f | H | $(CH_3)_2CHCH_2C(O)$ | $PhC(O)$ | $CH_2Ph$ |
| 602g | H | $CH_3C(O)CH_2C(O)$ | $PhC(O)$ | $CH_2Ph$ |
| 602h | H | $CH_3OC(O)C(O)$ | $PhC(O)$ | $CH_2Ph$ |
| 602i | H | $CH_3C(O)C(O)$ | $PhC(O)$ | $CH_2Ph$ |
| 602j | H | $CH_3OC(O)$ | $PhC(O)$ | $CH_2Ph$ |
| 602k | H | $CH_3C(O)$ | Boc | $CH_2Ph$ |
| 602l | $CH_3$ | $CH_3C(O)$ | Boc | $CH_2Ph$ |
| 602m | H | $CH_3S(O2)$ | $PhC(O)$ | $CH_3$ |
| 602p | H | $PhCH_2NHC(O)$ | $PhC(O)$ | $CH_3$ |
| 602q | H | ⟨tetrahydrofuran⟩-OCO | $PhC(O)$ | $CH_2Ph$ |
| 602r | H | $PhCH_2CH_2C(O)$ | $PhCH_2CH_2C(O)$ | $CH_2Ph$ |
| 602s | H | 4-pyridyl$CH_2C(O)$ | $PhC(O)$ | $CH_2Ph$ |

TABLE 9

| No. | Starting material | $R_3X$ | Step C method/ (% yield) | Step D method/ (% yield) |
|---|---|---|---|---|
| 603b | 600b | $PhCH_2C(O)Cl$ | A (98) | B (89) |
| 603c | 600b | $PhC(O)Cl$ | A (quant.) | B (quant.) |
| 603d | 600b | $CH_3C(O)Cl$ | A (quant.) | B (quant.) |
| 603e | 600b | $CH_3OCH_2C(O)Cl$ | A (59) | B (quant.) |
| 603f | 600b | $(CH_3)_2CHCH_2C(O)Cl$ | A (88) | B (95) |
| 603g | 600b | $CH_3C(O)CH_2CO_2H$ | B (quant.) | B (quant.) |
| 603h | 600b | $CH_3OC(O)C(O)Cl$ | A (96) | B (quant.) |
| 603i | 600b | $CH_3C(O)CO_2H$ | A (87) | B (94) |
| 603j | 600b | $CH_3OC(O)Cl$ | C (quant.) | B (quant.) |
| 603k | 600b | $CH_3C(O)Cl$ | A, Step C only (quant.) | not run |
| 603l | 600c | $CH_3C(O)Cl$ | A, Step C only (quant.) | not run |
| 603m | 600a/103 | $CH_3SO_3Cl$, $NEt_3$ instead of pyridine and THF instead of $CH_2Cl_2$ | A (76) | A (92) |
| 603p | 600a/103 | $PhCH_2C=N=O$ | D (80) | A (86) |
| 603q | 600b | ⟨tetrahydrofuran⟩-OCOCl | C (83) | B (71) |
| 603r | 600a/103 | $PhCH_2CH_2C(O)Cl$ | A | |
| 603s | 600b | 4-pyridyl$CH_2CO_2H$ | B (90) | B (98) |

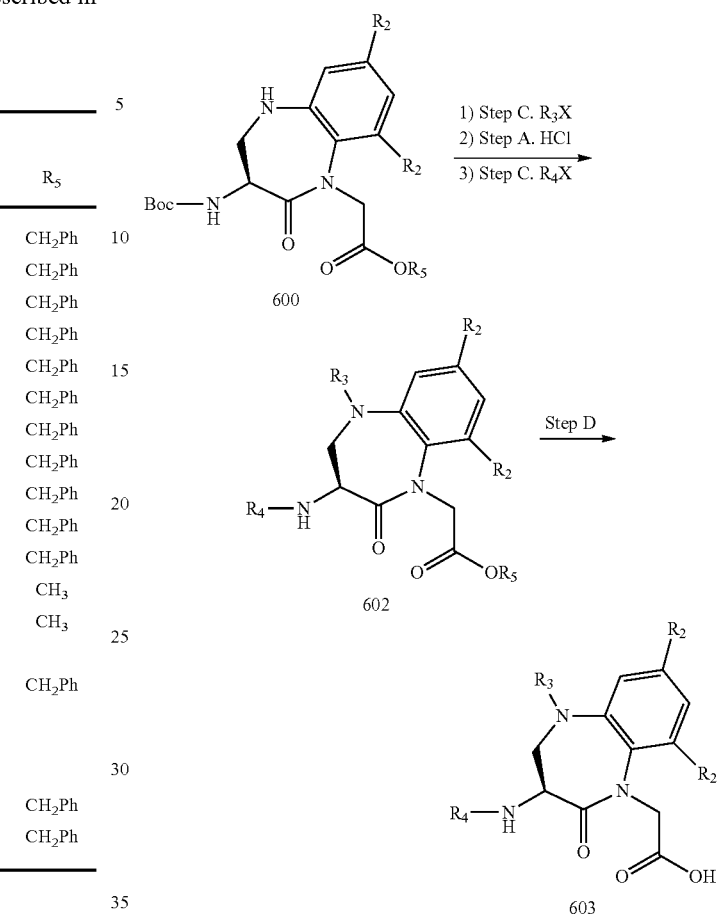

600 / 602 / 603

The compounds of Table 10 were prepared as described in Table 11 using the methods of Example 12.

TABLE 10

| Compound no. | $R_2$ | $R_3$ | $R_4$ | $R_5$ |
|---|---|---|---|---|
| 602n | H | $CH_3C(O)$ | Naphthylene-2-C(O) | $CH_2Ph$ |
| 602o | $CH_3$ | $CH_3C(O)$ | $PhC(O)$ | $CH_2Ph$ |
| 602t | H | 3-$CH_3PhCH_2C(O)$ | $PhC(O)$ | $CH_2Ph$ |
| 602u | H | $CH_3C(O)$ | Fmoc | $CH_2Ph$ |
| 602v | H | $PhCH_2CH_2CO$ | $PhCH_2$ | $CH_3$ |

TABLE 11

| No. | Starting material | 1) Step C. $R_3X$ method (% yield) | 3) Step C $R_4X$ method (% yield) | Step D method (% yield) |
|---|---|---|---|---|
| 603n | 602k | $CH_3C(O)Cl$ A (quant.) | naphthylene-2-C(O)Cl A (70) | B (quant.) |
| 603o | 602l | $CH_3C(O)Cl$ A (quant.) | $PhC(O)Cl$ A (73) | B (quant.) |
| 603t | 602k | $CH_3C(O)Cl$ A (quant.) | 3-$CH_3PhCH_2C(O)Cl$ A (93) | B (95) |
| 603u | 602k | $CH_3C(O)Cl$ A (quant.) | Fmoc-Cl C (82) | C (98) |
| 603v | 600a/103 | $PhCH_2CH_2C(O)Cl$ A | PhCHO E(40) | A (95) |

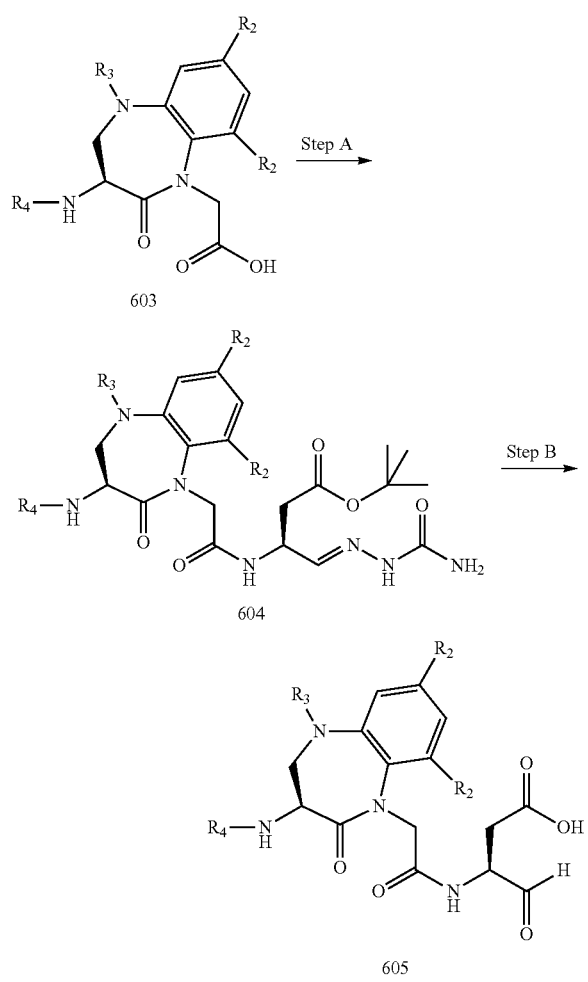

The compounds of Table 12 were prepared by the methods described below.

TABLE 12

| compound no. | $R_2$ | $R_3$ | $R_4$ |
|---|---|---|---|
| 605a | H | $PhCH_2CH_2C(O)$ | $PhC(O)$ |
| 605b | H | $PhCH_2C(O)$ | $PhC(O)$ |
| 605c | H | $PhC(O)$ | $PhC(O)$ |
| 605d | H | $CH_3C(O)$ | $PhC(O)$ |
| 605e | H | $CH_3OCH_2C(O)$ | $PhC(O)$ |
| 605f | H | $(CH_3)_2CHCH_2C(O)$ | $PhC(O)$ |
| 605g | H | $CH_3C(O)CH_2C(O)$ | $PhC(O)$ |
| 605h | H | $CH_3OC(O)C(O)$ | $PhC(O)$ |
| 605i | H | $CH_3C(O)C(O)$ | $PhC(O)$ |
| 605j | H | $CH_3OC(O)$ | $PhC(O)$ |
| 605m | H | $CH_3SO_3$ | $PhC(O)$ |
| 605n | H | $CH_3C(O)$ | Naphthyl-2-C(O) |
| 605o | $CH_3$ | $CH_3C(O)$ | $PhC(O)$ |
| 605p | H | $PhCH_2NHC(O)$ | $PhC(O)$ |
| 605q | H | ![tetrahydrofuranyl-OCO] | $PhC(O)$ |
| 605s | H | 4-pyridylCH$_2$C(O) | $PhC(O)$ |
| 605t | H | 3-CH$_3$PhCH$_2$C(O) | $PhC(O)$ |
| 605v | H | $PhCH_2CH_2C(O)$ | $PhCH_2$ |

(3S)-3-[(3S)-2-oxo-3-benzoylamino-5-(3-phenylpropionyl)-2,3,4,5-tetrahydro-1H-1,5-benzodiazepin-1-acetylamino]4-oxo-butyric acid (605a).

Step A. (3S)-3-(1-Fluorenylmethyloxycarbonylamino)-4-oxobutyric acid tert-butyl ester semicarbazone (210 mg, 0.45 mol, Prepared in a similar manner to the benzyloxycarbonyl analog in Graybill et al., *Int. J. Protein Res.*, 44, pp. 173-82 (1994).) was dissolved in 10 ml of DMF and 2 ml of diethylamine and stirred for 2 h. The reaction was concentrated in vacuo to give (3S)-3-amino-4-oxobutyric acid tert-butyl ester semicarbazone. The 0° C. solution of the above residue and 603a (200 mg, 0.42 mmol) in 5 ml of DMF and 5 ml of $CH_2Cl_2$ was treated with 1-hydroxybenzotriazole (57 mg, 0.42 mmol) and 1-(3-dimethylaminopropyl)-3-ethylcarbodiimide hydrochloride (98 mg, 0.51 mmol). The reaction was stirred at RT for 18 h, poured onto EtOAc (75 ml) and washed with aq. 0.3 N $KHSO_4$, sat. aq. $NaHCO_3$ and sat. aq. NaCl, dried over $NaSO_4$ and concentrated in vacuo. Chromatography (flash, $SiO_2$, 0% to 4% MeOH/0.1% $NH_4OH/CH_2Cl_2$) to give 240 mg (83%) of 604a.

Step B. 604a was stirred with 10 ml of 33% TFA/$H_2O$ for 4 h and concentrated in vacuo. The residue was dissolved in 7 ml of MeOH/acetic acid/37% aq. formaldehyde (5:1:1) and stirred for 18 h. Chromatography (Reverse Phase C18, 4.4 mm ID×25 cm, 15% to 70% $CH_3CN$/0.1% TFA/$H_2O$) gave 32 mg (16%) of 605a as a white solid: $^1H$ NMR ($CD_3OD$, existing as diastereomers of the hemiacetal) δ 7.85-7.78 (2H, d), 7.5-7.32 (6H, m), 7.32-7.28 (1H, m), 7.18-6.98 (5H, m), 4.92-4.85 (2H, m), 4.5-4.32 (2H, m), 4.31-4.20 (2H, m), 3.7-3.6 (1H, m), 2.90-2.75 (2H, m), 2.65-2.5 (1H, m), 2.48-2.25 (3H, m).

The following compounds were prepared by a similar method:

(3S)-3-[(3S)-2-oxo-3-benzoylamino-5-phenylacetyl-2,3,4,5-tetrahydro-1H-1,5-benzodiazepin-1-acetylamino]-4-oxo-butyric acid (605b). 148 mg (33%) as a white solid: $^1H$ NMR ($CD_3OD$) δ 7.9-6.9 (m, 16H), 4.9 (s, 2H), 4.5 (m, 1H), 4.4 (m, 2H), 3.75 (s, 1H), 3.6 (dd, 1H), 3.45 (dd, 1H), 2.7 (m, 1H), 2.5 (m, 1H).

(3S)-3-[(3S)-2-oxo-3-benzoylamino-5-benzoyl-2,3,4,5-tetrahydro-1H-1,5-benzodiazepin-1-acetylamino]-4-oxo-butyric acid (605c). 319 mg (56%) as a white solid: $^1H$ NMR ($CD_3OD$) δ 7.9-6.9 (m, 16H), 5.1 (m, 1H), 4.9 (dd, 1H), 4.7 (m, 1H), 4.6 (dd, 1H), 4.4 (m, 2H), 4.05 (m, 1H), 2.7 (m, 1H), 2.5 (m, 1H).

(3S)-3-[(3S)-2-oxo-3-benzoylamino-5-acetyl-2,3,4,5-tetrahydro-1H-1,5-benzodiazepin-1-acetylamino]-4-oxo-butyric acid (605d). 190 mg (38%) as a white solid: $^1H$ NMR ($CD_3OD$) δ 1.9 (d, H), 2.4 (m, 1H), 2.65 (m, 1H), 3.7 (m, 1H), 4.25 (m, 1H), 4.45 (m, 2H), 4.8-5.05 (m, 3H), 7.3-7.7 (m, 7H), 7.9 (d, 2H).

(3S)-3-[(3S)-2-oxo-3-benzoylamino-5-methoxyacetyl-2,3,4,5-tetrahydro-1H-1,5-benzodiazepin-1-acetylamino]-4-oxo-butyric acid (605e). 250 mg (78%) $^1H$ NMR ($CD_3OD$) δ 1.87 (bs), 1.95 (s, 2H), 2.1 (bs), 2.4 (m, 2H), 2.65 (m, 2H), 3.59 (bs), 3.75 (bs), 3.87 (bs), 4.19 (m), 4.37 (m), 4.50-4.78 (bm), 4.92 (m), 5.27 (bs), 7.41-7.58 (m, 7H), and 7.87 ppm (d, 2H).

(3S)-3-[(3S)-2-oxo-3-benzoylamino-5-(3-methylbutyryl)-2,3,4,5-tetrahydro-1H-1,5-benzodiazepin-1-acetylamino]-4-oxo-butyric acid (605f). 210.5 mg (46%) as a white solid: $^1H$ NMR ($CD_3OD$) δ 7.9-7.4 (m, 9H), 5.1 (m, 1H), 4.9 (m, 1H), 4.6 (dd, 1H), 4.4 (m, 2H), 4.1 (d, 1H), 3.8 (m, 1H), 3.5 (q, 1H), 2.7 (m, 1H), 2.5 (m, 1H), 2.0 (m, 3H), 1.2 (t, 1H), 0.9 (d, 3H), 0.8 (d, 3H).

(3S)-3-[(3S)-2-oxo-3-benzoylamino-5-acetoacetyl-2,3,4,5-tetrahydro-1H-1,5-benzodiazepin-1-acetylamino]-4-oxo-butyric acid (605g). 81 mg (19%) as a white solid: $^1$H NMR (CD$_3$OD) δ 7.9-7.3 (m, 11H), 4.9-4.8 (m, 2H), 4.6-4.4 (m, 3H), 4.3 (m, 1H), 3.75 (q, 1H), 3.55 (d, 1H), 2.7 (m, 1H), 2.5 (m, 1H), 2.05 (s, 3H).

(3S)-3-[(3S)-2-oxo-3-benzoylamino-5-methyloxalyl-2,3,4,5-tetrahydro-1H-1,5-benzodiazepin-1-acetylamino]-4-oxo-butyric acid (605h). 227 mg (54%) of a white solid: $^1$H NMR (CD$_3$OD) δ 2.5 (m, 1H), 2.7 (m, 1H), 3.55 (s, 3H), 3.8-4.0 (m, 2H), 4.4 (m, 1H), 4.6-4.8 (m, 2H), 4.95 (d, 1H), 5.1 (m, 1H), 7.3-7.7 (m, 7H), 7.9 (d, 2H), 8.6 (d, 1H).

(3S)-3-[(3S)-2-oxo-3-benzoylamino-5-acetylcarbonyl-2,3,4,5-tetrahydro-1H-1,5-benzodiazepin-1-acetylamino]-4-oxo-butyric acid (605i). 150 mg (37%) as a white solid: $^1$H NMR (CD$_3$OD) δ 7.9-7.3 (m, 12H), 5.1 (m, 1H), 4.65 (t, 1H), 4.55 (dd, 1H), 4.35 (m, 1H), 4.1 (d, 1H), 3.9 (q, 1H), 3.45 (q, 1H), 2.7 (m, 1H), 2.5 (m, 1H), 2.25 (s, 3H).

(3S)-3-[(3S)-2-oxo-3-benzoylamino-5-methoxycarbonyl-2,3,4,5-tetrahydro-1H-1,5-benzodiazepin-1-acetylamino]-4-oxo-butyric acid (605j). 234 mg (44%) as a white solid: $^1$H NMR (CD$_3$OD) δ 7.9-7.4 (m, 12H), 5.0 (m, 1H), 4.8-4.5 (m, 3H), 4.4 (m, 1H), 4.3 (t, 1H), 3.9-3.75 (m, 2H), 3.6 (s, 3H), 2.7 (m, 1H), 2.5 (m, 1H).

(3S)-3-[(3S)-2-oxo-3-benzoylamino-5-methanesulfonyl-2,3,4,5-tetrahydro-1H-1,5-benzodiazepin-1-acetylamino]-4-oxo-butyric acid (605m). 64.5 mg (34%) as a white solid: $^1$H NMR (DMSO-d$_6$, existing as diastereomers of the hemiacetal & open form of the aldehyde) δ 9.48 (0.2H, s), 8.85-8.72 (1H, m), 8.65-8.60 (0.8H, d), 8.30-8.26 (0.2H, d), 7.95-7.88 (2H, d), 7.6-7.45 (6H, m), 7.44-7.38 (1H, m), 5.78-5.75 (0.2H, d), 5.48 (0.6H, s), 4.85-4.70 (2H, m), 4.62-4.54 (1H, d), 4.50-4.40 (2H, m), 4.25-4.14 (1H, m), 3.9-3.85 (1H, m), 3.16 (3H, s), 3.05-2.3 (2, m).

(3S)-3-[(3S)-2-oxo-3-benzoylamino-5-(naphthlene-2-carbonyl)-2,3,4,5-tetrahydro-1H-1,5-benzodiazepin-1-acetylamino]-4-oxo-butyric acid (605n). 103 mg (17%) as a white solid: $^1$H NMR (CD$_3$OD) δ 1.9 (s, 3H), 2.5 (m, 1H), 2.65 (m, 1H), 3.75 (m, 1H), 4.3 (m, 1H), 4.5-4.7 (m, 3H), 4.85-5.1 (m, 2H), 7.3-7.65 (m, 6H), 7.85-8.05 (m, 4H), 8.45 (s, 1H).

(3S)-3-[(3S)-2-oxo-3-benzoylamino-5-acetyl-2,3,4,5-tetrahydro-7,9-dimethyl-1H-1,5-benzodiazepin-1-acetylamino]-4-oxo-butyric acid (605o). 42 mg (12%) as a white solid: $^1$H NMR (CD$_3$OD, existing as diastereomers of the hemiacetal) δ 7.85-7.74 (2H, m), 7.5-7.44 (1H, m), 7.43-7.35 (4H, m), 5.6-5.05 (2H, m), 4.82-4.42 (2H, m), 4.40-3.95 (2H, m), 3.6-3.5 (1H, m), 2.7-2.38 (2H, m), 2.32 (3H, s), 2.27 (3H, s), 1.92 (3H, s).

(3S)-3-[(3S)-2-oxo-3-benzoylamino-5-benzylaminocarbonyl-2,3,4,5-tetrahydro-1H-1,5-benzo diazepin-1-acetylamino]-4-oxo-butyric acid (605p). 165 mg (37%) as a white solid: $^1$H NMR (CD$_3$OD) δ 2.45 (m, 1H), 2.7 (m, 1H), 3.8 (m, 1H), 4.15-4.5 (m, 4H), 4.5-4.75 (m, 2H), 4.8-5.0 (m, 2H), 7.1-7.7 (m, 12H), 70.9 (d, 2H).

(3S)-3-[(3S)-2-Oxo-3-benzoylamino-5-[(3R,S)3-tetrahydrofuranylmethyoxycarbonyl]-2,3,4,5-tetrahydro-1H-1,5-benzodiazepin-1-acetylamino]-4-oxo-butyric acid (605q). 210 mg (66%) $^1$H NMR (CD$_3$OD) δ 1.95 (s, 2H), 2.4 (m, 2H), 2.65 (m, 2H), 3.29 (s, 3H), 3.78 (m), 3.87 (bs), 4.0 (d, 1H), 4.32 (m), 4.50-4.15 (m), 4.95 (m), 5.27 (bs), 7.45-7.65 (m, 7H), and 7.89 ppm (d, 2H).

(3S)-3-[(3S)-2-oxo-3-benzoylamino-5-(4-pyridylacetyl)-2,3,4,5-tetrahydro-1H-1,5-benzodiazepin-1-acetylamino]-4-oxo-butyric acid (605s). 128 mg (19%) as a white solid: $^1$H NMR (CD$_3$OD) δ 8.5-7.4 (m, 13H), 5.0 (m, 1H), 4.7 (m, 1H), 4.5 (m, 2H), 4.45-4.4 (m, 3H), 3.8-3.7 (m, 2H), 2.7 (m, 1H), 2.5 (m, 1H).

(3S)-3-[(3S)-2-Oxo-3-benzoylamino-5-(3-methylphenylacetyl)-2,3,4,5-tetrahydro-1H-1,5-benzodiazepin-1-acetylamino]-4-oxo-butyric acid (605t). 132 mg (24%) as a white solid: $^1$H NMR (CD$_3$OD) δ 7.8-6.7 (m, 13H), 4.9 (t, 1H), 4.75 (dd, 1H), 4.2 (dd, 1H), 4.1 (m, 2H), 3.8 (dd, 1H), 3.6 (q, 1H), 3.45 (dd, 1H), 3.3 (dd, 1H), 2.6 (m, 1H), 2.3 (m, 1H), 2.15 (s, 3H).

(3S)3-[(3S)2-oxo-3-benzylamino-5-(3-phenylpropionyl)-2,3,4,5-tetrahydro-1H-1,5-benzodiazepin-1-acetylamino]-4-oxo-butyric acid trifluoroacetic acid salt (605v). 88 mg (28%) as a white solid: $^1$H NMR (CD$_3$OD) δ 7.63-7.51 (2H, m), 7.5-7.35 (7H, m), 7.25-7.10 (3H, m), 7.1-7.02 (2H, m), 5.04-4.96 (1H, m), 4.75-4.57 (2H, m), 4.38-4.26 (2H, m), 4.24-4.12 (2H, m), 4.10-4.02 (1H, d), 4.88-4.80 (1H, m), 2.90-2.80 (2H, m), 2.78-2.63 (1H, m), 2.55-2.35 (2H, m), 2.34-2.22 (1H, m).

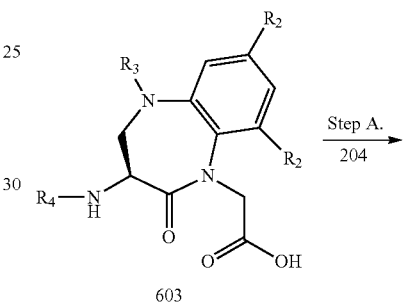

603

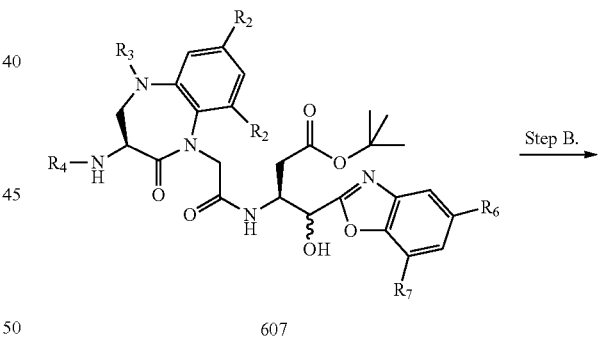

607

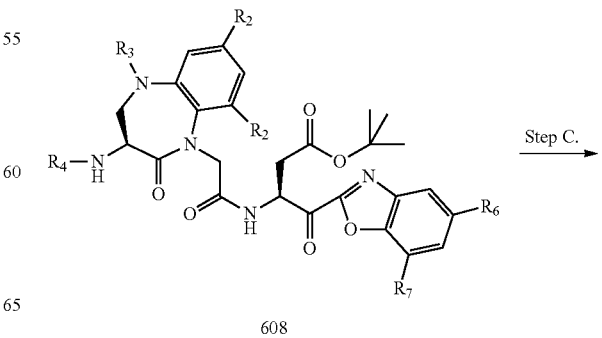

608

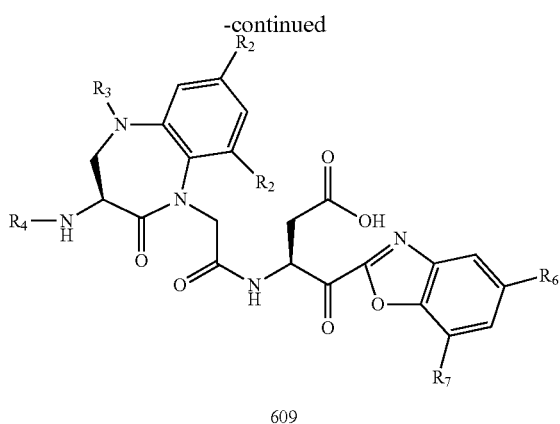

609

The compounds of Table 13 are described below.

TABLE 13

| # | $R_2$ | $R_3$ | $R_4$ | $R_6$ | $R_7$ |
|---|---|---|---|---|---|
| 609a | H | PhCH$_2$CH$_2$C(O) | PhCH$_2$CH$_2$C(O) | Cl | Cl |
| 609b | H | CH$_3$C(O) | PhC(O) | Cl | Cl |

(3S)-3-[(3S)-2-oxo-3-(3-phenylpropionylamino)-5-(3-phenylpropionyl)-2,3,4,5-tetrahydro-1H-1,5-benzodiazepin-1-acetylamino)]-4-(5,7-dichlorobenzoxazol-2-yl)-4-oxo-butyric acid (609a).

Step A. A solution of 204 (223 mg, 0.5 mmol) and 603r (300 mg; 0.36 mmol) in 4 ml of DMF and 4 ml of CH$_2$Cl$_2$ was treated with (Ph$_3$P)$_2$PdCl$_2$ (10 mg), 1-hydroxybenzotriazle (135 mg, 1.0 mmol) and 1-(3-dimethylaminopropyl)-3-ethylcarbodiimide hydrochloride (115 mg, 0.6 mmol). Tri-n-butyl tin hydride (219 mg, 0.75 mmol) was added dropwise to the reaction and stirred for 18 h. The reaction was poured onto EtOAc and washed with aq. 10% NaHSO$_4$, sat. aq. NaHCO$_3$ and sat. aq. NaCl, dried over Na$_2$SO$_4$ and concentrated in vacuo. Chromatography (flash, SiO$_2$, 0% to 50% EtOAc/hexane) gave 360 mg (86%) of 607a as a foam.

Step B. A solution of 607a (360 mg) in 5 ml of CH$_2$Cl$_2$ was added dropwise to a suspension of 1,1,1-triacetoxy-1,1-dihydro-1,2-benziodioxol-3(1H)-one (362 mg, 0.85 mmol) in 20 ml of CH$_2$Cl$_2$. The reaction was stirred for 4.5 h, diluted with CH$_2$Cl$_2$ and washed with a 1:1 mixture of sat. aq. NaHCO$_3$/sat. aq. Na$_2$S$_2$O$_3$, sat. aq. NaHCO$_3$ (2×) and sat. aq. NaCl, dried over Na$_2$SO$_4$ and concentrated in vacuo. Chromatography (flash, SiO$_2$, 20% EtOAc/CH$_2$Cl$_2$) gave 340 mg (95%) of the ketone 608a.

Step C. 608a (300 mg, 0.36 mmol) was dissolved in 25 ml of 25% TFA/CH$_2$Cl$_2$ and stirred at RT for 5 h and concentrated in vacuo. Chromatography (flash, SiO$_2$, 0 to 5% MeOH/CH$_2$Cl$_2$) gave 118 mg (42%) of 609a as a white solid: $^1$H NMR (CD$_3$OD) δ 7.62-6.65 (16H, m), 4.85-4.7 (1H, m), 4.68-4.42 (2H, m), 4.40-4.15 (2H, m), 3.48-3.28 (1H, m), 3.0-2.9 (1H, m), 2.9-2.6 (4H, m), 2.55-2.18 (3H, m), 2.16-1.96 (2H, m).

(3S)-3-[(3S)-2-oxo-3-benzoylamino-5-acetyl-2,3,4,5-tetrahydro-1H-1,5-benzodiazepin-1-acetylamino]-4-(5,7-dichlorobenzoxazol-2-yl)-4-oxo-butyric acid (609b) was prepared from 603d in a similar manner as 609a to give 287 mg (43% overall yield) as white solid: $^1$H NMR (DMSO-d$_6$) δ 1.6 (s, 3H), 2.7-3.1 (m, 2H), 3.45 (m, 1H), 4.4 (t, 1H), 4.7 (m, 2H), 4.95 (m, 1H), 5.2, 5.4 (2s, 1H), 7.2-7.65 (m, 8H), 7.9 (d, 2H), 8.8 (t, 1H), 8.9, 9.1 (2s, 1H), 12.6 (br, 1H).

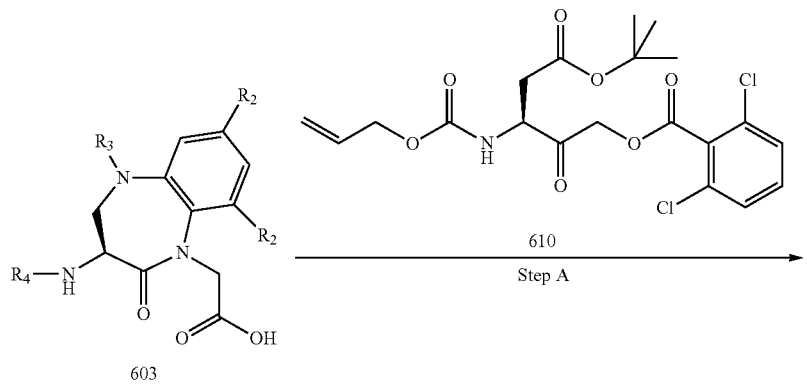

603

610

Step A

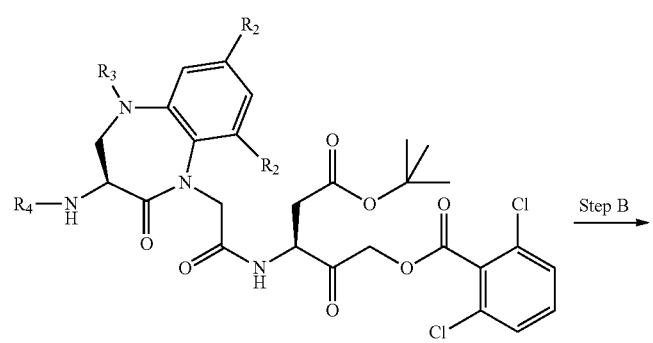

611

Step B

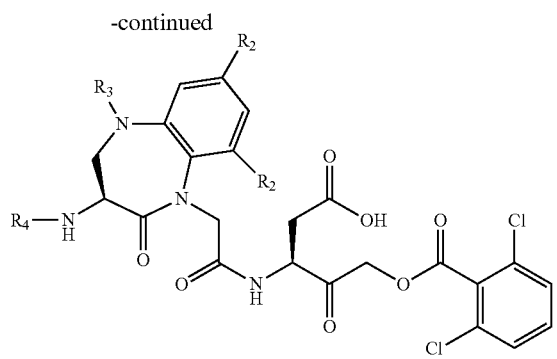

612

(3S)-3-[(3S)-2-oxo-3-benzoylamino-5-methanesulfonyl-2,3,4,5-tetrahydro-1H-1,5-benzodiazepine-1-acetylamino]-5-(2,6-dichlorobenzoyloxy)-4-oxo-pentanoic acid (612) was prepared by a method similar as 607a (Steps A and C only) using 603m (150 mg, 0.36 mmol) instead of 603r and (3S)-3-(allyloxycarbonylamino)-4-oxo-5-(2,6-dichlorobenzoyloxy)pentanoic acid t-butyl ester (110; 160 mg, 0.36 mmol, WO 93/16710) instead of 606a to give 612 (56%) as a white solid: $^1$H NMR (CDCl$_3$) 7.85-7.10 (12H, m), 5.4-4.65 (4H, m), 4.6-4.15 (4H, m), 3.10-2.72 (5H, s & m).

EXAMPLE 13

Compounds 619-635 were synthesized as described in Example 13 and Table 14.

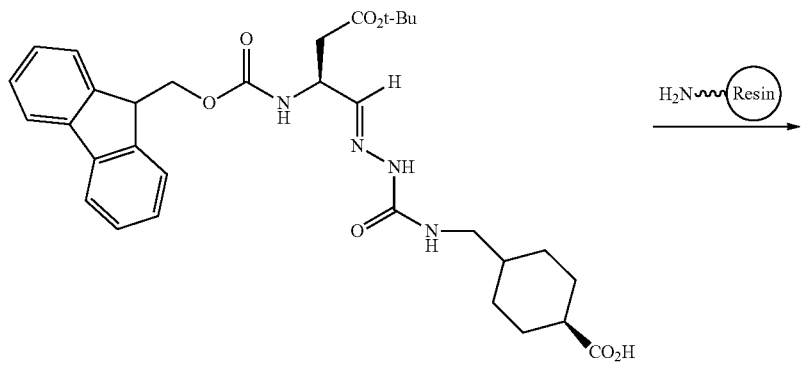

400

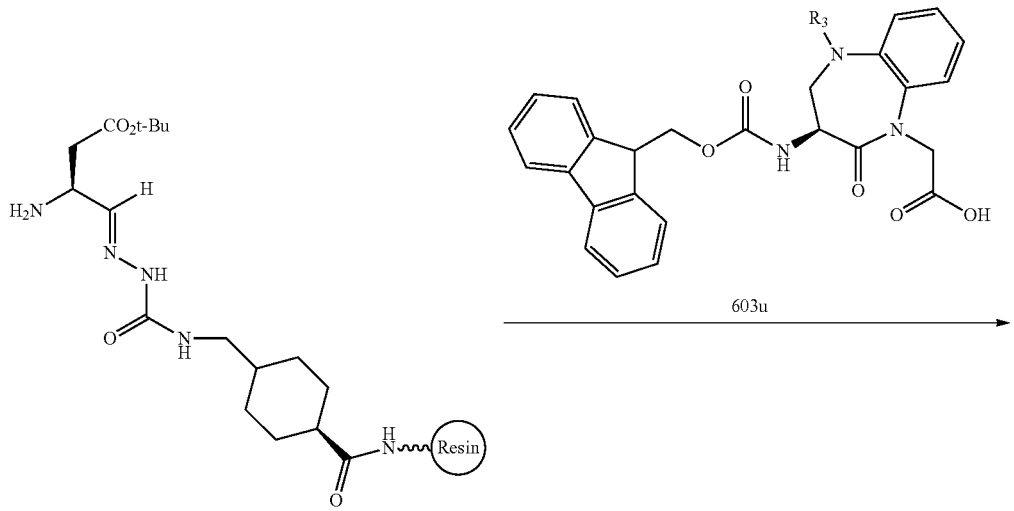

614

-continued
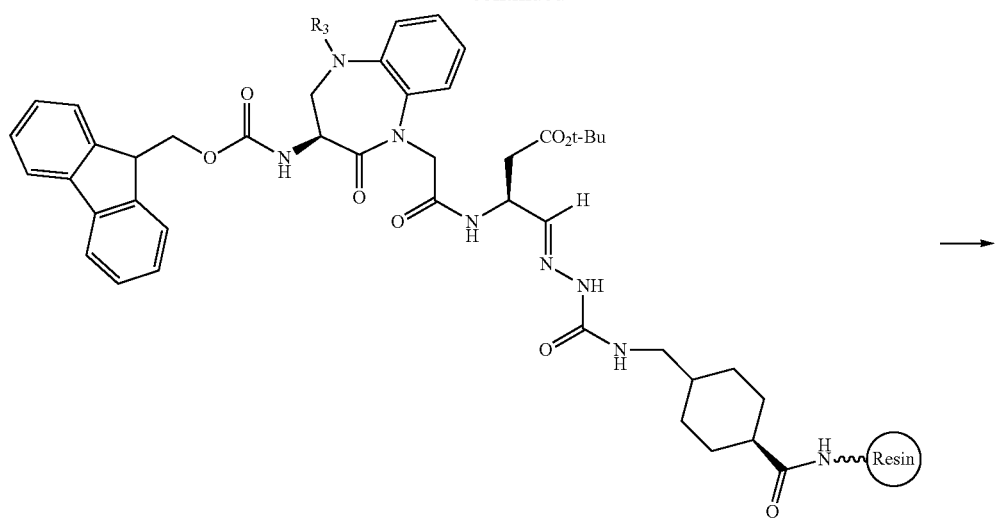
616
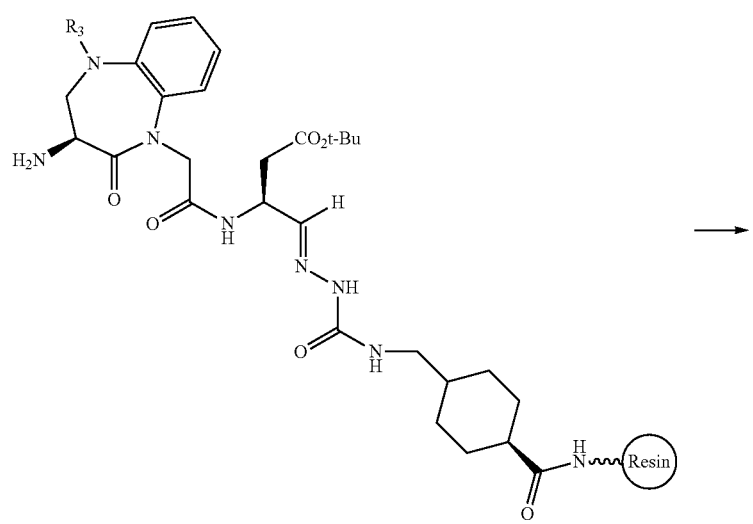
617
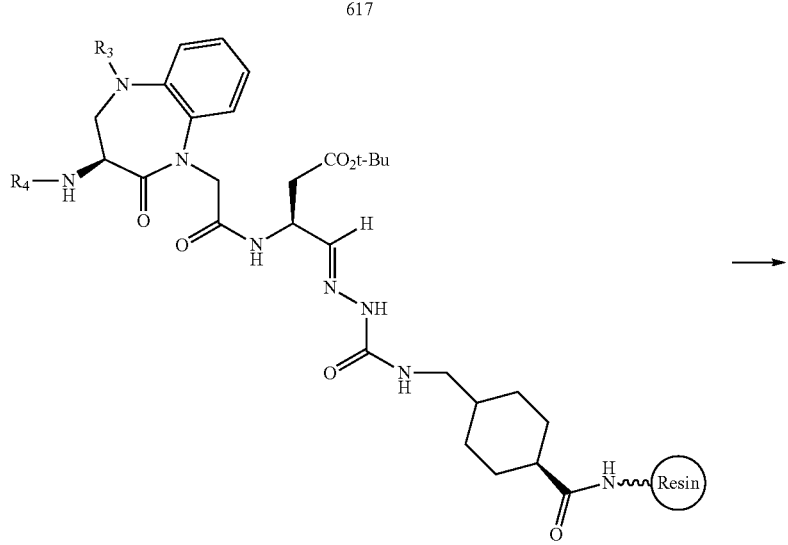
618
R₃ = CH₃C(O)

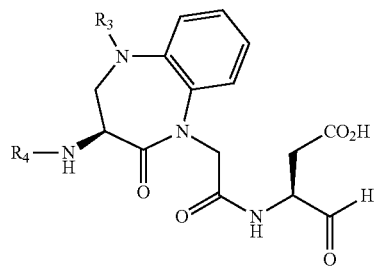

619-635

Syntheses of 619-635.

Step A. Synthesis of 614. TentaGel S® $NH_2$ resin (0.16 mmol/g, 10.0 g) was placed in a sintered glass funnel and washed with dimethylformamide (3×50 mL), 10% (v/v) diisopropylethylamine (DIEA) in dimethylformamide (2×50 mL) and finally with dimethylformamide (4×50 mL). Sufficient dimethylformamide was added to the resin to obtain a slurry followed by 400 (1.42 g, 2.4 mmol, prepared from (3S)3-(fluorenylmethyloxycarbonyl)-4-oxobutryic acid t-butyl ester according to A. M. Murphy et. al. *J. Am. Chem. Soc.,* 114, 3156-3157 (1992)), 1-hydroxybenzotriazole hydrate ($HOBT.H_2O$; 0.367 g, 2.4 mmol), O-benzotriazole-N,N,N,N'-tetramethyluronium hexafluorophosphate (HBTU; 0.91 g, 2.4 mmol), and DIEA (0.55 mL, 3.2 mmol). The reaction mixture was agitated overnight at room temperature using a wrist arm shaker. The resin was isolated on a sintered glass funnel by suction filtration and washed with dimethylformamide (3×50 mL). Unreacted amine groups were then capped by reacting the resin with 20% (v/v) acetic anhydride/dimethylformamide (2×25 mL) directly in the funnel (10 min/wash). The resin was washed with dimethylformamide (3×50 mL) and dichloromethane (3×50 mL) prior to drying overnight in vacuo to yield 614 (11.0 g, quantitative yield).

Step B. Synthesis of 616. Resin 614 (3.0 g, 0.16 mmol/g, 0.48 mmol) was swelled in a sintered glass funnel by washing with dimethylformamide (3×15 mL). The Fmoc protecting group was then cleaved with 25% (v/v) piperidine/dimethylformamide (15 mL) for 10 min (intermittent stirring) and then for 20 min with fresh piperidine reagent (15 ml). The resin was then washed with dimethylformamide (3×15 ml), followed by N-methypyrrolidone (2×15 mL). After transferring the resin to a 100 mL flask, N-methypyrrolidone was added to obtain a slurry followed by 603u (0.736 g, 0.72 mmol), $HOBT.H_2O$ (0.112 g, 0.73 mmol), HBTU (0.27 g, 0.73 mmol) and DIEA (0.26 mL, 1.5 mmol). The reaction mixture was agitated overnight at room temperature using a wrist arm shaker. The resin work-up and capping with 20% (v/v) acetic anhydride in dimethylformamide were performed as described for 614 to yield 616 (3.13 g, quantitative yield).

Step C. Synthesis of 617. This compound was prepared from resin 616 (0.24 g, 0.038 mmol) using an Advanced ChemTech 396 Multiple Peptide synthesizer.

The automated cycles consisted of a resin wash with dimethylformamide (3×1 mL), deprotection with 25% (v/v) piperidine in dimethylformamide (1 mL) for 3 min followed by fresh reagent (1 mL) for 10 min to yield resin 617. The resin was washed with dimethylformamide (3×1 mL) and N-methypyrrolidone (3×1 mL).

Step D. Method 1. (624). Resin 617 was acylated with a solution of 0.4M thiophene-3-carboxylic acid and 0.4M HOBT in N-methypyrrolidone (1 mL), a solution of 0.4M HBTU in N-methylpyrrolidone (0.5 mL) and a solution of 1.6M DIEA in N-methypyrrolidone (0.35 mL) and the reaction was shaken for 2 hr at room temperature. The acylation step was repeated. Finally, the resin was washed with dimethylformamide (3×1 mL), dichloromethane (3×1 mL) and dried in vacuo. The aldehyde was cleaved from the resin and globally deprotected by treatment with 95% TFA/5% H2O (v/v, 1.5 mL) for 30 min at room temperature. After washing the resin with cleavage reagent (1 mL), the combined filtrates were added to cold 1:1 ether:pentane (12 mL) and the resulting precipitate was isolated by centrifugation and decantation. The resulting pellet was dissolved in 10% acetonitrile/90% $H_2O$/0.1% TFA (15 mL) and lyophilized to obtain crude 624 as a white powder. The compound was purified by semi-prep RP-HPLC with a Rainin Microsorb™ C18 column (5u, 21.4×250 mm) eluting with a linear acetonitrile gradient (5%-45%) containing 0.1% TFA (v/v) over 45 min at 12 mL/min. Fractions containing the desired product were pooled and lyophilized to provide 624 (10.0 mg, 54%).

Step D. Method 1A. Synthesis of 627. Following a similar procedure as method 1, resin 617 was acylated with 4-(1-fluorenylmethoxycarbonylamino)benzoic acid and repeated. The Fmoc group was removed as described in Step C and the free amine was acetylated with 20% (v/v) acetic anhydride in dimethylformamide (1 mL) and 1.6M DIEA in N-methylpyrrolidone (0.35 mL) for 2 hr at room temperature. The acetylation step was repeated. Cleavage of the aldehyde from the resin gave 627 (4.2 mg, 20%).

Step D. Method 2. Synthesis of 632. Following a similar procedure as method 1, resin 617 was acylated with 0.5M cinnamoyl chloride in N-methypyrrolidone (1 mL) and 1.6M DIEA in N-methypyrrolidone (0.35 mL) for 2 hr at room temperature. The acylation step was repeated. Cleavage of the aldehyde from the resin gave 632 (11.1 mg, 58%).

Step D. Method 3. Synthesis of 629. Following a similar procedure as method 1, resin 617 was reacted with 1.0M benzenesulfonyl chloride in dichloromethane (0.5 mL) and 1M pyridine in dichloromethane (0.60 mL) for 4 hr at room temperature. The reaction was repeated. Cleavage of the aldehyde from the resin 629 (4.7 mg, 24%).

Analytical HPLC Methods:

(1) Waters DeltaPak C18, 300 A (5u, 3.9×150 mm). Linear acetonitrile gradient (5%-45%) containing 0.1% TFA (v/v) over 14 min at 1 mL/min.

TABLE 14

| Cmpd. | Structure | MF | MW | HPLC RT min | MS (M + H)+ | Syn. Method |
|---|---|---|---|---|---|---|
| 619 | 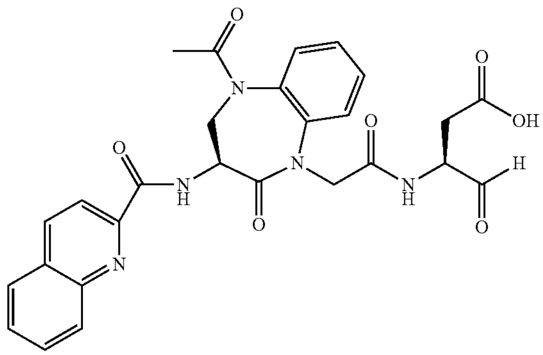 | C27H25N5O7 | 531.53 | 11.71 (1) 98% | 532 | 1 |
| 620 | 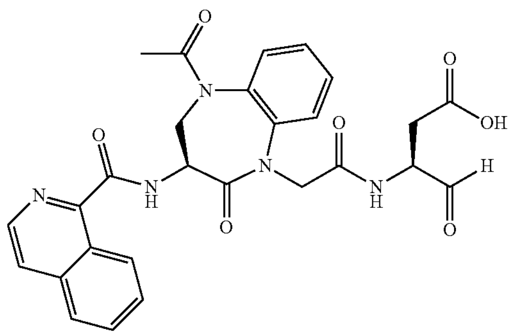 | C27H25N5O7 | 531.53 | 10.44 (1) 98% | 532 | 1 |
| 621 | 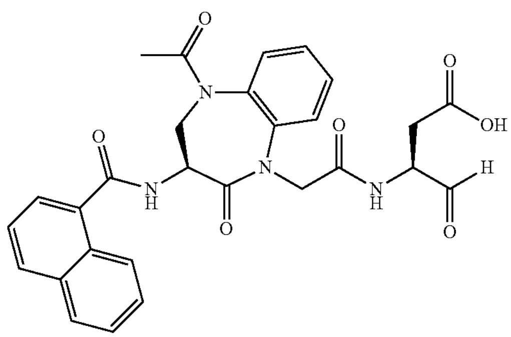 | C28H26N4O7 | 530.54 | 11.57 (1) 98% | (M + 2 Na)+ 553 | |
| 622 | 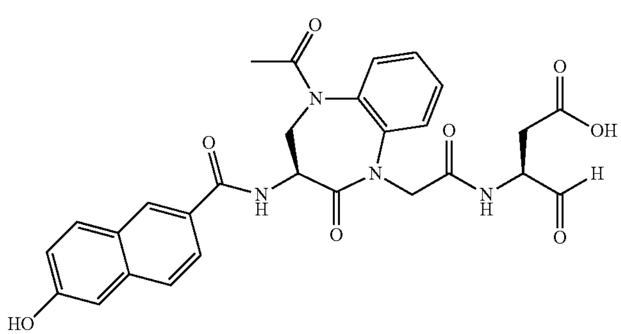 | C28H26N4O8 | 546.54 | 10.19 (1) 98% | (M + 1 Na)+ 569 | |

TABLE 14-continued

| Cmpd. | Structure | MF | MW | HPLC RT min | MS (M + H)+ | Syn. Method |
|---|---|---|---|---|---|---|
| 623 | 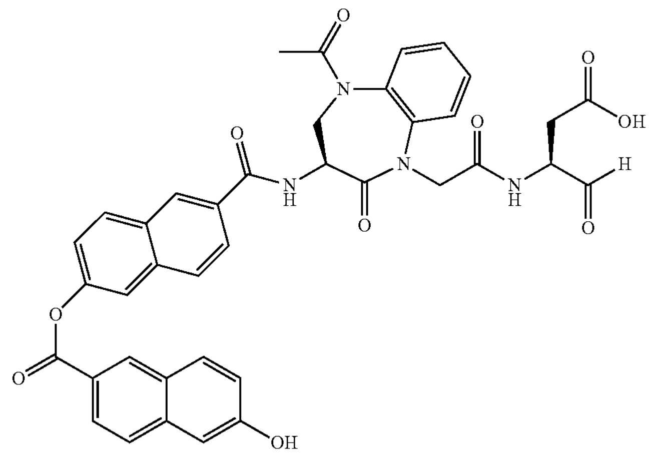 | C39H32N4O10 | 716.71 | 15.8 (1) 09% | (M−) 716 | 1 |
| 624 | 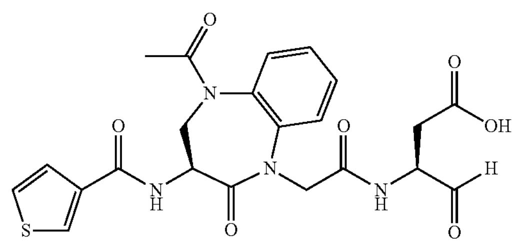 | C22H22N4O7S | 486.51 | 8.39 (1) 98% | 487 | 1 |
| 625 | 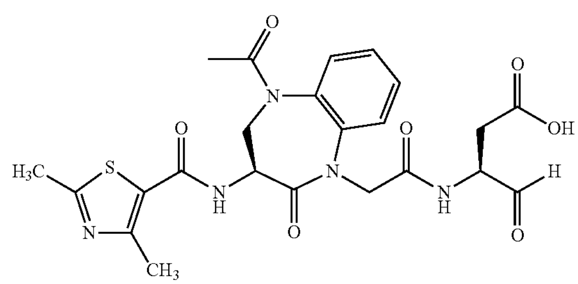 | C23H25N5O7S | 515.55 | 7.60 (1) 98% | 516 | 1 |
| 626 | 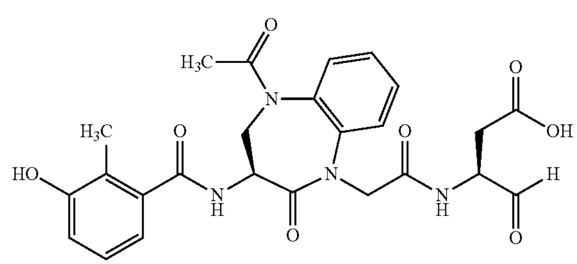 | C25H26N4O8 | 510.51 | 7.58 (1) 98% | 511 | 1 |
| 627 | 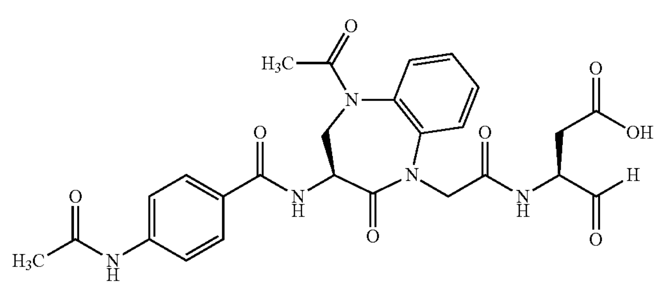 | C26H27N5O8 | 537.53 | 7.96 (1) 98% | 538 | 1A |

TABLE 14-continued

| Cmpd. | Structure | MF | MW | HPLC RT min | MS (M + H)+ | Syn. Method |
|---|---|---|---|---|---|---|
| 628 | 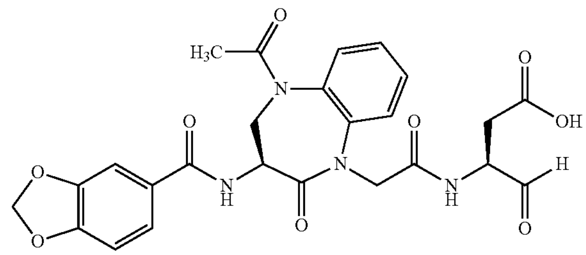 | C25H24N4O9 | 524.49 | 9.50 (1) 98% | 525 | 1 |
| 629 | 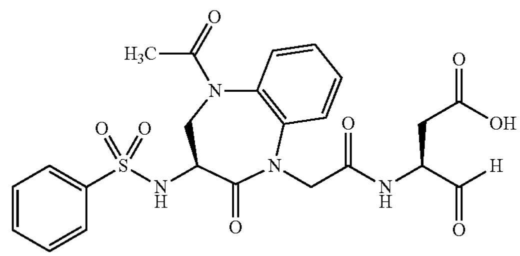 | C23H24N4O8S | 516.53 | 9.85 (1) 98% | 517 | 3 |
| 630 | 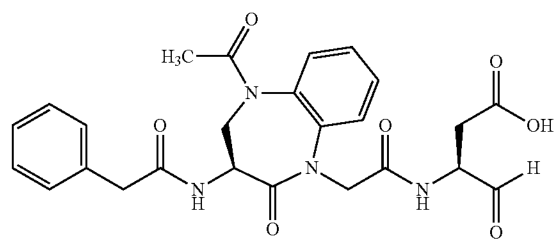 | C25H26N4O7 | 494.51 | 9.25 (1) 98% | 495 | 2 |
| 631 | 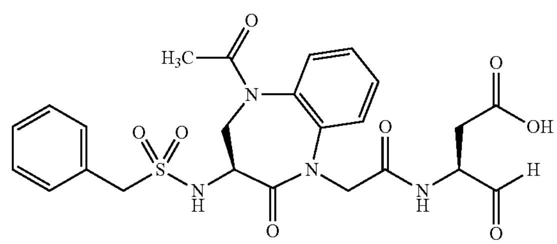 | C24H26N4O8S | 530.56 | 10.19 (1) 98% | 531 | 3 |
| 632 | 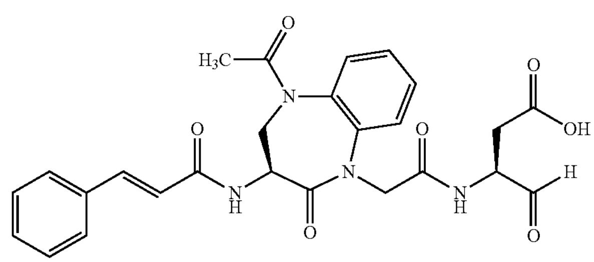 | C26H26N4O7 | 506.52 | 10.99 (1) 98% | 507 | 2 |
| 633 | 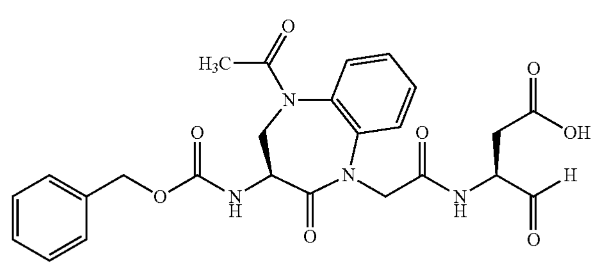 | C25H26N4O8 | 510.51 | 11.48 (1) 98% | 511 | 2 |

TABLE 14-continued

| Cmpd. | Structure | MF | MW | HPLC RT min | MS (M+H)+ | Syn. Method |
|---|---|---|---|---|---|---|
| 634 | 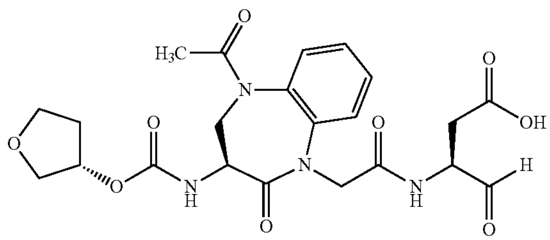 | C22H26N4O9 | 490.47 | 6.87 (1) 98% | 491 | 2 |
| 635 | 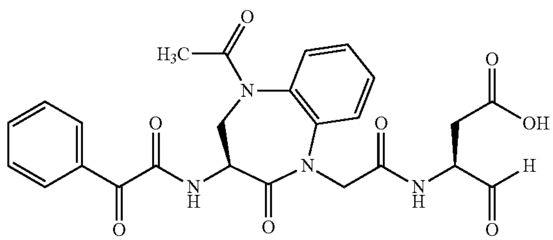 | C25H24N4O8 | 508.49 | 10.03 (1) 98% | 509 | 1 |

EXAMPLE 14

Compounds 1605a-j, 1605m, 1605n, 1605p, 1605t, and 1605v were synthesized as described below.

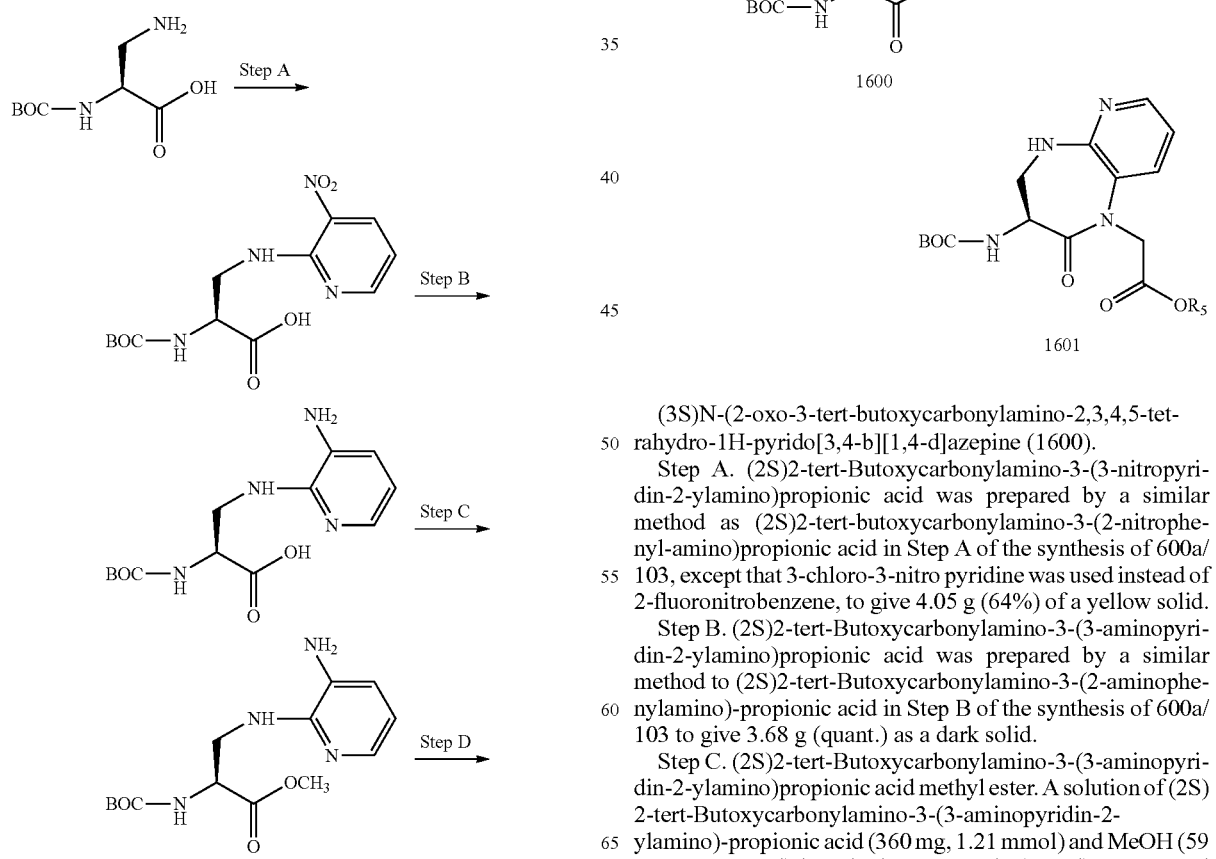

(3S)N-(2-oxo-3-tert-butoxycarbonylamino-2,3,4,5-tetrahydro-1H-pyrido[3,4-b][1,4-d]azepine (1600).

Step A. (2S)2-tert-Butoxycarbonylamino-3-(3-nitropyridin-2-ylamino)propionic acid was prepared by a similar method as (2S)2-tert-butoxycarbonylamino-3-(2-nitrophenyl-amino)propionic acid in Step A of the synthesis of 600a/103, except that 3-chloro-3-nitro pyridine was used instead of 2-fluoronitrobenzene, to give 4.05 g (64%) of a yellow solid.

Step B. (2S)2-tert-Butoxycarbonylamino-3-(3-aminopyridin-2-ylamino)propionic acid was prepared by a similar method to (2S)2-tert-Butoxycarbonylamino-3-(2-aminophenylamino)-propionic acid in Step B of the synthesis of 600a/103 to give 3.68 g (quant.) as a dark solid.

Step C. (2S)2-tert-Butoxycarbonylamino-3-(3-aminopyridin-2-ylamino)propionic acid methyl ester. A solution of (2S) 2-tert-Butoxycarbonylamino-3-(3-aminopyridin-2-ylamino)-propionic acid (360 mg, 1.21 mmol) and MeOH (59 mg, 1.82 mmol) in anhydrous $CH_2Cl_2$ (20 ml) was treated with 4-dimethylaminopyridine (DMAP, 163 mg, 1.33 mmol)

and 1-(3-dimethylaminopropyl)-3-ethylcarbodiimide hydrochloride (280 mg, 1.45 mmol). The reaction was stirred for 18 h, diluted with EtOAc (150 ml), washed with water (2×), sat. aq. NaHCO₃, and sat. aq. NaCl, dried over Na₂SO₄ and concentrated in vacuo. Chromatography (flash, SiO₂, 0 to 5% MeOH/CH₂Cl₂) gave 250 mg (67%) of the title compound as a light tan solid.

Step D. (3S)N-(2-Oxo-3-tert-butoxycarbonylamino-2,3,4,5-tetrahydro-1H-pyrido[3,4-b][1,4-d]azepine (1600). A solution of (2S)2-tert-butoxycarbonylamino-3-(3-aminopyridin-2-ylamino)prop ionic acid methyl ester (70 mg, 0.225 mol) and 25% sodium methoxide/MeOH (130 μl, 0.56 mmol) in anhydrous MeOH (4 ml) was heated at 60° C. for 16 h. The reaction was concentrated in vacuo, the residue dissolved in 2 ml of H₂O and extracted with EtOAc (3×). The combined extracts were dried over Na₂SO₄ and concentrated in vacuo. Chromatography (flash, SiO₂, 0 to 3% MeOH/CH₂Cl₂) gave 7.5 mg (3%) of 1600 as a light tan solid: ¹H NMR (CD₃OD) δ 7.96-7.92 (1H, d), 7.75-7.65 (1H, br. s), 7.14-7.08 (1H, d), 6.73-6.65 (1H, m), 5.83-5.75 (1H, br. s), 5.4-5.25 (1H, br. s), 4.6-4.5 (1H, m), 3.95-3.84 (1H, m), 3.55-3.48 (1H, m), 1.4 (9H, s)

Step E. 1601 is prepared from 1600 following the method in Step D for the preparation 600a/103.

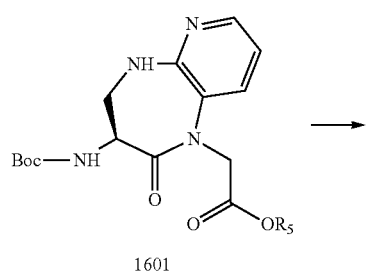

1601

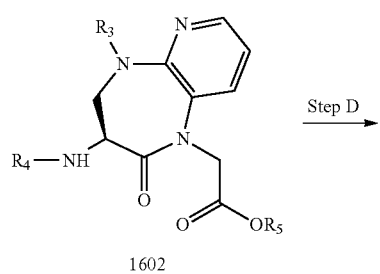

1602

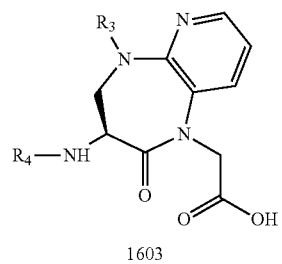

1603

Synthesis of 1603. 1603 is prepared from 1601 following the methods for the synthesis of 603 from 600.

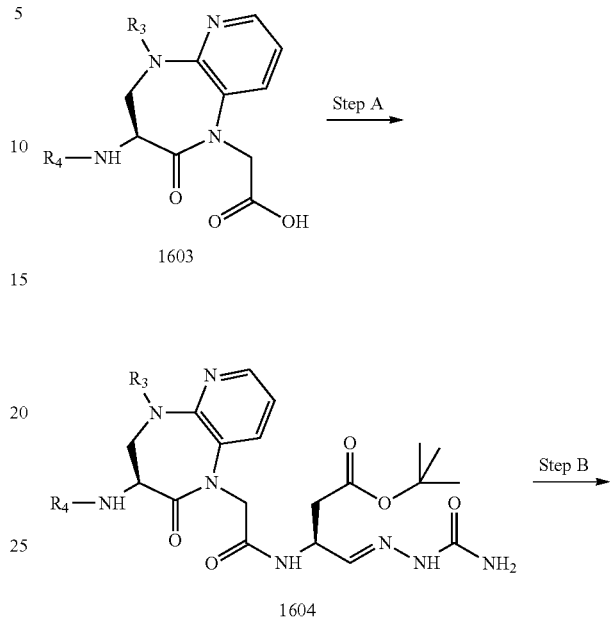

1603

1604

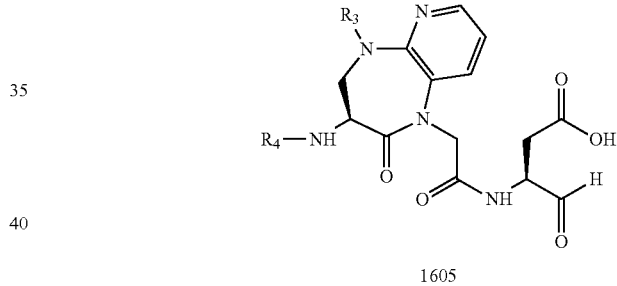

1605

Synthesis of 1605. 1605 is prepared from 1603 by methods described for the synthesis of 605 from 603.

TABLE 15

| 1605 | R₃ | R₄ |
|---|---|---|
| a | PhCH₂CH₂CO | PhCO |
| b | PhCH₂CO | PhCO |
| c | PhCO | PhCO |
| d | CH₃CO | PhCO |
| e | CH₃OCH₂CO | PhCO |
| f | (CH₃)₂CHCH₂CO | PhCO |
| g | CH₃COCH₂CO | PhCO |
| h | CH₃OCOCO | PhCO |
| i | CH₃COCO | PhCO |
| j | CH₃OCO | PhCO |
| m | CH₃SO₃ | PhCO |
| n | CH₃CO | Naphthyl-2-CO |
| p | PhCH₂NHCO | PhCO |
| t | 3-CH₃PhCH₂CO | PhCO |
| v | PhCH₂CH₂CO | PhCH₂ |

EXAMPLE 15
Compounds 1610-1621 are prepared from 1600 by methods similar to the methods used to prepare compounds 619-635 from 600a/103 and 600b.
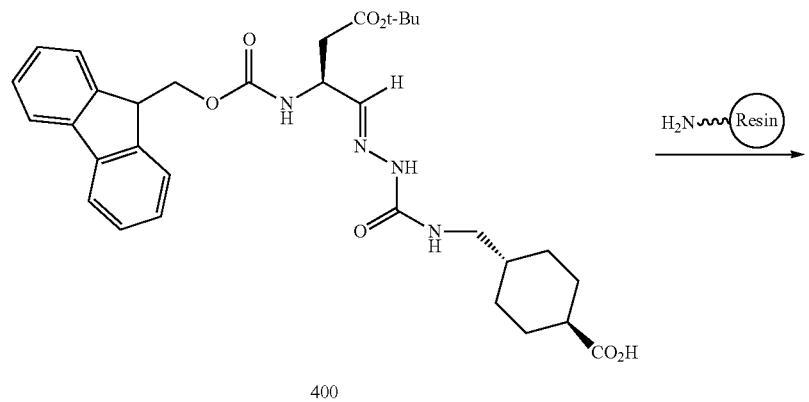
400
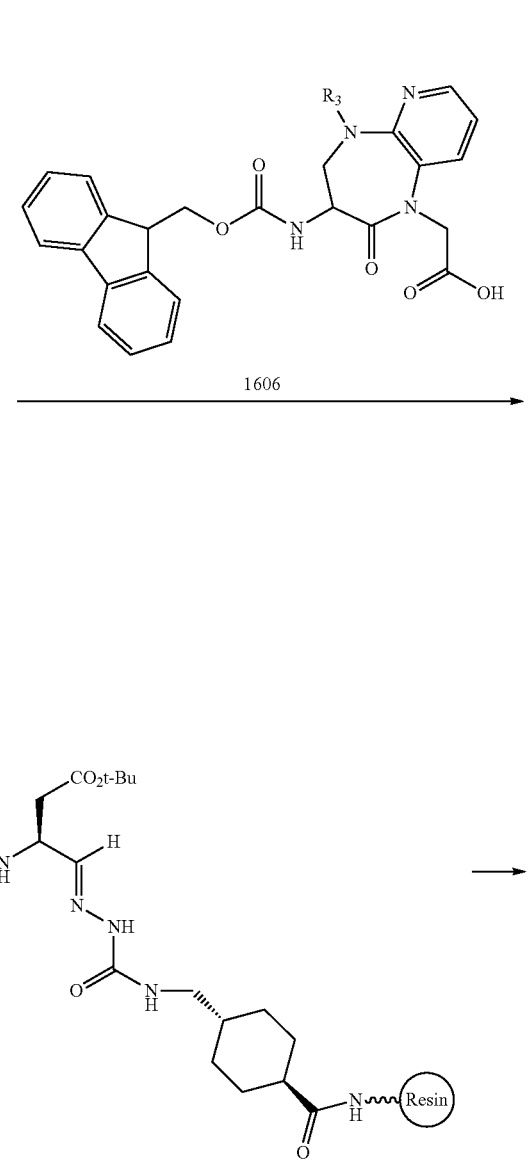
401
1607

-continued
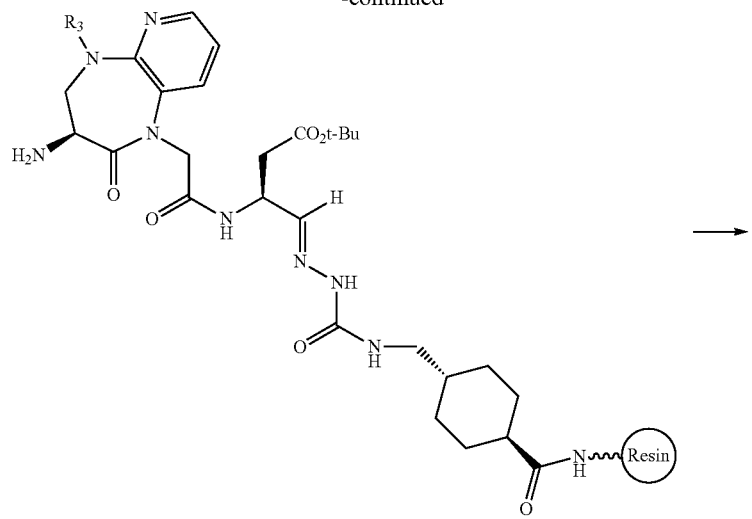
1608
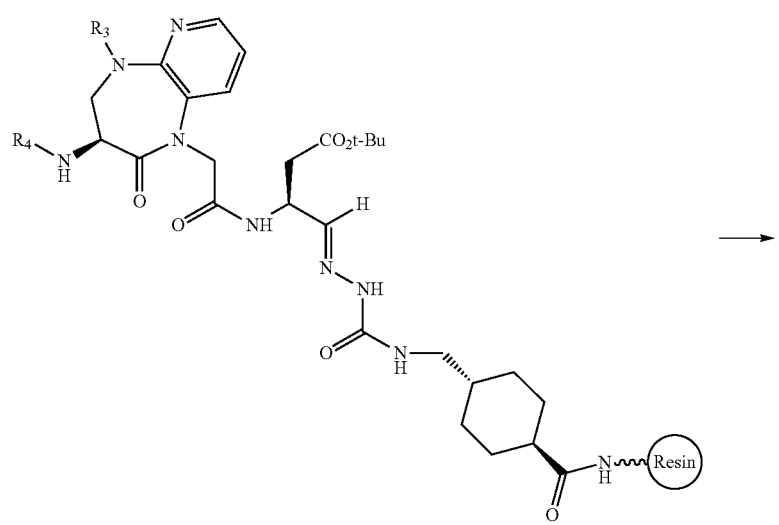
1609
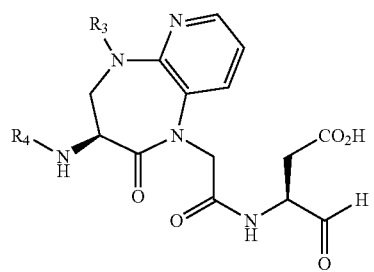
1610-1621 wherein for compounds 1610-1621,
a R₃=CH₃C(O)—
b R₃=CH₃OCH₂C(O)—:
R₄
1610 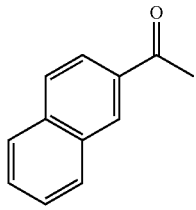
1611 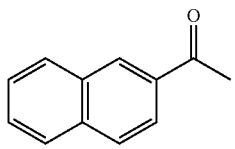
1612 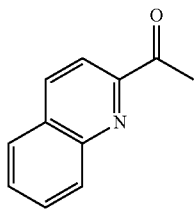
1613 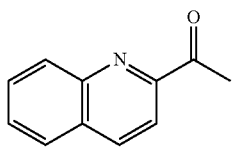
1614 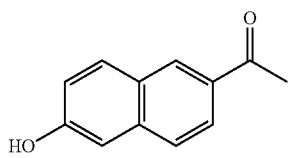
1615 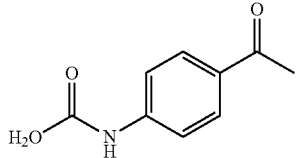
1616 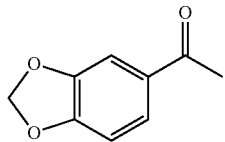
1617 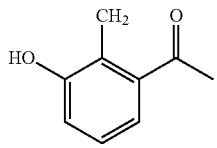
-continued
1618 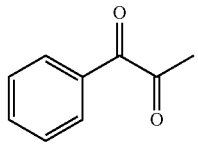
1619 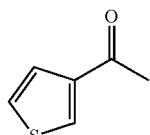
1620 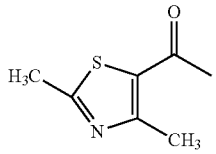
1621 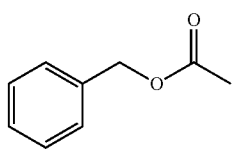
EXAMPLE 16
Compounds comprising scaffolds (e11), (y1), (y2), (z), and (e12) may be synthesized as described below.
Synthesis of Scaffold $R_1$, Wherein $R_1$ is (e11) and Wherein $Y_2$ is =O.
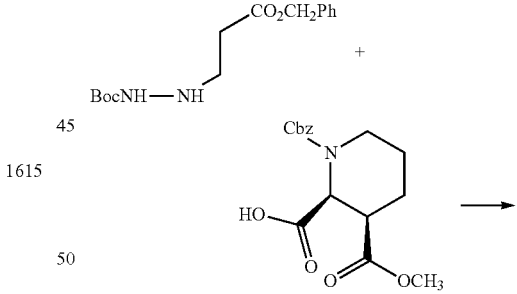
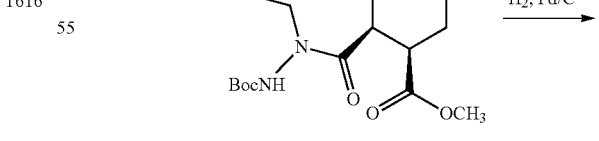

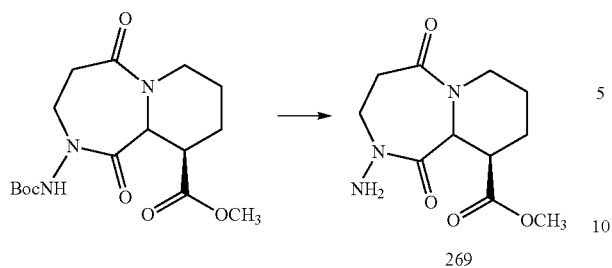
Synthesis of Scaffold $R_1$, Wherein $R_1$ is (y1) and Wherein y2 is =O.
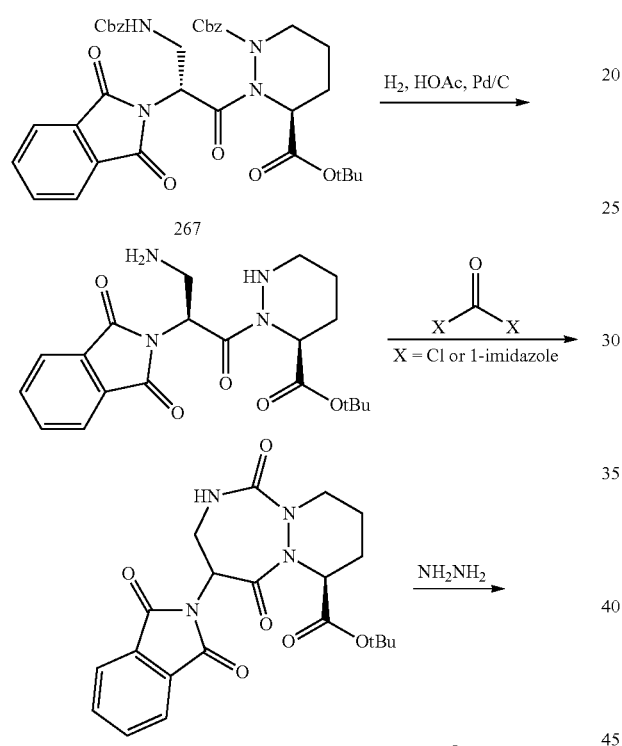
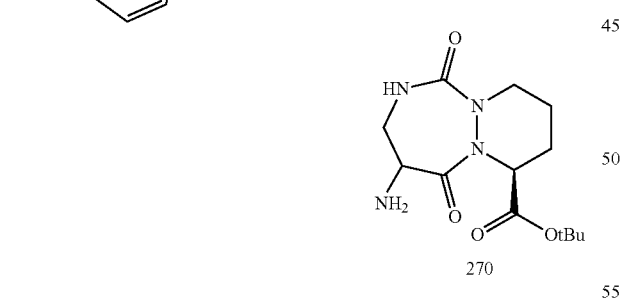
Synthesis of Scaffold $R_1$, Wherein $R_1$ is (y2) and Wherein $Y_2$ is $H_2$ and $X_7$ is O.
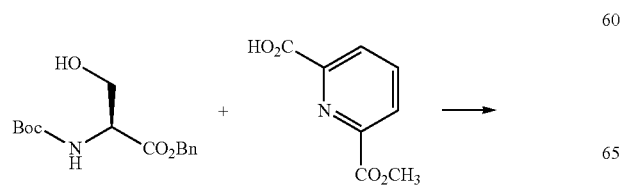
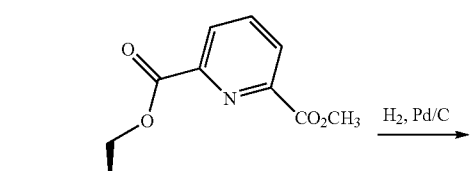
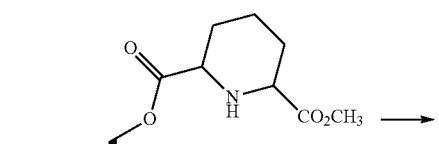
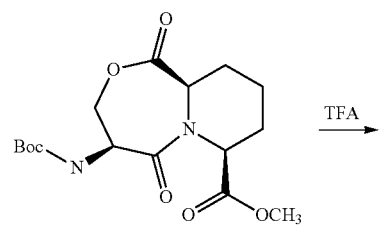
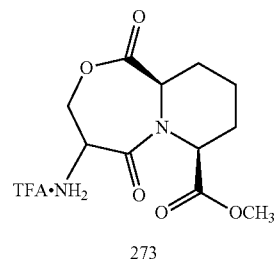
Synthesis of Scaffold $R_1$, Wherein $R_1$ is (y2) and Wherein $Y_2$ is =O and $X_7$ is NH.
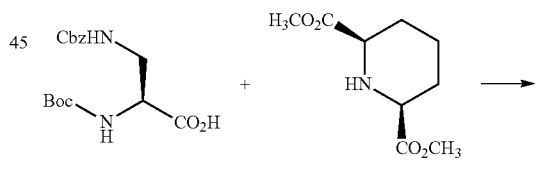
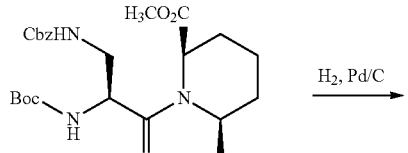
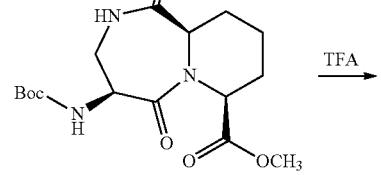

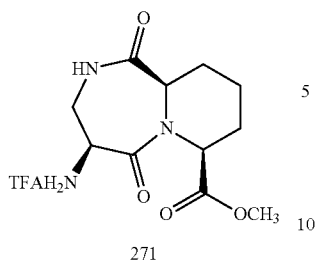
271
Synthesis of Scaffold $R_1$, Wherein $R_1$ is (y2) and Wherein $Y_2$ is $H_2$ and $X_7$ is NH.
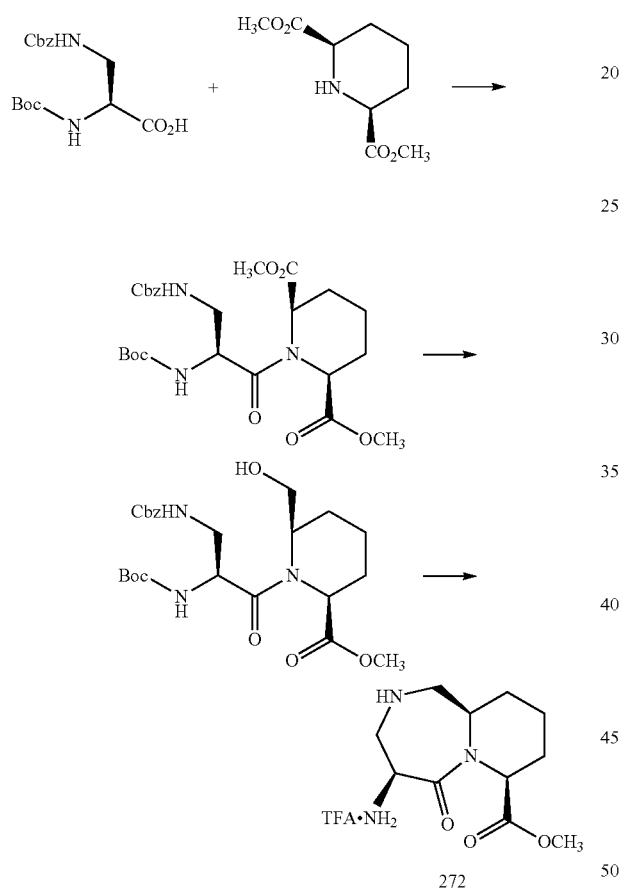
272
Synthesis of Scaffold $R_1$, Wherein $R_1$ is (z) and Wherein $Y_2$ is O.
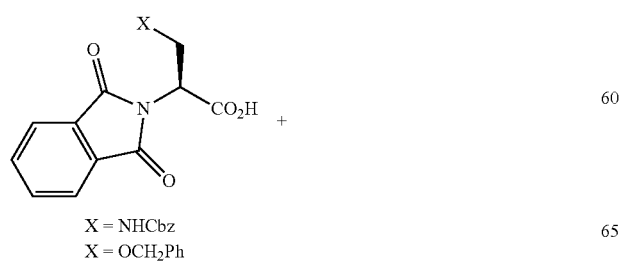
X = NHCbz
X = OCH$_2$Ph
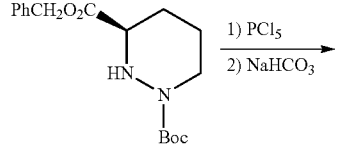
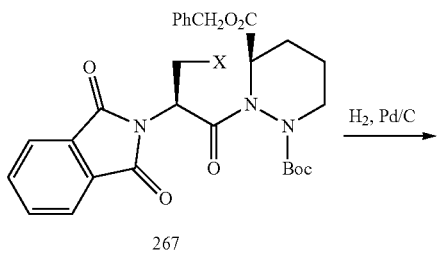
267
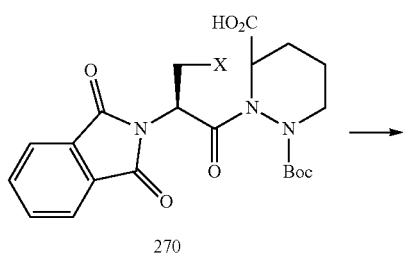
270
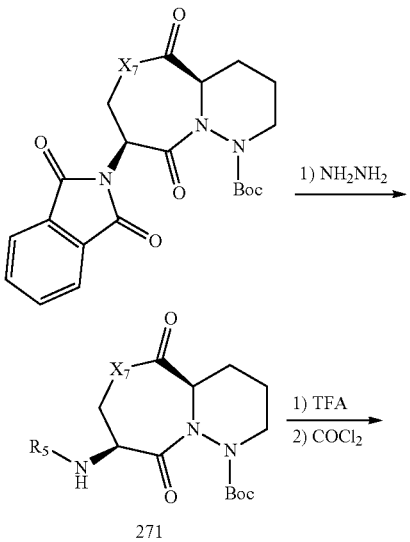
271
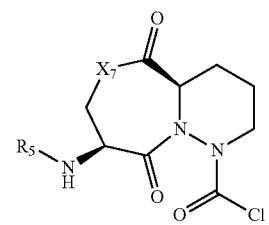
274 $X_7$ = NH
275 $X_7$ = O

379
Synthesis of Scaffold $R_1$, Wherein $R_1$ is (e12) and Wherein $Y_2$ is =O.
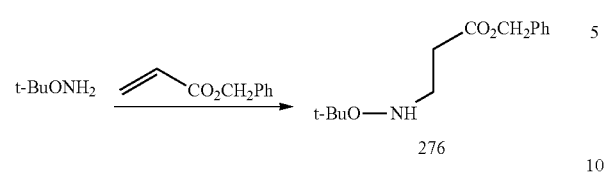
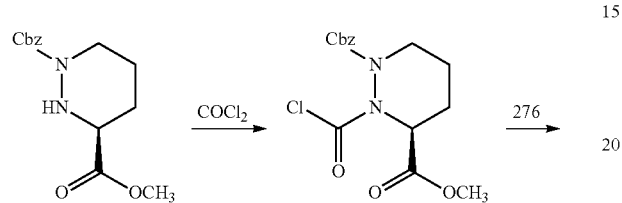
380
-continued
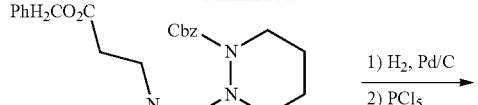
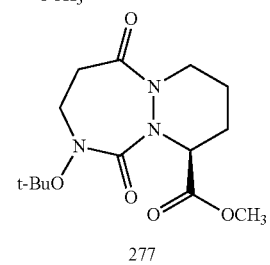
EXAMPLE 17
The preparation of compounds 2001, 2002, 2100a-e, and 2201 is described below.
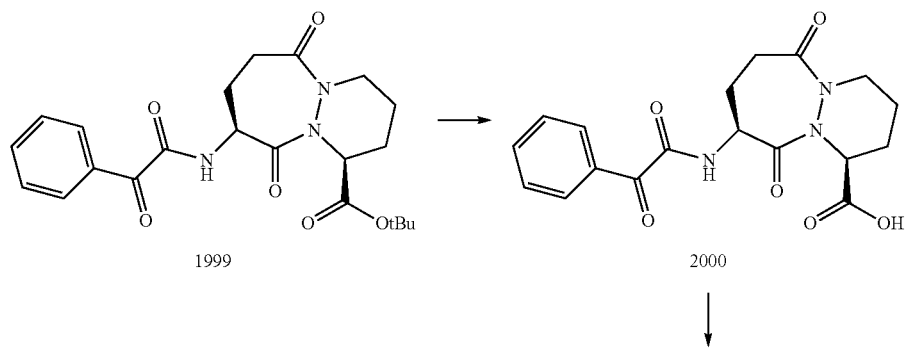
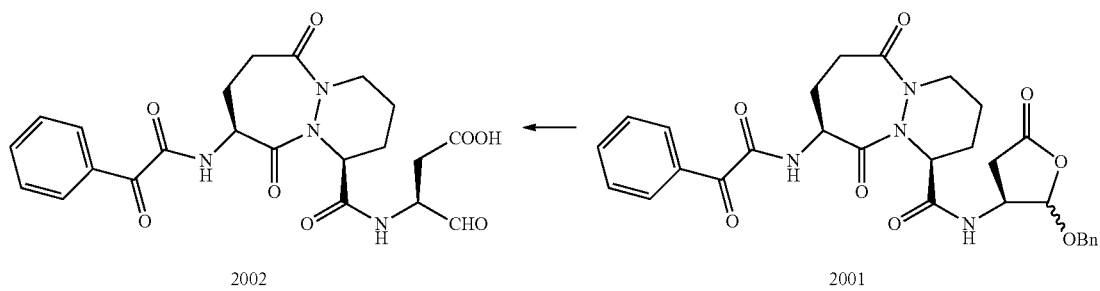

(1S,9S)9-Benzoylformylamino-6,10-dioxo-1,2,3,4,7,8,9,10-octahydro-6H-pyridazino[1,2-a]-[1,2]diazepine-1-carboxylic acid (2000). To a solution of t-butyl 9-amino-6,10-dioxo-1,2,3,4,7,8,9,10-octahydro-6H-pyridazino[1,2-a][1,2]diazepine-1-carboxylate (GB 2,128,984; 340 mg, 1.15 mmol) in $CH_2Cl_2$ was added benzoylformic acid (260 mg, 1.7 mmol), HOST (230 mg, 1.7 mmol) and EDC (340 mg, 1.7 mmol). The resulting mixture was stirred at ambient temperature for 16 hours, poured into 1N HCl and extracted with $CH_2Cl_2$. The organic extracts were further washed with saturated $NaHCO_3$, dried over $MgSO_4$ and concentrated to afford 1999 as a pale yellow solid. The solid was dissolved in $CH_2Cl_2$ (25 ml) and TFA (25 ml) and stirred overnight and concentrated in vacuo to give 560 mg of 2000 as an oil.

[1S,9S(2RS,3S)]9-Benzoylformylamino-6,10-dioxo-1,2,3,4,7,8,9,10-octahydro-N-(2(R,S)-benzyloxy-5-oxotetrahydrofuran-3-yl)-6H-pyridazino[1,2-a][1,2]-diazepine-1-carboxamide (2001), was synthesized from 2000 by methods similar to compound 213e to afford 410 mg (63%) of 2001 as a white solid: $^1$H NMR ($CDCl_3$; mixture of diastereomers) δ 8.25 (1H, d), 8.23 (1H, d), 7.78 (1H, dd), 7.65 (1H, bm), 7.50 (2H, m), 7.40-7.25 (4H, m), 6.55 (1H, d), 5.57 (1H, d), 5.10 (1H, t), 5.05-4.95 (2H, m), 4.90, (1H, d), 4.80 (1H, d), 4.72 (1H, bm), 4.65 (1H, m), 4.55 (1H, m), 4.45 (1H, t), 3.25 (1H, m), 3.15 (1H, m), 3.00 (2H, bm), 2.90 (1H, dd), 2.70 (1H, m), 2.47 (1H, dd), 2.45 (1H, m), 2.35 (1H, m), 2.00-1.75 (4H, m), 1.60 (1H, bm).

[3S(1S,9S)]3-(9-Benzoylformylamino-6,10-dioxo-1,2,3,4,7,8,9,10-octahydro-6H-pyridazino[1,2-a][1,2]diazepine-1-carboxamido)-4-oxobutanoic acid (2002). Compound 2001 (58.6 mg, 0.10 mmol) was treated with 15 ml of TFA/MeCN/water (1:2:3) and stirred at room temperature for 6.5 h. The reaction was extracted with ether. The aqueous layer was concentrated with azeotropic removal of the water using MeCN. The product was suspended in $CH_2Cl_2$, concentrated in vacuo and precipitated with ether to give 46.8 mg (99%) of 2002 as a white solid: $^1$H NMR ($CD_3OD$) δ 9.05 (0.25H, d), 8.15 (1H, d), 7.68 (1H, t), 7.64 (0.25H, d), 7.55 (3H, t), 7.35 (0.5H, m), 5.22 (1H, t), 4.90 (1H, m), 4.58 (1H, dd), 4.50 (1H, m), 4.28 (1H, bm), 3.45 (1H, m), 3.10 (1H, bt), 2.68 (1H, ddd), 2.60-2.45 (2H, m), 2.30 (1H, dd), 2.15-2.05 (2H, m), 1.90 (2H, bm), 1.68 (1H, bm).

(1S,9S(2RS,3S)) 9-Benzoylamino-6,10-dioxo-1,2,3,4,7,8,9,10-octahydro-N-(2-isopropoxy-5-oxo-tetrahydro-furan-3-yl)-6H-pyridazino[1,2-a][1,2]diazepine-1-carboxamide (2100a). A solution of 214e (101 mg, 0.23 mmol) in isopropanol (10 ml) was stirred at room temperature with a catalytic amount of p-toluenesulfonic acid (10 mg). After 75 minutes, the reaction mixture was poured into saturated $NaHCO_3$ and extracted with $CH_2Cl_2$. The combined extracts were dried over $Na_2SO_4$ and concentrated. Flash chromatography ($SiO_2$, $CH_2Cl_2$ to EtOAc) afforded 56 mg (51%) of 2100a as a white solid: $^1$H NMR ($CDCl_3$; mixture of diastereomers) 7.9-7.8 (2H, m), 7.6-7.5 (1H, m), 7.5-7.4 (2H, m), 7.1 (0.5H, d), 6.9 (0.5H, d), 6.4 (0.5H, d), 5.6 (0.5H, d), 5.3 (0.5H, s), 5.2-5.1 (1H, m), 4.95 (0.5H, m), 4.75-4.5 (1.5H, m), 4.35 (0.5H, t), 4.1 (0.5H, m), 3.98 (0.5H, m), 3.3-2.75 (4H, m), 2.5-2.4 (2H, m), 2.25 (1H, m), 2.1-1.9 (3H, m) 1.75-1.55 (2H, m).

[3S(1S,9S)]3-(9-Benzoylformylamino-6,10-dioxo-1,2,3,4,7,8,9,10-octahydro-6H-pyridazino[1,2-a][1,2]-diazepine-1-carboxamido)-4,4-diethoxy-butyric acid, ethyl ester (2100b). A solution of 214e (16 mg, 0.036 mmol) in ethanol (2 ml) was stirred at room temperature with a catalytic amount of p-toluenesulfonic acid (2 mg). After 5 days, the reaction mixture was poured into saturated $NaHCO_3$ and extracted with $CH_2Cl_2$. The combined extracts were dried over $Na_2SO_4$ and concentrated. Flash chromatography ($SiO_2$, $CH_2Cl_2$:EtOAc 95:5 v/v) afforded 16 mg (81%) of 2100b as a white solid: $^1$H NMR ($CDCl_3$) d 7.85-7.74 (2H, m), 7.55-7.38 (3H, m), 7.04-6.95 (1H, d), 6.61-6.48 (1H, d), 5.15-5.08 (1H, m), 4.63-4.53 (1H, m), 4.52-4.45 (1H, m), 4.42-4.35 (1H, m), 4.15-4.05 (2H, m), 3.74-3.60 (2H, m), 3.57-3.42 (2H, m), 3.39-3.28 (1H, m), 3.03-2.93 (1H, m), 2.92-2.82 (1H, m), 2.65-2.52 (2H, m), 2.42-2.25 (1H, m), 2.20-1.88 (4H, m), 1.76-1.50 (2H, m), 1.35-1.10 (9H, m).

[3S(1S,9S)]3-(9-Benzoylformylamino-6,10-dioxo-1,2,3,4,7,8,9,10-octahydro-6H-pyridazino[1,2-a][1,2]-diazepine-1-carboxamido)-4,4-dimethoxy-butyric acid methyl ester (2100c). A solution of 214e (165 mg, 0.37 mmol) in methanol (5 ml) was stirred at room temperature with a catalytic amount of p-toluenesulfonic acid (17.5 mg). After 4 days, the reaction mixture was diluted with EtOAc and washed with 10% $NaHCO_3$ (3×) and brine. The combined extracts were dried over $Na_2SO_4$ and concentrated. Flash chromatography ($SiO_2$, EtOAc) afforded 127 mg (68%) of 2100c as a white solid: $^1$H NMR ($CDCl_3$) δ 7.82 (2H, d), 7.55-7.50 (1H, m), 7.47-7.43 (2H, m), 7.02 (1H, d), 6.53 (1H, d), 5.20-5.10 (1H, m), 4.56-4.50 (1H, m), 4.45-4.50 (1H each, two m), 3.69 (3H, s), 3.41 (3H, s), 3.43 (3H, s), 3.35-3.25 (1H, m), 3.06-2.98 (1H, m), 2.94-2.83 (1H, m), 2.65-2.53 (2H, m), 2.35-2.32 (1H, m), 2.15-2.07 (1H, m), 2.00-1.89 (3H, m), 1.75-1.56 (2H, m).

[3S(1S,9S)]3-(9-Benzoylformylamino-6,10-dioxo-1,2,3,4,7,8,9,10-octahydro-6H-pyridazino[1,2-a][1,2]-diazepine-1-carboxamido)-4,4-diisopropoxy-butyric acid, isopropyl ester (2100d). A solution of 214e (53 mg, 0.12 mmol) in isopropanol (5 ml) was stirred at 50° C. with a catalytic amount of p-toluenesulfonic acid (5 mg). After 3 days the reaction mixture was poured into saturated $NaHCO_3$ and extracted with $CH_2Cl_2$. The combined extracts were dried over $Na_2SO_4$ and concentrated. Flash chromatography ($SiO_2$, $CH_2Cl_2$:EtOAc (4:1 to 1:1 v/v)) afforded 49 mg (68%) of 2100d as a white solid: $^1$H NMR ($CDCl_3$) δ 7.85 (2H, d), 7.50-7.43 (1H, m), 7.41-7.35 (2H, m), 7.02 (1H, d), 6.47 (1H, d), 5.13-5.07 (1H, m) 5.00-4.9 (1H, m), 4.61-4.55 (2H, m), 4.37-4.30 (1H, m), 3.80-3.70 (1H, m), 3.90-3.80 (1H, m), 3.42-3.35 (1H, m), 3.03-2.93 (1H, m), 2.91-2.81 (1H, m), 2.62-2.50 (2H, m), 2.38-2.33 (1H, m), 2.12-2.06 (1H, m), 1.97-1.81 (3H, m), 1.70-1.60 (2H, m), 1.28-1.05 (18H, m).

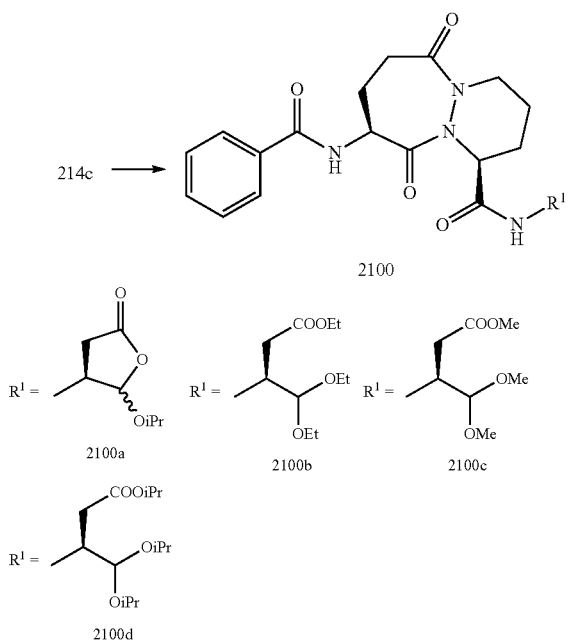

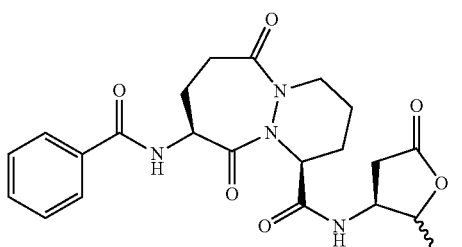

2100e

[1S,9S(2RS,3S)]9-Benzoylamino-6,10-dioxo-1,2,3,4,7,8,9,10-octahydro-N-(2-ethoxy-5-oxo-tetrahydro-furan-3-yl)-6H-pyridazino[1,2-a][1,2]-diazepine-1-carboxamide (2100e), was synthesized from 302 via methods used to synthesize 304a to afford 2100e, except ethanol and triethylorthoformate were used instead of methanol and trimethylorthoformate. Chromatography (SiO$_2$, 5% ethanol/CH$_2$Cl$_2$) afforded 92 mg (68%) of a white solid: $^1$H NMR (CDCl$_3$; mixture of diastereomers) δ 7.90-7.80 (2H, m), 7.60-7.50 (1H, m), 7.50-7.40 (2H, m), 7.30 (0.5H, d), 7.00 (0.5H, d), 6.50 (0.5H, d), 5.50 (0.5H, d), 5.20-5.10 (1.5H, m), 4.95 (0.5H, m), 4.75-4.65 (0.5H, m), 4.65-4.50 (1H, m), 4.38 (0.05H, t), 4.00-3.90 (0.5H, m), 3.85-3.75 (0.5H, m), 3.75-3.65 (0.5H, m), 3.65-3.55 (0.5H, m), 3.30-2.70 (4H, m), 2.50-2.35 (2H, m), 2.30 (1H, d), 2.15-1.90 (3H, m), 1.80-1.60 (2H, m), 1.25-1.20 (3H, two t)

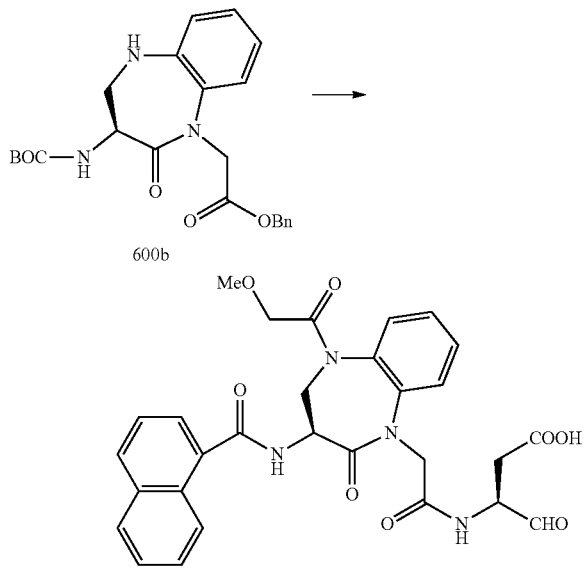

600b

2201

(3S)-3-[(3S)-2-oxo-3-(1-naphthoyl)amino-5-methoxy-acetyl-2,3,4,5-tetrahydro-1H-1,5-benzodiazepine-1-acetylamino]4-oxo-butyric acid (2201) was synthesized from 600b by the methods used to synthesize 605b to afford 2201: $^1$H NMR (CDCl$_3$) δ 8.30-8.22 (1H, m), 8.05-7.98 (1H, d), 7.96-7.83 (1H, m), 7.77-7.68 (1H, m), 7.67-7.40 (7H, m), 5.12-5.02 (1H, m), 4.98-4.41 (5H, m), 4.38-4.24 (1H, m), 4.07-4.00 (1H, d), 3.92-3.80 (2H, m), 3.32 (3H, s), 2.75-2.60 (1H, m), 2.58-2.35 (1H, m).

EXAMPLE 18

We obtained the following data for selected compounds of this invention using the methods described herein (Table 16, see Example 7; Tables 17 and 18, see Examples 1-4). The structures and preparations of compounds of this invention are described in Examples 28-31.

TABLE 16

Comparison of Prodrugs for Efficacy in LPS Challenged Mice: Inhibition of IL-1β Production. The percent inhibition of IL-1β production after treatment with a compound of the invention is shown as a function of time after LPS challenge ("—" indicates that no value was obtained at that relative time). Time of Compound Administration (relative to time of LPS challenge, PO, 50 mg/kg)

| Compound | −2 h | −1 h | 0 h | +1 h |
| --- | --- | --- | --- | --- |
| 213f | (−4) | — | 8 | — |
| 213h | 9 | — | 53 | — |
| 213i | (−11) | — | 62 | — |
| 213k | 0 | — | 68 | — |
| 213l | (−18) | — | 80 | — |
| 213m | 26 | — | 42 | — |
| 213o | 4 | — | 8 | — |
| 213p | 21 | — | 29 | — |
| 213q | 17 | — | 91 | — |
| 213r | 59 | — | 37 | — |
| 213x | 0 | — | 78 | — |
| 213y | 29 | — | 50 | — |
| 214e | 39 | — | 70 | 75 |
|  | 43 | 44 | 48 | 11 |
|  | — | — | — | 47 |
| 214k | 12 | — | 31 | — |
| 214l | 0 | — | 54 | — |
| 214m | 0 | — | 17 | — |
| 214w | 11 | — | 91 | — |
| 264l | 0 | — | 23 | — |
| 404 | — | — | — | 56 |
|  | 55 | — | 6 | — |
| 412 | 0 | — | 0 | — |
|  | 11 | — | 37 | — |
| 418 | — | — | — | 64 |
|  | 25 | — | 52 | — |
| 434 | — | — | — | 80 |
|  | 0 | — | 63 | — |
| 450 | 0 | — | 35 | — |
| 452 | — | — | — | 70 |
|  | 28 | — | 89 | — |
| 456 | — | — | — | 56 |
|  | 41 | — | 69 | — |
| 470 | 0 | — | 36 | — |
| 471 | 0 | — | 34 | — |
| 475 | 0 | — | 15 | — |
| 481 | 27 | — | 0 | — |
| 486 | 19 | — | 15 | — |
| 487 | 17 | — | 20 | — |
| 528 | 25 | — | 67 | — |
| 550f | 0 | — | 50 | — |
| 550h | 55 | — | 73 | — |
| 550i | (−10) | — | 23 | — |
| 550k | 36 | — | 34 | — |
| 550l | 9 | — | 38 | — |
| 550m | 45 | — | 52 | — |
| 550n | 19 | — | 65 | — |
| 550o | 19 | — | 64 | — |
| 550p | 30 | — | 60 | — |
| 655 | 0 | — | 68 | — |
| 656 | 31 | — | 16 | — |
| 662 | 41 | — | 75 | — |
| 668 | — | — | — | 53 |
| 695a | 49 | — | 78 | — |
| 1015 | 15 | — | 28 | — |
| 2001 | 64 | 62 | 58 | 55 |
| 2001a | 10 | — | 16 | — |
| 2002 | 5 | — | 87 | — |
| 2100h | 34 | — | 32 | — |

TABLE 16-continued

Comparison of Prodrugs for Efficacy in LPS Challenged Mice: Inhibition of IL-1β Production. The percent inhibition of IL-1β production after treatment with a compound of the invention is shown as a function of time after LPS challenge ("—" indicates that no value was obtained at that relative time). Time of Compound Administration (relative to time of LPS challenge, PO, 50 mg/kg)

| Compound | −2 h | −1 h | 0 h | +1 h |
|---|---|---|---|---|
| 2100i | 19 | — | 74 | — |
| 2100j | 48 | 41 | 0 | 33 |
| 2100k | 30 | 50 | 32 | 72 |
| 2100l | 52 | — | 28 | — |
| 2100m | 40 | — | 42 | — |
| 2100n | 21 | 9 | 64 | 73 |
| 2100o | 31 | 44 | 68 | 64 |

TABLE 17

Data for selected compounds of this invention obtained using the methods described in Examples 1-4.

| Compound | UV-Visible Ki (nM) | Cell PBMC avg. IC50 (nM) | Whole human blood IC50 (nM) | Clearance Mouse, i.v. ml/min/kg | Clearance Rat, i.v. ml/min/kg |
|---|---|---|---|---|---|
| 213f | | | 3000 | | |
| 213g | | | 2200 | | |
| 213h | | | 1500 | | |
| 213i | | | 1100 | | |
| 213j | | | | | |
| 213k | | | 2000 | | |
| 213l | | | 2000 | | |
| 213m | | | 2500 | | |
| 213o | | 5000 | 3300 | | |
| 213p | | | <300 | | |
| 213q | | | <300 | | |
| 213r | | | <300 | | |
| 213v | 0.5 | 1,100 | 1100 | 41 | 23 |
| 213x | | 4500 | 2500 | | |
| 213y | | | 930 | | |
| 214j | 4.2 | 2500 | 6000 | | |
| 214k | 0.2 | 500 | 580 | 22 | |
| 214l | 6 | 1900 | 1100 | 12 | |
| 214m | 1.5 | 530 | 2200 | | 33.4 |
| 214w | 0.6 | 620 | 370 | 15 | |
| 246b | 30000 | >30000 | | 87 | |
| 264l | | | 3000 | | |
| 265a | 2600 | 25000 | | | |
| 265c | 1100 | 4500 | | | 32 |
| 265d | 500 | 1500 | | | 35 |
| 265f | 1200 | | | | 24 |
| 280b | | | 13000 | | |
| 280c | | | 10000 | | 86 |
| 280d | | | 25000 | | |
| 283b | | | 1750 | | 41 |
| 283c | | | 4000 | | 50 |
| 283d | | >8000 | 10000 | | |
| 308c | 3000 | | | | |
| 308d | 3000 | | | | |
| 500 | 25 | 1800 | 1800 | | |
| 501 | 2.5 | 1800 | 1600 | | |
| 505c | | | 1500 | | |
| 505d | | >20000 | | | |
| 505f | | | 550 | | |
| 510a | 65 | 200 | | 267 | |
| 510d | 2300 | >20000 | | | |
| 511c | 730 | >20000 | 2200 | 78 | 40 |
| 528 | | | 2200 | | |
| 550f | | | 1100 | | |
| 550h | | | 1800 | | |
| 550i | | | 1400 | | |
| 550k | | | 3000 | | |
| 550l | | | 750 | | |
| 550m | | | 2000 | | |
| 550n | | | <300 | | |
| 550o | | 450 | 3000 | | |
| 550p | | | 2900 | | |
| 550q | | | 700 | | |
| 640 | 155 | 2250 | 3900 | | |
| 642 | 35 | 8000 | 2900 | | |
| 645 | 150 | | | | |
| 650 | 550 | 4000 | | | |
| 653 | 30 | 2300 | 6000 | | |
| 655 | | | | | |
| 656 | 0.6 | 2100 | 1600 | | 2.9 |
| 662 | 0.5 | 1800 | 800 | | 2.75 |
| 668 | 9 | 5200 | 3700 | | 29 |
| 669 | 14 | | 10000 | | |
| 670 | | | 4500 | | |
| 671 | 5 | 2000 | 2500 | | 33.2 |
| 677 | | | 610 | | |
| 678 | 5 | 2700 | 2200 | | |
| 680 | | | | | |
| 681 | 9 | 3000 | 5000 | | |
| 682 | | | 1300 | | |
| 683 | 400 | >20000 | >20000 | | |
| 684 | 15 | 5000 | 2800 | | |
| 686 | 4 | 4000 | 9000 | | |
| 688a | | | 3000 | | |
| 688b | | | 1300 | | |
| 689a | 0.8 | 910 | 2500 | | |
| 689b | 2.2 | 600 | 2000 | | |
| 690a | | | 1600 | | |
| 690b | | | | | |
| 691a | 2.1 | 2900 | 1200 | | 9.9 |
| 691b | 11.5 | 1,900 | 1400 | | |
| 692a | | | | | |
| 692b | | | 1800 | | |
| 693 | | | | | |
| 694 | 3 | 2600 | 2100 | | |
| 695a | | | | | |
| 695b | | | | | |
| 695c | | | 2500 | | |
| 696 | 4.5 | 2000 | 2900 | | 13 |
| 700 | 275 | | | | |
| 701 | 90 | | | | |
| 702 | 45 | >5000 | 20000 | | |
| 703 | 5 | 1400 | 20000 | | |
| 704 | 30 | 2600 | 9800 | | |
| 705 | 5 | 2300 | 3200 | | |
| 706 | 5 | 2400 | 5800 | | |
| 707 | 180 | | | | |
| 708 | 140 | | | | |
| 709 | 10 | 2100 | 14000 | | |
| 710 | 110 | | | | |
| 711 | 175 | | | | |
| 910 | 10 | 3400 | 3800 | | |
| 911 | 9 | 3500 | 1900 | | |
| 912 | 10 | 4200 | 3800 | | |
| 913 | 4.5 | 2400 | 7000 | | |
| 914 | 5.2 | 2600 | 2800 | | |
| 915 | 11.5 | >8000 | 1900 | | |
| 918 | 7 | | 1150 | | |
| 919 | 4 | 2000 | 4300 | | |
| 920 | 16 | 2100 | 3000 | | |
| 921 | 8.5 | 1800 | 3000 | | |
| 1018 | 170 | 4000 | 5500 | | 9.1 |
| 1052 | 100 | 2500 | | | 16 |
| 1053 | 27 | 2000 | >20000 | | 34 |
| 1056 | 170 | | | | 17 |
| 1075 | 120 | 5000 | 5500 | | 14.5 |
| 1095 | 360 | 6000 | | | 28 |
| 1105 | 250 | 3500 | 3000 | | |
| 1106 | 75 | 4000 | 1700 | | |
| 1107 | 65 | | | | |

TABLE 17-continued

Data for selected compounds of this invention
obtained using the methods described in Examples 1-4.

| Compound | UV-Visible $K_i$ (nM) | Cell PBMC avg. IC50 (nM) | Whole human blood IC50 (nM) | Clearance Mouse, i.v. ml/min/kg | Clearance Rat, i.v. ml/min/kg |
|---|---|---|---|---|---|
| 1108 | 22 | 1400 | 2600 | | |
| 1109 | 80 | | | | |
| 1110 | 45 | | | | |
| 1111 | 18 | 6050 | 4400 | | |
| 1112 | 3.5 | 1800 | 2300 | | |
| 1113 | 290 | | | | |
| 1114 | 125 | | | | |
| 1115 | 250 | | | | |
| 1116 | 215 | | | | |
| 1117 | 35 | 1700 | 1300 | | |
| 1118 | 380 | | | | |
| 1119 | 515 | | | | |
| 1120 | 95 | | | | |
| 1121 | 170 | | | | |
| 1122 | 400 | | | | |
| 1123 | 30 | 2,400 | 4500 | | |
| 1124 | 270 | | | | |
| 1125 | 55 | 2300 | 9000 | | |
| 2001a | | | 3000 | | |
| 2100f | | | | | |
| 2100g | | | | | |
| 2100h | | | 2000 | | |
| 2100i | | | | | |
| 2100j | 30000 | | 12000 | | |
| 2100k | 520 | 4000 | 600 | | |
| 2100l | | 750 | 2200 | | |
| 2100m | | | | | |
| 2100n | 670 | 770 | 4000 | | |
| 2100o | 670 | 1150 | 1500 | | |

We obtained the following data for selected compounds of this invention (Table 18) using the methods described herein (see Examples 1-4). The structures and preparations of compounds of this invention are described in Examples 28-31.

TABLE 18

| Cmpd. | Fluorescent Assay $k_{inact}$ $m^{-1}s^{-1}$ | Cell PBMC avg. IC50 (nM) | Whole human blood IC50 (nM) | Clearance Mouse, i.v. ml/min/kg | Clearance Rat, i.v. ml/min/kg |
|---|---|---|---|---|---|
| 286 | 370000 | 300 | 1600 | | 119 |
| 505 b | 190000 | 1500 | 2100 | 161 | 196 |
| 505 e | 420000 | 9000 | 1000 | | |

EXAMPLE 19

In Vivo Acute Assay for Efficacy as Anti-Inflammatory Agent

Results in the Table 19 show that 412f, 412d and 696a inhibit IL-1β production in LPS-challenged mice after oral administration using ethanol/PEG/water, β-cyclodextrin, labrosol/water or cremophor/water as vehicles. The compound was dosed at time of LPS challenge. The protocol is described in Example 7.

TABLE 19

Inhibition (%) of IL-1β production in LPS-challenged mice.

| Compound | 10 mg/kg dose | 25 mg/kg dose | 50 mg/kg dose |
|---|---|---|---|
| 412f | 17% | 25% | 32% |
| 412e | 5% | 17% | 61% |
| 696a | 0 | 45% | 52% |

EXAMPLE 20

Mouse Carrageenan Peritoneal Inflammation

Inflammation was induced in mice with an intraperitoneal (IP) injection of 10 mg carrageenan in 0.5 ml of saline (Griswold et al., *Inflammation,* 13, pp. 727-739 (1989)). Drugs are administered by oral gavage in ethanol/PEG/water, β-cyclodextrin, labrosol/water or cremophor/water vehicle. The mice are sacrificed at 4 hours post carrageenan administration, then injected IP with 2 ml of saline containing 5 U/ml heparin. After gentle massage of the peritoneum, a small incision is made, the contents collected and volume recorded. Samples are kept on ice until centrifuged (130×g, 8 mins at 4° C.) to remove cellular material, and the resultant supernatant stored at −20° C. IL-1β levels in the peritoneal fluid are determined by ELISA.

Results in the Table 20 show prodrug 412f inhibits IL-1β production in carrageenan-challenged mice after oral administration of drug. Compound 214e did not inhibit IL-1β production when dosed orally at 50 mg/kg.

TABLE 20

Inhibition (%) of IL-1β production by 412f and 412d in carrageenan-challenged mice.

| Dose (mg/kg) | Compound 412f | Compound 412d |
|---|---|---|
| 1 | 30% | 0 |
| 10 | 54% | 32% |
| 25 | 49% | 31% |
| 50 | 73% | 36% |
| 100 | 75% | 53% |

EXAMPLE 21

Type II Collagen-Induced Arthritis

Type II collagen-induced arthritis was established in male DBA/1J mice at described Wooley and Geiger (Wooley, P. H., *Methods in Enzmmology,* 162, pp. 361-373 (1988) and Geiger, T., *Clinical and Experimental Rheumatology,* 11, pp. 515-522 (1993)). Chick sternum Type II collagen (4 mg/kg in 10 mM acetic acid) was emulsified with an equal volume of Freund's complete adjuvant (FCA) by repeated passages (400) between two 10 ml glass syringes with a gauge 16 double-hub needle. Mice were immunized by intradermal injection (50 µl; 100 µl CII per mouse) of collagen emulsion 21 days later at the contra-lateral side of the tail base. Drugs were administered twice a day (10, 25 and 50 mg/kg) by oral gavage approximately 7 h apart. Vehicles used included ethanol/PEG/water, β-cyclodextrin, labrosol/water or cremophor/water. Drug treatments were initiated within 2 h of the CII booster immunization. Inflammation was scored on a 1 to 4 scale of increasing severity on the two front paws and the scores are added to give the final score.

Figure 12:
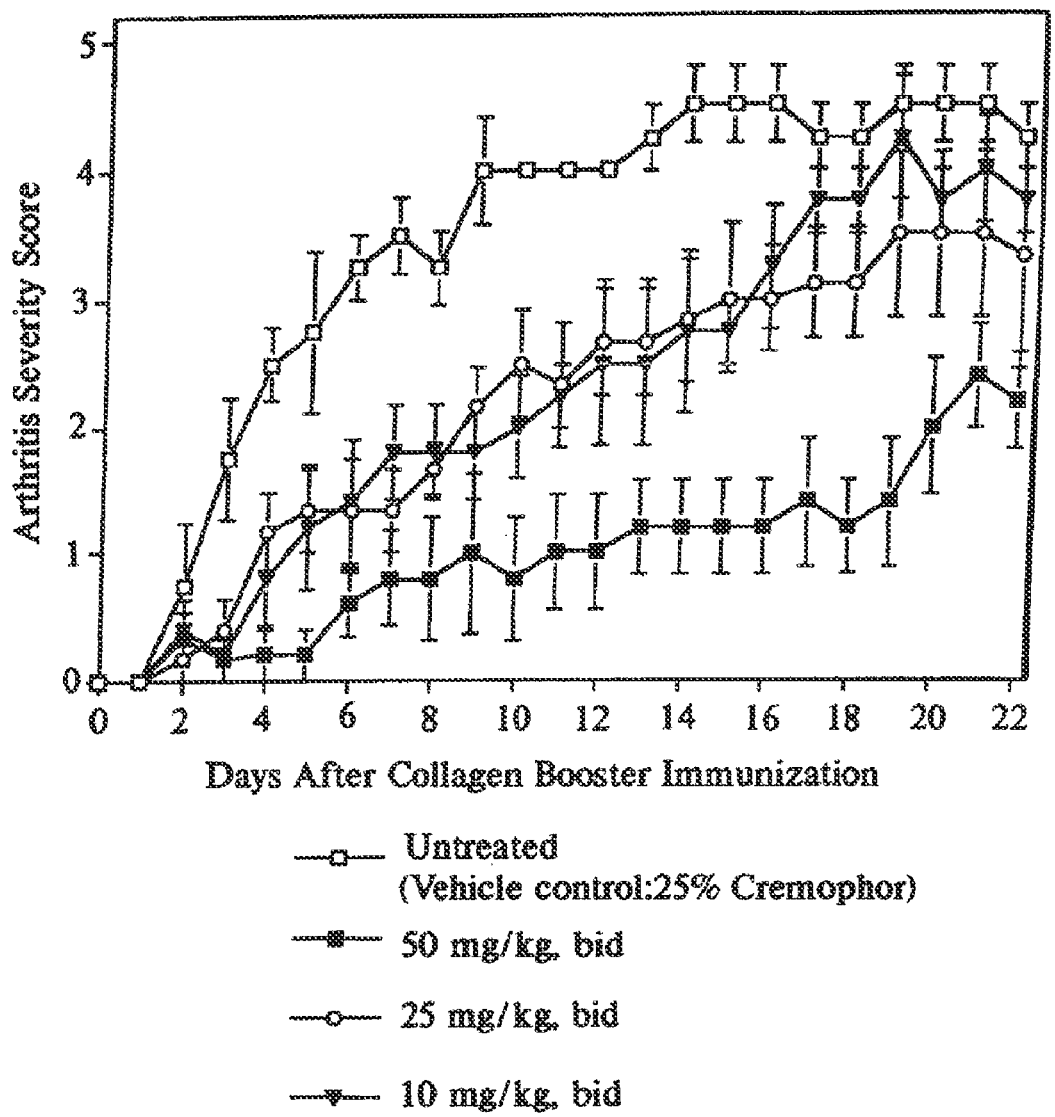
FIG. 12 Compound 412f blocks the progression of type II collagen-induced arthritis in male DBA/1J mice (Wooley, P. H., *Methods in Enzymology*, 162, pp. 361-373 (1988) and Geiger, T., *Clinical and Experimental Rheumatology*, 11, pp. 515-522 (1993)). Compound 412f was administered twice a day (10, 25 and 50 mg/kg), approximately 7 h apart, by oral gavage. Inflammation was measured on the Arthritis Severity Score on a 1 to 4 scale of increasing severity. The scores of the two front paws were added to give the final score (see Example 21).
Figure 13:
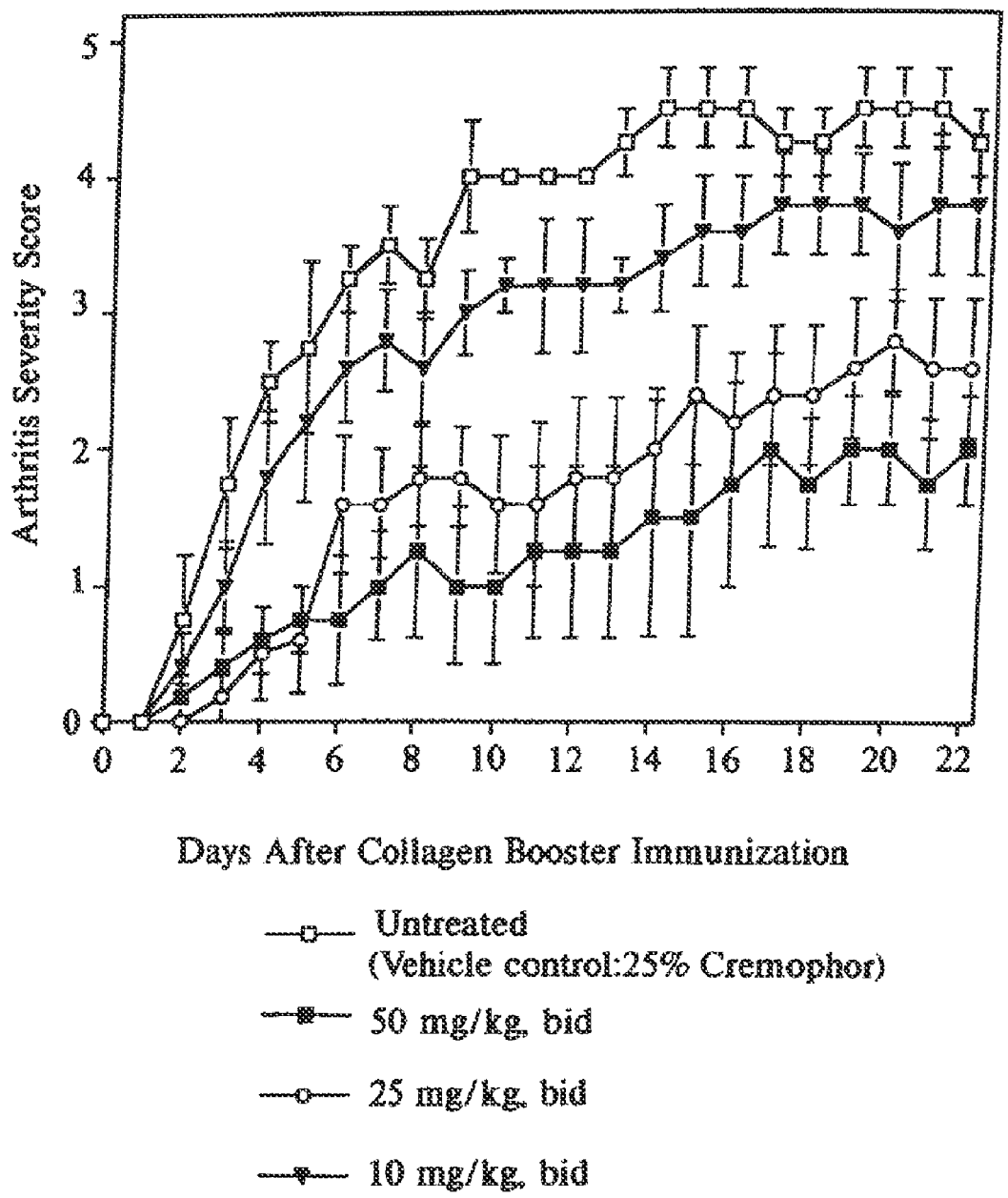
FIG. 13 Compound 412d blocks the progression of type II collagen-induced arthritis in male DBA/1J mice. The results were obtained as described for FIG. 12 and in Example 21.
Figure 14:
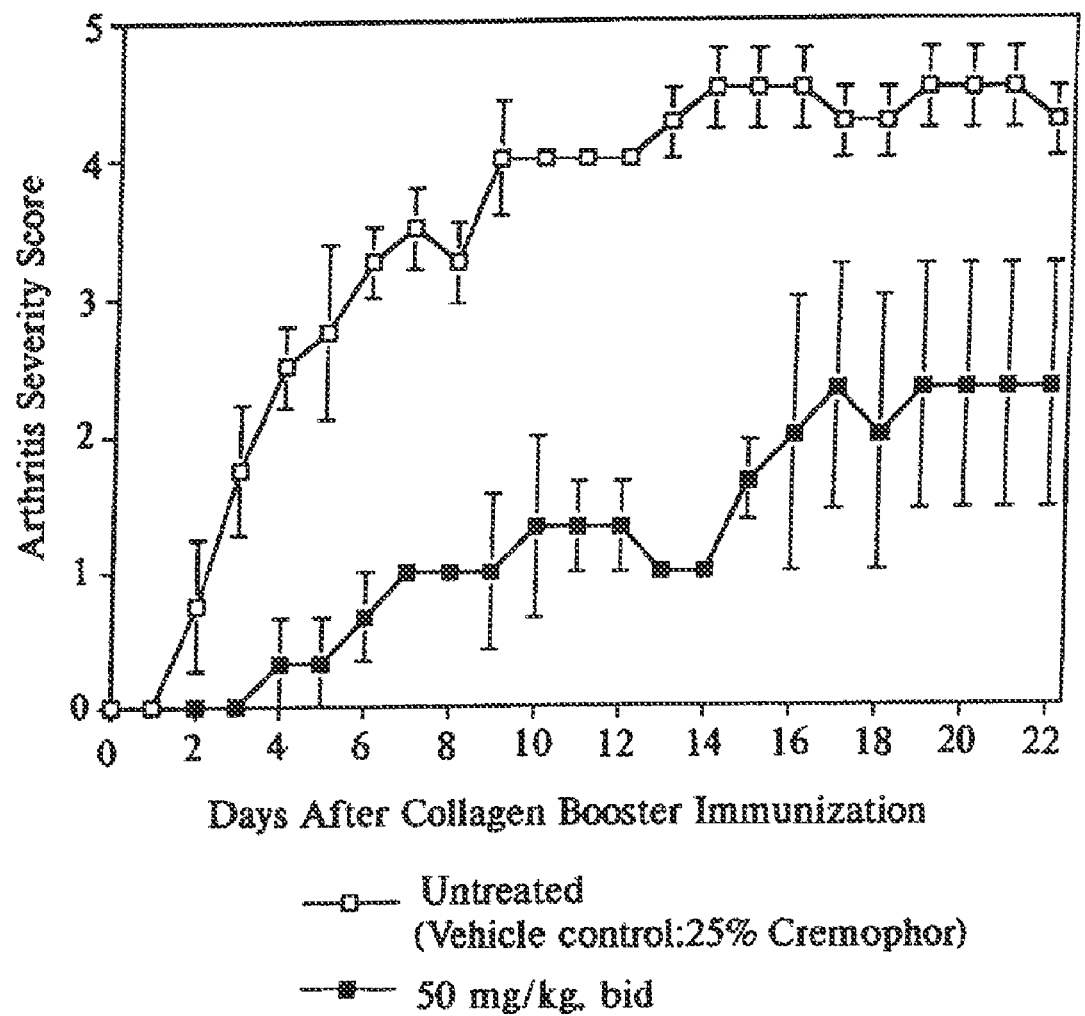
FIG. 14 Compound 696a blocks the progression of type II collagen-induced arthritis in male DBA/1J mice. The results were obtained as described for FIG. 12 and in Example 21.

Results in the FIGS. 12, 13 and 14 show prodrugs 412f, 412d and 696a inhibit inflammation in collagen-induced arthritits in mice after oral administration. Compound 214e did not inhibit inflammation when dosed (50 mg/kg) once a day by oral gavage.

EXAMPLE 22

In Vivo Bioavailability Determination

The drugs (10-100 mg/kg) were dosed orally to rats (10 mL/kg) in ethanol/PEG/water, β-cyclodextrin, labrosol/water or cremophor/water. Blood samples were drawn from the carotid artery at 0.25, 0.50, 1, 1.5, 2, 3, 4, 6, and 8 hours after dosing, centrifuged to plasma and stored at −70° C. until analysis. Aldehyde concentrations were determined using an enzymatic assay. Pharmacokinetic analysis of data was performed by non-linear regression using RStrip (MicroMath Software, UT). Drug availability values were determined as follows: (AUC of drug after oral prodrug dosing/AUC of drug after i.v. dosing of drug)×(dose i.v./dose p.o.)×100%.

Results in Table 21 show that prodrugs 412f, 412d and 696a give significant blood levels of drug and have good drug availability when dosed orally. Blood levels of 214e were not detected when it was dosed orally.

TABLE 21

Oral Bioavailability of 412f, 412d, 696a and 214e in Rat.

| Compound | Dose (mg/kg) | Cmax (µg/ml) | Drug Availability (%) |
|---|---|---|---|
| 412f | 25 | 2.4 | 32 |
| 412d | 25 | 2.6 | 35 |
| 696a | 50 | 1.2 | 10 |
| 214e | 45 | 0.2 | 0.9% |

EXAMPLE 23

ICE Cleaves and Activates Pro-IGIF

ICE and ICE Homolog Expression Plasmids

A 0.6 kb cDNA encoding full length murine pro-IGIF (H. Okamura et al., *Nature*, 378, p. 88 (1995) was ligated into the mammalian expression vector pCDLSRα (Y. Takebe et al., *Mol. Cell. Biol.*, 8, p. 466 (1988)).

Generally, plasmids (3 µg) encoding active ICE (above), or the three ICE-related enzymes TX, CPP32, and CMH-1 in the pCDLSRα expression vector (C. Faucheu et al., *EMBO*, 14, p. 1914 (1995); Y. Gu et al., *EMBO*, 14, p. 1923 (1995); J. A. Lippke et al., *J. Biol. Chem.*, 271, p. 1825 (1996)), were transfected into subconfluent monolayers of Cos cells in 35-mm dishes using the DEAE-dextran method (Y. Gu et al., *EMBO J.*, 14, p. 1923 (1995)). Twenty-four hours later, cells were lysed and the lysates subjected to SDS-PAGE and immunoblotting using an antiserum specific for IGIF (H. Okamura et al., *Nature*, 378, p. 88 (1995).

Polymerase chain reaction was used to introduce Nde I sites at the 5' and 3' ends of the murine pro-IGIF cDNA using the following primers: GGAATTCCATATGGCTGCCAT-GTCAGAAGAC (forward, SEQ ID NO: 11) and GGT-TAACCATATGCTAACTTTGATGTAAGTTAGTGAG (reverse, SEQ ID NO: 12) The resulting NdeI fragment was ligated into *E. coli* expression vector pET-15B (Novagen) at the NdeI site to create a plasmid that directs the synthesis of a polypeptide of 213 amino acids consisting of a 21-residue peptide (MGSSHHHHHHSSGLVPRGSHM (SEQ ID NO: 13), where LVPRGS (SEQ ID NO: 8) represents a thrombin cleavage site) fused in-frame to the N-terminus of pro-IGIF at Ala2, as confirmed by DNA sequencing of the plasmid and by N-terminal sequencing of the expressed proteins. *E. coli* strain BL21 (DE3) carrying the plasmid was induced with 0.8 mM isopropyl-1-thio-β-D-galactopyranoside for 1.5 hours at 37° C., harvested, and lysed by microfluidization (Microfluidic, Watertown, Mass.) in Buffer A (20 mM sodium phosphate, pH 7.0, 300 mM NaCl, 2 mM dithiothreitol, 10% glycerol, 1 mM phenylmethylsulfonyl fluoride, and 2.5 µg/ml leupeptin). Lysates were cleared by centrifugation at 100,000×g for 30 mM. (His)6-tagged pro-IGIF protein was then purified from the supernatant by Ni-NTA-agarose (Qiagen) chromatography under conditions recommended by the manufacturer.

In Vitro Pro-IGIF Cleavage Reactions

In vitro cleavage reactions (30 µl) contained 2 µg of purified pro-IGIF and various concentrations of the purified proteases in a buffer containing 20 mM Hepes, pH 7.2, 0.1% Triton X-100, 2 mM DTT, 1 mM PMSF and 2.5 µg/ml leupeptin and were incubated for 1 hour at 37° C. Conditions for cleavage by granzyme B were as described previously (Y. Gu et al., *J. Biol. Chem.*, 271, p. 10816 (1996)). Cleavage products were analyzed by SDS-PAGE on 16% gels and Coomassie Blue staining, and were subjected to N-terminal amino acid sequencing using an ABI automated peptide sequencer under conditions recommended by the manufacturer.

Kinetic Parameters of IGIF Cleavage by ICE

The kinetic parameters ($k_{cat}/K_M$, $K_M$, and $k_{cat}$) for IGIF cleavage by ICE were determined as follows. $^{35}$S-methionine-labeled pro-IGIF (3000 cpm, prepared by in vitro transcription and translation using, the TNT T7-coupled reticulocyte lysate system (Promega) and pro-IGIF cDNA in a pSP73 vector as template) were incubated in reaction mixtures of 60 µl containing 0.1 to 1 nM recombinant ICE and 190 nM to 12 µM of unlabeled pro-IGIF for 8-10 min at 37° C. Cleavage product concentrations were determined by SDS-PAGE and PhosphoImager analyses. The kinetic parameters were calculated by nonlinear regression fitting of the rate vs. concentration data to the Michaelis-Menten equation using the program Enzfitter (Biosoft).

IFN-γ Induction Assays

A.E7 Th1 cells (H. Quill and R. H. Schwartz, *J. Immunol.*, 138, p. 3704 (1987)) ($1.3 \times 10^5$ cells in 0.15 ml Click's medium supplemented with 10% FBS, 50 µM 2-mercaptoethanol and 50 units/ml IL-2) in 96-well plates were treated with IGIF for 18-20 hours and the culture supernatant were assayed for IFN-γ by ELISA (Endogen, Cambridge, Mass.).

EXAMPLE 24

Processing of Pro-IGIF by ICE In Cos Cells

Cos cells were transfected with various expression plasmid combinations as described in Example 23. Transfected Cos cells ($3.5 \times 10^5$ cells in a 35-mm dish) were labeled for 7 hours with 1 ml of methionine-free DMEM containing 2.5% normal DMEM, 1% dialyzed fetal bovine serum and 300 µCi/ml $^{35}$S-methionine ($^{35}$S-Express Protein Labeling-Mix, New England Nuclear). Cell lysates (prepared in 20 mM Hepes, pH 7.2, 150 mM NaCl, 0.1% Triton X-100, 5 mM N-ethylmaleimide, 1 mM PMSF, 2.5 µg/ml leupeptine) or conditioned medium were immunoprecipitated with an antiIGIF antibody that recognizes both the precursor and the mature forms of IGIF (H. Okamura et al., *Nature,* 378, p. 88 (1995)). Immunoprecipitated proteins were analyzed by SDS-PAGE (polyacrylamide gel electrophoresis) and fluorography (FIG. 2A).

We also measured the presence of IFN-γ inducing activity in the cell lysates and the conditioned media of transfected cells (FIG. 2B). Transfected Cos cells ($3.5 \times 10^5$ cells in a 35-mm dish) were grown in 1 ml medium for 18 hours. Media was harvested and used at 1:10 final dilution in the IFN-γ induction assay (Example 23). Cos cell pellets from the same transfection were lysed in 100 μl of 20 mM Hepes, pH 7.0, by freeze-thawing 3 times. Lysates were cleared by centrifugation as described above and were used at a 1:10 dilution in the assay.

EXAMPLE 25

IGIF is a Physiological Substrate of ICE

Wild type (ICE+/+) and ICE−/− mice were primed with heat-inactivated *P. acnes,* and Kupffer cells were isolated from these mice 7 days after priming and were then challenged with 1 μg/ml LPS for 3 hours. The amounts of IGIF in the conditioned media were measured by ELISA.

Wild type or ICE-deficient mice were injected intraperitoneally with heat-killed *p. acnes* as described (H. Okamura et al., *Infection and Immunity,* 63, p. 3966 (1995)). Kupffer cells were prepared seven days later according to Tsutsui et al. (H. Tsutsui et al., *Hepato-Gastroenterol.,* 39, p. 553 (1992)) except a nycodenz gradient was used instead of metrizamide. For each experiment, Kupffer cells from 2-3 animals were pooled and cultured in RPMI 1640 supplemented with 10% fetal calf serum and 1 μg/ml LPS. Cell lysates and conditioned medium were prepared 3 hours later.

Kupffer cells from wild type and ICE−/− mice were metabolically labeled with $^{35}$S-methionine as for Cos cells (described above in Example 24) except that methionine-free RPMI 1640 was used in place of DMEM. IGIF immunoprecipitation experiments were performed on cell lysates and conditioned media and immunoprecipitates were analyzed by SDS-PAGE and fluorography as described in Example 23. See FIG. 3.

EXAMPLE 26

Induction of IFN-γ Production In Vivo

LPS mixed with 0.5% carboxymethyl cellulose in PBS, pH 7.4, was administered to mice by intraperitoneal injection (30 mg/kg LPS) in a dose volume of 10 ml/kg. Blood was collected every 3 h for 24 h from groups of three ICE-deficient or wild type mice. Serum IFN-γ levels were determined by ELISA (Endogen).

EXAMPLE 27

IGIF and IFN-γ Inhibition Assays

Inhibition of IGIF processing by ICE inhibitors was measured in ICE inhibition assays as described herein (see Example 1 and Table 22).

Human PBMC Assays

Human buffy coat cells were obtained from blood donors and peripheral blood mononuclear cells (PBMC) were isolated by centrifugation in LeukoPrep tubes (Becton-Dickinson, Lincoln Park, N.J.). PBMC were added ($3 \times 10^6$/well) to 24 well Corning tissue culture plates and after 1 hr incubation at 37° C., non-adherent cells were removed by gently washing. Adherent mononuclear cells were stimulated with LPS (1 μg/ml) with or without ICE inhibitor in 2 ml RPMI-1640-10% FBS. After 16-18 hr incubation at 37° C., IGIF and IFN-γ were quantitated in culture supernatants by ELISA.

For example, we obtained the following data for compound 412 of this invention using the methods described herein. The structure of compound 412 is shown below.

TABLE 22

| compound | UV-Visible $K_i$ (nM) | Cell PBMC avg. IC50 (nM) |
|---|---|---|
| 412 | 1.3 | 580 |

EXAMPLE 28

Compounds of this invention may be prepared via various methods. The following illustrates a preferred method:

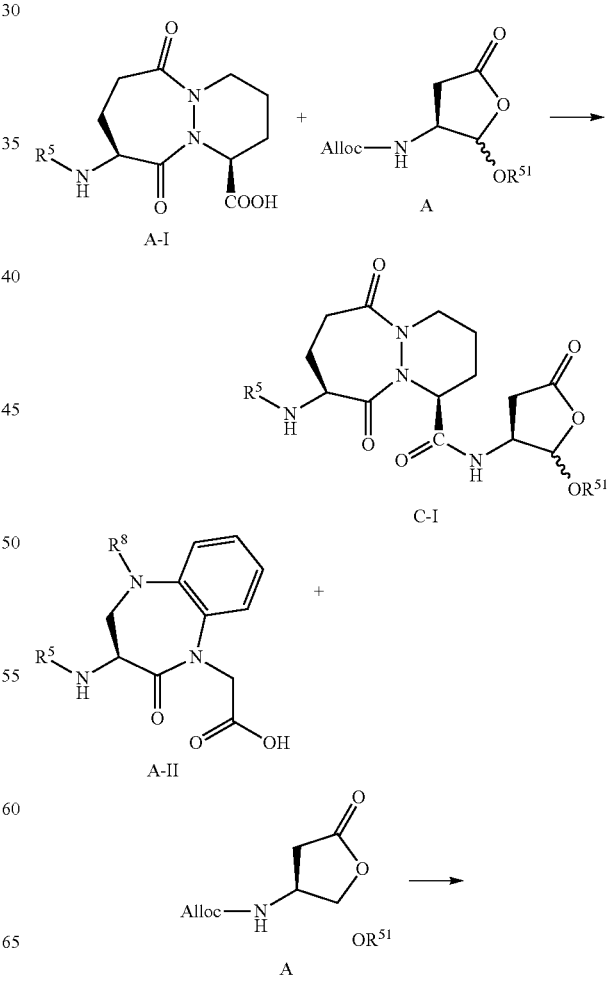

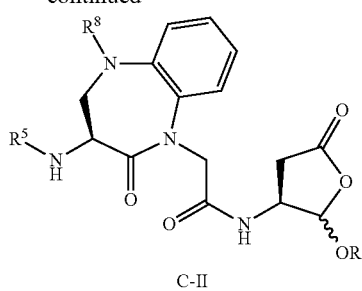

C-I

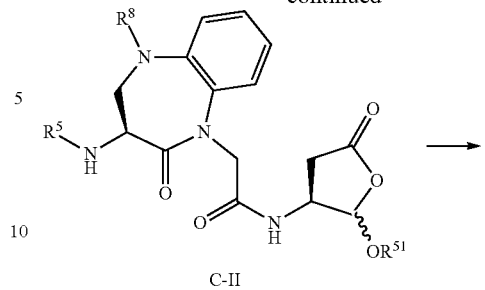

C-II

To a solution of A (1.1 equivalent) in $CH_2Cl_2$ (or DMF, or $CH_2Cl_2$:DMF (1:1)) is added triphenylphosphine (0-0.5 equivalent), a nucleophilic scavenger (2-50 equivalents) and tetrakis-triphenylphosphine palladium(0) (0.05-0.1 equivalent) at ambient temperature under inert atmosphere (nitrogen or argon). After 10 minutes, the above reaction mixture is optionally concentrated, then a solution of acid A-I or A-II in $CH_2Cl_2$ (or DMF, or $CH_2Cl_2$:DMF (1:1)) is added followed by addition of HOBT (1.1 equivalent) and EDC (1.1 equivalent). The resulting reaction mixture is allowed to stir at ambient temperature 1 hour-48 hours to provide coupled products C-I or C-II.

Various nucleophilic scavengers may be used in the above process. Merzouk and Guibe, *Tetrahedron Letters,* 33, pp. 477-480 (1992); Guibe and Balavoine, *Journal of Organic Chemistry,* 52, pp. 4984-4993 (1987)). Preferred nucleophilic scavengers that may be used include: dimedone, morpholine, trimethylsilyl dimethylamine and dimethyl barbituric acid. More preferred nuclophilic scavengers are trimethylsilyl dimethylamine (2-5 equivalents) and dimethyl barbituric (5-50 equivalents). When the nucleophilic scavenger is trimethylsilyl dimethylamine, the above reaction mixture must be concentrated prior to addition of A-I or A-II.

Other compounds of this invention may be prepared by hydrolyzing compounds represented by C-I and C-II to compounds represented by H-I and H-II as described in the following scheme:

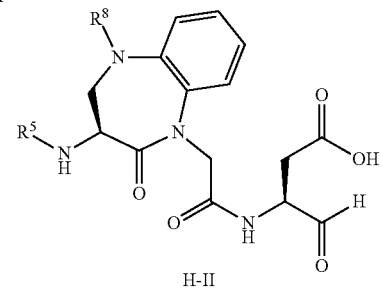

H-II

The hydrolysis may be carried out under various conditions, provided that the conditions include an acid and $H_2O$. Acids that may be used include p-toluensulfonic, methanesulfonic acid, sulfuric, perchloric, trifluoroacetic, and hydrochloric. For example, trifluoroacetic acid (1-90% by weight) or hydrochloric acid (0.1-30% by weight) in $CH_3CN/H_2O$ (1-90% $H_2O$ by weight) at between 0-50° C. may be used.

EXAMPLE 29

Compounds 213f, 213g, 213h, 213i, 213j, 213k, 213l, 213m, 214f, 214g, 214h, 214i, 214j, 214k, 214l, 214m, 550f, 550g, 550h, 550l, 550i, 550k, 550l and 550m were prepared as follows.

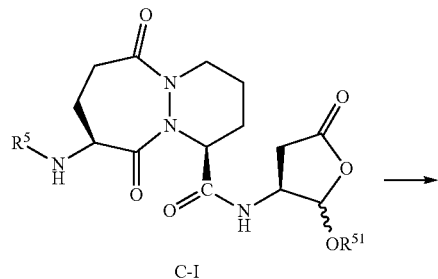

C-I

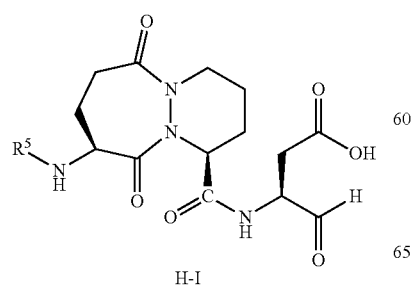

H-I

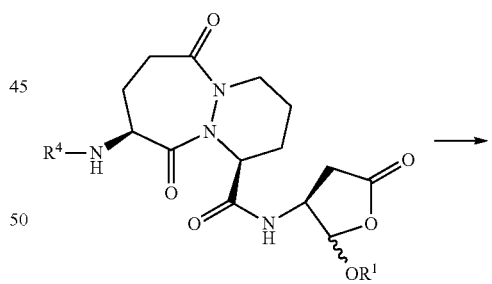

213f-m, $R^1$ = Bn
550f-m, $R_1$ = Et

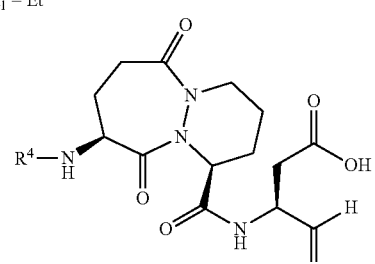

214f-m

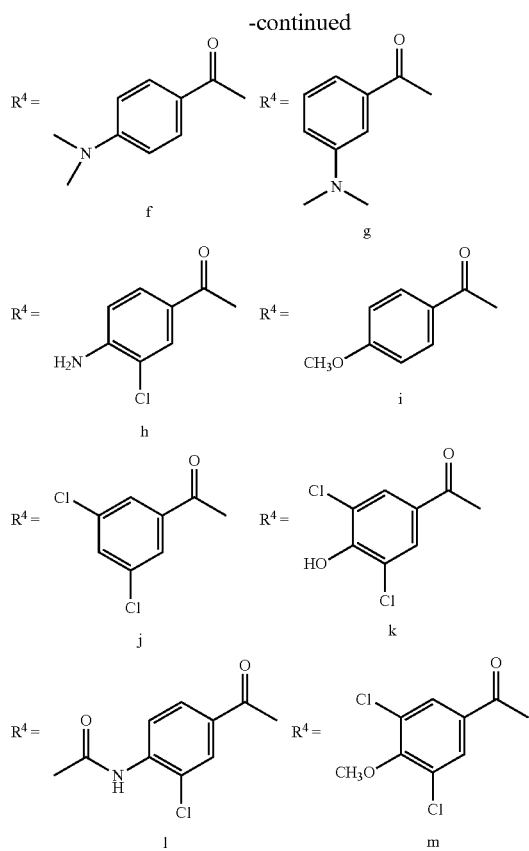

f
g
h
i
j
k
l
m

[1S,9S(2RS,3S)]9-[(4-Dimethylaminobenzoyl)amino]-6,10-dioxo-1,2,3,4,7,8,9,10-octahydro-N-(2-Benzyloxy-5-oxotetrahydrofuran-3-yl)-6H-pyridazino[1,2-a][1,2]diazepine-1-carboxamide (213f), was synthesized from 212f by the methods used to prepare 213e from 212e to afford 504 mg of 213f as a yellow solid, $^1$H NMR (CD$_3$OD) δ 1.10 (br. m, 0.25H), 1.30 (br. m, 2H), 1.50 (br. m, 1H), 1.65 (br. m, 1.5H), 1.80 (br. m, 0.25H), 1.90 (br. m, 0.25H), 1.95 (br. m, 0.5H), 2.05 (br. m, 0.25H), 2.15 (m, 1H), 2.3 (m, 1H), 2.5 (br. m, 1H), 2.6 (dd, 1H), 2.8 (m, 1H), 3.1 (br. s, 3H), 3.15 (br. m, 1H), 3.32 (br. s, 3H), 3.5 (m, 1H), 4.5 (br. m, 1H), 4.62 (br. d, 0.25H), 4.72 (m, 3H), 4.95 (m, 1H), 5.1 (br. t, 0.25H), 5.15 (br. t, 0.75H), 5.7 (d, 1H), 6.75 (d, 2H), 7.35 (br. s, 5H), 7.75 (d, 2H).

[1S,9S(2RS,3S)]9-[(3-Dimethylaminobenzoyl)amino]-6,10-dioxo-1,2,3,4,7,8,9,10-octahydro-N-(2-Benzyloxy-5-oxotetrahydrofuran-3-yl)-6H-pyridazino[1,2-a][1,2]diazepine-1-carboxamide (213g), was synthesized from 212g by the methods used to prepare 213e from 212e to afford 400 mg of 213g, $^1$H NMR (CD$_3$OD) δ 1.5 (br. m, 1H), 1.65 (br. m, 2H), 1.70 (br. m, 0.25H), 1.90 (br. m, 1H), 1.95 (br. m, 1H), 2.05 (br. m, 0.25H), 2.10 (m, 1H), 2.3 (m, 1H), 2.5 (m, 2H), 2.59 (d, 1H), 2.6 (d, 1H), 2.78 (d, 1H), 2.8 (d, 1H), 2.93 (br. s, 4H), 3.05 (br. m, 1H), 3.15 (br. m, 0.25H), 3.3 (br. s, 3H), 3.5 (m, 2H), 4.5 (br. m, 2H), 4.65 (d, 1H), 4.7 (br. m, 2H), 4.95 (br. m, 1H), 5.15 (br. t, 0.25H), 5.2 (br. t, 0.75H), 5.2 (d, 1H), 6.95 (d, 1H), 7.15 (d, 1H), 7.25 (br. s, 1H), 7.3 (br. t, 2H), 7.45 (br. s, 6H).

[1S,9S(2RS,3S)]9-[(3-Chloro-4-aminobenzoyl)amino]-6,10-dioxo-1,2,3,4,7,8,9,10-octahydro-N-(2-Benzyloxy-5-oxotetrahydrofuran-3-yl)-6H-pyridazino[1,2-a][1,2]diazepine-1-carboxamide (213h), was synthesized from 212h by the methods used to prepare 213e from 212e to afford 296 mg of 213h, $^1$H NMR (CDCl$_3$) δ 1.55-1.68 (m, 1H), 1.7-2.05 (m, 3H), 2.3-2.5 (m, 2H), 2.65-2.8 (m, 1H), 2.85-2.93 (m, 1H), 2.95-3.25 (m, 3H), 4.44-4.65 (m, 2H), 4.68-4.82 (m, 1H), 4.9-4.95 (d, 1H), 5.05-5.18 (m, 2H), 5.28 (s, 0.5H), 5.55-5.58 (d, 0.5H), 6.52-6.58 (d, 0.5H), 6.7-6.76 (m, 2H), 6.82-6.85 (d, 0.5H), 7.3-7.4 (m, 5H), 7.52-7.58 (m, 1H), 7.75 (s, 0.5H), 7.8 (s, 0.5H).

[1S,9S(2RS,3S)]9-[(4-Methoxybenzoyl)amino]-6,10-dioxo-1,2,3,4,7,8,9,10-octahydro-N-(2-Benzyloxy-5-oxotetrahydrofuran-3-yl)-6H-pyridazino[1,2-a][1,2]diazepine-1-carboxamide (213i), was synthesized from 212i by the methods used to prepare 213e from 212e to afford 1.1 g of 213i, $^1$H NMR (CDCl$_3$) δ 1.55-2.05 (m, 6H), 2.26-2.5 (m, 2H), 2.68-2.82 (m, 1H), 2.85-2.92 (m, 1H), 2.95-3.25 (m, 2H), 3.82 (s, 1.5H), 3.85 (s, 1.5H), 4.4-4.65 (m, 2H), 4.7-4.78 (m, 1H), 4.88-4.95 (m, 1H), 5.05-5.23 (m, 1H), 5.28 (s, 0.5H), 5.55-5.58 (d, 0.5H), 6.6-6.65 (m, 1H), 6.8-6.84 (m, 1H), 6.9-6.95 (m, 3H), 7.3-7.45 (m, 4H), 7.78-7.85 (m, 2H).

[1S,9S(2RS,3S)]9-[(3,5-Dichlorobenzoyl)amino]-6,10-dioxo-1,2,3,4,7,8,9,10-octahydro-N-(2-Benzyloxy-5-oxotetrahydrofuran-3-yl)-6H-pyridazino[1,2-a][1,2]diazepine-1-carboxamide (213j), was synthesized from 212j by the methods used to prepare 213e from 212e to afford 367 mg of 213j, $^1$H NMR (CDCl$_3$) δ 1.55-2.05 (m, 12H), 2.25 (d, 1H), 2.35 (m, 1H), 2.48 (m, 2H), 2.75 (m, 2H), 2.9 (m, 1H), 2.95-3.25 (m, 5H), 4.45 (t, 1H), 4.5-4.6 (m, 4H), 4.7 (m, 1H), 4.75 (d, 1H), 4.88 (m, 1H), 5.05 (m, 2H), 5.15 (q, 1H), 5.3 (s, 1H), 5.58 (d, 1H), 6.5 (d, 1H), 6.9 (d, 1H), 7.05 (d, 1H), 7.25-7.35 (m, 5H), 7.6 (s, 2H), 7.7 (s, 2H).

[1S,9S(2RS,3S)]9-[(3,5-Dichloro-4-hydroxybenzoyl)amino]-6,10-dioxo-1,2,3,4,7,8,9,10-octahydro-N-(2-Benzyloxy-5-oxotetrahydrofuran-3-yl)-6H-pyridazino[1,2-a][1,2]diazepine-1-carboxamide (213k), was synthesized from 212k by the methods used to prepare 213e from 212e to afford 593 mg of 213k, $^1$H NMR (CD$_3$OD) δ 1.5 (m, 1H), 1.6-1.7 (m, 2H), 1.75-1.95 (m, 4H), 2.15 (m, 2H), 2.3 (m, 1H), 2.6 (m, 1H), 2.7 (m, 1H), 3.05 (m, 2H), 3.15 (m, 1H), 3.5 (m, 2H), 4.45 (m, 2H), 4.65 (d, 1H), 4.7 (m, 1H), 4.95 (m, 1H), 5.15 (m, 1H), 5.4 (s, 1H), 5.7 (d, 1H), 7.3 (m, 5H), 7.85 (s, 2H).

[1S,9S(2RS,3S)]9-[(3-Chloro-4-acetamidobenzoyl)amino]-6,10-dioxo-1,2,3,4,7,8,9,10-octahydro-N-(2-Benzyloxy-5-oxotetrahydrofuran-3-yl)-6H-pyridazino[1,2-a][1,2]diazepine-1-carboxamide (213l), was synthesized from 212l by the methods used to prepare 213e from 212e to afford 133 mg of 213l, $^1$H NMR (CDCl$_3$) δ 1.55-1.7 (m, 1H), 1.75-2.05 (m, 3H), 2.25 (s, 1.5H), 2.27 (s, 1.5H), 2.3-2.48 (m, 2H), 2.7-2.83 (m, 1H), 2.85-2.94 (dd, 1H), 2.95-3.25 (m, 2H), 4.42-4.65 (m, 2H), 4.68-4.85 (m, 1H), 4.88-4.95 (m, 1H), 5.05-5.18 (m, 2H), 5.32 (s, 0.5H), 5.55-5.6 (d, 0.5H), 6.48-6.55 (d, 1H), 6.88-6.92 (d, 1H), 7.0-7.04 (d, 0.5H), 7.15-7.2 (d, 0.5H), 7.3-7.4 (m, 4H), 7.64-7.78 (m, 2H), 7.88-7.94 (m, 1H), 8.45-8.56 (m, 1H).

[1S,9S(2RS,3S)]9-[(3,5-Dichloro-4-methoxybenzoyl)amino]-6,10-dioxo-1,2,3,4,7,8,9,10-octahydro-N-(2-Benzyloxy-5-oxotetrahydrofuran-3-yl)-6H-pyridazino[1,2-a][1,2]diazepine-1-carboxamide (213m), was synthesized from 212m by the methods used to prepare 213e from 212e to afford 991 mg of 213m, $^1$H NMR (CDCl$_3$) δ 1.5-2.15 (m, 5H), 2.2-2.55 (m, 3H), 2.6-3.3 (m, 4H), 3.95 (2s, 3H), 4.45-4.7 (m, 2H), 4.7-4.85 (m, 1H), 4.8504.95 (m, 1H), 5.05-5.25 (m, 1H), 5.3 (s, 0.5H), 5.6 (d, 0.5H), 6.55 (d, 0.5H), 6.85 (d, 0.5H), 7.0 (d, 0.5H), 7.25-7.6 (m, 5.5H), 7.75 (s, 1H), 7.85 (s, 1H).

[1S,9S(2RS,3S)]9-[(4-Dimethylaminobenzoyl)amino]-6,10-dioxo-1,2,3,4,7,8,9,10-octahydro-N-(2-ethoxy-5-oxotetrahydrofuran-3-yl)-6H-pyridazino[1,2-a][1,2]diazepine-1-carboxamide (550f), was synthesized from 212f by the methods used to prepare 213e from 212e to afford 420 mg of 550f as an off white solid, $^1$H NMR (CDCl$_3$) δ 1.2-1.25 (br. t, 3H), 1.35 (m, 1H), 1.55 (br. m, 1H), 1.88-2.02 (br. m, 4H), 2.3 (d, 1H), 2.35 (m, 1H), 2.45 (m, 1H), 2.55-2.75 (m, 3H), 3.0 (s, 6H), 3.25 (m, 1H), 3.55 (m, 1H), 3.65 (m, 1H), 3.75 (m, 1H), 3.9 (m, 1H), 4.3 (t, 1H), 4.55 (m, 2H), 4.66 (br. m, 1H), 3.9 (m, 1H), 4.3 (t, 1H), 4.55 (m, 2H), 4.68 (br. m, 1H), 4.95 (br. m, 1H), 5.1 (br. m, 2H), 5.45 (d, 1H), 6.5 (m, 2H), 7.7 (m, 2H).

[1S,9S(2RS,3S)]9-[(3-Chloro-4-aminobenzoyl)amino]-6,10-dioxo-1,2,3,4,7,8,9,10-octahydro-N-(2-ethoxy-5-oxotetrahydrofuran-3-yl)-6H-pyridazino[1,2-a][1,2]diazepine-1-carboxamide (550h), was synthesized from 212h by the methods used to prepare 213e from 212e to afford 195 mg of 550h as a white solid, $^1$H NMR (DMSO-d$_6$) δ 1.1-1.18 (2t, 3H), 1.6-1.7 (m, 2H), 1.88-2.05 (m, 2H), 2.1-2.35 (m, 3H), 2.48-2.56 (m, 1H), 2.75-2.8 (m, 0.75H), 2.88-3.08 (m, 1.25H), 3.25-3.4 (m, 1H), 3.55-3.8 (m, 2H), 4.35-4.45 (m, 1H), 4.55-4.62 (m, 1H), 4.8-4.88 (m, 1H), 4.98-5.03 (m, 0.25H), 5.1-5.13 (m, 0.75H), 5.33 (s, 0.25H), 5.58-5.6 (d, 0.75H), 5.9-6.0 (br. s, 2H), 6.8-6.85 (d, 1H), 7.58-7.62 (d, 1H), 7.82 (s, 1H), 8.22-8.28 (d, 1H), 8.48-8.52 (d, 0.75H), 8.72-8.76 (d, 0.25H).

[1S,9S(2RS,3S)]9-[(4-Methoxybenzoyl)amino]-6,10-dioxo-1,2,3,4,7,8,9,10-octahydro-N-(2-ethoxy-5-oxotetrahydrofuran-3-yl)-6H-pyridazino[1,2-a][1,2]diazepine-1-carboxamide (550i), was synthesized from 212i by the methods used to prepare 213e from 212e to afford 135 mg of 550i, $^1$H NMR (CDCl$_3$) δ 1.18-1.28 (2t, 3H), 1.6-1.75 (m, 1.5H), 1.9-2.1 (m, 3.5H), 2.22-2.3 (d, 0.5H), 2.38-2.47 (m, 1.5H), 2.7-2.8 (m, 0.5H), 2.8-2.93 (m, 1H), 2.94-3.15 (m, 1.5H), 3.15-3.28 (m, 1H), 3.55-3.62 (q, 0.5H), 3.62-3.73 (q, 0.5H), 3.78-3.88 (q, 0.5H), 3.88 (s, 3H), 3.9-3.95 (q, 0.5H), 4.33-4.4 (m, 0.5H), 4.5-4.55 (m, 1H), 4.68-4.76 (m, 0.5H), 4.9-4.95 (m, 0.5H), 5.1-5.2 (m, 1.5H), 5.18 (s, 0.5H), 5.48-5.52 (d, 0.5H), 6.48-6.55 (d, 0.5H), 6.85-6.9 (m, 1H), 6.9-6.95 (m, 2H), 7.34-7.38 (d, 0.5H), 7.78-7.85 (m, 2H).

[1S,9S(2RS,3S)]9-[(3,5-Dichloro-4-hydroxybenzoyl)amino]-6,10-dioxo-1,2,3,4,7,8,9,10-octahydro-N-(2-ethoxy-5-oxotetrahydrofuran-3-yl)-6H-pyridazino[1,2-a][1,2]diazepine-1-carboxamide (550k), was synthesized from 212k by the methods used to prepare 213e from 212e to afford 174 mg of 550k as a white solid, $^1$H NMR (DMSO-d$_6$) δ 1.15 (2t, 3H), 1.6-1.75 (m, 2H), 1.9-2.05 (m, 2H), 2.1-2.4 (m, 5H), 2.5-2.55 (m, 1H), 2.7-2.8 (m, 0.5H), 2.85-3.0 (m, 1H), 3.0-3.1 (m, 0.5H), 3.55-3.7 (m, 1H), 3.7-3.8 (m, 1H), 4.2 (t, 0.5H), 4.35-4.45 (m, 0.5H), 4.55-4.65 (m, 0.5H), 4.8-4.9 (m, 0.5H), 5.05 (t, 0.5H), 5.15 (t, 0.5H), 5.35 (s, 0.5H), 5.6 (d, 0.5H), 7.95 (s, 2H), 8.5 (d, 0.5H), 8.65 (d, 1H), 8.75 (d, 0.5H), 10.9 (br. s, 1H).

[1S,9S(2RS,3S)]9-[(3-Chloro-4-acetamidobenzoyl)amino]-6,10-dioxo-1,2,3,4,7,8,9,10-octahydro-N-(2-ethoxy-5-oxotetrahydrofuran-3-yl)-6H-pyridazino[1,2-a][1,2]diazepine-1-carboxamide (550l), was synthesized from 212l by the methods used to prepare 213e from 212e to afford 151 mg of 550l, $^1$H NMR (CDCl$_3$) δ 1.2-1.28 (2t, 3H), 1.6-1.72 (m, 1.5H), 1.88-2.15 (m, 3.5H), 2.22-2.28 (m, 0.5H), 2.28 (s, 3H), 2.38-2.48 (m, 1.5H), 2.66-2.92 (m, 1.5H), 2.95-3.14 (m, 1.5H), 3.2-3.34 (m, 1H), 3.56-3.63 (q, 0.5H), 3.63-3.72 (q, 0.5H), 3.8-3.85 (q, 0.5H), 3.9-3.95 (q, 0.5H), 4.32-4.38 (m, 0.5H), 4.5-4.62 (m, 1H), 4.68-4.75 (m, 0.5H), 4.88-4.92 (m, 0.5H), 5.08-5.2 (m, 1.5H), 5.18 (s, 0.5H), 5.46-5.5 (d, 0.5H), 6.5-6.55 (d, 0.5H), 6.98-7.05 (m, 1H), 7.42-7.48 (d, 0.5H), 7.63-7.78 (m, 2.5H), 7.9-7.94 (d, 0.5H), 8.44-8.52 (m, 1H).

[1S,9S(2R8,3S)]9-[(3,5-Dichloro-4-methoxybenzoyl)amino]-6,10-dioxo-1,2,3,4,7,8,9,10-octahydro-N-(2-ethoxy-5-oxotetrahydrofuran-3-yl)-6H-pyridazino[1,2-a][1,2]diazepine-1-carboxamide (550m), was synthesized from 212m by the methods used to prepare 213e from 212e to afford 301 mg of 550m as a white solid, $^1$H NMR (CDCl$_3$) δ 1.2-1.35 (2t, 3H), 1.5-1.8 (m, 2H), 1.9-2.15 (5H), 2.25 (d, 0.5H), 2.4-2.5 (m, 2H), 2.65-2.8 (m, 0.5H), 2.8-3.0 (m, 0.5H), 3.0-3.2 (m, 1H), 3.2-3.35 (m, 0.5H), 3.55-3.65 (m, 0.5H), 3.65-3.75 (m, 0.5H), 3.8-3.9 (m, 0.5H), 3.9-4.0 (m, 0.5H), 4.4-4.45 (m, 0.5H), 4.55-4.65 (m, 0.5H), 4.7-4.8 (m, 0.5H), 4.85-4.95 (m, 0.5H), 5.05-5.2 (m, 0.5H), 5.2 (s, 0.5H), 5.5 (d, 0.5H), 6.5 (d, 0.5H), 6.9 (d, 0.5H), 6.95 (d, 0.5H), 7.35 (d, 0.5H), 7.75 (s, 1H), 7.85 (s, 1H).

[3S(1S,9S)]3-(9-(3,5-Dichlorobenzoyl)amino-6,10-dioxo-1,2,3,4,7,8,9,10-octahydro-6H-pyridazino[1,2-a][1,2]diazepine-1-carboxamido)-4-oxobutanoic acid (214j), was synthesized from 213j by the method used to prepare 2002 from 2001 to afford 62 mg of 214j as a white solid, $^1$H NMR (CD$_3$OD) δ 0.9 (t, 1H), 1.3 (br. s, 1H), 1.7 (br. m, 1H), 1.9 (br. m, 1H), 2.1 (br. s, 1H), 2.25 (q, 1H), 2.35 (m, 1H), 2.48 (m, 2H), 2.65 (t, 1H), 3.15 (br. t, 1H), 3.5 (br. m, 1H), 4.3 (br. s, 1H), 4.55 (m, 2H), 4.95 (t, 1H), 5.25 (br. s, 1H), 7.6 (br. s, 1H), 7.85 (br. s, 1H).

[3S(1S,9S)]3-(9-(3,5-Dichloro-4-hydroxybenzoyl)amino-6,10-dioxo-1,2,3,4,7,8,9,10-octahydro-6H-pyridazino[1,2-a][1,2]diazepine-1-carboxamido)-4-oxobutanoic acid (214k), was synthesized from 213k by the method used to prepare 2002 from 2001 to afford 80 mg of 214k as a white solid, $^1$H NMR (CD$_3$OD) δ 1.6-1.7 (m, 1H), 1.8-2.0 (m, 2H), 2.0-2.1 (m, 2H), 2.15-2.25 (m, 1H), 2.3-2.4 (m, 1H), 2.4-2.55 (m, 2H), 2.6-2.75 (m, 1H), 3.05-3.2 (m, 1H), 3.4-3.6 (m, 2H), 4.2-4.3 (m, 1H), 4.45-4.6 (m, 1H), 4.8-5.0 (m, 1H), 5.1-5.2 (m, 1H), 7.85 (s, 2H).

[3S(1S,9S)]3-(9-(3-Chloro-4-acetamidobenzoyl)amino-6,10-dioxo-1,2,3,4,7,8,9,10-octahydro-6H-pyridazino[1,2-a][1,2]diazepine-1-carboxamido)-4-oxobutanoic acid (214l), was synthesized from 213l by the method used to prepare 2002 from 2001 to afford 91 mg of 214l as a white solid, $^1$H NMR (DMSO-d$_6$) δ 1.65 (br. m, 6H), 1.9 (br. m, 6H), 2.15 (s, 3H), 2.3 (m, 3H), 2.6-2.85 (m, 3H), 2.9 (m, 2H), 3.0 (m, 1H), 4.15 (br. q, 1H), 4.4 (m, 3H), 5.0 (m, 1H), 5.15 (m, 1H), 5.45 (s, 1H), 7.8 (d, 2H), 7.95 (d, 1H), 8.05 (s, 1H), 8.65 (m, 2H), 9.65 (s, 1H).

[3S(1S,9S)]3-(9-(3,5-Dichlorobenzoyl)amino-6,10-dioxo-1,2,3,4,7,8,9,10-octahydro-6H-pyridazino[1,2-a][1,2]diazepine-1-carboxamido)-4-oxobutanoic acid (214m), was synthesized from 213m by the method used to prepare 2002 from 2001 to afford 105 mg of 214m as a white solid, $^1$H NMR (CD$_3$OD) δ 1.6-1.75 (m, 1H), 1.85-1.95 (m, 1H), 2.0-2.1 (m, 2H), 2.15-2.25 (m, 1H), 2.3-2.4 (m, 1H), 2.45-2.55 (m, 2H), 2.65-2.75 (m, 1H), 3.4-3.55 (m, 2H), 3.95 (s, 3H), 4.2-4.3 (m, 1H), 4.45-4.6 (m, 1H), 4.9-5.0 (m, 1H), 5.15-5.2 (m, 1H), 7.9 (s, 2H).

Compounds 308c and 308d were prepared as follows.

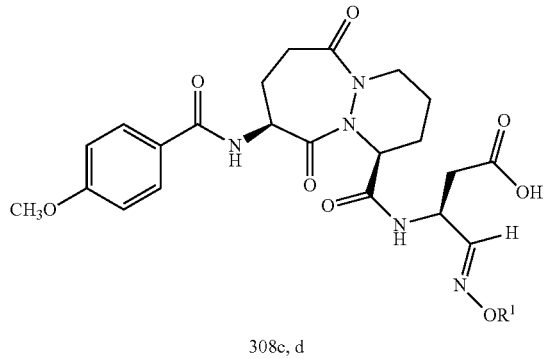

308c, d c R[1] = Me    d R[1] =

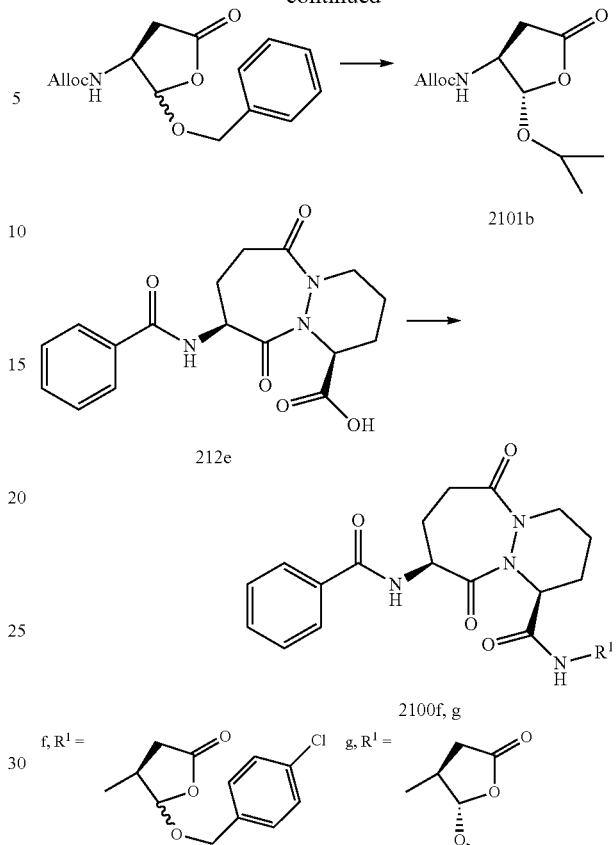

[3S(1S,9S)3-(9-(4-Methoxybenzoyl)amino-6,10-dioxo-1,2,3,4,7,8,9,10-octahydro-6H-pyridazino[1,2-a][1,2]diazepine-1-carboxamido)-amino]-4-oxobutanoic acid, O-methyl oxime (308c), was synthesized from 212e via the methods used to prepare 308b from 212e to afford 266 mg of 308c $^1$H NMR (CDCl$_3$) δ 1.6-1.7 (m, 1H), 1.88-1.98 (m, 3H), 2.02-2.15 (m, 1H), 2.3-2.4 (m, 1H), 2.65-2.95 (m, 3H), 3.04-3.09 (m, 1H), 3.12-3.25 (m, 1H), 3.84 (s, 3H), 3.86 (s, 3H), 4.5-4.58 (m, 1H), 4.88-4.95 (m, 1H), 5.1-5.25 (m, 2H), 6.86-6.9 (d, 2H), 7.15-7.25 (m, 2H), 7.36-7.4 (m, 1H), 7.75-7.8 (d, 2H).

[3S(1S,9S)3-(9-(4-Methoxybenzoyl)amino-6,10-dioxo-1,2,3,4,7,8,9,10-octahydro-6H-pyridazino[1,2-a][1,2]diazepine-1-carboxamido)-amino]-4-oxobutanoic acid, O-benzyl oxime (308d), was synthesized from 212e via the methods used to prepare 308b from 212e to afford 270 mg of 308d, $^1$H NMR (CDCl$_3$) δ 1.55-1.65 (m, 1H), 1.8-2.1 (m, 4H), 2.3-2.4 (m, 1H), 2.65-2.88 (m, 3H), 2.9-3.3 (m, 3H), 4.5-4.58 (m, 1H), 4.88-4.95 (m, 1H), 5.05 (s, 2H), 5.1-5.2 (m, 1H), 6.82-6.95 (m, 2H), 7.02-7.15 (m, 2H), 7.28 (m, 5H), 7.45 (m, 1H), 7.72 (d, 2H).

Compounds 2100f, 2100g, 2100h, 2100i and 2100j were prepared as described below.

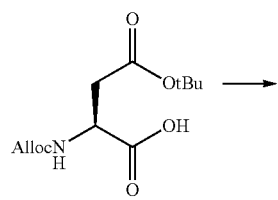

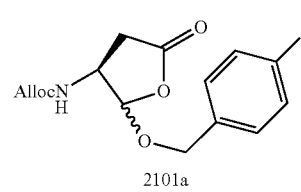

2101a (3S,2RS)3-Allyloxycarbonylamino-2-(4-chlorobenzyl)oxy-5-oxotetrahydrofuran (2101a), was synthesized from allyloxycarbonylamino-β-tert-butyl aspartate by the methods employed by Chapman (*Bioorg. & Med. Chem. Lett.*, 2, pp. 615-618 (1992)) to prepare (3S,2RS)3-allyloxycarbonylamino-2-benzyloxy-5-oxotetrahydrofuran using 4-chlorobenzyl alcohol instead of benzyl alcohol to afford 1.84 g of 2101a as a crystalline solid.

[1S,9S(2RS,3S)]9-Benzoylamino-6,10-dioxo-1,2,3,4,7,8,9,10-octahydro-N-(2-(4-chlorobenzyl)oxy-5-oxotetrahydrofuran-3-yl)-6H-pyridazino[1,2-a][1,2]diazepine-1-carboxamide (2100f), was synthesized from 212e by the methods used to prepare 213e from 212e using 2101a to afford 380 mg of 2100f, $^1$H NMR (CDCl$_3$) δ 1.8-2.0 (m, 10H), 2.30 (d, 1H), 2.31-2.5 (m, 3H), 2.7-2.9 (m, 3H), 3.05 (m, 2H), 3.1-3.2 (m, 4H), 4.45 (q, 1H), 4.5-4.6 (m, 3H), 4.7 (d, 2H), 4.85 (d, 1H), 4.9 (t, 1H), 5.2 (t, 1H), 5.15 (m, 2H), 5.25 (s, 1H), 5.55 (d, 1H), 6.5 (d, 1H), 6.9 (d, 1H), 6.95 (d, 1H), 7.25 (m, 3H), 7.35 (t, 2H), 7.45 (m, 2H), 7.55 (1H), 7.8 (m, 3H).

(3S,2RS)3-Allyloxycarbonylamino-2-anti-isopropoxy-5-oxotetrahydrofuran (2101b), was synthesized from (3S,2RS)3-allyloxycarbonylamino-2-benzyloxy-5-oxotetrahydrofuran via the method used to prepare 2100d from 214e using H$_2$SO$_4$ instead of pTSA to afford 2101b.

[1S,9S(2RS,3S)]9-Benzoylamino-6,10-dioxo-1,2,3,4,7,8,9,10-octahydro-N-(2-anti-isopropoxy-5-oxotetrahydrofuran-3-yl)-6H-pyridazino[1,2-a][1,2]diazepine-1-carboxamide (2100 g), was synthesized from 212e by the methods used to prepare 213e from 212e using 2101b to afford 31 mg of 2100g, $^1$H NMR (CDCl$_3$) δ 1.19 (d), 1.94 (br s), 2.00-2.12 (m), 2.24 (d), 2.42 (dd), 2.71-2.83 (m), 3.02 (dd), 3.12-3.27 (overlapping m), 3.93 (m), 4.32-4.37 (m), 4.52-4.63 (m), 4.90-4.95 (m), 5.12-5.20 (m), 5.28 (s), 6.93 (d), 7.10 (d), 7.41-7.50 (m), 7.51-7.58 (m), 7.84 (d).

214e → 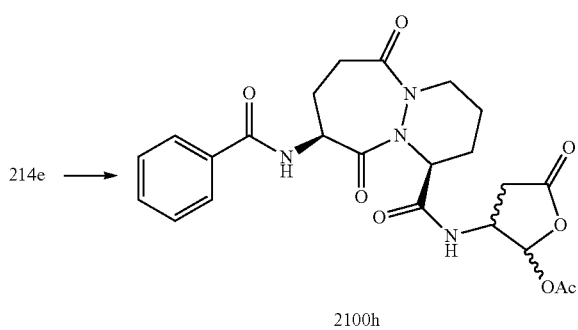

2100h

[1S,9S(2RS,3RS)]9-Benzoylamino-6,10-dioxo-1,2,3,4,7,8,9,10-octahydro-N-(2-acetoxy-5-oxotetrahydrofuran-3-yl)-6H-pyridazino[1,2-a][1,2]diazepine-1-carboxamide (2100h).

A solution of 214e (287 mg, 0.65 mmol) in pyridine (5 mL) was treated with Ac$_2$O (0.4 mL, 3.62 mmol). After 6 hours, the reaction mixture was poured into 5% NaHSO$_4$ and extracted 3 times with EtOAc. The combined organics were washed with brine, dried over Na$_2$SO$_4$ and concentrated in vacuo. Chromatography (SiO$_2$, EtOAc) afforded 119 mg of 2100h, $^1$HNMR (CDCl$_3$, mixture of four diastereoisomers) δ 1.80-2.05 (m), 2.12 (s), 2.13 (s), 2.19 (s), 2.22 (d), 2.67-2.75 (m), 2.80-2.95 (m), 3.00-3.20 (m), 3.21-3.33 (m), 3.50-3.95 (four discrete multiplets), 4.19 (m), 4.55 (m), 4.57-4.65 (m), 4.69 (m), 4.85-4.95 (m), 5.04 (m), 5.10 (s), 5.10-5.22 (m), 6.46 (d), 6.03 (s), 6.50 (d), 6.58 (d), 6.75 (d), 6.95-7.05 (m), 7.22 (m), 7.30 (m), 7.71 (d), 7.75-7.83 (m).

2100b → 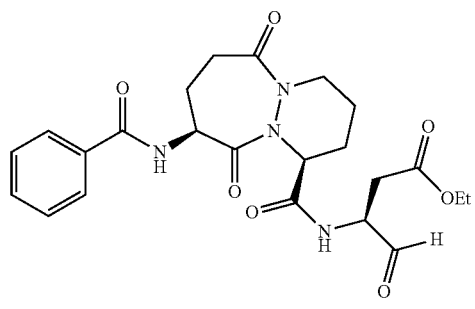

2100i

[3S(1S,9S)]3-(9-Benzoylamino-6,10-dioxo-1,2,3,4,7,8,9,10-octahydro-6H-pyridazino[1,2-a][1,2]diazepine-1-carboxamido)-4-oxobutanoic acid ethyl ester (2100i). To a solution of 2100b (1.5 g, 2.7 mmol) in CH$_3$CN (10 mL) was added 1N HCl at ambient temperature. After 6 hours solid NaHCO$_3$ was added and the product extracted with EtOAc, dried over MgSO$_4$ and concentrated in vacuo. Chromatography (SiO$_2$, 30-100% CH$_2$Cl$_2$ in EtOAc) afforded 123 mg of 2100i, $^1$H NMR (CDCl$_3$) δ 1.25 (t, 3H), 1.6-1.8 (m, 1H), 1.9-2.2 (m, 5H), 2.4-2.5 (m, 1H), 2.75-2.9 (m, 2H), 3.0-3.1 (m, 2H), 3.2-3.25 (m, 1H), 4.05-4.2 (m, 1H), 4.5-4.7 (m, 1H), 5.1-5.25 (m, 1H), 7.0-7.2 (m, 2H), 7.4-7.45 (m, 2H), 7.5 (t, 1H), 7.8 (t, 2H), 9.5 (s, 1H).

2100i → 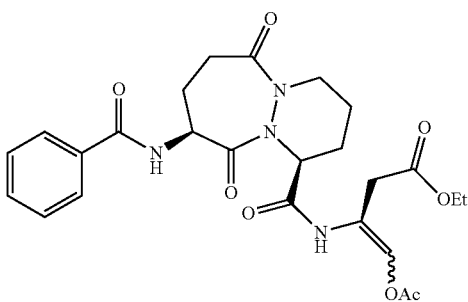

2100j

[3S(1S,9S)]3-(9-Benzoylamino-6,10-dioxo-1,2,3,4,7,8,9,10-octahydro-6H-pyridazino[1,2-a][1,2]diazepine-1-carboxamido)-4-acetoxy-3-butenoic acid ethyl ester (2100j), was synthesized from 2100i via the method used to prepare 2100h from 214e to afford 347 mg of 2100j, $^1$H NMR (CDCl$_3$) δ 1.3 (t, 3H), 1.6-1.8 (m, 2H), 1.9-2.25 (m, 4H), 2.25 (s, 3H), 2.3-2.45 (m, 1H), 2.8-3.0 (m, 1H), 3.0-3.25 (m, 2H), 3.4-3.45 (m, 2H), 4.1-4.2 (m, 2H), 4.55-4.7 (m, 1H), 5.1-5.25 (m, 1H), 6.8 (s, 1H), 7.0-7.1 (m, 2H), 7.5 (t, 1H), 7.8 (t, 2H), 9.5 (s, 1H).

Compounds 500 and 501 are described in Table 23. These compounds were prepared by methods similar to the methods used to prepare compounds 404-449 (see, Example 11).

TABLE 23

| Compound Structure | MF | MW | HPLC RT min (method) Purity | MS (M + H)+ |
|---|---|---|---|---|
| 500 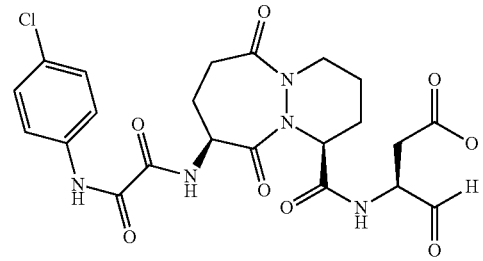 | C22H24ClN5O8 | 521.92 | 11.448 (A) 0.991 | 523.1 |

TABLE 23-continued
| Compound Structure | MF | MW | HPLC RT min (method) Purity | MS (M + H)+ |
|---|---|---|---|---|
| 501 | C24H28N4O10 | 532.51 | 10.13 0.97 | 533 |
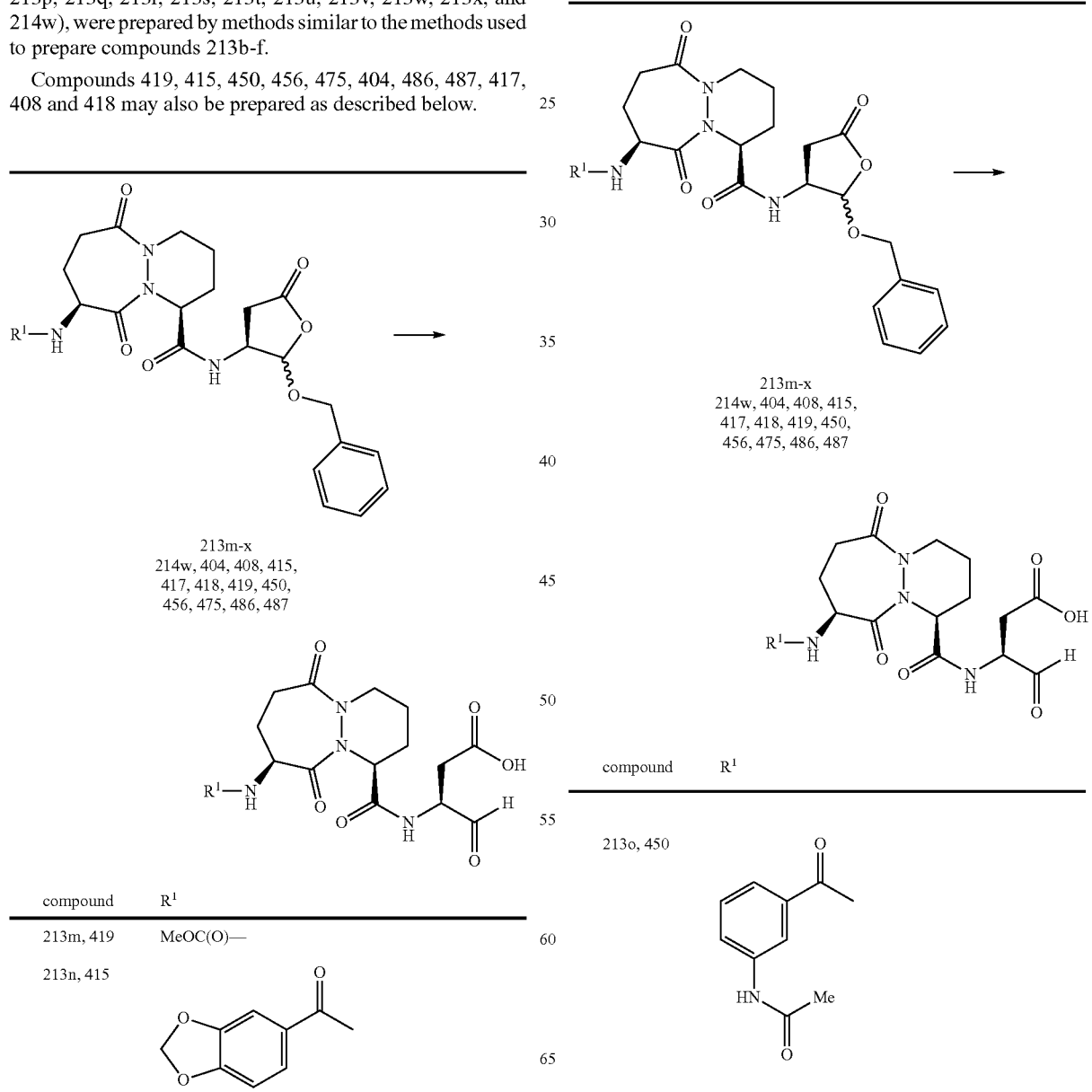
The compounds described below (213m, 213n, 213o, 213p, 213q, 213r, 213s, 213t, 213u, 213v, 213w, 213x, and 214w), were prepared by methods similar to the methods used to prepare compounds 213b-f.
Compounds 419, 415, 450, 456, 475, 404, 486, 487, 417, 408 and 418 may also be prepared as described below.

405
-continued
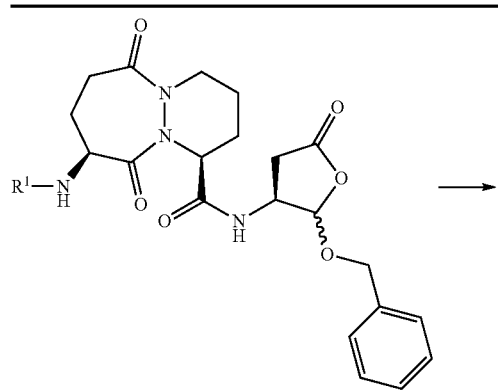
213m-x
214w, 404, 408, 415,
417, 418, 419, 450,
456, 475, 486, 487
→
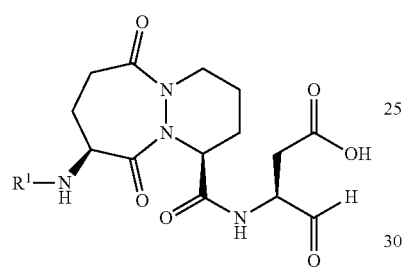
| compound | R¹ |
|---|---|
| 213p, 456 | 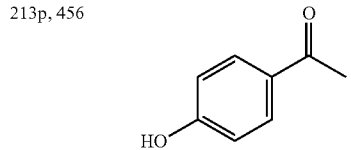 |
| 213q, 475 | 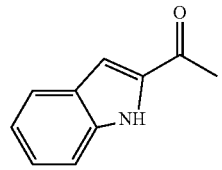 |
| 213r, 404 | 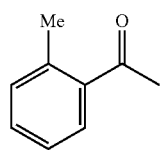 |
| 213s, 486 | 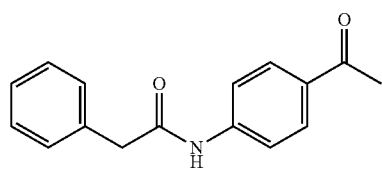 |
| 213t, 487 | 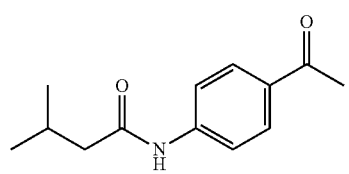 |
406
-continued
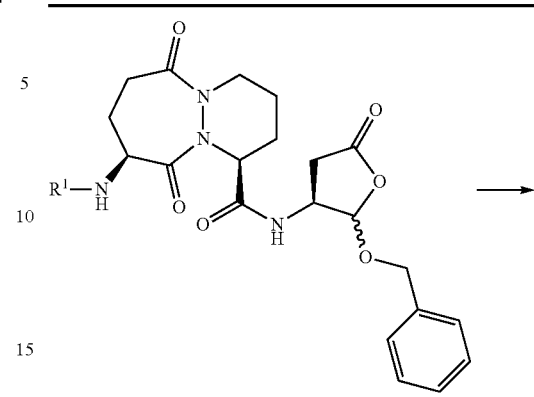
213m-x
214w, 404, 408, 415,
417, 418, 419, 450,
456, 475, 486, 487
→
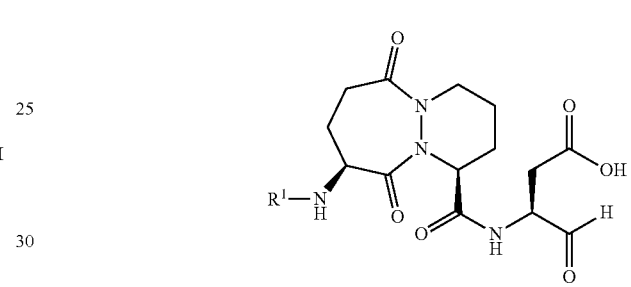
| compound | R¹ |
|---|---|
| 213u, 417 | 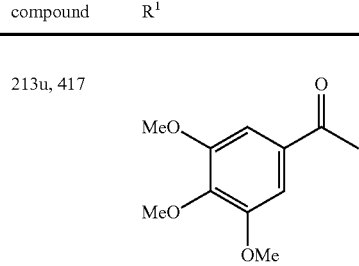 |
| 213v, 408 | 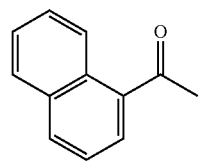 |
| 213w, 214w | 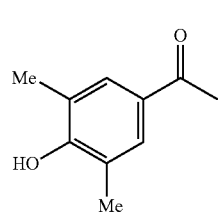 |
| 213x, 418 | 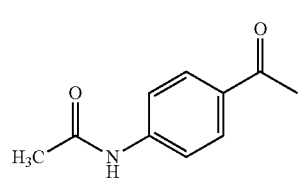 |

[1S,9S(2RS,3S)]N-(2-Benzyloxy-5-oxotetrahydrofuran-3-yl)-6,10-dioxo-9-(3,4-methylenedioxybenzoylamino)-1,2,3,4,7,8,9,10-octahydro-6H-pyridazino[1,2-a][1,2]diazepine-1-carboxamide (213n), was isolated as a mixture of diastereomers (syn:anti isomer ratio 6:4) (1.43 g, 82%) as a white solid: mp. 206-10° C.; IR (KBr) 3288, 1787, 1680, 1657, 1651, 1619, 1548, 1440, 1256, 1135; $^1$H NMR (D$_6$-DMSO) δ 8.75 (0.4H, d), 8.55 (0.6H, d), 8.45 and 8.43 (1H, 2×d), 7.50 (1H, d), 7.42 (1H, s), 7.40-7.27 (5H, m), 7.01 (1H, d), 6.11 (2H, s), 5.67 (0.6H, d), 5.43 (0.4H, s), 5.10-5.00 (1H, m), 4.90-4.59 (3.5H, m), 4.45-4.25 (1.5H, m), 3.47-3.20 (1H, m), 3.20-2.70 (2H, m), 2.65-2.35 (1H, m), 2.35-2.00 (3H, m), 2.00-1.75 (2H, m), 1.65-1.40 (2H, m). Anal. Calcd for C$_{29}$H$_{30}$N$_4$O$_9$: C, 60.20; H, 5.23; N, 9.68. Found: C, 60.08; H, 5.32; N, 9.50. MS (ES$^+$) 580 (M$^+$+2, 35%), 579 (M$^+$+1, 100), 404 (5), 367 (5), 236 (7), 107 (5).

[1S,9S(2RS,3S)]9-[(3-Acetamido)benzamido]-N-(2-benzyloxy-5-oxotetrahydrofuran-3-yl)-6,10-dioxo-1,2,3,4,7,8,9,10-octahydro-6H-pyridazino[1,2-a][1,2]diazepine-1-carboxamide (213o), anti-isomer as a white foamy solid (0.73 g, 69%): mp. 135-40° C.; [α]$_D^{21}$ −37.3° (c 0.1, CH$_2$Cl$_2$); IR (KBr) 3452, 3310, 1790, 1664, 1659, 1650, 1549, 1425, 1258, 1121; $^1$H NMR (D$_6$-DMSO) δ 10.11 (1H, s), 8.77 (1H, d), 8.57 (1H, d), 8.01 (1H, s), 7.76 (1H, d), 7.55 (1H, d), 7.45-7.25 (6H, m), 5.43 (1H, s), 5.08-5.00 (1H, m), 4.95-4.73 (1H, m), 4.76 and 4.68 (2H, dd), 3.40-3.20 (1H, m), 3.09 (1H, dd), 3.02-2.75 (1H, m), 2.45-2.06 (4H, m), 2.06 (3H, s), 2.00-1.75 (2H, m), 1.70-1.40 (2H, m). Anal. Calcd for C$_{30}$H$_{33}$N$_5$O$_8$.0.75H$_2$O: C, 59.54; H, 5.75; N, 11.57. Found: C, 59.40; H, 5.62; N, 11.50. MS (ES$^+$) 593 (M$^+$+2, 33%), 592 (M$^+$+1, 100), 574 (7), 487 (7), 475 (6), 385 (9), 373 (26), 318 (14), 296 (11), 266 (10), 221 (22).

[1S,9S(2RS,3S)]N-(2-Benzyloxy-5-oxotetrahydrofuran-3-yl)-6,10-dioxo-9-(4-hydroxybenzoyl)amino-1,2,3,4,7,8,9,10-octahydro-6H-pyridazino[1,2-a][1,2]diazepine-1-carboxamide (213p), was isolated as a foam (1.2 g, 77%): [α]$_D^{20}$ −115° (c 0.20, CH$_2$Cl$_2$); IR (KBr) 3368, 2946, 1794, 1654, 1609, 1540, 1505, 1421, 1277, 1175, 1119, 980; $^1$H NMR (D$_6$-DMSO) δ 10.1 (1H, s), 8.80 (0.5H, d, J=6.6), 8.60 (0.5H, d, J=7.2), 8.40-8.36 (1H, 2d), 7.82 (2H, d, J=8.0), 7.41 (5H, bs), 6.86 (2H, d, J 8.6), 5.72 (0.5H, d, J=5.0), 5.49 (0.5H, bs), 5.13-5.07 (1H, m), 4.95-4.65 (2.5H, m), 4.49-4.38 (2.5H, m), 3.49-3.30 (2H, m), 3.21, 2.79 (2H, m), 2.40-1.41 (7H, m). MS (ES$^+$) 551.

[1S,9S(2RS,3S)]N-(2-Benzyloxy-5-oxotetrahydrofuran-3-yl)-6,10-dioxo-9-(indol-2-oylamino)-1,2,3,4,7,8,9,10-octahydro-6H-pyridazino[1,2-a][1,2]diazepine-1-carboxamide (213q), was isolated as a white glassy solid (80%): mp. 145-149° C.; [α]$_D^{23}$ −56.0° (c 0.05, CH$_2$Cl$_2$); IR (KBr) 3399-3319, 1791, 1657, 1543, 1420, 1253, 1119; $^1$H NMR (CDCl$_3$) δ 9.54 (1H, s), 7.65 (1H, d, J=7.9), 7.51 (1H, d, J=6.9), 7.44-7.25 (7H, m), 7.18-7.06 (3H, m), 5.30-5.20 (1H, m), 5.27 (1H, s), 4.84 (1H, m), 4.79 (1H, d, J=11.4), 4.56 (1H, d, J=11.3), 4.47 (2H, m), 3.28 (1H, m), 3.10-2.97 (2H, m), 2.71 (1H, m), 2.47-2.37 (1H, m), 2.26 (1H, d, J=17.9), 2.09 (1H, m), 1.83, 1.70, 1.51 (4H, 3m).

[1S,9S(2RS,3S)]N-(2-Benzyloxy-5-oxotetrahydrofuran-3-yl)-6,10-dioxo-1,2,3,4,7,8,9,10-octahydro-9-(2-toluoylamino)-6H-pyridazino[1,2-a][1,2]diazepine-1-carboxamide (213r), was isolated as a mixture of diastereomers (syn:anti isomer ratio 55:45) as a white foamy solid (1.46 g, 89%): mp. 106-10° C.; IR (KBr) 3306, 2947, 1791, 1659, 1650, 1535, 1421, 1256, 1122; $^1$H NMR (D$_6$-DMSO) δ 8.76 (0.45H, d), 8.56 (0.55H, d), 8.49 and 8.47 (1H, 2xd), 7.41-7.19 (9H, m), 5.67 (0.55H, d), 5.43 (0.45H, d), 5.11-5.02 (1H, m), 4.86-4.55 (3.5H, m), 4.45-4.25 (1.5H, m), 3.40-3.20 (1H, m), 3.20-2.70 (2H, m), 2.65-2.40 (1H, m), 2.34 (3H, s), 2.30-1.70 (5H, m), 1.65-1.40 (2H, m). Anal. Calcd for C$_{29}$H$_{32}$N$_4$O$_7$: C, 62.66; H, 5.95; N, 10.08. Found: C, 62.91; H, 6.00; N, 9.70. MS (ES$^+$) 550 (M$^+$+2, 43%), 549 (M$^+$+1, 100), 374 (3), 280 (4), 279 (20), 118 (5).

[1S,9S(2RS,3S)]N-(2-Benzyloxy-5-oxotetrahydrofuran-3-yl)-6,10-dioxo-1,2,3,4,7,8,9,10-octahydro-9-[4-(phenylacetamido)benzamido]-6H-pyridazino[1,2-a][1,2]diazepin-1-carboxamide (213s), was isolated as the anti-isomer as a white foamy solid (0.64 g, 77%): mp. 137-41° C.; [α]$_D^{21}$ −48.2° (c 0.05, CH$_3$OH); IR (KBr) 3477, 3314, 1791, 1659, 1599, 1529, 1499, 1406, 1256, 1122; $^1$H NMR (D$_6$-DMSO) δ 10.45 (1H, s), 8.76 (1H, d), 8.50 (1H, d), 7.86 (2H, d), 7.69 (2H, d), 7.41-7.20 (10H, m), 5.43 (1H, s), 5.08-4.98 (1H, m), 4.90-4.73 (1H, m), 4.76 and 4.68 (2H, dd), 3.67 (2H, s), 3.40-3.20 (1H, m), 3.09 (1H, dd), 3.02-2.75 (1H, m), 2.39 (1H, dd), 2.30-2.00 (3H, m), 2.00-1.75 (2H, m), 1.70-1.40 (2H, m). Anal. Calcd for C$_{36}$H$_{37}$N$_5$O$_8$.0.5H$_2$O: C, 63.90; H, 5.66; N, 10.35. Found: C, 63.68; H, 5.67; N, 10.24. MS (ES$^+$) 669 (M$^+$+2, 40%), 668 (M$^+$+1, 100), 640 (12), 435 (18), 425 (23), 403 (33), 328 (17), 302, (32), 274 (22), 197 (16), 138 (17).

[1S,9S(2RS,3S)]N-(2-Benzyloxy-5-oxotetrahydrofuran-3-yl)-6,10-dioxo-9-[4-(3-methylbutan-1-oylamino)benzamido]-1,2,3,4,7,8,9,10-octahydro-6H-pyridazino[1,2-a][1,2]diazepine-1-carboxamide (213t), was isolated as a white foamy solid (0.63 g, 80%): mp. 159-64° C.; [α]$_D^{21}$ −37.0° (c 0.05, CH$_3$OH); IR (KBr) 3463, 3321, 1790, 1680, 1658, 1650, 1644, 1595, 1525, 1501, 1408, 1251, 1113, 933; $^1$H NMR (D$_6$-DMSO) δ 10.13 (1H, s), 8.76 (1H, d), 8.48 (1H, d), 7.85 (2H, d), 7.68 (2H, d), 7.40-7.25 (5H, m), 5.43 (1H, s), 5.08-4.95 (1H, m), 4.92-4.73 (1H, m), 4.76 and 4.68 (2H, dd), 3.40-3.20 (1H, m), 3.09 (1H, dd), 3.02-2.75 (1H, m), 2.39 (1H, dd), 2.35-2.00 (6H, m), 2.00-1.75 (2H, m), 1.70-1.40 (2H, m), 0.93 (6H, d). Anal. Calcd for C$_{33}$H$_{39}$N$_5$O$_8$.0.5H$_2$O: C, 61.67; H, 6.27; N, 10.90. Found: C, 61.49; H, 6.24; N, 10.86. MS (ES$^+$) 635 (M$^+$+2, 39%), 634 (M$^+$+1, 100), 484 (10), 427 (9), 274 (18), 268 (37), 204 (19), 117 (13).

[1S,9S(2RS,3S)]N-(2-Benzyloxy-5-oxotetrahydrofuran-3-yl)-6,10-dioxo-1,2,3,4,7,8,9,10-octahydro-9-(3,4,5-trimethoxybenzoylamino)-6H-pyridazino[1,2-a][1,2]diazepine-1-carboxamide (213u), was isolated as a white solid (81%): mp. 120-132° C.; IR (KBr) 3361-3334, 1792, 1659, 1585, 1536, 1499, 1457, 1416, 1340, 1236, 1126, 989; $^1$H NMR (CDCl$_3$) δ 7.39-7.29 (6H, m), 7.12 (1H, s), 7.03 (1H, s), 6.92, 6.83, 6.48 (approx 3H, 3d, J=8.1, 7.5, 8.1), 5.57 (d, J=5.3), 5.27 (1H, s), 5.23-5.06, 4.91-4.71, 4.64-4.43, (6H, 3m), 3.92, 3.91, 3.89, 3.88 (9H, 4s), 3.32-2.70, 2.52-2.08, 1.91, 1.63 (1H, 4m).

[1S,9S(2RS,3S)]N-(2-Benzyloxy-5-oxotetrahydrofuran-3-yl)-6,10-dioxo-9-(naphth-1-oylamino)-1,2,3,4,7,8,9,10-octahydro-6H-pyridazino[1,2-a][1,2]diazepine-1-carboxamide (213v), was isolated as a white solid (78%): mp. 121-7° C.; IR (KBr) 3534-3331, 1791, 1659, 1528, 1420, 1256, 1122; $^1$H NMR (CDCl$_3$) δ 8.34-8.29 (1H, m), 7.98-7.87 (2H, m), 7.68-7.45 (4H, m), 7.34-7.24 (5H, m), 7.04 (d, J=6.8), 6.78 (d, J=7.8), 6.66 (d, J=7.7), 6.48 (2H, d, J=7.5) 5.56 (d, J=5.4), 5.15 (1H, s), 5.30-5.14, 5.0, 4.89 (d, J=11.2), 4.71-4.41 (6H), 3.18-2.80, 2.50-2.27, 2.08-1.60 (11H, 3m).

[1S,9S(2RS,3S)]N-(2-Benzyloxy-5-oxotetrahydrofuran-3-yl)-6,10-dioxo-9-(4-hydroxy-3,5-dimethylbenzoyl)amino-1,2,3,4,7,8,9,10-octahydro-6H-pyridazino[1,2-a][1,2]diazepine-1-carboxamide (213w), was isolated as a mixture of diastereoisomers (65/35) as a white solid (0.9 g, 65%): mp. 110-115° C. (decomp.); IR (KBr) 3409, 2945, 1792, 1658, 1606, 1534, 1486, 1420, 1330, 1276, 1209, 1122, 980, 960; $^1$H NMR (CDCl$_3$) δ 7.66 (0.35H, d, J=6.9), 7.46-7.20 (7H, m), 6.93 (0.35H, d, J=7.7), 6.85 (0.65H, d, J=7.6), 6.73 (0.65H, d, J=7.6), 5.96 (0.35H, bs), 5.85 (0.65H, bs), 5.56 (0.65H, d, J=5.2), 5.28 (0.35H, bs), 5.20-4.98 (2H, m), 4.96-4.40 (4H, m), 3.28-2.55 (3H, m), 2.53-2.32 (1H, m), 2.23 (6H, 2s), 2.03-1.40 (7H, m). MS (ES$^-$) 577, (ES$^+$) 579.

[1S,9S(2RS,3S)]9-[4-(Acetylamino)benzoylamino]-N-(2-benzyloxy-5-oxo-tetrahydrofuran-3-yl)-6,10-dioxo-1,2,3,4,7,8,9,10-octahydro-6H-pyridazino[1,2-a][1,2]diazepine-1-carboximide (213x), was isolated as a colourless powder (691 mg, 86%): mp. 150-70° C.; $[\alpha]_D^{22}$ –10.1° (c 0.10, Me$_2$CO); IR (KBr) 3313, 1791, 1679, 1654, 1597, 1528, 1501, 1457, 1407, 1371, 1315, 1255, 1184, 1122, 933; $^1$H NMR (d6-DMSO) δ 8.75 (1H, d), 8.47 (1H, d), 7.84 (2H, d), 7.66 (2H, d), 7.35 (5H, m), 5.43 (1H, s), 5.06-5.00 (1H, m), 4.90-4.64 (3H, m), 4.46-4.26 (2H, m), 3.16-2.86 (2H, m), 2.45-2.05 (5H, m), 2.07 (3H, s), 2.00-1.84 (2H, m), 1.68-1.56 (2H, m); Anal. Calcd for C$_{30}$H$_{33}$N$_5$O$_8$.H$_2$O: C, 59.11; H, 5.79; N, 11.49. Found: C, 59.38; H, 5.66; N, 11.31; M.S. (ES$^+$) 614 (100%), 592 (M$^+$+1.66).

[3S(1S,9S)]3-[(6,10-Dioxo-9-(3,4-methylenedioxybenzoylamino)-1,2,3,4,7,8,9,10-octahydro-6H-pyridazino[1,2-a][1,2]diazepine-1-carboxamido]-4-oxobutanoic acid (415), was prepared by a similar method as compound 214e to afford a white solid (297 mg, 84%): mp. 158-62° C.; $[\alpha]_D^{24}$ –109.5° (c 0.1, CH$_3$OH); IR (KBr) 3700-2500 (br), 1783, 1659, 1650, 1538, 1486, 1439, 1257, 1037; $^1$H NMR (CD$_3$OD) δ 7.48 (1H, dd), 7.35 (1H, d), 6.88 (1H, d), 6.03 (2H, s), 5.25-5.15 (1H, m), 5.02-4.90 (1H, m), 4.63-4.45 (2H, m), 4.30-4.20 (1H, m), 3.57-3.30 (1H, m), 3.20-3.05 (1H, m), 2.75-2.10 (5H, m), 2.10-1.60 (4H, m). MS (ES$^+$) 488 (M+, 25%), 487 (M$^+$–1, 100), 443 (8), 387 (3), 315 (5), 150 (6), 127 (5), 113 (8). Accurate mass calculated for C$_{22}$H$_{25}$N$_4$O$_9$ (MH$^+$): 489.1621. Found 489.1648.

[3S(1S,9S)]3-{(9-[(3-Acetamido)benzamido]-6,10-dioxo-1,2,3,4,7,8,9,10-octahydro-6H-pyridazino[1,2-a][1,2]diazepine-1-carboxamido}-4-oxobutanoic acid (450), was prepared by a similar method as compound 214e to afford a white foamy solid (378 mg, 94%): mp. 175-9° C.; $[\alpha]_D^{22}$ –91.7° (c 0.1, CH$_3$OH); IR (KBr) 3700-2500 (br), 3319, 1659, 1590, 1553, 1427, 1260; $^1$H NMR (CD$_3$OD) δ 8.01 (1H, d), 7.74 (1H, dd), 7.58 (1H, d), 7.45-7.35 (1H, m), 5.25-5.15 (1H, m), 5.05-4.90 (1H, m), 4.60-4.45 (2H, m), 4.30-4.20 (1H, m), 3.55-3.30 (1H, m), 3.20-3.00 (1H, m), 2.75-2.20 (5H, m), 2.14 (3H, s), 2.20-1.60 (4H). Anal. Calcd for C$_{23}$H$_{27}$N$_5$O$_8$.1.5H$_2$O: C, 52.27; H, 5.72; N, 13.25. Found: C, 52.31; H, 5.86; N, 12.85. MS (ES$^+$) 501 (M+, 26%), 500-1, 100), 328 (2), 149 (3), 113 (3).

[3S(1S,9S)]3-[4-(Hydroxybenzoyl)amino-6,10-dioxo-1,2,3,4,7,8,9,10-octahydro-6H-pyridazino[1,2-a][1,2]diazepine-1-carboxamido]-4-oxobutanoic acid (456), was prepared by a similar method as compound 214e to afford a white solid (0.73 g, 72%): mp. >260° C.; $[\alpha]_D^{20}$ –66° (c 0.34, MeOH); IR (KBr) 3401, 2946, 1651, 1609, 1584, 1506, 1426, 1277, 1257, 1177; $^1$H NMR (D$_6$-DMSO) δ 10.2 (1H, very bs), 9.17 (1H, bs), 8.65 (1H, s), 8.37 (1H, d, J 5.4), 7.81 (2H, d, J=8.2), 6.87 (2H, d, J=8.4), 5.24 (1H, m), 4.92-4.86 (1H, m), 4.41-4.32 (2H, m), 3.68-3.21 (3H, m), 3.12-2.79 (1H, m), 2.50-1.42 (7H, m). MS (ES$^+$) 459.

[3S(1S,9S)]3-[6,10-Dioxo-9-(indol-2-oylamino)-1,2,3,4,7,8,9,10-octahydro-6H-pyridazino[1,2-a][1,2]diazepine-1-carboxamido]-4-oxobutanoic acid (475), was prepared by a similar method to that described for compound 214e to afford a white solid (79%): mp. 150° C. (softens) 190-210° C.; $[\alpha]_D^{23}$ –97.5° (c 0.1, CH$_3$OH); IR (KBr) 3319, 1658, 1650, 1549, 1421, 1256; $^1$H NMR (CD$_3$OD) δ 7.61 (1H, d, J=8.0), 7.43 (1H, d, J=8.1), 7.21 (2H, m), 7.05 (1H, m), 5.21 (1H, m), 5.07-4.77 (1H, m), 4.54 (2H, m), 4.23 (1H, m), 3.46 (1H, m), 3.14 (1H, m), 2.66-1.71 (9H, m). MS (ES$^+$, m/z), 482 (M$^+$–1, 100%).

[3S(1S,9S)]3-[6,10-Dioxo-1,2,3,4,7,8,9,10-octahydro-9-(2-toluoylamino)-6H-pyridazino[1,2-a][1,2]diazepine-1-carboxamido]-4-oxobutanoic acid (404), was prepared by a similar method as compound 214e to afford a white solid (0.79 g, 86%): mp. 156-9° C.; $[\alpha]_D^{25}$ –119.7° (c 0.1, CH$_3$OH); IR (KBr) 3700-2500 (br), 3387, 3309, 2956, 1785, 1659, 1650, 1535, 1422, 1278; $^1$H NMR (CD$_3$OD) δ 7.46-7.15 (4H, m), 5.25-5.15 (1H, m), 5.02-4.90 (1H, m), 4.58-4.45 (2H, m), 4.30-4.20 (1H, m), 3.55-3.30 (1H, m), 3.20-3.05 (1H, m), 2.80-2.20 (4H, m), 2.41 (3H, s), 2.20-1.60 (5H, m). MS (ES$^+$) 458 (M+, 27%), 457 (M$^+$–1, 100), 413 (13), 339 (8), 285 (5), 134 (6), 127 (11). Accurate mass calculated for C$_{22}$H$_{27}$N$_4$O$_7$ (MH$^+$): 459.1880. Found 459.1854.

[3S(1S,9S)]3-[6,10-Dioxo-1,2,3,4,7,8,9,10-octahydro-9-[4-(phenylacetamido)benzamido]-6H-pyridazino[1,2-a][1,2]diazepine-1-carboxamido]-4-oxobutanoic acid (486), was prepared by a similar method as compound 214e to afford a white solid (325 mg, 89%): mp. 165-9° C.; $[\alpha]_D^{22}$ –69.1° (c 0.1, CH$_3$OH); IR (KBr) 3700-2500 (br), 3318, 1658, 1599, 1530, 1505, 1407, 1258; $^1$H NMR (CD$_3$OD) δ 7.85 (2H, d), 7.69 (2H, d), 7.38-7.20 (5H, m), 5.25-5.15 (1H, m), 5.05-4.90 (1H, m), 4.57-4.45 (2H, m), 4.30-4.20 (1H, m), 3.70 (2H, s), 3.55-3.30 (1H, m), 3.20-3.00 (1H, m), 2.75-1.60 (9H, m). Anal. Calcd for C$_{29}$H$_{31}$N$_5$O$_8$.1.5H$_2$O: C, 57.61; H, 5.67; N, 11.58. Found: C, 57.81; H, 5.74; N, 11.47. MS (ES$^+$) 577 (M+, 33%), 576 (M$^+$–1, 100), 502 (2).

[3S(1S,9S)]3-{6,10-Dioxo-9-[4-(3-methylbutan-1-oylamino)benzamido]-1,2,3,4,7,8,9,10-octahydro-6H-pyridazino[1,2-a][1,2]diazepine-1-carboxamido}-4-oxobutanoic acid (487), was prepared by a similar method as compound 214e to afford a white foamy solid (335 mg, 93%): mp. 176-80° C.; $[\alpha]_D^{22}$ –88.0° (c0.1, CH$_3$OH); IR (KBr) 3700-2500 (br), 3321, 2960, 1781, 1660, 1597, 1529, 1407, 1258, 1187; $^1$H NMR (CD$_3$OD) δ 7.86 (2H, d), 7.69 (2H, d), 5.25-5.15 (1H, m), 5.05-4.90 (1H, m), 4.60-4.45 (2H, m), 4.30-4.20 (1H, m), 3.57-3.30 (1H, m), 3.20-3.00 (1H, m), 2.75-1.60 (12H, m), 1.00 (6H, d). Anal. Calcd for C$_{20}$H$_{33}$N$_5$O$_8$.H$_2$O: C, 55.61; H, 6.28; N, 12.45. Found: C, 56.00; H, 6.37; N, 12.15. MS (ES$^+$) 543 (M+, 31%), 542 (M$^+$–1, 100), 498 (2), 468 (3).

[3S(1S,9S)]3-[6,10-Dioxo-1,2,3,4,7,8,9,10-octahydro-9-(3,4,5-trimethoxybenzoylamino)-6H-pyridazino[1,2-a][1,2]diazepine-1-carboxamido]-4-oxobutanoic acid (417), was prepared by a similar method to that described for compound 214e to afford a white solid (0.63 g, 92%): mp. 145-155° C. (approx., not sharp); $[\alpha]_D^{27}$ –114.6° (c 0.11, CH$_3$OH); IR (KBr) 3327, 1658, 1586, 1548, 1501, 1416, 1341, 1238, 1126; $^1$H NMR (CD$_3$OD) δ 7.22 (2H, s), 5.21 (1H, m), 5.00 (1H, m), 4.56, 4.49 (2H, 2m), 4.25 (1H, m), 3.88 (6H, s), 3.80 (3H, s), 3.55-3.43 (1H, m), 3.12 (1H, m), 2.71-1.70 (9H, m). Anal. Calcd for C$_{24}$H$_{30}$N$_4$O$_{10}$.2H$_2$O: C, 50.52; H, 6.01; N, 9.82. Found: C, 50.49; H, 6.05; N, 9.68. MS (ES$^+$, m/z) 533 (M$^+$–1, 100%).

[3S(1S,9S)]3-[6,10-Dioxo-9-(naphth-1-oylamino)-1,2,3,4,7,8,9,10-octahydro-6H-pyridazino[1,2-a][1,2]diazepine-1-carboxamido]-4-oxobutanoic acid (408), was prepared by a similar method to that described for compound 214e to afford a white solid (73%): mp. 157-165° C. (not sharp); $[\alpha]_D^{27}$ –140.5° (c 0.1, CH$_3$OH); IR (KBr) 3325, 1658, 1531, 1420, 1278, 1257; $^1$H NMR (CD$_3$OD) δ 8.33-8.28 (1H, m), 8.01-7.78 (2H, m), 7.71 (1H, d, J=6.0), 7.59-7.52 (3H, m), 5.27 (1H, m), 5.12-5.03 (1H, m), 4.55 (2H, m), 4.25 (1H, m), 3.64-3.43 (1H, m), 3.24-3.12 (1H, m), 2.80-1.67 (9H, m).

Anal. Calcd for $C_{26}H_{26}N_4O_7 \cdot 2H_2O$: C, 56.60; H, 5.70; N, 10.56. Found: C, 56.70; H, 5.80; N, 10.33. MS (ES+, m/z), 493 (M+−1, 100%).

[3S(1S,9S)]3-[6,10-Dioxo-4-(hydroxy-3,5-dimethylbenzoyl)amino-1,2,3,4,7,8,9,10-octahydro-6H-pyridazino[1,2-a][1,2]diazepine-1-carboxamido]-4-oxobutanoic acid (214w), was prepared by a similar method as compound 214e to afford 210 mg (62%) of a white solid: mp. >260° C.; $[\alpha]_D^{20}$ −93° (c 0.20, MeOH); IR (KBr) 3401, 2948, 1651, 1604, 1559, 1486, 1421, 1325, 1276, 1210; $^1$H NMR ($D_6$-DMSO) δ 9.39 (1H, bs), 8.29 (1H, d, J=5.9), 7.55 (2H, s), 6.64 (1H, d, J=6.1), 5.79 (1H, s), 5.25-5.21 (1H, m), 1.90-1.82 (1H, m), 4.41-3.69 (2H, m), 3.47-3.20 (3H, m), 2.97-2.91 (1H, m), 2.23 (6H, s), 2.25-1.60 (7H, m).

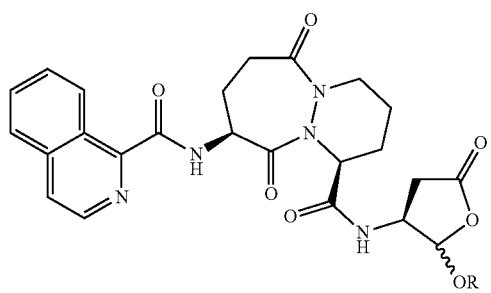

550q R = Et
213y R = Bn

[1S,9S(2RS,3S)]N-(2-Ethoxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide (550q), was synthesized via methods used to prepare 213e to afford 550q.

[1S,9S(2RS,3S)]N-(2-Benzyloxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide (213y), was synthesized via methods used to prepare 213e to afford 213y.

412 a-f

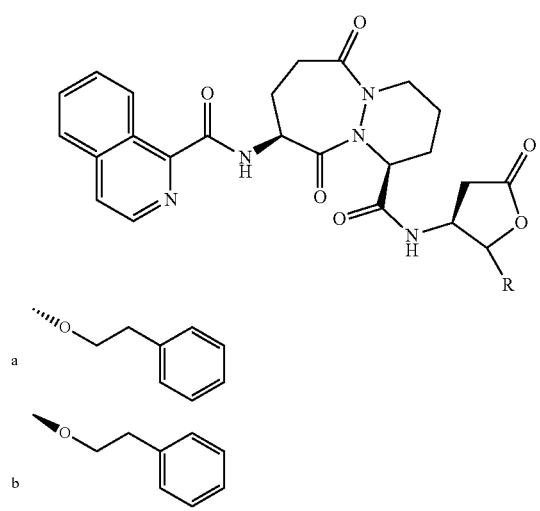

-continued

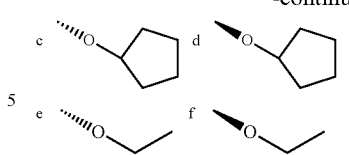

[1S,9S(2S,3S)]N-(2-Phenethoxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide, (412a) was synthesized via methods used to prepare 550q using 513a-1 to afford 412a.

[1S,9S(2R,3S)]N-(2-Phenethoxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide, (412b) was synthesized via methods used to prepare 550q using 513a-2 to afford 412b.

[1S,9S(2S,3S)]N-(2-Cyclopentoxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide, (412c) was synthesized via methods used to prepare 550q using 513b-1 to afford 412c.

[1S,9S(2R,3S)]N-(2-Cyclopentoxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide, (412d) was synthesized via methods used to prepare 550q using 513b-2 to afford 412d: $^1$H NMR (CDCl$_3$) δ 9.5 (1H, d), 8.9 (1H, d), 8.5 (1H, d), 7.9-7.8 (2H, m), 7.8-7.65 (2H, m), 6.55 (1H, d), 5.55 (1H, d), 5.25-5.1 (2H, m), 4.75-4.65 (1H, m), 4.65-4.6 (1H, m), 4.4-4.3 (1H, m), 3.25-3.15 (1H, m), 3.15-3.05 (1H, m), 2.95-2.8 (2H, m), 2.55-2.4 (2H, m), 2.15-1.5 (14H, m).

[1S,9S(2S,3S)]N-(2-Ethoxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide, (412e) was synthesized via methods used to prepare 550q using 513f-1 to afford 412e.

[1S,9S(2R,3S)]N-(2-Ethoxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide, (412f) was synthesized via methods used to prepare 550q using 513f-2 to afford 412f.

Compounds 410 and 412 were prepared via methods used to prepare 605 from 604.

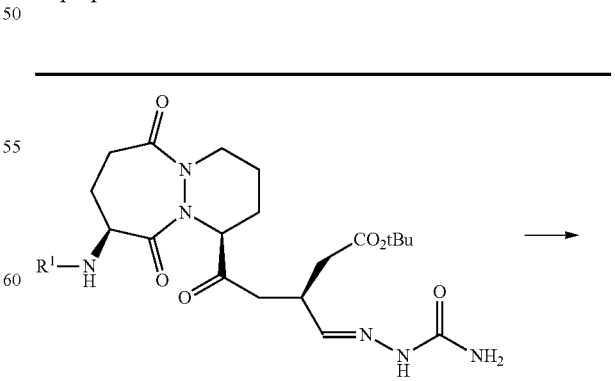

502y, 502z

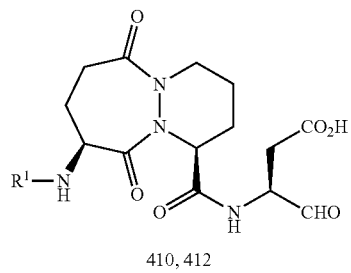

| compound | R¹ |
|---|---|
| 502y, 410 | 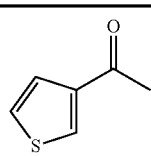 |
| 502z, 412 | 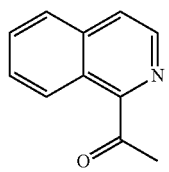 |

[3S(1S,9S)]3-[(6,10-Dioxo-1,2,3,4,7,8,9,10-octahydro-6H-pyridazino[1,2-a][1,2]diazepine-9-(thiophene-3-yl-carbonylamino)-1-carboxamido]-4-oxobutanoic acid (410), was purified by flash chromatography (5-25% methanol in dichloromethane) to give 296 mg (94%) of a colourless solid: mp. 90-200° C.; IR (KBr) 3338, 3096, 2950, 1787, 1726, 1657, 1546, 1420, 1279, 1258, 1125, 1092, 984, 933; $^1$H NMR (CD$_3$OD) δ 8.41 (1H, d), 8.13 (1H, d), 7.54-7.41 (3H, m), 7.20 (1H, d), 5.19-5.11 (1H, m), 4.54-4.30 (1H, m), 3.27 (1H, m), 3.18-3.03 (1H, m), 2.81-2.64 (2H, m), 2.56-1.59 (7H, m). Anal. Calcd for C$_{19}$H$_{22}$N$_4$O$_7$S.2.5H$_2$O: C, 46.05; H, 5.49; N, 11.31. Found: C, 46.36; H, 5.25; N, 11.10. MS (ES$^+$) 449 (M−1, 80%), 113 (100). Accurate mass calculated for C$_{19}$H$_{23}$N$_4$O$_7$S (MH$^+$): 451.1287. Found: 451.1295.

[3S(1S,9S)]3-[6,10-Dioxo-9-(isoquinolin-1-oylamino)-1,2,3,4,7,8,9,10-octahydro-6H-pyridazino[1,2-a][1,2]diazepine-1-carboxamido]-4-oxobutanoic acid (412) was prepared by a similar method to that described for compound 605 to afford a white glassy solid (69%): mp. 138-141° C.; [α]$_D^{23}$ −105.5° (c 0.5, CH$_2$Cl$_2$); IR (KBr) 3375, 1787, 1659, 1515, 1421, 1278, 1256; $^1$H NMR (CDCl$_3$) δ 9.32 (1H, m), 8.79 (1H, m), 8.47 (1H, m), 7.86-7.64 (4H, m), 5.31, 5.18, 4.59, 4.37 (4 or 5H, m), 3.55-2.76, 2.49-2.39, 2.05, 1.65 (11H, 4m). Anal. Calcd for C$_{24}$H$_2$O$_5$O$_7$.1.5H$_2$O: C, 55.17; H, 5.40; N, 13.40. Found: C, 54.87; H, 5.22; N, 13.15. MS (ES$^+$, m/z) 494 (M$^+$−1, 100%).

[3S(1S,9S)]t-Butyl 3-[6,10-dioxo-1,2,3,4,7,8,9,10-octahydro-9-(thiophene-3-yl)-6H-pyridazino[1,2-a][1,2]diazepine-carbonylamino]-1-carboxamido]-4-oxobutanoate semicarbazone (502y), was synthesized via methods used to prepare 604 from 603 to afford a pale cream powder: mp. 120-180° C.; [α]$_D^{23}$ −109° (c 0.18, CH$_2$Cl$_2$); IR (KBr) 3478, 3327, 1670, 1582, 1543, 1421, 1279, 1257, 1155; $^1$H NMR (CDCl$_3$, CD$_3$OD) δ 8.04 (1H, m), 7.49 (1H, m), 7.38 (1H, m), 7.17 (1H, m), 5.17-5.01 (2H, m), 4.86 (1H, m), 4.61-4.50 (1H, m), 3.45-3.29 (2H, m), 3.21-3.03 (1H, m), 2.79-2.54 (3H, m), 2.43-2.33 (1H, m), 2.11-1.66 (5H, m), 1.44 (9H, s). Anal. Calcd for C$_{24}$H$_{33}$N$_7$O$_7$S.H$_2$O: C, 49.56; H, 6.07; N, 16.86; S, 5.51. Found: C, 49.51; H, 5.93; N, 16.31; S, 5.17. MS (ES$^+$) 586 (100%), 564 (M$^+$+1, 1.59). Accurate mass calculated for C$_{24}$H$_{34}$N$_7$O$_7$S (MH$^+$): 564.2240. Found: 564.2267.

[3S(1S,9S)]t-Butyl 3-[6,10-dioxo-9-(isoquinolin-1-oylamino)-1,2,3,4,7,8,9,10-octahydro-6H-pyridazino[1,2-a][1,2]diazepine-1-carboxamido]-4-oxobutanoate semicarbazone (502z), was prepared by a similar method to that described for compound 604 to afford a pale yellow solid (90%): mp. 142-145° C.; [α]$_D^{24}$ −136.5° (c 0.06, CH$_2$Cl$_2$); $^1$H NMR (CDCl$_3$) δ 9.51-9.46 (1H, m), 9.11 (1H, s), 8.83 (1H, d, J=7.8), 8.53 (1H, d, J=5.5), 7.89-7.83 (2H, m), 7.77-7.65 (2H, m), 7.55 (1H, d, J=7.2), 7.18 (1H, d, J=2.7), 5.26-5.12 (2H, m), 4.87 (1H, m), 4.59 (1H, m), 3.25-3.12 (2H, m), 2.95-2.76 (2H, m), 2.59-2.38, 2.18-1.94, 1.70 (5H, 3m), 1.44 (9H, s).

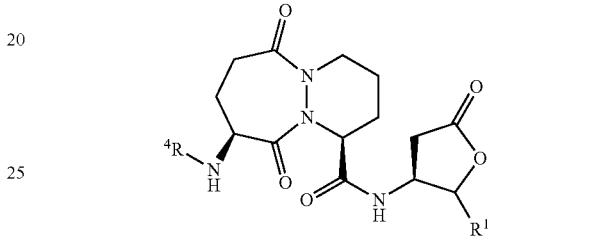

| compound | R⁴ | R¹ |
|---|---|---|
| 415a | 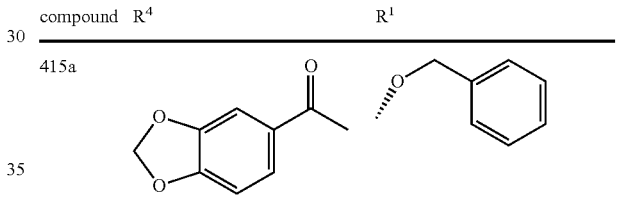 | |
| 415b | 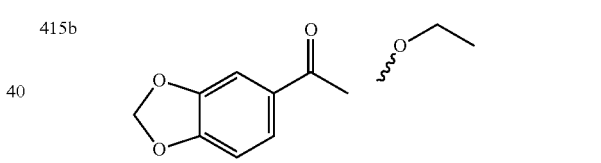 | |
| 415c | 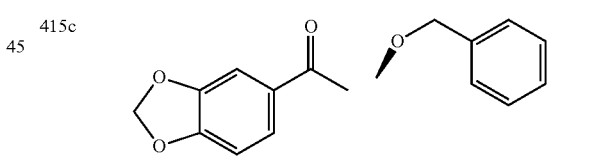 | |
| 214w-1 | 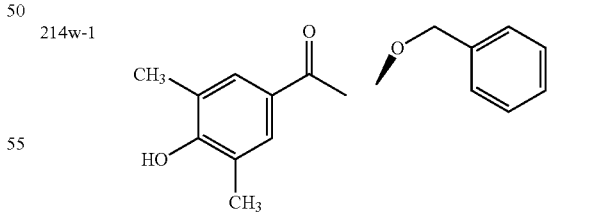 | |
| 214w-2 | 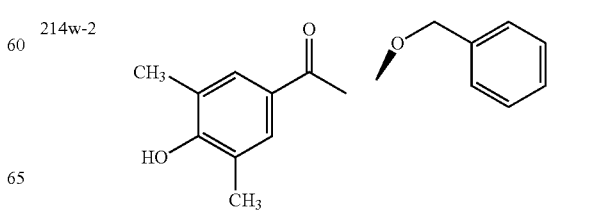 | |

415
-continued

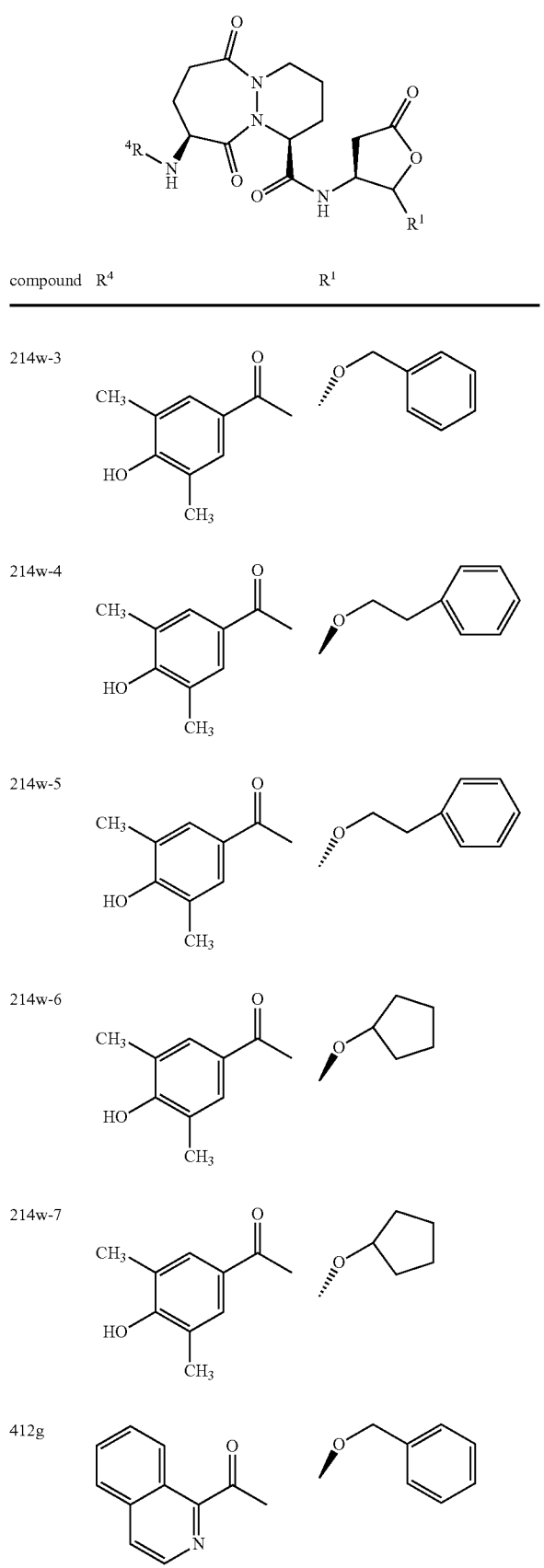

| compound | R⁴ | R¹ |
|---|---|---|
| 214w-3 | 3,5-dimethyl-4-hydroxyphenyl ketone | benzyloxy |
| 214w-4 | 3,5-dimethyl-4-hydroxyphenyl ketone | phenethoxy |
| 214w-5 | 3,5-dimethyl-4-hydroxyphenyl ketone | phenethoxy |
| 214w-6 | 3,5-dimethyl-4-hydroxyphenyl ketone | cyclopentoxy |
| 214w-7 | 3,5-dimethyl-4-hydroxyphenyl ketone | cyclopentoxy |
| 412g | isoquinolin-1-yl ketone | benzyloxy |
| 412h | isoquinolin-1-yl ketone | benzyloxy |

[1S,9S(2S,3S)]N-(2-Benzyloxy-5-oxotetrahydrofuran-3-yl)-6,10-dioxo-9-(methylenedioxybenzoylamino)-1,2,3,4,7,8,9,10-octahydro-6-H-pyridazino[1,2-a][1,2]diazepine-1-carboxamide, (415a) was synthesized via methods used to prepare 550q to afford 415a.

[1S,9S(2RS,3S)]N-(2-Ethoxy-5-oxotetrahydrofuran-3-yl)-6,10-dioxo-9-(methylenedioxy benzoylamino)-1,2,3,4,7,8,9,10-octahydro-6-H-pyridazino[1,2-a][1,2]diazepine-1-carboxamide, (415b) was synthesized via methods used to prepare 550q to afford 415b.

[1S,9S(2R,3S)]N-(2-Benzyloxy-5-oxotetrahydrofuran-3-yl)-6,10-dioxo-9-(methylenedioxy benzoylamino)-1,2,3,4,7,8,9,10-octahydro-6-H-pyridazino[1,2-a][1,2]diazepine-1-carboxamide, (415c) was synthesized via methods used to prepare 550q to afford 415c.

[1S,9S(2RS,3S)]N-(2-Benzyloxy-5-oxotetrahydrofuran-3-yl)-6,10-dioxo-9-(3,5-dimethyl-4-hydroxybenzoylamino)-1,2,3,4,7,8,9,10-octahydro-6-H-pyridazino[1,2-a][1,2]diazepine-1-carboxamide, (214w-1) was synthesized via methods used to prepare 550q to afford 214w-1.

[1S,9S(2R,3S)]N-(2-Benzyloxy-5-oxotetrahydrofuran-3-yl)-6,10-dioxo-9-(3,5-dimethyl-4-hydroxybenzoylamino)-1,2,3,4,7,8,9,10-octahydro-6-H-pyridazino[1,2-a][1,2]diazepine-1-carboxamide, (214w-2) was synthesized via methods used to prepare 550q to afford 214w-2.

[1S,9S(2S,3S)]N-(2-Benzyloxy-5-oxotetrahydrofuran-3-yl)-6,10-dioxo-9-(3,5-dimethyl-4-hydroxybenzoylamino)-1,2,3,4,7,8,9,10-octahydro-6-H-pyridazino[1,2-a][1,2]diazepine-1-carboxamide, (214w-3) was synthesized via methods used to prepare 550q to afford 214w-3.

[1S,9S(2R,3S)]N-(2-Phenethoxy-5-oxotetrahydrofuran-3-yl)-6,10-dioxo-9-(3,5-dimethyl-4-hydroxybenzoylamino)-1,2,3,4,7,8,9,10-octahydro-6-H-pyridazino[1,2-a][1,2]diazepine-1-carboxamide, (214w-4) was synthesized via methods used to prepare 550q to afford 214w-4.

[1S,9S(2S,3S)]N-(2-Phenethoxy-5-oxotetrahydrofuran-3-yl)-6,10-dioxo-9-(3,5-dimethyl-4-hydroxybenzoylamino)-1,2,3,4,7,8,9,10-octahydro-6-H-pyridazino[1,2-a][1,2]diazepine-1-carboxamide, (214w-5) was synthesized via methods used to prepare 550q to afford 214w-5.

[1S,9S(2R,3S)]N-(2-Cyclopentoxy-5-oxotetrahydrofuran-3-yl)-6,10-dioxo-9-(3,5-dimethyl-4-hydroxybenzoylamino)-1,2,3,4,7,8,9,10-octahydro-6-H-pyridazino[1,2-a][1,2]diazepine-1-carboxamide, (214w-6) was synthesized via methods used to prepare 550q to afford 214w-6.

[1S,9S(2S,3S)]N-(2-Cyclopentoxy-5-oxotetrahydrofuran-3-yl)-6,10-dioxo-9-(3,5-dimethyl-4-hydroxybenzoylamino)-1,2,3,4,7,8,9,10-octahydro-6-H-pyridazino[1,2-a][1,2]diazepine-1-carboxamide, (214w-7) was synthesized via methods used to prepare 550q to afford 214w-7.

[1S,9S(2R,3S)]N-(2-Benzyloxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide, (412g) was synthesized via methods used to prepare 550q to afford 412g.

[1S,9S(2S,3S)]N-(2-Benzyloxy-5-oxotetrahydrofuran-3-yl)-6,10-dioxo-9-(isoquinolin-1-oylamino)-1,2,3,4,7,8,9,10-octahydro-6-H-pyridazino[1,2-a][1,2]diazepine-1-carboxamide, (412h) was synthesized via methods used to prepare 550q to afford 412h.

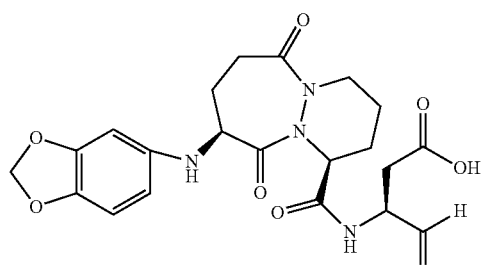

415

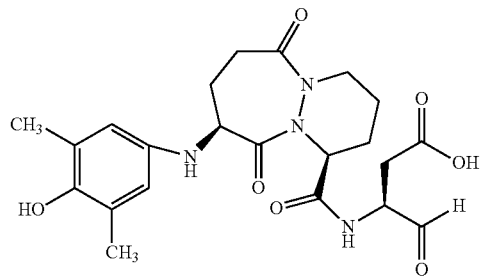

214w

[3S(1S,9S)]3-(9-(4,5-Methylenedioxybenzoyl)amino-6,10-dioxo-1,2,3,4,7,8,9,10-octahydro-6H-pyridazino[1,2-a][1,2]diazepine-1-carboxamido)-4-oxobutanoic acid (415), was synthesized by the method used to prepare 2002 from 2001 to afford 415.

[3S(1S,9S)]3-(9-(3,5-Dichloro-4-hydroxybenzoyl)amino-6,10-dioxo-1,2,3,4,7,8,9,10-octahydro-6H-pyridazino[1,2-a][1,2]diazepine-1-carboxamido)-4-oxobutanoic acid (214w), was synthesized by the method used to prepare 2002 from 2001 to afford 214w.

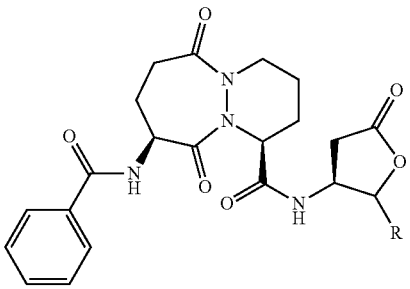

2100k-o

| compound | R |
| --- | --- |
| 2100k | 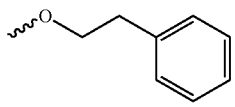 |
| 2100l | 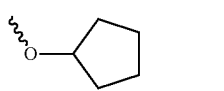 |
| 2100m | 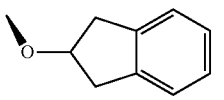 |
| 2100n | 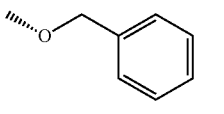 |
| 2100o | 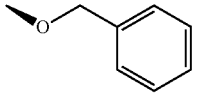 |

[1S,9S(2RS,3S)]9-Benzoylamino-6,10-dioxo-1,2,3,4,7,8,9,10-octahydro-N-(2-phenethyloxy-5-oxotetrahydrofuran-3-yl)-6H-pyridazino[1,2-a][1,2]diazepine-1-carboxamide (2100k), was prepared by a similar method as compound 213e to afford a mixture of diastereoisomers (75/25) as a white solid (258 mg, 83%): mp. 101° C.; $[\alpha]_D^{25}$ −96° (c 0.2, CH$_2$Cl$_2$); IR (KBr) 3328, 2935, 2978, 1732, 1669, 1603, 1483, 1450, 1414, 1237, 1155, 1082, 989, 755; $^1$H NMR (CDCl$_3$) δ 7.84-7.80 (2H, m), 7.54-7.17 (8H, m), 7.06-6.99 (1H, m), 6.25 (1H, d, J=7.9H), 5.41 (0.75H, d, J=5.4H), 5.31 (0.25H, bs), 5.23-5.09 (1H, m), 4.93-4.87 (1H, m), 4.68-4.51 (2H, m), 4.40-4.33 (0.25H, m), 4.24-4.14 (0.75H, m), 3.95-3.70 (1H, m), 3.30-3.13 (1H, m), 3.14-2.78 (5H, m), 2.47-2.21 (2H, m), 2.05-1.50 (5H, m). Anal. Calcd for C$_{29}$H$_{32}$N$_4$O$_7$.0.5H$_2$O: C, 62.47; H, 5.97; N, 10.05. Found: C, 62.17; H, 5.83; N, 9.97. MS (ES$^+$) 549.

[1S,9S(2RS,3S)]9-Benzamido-N-(2-cyclopentyloxy-5-oxo-tetrahydrofuran-3-yl)-6,10-dioxo-1,2,3,4,7,8,9,10-octahydro-6H-pyridazino[1,2-a][1,2]diazepine-1-carboxamide (2100l), was prepared by a similar method as 213e, (74%) as a colourless solid: mp. 172-80° C.; $[\alpha]_D^{23}$ −91.5° (c 0.1, CH$_2$Cl$_2$); IR (KBr) 3290, 1792, 1677, 1657, 1642, 1544, 1425, 1280, 1259, 1124, 977; $^1$H NMR (CDCl$_3$) δ 7.80 (2H, m), 7.46 (3.5H, m), 7.00 (1H, d, J=6.7), 6.48 (0.5H, d, J=7.9), 5.55 (0.5H, d, J=5.3), 5.19 (2H, s+m), 4.93 (0.5H, m), 4.62 (1.5H, m), 4.34 (1H, m), 4.18 (0.5H, m), 3.28-2.70 (4H, m), 2.49-2.29 (2H, m), 205-1.48 (15H, m).

[1S,9S(2R,3S)]9-Benzamido-6,10-dioxo-N-[2-(2-indanyloxy)-5-oxo-tetrahydrofuran-3-yl]-1,2,3,4,7,8,9,10-octahydro-6H-pyridazino[1,2-a][1,2]diazepine-1-carboxamide (2100m), was prepared by a similar method as 213e, (76%) as a colourless solid: mp. ~140° C., remelts 187-9° C.; $[\alpha]_D^{23}$ −96.9° (c 0.11, CH$_2$Cl$_2$); IR (KBr) 3507, 3308, 3251, 1772, 1660, 1641, 1566, 1545, 1457, 1424, 1346, 1326, 1302, 1275, 1258, 1136, 1085, 1018, 981; $^1$H NMR (CDCl$_3$) δ 7.78 (2H, m), 7.53 (3H, m), 7.19 (4H, m), 6.91 (1H, d, J=7.4), 6.27 (1H, d, J=7.6), 5.66 (1H, d, J=5.3), 5.10 (1H, m), 4.96 (1H, m), 4.75 (2H, m), 4.52 (1H, m), 3.08 (3H, m), 3.03-2.71 (5H, m), 2.48-2.31 (2H, m), 1.90-1.40 (4H, m), 1.22 (1H, m).

[1S,9S(2S,3S)]9-Benzoylamino-N-(2-benzyloxy-5-oxotetrahydrofuran-3-yl)-6,10-dioxo-1,2,3,4,7,8,9,10-octahydro-6H-pyridazino[1,2-a][1,2]diazepine-1-carboxamide (2100n), was prepared by a similar method to that described for compound 213e to afford a white glassy solid (76%): mp. 112-5° C.; $[\alpha]_D^{23}$ −62.0° (c 0.1, CH$_2$Cl$_2$); IR (KBr) 3305, 1789, 1677, 1665, 1535, 1422, 1279, 1256, 1119, 942, 700; $^1$H NMR (CDCl$_3$) δ 7.84 (2H, m), 7.58-7.27 (9H, m), 6.99 (1H, d, J=7.8), 5.23 (1H, s), 5.23-5.11 (1H, m), 4.89 (1H, m), 4.76 (1H, d, J=11.3), 4.55 (1H, d, J=11.4), 4.58-4.43 (2H, m), 3.30-2.96, 2.81-2.69, 2.46-2.37, 2.16-1.66 (10H, 4m), 2.27 (1H, d, J=17.8). Anal. Calcd for C$_{20}$H$_{30}$N$_4$O$_7$.0.5H$_2$O: C, 61.87; H, 5.75; N, 10.32. Found: C, 61.88; H, 5.70; N, 10.33. MS (ES$^+$, m/z) 535 (M$^+$+1, 100%).

[1S,9S(2R,3S)]9-Benzoylamino-N-(2-benzyloxy-5-oxotetrahydrofuran-3-yl)-6,10-dioxo-1,2,3,4,7,8,9,10-octahydro-6H-pyridazino[1,2-a][1,2]diazepine-1-carboxamide (2100o), (containing about 7% of (2S)), was prepared by a similar method to that described for compound 213e to afford a white glassy solid (81%): mp. 115-7° C.; $[\alpha]_D^{23}$ −121.8° (c 0.11, CH$_2$Cl$_2$); IR (KBr) 3326, 1792, 1659, 1535, 1421, 1278, 1257, 1124, 978; $^1$H NMR (CDCl$_3$) δ 7.82 (2H, m), 7.58-7.24 (8H, m), 6.90 (1H, d, J=7.3), 6.49 (1H, d, J=7.7), 5.57 (1H, d, J=5.5), 5.11 (2H, m), 4.91 (1H, d, J=11.4), 4.57 (1H, d, J=11.1), 4.81-4.68 (1H, m), 4.65-4.54 (1H, m), 3.18-2.71 2.52-2.30, 2.05-1.62 (11H, 3m). Anal. Calcd for C$_{28}$H$_{30}$N$_4$O$_7$.0.5H$_2$O: C, 61.87; H, 5.75; N, 10.32. Found: C, 61.70; H, 5.71; N, 10.15. MS (ES$^+$, m/z) 535 (M$^+$+1, 94.3%), 557 (100%).

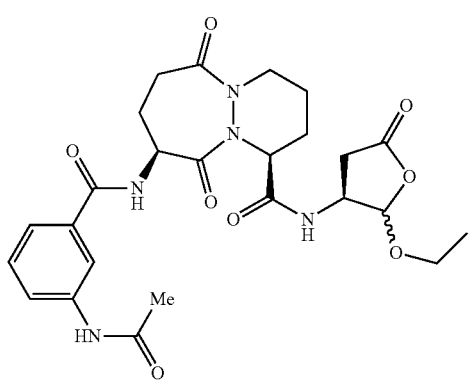

550n

[1S,9S(2RS,3S)]9-(3-Acetamido) benzoylamino-6,10-dioxo-N-(2-ethoxy-5-oxo-tetrahydrofuran-3-yl)-1,2,3,4,7,8,9,10-octahydro-6H-pyridazino[1,2-a][1,2]diazepine-1-carboxamide (550n), was prepared by a similar method as compound 213e to afford a mixture of diastereoisomers (65/35) as a tan powder (390 mg, 28%): mp. 139-145° C.; $[\alpha]D^{23}$ −104° (c 0.2, MeOH); IR (KBr) 3318, 2405, 2369, 1792, 1660, 1591, 1549, 1484, 1422, 1257, 1117; $^1$H NMR (D$_6$-DMSO) δ 10.1 (1H, s), 8.80 (0.65H, d, J=6.6), 8.58 (0.35H, d, J=6.6), 8.59 (1H, d, J=7.0), 8.06 (1H, bs), 7.83-7.79 (1H, m), 7.61-7.57 (1H, m), 7.47-7.39 (1H, m), 5.61 (0.35H, d, J=5.0), 5.37 (0.65H, bs), 5.17-5.14 (0.35H, m), 5.08-5.06 (0.65H, m), 4.92-4.86 (1H, m), 4.67-4.61 (0.35H, m), 4.47-4.41 (0.65H, m), 4.28-4.11 (1H, 2m), 3.80-3.59 (2H, m), 3.23-2.75 (3H, m), 2.61-1.48 (7H, m), 2.10 (3H, s), 1.25 and 1.17 (3H, 2t, J=5.8). MS (ES$^+$) 528.

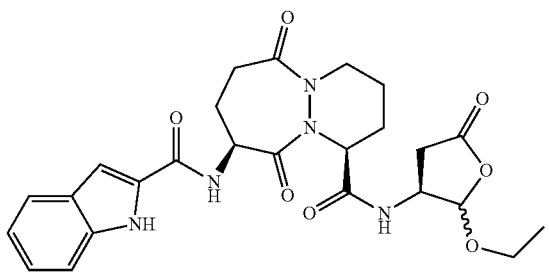

550o

[1S,9S(2RS,3S)]6,10-Dioxo-N-(2-ethoxy-5-oxotetrahydrofuran-3-yl)-9-(2-indoloylamino)-1,2,3,4,7,8,9,10-octahydro-6H-pyridazino[1,2-a][1,2]diazepine-1-carboxamide (550o), was synthesized by a similar method as compound 213e to afford a colourless solid (1.071 g, 80%): mp. 155-70° C.; $[\alpha]_D^{22}$ −75.8° (c 0.26, CH$_2$Cl$_2$); IR (KBr) 3314, 2941, 1791, 1658, 1545, 1420, 1341, 1312, 1252, 1181, 1118, 939, 749; $^1$H NMR (CDCl$_3$) δ 9.45 (0.5H, s), 9.34 (0.5H, s), 7.68-7.62 (1H, m), 7.49-7.39 (2H, m), 7.33-7.26 (1H, m), 7.18-7.03 (3H, m), 5.49 (0.5H, d), 5.30 (0.5H, s), 5.26-5.13 (1H, m), 4.90-4.83 (0.5H, m), 4.76-4.49 (1H, m), 4.42-4.35 (0.5H, m), 3.97-3.74 (1H, m), 3.72-3.53 (1H, m), 3.35-2.64 (4H, m), 2.50-2.37 (1H, m), 2.20-1.82 (5H, m), 1.69-1.50 (2H, m), 1.30-1.19 (3H, m).

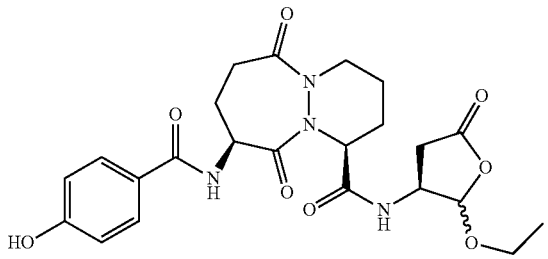

550p

[1S,9S(2RS,3S)]6,10-Dioxo-N-(2-ethoxy-5-oxotetrahydrofuran-3-yl)-9-(4-hydroxybenzoyl)amino-1,2,3,4,7,8,9,10-octahydro-6H-pyridazino[1,2-a][1,2]diazepine-1-carboxamide (550p), was prepared by a similar method as compound 213e to afford a mixture of diastereoisomers as a white foam (820 mg, 47%): $[\alpha]_D^{24}$−75° (c 0.16, CH$_2$Cl$_2$); IR (KBr) 3401, 2937, 1791, 1657, 1609, 1539, 1505, 1423, 1277, 1177, 1118; $^1$H NMR (CDCl$_3$) δ 8.07-8.05 (1H, m), 7.67 (2H, d, J=7.9), 7.38-7.29 (2H, m), 6.80 (2H, d, J=8.5), 5.49 (0.5H, d, J=4.6), 5.23 (0.5H, bs), 5.24-5.20 (1H, m), 5.12-5.08 (1H, m), 4.68-4.29 (2H, m), 3.92-3.45 (3H, m), 3.32-2.30 (2H, m), 2.80-1.56 (11H, m), 1.21 (3H, t, J=7.0H).

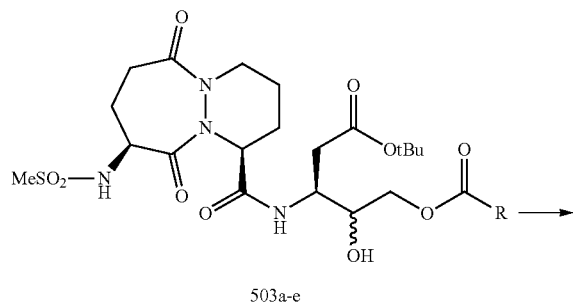

503a-e

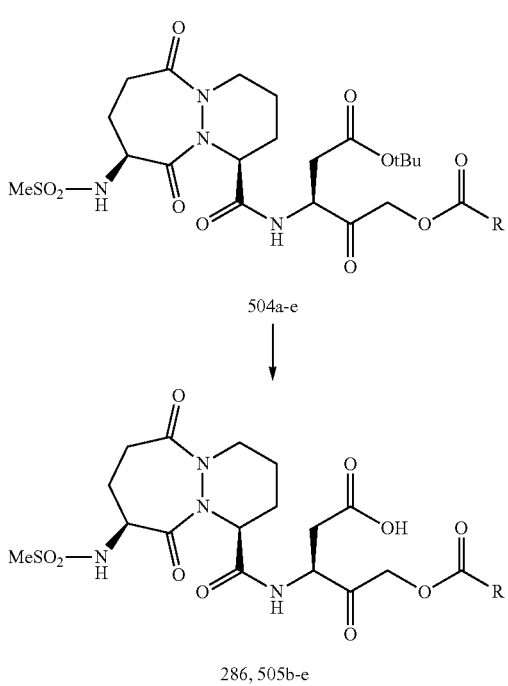

504a-e

↓

286, 505b-e

| compound | R |
|---|---|
| 503a 504a 286 | ![1-naphthyl] |
| 503b 504b 505b | ![4-methyl-5-methyl-3-phenylisoxazolyl with Me, Me, Ph, N] |
| 503c 504c 505c | ![2-phenoxyphenyl] |
| 503d 504d 505d | ![3-phenoxyphenyl] |
| 503e 504e 505e | 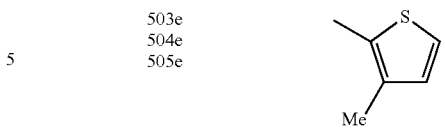 |

[3S,4R(1S,9S)]t-Butyl 3-(6,10-dioxo-9-methanesulpho-nylamino-1,2,3,4,7,8,9,10-octahydro-6H-pyridazino[1,2-a][1,2]diazepine-1-carboxamido)-4-hydroxy-5-(1-naphthoy-loxy)pentanoate (503a), was prepared from 212b and (3S,4R) t-butyl (N-allyloxycarbonyl)-3-amino-4-hydroxy-5-(1-naphthoyloxy)pentanoate by the method described for (213e) to afford 533 mg (81%) of an off-white foam: $[\alpha]_D^{22}$ −81.4° (c 0.5, $CH_2Cl_2$); IR(KBr) 3342, 2976, 1719, 1664, 1328, 1278, 1246, 1153, 1137. $^1$H NMR ($CDCl_3$) δ 8.86 (1H, d, J=8.4), 8.21 (1H, dd, J=1.3, 7.3), 8.03 (1H, d, J=8.1), 7.88 (1H, d, J=8.6), 7.66-7.45 (3H, m), 7.23 (1H, d, J=8.6), 5.96 (1H, d, J=9.2), 5.30 (1H, m), 4.59-4.33 (5H, m), 4.24 (1H, m), 3.96 (1H, brd), 3.29 (1H, m), 2.95 (1H, m), 2.93 (3H, s), 2.69-2.50 (3H, m), 2.36 (1H, m), 1.96 (4H, m), 1.62 (1H, m), 1.41 (9H, s). Anal. Calcd for $C_{31}H_{40}N_4O_{10}S\cdot0.25H_2O$: C, 55.97; H, 6.14; N, 8.42. Found: C, 55.90; H, 6.11; N, 8.23. M.S. ($ES^+$) 683 (M+Na, 100%), 661 (M+1,39), 605 (78).

[3S(1S,9S)]t-Butyl 3-(6,10-dioxo-9-methanesulphony-lamino-1,2,3,4,7,8,9,10-octahydro-6H-pyridazino[1,2-a][1,2]diazepine-1-carboxamido)-5-(1-naphthoyloxy)-4-oxopen-tanoate (504a), was synthesized from 503a via method used to prepare 216e from 215e to afford 446 mg (91%) of a colourless foam: $[\alpha]_D^{21}$ −111.6° (c 0.5, $CH_2Cl_2$); IR (KBr) 3319, 2978, 2936, 1723, 1670, 1413, 1370, 1329, 1278, 1246, 1153. $^1$H NMR ($CDCl_3$) δ 8.87 (1H, d, J=8.9), 8.29 (1H, d, J=7.2), 8.06 (1H, d, J=8.3), 7.90 (1H, d, J=8.2), 7.66-7.48 (3H, m), 7.37 (1H, d, J=8.1), 5.61 (1H, d, J=9.0), 5.31 (1H, m), 5.22 (1H, AB, J=16.9), 5.09 (1H, AB, J=16.92), 4.99 (1H, m), 4.65-4.43 (2H, m), 3.28 (1H, m), 2.96 (3H, s), 2.86 (2H, m), 2.59 (1H, m) 2.38 (1H, dd, J=6.8, 13.2), 2.21-1.70 (6H, m), 1.45 (9H, s). Anal. Calcd for $C_{31}H_{38}O_4O_{10}\cdot0.25H_2O$. C, 56.14; H, 5.85; N, 8.45. Found: C, 56.11; H, 5.83; N, 8.29. M.S. ($ES^+$) 657 (M−1, 100%).

[3S(1S,9S)]3-(6,10-Dioxo-9-methanesulphonylamino-1,2,3,4,7,8,9,10-octahydro-6H-pyridazino[1,2-a][1,2]diaz-epine-1-carboxamido)-5-(1-naphthoyloxy)-4-oxopentanoic acid (286), was prepared from 504a by the method described for 217 to afford 356 mg (93%) of a white powder: mp 120-123° C.; $[\alpha]_D^{23}$ −121° (c 0.194, $CH_2Cl_2$); IR (KBr) 3314, 2937, 1722, 1663, 1412, 1328, 1278, 1245, 1195, 1132. $^1$H NMR (d6-DMSO) 512.63 (1H, brs), 8.94 (1H, d, J=7.4), 8.78 (1H, d, J=8.6), 8.26 (2H, m), 8.11 (1H, d, J=8.0), 7.77-7.62 (4H, m), 5.28 (2H, s), 5.21 (1H, m), 4.82 (1H, m), 4.44-4.29 (2H, m), 3.31 (1H, m), 2.98 (3H, s), 2.98-2.86 (2H, m), 2.72 (1H, dd, J=7.3, 16.9), 2.40 (1H, m), 2.24-1.84 (4H, m), 1.69 (2H, m). Anal. Calcd for $C_{27}H_{30}N_4O_{10}S\cdot H_2O$: C, 52.25; H, 5.20; N, 9.03. Found: C, 52.11; H, 4.97; N, 8.89. M.S. ($ES^+$) 601 (M−1, 100%).

[3S,4RS(1S,9S)]t-Butyl 3-[6,10-dioxo-1,2,3,4,7,8,9,10-octahydro-6H-pyridazino[1,2-a][1,2]diazepine-9-(methane-sulphonylamino)-1-carboxamido]-4-hydroxy-5-(5-methyl-3-phenylisoxazoyloxy)pentanoate (503b), was synthesized by a similar method as compound 213e, to afford an off-white powder (671 mg, 88%): mp. 90-120° C.; IR (KBr) 3345, 2977, 1727, 1664, 1532, 1450, 1423, 1369, 1323, 1310, 1276, 1257, 1154, 1101, 990, 766; $^1$H NMR ($CDCl_3$) δ 7.61-7.55 (2H, m), 7.51-7.42 (3H, m), 6.86 (1H, d), 5.69 (1H, d), 5.21 (1H, m), 4.64-4.38 (2H, m), 4.15-4.05 (3H, m), 3.84 (1H, m), 3.31-3.14 (2H, m), 2.97-2.87 (1H, m), 2.94 (3H, s), 2.76 (3H, s), 2.64-2.48 (3H, m), 2.39-2.29 (1H, m), 2.04-1.61 (5H, m).

Anal. Calcd for $C_{31}H_{41}N_5O_{11}S.H_2O$: C, 52.46; H, 6.11; N, 9.87; S, 4.52. Found: C, 52.34; H, 5.92; N, 9.56; S, 4.44. MS (ES$^+$) 714 (47%), 692 (M$^+$+1, 84), 636 (100).

[3S(1S,9S)]t-Butyl 3-[6,10-dioxo-9-(methanesulphonylamino)-1,2,3,4,7,8,9,10-octahydro-6H-pyridazino[1,2-a][1,2]diazepine-1-carboxamido]-5-(5-methyl-3-phenylisoxazoyloxy)-4-oxopentanoate (504b), was synthesized by a similar method as compound 216b to afford a colourless powder (601 mg, 93%): mp. 75-115° C.; $[\alpha]_D^{23}$ −104° (c 0.26, $CH_2Cl_2$); IR (KBr) 3324, 2977, 2935, 1730, 1670, 1525, 1452, 1422, 1369, 1317, 1276, 1256, 1222, 1155, 1107, 990, 766; $^1$H NMR (CDCl$_3$) δ 7.68-7.61 (2H, m), 7.47-7.38 (3H, m), 7.32-7.24 (1H, m), 5.56 (1H, d), 5.36-5.24 (1H, m), 5.04 (1H, d), 4.88 (1H, d), 4.86-4.77 (1H, m), 4.64-4.39 (2H, m), 3.32-3.17 (1H, m), 2.97-2.85 (1H, m), 2.93 (3H, s), 2.76 (3H, s), 2.80-2.71 (1H, m), 2.65-2.49 (1H, m), 2.41-2.30 (1H, m), 2.12-1.61 (6H, m), 1.42 (9H, s). Anal. Calcd for $C_{31}H_{39}N_5O_{11}S.H_2O$: C, 52.61; H, 5.84; N, 9.90; S, 4.53. Found: C, 52.94; H, 5.69; N, 9.72; S, 4.51. MS (ES$^+$) 712 (31%), 707 (100), 690 (M$^+$+1, 41), 634 (55).

[3S(1S,9S)]3-[6,10-Dioxo-9-(methanesulphonylamino)-1,2,3,4,7,8,9,10-octahydro-6H-pyridazino[1,2-a][1,2]diazepine-1-carboxamido]-5-(5-methyl-3-phenylisoxazoyloxy)-4-oxopentanoic acid (505b), was synthesized by a similar method as compound 217 to afford a colourless powder (499 mg, 96%): mp. 95-145° C.; $[\alpha]_D^{22}$ −137° (c 0.12, MeOH); IR (KBr) 3323, 2936, 1732, 1665, 1529, 1452, 1421, 1312, 1275, 1256, 1221, 1183, 1153, 1135, 1101, 990; $^1$H NMR (CD$_3$OD) δ 7.67-7.56 (2H, m), 7.49-7.38 (4H, m), 5.23-5.12 (1H, m), 5.02 (1H, d), 4.79-4.73 (1H, m), 4.52-4.34 (3H, m), 3.48-3.25 (2H, m), 3.03-2.85 (2H, m), 2.94 (3H, s), 2.74 (3H, s), 2.79-2.66 (1H, m), 2.52-2.38 (1H, m), 2.29-2.14 (1H, m), 2.04-1.70 (4H, m). Anal. Calcd for $C_{27}H_{31}N_5O_{11}S.H_2O$: C, 49.77; H, 5.18; N, 10.75; S, 4.92. Found: C, 49.83; H, 5.01; N, 10.27; S, 4.84. MS (ES$^+$) 746 (42%), 632 (M−1, 100), 386 (60). Accurate mass calculated for $C_{27}H_{32}N_5O_{11}S$ (MH$^+$): 634.1819. Found: 634.1807.

[3S,4RS(1S,9S)]t-Butyl 3-[6,10-dioxo-9-(methanesulphonylamino)-1,2,3,4,7,8,9,10-octahydro-6H-pyridazino[1,2-a][1,2]diazepine-1-carboxamido]-4-hydroxy-5-(2-phenoxybenzoyloxy)pentanoate (503c), was synthesized by a similar method as compound 213e to afford a colourless solid (446 mg, 84%): IR (KBr) 3345, 2976, 2935, 1727, 1664, 1603, 1535, 1483, 1451, 1416, 1395, 1369, 1328, 1297, 1277, 1237, 1155, 1135, 1076, 990, 755; $^1$H NMR (CDCl$_3$) δ 7.98-7.89 (1H, m), 7.55-7.45 (1H, m), 7.39-7.18 (3H, m), 7.14-7.07 (1H, m), 7.00-6.90 (3H, m), 6.75 (1H, d), 5.57-5.50 (1H, m), 5.21-5.09 (1H, m), 4.64-4.42 (2H, m), 4.36-4.12 (3H, m), 3.95-3.87 (1H, m), 3.39-3.18 (1H, m), 3.00-2.82 (1H, m), 2.95 (3H, s), 2.69-2.48 (3H, m), 2.42-2.28 (1H, m), 2.07-1.62 (6H, m), 1.42 (9H, s). Anal. Calcd for $C_{33}H_{42}N_4O_{11}S.H_2O$: C, 54.99; H, 6.15; N, 7.77; S, 4.45. Found: C, 54.95; H, 5.95; N, 7.34; S, 4.20. MS (ES$^+$) 725 (26%), 720 (47), 703 (M$^+$+1, 34), 433 (100), 403 (89).

[3S(1S,9S)]t-Butyl 3-[6,10-dioxo-9-(methanesulphonylamino)-1,2,3,4,7,8,9,10-octahydro-6H-pyridazino[1,2-a][1,2]diazepine-1-carboxamido]-4-oxo-5-(2-phenoxybenzoyloxy)pentanoate (504c), was synthesized by a similar method as compound 216e to afford a colourless powder: mp. 85-100° C.; $[\alpha]_D^{22}$−91.3° (c 0.52, $CH_2Cl_2$); IR (KBr) 3328, 2978, 2935, 1732, 1669, 1603, 1524, 1483, 1450, 1396, 1369, 1296, 1276, 1237, 1155, 1132, 1082, 989, 755; $^1$H NMR (CDCl$_3$) δ 8.03-7.98 (1H, m), 7.52-7.44 (1H, m), 7.37-7.07 (5H, m), 7.01-6.92 (3H, m), 5.52 (1H, d), 5.28-5.20 (1H, m), 5.06-4.84 (3H, m), 4.64-4.39 (2H, m), 3.32-3.14 (1H, m), 2.99-2.88 (1H, m), 2.94 (3H, s), 2.65-2.45 (2H, m), 2.39-2.29 (1H, m), 2.12-1.58 (6H, m), 1.40 (9H, s). Anal. Calcd for $C_{33}H_{40}N_4O_{11}S$: C, 56.56; H, 5.75; N, 8.00; S, 4.58. Found: C, 56.37; H, 5.84; N, 7.69; S, 4.37. MS (ES$^+$) 723 (30%), 718 (100), 701 (M$^+$+1, 23), 645 (59).

[3S(1S,9S)]3-[6,10-Dioxo-9-(methanesulphonylamino)-1,2,3,4,7,8,9,10-octahydro-6H-pyridazino[1,2-a][1,2]diazepine-1-carboxamido]-4-oxo-5-(2-phenoxybenzoyloxy)pentanoic acid (505c), was synthesized by a similar method as compound 217 to afford a colourless foam (252 mg, 72%): mp. 90-125° C.; $[\alpha]_D^{23}$ −133° (c 0.11, MeOH); IR (KBr) 3314, 2938, 1792, 1734, 1663, 1604, 1535, 1483, 1448, 1415, 1250, 1132, 756; $^1$H NMR (D$_5$-DMSO) δ 8.81-8.76 (1H, m), 7.92 (1H, d), 7.68-7.54 (2H, m), 7.41-7.25 (3H, m), 7.16-6.91 (4H, m), 5.13-4.98 (2H, m), 4.72-4.63 (1H, m), 4.37-4.21 (2H, m), 2.92 (3H, s), 2.90-2.60 (3H, m), 2.35-2.26 (1H, m), 2.17-2.05 (2H, m), 1.99-1.80 (2H, m), 1.61-1.50 (1H, m). Anal. Calcd for $C_{29}H_{32}N_4O_{11}S.0.5H_2O$: C, 53.29; H, 5.09; N, 8.57; S, 4.90. Found: C, 53.57; H, 5.18; N, 8.32; S, 4.75. MS (ES$^+$) 643 (M−1, 100%).

[3S,4RS(1S,9S)]t-Butyl 3-[6,10-dioxo-9-(methanesulphonylamino)-1,2,3,4,7,8,9,10-octahydro-6H-pyridazino[1,2-a][1,2]diazepine-1-carboxamido]-4-hydroxy-5-(3-phenoxybenzoyloxy)pentanoate (503d), was synthesized by a similar method as compound 213e to afford a colourless solid (563 mg, 90%): IR (KBr) 3349, 2978, 2935, 1724, 1664, 1583, 1536, 1489, 1443, 1370, 1327, 1271, 1226, 1189, 1155, 1073, 990, 755; $^1$H NMR (CDCl$_3$) δ 7.77 (1H, d), 7.67 (1H, m), 7.45-7.10 (6H, m), 7.00 (2H, d), 5.93-5.80 (1H, m), 5.36-5.30 (1H, m), 4.63-4.24 (5H, m), 4.15-4.09 (1H, m), 3.37-3.22 (1H, m), 2.98-2.74 (1H, m), 2.94 (3H, s), 2.70-2.47 (3H, m), 2.40-2.30 (1H, m), 2.15-1.60 (5H, m), 1.42 (9H, s). Anal. Calcd for $C_{33}H_{42}N_4O_{11}S.H_2O$: C, 54.99; H, 6.15; N, 7.77; S, 4.45. Found: C, 54.60; H, 5.88; N, 7.49; S, 4.50. MS (ES$^+$) 725 (19%), 720 (91), 703 (M$^+$+1, 74), 647 (76), 629 (100), 433 (78).

[3S(1S,9S)]t-Butyl 3-[6,10-dioxo-9-(methanesulphonylamino)-1,2,3,4,7,8,9,10-octahydro-6H-pyridazino[1,2-a][1,2]diazepine-1-carboxamido]-4-oxo-5-(3-phenoxybenzoyloxy)pentanoate (504d), was synthesized by a similar method as compound 216e to afford a colourless powder (466 mg, 85%): mp. 75-100° C.; $[\alpha]D^{22}$ −99.3° (c 0.60, $CH_2Cl_2$); IR (KBr) 3335, 2978, 2937, 1728, 1669, 1584, 1525, 1487, 1444, 1416, 1369, 1328, 1272, 1227, 1188, 1155, 989, 754; $^1$H NMR (CDCl$_3$) δ 7.82-7.77 (1H, m), 7.66-7.65 (1H, m), 7.46-7.32 (4H, m), 7.26-7.10 (2H, m), 7.04-6.98 (2H, m), 5.68 (1H, d), 5.37-5.31 (1H, m), 5.11 (1H, d), 5.02-4.88 (2H, m), 4.66-4.42 (2H, m), 3.35-3.17 (1H, m), 2.98-2.89 (1H, m), 2.96 (3H, s), 2.84-2.78 (1H, m), 2.72-2.47 (2H, m), 2.42-2.32 (1H, m), 2.14-1.58 (6H, m), 1.43 (9H, s). Anal. Calcd for $C_{33}H_{40}N_4O_{11}S$: C, 56.56; H, 5.75; N, 8.00. Found: C, 56.36; H, 5.82; N, 7.71. MS (ES$^+$) 723 (56%), 718 (90), 701 (M$^+$+1, 36), 645 (100).

[3S(1S,9S)]3-[6,10-Dioxo-9-(methanesulphonylamino)-1,2,3,4,7,8,9,10-octahydro-6H-pyridazino[1,2-a][1,2]diazepine-1-carboxamido]-4-oxo-5-(3-phenoxybenzoyloxy)pentanoic acid (505d), was synthesized by a similar method as compound 217 to afford a colourless foam (353 mg, 73%): mp. 80-115° C.; $[\alpha]_D^{23}$ −138° (c 0.11, MeOH); IR (KBr) 3327, 2937, 1728, 1666, 1584, 1529, 1487, 1443, 1413, 1328, 1273, 1227, 1189, 1155, 1134, 989, 754; $^1$H NMR (D$_6$-DMSO) δ 8.82 (1H, d), 7.76-7.72 (1H, m), 7.61-7.53 (2H, m), 7.48-7.32 (4H, m), 7.24-7.17 (1H, m), 7.11-7.06 (2H, m), 5.14-5.06 (3H, m), 4.73-4.64 (1H, m), 4.38-4.24 (2H, m), 2.92 (3H, s), 2.89-2.61 (3H, m), 2.38-2.27 (1H, m), 2.19-2.06 (2H, m), 2.02-1.79 (3H, m), 1.63-1.52 (1H, m). Anal. Calcd for C$_{29}$H$_{32}$N$_4$O$_{11}$S.0.5H$_2$O: C, 53.29; H, 5.09; N, 8.57; S, 4.90. Found: C, 53.24; H, 5.14; N, 8.34; S, 4.86. MS (ES$^+$) 643 (M−1, 100%), 385 (62).

[3S,4R(1S,9S)]t-Butyl 5-(3-chlorothien-2-oyloxy)-3-(6,10-dioxo-9-methanesulphonylamino-1,2,3,4,7,8,9,10-octahydro-6H-pyridazino[1,2-a][1,2]diazepine-1-carboxamido)-4-hydroxypentanoate (503e), was prepared by a similar method to that described for compound 213e, to afford an off white solid (70%): mp. 100-103° C.; $[\alpha]_D^{25}$ −84.0° (c 0.05, CH$_2$Cl$_2$); IR (KBr) 3459-3359, 1722, 1664, 1514, 1368, 1328, 1278, 1247, 1155; $^1$H NMR (CDCl$_3$) δ 7.52 (1H, m), 7.06-6.99 (2H, m), 5.69 (1H, d, J=9.0), 5.23 (1H, m), 4.61-4.16 (6H, m), 3.36-3.19 (1H, m), 2.96 (3H, s), 2.67-2.49, 2.42-2.32, 2.06-1.89, 1.69 (10H, 4m), 1.43 (9H, s).

[3S(1S,9S)]t-Butyl 5-(3-chlorothien-2-oyloxy)-3-(6,10-dioxo-9-methanesulphonylamino-1,2,3,4,7,8,9,10-octahydro-6H-pyridazino[1,2-a][1,2]diazepine-1-carboxamido)-4-oxopentanoate (504e), was prepared by a similar method to that described for compound 216e, to afford a white solid (98%): mp. 91-98° C.; $[\alpha]_D^{25}$ −112.5° C. (c 0.06, CH$_2$Cl$_2$); IR (KBr) 3453-3364, 1727, 1668, 1513, 1420, 1368, 1245, 1155; $^1$H NMR (CDCl$_3$) δ 7.54 (1H, d, J=5.3), 7.18 (1H, d, J=7.18), 7.05 (1H, d, J=5.4), 5.42 (1H, d, J=8.9), 5.25 (1H, m), 5.02 (2H, m), 4.96-4.87 (1H, m), 4.65-4.42 (2H, m), 3.34-3.17 (1H, m), 2.97-2.93 (1H, m), 2.97 (3H, s), 2.87-2.78, 2.73-2.50, 2.38-2.32, 2.13-1.88, 1.69-1.60 (9H, 5m), 1.44 (9H, s).

[3S(1S,9S)]5-(3-Chlorothien-2-oyloxy)-3-(6,10-dioxo-9-methanesulphonylamino-1,2,3,4,7,8,9,10-octahydro-6H-pyridazino[1,2-a][1,2]diazepine-1-carboxamido)-4-oxopentanoic acid (505e). A solution of 217 (0.33 g, 0.51 mmol) in dry dichloromethane (3 ml) was cooled (ice/water) with protection from moisture. Trifluoroacetic acid (2 ml) was added with stirring. The solution was kept at room temperature for 2 h after removal of the cooling bath, then concentrated in vacuo. The residue was evaporated three times from dichloromethane, triturated with diethyl ether and filtered. The solid was purified by flash chromatography (silica gel, 0-6% methanol in dichloromethane) to give the product as a white glassy solid (0.296 g, 98%): mp 110-122° C.; $[\alpha]_D^{22}$ −163.5° (c 0.1, CH$_3$OH); IR (KBr) 3514-3337, 1726, 1664, 1513, 1420, 1245, 1152, 1134, 990; $^1$H NMR (CD$_3$OD) δ 7.79 (1H, d, J=5.2), 7.12 (1H, d, J=5.2), 5.20 (1H, m), 5.02-4.72 (2H, m, masked by H$_2$O), 4.59-4.32 (3H, m), 3.48-3.29, 3.08-2.75, 2.50-2.41, 2.31-2.22, 2.08-1.89, 1.72-1.63 (11H, 6m), 2.95 (3H, s).

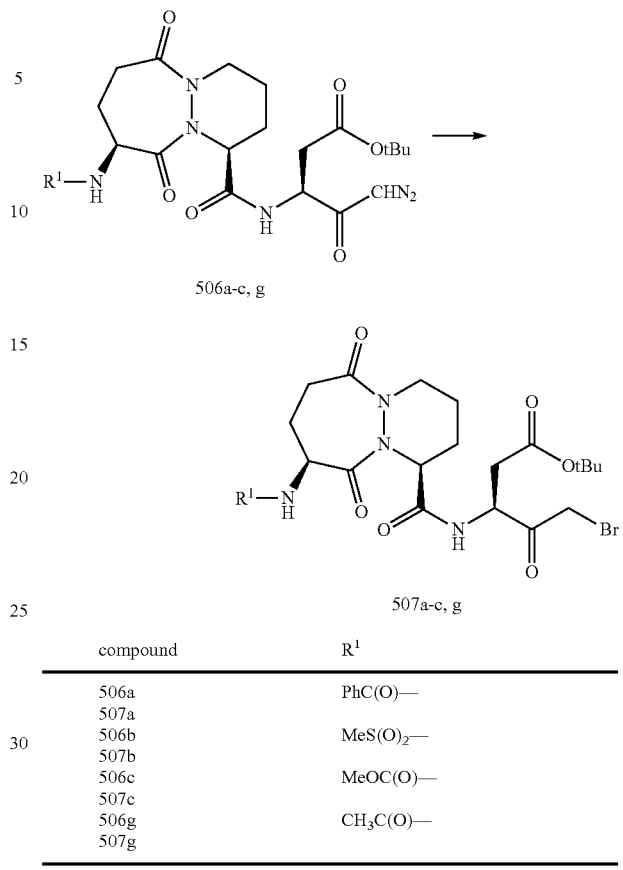

| compound | R$^1$ |
|---|---|
| 506a | PhC(O)— |
| 507a | |
| 506b | MeS(O)$_2$— |
| 507b | |
| 506c | MeOC(O)— |
| 507c | |
| 506g | CH$_3$C(O)— |
| 507g | |

[3S(1S,9S)]t-Butyl 3-(9-benzoylamino-6,10-dioxo-1,2,3,4,7,8,9,10-octahydro-6H-pyridazino[1,2-a][1,2]diazepine-1-carboxamido)-5-diazo-4-oxopentanoate (506a). A solution of 212e (321 mg, 0.929 mmol) and (3S)t-butyl 3-amino-5-diazo-4-oxopentanoate (198 mg, 0.929 mmol) in dichloromethane (3 ml) was cooled to 0° and N,N-diisopropylethylamine (0.16 ml, 1.86 mmol) and [2-(1H-benzotriazol-1-yl)-1,1,3,3-tetramethyl-uronium tetrafluoroborate (328 mg, 1.02 mmol) were added. The solution was stirred overnight at room temperature, diluted with ethyl acetate and washed with 1M NaHSO$_4$ (×2), aqueous NaHCO$_3$ (×2), brine, dried over magnesium sulphate and evaporated. Chromatography on silica gel eluting with ethyl acetate gave 506a (425 mg, 85%) as a colourless foam: $[\alpha]_D^{23}$ −124.9° (c 0.2, CH$_2$Cl$_2$); IR (KBr) 3332, 2111, 1728, 1658, 1532, 1421, 1392, 1367, 1279, 1256, 1155; $^1$H NMR (CDCl$_3$) δ 7.82 (2H, m), 7.49 (3H, m), 7.28 (1H, d, J=9.3), 7.05 (1H, d, J=7.3), 5.06 (1H, s), 5.18 (2H, m), 4.78 (1H, m), 4.62 (1H, m), 3.29 (1H, m), 3.08-2.79 (3H, m), 2.58 (1H, dd, J=16.8, 5.6), 2.20-1.85 (4H, m), 1.70 (1H, m), 1.45 (9H, s). MS (ES$^+$) 539.58 (M−1, 97.9%) 529.59 (100).

[3S(1S,9S)]t-Butyl 5-diazo-3-[6,10-dioxo-(9-methanesulphonamido)-1,2,3,4,7,8,9,10-octahydro-6H-pyridazino[1,2-a][1,2]diazepine-1-carboxamido]-4-oxopentanoate (506b), was prepared by a similar method as compound 506a. 74% as yellow orange solid: mp. 75° C. (decamp.); $[\alpha]_D^{20}$ −92.0° (c 0.036, CH$_2$Cl$_2$); IR (KBr) 3438, 2904, 2113, 1728, 1669, 1523, 1368, 1328, 1155; $^1$H NMR (CDCl$_3$) δ 7.48 (1H, d, J=8.1), 5.83-5.68 (1H, m), 5.55-5.50 (1H, m), 5.43-5.14 (1H, m), 4.83-4.45 (3H, m), 3.40-3.19 (1H, m), 2.98 (3H, s), 2.92-2.30 (4H, m), 2.24-1.70 (6H, m), 1.43 (9H, s).

[3S(1S,9S)]t-Butyl 5-diazo-3-[6,10-dioxo-(9-methoxycarbonyl)amino-1,2,3,4,7,8,9,10-octahydro-6H-pyridazino[1,2-a][1,2]diazepine-1-carboxamido]-4-oxopentanoate (506c), was prepared by a similar method as compound 506a to afford a pale yellow foam (405 mg, 82%): $[\alpha]_D^{20}$ −144° (c 0.2, CH$_2$Cl$_2$); IR (KBr) 3339, 2978, 2958, 2112, 1728, 1674, 1530, 1459, 1415, 1367, 1274, 1252, 1154, 1063; $^1$H NMR (CDCl$_3$) δ 7.23 (1H, d, J=8.2), 5.51-5.31 (2H, m), 5.21-5.16 (1H, m), 4.77-4.55 (3H, m), 3.68 (3H, s), 3.35-3.18 (1H, m), 3.04-2.51 (4H, m), 2.40-2.30 (1H, m), 2.09-1.66 (5H, m), 1.45 (9H, s). MS (ES$^+$) 493.

[3S(1S,9S)]t-Butyl 3-(9-acetylamino-6,10-dioxo-1,2,3,4,7,8,9,10-octahydro-6H-pyridazino[1,2-a][1,2]diazepine-1-carboxamido)-5-diazo-4-oxopentanoate (506g), was prepared by a similar method as compound 506a. 81%: $[\alpha]_D^{28}$ −146.7° (c 0.4, CH$_2$Cl$_2$); IR (KBr) 3438, 2904, 2113, 1728, 1669, 1523, 1368, 1328, 1155; $^1$H NMR (CDCl$_3$) δ 7.32 (1H, d), 6.43 (1H, d), 5.50 (1H, s), 5.22 (1H, m), 4.94 (1H, m), 4.77 (1H, m), 4.60 (1H, m), 3.24 (1H, m), 3.03-2.52 (4H, m), 2.36 (1H, m), 2.10-1.64 (5H, m), 2.02 (3H, s), 1.45 (9H, s). Anal. Calcd for C$_{21}$H$_{20}$N$_6$O$_7$: C, 52.69; H, 6.32; N, 17.05. Found: C, 52.51; H, 6.27; N, 17.36. MS (ES$^+$) 477 (M$^+$−1, 100%).

[3S(1S,9S)]t-Butyl 5-bromo-3-(9-benzoylamino-6,10-dioxo-1,2,3,4,7,8,9,10-octahydro-6H-pyridazino[1,2-a].[1,2]diazepine-1-carboxamido)-4-oxopentanoate (507a). 506a (3.0 g, 5.55 mmol) in dry dichloromethane (40 ml) was cooled to 0° and 30% hydrobromic acid in acetic acid (1.1 ml, 5.55 mmol) was added dropwise over 4 min. The mixture was stirred at 0° for 9 min and quenched with aqueous sodium bicarbonate. The product was extracted into ethyl acetate, washed with aqueous sodium bicarbonate, brine, dried (MgSO$_4$) and evaporated to give 2.97 g (92%) of a colourless foam: $[\alpha]_D^{23}$ −82.3° (c 0.23, CH$_2$Cl$_2$); IR (KBr) 3333, 1726, 1659, 1530, 1458, 1447, 1422, 1395, 1368, 1279, 1256, 1222, 1155, 728; $^1$H NMR (CDCl$_3$) δ 7.81 (2H, m), 7.50 (3H, m), 7.11 (1H, d, J=8.0), 7.01 (1H, d, J=7.4), 5.20 (2H, m), 5.00 (1H, m), 4.06 (2H, s), 3.28 (1H, m), 3.20-2.70 (4H, m), 2.42 (1H, m), 2.10-1.85 (4H, m), 1.72 (1H, m), 1.44 (9H, s). Anal. Calcd for C$_{26}$H$_{33}$N$_4$O$_7$Br.0.7H$_2$O: C, 51.53; H, 5.72 N, 9.24. Found: C, 51.55; H, 5.52; N, 9.09. MS (ES$^+$) 595, 593 (M$^+$+1).

[3S(1S,9S)]t-Butyl 5-bromo-3-(6,10-dioxo-9-methanesulphonamido-1,2,3,4,7,8,9,10-octahydro-6H-pyridazino[1,2-a][1,2]diazepine-1-carboxamido)-4-oxopentanoate (507b), was prepared by a similar method as compound 507a. (68%) as an orange foam: $[\alpha]_D^{20}$ −135° (c 0.053, CH$_2$Cl$_2$); IR (KBr) 3429, 2944, 2935, 1723, 1670, 1458, 1408, 1327, 1225, 1154, 991; $^1$H NMR (CDCl$_3$) δ 7.38 (1H, d, J=8.2), 5.69 (1H, d, J=9.3), 5.43-5.34 (1H, m), 5.07-4.97 (1H, m), 4.70-4.42 (2H, m), 4.12 (2H, s), 3.35-3.17 (1H, m), 3.10-2.69 (4H, m), 2.98 (3H, s), 2.43-2.33 (1H, m), 2.15-1.65 (5H, m), 1.43 (9H, s). Anal. Calcd for C$_{20}$H$_{31}$BrN$_4$O$_8$S: C, 42.33; H, 5.51; N, 9.87. Found: C, 42.69; H, 5.52; N, 9.97.

[3S(1S,9S)]t-Butyl 5-bromo-3-(6,10-dioxo-9-(methoxycarbonyl)amino-1,2,3,4,7,8,9,10-octahydro-6H-pyridazino[1,2-a][1,2]diazepine-1-carboxamido)-4-oxopentanoate (507c), was prepared by a similar method as compound 507a to afford a pale yellow foam (320 mg, 78%): $[\alpha]_D^{20}$ −107° (c 0.2, CH$_2$Cl$_2$); IR (KBr) 3401, 2956, 1726, 1670, 1528, 1452, 1415, 1395, 1368, 1276, 1251, 1155, 1064; $^1$H NMR (CDCl$_3$) δ 7.07 (1H, d, J=7.6), 5.47 (1H, d, J=8.1), 5.21-5.16 (1H, m), 5.03-4.94 (1H, m), 4.75-4.56 (2H, m), 4.06 (2H, s), 3.69 (3H, s), 3.31-3.13 (1H, m), 3.03-2.92 (2H, m), 2.81-2.58 (2H, m), 2.41-2.31 (1H, m), 2.10-1.66 (5H, m), 1.44 (9H, s).

[3S(1S,9S)]t-Butyl 3-(9-acetylamino-6,10-dioxo-1,2,3,4,7,8,9,10-octahydro-6H-pyridazino[1,2-a][1,2]diazepine-1-carboxamido]-5-bromo-4-oxopentanoate (507g), was prepared by a similar method as compound 507a to afford a pale yellow foam (84%): $[\alpha]_D^{22}$ −109.6° (c 0.1, CH$_2$Cl$_2$); IR (KBr) 3324, 1727, 1659, 1535, 1458, 1444, 1423, 1369, 1279, 1256, 1223, 1155; $^1$H NMR (CDCl$_3$) δ 7.12 (1H, d, J=7.8), 6.33 (1H, d, J=7.5), 5.19 (1H, m), 4.97 (2H, m), 4.58 (1H, m), 4.06 (2H, s), 3.20 (1H, m), 3.05-2.69 (4H, m), 2.35 (1H, m), 2.14-1.68 (5H, m), 2.03 (3H, s), 1.44 (9H, s). Anal. Calcd for C$_{21}$H$_{31}$BrN$_4$O$_7$.0.3H$_2$O: C, 46.99; H, 5.93; N, 10.44. Found: C, 46.97; H, 5.90; N, 10.35.

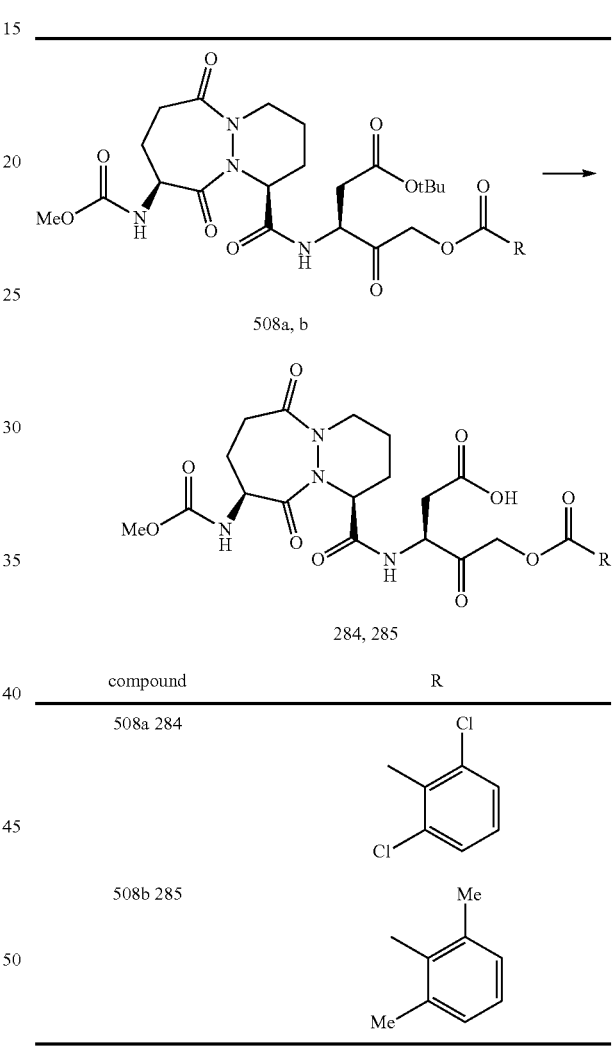

| compound | R |
|---|---|
| 508a 284 | 2,6-dichloro-phenyl |
| 508b 285 | 2,6-dimethyl-phenyl |

[3S(1S,9S)]t-Butyl 5-(2,6-dichlorobenzoyloxy)-3-[(6,10-dioxo-9-(methoxycarbonyl)amino-1,2,3,4,7,8,9,10-octahydro-6H-pyridazino[1,2-a][1,2]diazepine-1-carboxamido]-4-oxobutanoate (508a). To a solution of 506c (547 mg, 1 mmol) in DMF (4 ml) was added potassium fluoride (145 mg, 2.5 mmol, 2.5 equiv). After 10 min stirring at room temperature, 2,6-dichlorobenzoic acid (229 mg, 1.2 mmol, 1.2 equiv) was added. After 3 h reaction at room temperature, ethyl acetate (30 ml) was added. The solution was washed with a saturated solution of sodium bicarbonate (30 ml), brine, dried over MgSO$_4$ and concentrated in vacuo to afford 590 mg (90%) of a pale yellow foam: $[\alpha]_D^{22}$ −85° (c 0.20, CH$_2$Cl$_2$); IR (KBr) 3400, 2956, 1737, 1675, 1528, 1434, 1414, 1368, 1344, 1272, 1197, 1152, 1061; $^1$H NMR (CDCl$_3$) δ 7.36-7.33 (3H, m), 7.04 (1H, d, J=8.0), 5.46 (1H, d, J=7.8), 5.19-5.16 (1H, m), 5.08 (2H, AB), 4.97-4.55 (1H, m), 4.69-4.55 (2H, m), 3.68 (3H, s), 3.30-3.10 (1H, m), 3.01-2.50 (4H, m), 2.40-2.33 (1H, m), 2.15-1.60 (5H, m), 1.44 (9H, s). Anal. Calcd for C$_{28}$H$_{34}$Cl$_2$N$_4$O$_{10}$: C, 51.15; H, 5.21; N, 8.52. Found: C, 51.35; H, 5.32; N, 8.56.

[3S(1S,9S)]5-(2,6-Dichlorobenzoyloxy)-3-[6,10-dioxo-9-(methoxycarbonyl)amino-1,2,3,4,7,8,9,10-octahydro-6H-pyridazino[1,2-a][1,2]diazepine-1-carboxamido]-4-oxopentanoic acid (284), was synthesized from 508a via method used to prepare 505 from 504 which afforded 330 mg (65%) of a white solid: mp. 115° C. (decomp.); [α]$_D$$^{20}$ −107° (c 0.2, CH$_2$Cl$_2$); IR (KBr) 3340, 2954, 1738, 1664, 1530, 1434, 1272, 1198, 1148, 1060; $^1$H NMR (D$_6$-DMSO) δ 8.91 (1H, d, J=7.2H), 7.67-7.63 (3H, m), 7.54 (1H, d, J=8.0), 5.24 (2H, s), 5.20-5.15 (1H, m), 4.79-4.70 (1H, m), 4.46-4.37 (2H, m), 3.58 (3H, s), 3.33-3.20 (1H, m), 2.94-2.55 (4H, m), 2.30-1.60 (6H, m). Anal. Calcd for C$_{24}$H$_{26}$C$_{12}$N$_4$O$_{10}$·H$_2$O: C, 46.54; H, 4.56; N, 9.05. Found: C, 46.36; H, 4.14; N, 8.88.

[3S(1S,9S)]t-Butyl 5-(2,6-dimethylbenzoyloxy)-3-[6,10-dioxo-9-(methoxycarbonyl)amino-1,2,3,4,7,8,9,10-octahydro-6H-pyridazino[1,2-a][1,2]diazepine-1-carboxamido]-4-oxopentanoate (508b), was synthesized by a similar method as compound 508a to afford a pale yellow foam (460 mg, 82%): [α]$_D$$^{22}$ −115° (c 0.20, CH$_2$Cl$_2$); IR (KBr) 3413, 2960, 1729, 1675, 1528, 1514, 1461, 1421, 1368, 1265, 1116, 1096; $^1$H NMR (CDCl$_3$) δ 7.27-7.03 (4H, m), 5.48 (1H, d, J=8.2), 5.20-5.14 (1H, m), 5.04 (2H, AB), 4.93-4.86 (1H, m), 4.80-4.56 (2H, m), 3.77 (3H, s), 3.32-3.15 (1H, m), 3.00-2.56 (4H, m), 2.37 (6H, s), 2.19-1.77 (5H, m), 1.45 (9H, s), 2.41-2.25 (1H, m). MS (ES$^+$) 617.

[3S(1S,9S)]5-(2,6-Dimethylbenzoyloxy)-3-[6,10-dioxo-9-(methoxycarbonyl)amino-1,2,3,4,7,8,9,10-octahydro-6H-pyridazino[1,2-a][1,2]diazepine-1-carboxamido]-4-oxopentanoic acid (285), was synthesized by a similar method as compound 284 to afford a white solid (303 mg, 78%): mp. 110° C. (decomp.); [α]$_D$$^{20}$ −128° (c 0.10, CH$_2$Cl$_2$); IR (KBr) 3339, 2958, 1731, 1666, 1529, 1420, 1266, 1248, 1115, 1070; $^1$H NMR (D$_6$-DMSO) δ 8.90 (1H, d, J=7.4), 7.54 (1H, d, J=7.9), 7.36-7.28 (1H, m), 7.17-7.14 (2H, m), 5.19-5.15 (3H, m), 4.84-4.74 (1H, m), 4.45-4.37 (2H, m), 3.59 (3H, s), 3.45-3.25 (1H, m), 2.95-2.64 (4H, m), 2.35 (6H, s), 2.30-1.60 (6H, m). Anal. Calcd for C$_{26}$H$_{32}$N$_4$O$_{10}$·H$_2$O: C, 53.98; H, 5.92; N, 9.68. Found: C, 53.50; H, 5.52; N, 9.49. MS (ES$^+$) 559.

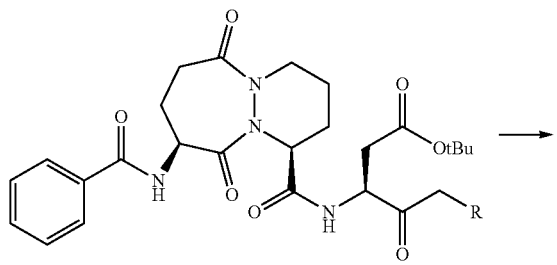

509a-d

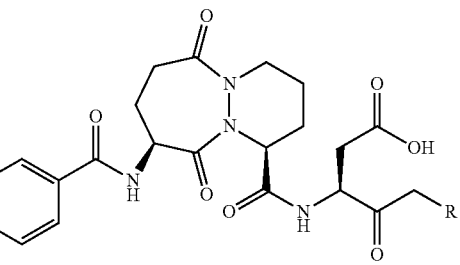

510a, 280, 283, 510d

| compound | R |
|---|---|
| 509a 510a | 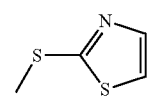 |
| 509b 280 | 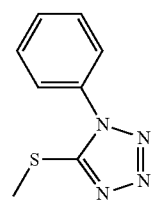 |

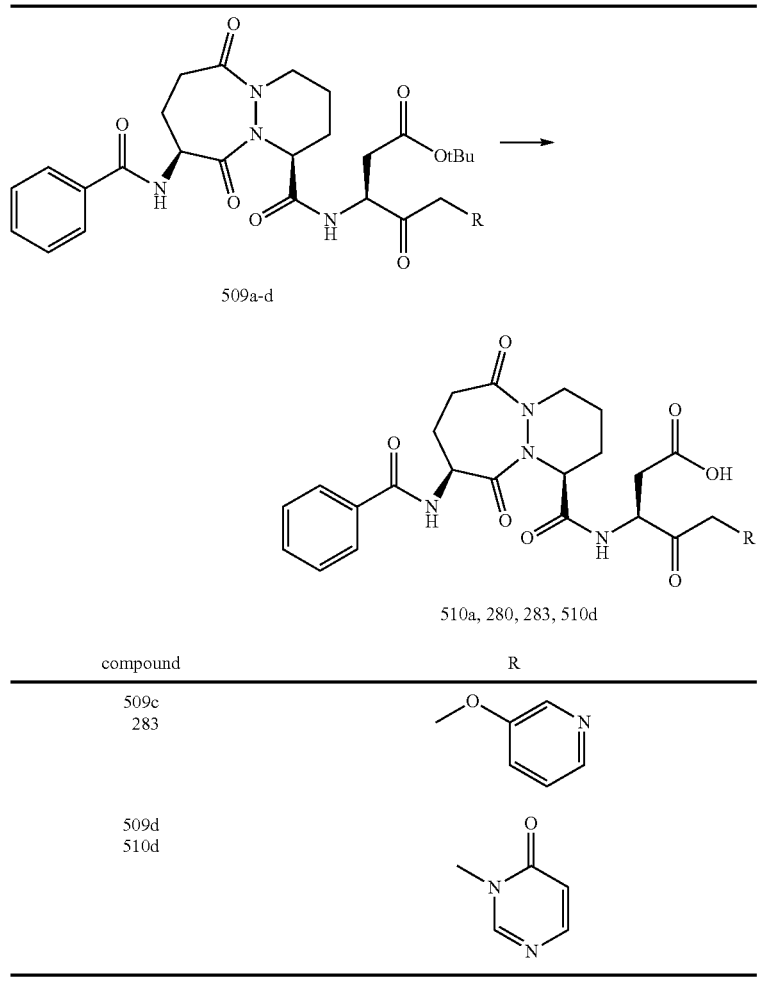

| compound | R |
|---|---|
| 509c 283 | (3-methoxypyridin-2-yl) |
| 509d 510d | (1-methyl-4-oxo-1H-pyrimidin-yl) |

[3S(1S,9S)]3-(9-Benzoylamino-6,10-dioxo-1,2,3,4,7,8,9,10-octahydro-6H-pyridazino[1,2-a][1,2]diazepine-1-carboxamido)-5-(2-mercaptothiazole)-4-oxopentanoic acid (510a). A solution of 506a (2.27 g, 4.2 mmol) in dry dichloromethane (50 ml) was treated with 30% hydrobromic acid in acetic acid (1.84 ml, 9.2 mmol, 2.2 equiv) at 0° C., under nitrogen. After 10 min stirring at 0° C. the reaction was complete and a white solid crystallised in the medium. The solid was filtered and washed with ethylacetate and diethylether to afford 2.20 g (100%) of [3S(1S,9S)]5-bromo-3-(9-benzoylamino-6,10-dioxo-1,2,3,4,7,8,9,10-octahydro-6H-pyridazino[1,2-a][1,2]diazepine-1-carboxamido)-4-oxopentanoic acid which was used without further purification: $^1$H NMR (D$_6$-DMSO) δ 8.87 (1H, d, J=7.3), 8.63 (1H, d, J=7.6), 7.91-7.87 (2H, m), 7.60-7.44 (3H, m), 6.92 (1H, bs), 5.14-5.09 (1H, m), 4.92-4.65 (2H, m), 4.43 (2H, AB), 4.41-4.35 (1H, m), 3.33-3.22 (1H, m), 2.98-2.90 (1H, m), 2.89-2.57 (2H, m), 2.35-2.15 (3H, m), 1.99-1.91 (2H, m), 1.75-1.60 (2H, m). A solution of the bromoketone (535 mg, 1 mmol) in dry DMF (10 ml) was treated with potassium fluoride (150 mg, 2.5 mmol, 2.5 equiv), under nitrogen. After 5 min stirring at room temperature, 2-mercaptothiazole (140 mg, 1.2 mmol, 1.2 equiv) was added. After overnight reaction ethylacetate (150 ml) was added and the organic solution was washed with brine, dried over magnesium sulphate and reduced in vacuo. The residue was crystallised in diethyl ether, filtered and purified on silica gel using a gradient of MeOH (0% to 5%) in dichloromethane. Evaporation afforded 344 mg (60%) of a white solid: mp. 90-95° C. (decomp.); $[\alpha]_D^{20}$ −82° (c 0.2, CH$_2$Cl$_2$); IR (KBr) 3328, 2941, 1745, 1659, 1535, 1422, 1276, 1255, 1223, 1072; $^1$H NMR (D$_6$-DMSO) δ 8.92 (1H, d, J=7.6), 8.68 (1H, d, J=7.6), 7.98-7.90 (2H, m), 7.75-7.67 (1H, m), 7.64-7.50 (4H, m), 5.22-5.18 (1H, m), 4.95-4.74 (2H, m), 4.58-4.38 (3H, m), 3.52-3.19 (1H, m), 3.05-2.65 (4H, m), 2.40-1.50 (6H, m). Anal. Calcd for C$_{25}$H$_{27}$N$_5$O$_4$S$_2$—H$_2$O: C, 50.75; H, 4.94 N, 11.84. Found: C, 51.34; H, 4.70; N, 11.58. MS (ES$^+$) 572.

[3S(1S,9S)]t-Butyl 3-(9-benzoylamino-6,10-dioxo-1,2,3,4,7,8,9,10-octahydro-6H-pyridazino[1,2-a][1,2]diazepine-1-carboxamido)-4-oxo-5-(1-phenyl-1H-tetrazole-5-thio)pentanoate (509b). 507a (100 mg, 0.17 mmol) in dry dimethylformamide (1.5 ml) was treated with 1-phenyl-1H-tetrazole-5-thiol (33 mg, 0.187 mmol) and potassium fluoride (15 mg, 0.34 mmol). The mixture was stirred at room temperature for 2 h, diluted with ethyl acetate, washed with aqueous sodium bicarbonate (×2), brine, dried (MgSO$_4$) and evaporated. The product was purified by flash chromatography on silica gel eluting with ethyl acetate to give 103 mg (88%) as a colourless foam: $[\alpha]_D^{23}$ −92.2° (c 0.1, CH$_2$Cl$_2$); IR (KBr) 3334, 1726, 1660, 1528, 1501, 1417, 1394, 1368, 1279, 1253, 1155; $^1$H NMR (CDCl$_3$) δ 7.82 (2H, m), 7.60-7.40 (8H, m), 7.39 (1H, d, J=8.1), 7.05 (1H, d, J=7.3), 5.26 (1H, m), 5.15 (1H, m), 4.99 (1H, m), 4.60 (2H, m), 4.30 (1H, d, J=17.2H), 3.32 (1H, m), 3.10-2.75 (4H, m), 2.40 (1H, m), 2.24 (1H, m), 1.90 (3H, m), 1.75 (1H, m), 1.44 (9H, s). MS (ES+) 691.47 (M++1).

[3S(1S,9S)]3-(9-Benzoylamino-6,10-dioxo-1,2,3,4,7,8,9,10-octahydro-6H-pyridazino[1,2-a][1,2]diazepine-1-carboxamido)-4-oxo-5-(1-phenyl-1H-tetrazole-5-thio) pentanoic acid (280), was synthesized via method used to prepare 505 from 504. 509b (98 mg, 0.142 mmol) in dichloromethane (1 ml) was cooled to 0° and trifluoroacetic acid (1 ml) was added. The mixture was stirred at 0° for 15 min and at room temperature for 30 min before evaporation under reduced pressure. The residue was triturated with dry toluene and evaporated. Chromatography on silica gel eluting with 10% methanol in dichloromethane gave a colourless glass which was crystallised from dichloromethane/diethyl ether to give 62 mg (69%) of colourless solid: mp. 145° C. (decomp.); $[\alpha]_D^{22}$ −80.9° (c 0.1, $CH_2Cl_2$); IR (KBr) 3400, 1727, 1658, 1530, 1501, 1460, 1445, 1416, 1280, 1254; $^1H$ NMR (CDCl$_3$) δ 8.00 (1H, m), 7.79 (2H, d, J=6.7), 7.58-7.30 (9H, m), 5.25 (2H, m), 4.94 (1H, m), 4.53 (2H, m), 4.35 (1H, m), 3.35 (1H, m), 3.01 (3H, m), 2.73 (1H, m), 2.38 (1H, m), 1.98 (4H, m), 1.64 (1H, m). Anal. Calcd for $C_{29}H_{30}N_8O_7S.0.2TFA$: C, 53.71; H, 4.63 N, 17.04. Found: C, 53.97; H, 4.92; N, 16.77. MS (ES+) 633.55 (M+−1).

[3S(1S,9S)]t-Butyl 3-[9-benzoylamino-6,10-dioxo-1,2,3,4,7,8,9,10-octahydro-6H-pyridazino[1,2-a][1,2]diazepine-1-carboxamido]-4-oxo-5-(3-pyridyloxy)pentanoate (509c), was prepared by a similar method as compound 509b to afford a colourless glass (34%): $[\alpha]_D^{22}$ −77.1° (c 0.25, $CH_2Cl_2$); IR (film) 3311, 1724, 1658, 1603, 1578, 1536, 1488, 1458, 1426, 1368, 1340, 1279, 1256, 1231, 1155, 707; $^1H$ NMR (CDCl$_3$) δ 8.29 (2H, m), 7.84 (2H, m), 7.48 (4H, m), 7.22 (3H, m), 5.20 (2H, m), 4.90 (2H, m), 4.58 (1H, m), 3.29 (1H, m), 3.20-2.70 (4H, m), 2.38 (2H, m), 1.96 (4H, m), 1.68 (1H, m), 1.42 (9H, s). MS (ES+) 608.54 (M+1).

[3S(1S,9S)]3-[9-Benzoylamino-6,10-dioxo-1,2,3,4,7,8,9,10-octahydro-6H-pyridazino[1,2-a][1,2]diazepine-1-carboxamido]-4-oxo-5-(3-pyridyloxy)pentanoic acid (283), was prepared by a similar method as compound 280 to afford a colourless foam (100%): mp. ~125° C.; $[\alpha]_D^{19}$ −84.1° (c 0.1, 20% MeOH/$CH_2Cl_2$); IR (KBr) 3401, 1736, 1663, 1538, 1489, 1459, 1425, 1281, 1258, 1200, 1134; $^1H$ NMR (CD$_3$OD/CDCl$_3$) δ 8.38 (2H, m), 7.84-7.40 (8H, m), 5.16 (4H, m), 4.80 (1H, m), 4.56 (1H, m), 3.50 (1H, m), 3.12 (2H, m), 2.82 (2H, m), 2.37 (1H, m), 2.10-1.65 (5H, m). Anal. Calcd for $C_{27}H_{29}N_5O_8.0.4H_2O$: C, 51.77; H, 4.61; N, 10.41. Found: C, 52.19; H, 4.93; N, 9.99.

[3S(1S,9S)]t-Butyl 3-[6,10-dioxo-1,2,3,4,7,8,9,10-octahydro-9-(phenycarbonylamino)-6H-pyridazino[1,2-a][1,2]diazepine-1-carboxamido]-4-oxo-5-{2-[4(3H)-pyrimidone]}pentanoate (509d), was synthesized by a similar method as compound 509b to afford a colourless solid (49.6 mg, 82%): $^1H$ NMR (CDCl$_3$) δ 8.02 (1H, s), 7.95-7.86 (1H, m), 7.84-7.76 (2H, m), 7.62-7.35 (4H, m), 7.22-7.07 (1H, m), 6.43 (1H, d), 5.26-5.08 (2H, m), 5.03-4.72 (3H, m), 4.66-4.50 (1H, m), 3.43-3.19 (1H, m), 3.15-2.97 (1H, m), 2.86-2.72 (3H, m), 2.48-2.31 (1H, m), 2.18-1.60 (6H, m), 1.43 (9H, s).

[3S(1S,9S)]3-[6,10-Dioxo-1,2,3,4,7,8,9,10-octahydro-9-(phenycarbonylamino)-6H-pyridazino[1,2-a][1,2]diazepine-1-carboxamido]-4-oxo-5-{2-[4(3H)-pyrimidone]}pentanoic acid (510d), was synthesized by a similar method as compound 280 to afford a colourless solid (25.7 mg, 57%): mp. 140-80° C.; IR (KBr) 3391, 2945, 1733, 1664, 1530, 1422, 1363, 1277, 1259, 1204; $^1H$ NMR (CD$_3$OD) δ 8.23 (1H, s), 7.94 (1H, d), 7.87 (2H, d), 7.54-7.42 (3H, m), 6.48 (1H, d), 5.22-5.15 (1H, m), 4.57-4.46 (1H, m), 3.62-3.41 (1H, m), 3.22-3.13 (1H, m), 3.02-2.81 (2H, m), 2.70-1.80 (6H, m). Anal. Calcd for $C_{26}H_{28}N_6O_8.1.5H_2O$: C, 54.30; H, 5.35; N, 14.61. Found: C, 54.14; H, 5.35; N, 13.04. MS (ES+) 551 (M−1, 100%). Accurate mass calculated for $C_{26}H_{29}N_6O_8$ (MH+): 553.2047. Found: 553.2080.

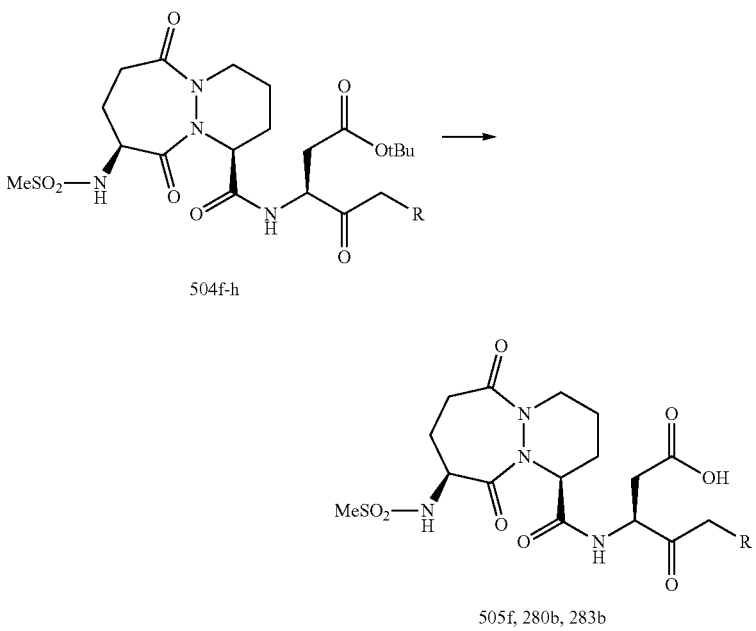

| compound | R |

| | |
|---|---|
| 504f 505f | 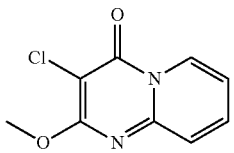 |
| 504g 280b | 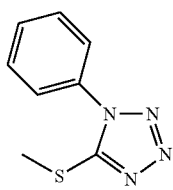 |
| 504h 283b | 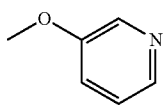 |

[3S(1S,9S)]5-(3-Chloro-2-oxy-4H-pyrido[1,2-a]pyrimidin-4-one)-3-[6,10-dioxo-9-(methylsulphonyl)amino-1,2,3,4,7,8,9,10-octahydro-6H-pyridazino[1,2-a][1,2]diazepine-1-carboxamido]-4-oxopentanoic acid (505f), was prepared by a similar method as compound 508a using 507b and 3-chloro-2-hydroxy-4H-pyrido[1,2-a]pyrimidin-4-one and directly followed by the hydrolysis of 504f with trifluoroacetic to afford a tan powder (65 mg, 30%): $[\alpha]_D^{20}$ -128° (c 0.10, MeOH); IR (KBr) 3414, 2928, 1667, 1527, 2459, 1407, 1328, 1274, 1153, 1134; $^1$H NMR (MeOD) δ 9.35 (1H, d, J=6.6H), 8.34 (1H, t, J=7.2H), 7.99-7.95 (1H, m), 7.76-7.69 (1H, m), 5.85-5.45 (3H, m), 5.30-5.21 (1H, m), 4.93-4.66 (2H, m), 3.81-3.65 (1H, m), 3.66 (3H, m), 3.45-2.52 (4H, m), 2.52-1.71 (6H, m). D. J. Hlasta et al., J. Med. Chem. 1995, 38, 4687-4692.

[3S(1S,9S)]t-Butyl 3-(6,10-dioxo-9-methanesulphonamido-1,2,3,4,7,8,9,10-octahydro-6H-pyridazino[1,2-a][1,2]diazepine-1-carboxamido)-4-oxo-5-(1-phenyl-1H-tetrazole-5-thio)pentanoate (504g), was prepared by a similar method as compound 509b, (83%) as a colourless foam: $[\alpha]_D^{23}$ -112.7° (c 0.2, CH$_2$Cl$_2$); IR (KBr) 3312, 1726, 1668, 1501, 1413, 1395, 1369, 1328, 1276, 1254, 1155; $^1$H NMR (CDCl$_3$) δ 7.59 (5H, m), 7.48 (1H, d, J=8.0), 5.68 (1H, d, J=9.0), 5.37 (1H, m), 4.95 (1H, m), 4.62-4.31 (4H, m), 3.36 (1H, m), 2.98 (3H, s), 2.88 (4H, m), 2.66 (1H, m), 2.42 (2H, m), 1.98 (1H, m), 1.75 (1H, m), 1.43 (9H, s).

[3S(1S,9S)]3-(6,10-Dioxo-9-methanesulphonamido-1,2,3,4,7,8,9,10-octahydro-6H-pyridazino[1,2-a][1,2]diazepine-1-carboxamido)-4-oxo-5-(1-phenyl-1H-tetrazole-5-thio)pentanoic acid (280b), was prepared by a similar method as compound 280, (100%) as a colourless foam: mp. 120-5° C.; $[\alpha]_D^{25}$ -112.4° (c 0.1, CH$_2$Cl$_2$); IR (KBr) 3328, 1730, 1664, 1529, 1501, 1410, 1328, 1277, 1219, 1153, 1134, 991; $^1$H NMR (CDCl$_3$) δ 8.07 (1H, d, J=7.8), 7.58 (5H, s), 6.41 (1H, d, J=9.5), 5.32 (1H, m), 5.04 (1H, m), 4.70 (1H, d, J=17.5), 4.60 (3H, m), 3.50-2.9 (3H, m), 2.98 (3H, s), 2.45 (2H, m), 2.06 (4H, m), 1.68 (1H, m).

[3S(1S,9S)]t-Butyl 3-(6,10-dioxo-9-methanesulphonamido-1,2,3,4,7,8,9,10-octahydro-6H-pyridazino[1,2-a][1,2]diazepine-1-carboxamido)-4-oxo-5-(3-pyridyloxy)pentanoate (504h), was prepared by a similar method as compound 509b (24%) as a colourless foam: $[\alpha]_D^{23}$ -101.0° (c 0.2, CH$_2$Cl$_2$); IR (KBr) 3330, 1727, 1669, 1425, 1396, 1369, 1328, 1276, 1256, 1231, 1155, 1137, 991; $^1$H NMR (CDCl$_3$) δ 8.28 (2H, br d, J=9.4), 7.71 (1H, d, J=7.9), 7.22 (2H, s), 6.03 (1H, d, J=9.4), 5.36 (1H, m), 4.95 (2H, m), 4.52 (2H, m), 3.29 (1H, m), 3.07 (3H, s), 3.23-2.75 (3H, m), 2.66-2.35 (2H, m), 2.30-1.60 (5H, m), 1.42 (9H, s).

[3S(1S,9S)]3-(6,10-Dioxo-9-methanesulphonamido-1,2,3,4,7,8,9,10-octahydro-6H-pyridazino[1,2-a][1,2]diazepine-1-carboxamido)-4-oxo-5(3-pyridyloxy)pentanoic acid (283b), was prepared by a similar method as compound 280, (100%) as a colourless foam: mp. 120-5° C.; $[\alpha]_D^{25}$ -85.2° (c 0.1, 10% CH$_3$OH/CH$_2$Cl$_2$); IR (KBr) 3337, 1738, 1667, 1560, 1457, 1424, 1326, 1317, 1278, 1258, 1200, 1189, 1150, 1133, 991; $^1$H NMR (CDCl$_3$/CD$_3$OD) δ 8.35 (2H, m), 7.54 (2H, m), 5.32 (2H, m), 4.83 (2H, m), 4.45 (2H, m), 3.43-2.77 (4H, m), 2.97 (3H, s), 2.42 (2H, m), 2.05-1.72 (5H, m).

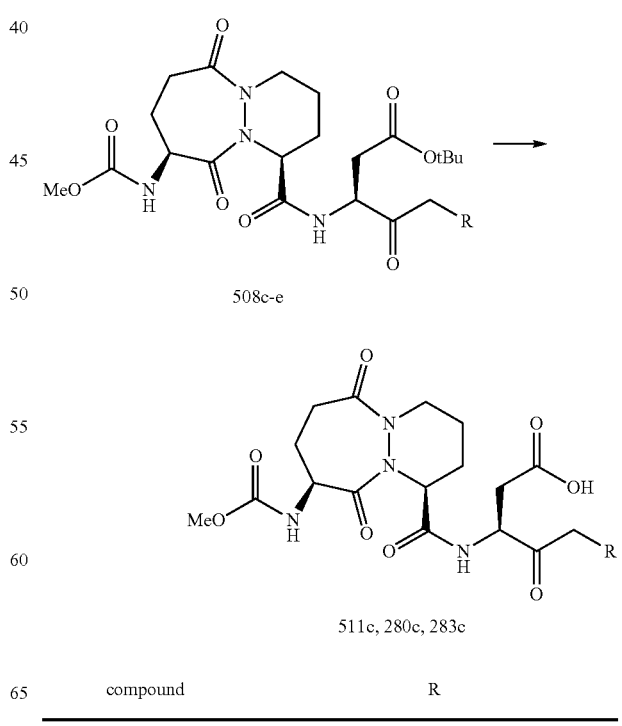

| | |
|---|---|
| 508c 511c | 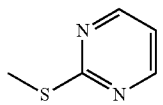 |
| 508d 280c | 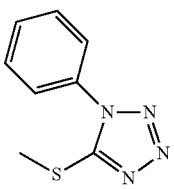 |
| 508e 283c | 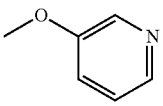 |

[3S(1S,9S)]t-Butyl 3-[6,10-dioxo-9-(methoxycarbonyl)amino-1,2,3,4,7,8,9,10-octahydro-6H-pyridazino[1,2-a][1,2]diazepine-1-carboxamido)-5-(2-mercaptopyrimidine)-4-oxo-pentanoate (508c), was prepared by a similar method as compound 509b to afford 544 mg (97%) of a pale yellow foam: $[\alpha]_D^{20}$ −86° (c 0.19, CH$_2$Cl$_2$); IR (KBr) 3426, 2947, 1725, 1669, 1551, 1418, 1383, 1253, 1155, 1064; $^1$H NMR (CDCl$_3$) δ 8.49 (2H, d, J=4.8), 7.13 (1H, d, J=7.9), 7.03-6.98 (1H, m), 5.47 (1H, d, J=7.9), 5.23-5.19 (1H, m), 5.09-5.01 (1H, m), 4.84-4.51 (2H, m), 4.04 (2H, AB), 3.69 (3H, s), 3.38-3.19 (1H, m), 3.06-2.64 (4H, m), 2.40-1.76 (6H, m), 1.43 (9H, s). Anal. Calcd for C$_{25}$H$_{34}$N$_6$O$_8$S: C, 51.89; H, 5.92; N, 14.52. Found: C, 51.49; H, 6.04; N, 13.87. MS (ES$^+$) 579.

[3S(1S,9S)]3-[6,10-Dioxo-9-(methoxycarbonyl)-amino-1,2,3,4,7,8,9,10-octahydro-6H-pyridazino[1,2-a][1,2]diazepine-1-carboxamido]-5-(2-mercaptopyrimidine)-4-oxo-pentanoic acid (511c), was prepared by a similar method as compound 280 to afford 370 mg (79%) of a white powder: mp. 105° C. (dec); $[\alpha]_D^{22}$ −94° (c 0.20, CH$_2$Cl$_2$); IR (KBr) 3316, 3057, 2957, 1724, 1664, 1252, 1416, 1384, 1254, 1189, 1063; $^1$H NMR (D$_6$-DMSO) δ 8.85 (1H, d, J=7.8), 8.62 (2H, d, J=4.7), 7.53 (1H, d, J=8.0), 7.28-7.23 (1H, m), 5.21-5.17 (1H, m), 4.87-4.79 (1H, m), 4.47-4.35 (2H, m), 4.23 (1H, AB), 3.58 (3H, s), 3.30-3.21 (1H, m), 2.95-2.50 (4H, m), 2.35-1.60 (6H, m). Anal. Calcd for C$_{21}$H$_{26}$N$_6$O$_8$S.H$_2$O: C, 46.66; H, 5.22; N, 15.55. Found: C, 46.66; H, 5.13; N, 15.07. MS (ES$^+$) 523, (ES$^+$) 521.

[3S(1S,9S)]t-Butyl 3-[(6,10-dioxo-9-(methoxycarbonylamino)-1,2,3,4,7,8,9,10-octahydro-6H-pyridazino[1,2-a][1,2]diazepine-1-carboxamido]-4-oxo-5-[5-(1-phenyltetrazolyl)-thio]pentanoate (508d), was synthesized by a similar method as compound 509b to afford a colourless solid (269 mg, 87%): mp. 80-110° C.; $[\alpha]_D^{23}$ −108° (c 0.60 CH$_2$Cl$_2$); IR (KBr) 3315, 2977, 1727, 1688, 1527, 1501, 1458, 1418, 1368, 1279, 1250, 1155, 1064; $^1$H NMR (CDCl$_3$) δ 7.70 (1H, d), 7.63-7.53 (5H, m), 5.84 (1H, d), 5.34-5.27 (1H, m), 5.05-4.92 (1H, m), 4.78-4.54 (3H, m), 4.38 (1H, d), 3.66 (3H, s), 3.37-3.19 (1H, m), 3.07-2.94 (1H, m), 2.91-2.82 (2H, m), 2.71-2.56 (1H, m), 2.40-2.30 (1H, m), 2.19-2.13 (1H, m), 2.08-1.68 (4H, m), 1.42 (9H, s). MS (ES$^+$) 667 (31%), 645 (M$^+$+1, 100), 589 (62).

[3S(1S,9S)]3-[6,10-Dioxo-9-(methoxycarbonylamino)-1,2,3,4,7,8,9,10-octahydro-6H-pyridazino[1,2-a][1,2]diazepine-1-carboxamido]-4-oxo-5-[5-(1-phenyltetrazolyl)-thio]pentanoic acid (280c), was synthesized by a similar method as compound 280 to afford a pale cream solid (203 mg, 88%): mp. 105-130° C.; $[\alpha]_D^{22}$ −235° (c 0.11 MeOH); IR (KBr) 3342, 2951, 1727, 1667, 1529, 1501, 1459, 1416, 1276, 1252, 1225, 1192, 1062; $^1$H NMR (D$_6$-DMSO) δ 8.89 (1H, d), 7.69 (5H, s), 7.50 (1H, d), 5.18-5.11 (1H, m), 4.79-4.69 (1H, m), 4.57 (2H, s), 4.42-4.32 (1H, m), 3.54 (3H, s), 2.92-2.63 (3H, m), 2.21-1.82 (5H, m), 1.65-1.57 (1H, m). MS (ES$^+$) 587 (M−1, 100%).

[3S(1S,9S)]t-Butyl 3-[6,10-dioxo-9-(methoxycarbonylamino)-1,2,3,4,7,8,9,10-octahydro-6H-pyridazino[1,2-a][1,2]diazepine-1-carboxamido]-4-oxo-5-(3-pyridinyloxy) pentanoate (508e), was synthesized by a similar method as compound 509b to afford a pale orange solid (199 mg, 25%): mp. 80-120° C.; $[\alpha]_D^{23}$ −89° (c 0.51 CH$_2$Cl$_2$); IR (KBr) 3333, 2978, 1726, 1669, 1578, 1536, 1478, 1426, 1368, 1277, 1253, 1232, 1155, 1064; $^1$H NMR (CDCl$_3$) δ 8.41-8.18 (2H, m), 7.81 (1H, d), 7.26-7.20 (2H, s), 5.91 (1H, d), 5.24-5.16 (1H, m), 5.07-4.86 (3H, m), 4.81-4.51 (2H, m), 3.67 (3H, s), 3.34-3.16 (1H, m), 3.10-2.81 (3H, m), 2.72-2.54 (1H, m), 2.41-2.31 (1H, m), 2.07-1.62 (5H, m), 1.47 (9H s). MS (ES$^+$) 562 (M$^+$+1, 100%), 506 (38).

[3S(1S,9S)]3-[6,10-Dioxo-9-(methoxycarbonylamino)-1,2,3,4,7,8,9,10-octahydro-6H-pyridazino[1,2-a][1,2]diazepine-1-carboxamido]-4-oxo-5-(3-pyridinyloxy)pentanoic acid (283c), was synthesized by a similar method as compound 280 to afford an off-white powder (167 mg, 98%): mp. 90-105° C.; $[\alpha]_D^{22}$ −106° (c 0.11 MeOH); IR (KBr) 3325, 3070, 2956, 1669, 1544, 1423, 1256, 1199, 1133, 1062; $^1$H NMR (D$_6$-DMSO) δ 8.95 (1H, d), 8.45-8.20 (2H, m), 7.53-7.45 (3H, m), 5.19-5.08 (3H, m), 4.70-4.62 (1H, m), 4.41-4.30 (2H, m), 3.53 (3H, s), 2.92-2.68 (3H, m), 2.22-2.06 (2H, m), 1.95-1.82 (2H, m), 1.63-1.53 (1H, m). MS (ES$^+$) 506 (M$^+$+1, 100%).

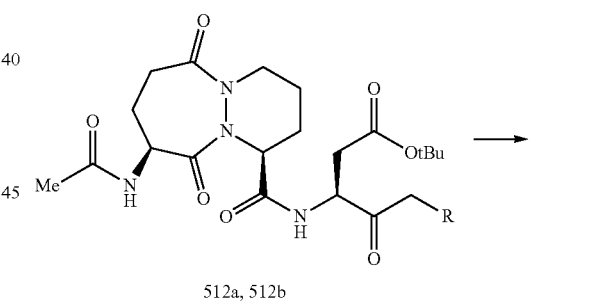

512a, 512b

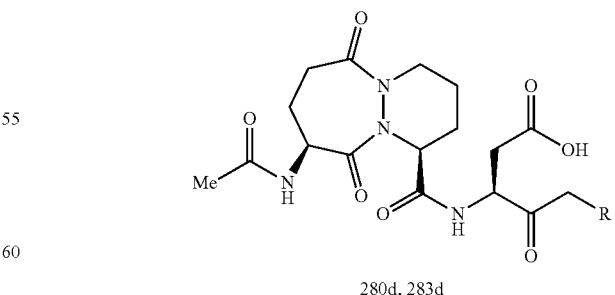

280d, 283d compound     R

| | |
|---|---|
| 512a<br>280d | 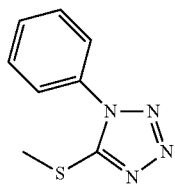 |
| 512b<br>283d | 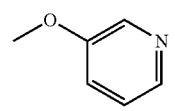 |

[3S(1S,9S)]t-Butyl 3-(9-acetamido-6,10-dioxo-1,2,3,4,7,8,9,10-octahydro-6H-pyridazino[1,2-a][1,2]diazepine-1-carboxamido)-4-oxo-5-(1-phenyl-1H-tetrazole-5-thio)pentanoate (512a), was prepared by a similar method as compound 509b, to afford (83%) as a colourless foam: $[\alpha]_D^{23}$ −129.6° (c 0.1, $CH_2Cl_2$); IR (KBr) 3323, 1726, 1664, 1531, 1501, 1444, 1415, 1394, 1369, 1279, 1254, 1156; $^1$H NMR ($CDCl_3$) δ 7.59 (5H, s), 7.37 (1H, d, J=7.9), 6.38 (1H, d, J=7.4), 5.27 (1H, m), 4.98 (2H, m), 4.58 (2H, d+m), 4.28 (1H, d, J=17.2), 3.28 (1H, m), 3.10-2.65 (4H, m), 2.31 (2H, m), 2.03 (3H, s), 2.10-1.72 (4H, m), 1.48 (9H, s).

[3S(1S,9S)]3-(9-Acetamido-6,10-dioxo-1,2,3,4,7,8,9,10-octahydro-6H-pyridazino[1,2-a][1,2]diazepine-1-carboxamido)-4-oxo-5-(1-phenyl-1H-tetrazole-5-thio)pentanoic acid (280d), was prepared by a similar method as compound 280, to afford (77%) as a colourless foam: $[\alpha]_D^{22}$ −93.3° (c 0.1, $CH_2Cl_2$); IR (KBr) 3316, 1728, 1659, 1531, 1501, 1415, 1341, 1278, 1253, 1222, 1185; $^1$H NMR ($CDCl_3$) δ 8.05 (1H, d, J=7.9), 7.57 (5H, br s), 5.30 (1H, m), 5.01 (2H, m), 4.70-4.10 (4H, m), 3.40-2.85 (4H, m), 2.62 (1H, m), 2.33 (1H, m), 2.27-1.65 (5H, m), 2.01 (3H, s).

[3S(1S,9S)]t-Butyl 3-(9-acetamido-6,10-dioxo-1,2,3,4,7,8,9,10-octahydro-6H-pyridazino[1,2-a](1,2]diazepine-1-carboxamido)-4-oxo-5-(3-pyridyloxy)pentanoate (512b), was prepared by a similar method as compound 509b, to afford (9%) as a colourless foam: IR (KBr) 3333, 1727, 1661, 1542, 1427, 1369, 1279, 1257, 1232, 1156; $^1$H NMR ($CDCl_3$) δ 8.30 (2H, m), 7.20 (3H, m), 6.45 (1H, d, J=7.4), 5.17 (1H, m), 4.91 (3H, m), 4.55 (1H, m), 3.27 (1H, m), 3.14-2.70 (4H, m), 2.41 (1H, m), 2.04 (3H, s), 2.10-1.65 (6H, m), 1.44 (9H, s).

[3S(1S,9S)]3-(9-Acetamido-6,10-dioxo-1,2,3,4,7,8,9,10-octahydro-6H-pyridazino[1,2-a][1,2]diazepine-1-carboxamido)-4-oxo-5-(3-pyridyloxy)pentanoic acid (283d), was prepared by a similar method as compound 280. (100%) as a colourless foam: $[\alpha]_D^{22}$ −106.0° (c 0.2, 10% $CH_3OH/CH_2Cl_2$); IR (KBr) 3312, 1735, 1664, 1549, 1426, 1279, 1258, 1200, 1135; $^1$H NMR ($CDCl_3$) δ 8.27 (2H, m), 7.46 (2H, m), 5.09 (1H, m), 4.79 (3H, m), 4.47 (1H, m), 3.40 (1H, m), 3.30-2.70 (3H, m), 2.54 (1H, m), 2.30 (1H, m), 1.98 (3H, s), 2.05-1.65 (4H, m).

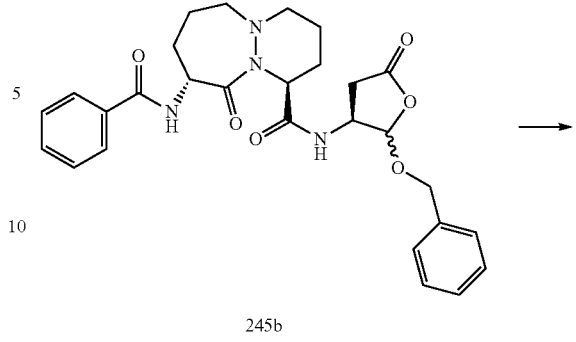

245b

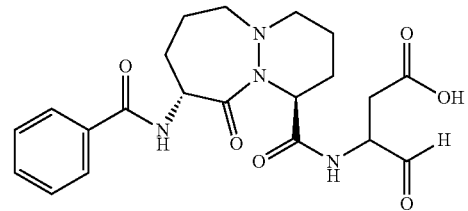

246b

[1S,9R(2RS,3S)]9-Benzoylamino-N-(2-benzyloxy-5-oxotetrahydrofuran-3-yl)-1,2,3,4,7,8,9,10-octahydro-10-oxo-6H-pyridazino[1,2-a][1,2]diazepine-1-carboxamide (245b), was prepared from (1S,9R) 9-Benzoylamino-1,2,3,4,7,8,9,10-octahydro-10-oxo-6H-pyridazino[1,2-a][1,2]diazepine-1-carboxylic acid by the method described for 245 to afford 416 mg (85%) of a colourless foam (~1:1 mixture of diastereoisomers): IR (KBr) 3392, 3302, 2942, 1792, 1642, 1529, 1520, 1454, 1119; $^1$H NMR ($CDCl_3$) δ 7.79 (2H, m), 7.51-7.09 (10H, m), 5.52 (0.5H, d, J=5.3), 5.51 (0.5H, s), 5.36 (1H, m), 4.84 (1H, m), 4.74-4.59 (1.5H, m), 4.51 (1H, m), 4.38 (0.5H, m), 3.22-2.83 (5H, m), 2.51 (1H, m), 2.25 (2H, m), 2.01-1.46 (6H, m). Anal. Calcd for $C_{28}H_{32}N_4O_6 \cdot 0.75H_2O$: C, 62.97; H, 6.32; N, 10.49. Found: C, 63.10; H, 6.16; N, 10.21. MS ($ES^+$) 521 (M+1, 100%).

[3S(1S,9R)]3-(9-Benzoylamino-1,2,3,4,7,8,9,10-octahydro-10-oxo-6H-pyridazino[1,2-a][1,2]diazepine-1-carboxamido)-4-oxobutanoic acid (246b), was prepared from 245b by the method described for 246 to afford 104 mg (33%) of a white powder: mp. 115-119° C.; $[\alpha]_D^{24}$ −19.8° (c 0.2 MeOH); IR (KBr) 3293, 2944, 1786, 1639, 1578, 1537, 1489, 1450, 1329, 1162, 1124; $^1$H NMR ($CD_3OD$) δ 7.85 (2H, d, J=7.0), 7.49 (3H, m), 5.49 (1H, m), 4.55 (1H, m), 4.30 (2H, m), 3.40 (1H, m), 3.19-2.89 (3H, m), 2.63 (2H, m), 2.16-1.81 (5H, m), 1.60 (3H, m). Anal. Calcd for $C_{21}H_{26}N_4O_6 \cdot H_2O$: C, 56.24; H, 6.29; N, 12.49. Found: C, 56.54; H, 6.05; N, 12.29. MS ($ES^+$) 429 (M−1, 100%).

Compounds 513a-j were prepared as described below.
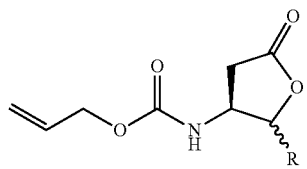
513a-f
| compound | R |
|---|---|
| 513a | 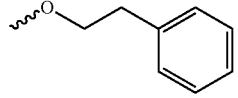 |
| 513a-1 | 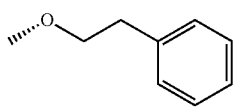 |
| 513a-2 | 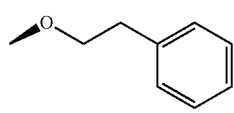 |
| 513b | 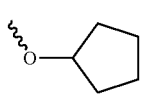 |
| 513b-1 | 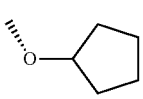 |
| 513b-2 | 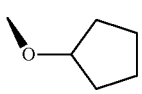 |
| 513c | 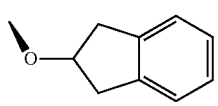 |
| 513d | 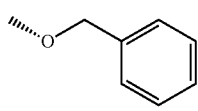 |
| 513e | 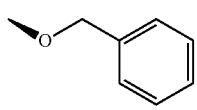 |

| | |
|---|---|
| 513f | 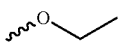 |
| 513f-1 | 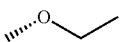 |
| 513f-2 | 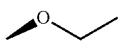 |

513g

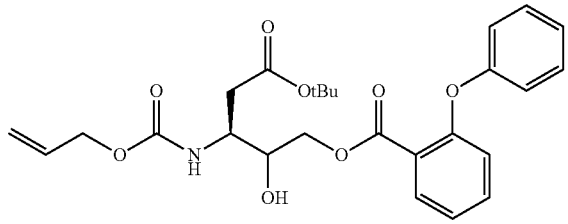

513h

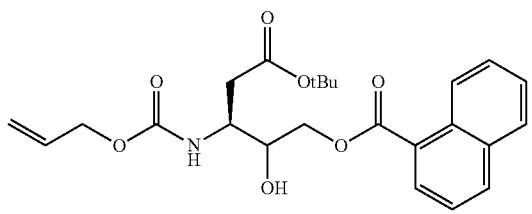

513i

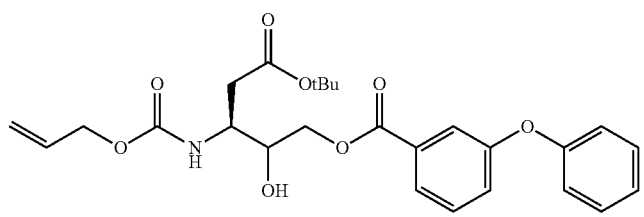

513j

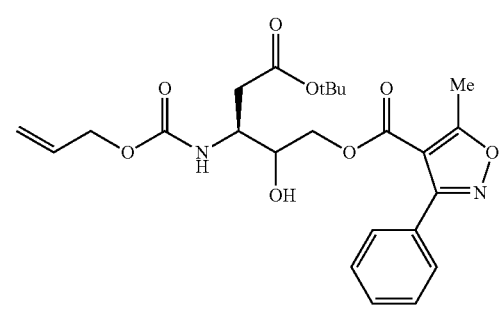

(2RS,3S)3-(Allyloxycarbonyl)amino-2-(2-phenethyloxy)-5-oxotetrahydrofuran (513a), was prepared by a similar method as compound 513d/e to afford a mixture of diastereoisomers (670 mg, 50%) as an oil: IR (KBr) 3331, 2946, 1790, 1723, 1713, 1531, 1329, 1257, 1164, 1120, 1060, 977, 937, 701; $^1$H NMR (CDCl$_3$) δ 7.36-7.18 (5H, m), 5.99-5.83 (1H, m), 5.41-5.34 (2H, m), 5.28-5.18 (2H, m), 4.59-4.56 (2H, m), 4.32-3.96 (2H, m), 3.85-3.73 (1H, m), 3.02-2.76 (3H, m), 2.49-2.34 (1H, m).

(2RS,3S)3-(Allyloxycarbonyl)amino-2-cyclopentyloxy-5-oxotetrahydrofuran (513b), was prepared as 513d/e to afford 8 g (51%) of a mixture of diastereoisomers as a clear oil: $[α]_D^{20}$ −13° (c 0.25, CH$_2$Cl$_2$); IR (KBr) 3325, 2959, 2875, 1790, 1723, 1535, 1420, 1328, 1257, 1120, 1049, 973, 937; $^1$H NMR (CDCl$_3$) δ 6.02-5.80 (1H, m), 5.53-5.46 (2H, m), 5.37-5.21 (2H, m), 4.58 (2H, d, J=5.5), 4.50-4.46 (0.5H, m), 4.34-4.25 (1H, m), 4.19-4.12 (0.5H, m), 3.06-2.77 (1H, m), 2.53-2.35 (1H, m), 1.85-1.50 (8H, m). Anal. Calcd for C$_{13}$H$_{19}$NO$_5$: C, 57.98; H, 7.11; N, 5.20. Found: C, 56.62; H, 7.22; N, 4.95. MS (ES$^+$) 270.

(2R,3S)-3-Allyloxycarbonylamino-2-(indan-2-yloxy)-5-oxotetrahydrofuran (513c), was synthesized by a similar method as compound 513d/e to afford a single isomer (20%) as a pale yellow oil: $[α]_D^{24}$ −63.1° (c 0.2, CH$_2$Cl$_2$); IR (film) 3338, 2948, 1791, 1723, 1529, 1421, 1330, 1253, 1122, 984, 929, 746; $^1$H NMR (CDCl$_3$) δ 7.20 (4H, m), 5.87 (1H, m), 5.61 (1H, d, J=5.4), 5.33-5.10 (2H, m), 4.70 (1H, m), 4.56 (3H, m), 3.33-3.19 (2H, m), 3.10-2.94 (2H, m), 2.81 (1H, dd, J=8.3, 17.3), 2.43 (1H, dd, J=10.5, 17.3).

(2R,3S)3-Allyloxycarbonylamino-2-benzyloxy-5-oxotetrahydro-furan (513d) and (2S,3S)3-Allyloxycarbonylamino-2-benzyloxy-5-oxo-tetrahydrofuran (513d/e), were prepared [via method described by Chapman *Biorg. & Med. Chem. Lett.*, 2, pp. 615-618 (1992)]. Following work-up by extraction with ethylacetate and washing with NaHCO$_3$, the product was dried (MgSO$_4$), filtered and evaporated to yield an oil which contained product and benzyl alcohol. Hexane (200 ml) (200 ml hexane for every 56 g of AllocAsp(CO$_2$tBu)CH$_2$OH used) was added and the mixture stirred and cooled overnight. This afforded an oily solid. The liquors were decanted and retained for chromatography. The oily residue was dissolved in ethyl acetate and evaporated to afford an oil which was crystallised from 10% ethyl acetate in hexane (~500 ml). The solid was filtered to afford 513d (12.2 g, 19%): mp. 108-110° C.; $[\alpha]_D^{24}$ +75.72° (c 0.25, CH$_2$Cl$_2$); IR (KBr) 3361, 1778, 1720, 1517, 1262, 1236, 1222, 1135, 1121, 944, 930, 760; $^1$H NMR (CDCl$_3$) δ 7.38 (5H, m), 5.90 (1H, m), 5.50 (1H, s), 5.37 (0.5H, m), 5.26 (2.5H, m), 4.87 (1H, ABq), 4.63 (3H, m), 4.31 (1H, m), 3.07 (1H, dd), 2.46 (1H, dd). Anal. Calcd for C$_{15}$H$_{17}$NO$_5$: C, 61.85; H, 5.88; N, 4.81. Found: C, 61.85; H, 5.89; N, 4.80.

The liquors were combined and evaporated to yield an oil (~200 g) containing benzyl alcohol. Hexane/ethyl acetate (9:1, 100 ml) was added and the product purified by chromatography eluting with 10% ethyl acetate in hexane to remove the excess benzyl alcohol, and then dichloromethane/hexane (1:1 containing 10% ethyl acetate). This afforded 513e containing some 513d (20.5 g, 32%): mp. 45-48° C.; $[\alpha]_D^{24}$ −71.26° (c 0.25, CH$_2$Cl$_2$); IR (KBr) 3332, 1804, 1691, 1536, 1279, 1252, 1125, 976. $^1$H NMR (CDCl$_3$) δ 7.38 (5H, m), 5.91 (1H, m), 5.54 (1H, d, J=5.2), 5.38 (3H, m); 4.90 (1H, ABq); 4.60 (4H, m), 2.86 (1H, dd); 2.52 (1H, dd). Anal. Calcd for C$_{15}$H$_{17}$NO$_5$.0.1H$_2$O C, 61.47; H, 5.91; N, 4.78. Found: C, 61.42; H, 5.88; N, 4.81.

(2RS,3R)3-(Allyloxycarbonylamino)-2-ethoxy-5-oxotetrahydrofuran (513f), was synthesized by a similar method as 513d/e to afford a colourless oil (152 mg, 79%): IR (film) 3334, 2983, 2941, 1783, 1727, 1713, 1547, 1529, 1422, 1378, 1331, 1313, 1164, 1122, 1060, 938; $^1$H NMR (CDCl$_3$) δ 6.09-5.82 (2H, m), 5.50-5.18 (3H, m), 4.64-4.54 (2H, m), 4.27-4.16 (1H, m), 3.95-3.78 (1H, m), 3.73-3.56 (1H, m), 3.05-2.77 (1H, m), 2.56-2.37 (1H, m), 1.35-1.17 (4H, m). Anal. Calcd for C$_{10}$H$_{15}$NO$_5$: C, 52.40; H, 6.60; N, 6.11. Found: C, 52.16; H, 6.62; N, 5.99. MS (ES$^+$) 229 (M$^+$+1, 100%).

(3S,4RS)t-Butyl 3-(allyloxycarbonylamino)-4-hydroxy-5-(2-phenoxybenzoyloxy)pentanoate (513g). 4-Dimethylamino-pyridine (76.0 mg, 622 mmol) was added to a solution of 2-phenoxybenzoyl chloride (579 mg, 2.49 mmol) and 517 (600 mg, 2.07=1) in pyridine (10 ml). The mixture was stirred at room temperature for 18 h before adding brine (25 ml) and extracting with ethyl acetate (30 ml, 20 ml). The combined organic extracts were washed with 1M hydrochloric acid (3×25 ml), saturated aqueous sodium hydrogen carbonate (2×25 ml) and brine (25 ml), dried (MgSO$_4$) and concentrated. The pale orange oil was purified by flash column chromatography (1-10% acetone in dichloromethane) to afford 447 mg (44%) of colourless oil: IR (film) 3375, 2980, 1721, 1712, 1602, 1579, 1514, 1484, 1451, 1368, 1294, 1250, 1234, 1161, 1137, 1081, 754; $^1$H NMR (CDCl$_3$) δ 7.98-7.93 (1H, m), 7.50-7.41 (1H, m), 7.35-7.25 (2H, m), 7.22-7.03 (3H, m), 6.95 (3H, d), 5.95-5.76 (1H, m), 5.57 (1H, d), 5.30-5.13 (2H, m), 4.51 (2H, d), 4.25 (2H, d), 4.18-4.04 (1H, m), 3.88 (1H, m), 3.50 (1H, m), 2.51 (2H, m), 1.41 (9H, s). MS (ES$^+$) 508 (57%), 503 (76), 486 (M$^+$+1, 45), 468 (27), 412 (100). Accurate mass calculated for C$_{26}$H$_{32}$NO$_8$ (MH$^+$): 486.2128. Found: 486.2158.

(3S,4R)t-Butyl (N-allyloxycarbonyl)-3-amino-4-hydroxy-5-(1-naphthoyloxy)pentanoate (513h), was prepared from (3S,4R)t-Butyl (N-allyloxycarbonyl)-3-amino-4,5-dihydroxypentanoate by the method described for 513g to afford 562 mg (85%) of a colourless oil: IR(film) 3418, 2980, 1722, 1711, 1512, 1368, 1278, 1245, 1198, 1157, 1139; $^1$H NMR (CDCl$_3$) δ 8.90 (1H, d, J=8.6), 8.21 (1H, dd, J=1.2, 7.3), 8.04 (1H, d, J=8.2), 7.89 (1H, dd, J=1.5, 7.9), 7.67-7.46 (3H, m), 5.88 (1H, m), 5.49 (1H, d, J=9.0), 5.35-5.18 (2H, m), 4.57-4.46 (4H, m), 4.19 (2H, m), 2.67 (2H, m), 1.40 (9H, s). Anal. Calcd for C$_{24}$H$_{29}$NO$_7$: C, 65.00; H, 6.59; N, 3.16. Found: C, 64.74; H, 6.56; N, 3.09. M.S. (ES$^+$) 466 (M+Na, 100%), 444 (M+1, 39), 388 (44).

(3S,4RS)t-Butyl 3-(allyloxycarbonylamino)-4-hydroxy-5-(3-henoxybenzoyloxy)pentanoate (513i), was synthesized by a similar method as compound 513g to afford a colourless oil (569 mg, 85%): IR (film) 3400, 1723, 1712, 1584, 1528, 1489, 1443, 1367, 1276, 1232, 1190, 1161, 1098, 1074, 995, 755; $^1$H NMR (CDCl$_3$) δ 8.65-8.59 (1H, d), 7.84-7.66 (2H, m), 7.45-711 (5H, m), 7.05-6.97 (2H, m), 6.00-5.78 (1H, m), 5.54-5.14 (2H, m), 4.62-4.52 (2H, m), 4.42-4.32 (2H, m), 4.08-4.22 (2H, m), 2.78-2.47 (2H, m), 1.44 (9H, s). MS (ES$^+$) 508 (100%), 486 (M$^+$+1, 33. Accurate mass calculated for C$_{26}$H$_{32}$NO$_8$ (MH$^+$): 486.2128. Found: 486.2121.

(3S,4RS)t-Butyl 3-(allyloxycarbonylamino)-4-hydroxy-5-(5-methyl-3-phenylisoxazoloyloxy)pentanoate (513j), was synthesized by a similar method as compound 513g to afford a pale orange oil (905 mg, 91%): IR (film) 3418, 3383, 2980, 1722, 1711, 1601, 1517, 1450, 1424, 1368, 1308, 1252, 1154, 1100, 994, 767, 698; $^1$H NMR (CDCl$_3$) δ 7.62-7.55 (2H, m), 7.51-7.42 (3H, m), 5.98-5.76 (1H, m), 5.33-5.18 (2H, m), 4.53 (2H, d), 4.18 (2H, d), 3.91 (1H, m), 3.80 (1H, m), 2.76 (3H, s), 2.50 (2H, m), 1.43 (9H, s). Anal. Calcd for C$_{24}$H$_{30}$N$_2$O$_8$.0.5H$_2$O: C, 59.62; H, 6.46; N, 5.79. Found: C, 59.46; H, 6.24; N, 5.72. MS (ES$^+$) 497 (100%), 475 (M$^+$+1, 15), 419 (48).

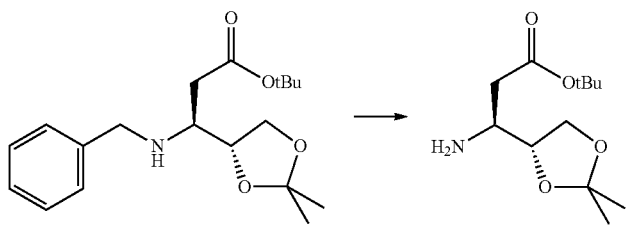

514        515

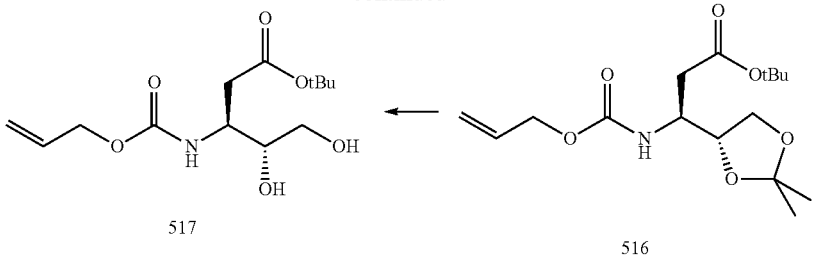

(3S,4R)t-Butyl 3-benzylamino-4,5-(dimethylmethylenedioxy)-pentanoate (514), was prepared by the method described in H. Matsunaga, et al. *Tetrahedron Letters* 24, pp. 3009-3012 (1983) as a pure diastereomer (60%) as an oil: $[\alpha]_D^{23}$ −36.9° (c 0.5, dichloromethane); IR (film) 2982, 2934, 1726, 1455, 1369, 1257, 1214, 1157, 1068; $^1$H NMR (CDCl$_3$) δ 7.31 (5H, m), 4.10 (1H, q, J=6.0), 4.05-3.75 (4H, m), 3.10 (1H, q, J=6.0), 2.40 (2H, m), 1.42 (9H, s), 1.40 (3H, s), 1.34 (3H, s).

(3S,4R)t-Butyl 3-(allyloxycarbonylamino)-4,5-(dimethylmethylenedioxy)pentanoate (516). 514 (3.02 g, 9.00 mmol) and 10% palladium on carbon (300 mg) in ethanol (30 ml) were stirred under hydrogen for 2 h. The suspension was filtered through celite and a 0.45 mm membrane and the filtrate concentrated to give a colourless oil 515 (2.106 g, 95%) which was used without purification. The oil (1.93 g, 7.88 mmol) was dissolved in water (10 ml) and 1,4-dioxan and sodium hydrogen carbonate added (695 mg, 8.27 mmol). The mixture was cooled to 0° C. and allyl chloroformate (1.04 g, 919 ml, 8.66 mmol) added dropwise. After 3 h the mixture was extracted with ether (2×50 ml). The combined ether extracts were washed with water (2×25 ml) and brine (25 ml), dried (MgSO$_4$) and concentrated to give a colourless oil. Flash column chromatography (10-35% ethylacetate in hexane) afforded a colourless solid (2.69 g, 95%): mp. 64-5° C.; $[\alpha]_D^{23}$ −21° (c 1.00, CH$_2$Cl$_2$); IR (KBr) 3329, 1735, 1702; $^1$H NMR (CDCl$_3$) δ 6.00-5.82 (1H, m), 5.36-5.14 (2H, m), 542 (1H, s), 4.56 (1H, d), 4.40-4.08 (2H, m), 4.03 (1H, m) 3.70 (1H, m), 2.52 (2H, m), 1.44 (12H, 2×s), 1.33 (3H, s); Anal. Calcd for C$_{16}$H$_{27}$NO$_6$: C, 58.34; H, 8.26; N, 4.25. Found: C, 58.12; H, 8.16; N, 4.19; MS (+FAB) 320 (M$^+$+1, 41%), 274 (70), 216 (100).

(3S,4R)t-Butyl 3-(allyloxycarbonylamino)-4,5-dihydroxy pentanoate (517). A solution 516 (2.44 g, 7.41 mmol) in 80% aqueous acetic acid (25 ml) was stirred at room temperature for 24 h then concentrated and azeotroped with toluene (2×25 ml). The residue was treated with brine (25 ml) and extracted with ethylacetate (2×25 ml). The organic fractions were dried (MgSO$_4$) and concentrated to afford a colourless oil. Flash chromatography (20-80% ethyl acetate in dichloromethane) gave a colourless solid (1.99 g, 90%): mp. 74-5° C.; $[\alpha]_D^{25}$ −1.3° (c 1.0, CH$_2$Cl$_2$); IR (KBr) 1723, 1691; $^1$H NMR (CDCl$_3$) δ 6.02-5.78 (1H, m), 5.35-5.16 (2H, m), 4.55 (2H, d), 4.16-4.04 (2H, m), 2.76 (2H, s), 3.56 (2H, m), 2.56 (2H, m), 1.43 (9H, s); Anal. Calcd for C$_{13}$H$_{23}$NO$_6$. C, 53.97; H, 8.01; N, 4.84. Found: C, 53.79; H, 7.88; N, 4.81; MS (+FAB) 290 (M$^+$+1, 44%), 234 (100).

EXAMPLE 30

Compounds 1105-1125 were prepared as follows. Physical data for these compounds is listed in Table 24.

TABLE 24

| Compound | Structure | MF | MW | HPLC RT min (method) Purity | MS (M + Na)+ |
|---|---|---|---|---|---|
| 1105 | ![structure] | C22H27N5O7 | 473.49 | 12.769 (1) 99% | 496.9 |
| 1106 | ![structure] | C21H23N5O8 | 473.45 | 12.137 (1) 99% | 496.9 |

TABLE 24-continued

| Compound | Structure | MF | MW | HPLC RT min (method) Purity | MS (M + Na)+ |
|---|---|---|---|---|---|
| 1107 | 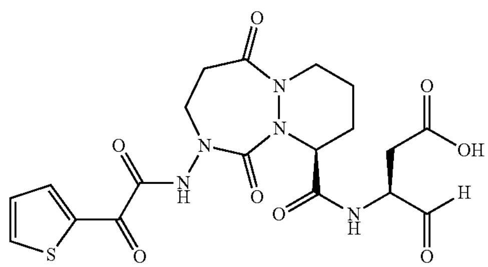 | C19H21N5O8S | 479.47 | 11.272 (1) 97% | 502.9 |
| 1108 | 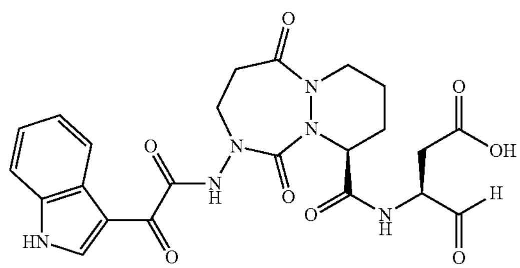 | C23H24N6O8 | 512.48 | 13.699 (1) 97% | 536.4 |
| 1109 | 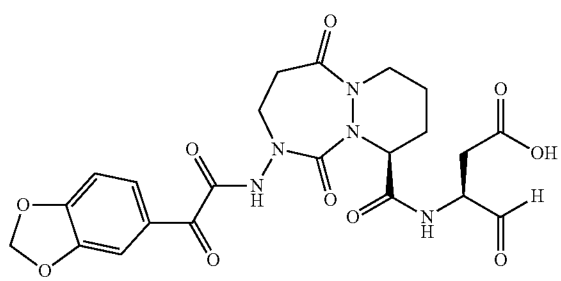 | C22H23N5O10 | 517.46 | 12.341 (1) 92% | 541.2 |
| 1110 | 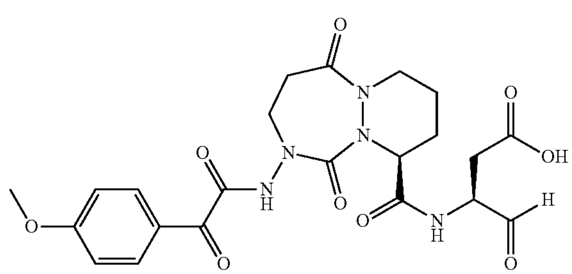 | C22H25N5O9 | 503.47 | 12.991 (1) 96% | 527.9 |
| 1111 | 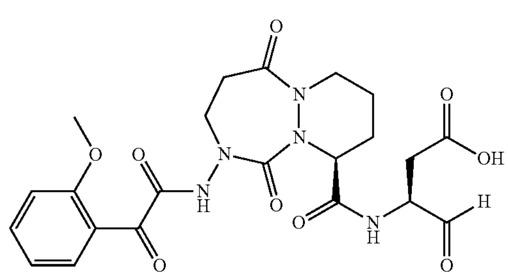 | C22H25N5O9 | 503.47 | 10.951 (1) 99% | 526.7 |

TABLE 24-continued

| Compound | Structure | MF | MW | HPLC RT min (method) Purity | MS (M + Na)+ |
|---|---|---|---|---|---|
| 1112 | 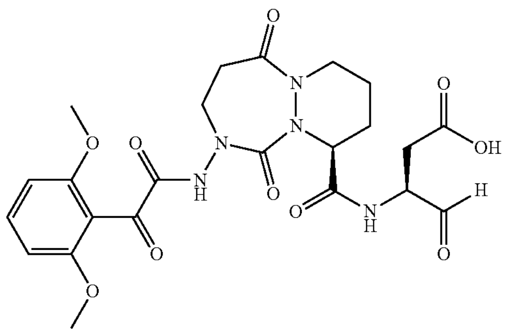 | C23H27N5O10 | 533.50 | 11.377 (1) 98% | 557.2 |
| 1113 | 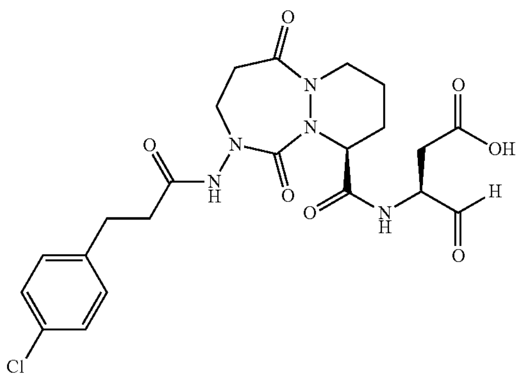 | C22H26ClN5O7 | 507.93 | 16.317 (1) 98% | 531.5 |
| 1114 | 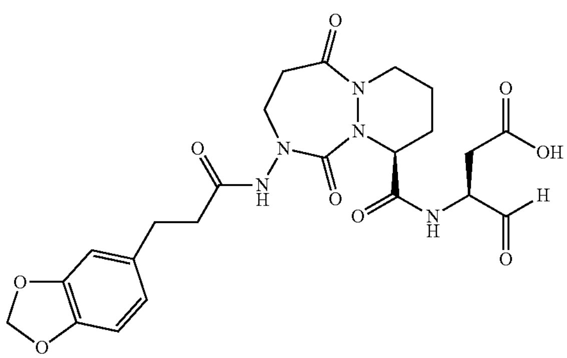 | C23H27N5O9 | 517.50 | 12.902 (1) 99% | 542.4 |
| 1115 | 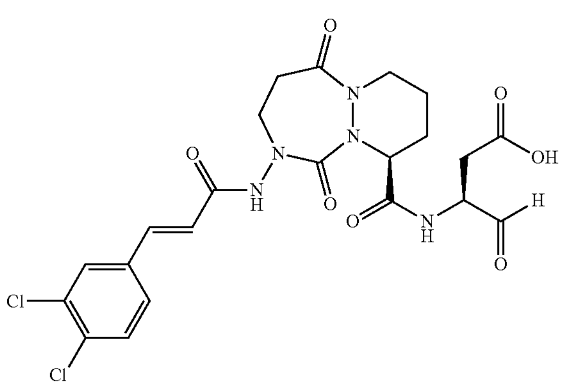 | C22H23Cl2N5O7 | 540.36 | 12.529 (2) 97% | 563.4 |

TABLE 24-continued

| Compound | Structure | MF | MW | HPLC RT min (method) Purity | MS (M + Na)+ |
|---|---|---|---|---|---|
| 1116 | 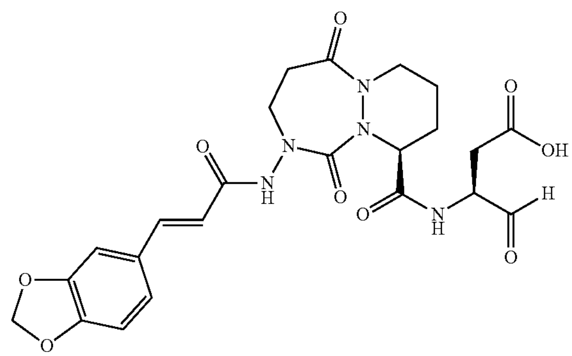 | C23H25N5O9 | 515.48 | 14.144 (1) 85% | 538.8 |
| 1117 | 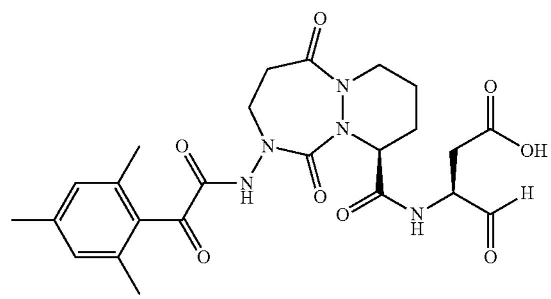 | C24H29N5O8 | 515.53 | 11.551 (2) 97% | 538.8 |
| 1118 | 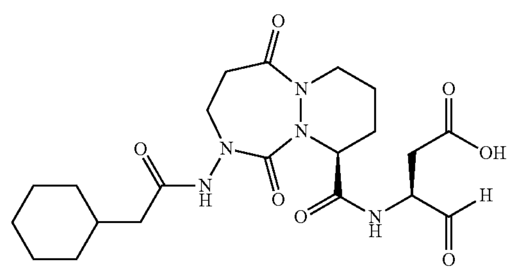 | C21H31N5O7 | 465.51 | 13.974 (1) 96% | 488.9 |
| 1119 | 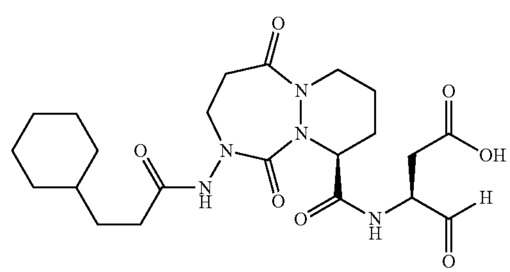 | C22H33N5O7 | 479.54 | 11.079 (2) 95% | 502.9 |
| 1120 | 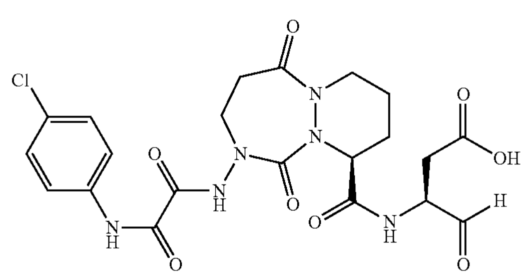 | C21H23ClN6O8 | 522.91 | 16.796 (1) 99% | 547.3 |

TABLE 24-continued

| Compound | Structure | MF | MW | HPLC RT min (method) Purity | MS (M + Na)+ |
|---|---|---|---|---|---|
| 1121 | 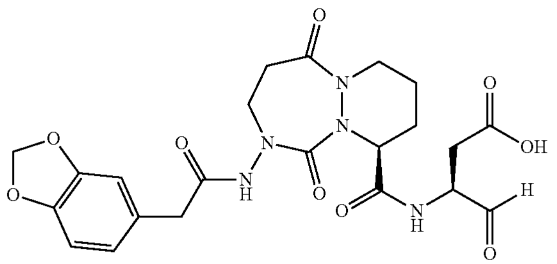 | C22H25N5O9 | 503.47 | 11.131 (1) 99% | 527.9 |
| 1122 | 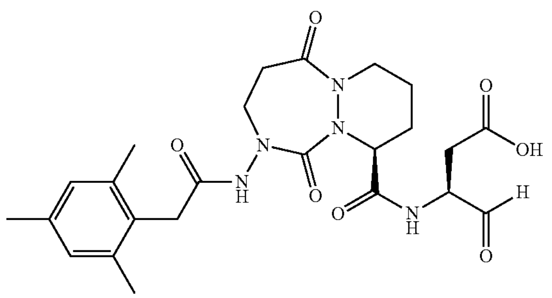 | C24H31N5O7 | 501.54 | 10.892 (2) 98% | 525.5 |
| 1123 | 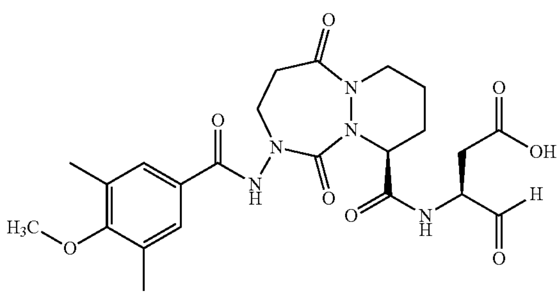 | C26H24N4O10 | 552.50 | 15.85 >0.98 | 574 |
| 1124 | 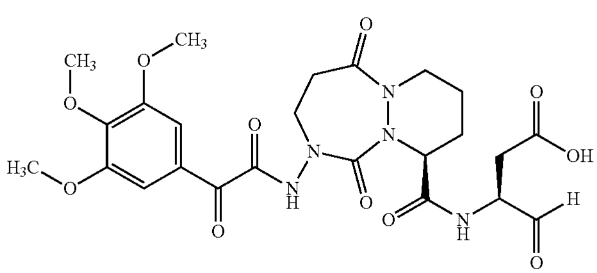 | C24H29N5O11 | 563.53 | 13.336 (1) 99% | 587 |
| 1125 | 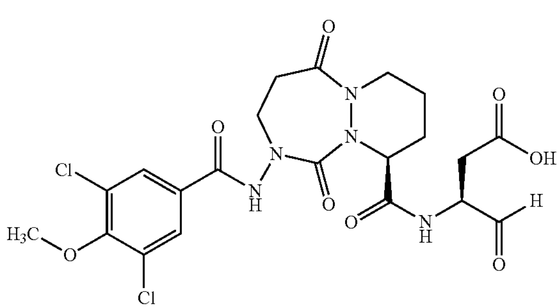 | C21H23Cl2N5O8 | 544.35 | 8.99 0.95 | 566 |

457 458
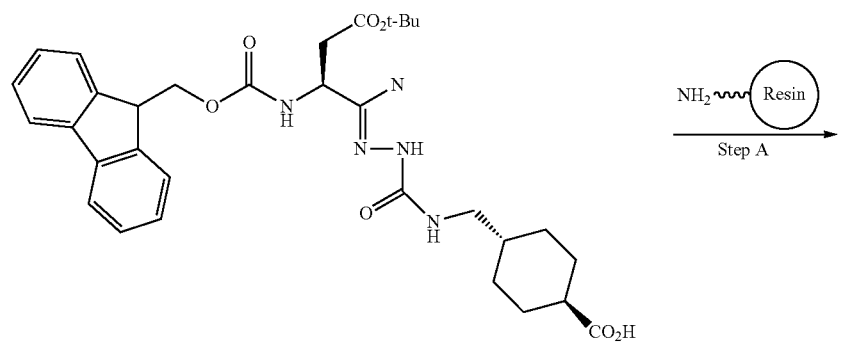
400
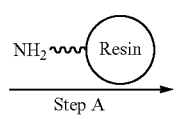
Step A
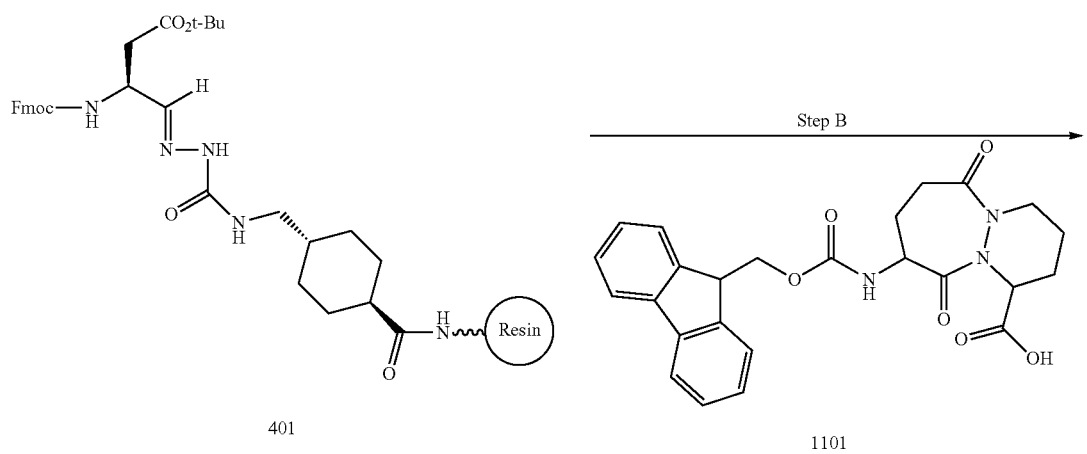
401    1101
Step B
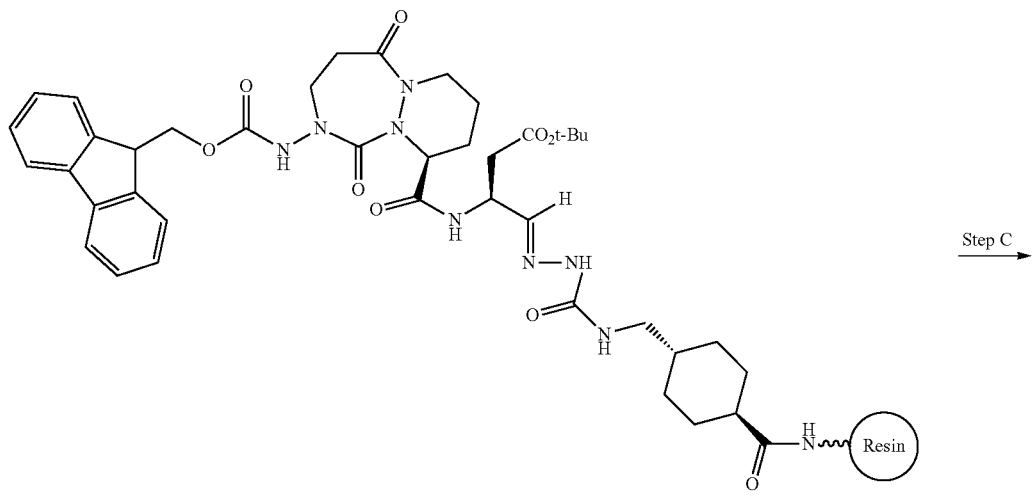
1102
Step C

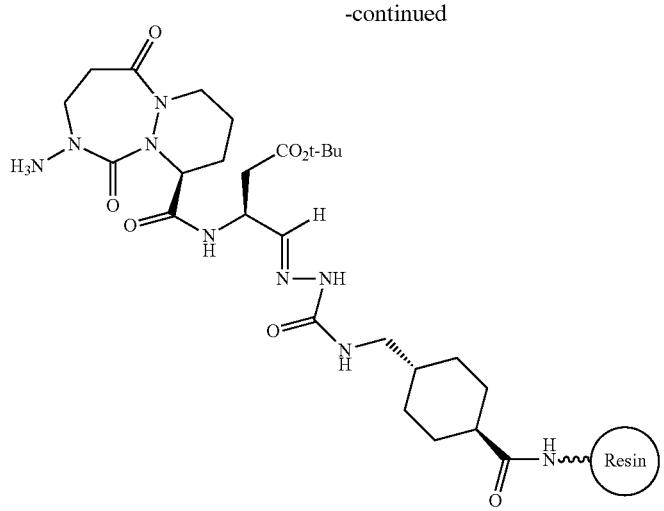
1103
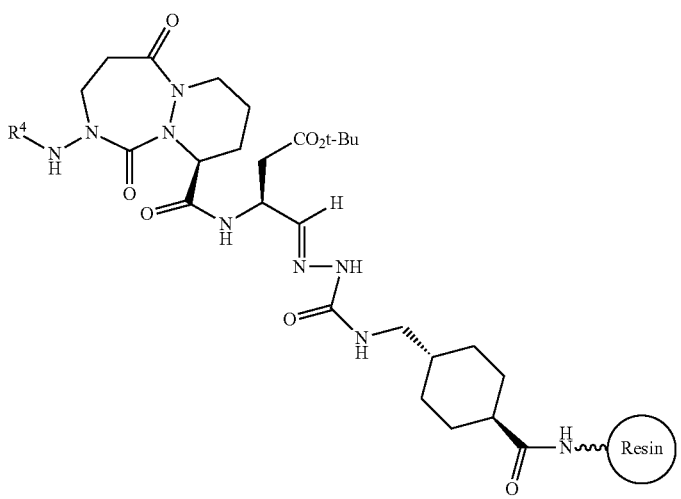
1104
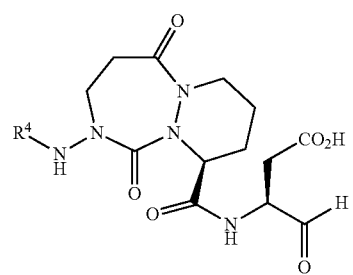
1105-1125

Step A. Synthesis of 401. TentaGel S® $NH_2$ resin (0.25 mmol/g, 5.25 g) was placed in a sintered glass shaker vessel and washed with dimethylacetamide (3×15 mL). Compound 400 (1.36 g, 2.3 mmol) was dissolved in DMA (10 mL) and O-benzotriazole-N,N,N',N'-tetramethyluronium hexafluorophosphate (HBTU; 0.88 g, 2.3 mmol), and DIEA (0.8 mL, 4.6 mmol) were added. The solution was transferred to the resin and a further 5 mL DMA added. The reaction mixture was agitated for 1.5 h at room temperature using a wrist arm shaker. The resin was filtered and washed with dimethylacetamide (4×15 mL).

Step B. Synthesis of 1102. Resin 401 was deprotected with 20% (v/v) piperidine/dimethylacetamide (15 mL) for 10 min (shaking) and then for 10 min with fresh piperidine reagent (15 ml). The resin was then washed with dimethylacetamide (6×15 ml), followed by N-methypyrrolidone (2×25 mL).

Compound 1101 (0.979 g, 2.11 mmol) was dissolved in dimethylacetamide (8 mL). HBTU (0.81 g, 2.1 mmol) and DIEA (0.75 mL, 4.3 mmol) were added and the solution added to the resin, followed by dimethylacetamide (4 mL). The reaction mixture was agitated for 2 h at room temperature using a wrist arm shaker. The resin work-up was performed as described for 401 to yield 1102.

Step C. Synthesis of 1103. This compound was prepared from resin 1102 (0.040 mmol) using an Advanced ChemTech 396 Multiple Peptide synthesizer. The automated cycles consisted of a resin wash with dimethylformamide (2×1 mL), deprotection with 25% (v/v) piperidine in dimethylformamide (1 mL) for 3 min followed by fresh reagent (1 mL) for 10, min to yield resin 1103. The resin was washed with dimethylformamide (3×1 mL) and N-methylpyrrolidone (3×1 mL).

Resin 1103 was acylated with a solution of 0.4M carboxylic acid and 0.4M HOBT in N-methypyrrolidone (0.5 mL), a solution of 0.4M HBTU in N-methylpyrrolidone (0.5 mL) and a solution of 1.6M DIEA in N-methylpyrrolidone (0.25 mL) and the reaction was shaken for 2 hr at room temperature. The acylation step was repeated. Finally, the resin was washed with N-methylpyrrolidone (1×1 mL), dimethylformamide (4×1 mL), dichloromethane (5×1 mL) and dried in vacuo. The aldehyde was cleaved from the resin and globally deprotected by treatment with 95% TFA/5% $H_2O$ (v/v, 1.5 mL) for 30 min at room temperature. After washing the resin with cleavage reagent (1 mL), the combined filtrates were added to cold 1:1 ether:hexane (10 mL) and the resulting precipitate was isolated by centrifugation and decantation. The resulting pellet was dissolved in 10% acetonitrile/90% $H_2O$/0.1% TFA (5 mL) and lyophilized to obtain crude 1105-1125 as a white powder. The compound was purified by semi-preparative RP-HPLC with a Rainin Microsorb™ C18 column (5μ, 21.4×250 mm) eluting with a linear acetonitrile gradient (8%-48%) containing 0.1% TFA (v/v) over 30 min at 12 mL/min. Fractions containing the desired product were pooled and lyophilized to provide 1105-1125 (10.8 mg, 63%).

Analytical HPLC Methods:

(1) Waters DeltaPak C18, 300 Å (5μ, 3.9×150 mm). Linear acetonitrile gradient (0%-25%) containing 0.1% TFA (v/v) over 14 min at 1 mL/min.

(2) Waters DeltaPak C18, 300 Å (5μ, 3.9×150 mm). Linear acetonitrile gradient (5%-45%) containing 0.1% TFA (v/v) over 14 min at 1 mL/min.

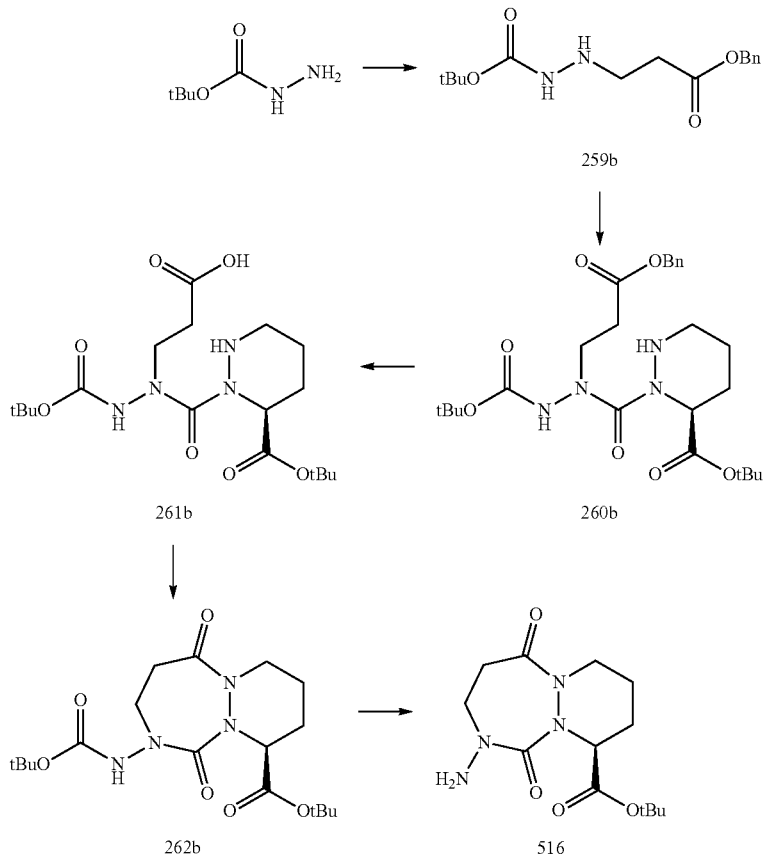

Benzyl 3-(N'-t-butyloxycarbonylhydrazino)propionate (259b), was synthesized via method used to prepare 259 from 258 to afford a waxy solid (87 g, 51%): mp 54-55° C.; IR (film) 3324, 2978, 1732, 1713, 1455, 1367, 1277, 1254, 1171; $^1$H NMR (CDCl$_3$) δ 7.35 (5H, m), 6.15 (1H, bs), 5.13 (2H, s), 3.15 (2H, t, J=6.5), 2.54 (2H, t, J=6.5), 1.45 (9H, s). Anal. Calcd for C$_{15}$H$_{22}$N$_2$O$_3$: C, 61.21; H, 7.53; N, 9.52. Found: C, 61.29; H, 7.51; N, 9.51. MS (ES$^+$) 295 (M$^+$+1).

(3S)1-Benzyl 3-t-butyl 2-(N-2-benzyloxycarbonylethyl-NI-2-butoxycarbonylhydrazino) carbonyl hexahydropyridazine dicarboxylate (260b), was synthesized via method used to prepare 260 from 259 to afford a gum (81 g) which was used in the next step without purification. Analytical data for a pure sample: IR (film) 3318, 2976, 1733, 1451, 1412, 1393, 1366, 1256, 1161; $^1$H NMR (CDCl$_3$) δ 7.34 (10H, m), 6.68 (0.5H, bs), 5.11 (4H, m), 4.63 (0.5H, bs), 4.14 (1H, m), 3.53 (2H, m), 3.08 (1H, m), 2.63 (2H, m), 2.10-1.60 (4H, m), 1.60-1.35 (19H, m+2×s).

(3S)t-Butyl 2-(N'-t-butoxycarbonyl-N-2-carboxyethylhydrazino)-carbonylhexahydropyridazine 3-carboxylate (261b), was synthesized via method used to prepare 261 from 260 to give a gum which was purified by flash chromatography (1:1 ethyl acetate/dichloromethane) to give the title compound 261b (36.0 g, 79.4% over 2 stages): IR (film) 3267, 2979, 2937, 1728, 1668, 1394, 1369, 1245, 1159; $^1$H NMR (CDCl$_3$) δ 7.6 (1H, bs), 6.8 (1H, vbs), 4.47 (1H, bs), 3.73 (2H, bs), 2.98 (1H, bs), 2.66 (3H, m), 2.04 (1H, bs), 1.84 (1H, m), 1.6-1.2 (21H, m+s).

(4S)t-Butyl 7-t-butoxycarbonylamino-6,10-dioxo-1,2,3,4,7,8,9,10-octahydro-6H-pyridazino[1,2-a][1,2,4]triazepine-4-carboxylate (262b), was synthesized via method used to prepare 262 from 261 to give the title compound 262b, (18.6 g, 54%) as an oil: [α]$_D^{20}$ +47.7° (c 0.236, CH$_2$Cl$_2$); IR (film) 3291, 2978, 1738, 1727, 1690, 1678, 1439, 1243, 1164; $^1$H NMR (CDCl$_3$) δ 6.59 (1H, s), 5.06 (1H, m), 4.47 (1H, m), 3.85 (3H, m), 2.82 (1H, m), 2.37 (1H, m), 2.22 (1H, m), 1.92 (1H, m), 1.63 (2H, m), 1.48 and 1.46 (18H, 2×s). MS (ES$^+$) 399 (M$^+$+1).

(4S)t-Butyl 7-amino-6,10-dioxo-1,2,3,4,7,8,9,10-octahydro-6H-pyridazino[1,2-a][1,2,4]triazepine-4-carboxylate (518). Compound 262b (2.43 g, 6.1 mmol) was dissolved in 1M hydrogen chloride in ethyl acetate (30 ml) and stirred at room temperature for 20 h. Solid sodium bicarbonate (4g, 46.5 mmol) and water 20 ml were added and the mixture stirred for 5 min before separating and extracting the aqueous portion with ethyl acetate. The combined organic solution was washed with water, saturated salt, dried (MgSO$_4$) and concentrated. Purification by flash chromatography (50% ethyl acetate in dichloromethane—100% ethyl acetate) gave the pure product 518 (1.08 g, 59%) as an unstable oil: [α]$_D^{20}$ +82° (c 0.55, CH$_2$Cl$_2$); IR (film) 3331, 2977, 1731, 1680, 1664, 1439, 1420, 1315, 1158; $^1$H NMR (CDCl$_3$) δ 5.08 (1H, m), 4.48 (1H, m), 3.80 (2H, Abq), 3.70 (2H, bs, exch with D$_2$O), 3.53 (1H, m), 2.75 (1H, m), 2.30 (2H, m), 1.88 (1H, m), 1.71 (2H, m), 1.47 (9H, s).

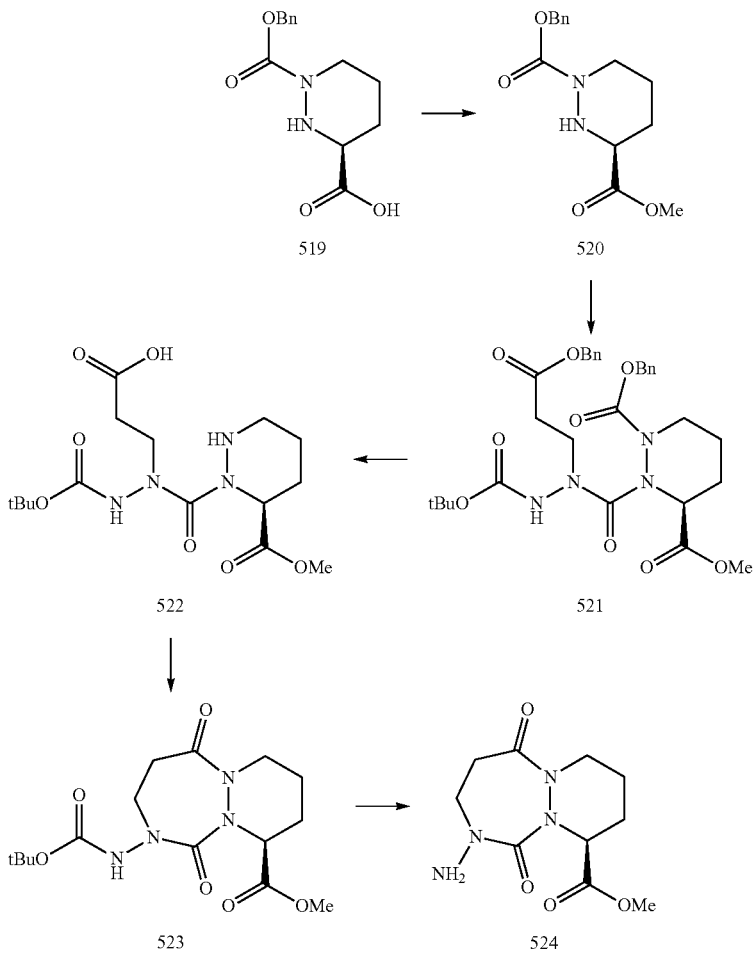

(3S) Methyl 1-benzyloxycarbonyl-hexahydropyridazine-3-carboxylate (520). 519 (9.4 g, 35.6 mmol) was suspended in methanol (230 ml) and cooled to 0° C. in an ice bath. Thionyl chloride (3 ml, 4.89 g, 41.1 mmol) was added dropwise over 30 min and the mixture stirred at ambient temperature for 48 h. The solvent was removed in vacuo at 30° C. and the oily residue dissolved in ethyl acetate (500 ml). The organic solution was washed with saturated sodium bicarbonate, water and brine, dried (MgSO$_4$) and concentrated to give 520 (7.84 g, 79%) as an oil: $[\alpha]_D^{22}$ −25.9° (c 0.615, CH$_2$Cl$_2$); IR (film) 2953, 1739, 1703, 1694, 1440, 1403, 1357, 1261, 1241, 1174; $^1$H NMR (CDCl$_3$) δ 7.36 (5H, s), 5.18 (2H, s), 4.00 (1H, bd), 3.73 (3H, s), 3.55 (1H, dd), 3.12 (1H, t), 2.06 (1H, m), 1.73 (3H, m). Anal. Calcd for C$_{14}$H$_{17}$N$_2$O$_4$.0.25H$_2$O: C, 59.46; H, 6.59; N, 9.91. Found: C, 59.44; H, 6.46; N, 10.09.

(3S)1-Benzyl 3-methyl 2-(N-2-benzyloxycarbonylethyl-NI-t-butoxycarbonylhydrazino)carbonyl hexahydropyridazine dicarboxylate (521). Using a similar method to that described for 260 above, 521 was prepared, 96% as a crude oil: $[\alpha]_D^{22}$ −22.16° (c 0.25, CH$_2$Cl$_2$); IR (film) 3316, 2976, 2953, 1738, 1726, 1714, 1690, 1367, 1260, 1167; $^1$H NMR (CDCl$_3$) δ 7.25 (10H, m), 6.82 (1H, bs), 5.10 (4H, m), 4.80 (1H, bs), 4.3-3.4 (6H, m), 3.10 (1H, m), 2.59 (2H, m), 1.95 (2H, m), 1.44 (10H, m+s).

(3S) Methyl 2-(N'-t-butoxycarbonyl-N-2-carboxyethylhydrazino)-carbonyl hexahydropyridazine 3-carboxylate (522). Using a similar method to that described for 261 above, 522 was prepared, 92% as a white solid: mp. 146-148° C. (decamp); $[\alpha]_D^{22}$ +27.8° (c 0.25, CH$_2$Cl$_2$); IR (KBr) 3346, 1740, 1710, 1626, 1497, 1290, 1250, 1206, 1179, 1159; $^1$H NMR (CDCl$_3$) δ 7.60 (1H, bs), 7.5-5.5 (1H, vbs), 4.64 (1H, bs), 3.76 (5H, m+s), 3.00 (1H, m), 2.70 (3H, m), 2.16 (1H, m), 1.92 (1H, m), 1.56 (1H, m), 1.46 (11H, m+s). Anal. Calcd for C$_{15}$H$_2$O$_4$O$_7$: C, 48.12; H, 7.00; N, 14.96. Found: C, 48.21; H, 6.96; N, 14.86. MS (ES$^+$) 373 (M$^-$−1).

(4S) Methyl 7-t-butoxycarbonylamino-6,10-dioxo-1,2,3,4,7,8,9,10-octahydro-6H-pyridazino[1,2-a][1,2,4]triazepine-4-carboxylate (523). 522 (7.15 g, 19.1 mmol) was dissolved in dichloromethane (100 ml), containing dimethylformamide (0.5 ml), and cooled to 0° C. Thionyl chloride (1.6 ml, 2.61 g, 22 mmol) and N-ethyl morpholine (4.86 ml, 440 mg, 38.2 mmol) were added and the mixture stirred for 2 h. The organic mixture was washed with 2M sodium bisulphate (50 ml), saturated sodium bicarbonate (50 ml) and brine (50 ml), dried (MgSO$_4$) and concentrated. The residues were triturated with ether to give 523 as a white solid (5.73 g, 84%): mp. 186-188° C. (decomp); $[\alpha]_D^{22}$ +65.3° (c 0.25, CH$_2$Cl$_2$); IR (KBr) 3298, 2978, 1750, 1720, 1682, 1658, 1455, 1423, 1369, 1316, 1241, 1212, 1160; $^1$H NMR (CDCl$_3$) δ 6.56 (1H, s), 5.17 (1H, dd), 4.48 (1H, bd), 3.81 (3H, m), 3.75 (3H, s), 2.83 (1H, dt), 2.40 (1H, m), 2.28 (1H, m), 1.95 (1H, m), 1.67 (1H, m), 1.47 (9H, s). Anal. Calcd for C$_{15}$H$_{24}$N$_4$O$_6$.⅛H$_2$O: C, 50.13; H, 6.82; N, 15.59. Found: C, 50.12; H, 6.71; N, 15.58. MS (ES$^+$) 357 (M$^+$−1, 46%), 301 (100%).

(4S) Methyl 7-amino-6,10-dioxo-1,2,3,4,7,8,9,10-octahydro-6H-pyridazino[1,2-a][1,2,4]triazepine-4-carboxylate (524), was synthesized from 523 via method used to prepare 518.

Compounds 262a-k were synthesized via methods used to prepare 211b-f.

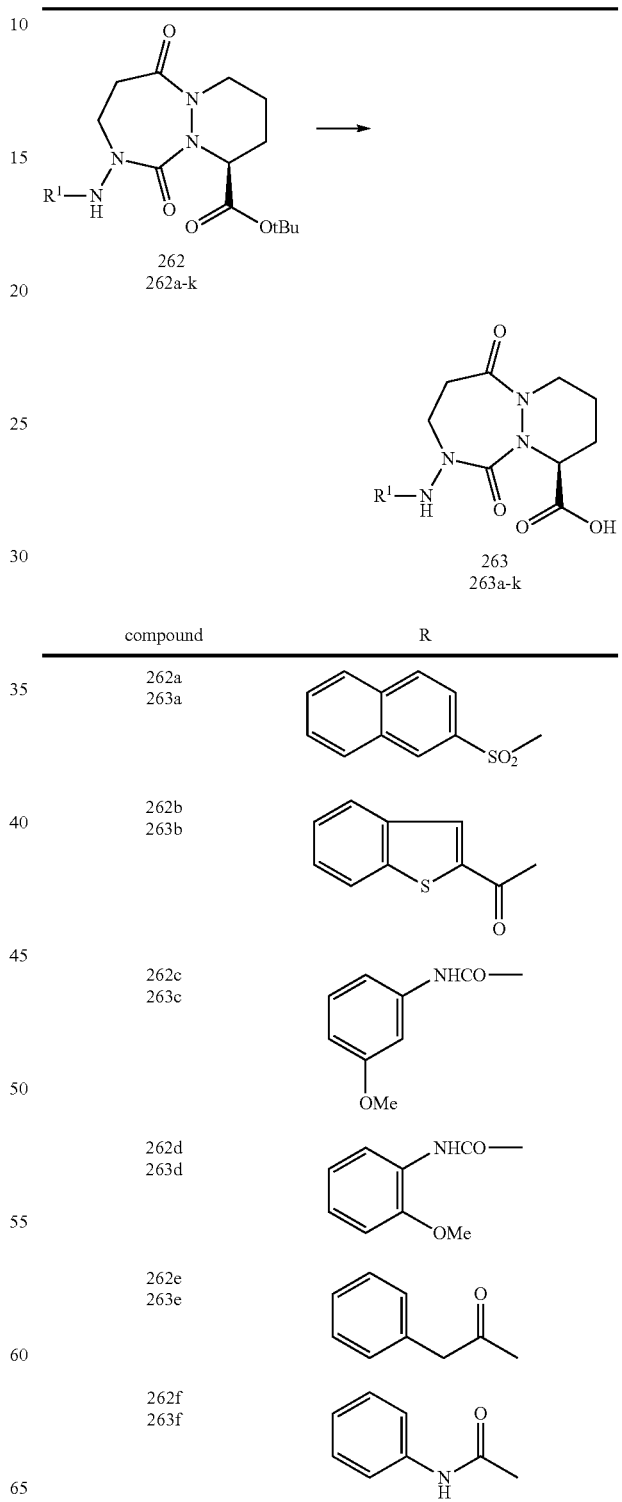

-continued

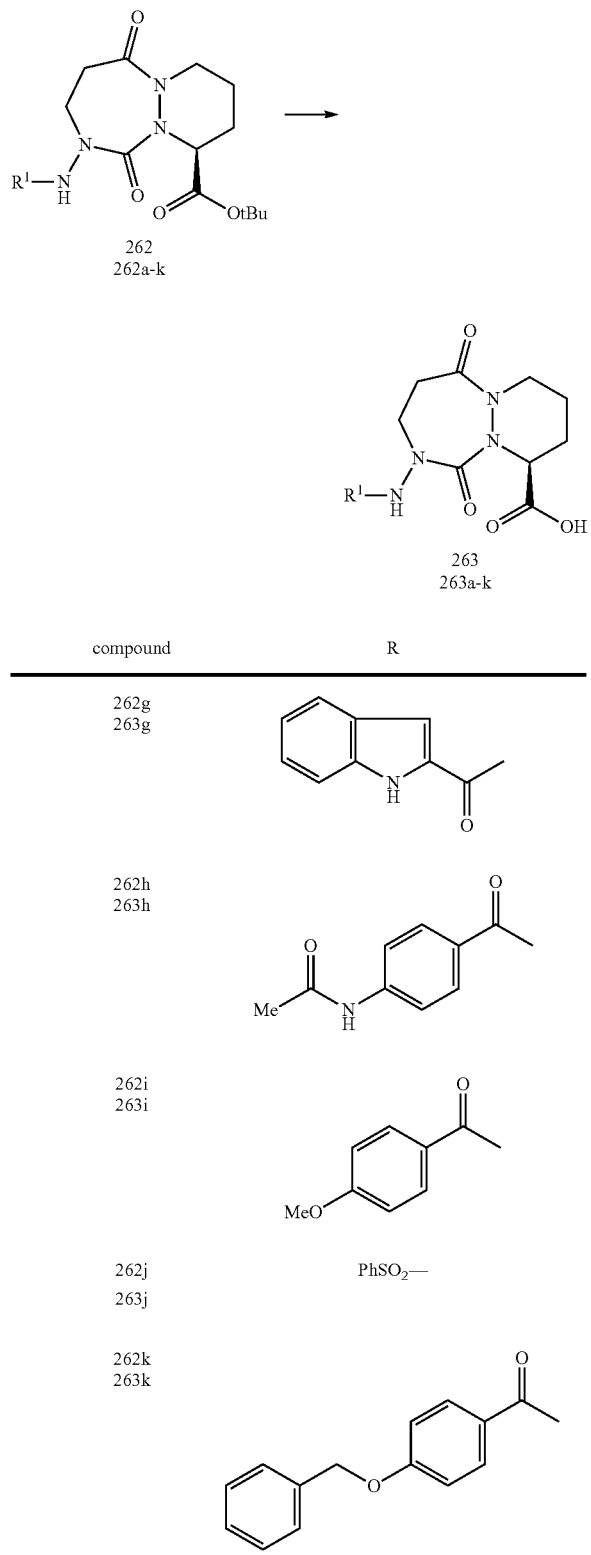

| compound | R |
|---|---|
| 262g 263g | (indol-2-yl carbonyl) |
| 262h 263h | (4-acetamidophenyl ketone via Me-C(O)-NH-C6H4-C(O)-) |
| 262i 263i | (4-methoxyphenyl ketone, MeO-C6H4-C(O)-) |
| 262j 263j | PhSO2— |
| 262k 263k | (4-benzyloxyphenyl ketone, PhCH2O-C6H4-C(O)-) |

(4S)t-Butyl 6,10-dioxo-7-(2-naphthyl)sulfonamide-1,2,3,4,7,8,9,10-octahydro-6H-pyridazino[1,2-a][1,2,4]triazepine-4-carboxylate (262a). 443 mg (91%) of the title compound was obtained: mp. 56-7° C.; $[\alpha]_D^{25}$ +76° (c 0.15, CH$_2$Cl$_2$); IR (KBr) 3429, 2979, 1734, 1675, 1418, 1369, 1339, 1323, 1244, 1164, 665; $^1$H NMR (CDCl$_2$) δ 8.45 (1H, s), 8.00-7.59 (7H, m), 4.69-4.65 (1H, m), 4.25-4.12 (1H, m), 4.10-3.99 (1H, m), 3.73-3.55 (2H, m), 2.40-2.30 (1H, m), 1.99-1.91 (1H, m), 1.82-1.62 (2H, m), 1.48-1.46 (2H, m), 1.37 (9H, s). Anal. Calcd for C$_{23}$H$_{20}$O$_6$S.H$_2$O: C, 54.53; H, 5.97; N, 11.06. Found: C, 54.60; H, 5.73; N, 10.95. MS (ES$^+$) 489.

(4S)t-Butyl 6,10-dioxo-7-(3-methoxyphenylureido)-1,2,3,4,7,8,9,10-octahydro-6H-pyridazino[1,2-a][1,2,4]triazepine-4-carboxylate (262c), 120 mg (80%) of colourless foam was obtained: $[\alpha]_D^{22}$ +22.6° (c 0.1, CH$_2$Cl$_2$); IR (KBr) 3316, 1732, 1671, 1609, 1551, 1495, 1455, 1432, 1316, 1288, 1245, 1218, 1158, 1122, 1023; $^1$H NMR (CDCl$_3$) δ 7.16 (4H, m), 6.79 (1H, m) 6.60 (1H, m), 5.11 (1H, m), 4.59 (1H, m), 3.89 (2H, m), 3.77 (3H, s), 3.72 (2H, m), 2.85 (1H, m).

(4S)t-Butyl 6,10-dioxo-7-(2-methoxyphenylureido)-1,2,3,4,7,8,9,10-octahydro-6H-pyridazino[1,2-a][1,2,4]triazepine-4-carboxylate (262d), (81%) was obtained as colourless foam: $[\alpha]_D^{22}$ +3.7° (c 0.1, CH$_2$Cl$_2$); IR (KBr) 3468, 3446, 3269, 1734, 1698, 1667, 1609, 1555, 1490, 1461, 1433, 1423, 1296, 1246, 1215, 1173, 1157, 1028, 756; $^1$H NMR (CDCl$_3$) δ 8.23 (1H, m), 7.95 (1H, s), 6.95 (4H, m), 5.15 (1H, m), 4.60 (1H, m), 3.98-3.65 (4H, m), 3.89 (3H, s), 2.90 (1H, m), 2.48 (1H, m), 2.25 (1H, m), 2.05-1.65 (2H, m), 1.48 (9H, s).

(4S)t-Butyl 6,10-dioxo-1,2,3,4,7,8,9,10-octahydro-7-phenylacetylamino-6H-pyridazino[1,2-a][1,2,4]triazepine-4-carboxylate (262e), was obtained as a white foamy solid (155 mg, 53%): mp. 53-7° C.; $[\alpha]_D^{22}$ +57.4° (c 0.1, CH$_2$Cl$_2$); IR (KBr) 3271, 2978, 1733, 1680, 1437, 1314, 1245, 1156; $^1$H NMR (CDCl$_3$) δ 7.46 (1H, s), 7.42-7.20 (5H, m), 5.03 (1H, dd), 4.52-4.40 (1H, m), 3.96-3.70 (2H, m), 3.70-3.49 (1H, m), 3.63 (2H, s), 2.92-2.75 (1H, m), 2.43-2.33 (1H, m), 2.33-2.15 (1H, m), 2.00-1.50 (3H, m), 1.45 (9H, s). Anal. Calcd for C$_{21}$H$_{28}$N$_4$O$_5$.0.25H$_2$O: C, 59.91; H, 6.82; N, 13.31. Found: C, 60.19; H, 6.80; N, 13.30. MS (ES$^+$) 418 (M$^+$+2, 25%), 417 (M$^+$+1, 100), 362 (9), 361 (45).

(4S)t-Butyl 6,10-dioxo-1,2,3,4,7,8,9,10-octahydro-7-(3-phenylureido)-6H-pyridazino[1,2-a][1,2,4]triazepine-4-carboxylate (262f), was obtained as a white solid (273 mg, 93%): mp. 102-6° C.; $[\alpha]_D^{22}$ +7.5° (c 0.07, CH$_2$Cl$_2$); IR (KBr) 3320, 2979, 1731, 1676, 1669, 1601, 1549, 1444, 1314, 1240, 1156; $^1$H NMR (CDCl$_3$) δ 7.37-7.20 (6H, m), 7.08-6.98 (1H, m), 5.12 (1H, dd), 4.64-4.55 (1H, m), 4.02-3.78 (2H, m), 3.75-3.65 (1H, m), 2.94-2.75 (1H, m), 2.57-2.35 (1H, m), 2.35-2.20 (1H, m), 2.00-1.50 (3H, m), 1.48 (9H, s). Anal. Calcd for C$_{20}$H$_{27}$N$_5$O$_5$.0.4H$_2$O: C, 56.56; H, 6.60; N, 16.49. Found: C, 56.89; H, 6.58; N, 16.07. MS (ES$^+$) 419 (M$^+$+2, 24%), 418 (M$^+$+1, 100), 363 (15), 362 (81), 242 (10).

(4S)t-Butyl 6,10-dioxo-7-(indole-2-carboxamido)-1,2,3,4,7,8,9,10-octahydro-6H-pyridazino[1,2-a][1,2,4]triazepine-4-carboxylate (262g), (13 g) was obtained as a white solid (298 mg, 70%): mp. 138-43° C.; $[\alpha]_D^{23}$ +69.8° (c 0.1, CH$_2$Cl$_2$); IR (KBr) 3282, 2978, 1733, 1664, 1536, 1421, 1310, 1156, 748; $^1$H NMR (CDCl$_3$) δ 9.67 (1H, s), 9.53 (1H, s), 7.50 (1H, d), 7.30-7.15 (2H, m), 7.10-7.00 (1H, m), 6.93 (1H, s), 5.16-5.12 (1H, m), 4.60-4.50 (1H, m), 4.05-3.85 (2H, m), 3.85-3.70 (1H, m), 3.05-2.90 (1H, m), 2.55-2.35 (1H, m), 2.35-2.20 (1H, m), 2.00-1.85 (1H, m), 1.85-1.50 (2H, m), 1.47 (9H, s). Anal. Calcd for C$_{22}$H$_{27}$N$_5$O$_5$.0.45H$_2$O: C,58.77; H, 6.26; N, 15.58. Found: C, 59.14; H, 6.24; N, 15.18.

MS (ES⁺) 433 (M⁺+2, 26%), 442 (M⁺+1, 100), 387 (17), 386 (79), 285 (20), 229 (85), 211 (26), 185 (15), 183 (57), 139 (9).

(4S)t-Butyl 7-[(4-acetamido)benzamido]-6,10-dioxo-1,2,3,4,7,8,9,10-octahydro-6H-pyridazino[1,2-a][1,2,4]-triazepine-4-carboxylate (262h), was obtained as a white solid (325 mg, 73%): mp. 209-12° C.; $[\alpha]_D^{24}$ +62.4° (c 0.2, CH$_2$Cl$_2$); IR (KBr) 3513, 3269, 2980, 1731, 1680, 1653, 1599, 1531, 1314, 1158; $^1$H NMR (CDCl$_3$) δ 9.40 (1H, s), 8.75 (1H, s), 7.72 (2H, d), 7.47 (2H, d), 5.15-5.05 (1H, m), 4.55-4.45 (1H, m), 4.05-3.70 (3H, m), 3.00-2.80 (1H, m), 2.45-2.35 (1H, m), 2.30-2.15 (1H, m), 2.10 (3H, s), 2.00-1.80 (1H, m), 1.80-1.50 (2H, m), 1.48 (9H, s). Anal. Calcd for C$_{22}$H$_{29}$N$_5$O$_6$: C, 57.51; H, 6.36; N, 15.24. Found: C, 57.41; H, 6.38; N, 15.12. MS (ES⁺) 461 (M⁺+2, 26%), 460 (M⁺+1, 100), 405 (12), 404 (55), 354 (7), 285 (23), 229 (52), 183 (22).

(4S)t-Butyl 6,10-dioxo-7-(4-methoxybenzoylamino)-octahydro-6H-pyridazino[1,2-a][1,2,4]triazepine-carboxylate (262i), was obtained as a white glassy solid (76%): mp. 85-9° C.; $[\alpha]_D^{25}$ +66.4° (c 0.11, CH$_2$Cl$_2$); IR (KBr) 1732, 1668, 1607, 1502, 1440, 1312, 1295, 1258, 1176, 1157, 1025; $^1$H NMR (CDCl$_3$) δ 8.25 (1H, s), 7.77 (2H, m), 6.90 (2H, m), 5.11-5.07 (1H, m), 4.55-4.48 (1H, m), 4.01-3.91 (2H, m), 3.86-3.78 (1H, m), 3.85 (3H, s), 2.98 (1H, m), 2.46-2.40 (1H, m), 2.26-2.20 (1H, m), 2.05-1.80 (1H, m), 1.70-1.64 (2H, m), 1.48 (9H, s).

(4S)t-Butyl 6,10-dioxo-1,2,3,4,7,8,9,10-octahydro-7-phenylsulphonylamino-6H-pyridazino[1,2-a][1,2,4]triazepine-4-carboxylate (262j), was obtained as a white crystalline solid (79%): mp. 182-3° C. (dec); $[\alpha]_D^{22}$ +92.1° (c 0.4, CH$_2$Cl$_2$); IR (KBr) 3283, 1732, 1684, 1448, 1430, 1404, 1369, 1338, 1306, 1285, 1242, 1169, 1091, 692; $^1$H NMR (CDCl$_3$) δ 7.89 (2H, d, J=7.4), 7.76 (1H, s), 7.64-7.49 (3H, m), 4.83 (1H, m), 4.35 (1H, brd, J=13.0), 4.00 (1H, m), 3.74-3.63 (2H, m), 2.39-2.26 (2H, m), 2.06 (1H, m), 1.50-1.41 (10H, m). Anal. Calcd for C$_{19}$H$_{26}$SN$_4$O$_6$: C, 52.04; H, 5.98 N, 12.78. Found: C, 52.11; H, 5.95; N, 12.71. MS (ES⁺) 437 (M⁺−1, 100%).

(3S)t-Butyl (7-(4-benzyloxyphenyl)carbonylamino-6,10-dioxo-1,2,3,4,7,8,9,10-octahydro-6H-pyridazino[1,2-a][1,2,4]triazepine-4-carboxylate (262k), (83%) was obtained: $[\alpha]_D^{22}$ +42.3°. (c 0.11, CH$_2$Cl$_2$). IR (KBr) 3287, 2997, 2935, 1735, 1681, 1606, 1501, 1296, 1248, 1173, 1155. $^1$H NMR (CDCl$_3$) δ 9.23 (1H, s), 7.73 (2H, d), 7.38 (5H, m), 6.85 (2H, d), 5.08 (1H, m), 5.02 (2H, s), 4.48 (1H, bd), 4.15-3.65 (3H, m), 2.96 (1H, m), 2.45-2.10 (2H, m), 1.88 (2H, m), 1.63 (2H, m), 1.48 (9H, s). M.S. (ES⁺509 (M⁺+1).

Compounds 263a-k were synthesized via methods used to prepare 212b-f.

(4S)6,10-Dioxo-7-(2-naphthalenesulfonyl)amino-1,2,3,4,7,8,9,10-octahydro-6H-pyridazino[1,2-a][1,2,4]triazepine-4-carboxylic acid (263a), 348 mg (94%) obtained as a white foamy solid: mp: $[\alpha]_D^{21}$ +171° (c 0.056, CH$_2$Cl$_2$); IR (KBr) 3426, 3233, 2953, 1734, 1663, 1481, 1415, 1340, 1214, 1167, 1132, 1075, 668; $^1$H NMR (CDCl$_3$) δ 8.44 (1H, s), 8.00-7.60 (7H, m), 4.85-4.83 (1H, m), 4.25-4.00 (1H, m), 4.07-3.90 (1H, m), 3.70-3.46 (2H, m), 2.38-2.30 (1H, m), 2.12-2.01 (1H, m), 1.91-1.83 (1H, m), 1.46-1.26 (1H, m), 1.13-1.06 (1H, m), 0.90-0.77 (1H, m). MS (ES⁺) 431.

(4S)7-(Benzo[b]thiophene-2-carbonyl)amino-6,10-dioxo-1,2,3,4,7,8,9,10-octahydro-6H-pyridazino[1,2-a][1,2,4]triazepine-4-carboxylic acid (263b). 200 mg (100%) was obtained as a white solid: mp. 155° C.; $[\alpha]_D^{20}$ 13 (c 0.07, CH$_2$Cl$_2$); IR (KBr) 3431, 2935, 1734, 1663, 1531, 1435, 1292, 1177; $^1$H NMR (CDCl$_3$) δ 9.73 (1H, bs), 7.73-7.27 (5H, m), 5.35-5.25 (1H, m), 4.56-4.48 (1H, m), 4.05-3.65 (3H, m), 3.12-3.00 (1H, m), 2.50-2.45 (1H, m), 2.30-2.20 (1H, m), 2.10-2.00 (1H, m), 1.75-1.61 (2H, m). MS (ES⁺) 401.

(4S)6,10-Dioxo-7-(3-methoxyphenylureido)-1,2,3,4,7,8,9,10-octahydro-6H-pyridazino[1,2-a][1,2,4]triazepine-4-carboxylic acid (263c), 216 mg, (100+%) obtained as a colourless foam: $[\alpha]_D^{23}$ 32.5° (c 0.1, CH$_2$Cl$_2$); IR (KBr) 3326, 1730, 1661, 1610, 1555, 1495, 1431, 1314, 1288, 1217, 1175, 1161; $^1$H NMR (CDCl$_3$) δ 7.87 (1H, s), 7.58 (1H, s), 7.19 (2H, m), 6.82 (1H, m), 6.62 (1H, m), 5.21 (1H, m), 4.55 (1H, m), 3.76 (3H, s), 4.0-3.65 (4H, m), 2.85 (2H, m), 2.35 (2H, m), 1.75 (1H, m), 1.71 (2H, m).

(4S)6,10-Dioxo-7-(2-methoxyphenylureido)-1,2,3,4,7,8,9,10-octahydro-6H-pyridazino[1,2-a][1,2,4]triazepine-4-carboxylic acid (263d), (100+%) obtained as colourless foam: $[\alpha]_D^{24}$ +11.7° (c 0.1, CH$_2$Cl$_2$); IR (KBr) 3394, 3325, 1666, 1603, 1543, 1490, 1463, 1438, 1329, 1311, 1292, 1249, 1214, 1176, 1119, 1024, 752; $^1$H NMR (CDCl$_3$) δ 8.15 (1H, m), 7.97 (2H, m), 7.15-6.84 (3H, m), 5.29 (1H, m), 4.62 (1H, m), 4.04-3.65 (4H, m), 3.89 (3H, s), 2.92 (1H, m), 2.50 (1H, m), 2.30 (1H, m), 2.10-1.75 (2H, m).

(4S)6,10-Dioxo-1,2,3,4,7,8,9,10-octahydro-7-phenylacetyl-amino-6H-pyridazino[1,2-a][1,2,4]triazepine-4-carboxylic acid (263e), obtained as a white foamy solid (117 mg, 98%):

mp. 109-14° C.; $[\alpha]_D^{24}$ +82.6° (c 0.06, CH$_2$Cl$_2$); IR (KBr) 3700-2250 (br), 3437, 3274, 2959, 1733, 1664, 1481, 1437, 1310, 1177; $^1$H NMR (CDCl$_3$) δ 7.99 (1H, s), 7.40-7.15 (5H, m), 5.15-5.10 (1H, m), 5.25-4.70 (1H, bs), 4.50-4.35 (1H, m), 3.95-3.50 (3H, m), 3.61 (2H, s), 2.93-2.78 (1H, m), 2.40-2.20 (2H, m), 2.10-1.80 (1H, m), 1.80-1.60 (2H, m). Anal. Calcd for C$_{17}$H$_{20}$N$_4$O$_5$.1H$_2$O: C, 53.96; H, 5.86; N, 14.81. Found: C, 54.12; H, 5.50; N, 14.68. MS (ES⁺) 360 (M+, 21%), 359 (M⁺−1, 100), 196 (14), 182 (14), 111 (7).

(4S)6,10-Dioxo-1,2,3,4,7,8,9,10-octahydro-7-(3-phenylureido)-6H-pyridazino[1,2-a][1,2,4]triazepine-4-carboxylic acid (263f), obtained as a white foamy solid (199 mg, 92%): mp. 149-52° C.; $[\alpha]_D^{24}$ +92.0° (c 0.01, CH$_3$OH); IR (KBr) 3700-2300 (br), 3319, 2956, 1726, 1664, 1600, 1548, 1500, 1444, 1313, 1238, 755; $^1$H NMR (D$_6$-DMSO) δ 8.90 (1H, s), 8.24 (1H, s), 7.42 (2H, d), 7.30-7.20 (2H, m), 7.00-6.90 (1H, m), 4.98-4.92 (1H, m), 4.32-4.22 (1H, m), 3.80-3.55 (3H, m), 2.85-2.70 (1H, m), 2.30-2.20 (1H, m), 2.20-2.00 (1H, m), 1.90-1.35 (3H, m). Anal. Calcd for C$_{16}$H$_{19}$N$_5$O$_5$.0.75H$_2$O: C, 51.26; H, 5.51; N, 18.68. Found: C, 51.11; H, 5.23; N, 18.42. MS (ES⁺) 361 (M+, 20%), 360 (M⁺−1, 100), 241 (11), 240 (89), 196 (15), 175 (29), 111 (12).

(4S)6,10-Dioxo-7-(indole-2-carboxamido)-1,2,3,4,7,8,9,10-octahydro-6H-pyridazino[1,2-a][1,2,4]triazepine-4-carboxylic acid (263 g), was obtained as a white solid (259 mg, 92%) mp. 248-51° C.; [α]$_D^{24}$ +94.0° (c 0.01, CH$_3$OH); IR (KBr) 3700-2300 (br) 3341, 2956, 1738, 1668, 1651, 1529, 1425, 1311, 1259, 751; $^1$H NMR (D$_6$-DMSO) δ 13.29 (1H, bs), 11.72 (1H, s), 10.64 (1H, s), 7.65 (1H, d), 7.45 (1H, d), 7.26-7.15 (1H, m), 7.17 (1H, s), 7.10-7.00 (1H, m), 5.05-4.95 (1H, m), 4.40-4.25 (1H, m), 3.90-3.50 (3H, m), 2.88-2.75 (1H, m), 2.38-2.20 (1H, m), 2.20-2.00 (1H, m), 1.90-1.35 (3H). Anal. Calcd for C$_{18}$H$_{19}$N$_5$O$_5$.0.5H$_2$O: C, 53.59; H, 5.25; N, 17.35. Found: C, 53.66; H, 4.88; N, 17.11. MS (ES$^+$) 385 (M+, 23%), 384 (M$^+$−1, 100), 298 (6), 253 (8), 227 (10), 199 (23), 196 (10), 173 (9), 126 (21).

(4S)7-[(4-Acetamido)benzamido]-6,10-dioxo-1,2,3,4,7,8,9,10-octahydro-6H-pyridazino[1,2-a][1,2,4]triazepine-4-carboxylic acid (263h), was obtained as a white solid (282 mg, 99%): mp. 210-5° C.; [α]$_D^{24}$ +74.5° (c 0.01, CH$_3$OH); IR (KBr) 3700-2300 (br) 3444, 3316, 2960, 1664, 1599, 1531, 1439, 1301, 1184; $^1$H NMR (D$_6$-DMSO) δ 13.30 (1H, bs), 10.50 (1H, s), 10.25 (1H, s), 7.80 (2H, d), 7.68 (2H, d), 5.00-4.90 (1H, m), 4.35-4.25 (1H, m), 3.90-3.40 (3H, m), 2.88-2.70 (1H, m), 2.35-2.25 (1H, m), 2.25-1.95 (1H, m), 2.08 (3H, s), 1.95-1.35 (3H, m). MS (ES$^+$) 403 (M+, 10%), 402 (M$^+$−1, 100), 358 (10), 247 (10), 227 (16), 219 (51), 198 (12), 184 (17).

(4S)6,10-Dioxo-7-(4-methoxybenzoylamino)-octahydro-6H-pyridazino[1,2-a][1,2,4]triazepine-carboxylic acid (263i), was obtained as a white glassy solid (approx 100%) used without purification: $^1$H NMR (CDCl$_3$) δ 9.23 (1H, s), 7.72 (2H, d, J=8.8), 6.81 (2H, d, J=8.9), 5.22 (1H, m), 4.51 (1H, m), 3.97-3.72 (2H, m), 3.81 (3H, s), 3.03 (1H, m), 2.51-2.46 (1H, m), 2.31-2.25 (1H, m), 2.03 (1H, m), 1.72 (2H, m).

(4S)6,10-Dioxo-1,2,3,4,7,8,9,10-octahydro-7-phenylsulphonylamino-6H-pyridazino[1,2-a][1,2,4]triazepine-4-carboxylic acid (263j), was obtained as a white solid (100%): mp. 73-83° C. (dec); [α]$_D^{22}$ +104.7° (c 0.3, CH$_2$Cl$_2$); IR (KBr) 3600-2500 (br), 3208, 1734, 1666, 1481, 1448, 1416, 1338, 1311, 1214, 1171, 1091, 729, 689; $^1$H NMR (CDCl$_3$) δ 7.87 (3H, m), 7.70-7.50 (3H, m), 7.16 (1H, brs), 4.99 (1H, m), 4.37 (1H, brd, J=12.8), 3.92 (1H, m), 3.67 (2H, m), 2.36 (2H, m), 2.13 (1H, brd, J=12.2), 1.56 (3H, m). Anal. Calcd for C$_{15}$H$_{18}$SN$_4$O$_6$.0.25CF$_3$CO$_2$H: C, 45.31; H, 4.48 N, 13.64. Found: C, 45.48; H, 4.71; N, 13.43. MS (ES$^+$) 383 (MH$^+$, 100%). Accurate mass calculated for C$_{15}$H$_{19}$SN$_4$O$_6$ (MH$^+$): 383.1025. Found: 383.1007.

(4S)7-(4-Benzyloxyphenyl)carbonylamino-6,10-dioxo-1,2,3,4,7,8,9,10-octahydro-6H-pyridazino[1,2-a][1,2,4]triazepine-4-carboxylic acid (263k), (100%) obtained: mp. 130-142° C.; IR (KBr) 3272, 2945, 1738, 1650, 1611, 1501, 1445, 1309, 1255, 1171; $^1$H NMR (CDCl$_3$) δ 9.35 (1H, s), 7.74 (2H, d), 7.38 (5H, m), 6.85 (2H, d), 5.40 (1H, bs), 5.19 (1H, s), 5.02 (2H, s), 4.49 (1H, d), 3.92 (2H, m), 3.68 (1H, m), 2.99 (1H, bs), 2.43 (1H, bs), 2.22 (1H, bs), 1.99 (1H, bs), 1.68 (2H, bs).

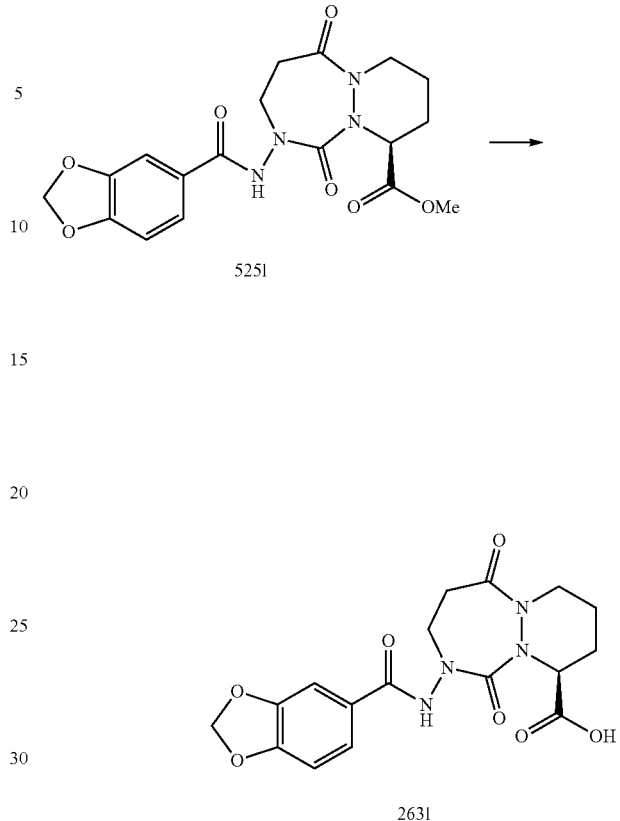

(4S) Methyl 6,10-dioxo-7-(3,4-methylenedioxybenzoylamino)-1,2,3,4,7,8,9,10-octahydro-6H-pyridazino[1,2-a][1,2,4]triazepine-4-carboxylate (5251), was synthesized via method used to prepare 211 to afford a white crystalline solid (3.35 g, 83%): mp. 214-5° C.; [α]$_D^{20}$ +75.2, (c 0.1, CH$_2$Cl$_2$); IR (KBr) 3272, 2955, 1747, 1664, 1610, 1485, 1443, 1265, 1040; $^1$H NMR (CDCl$_3$) δ 8.66 (1H, s), 7.32 (1H, dd), 7.23 (1H, d), 6.76 (1H, d), 6.02 (2H, s), 5.20 (1H, dd), 4.55-4.45 (1H, m), 4.03-3.70 (3H, m), 3.78 (3H, s), 3.05-2.88 (1H, m), 2.47-2.35 (1H, m), 2.35-2.20 (1H, m), 2.10-1.90 (1H, m), 1.85-1.50 (2H, m). Anal. Calcd for C$_{18}$H$_{20}$N$_4$O$_7$.0.5H$_2$O: C, 52.87; H, 5.06; N, 13.70. Found: C, 52.84; H, 5.00; N, 13.66. MS (ES$^+$) 406 (M$^+$+2, 20%), 405 (M$^+$+1, 100), 391 (10), 162 (6), 148 (3), 105 (2).

(4S)6,10-Dioxo-7-(3,4-methylenedioxybenzoylamino)-1,2,3,4,7,8,9,10-octahydro-6H-pyridazino[1,2-a][1,2,4]triazepine-4-carboxylic acid (2631). A suspension of 5251 (3.32 g, 8.2 mmol) in tetrahydrofuran (60 ml) was treated with a solution of LiOH.H$_2$O (0.69 g, 16.4 mmol, 2.0 equiv) in water (20 ml). The resulting mixture was stirred for 1 h, concentrated and the residue dissolved in water (50 ml). The solution was acidified using 2M. NaHSO$_4$ and the product extracted with EtOAc (100 ml and 50 ml portions). The combined extract was washed once with brine (2×50 ml), dried (MgSO$_4$) and concentrated to afford 2631 as a white crystalline solid (2.87 g, 90%): mp. 154-8° C.; [α]$_D^{20}$ +85.6° (c 0.01, CH$_3$OH); IR (KBr) 3700-2300 (br), 3248, 2942, 1733, 1681, 1658, 1648, 1536, 1486, 1440, 1297, 1255, 1037; $^1$H NMR (D$_6$-DMSO) δ 13.23 (1H, bs), 10.45 (1H, s), 7.45 (1H, d), 7.35 (1H, s), 7.03 (1H, d), 6.12 (2H, s), 5.00-4.93 (1H, m), 4.35-4.25 (1H, m), 3.90-3.40 (3H, m), 2.95-2.70 (1H, m), 2.40-2.25 (1H, m), 2.15-2.00 (1H, m), 1.91-1.40 (3H, m). Anal. Calcd for C$_{17}$H$_{18}$N$_4$O$_7$.0.8H$_2$O: C, 50.45; H, 4.88; N, 13.84. Found: C, 50.80; H, 4.95; N, 13.36. MS (ES$^+$) 390 (M$^+$, 19%), 389 (M$^+$−1, 100), 345 (9), 204 (31), 182 (27), 111 (12).

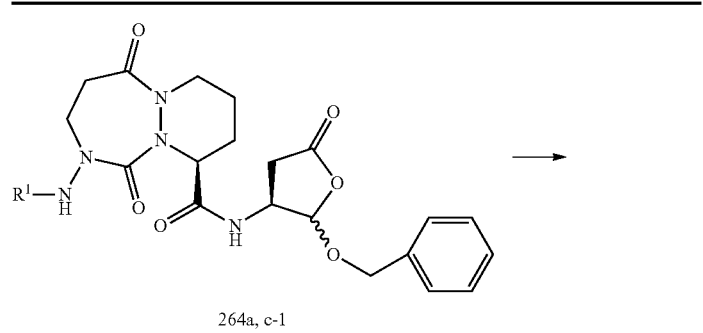
264a, c-1
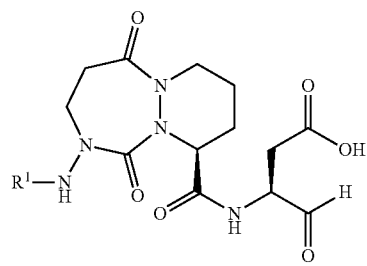
265a, c, d, f
1015, 1018, 1027,
1052, 1056, 1075, 1095
| compound | R[1] |
|---|---|
| 264a 265a | ![naphthalene-SO2] |
| 264c 265c | ![3-methoxyacetanilide] |
| 264d 265d | ![2-methoxyacetanilide] |
| 264e 1095 | ![phenylacetone] |
| 264f 265f | ![acetanilide] |
| 264g 1075 | ![2-acetylindole] |

| | |
|---|---|
| 264h 1018 | 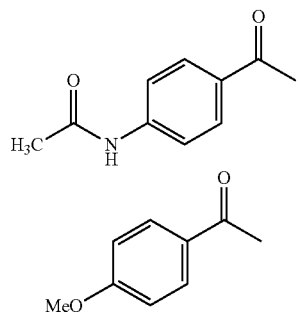 |
| 264i 1052 | 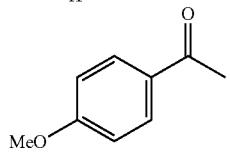 |
| 264j 1027 | 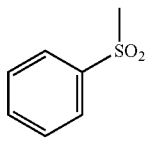 |
| 264k 1056 | 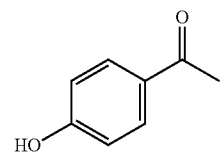 |
| 264l 1015 | 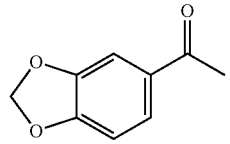 |

[4S(2S,3S)]N-(2-Benzyloxy-5-oxo-tetrahydrofuran-3-yl)-6,10-dioxo-7-(2-naphthalenesulfonyl)amino-1,2,3,4,7,8,9,10-octahydro-6H-pyridazino[1,2-a][1,2,4]triazepine-4-carboxamide (264a), was synthesized by a similar method as compound 213e to afford a white solid (240 mg, 82%): IR (KBr) 3380, 3066, 2947, 1789, 1750, 1691, 1454, 1417, 1368, 1298, 1262, 1235, 1193, 1118, 756, 696; $^1$H NMR (D$_6$-DMSO) δ 8.59 (1H, d, J=6.8), 8.48 (1H, s), 8.25-8.09 (3H, m), 7.85-7.75 (3H, m), 7.36 (5H, m), 5.39 (1H, m), 4.21 (2H, AB, J=14.2), 4.53-4.49 (1H, m), 4.25-4.10 (2H, m), 3.65-3.44 (3H, m), 3.13-2.99 (1H, m), 2.43-2.16 (1H, m), 1.72-0.72 (7H, m). Anal. Calcd for C$_{30}$H$_{31}$N$_5$O$_8$S: C, 57.96; H, 5.03; N, 11.27. Found: C, 57.28; H, 5.14; N, 10.48. MS (ES$^+$) 622.

[4S(2S,3S)]N-(2-Benzyloxy-5-oxo-tetrahydrofuran-3-yl)-6,10-dioxo-7-(3-methoxyphenylureido)-1,2,3,4,7,8,9,10-octahydro-6H-pyridazino[1,2-a][1,2,4]triazepine-1-carboxamide (264c), was prepared by a similar method as 213e, (55%) as a colourless foam: mp. 135-40° C.; (a)$_D^{22}$ +51.6° (c 0.1, CH$_2$Cl$_2$); IR (KBr) 3314, 1790, 1664, 1608, 1543, 1496, 1455, 1428, 1325, 1287, 1250, 1218, 1160, 1118; $^1$H NMR (CDCl$_3$) δ 8.00 (1H, d, J=7.1), 7.66 (1H, s), 7.55 (1H, s), 7.28 (5H, m), 7.14 (2H, m), 6.87 (1H, d, J=7.4), 6.59 (1H, m), 5.42 (1H, s), 4.66 (5H, m), 3.90-3.65 (4H, m), 3.73 (3H, s), 2.98 (2H, m), 2.38 (2H, m), 2.01-1.65 (3H, m).

[4S(2S,3S)]N-(2-Benzyloxy-5-oxo-tetrahydrofuran-3-yl)-6,10-dioxo-7-(2-methoxyphenylureido)-1,2,3,4,7,8,9,10-octahydro-6H-pyridazino[1,2-a][1,2,4]triazepine-1-carboxamide (264d), was prepared by a similar method as 213e, (72%) as colourless foam: [α]$_D^{22}$ +21.4° (c 0.1, CH$_2$Cl$_2$); IR (KBr) 3302, 1791, 1689, 1678, 1664, 1602, 1536, 1489, 1461, 1437, 1420, 1249, 1119, 1023, 942, 751; $^1$H NMR (CDCl$_3$) δ 8.07 (1H, d, J=7.7), 7.82 (1H, s), 7.68 (1H, d, J=6.7), 7.49 (1H, s), 7.34 (5H, m), 6.96 (3H, m), 5.47 (1H, s), 4.82 (2H, d+m, J=11.5), 4.63 (1H, d, J=11.5), 4.49 (2H, m), 3.85 (4H, s+m), 3.68 (2H, m), 3.01 (2H, m), 2.46 (2H, m), 1.95 (3H, m), 1.57 (1H, m).

[4S(2RS,3S)]N-(2-Benzyloxy-5-oxotetrahydrofuran-3-yl)-6,10-dioxo-1,2,3,4,7,8,9,10-octahydro-7-phenylacetylamino-6H-pyridazino[1,2-a][1,2,4]triazepine-4-carboxamide (264e) was synthesized via a similar method as used to prepare 213e to afford a mixture of diastereomers (Syn:anti isomer ratio 9:1) as a white glassy solid (128 mg, 78%): mp. 103-8° C.; IR (KBr) 3419, 3302, 1793, 1664, 1535, 1421, 1327, 1256, 1123, 973; $^1$H NMR (D$_6$-DMSO) δ 10.20 (0.9H, s), 9.35 (0.1H, s), 8.74 (0.1H, d), 8.49 (0.9H, d), 7.36-7.15 (10H, m), 5.67 (0.9H, d), 5.44 (0.1H, s), 4.85-4.75 (1H, m), 4.74-4.60 (1H, m), 4.77 and 4.63 (2H, dd), 4.30-4.10 (1H, m), 3.80-3.40 (3H, m), 3.43 (2H, s), 3.10-2.40 (3H, m), 2.25-2.15 (1H, m), 2.00-1.35 (4H, m). Anal. Calcd for C$_{28}$H$_{31}$N$_5$O$_7$.0.5H$_2$O: C, 60.21; H, 5.77; N, 12.53. Found: C, 60.38; H, 5.83; N, 12.13. MS (ES$^+$) 551 (M$^+$+2, 33%), 550 (M$^+$+1, 100), 480 (7), 343 (8), 279 (4).

[4S(2RS,3S)]N-(2-Benzyloxy-5-oxotetrahydrofuran-3-yl)-6,10-dioxo-1,2,3,4,7,8,9,10-octahydro-7-(3-phenylureido)-6H-pyridazino[1,2-a][1,2,4]triazepine-4-carboxamide (264f), was prepared by a similar method as compound 213e to afford the pure syn-isomer as a white foamy solid (225 mg, 82%): mp. 130-5° C.; [α]$_D^{24}$ +10.8° (c 0.1, CH$_2$Cl$_2$); IR (KBr) 3316, 1791, 1688, 1676, 1664, 1601, 1536, 1445, 1314, 1242, 973; $^1$H NMR (D$_6$-DMSO) δ 8.84 (1H, s), 8.49 (1H, d), 8.19 (1H, s), 7.45-7.18 (9H, m), 7.00-6.90 (1H, m), 5.68 (1H, d), 4.90-4.81 (1H, m), 4.75-4.60 (1H, m), 4.78 and 4.63 (2H, dd), 4.30-4.20 (1H, m), 3.75-3.55 (3H, m), 2.85-2.55 (3H, m), 2.25-2.15 (1H, m), 2.00-1.35 (4H, m). Anal. Calcd for $C_{27}H_{30}N_6O_7.0.5H_2O$: C, 57.95; H, 5.58; N, 15.02. Found: C, 58.12; H, 5.64; N, 14.81. MS (ES+) 552 (M++2, 30%), 551 (M++1, 100), 362 (19), 299 (10), 279 (4).

[4S(2S,3S)]N-(2-Benzyloxy-5-oxotetrahydrofuran-3-yl)-6,10-dioxo-7-(indole-2-carboxamido)-1,2,3,4,7,8,9,10-octahydro-6H-pyridazino[1,2-a][1,2,4]triazepine-4-carboxamide (264g), was prepared by a similar method as compound 213e to afford the pure anti-isomer as a white solid (284 mg, 80%): mp. 148-53° C.; $[\alpha]_D^{24}$ +72.00 (c 0.1, $CH_2Cl_2$); IR (KBr) 3404, 3295, 1789, 1660, 1536, 1421, 1310, 1260, 1122, 749; $^1$H NMR ($D_6$-DMSO) δ 11.72 (1H, s), 10.58 (1H, s), 8.73 (1H, d), 7.65 (1H, d), 7.58-7.27 (6H, m), 7.27-7.10 (1H, m), 7.17 (1H, s), 7.10-7.00 (1H, m), 5.46 (1H, s), 4.90-4.85 (1H, m), 4.77 and 4.68 (2H, dd), 4.35-4.25 (2H, m), 3.95-3.55 (3H, m), 3.09 (1H, dd), 2.95-2.80 (1H, m), 2.47-2.25 (2H, m), 2.10-1.35 (4H, m). MS (ES+) 574 (M+, 35%), 573 (M+−1, 100), 384 (16), 383 (69), 341 (23), 327 (12), 267 (13), 200 (22).

[4S(2RS,3S)]7-[(4-Acetamido)benzamido]-N-(2-benzyloxy-5-oxotetrahydrofuran-3-yl)-6,10-dioxo-1,2,3,4,7,8,9,10-octahydro-6H-pyridazino[1,2-a][1,2,4]triazepine-4-carboxamide (264h), was prepared by a similar method as compound 213e to afford a mixture of diastereomers (Syn:anti isomer ratio 9:1) as a white solid (276 mg, 70%): mp. 147-52° C.; IR (KBr) 3444, 3304, 1793, 1665, 1602, 1531, 1505, 1423, 1294, 1264, 1181, 1123, 966; $^1$H NMR ($D_6$-DMSO) δ 10.41 (1H, s), 10.22 (1H, s), 8.71 (0.1H, d), 8.48 (0.9H, d), 7.78 (2H, d), 7.67 (2H, d), 7.35-7.30 (5H, m), 5.68 (0.9H, d), 5.45 (0.1H, s), 4.88-4.80 (1H, m), 4.75-4.60 (1H, m), 4.77 and 4.63 (2H, dd), 4.30-4.20 (1H, m), 3.90-3.50 (3H, m), 3.10-2.50 (3H, m), 2.35-2.20 (1H, m), 2.07 (3H, s), 2.05-1.35 (4H, m). Anal. Calcd for $C_{29}H_{32}N_6O_8.1H_2O$: C, 57.04; H, 5.61; N, 13.76. Found: C, 56.79; H, 5.50; N, 13.53. MS (ES+) 594 (M++2, 34%), 593 (M++1, 100), 387 (8), 386 (38), 358 (8), 162 (19).

[4S(2RS,3S)]N-(2-Benzyloxy-5-oxotetrahydrofuran-3-yl)-6,10-dioxo-7-(4-methoxybenzoylamino)-octahydro-6H-pyridazino[1,2-a][1,2,4]triazepine-4-carboxamide (264i), was prepared by a similar method to that described for compound 213e to afford a white solid (70%): mp. 116-118° C.; IR (KBr) 3315, 2951, 1793, 1664, 1607, 1502, 1258, 1177; $^1$H NMR ($CDCl_3$) δ 8.07 (1H, s), 7.77 (2H, d, J=8.6), 7.35 (5H, m), 6.94 (2H, d, J=8.5), 6.74 (1H), 4.89 (1H, d, J=11.1), 4.74 (1H, m), 4.60 (1H, d, J=11.0), 4.48, 4.41 (1H, 2m), 3.86 (3H, s), 3.79, 3.71-3.53 (3H, 2m), 2.87 (2H, m), 2.44 (1H, m), 2.18, 1.91, 1.68 (5H, 3m).

[4S(2S,3S)]N-(2-Benzyloxy-5-oxotetrahydrofuran-3-yl)6,10-dioxo-1,2,3,4,7,8,9,10-octahydro-7-phenylsulphonylamino-6H-pyridazino[1,2-a][1,2,4]triazepine-4-carboxamide (264j), was synthesized by a similar method as compound 213e to afford a foam (88%): $[\alpha]_D^{24}$ +74.2° (c 0.36, $CH_2Cl_2$); IR (KBr) 3332, 3235, 1793, 1664, 1537, 1448, 1416, 1337, 1169, 118, 1092, 940, 690; $^1$H NMR ($CDCl_3$) δ 7.99 (1H, s), 7.88 (2H, d, J=6.8), 7.64-7.48 (3H, m), 7.34 (5H, s), 7.13 (1H, d, J=6.9), 5.39 (1H, s), 4.81 (2H, m), 4.62 (1H, d, J=11.5), 4.48 (1H, m), 4.33 (1H, m), 3.85 (1H, m), 3.59 (2H, m), 3.03 (1H, dd, J=7.6, 18.2), 2.49-2.28 (3H, m), 1.94-1.40 (4H, m). Anal. Calcd for $C_{26}H_{29}SN_5O_8$: C, 54.63; H, 5.11 N, 12.25. Found: C, 54.42; H, 5.28; N, 11.62. MS (ES+) 572 (MH+, 100%). Accurate mass calculated for $C_{26}H_{30}SN_5O_8$ (MH+): 572.1815. Found: 572.1802.

[4S(2RS,3S)]7-(4-Benzyloxyphenyl)carbonylamino-N-(2-benzyloxy-5-oxotetrahydrofuran-3-yl)-6,10-dioxo-1,2,3,4,7,8,9,10-octahydro-6H-pyridazino[1,2-a][1,2,4]triazepine-4-carboxamide (264k), was prepared by the method used for 213e (96%): IR (KBr) 3294, 2946, 1793, 1658, 1606, 1535, 1501, 1248, 1174, 1119. $^1$H NMR ($CDCl_3$) δ 8.91 (1H, s), 7.85 (3H, m), 7.4 (10H, m), 7.02 (2H, d), 5.35 (1H, s), 5.10 (2H, s), 4.8-4.3 (5H, m), 4.00 (1H, bs), 3.78 (2H, m), 2.90 (2H, m), 2.5-1.5 (6H, m).

[4S(2RS,3S)]N-(2-Benzyloxy-5-oxotetrahydrofuran-3-yl)-6,10-dioxo-7-(3,4-methylenedioxybenzoylamino)-1,2,3,4,7,8,9,10-octahydro-6H-pyridazino[1,2-a][1,2,4]triazepine-4-carboxamide (264l), was prepared by a similar method as compound 213e to afford a mixture of diastereomers (syn:anti isomer ratio 1:1) as a white solid (1.72 g, 71%): mp. 148-60° C.; IR (KBr) 3314, 1780, 1677, 1658, 1651, 1550, 1485, 1439, 1258, 1132, 1038, 943; $^1$H NMR ($D_6$-DMSO) δ 10.39 (1H, s), 8.71 (0.5H, d), 8.49 (0.5H, d), 7.44 (1H, d), 7.42-7.30 (6H, m), 7.03 (1H, d), 6.12 (2H, s), 5.68 (0.5H, d), 5.45 (0.5H, s), 4.90-4.82 (1H, m), 4.82-4.58 (2.5H, m), 4.40-4.10 (1.5H, m), 3.90-3.65 (2H, m), 3.65-3.43 (1H, m), 3.09 (0.5H, dd), 2.90-2.55 (1.5H, m), 2.45-2.10 (2H, m), 2.10-1.35 (4H, m). Anal. Calcd for $C_{28}H_{29}N_5O_9.0.2H_2O$: C, 57.67; H, 5.08; N, 12.01. Found: C, 58.01; H, 5.33; N, 11.51. MS (ES+) 581 (M++2, 33%), 580 (M+, 100), 374 (9), 373 (48), 345 (12), 261 (4), 239 (7), 149 (9).

[3S(4S)]3-[6,10-Dioxo-7-(2-naphthalenesulfonyl)amino-1,2,3,4,7,8,9,10-octahydro-6H-pyridazino[1,2-a][1,2,4]triazepine-4-carboxamido]-4-oxobutanoic acid (265a), was prepared by a similar method as compound 265 to afford a white solid (37 mg, 17%): mp. 126-30° C. (dec); $[\alpha]_D^{20}$ +30° (c 0.05, MeOH); IR (KBr) 3371, 2935, 1785, 1663, 1538, 1418, 1339, 1164, 669; $^1$H NMR ($CD_3OD$) δ 8.44 (1H, s), 8.06-7.50 (7H, m), 7.22 (1H, d, J=8.4), 4.58-4.57 (1H, m), 4.46-4.42 (1H, m), 4.16-4.09 (2H, m), 3.85-3.50 (3H, m), 2.84-2.78 (1H, m), 2.64-2.51 (1H, m), 2.44-2.15 (2H, m), 1.81-0.89 (4H, m). Anal. Calcd for $C_{23}H_{25}N_5O_8S.H_2O$: C, 50.27; H, 4.95; N, 12.74. Found: C, 50.33; H, 5.04; N, 12.60. MS (ES+) 530.

[3S(4S)]3-[6,10-Dioxo-7-(3-methoxyphenylureido)-1,2,3,4,7,8,9,10-octahydro-6H-pyridazino[1,2-a][1,2,4]triazepine-4-carboxamido]-4-oxobutanoic acid (265c), was prepared by a similar method as 265, (90%) as a colourless solid: mp. ~150° C. (decomp.); $[\alpha]_D^{23}$ +94.8° (c 0.1, 20% MeOH/$CH_2Cl_2$); IR (KBr) 3330, 1780, 1660, 1610, 1550, 1495, 1428, 1326, 1287, 1251, 1223, 1160; $^1$H NMR ($CD_3OD$) δ 7.16 (2H, m), 6.89 (1H, d, J=7.8), 4.58 (1H, m), 4.37 (2H, m), 3.76 (6H, s+m), 2.95 (1H, m), 2.67 (1H, m), 2.33 (1H, m), 2.20-1.85 (3H, m), 1.66 (1H, m).

[3S(4S)]3-[6,10-Dioxo-7-(2-methoxyphenylureido)-1,2,3,4,7,8,9,10-octahydro-6H-pyridazino[1,2-a][1,2,4]-triazepine-4-carboxamido]-4-oxobutanoic acid (265d), was prepared by a similar method as 265, (85%) as a colourless solid: mp. ~176-85° C.; $[\alpha]_D^{23}$ +11.0° (c 0.1, MeOH); IR (KBr) 3392, 3328, 1784w, 1665, 1603, 1537, 1490, 1462, 1437, 1337, 1290, 1290, 1217, 1177, 1119, 1023; $^1$H NMR ($CD_3OD$) δ 8.02 (2H, m), 6.95 (4H, m), 5.05 (1H, m), 4.60 (2H, m), 3.92 (4H, s+m), 3.00 (2H, m), 2.68 (1H, m), 2.39 (1H, m), 2.00 (4H, m), 1.69 (1H, m).

[3S(4S)]3-(6,10-Dioxo-1,2,3,4,7,8,9,10-octahydro-7-phenylacetylamino-6H-pyridazino[1,2-a][1,2,4]triazepine-4-carboxamido)-4-oxobutanoic acid (1095), was prepared by a similar method as compound 265 to afford a white solid (84 mg, 90%): mp. 180-6° C.; $[\alpha]_D^{22}$ +22.3° (c 0.065, $CH_3OH$); IR (KBr) 3700-2300 (br), 3287, 1664, 1536, 1425, 1261, 1181; $^1$H NMR ($CD_3OD$) δ 7.35-7.20 (5H, m), 5.00-4.90 (1H, m), 4.60-4.50 (1H, m), 4.50-4.10 (2H, m), 3.90-3.50 (3H, m), 3.54 (2H, s), 3.00-2.80 (1H, m), 2.80-2.40 (2H, m), 2.35-2.20 (1H, m), 2.20-1.50 (4H, m). MS (ES+) 459 (M+24%), 458 (M+−1, 100), 358 (27), 175 (9), 149 (7), 137 (12). Accurate mass calculated for $C_{21}H_{26}N_5O_7$ (MH+): 460.1832. found: 460.1840.

[3S(4S)]3-[6,10-Dioxo-1,2,3,4,7,8,9,10-octahydro-7-(3-phenylureido)-6H-pyridazino[1,2-a][1,2,4]triazepine-4-carboxamido]-4-oxobutanoic acid (265f), was prepared by a similar method as compound 265 to afford a white foamy solid (130 mg, 88%): mp. 157-62° C.; $[\alpha]_D^{24}$ +41.7° (c 0.1, CH$_3$OH); IR (KBr) 3700-2300 (br), 3325, 1782, 1663, 1547, 1443, 1315, 1242, 1181; $^1$H NMR (CD$_3$OD) δ 7.40 (2H, dd), 7.35-7.20 (2H, m), 7.06-6.95 (1H, m), 5.05-4.95 (1H, m), 4.64-4.54 (1H, m), 4.50-4.35 (1H, m), 4.35-4.15 (1H, m), 3.90-3.69 (3H, m), 3.00-2.85 (1H, m), 2.80-2.45 (3H, m), 3.40-1.50 (4H, m). MS (ES$^{4+}$) 460 (M+, 24%), 459 (M$^+$-1, 100), 341 (9), 340 (54), 296 (6), 239 (9).

[3S(4S)]3-[6,10-Dioxo-7-(indole-2-carboxamido)-1,2,3,4,7,8,9,10-octahydro-6H-pyridazino[1,2-a][1,2,4]triazepine-4-carboxamido]-4-oxobutanoic acid (1075), was prepared by a similar method as compound 265 to afford a white solid (184 mg, 83%): mp. 210-5° C.; $[\alpha]_D^{24}$ +43.9°, (c 0.1, CH$_3$OH); IR (KBr) 3700-2300 (br), 3309, 1660, 1537, 1423, 1311, 1262, 1184; $^1$H NMR (CD$_3$OD) δ 7.61 (1H, d), 7.45 (1H, d), 7.28-7.15 (1H, m), 7.15-7.00 (1H, m), 7.13 (1H, s), 5.12-4.96 (1H, m), 4.62-4.55 (1H, m), 4.50-4.25 (2H, m), 4.00-3.69 (3H, m), 3.05-2.90 (1H, m), 2.80-2.30 (3H, m), 2.25-1.50 (4H, m). MS (ES$^+$) 484 (M+, 26%), 483 (M$^+$-1, 100), 383 (25), 245 (12), 208 (11), 200 (21), 174 (31), 137 (18).

[3S(4S)]3-{7-[(4-Acetamido) benzamido]-6,10-Dioxo-1,2,3,4,7,8,9,10-octahydro-6H-pyridazino[1,2-a][1,2,4]-triazepine-4-carboxamido}-4-oxobutanoic acid (1018), was prepared by a similar method as compound 265 to afford a white solid (177 mg, 82%): mp. 235-40° C.; $[\alpha]_D^{23}$ +27.3° (c 0.1, CH$_3$OH); IR (KBr) 3700-2300 (br), 3311, 2957, 1662, 1599, 1531, 1318, 1266, 1182; $^1$H NMR (CD$_3$OD) δ 7.83 (2H, d), 7.69 (2H, d), 5.10-4.95 (1H, m), 4.64-4.55 (1H, m), 4.50-4.35 (1H, m), 4.32-4.22 (1H, m), 4.00-3.65 (3H, m), 3.05-2.90 (1H, m), 2.80-2.30 (3H, m), 2.15 (3H, s), 2.15-1.50 (4H, m). Anal. Calcd for C$_{22}$H$_{26}$N$_6$O$_8$.1.5H$_2$O: C, 49.90; H, 5.52; N, 15.87. Found: C, 50.21; H, 5.41; N, 15.49. MS (ES$^+$) 502 (M+, 28%), 501 (M$^+$-1, 100), 401 (8), 218 (4), 119 (2), 118 (5), 113 (16).

[3S(4S)]3-[6,10-Dioxo-7-(4-methoxybenzoylamino)-octahydro-6H-pyridazino[1,2-a][1,2,4]triazepine-4-carboxamido]-4-oxobutanoic acid (1052), was synthesized via method used to prepare 265 to afford a white solid (0.194g, 100%): mp. 138-142° C.; $[\alpha]_D^{20}$ +36.3° (c 0.19, CH$_3$OH); IR (KBr) 3434-2962, 1782, 1660, 1607, 1537, 1504, 1441, 1424, 1313, 1293, 1258, 1177; $^1$H NMR (CD$_3$OD) δ 7.11 (2H, d, J=8.8), 6.90 (2H, d, J=8.9), 4.48 (1H, m), 4.34, 4.28 (1H, 2m), 4.15 (1H, m), 3.75 (3H, s), 3.75, 3.70 (3H, m), 2.88, 2.49, 2.28, 2.23, 2.00, 1.86, 1.79, 1.58 (8H, m).

[3S(4S)]3-(6,10-Dioxo-1,2,3,4,7,8,9,10-octahydro-7-phenylsulphonylamino-6H-pyridazino[1,2-a][1,2,4]triazepine-4-carboxamido)-4-oxobutanoic acid (1027), was synthesized by a similar method as compound 265 to afford a white foam (88%): $[\alpha]_D^{24}$ +22.6° (c 0.17, MeOH); IR (KBr) 3349, 1789, 1663, 1537, 1448, 1337, 1169, 1092, 690; $^1$H NMR (CD$_3$OD) δ 7.82 (2H, d, J=7.8), 7.57 (3H, m), 4.74 (1H, m), 4.47 (1H, m), 4.24-4.10 (2H, m), 3.72-3.47 (4H, m), 2.62-2.48 (3H, m), 2.20 (1H, m), 1.94-1.35 (3H, m). MS (ES$^+$) 480 (M$^+$-1, 100%). Accurate mass calculated for C$_{19}$H$_{24}$SN$_5$O$_8$ (MH$^+$): 482.1346. Found: 482.1325.

[3S(4S)]3-[6,10-Dioxo-7-(4-hydroxybenzoylamino)-1,2,3,4,7,8,9,10-octahydro-6H-pyridazino[1,2-a][1,2,4]triazepine-4-carboxamido]-4-oxobutanoic acid (1056), was prepared by the method used for 265 (95%): mp. >300° C.; IR (KBr) 3392, 1660, 1610, 1507, 1442, 1280, 1171, 1149, 1133.

$^1$H NMR (CD$_3$OD) δ 7.74 (2H, d J=8.7), 6.84 (2H, d J=8.7) 4.58 (1H, m), 4.41 (1H, bd, J=12.6), 4.28 (1H, m), 3.85 (3H, m), 2.98 (1H, m), 2.8-2.3 (3H, m), 2.3-1.6 (4H, m).

[3S(4S)]3-[6,10-Dioxo-7-(3,4-methylenedioxybenzoylamino)-1,2,3,4,7,8,9,10-octahydro-6H-pyridazino[1,2-a][1,2,4]triazepine-4-carboxamido]-4-oxobutanoic acid (1015), was prepared by a similar method as used for 265 to afford a white solid (142 mg, 58%): mp. 170-5° C.; $[\alpha]_D^{25}$+32.7° (c 0.1, CH$_3$OH); IR (KBr) 3700-2500 (br), 3325, 2969, 1784, 1662, 1485, 1440, 1292, 1258, 1037; $^1$H NMR (CD$_3$OD) δ 7.45 (1H, dd), 7.32 (1H, d), 6.90 (1H, d), 6.05 (2H, s), 5.10-4.90 (1H, m), 4.62-4.54 (1H, m), 4.45-4.35 (1H, m), 4.33-4.22 (1H, m), 3.95-3.65 (3H, m), 3.05-2.90 (1H, m), 2.80-2.30 (3H, m), 2.20-1.50 (4H, m).

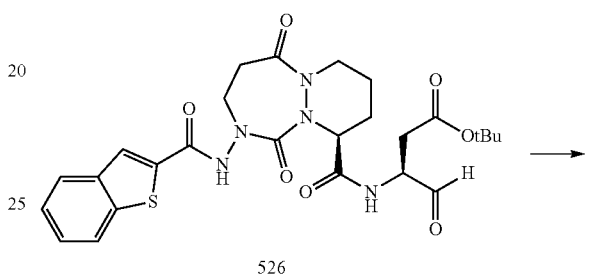

526

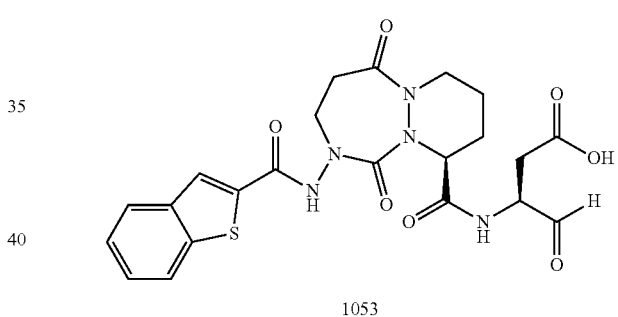

1053

[3S(4S)]t-Butyl 3-[7-(benzo[b]thiophene-2-carbonyl) amino-6,10-dioxo-1,2,3,4,7,8,9,10-octahydro-6H-pyridazino[1,2-a][1,2,4]triazepine]-4-oxobutanoate semicarbazone (526), was prepared by a similar method as used for 502 to afford a glassy solid: $[\alpha]_D^{20}$ +34° (c 0.13, CH$_2$Cl$_2$); IR (KBr) 3437, 2929, 1670, 1530, 1428, 1288, 1156; $^1$H NMR (CDCl$_3$) δ 10.0 (1H, bs), 9.74 (1H, bs), 7.93 (1H, s), 7.80-7.60 (2H, m), 7.40-7.18 (3H, m), 6.15-5.30 (2H, bs), 5.00-4.85 (2H, m), 4.50-4.25 (1H, m), 3.95-3.75 (3H, m), 3.12-2.78 (2H, m), 2.73-1.60 (7H, m), 1.36 (9H, s). Anal. Calcd for C$_{27}$H$_{34}$N$_8$O$_7$S: C, 52.76; H, 5.58; N, 18.23. Found: C, 52.25; H, 5.74; N, 16.30. MS (ES$^+$) 615.

[3S(4S)]3-[7-(Benzo[b]thiophene-2-carbonyl)amino-6,10-dioxo-1,2,3,4,7,8,9,10-octahydro-6H-pyridazino[1,2-a][1,2,4]triazepine-4-carboxamido]-4-oxobutanoic acid (1053), was prepared by a similar method as used for 214 to afford a white solid (106 mg, 73%): $[\alpha]_D^{20}$ +22° (c 0.10, MeOH); IR (KBr) 3428, 2944, 1733, 1652, 1532, 1433, 1337, 1288, 1186; $^1$H NMR (CD$_3$OD) δ 7.95 (1H, s), 7.90-7.85 (2H, m), 7.43-7.35 (2H, m), 4.98 (1H, m), 4.65-4.52 (1H, m), 4.40-4.20 (2H, m), 3.85-3.70 (3H, m), 3.30-3.25 (3H, m), 3.03-2.85 (1H, m), 2.70-2.31 (3H, m), 2.10-1.55 (4H, m). MS (ES$^+$) 500 (as methyl acetal of the aldehyde).

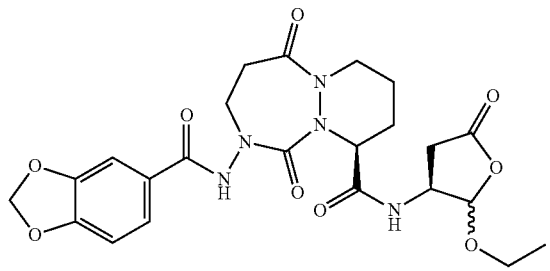

528

[4S(2RS,3S)]6,10-Dioxo-N-(2-ethoxy-5-oxotetrahydrofuran-3-yl)-7-(3,4-methylenedioxybenzoylamino)-1,2,3,4,7,8,9,10-octahydro-6H-pyridazino[1,2-a][1,2,4]triazepine-4-carboxamide (528), was prepared by a similar method as compound 213e to afford a mixture of diastereomers (Syn:anti isomer ratio 1:1) as a creamy white foamy solid (1.05 g, 58%): mp. 124-32° C.; IR (KBr) 3312, 2979, 1790, 1664, 1610, 1532, 1485, 1285, 1120, 1037, 932; $^1$H NMR (D$_6$-DMSO) δ 10.39 (1H, s), 8.71 (0.5H, d), 8.43 (0.5H, d), 7.45 (1H, d), 7.36 (1H, s), 7.04 (1H, d), 6.12 (2H, s), 5.58 (0.5H, d), 5.34 (0.5H, s), 4.95-4.85 (1H, m), 4.70-4.52 (0.5H, m), 4.35-4.10 (1.5H, m), 3.95-3.50 (5H, m), 3.03 (0.5H, dd), 2.90-2.55 (1.5H, m), 2.46-2.20 (2H, m), 2.10-2.40 (4H, m), 1.16-1.13 (3H, 2×t). Anal. Calcd for C$_{23}$H$_{27}$N$_5$O$_9$.0.6H$_2$O: C, 52.29; H, 5.38; N, 13.26. Found: C, 52.53; H, 5.35; N, 12.78. MS (ES$^+$) 519 (M$^+$+2, 27%), 518 (M$^+$+1, 100), 472 (7), 374 (12), 373 (53), 345 (14), 149 (12).

EXAMPLE 31

Compounds 640, 642, 645, 650, 653, 655, 656, 662, 668, 669, 670, 671, 677, 678, 681, 682, 683, 684, 686, 688a, 688b, 6891, 689b, 690a, 690b, 691a, 691b, 695a, 695b, 695c, 692a, 692b, 693 and 694 were prepared as follows.

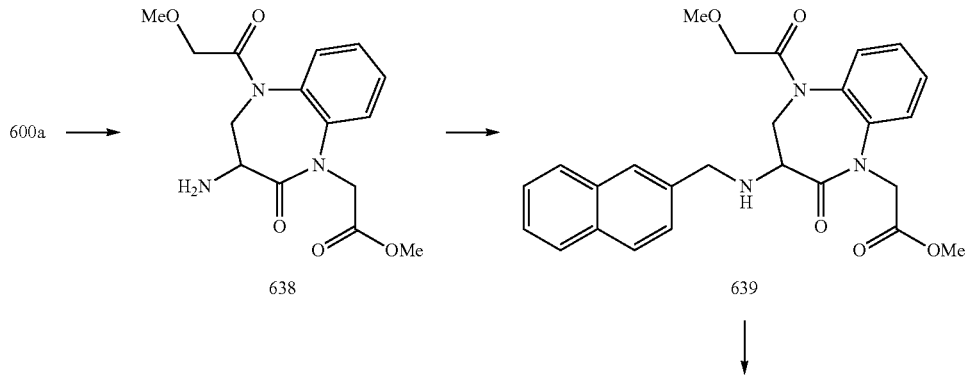

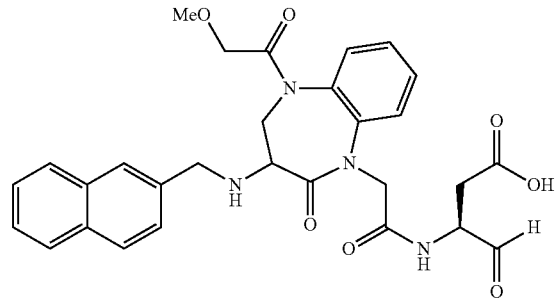

640

(3S)-2-oxo-3-amino-5-methoxyacetyl-2,3,4,5-tetrahydro-1H-1,5-benzodiazepine-1-acetic acid methyl ester (638), was synthesized from 600a by methods similar to those used for making 602m from 600a to afford 2.4 g of 638 as a white solid.

(3S)-2-oxo-3-(2-naphthylmethylene)amino-5-methoxyacetyl-2,3,4,5-tetrahydro-1H-1,5-benzodiazepine-1-acetic acid methyl ester (639). To a solution of 638 (630 mg, 1.76 mmol) and 2-naphthylmethyl bromide (428 mg, 1.94 mmol) in CH$_3$CN was added K$_2$CO$_3$ (608 mg, 4.4 mmol). The resulting mixture was stirred at ambient temperature. After 18 hours, the reaction mixture was diluted with CH$_2$Cl$_2$, washed with water then brine, dried over Na$_2$SO$_4$ then concentrated in vacuo. Flash chromatography (SiO$_2$, 0 to 20% EtOAc/CH$_2$Cl$_2$) afforded 450 mg of 639.

(3S)-3-[(3S)-2-oxo-3-(2-naphthylmethylene)amino-5-methoxyacetyl-2,3,4,5-tetrahydro-1H-1,5-benzodiazepine-1-acetylamino]-4-oxo-butyric acid (640), was synthesized by methods used to make 605v from 602v to afford 205 mg of 640 as a white solid, $^1$H NMR (CDCl$_3$) δ 2.4-2.55 (m, 1H), 2.65-2.8 (m, 1H), 3.2 (s, 3H), 3.72-3.78 (m, 1H), 3.85-4.0 (m, 2H), 4.22-4.28 (d, 1H), 4.26-4.5 (m, 4H), 4.58-4.75 (m, 1H), 4.78-4.85 (m, 1H), 5.0-5.08 (t, 1H), 7.35-7.65 (m, 7H), 7.85-8.02 (m, 4H).

638 ⟶

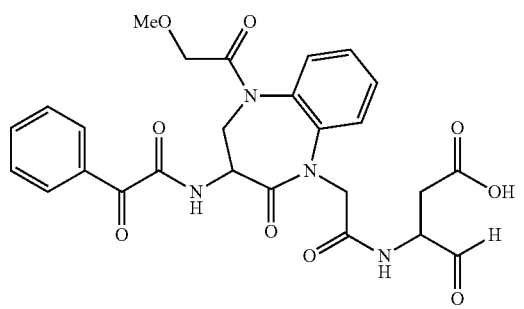

642

(3S)-3-[(3S)-2-oxo-3-benzoylformylamino-5-methoxyacetyl-2,3,4,5-tetrahydro-1H-1,5-benzodiazepine-1-acetylamino]-4-oxo-butyric acid (642), was synthesized from 638 by similar methods used to make 605m to afford 213 mg of 642, $^1$H NMR (CD$_3$OD) δ 2.5 (m, 1H), 2.68 (ddd, 1H), 3.25 (s, 2H), 3.3 (s, 3H), 3.78 (m, 2H), 4.0 (d, 1H), 4.3 (m, 1H), 4.6 (m, 2H), 4.85 (br. s, 2H), 7.08-7.22 (m, 2H), 7.35 (m, 1H), 7.4-7.65 (m, 4H), 7.7 (dd, 1H), 8.1 (dd, 1H).

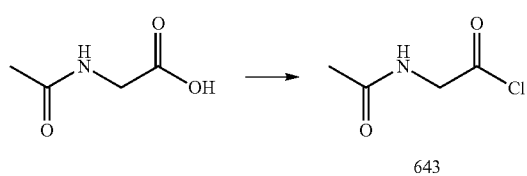

643

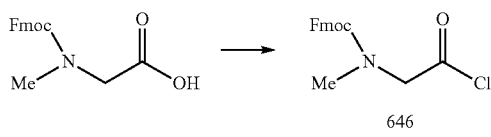

646

600b ⟶

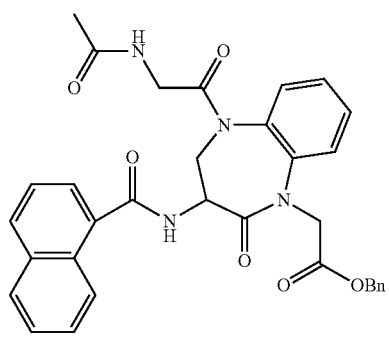

644

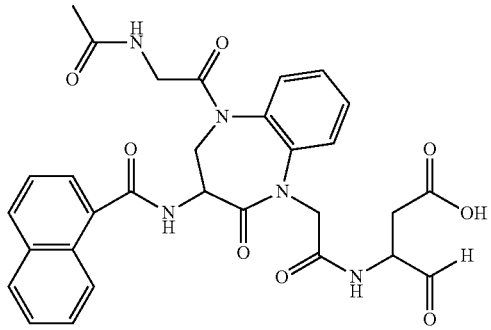

645

2-Acetamido-acetyl chloride (643). To a suspension of N-acetyl glycine (200 mg, 1.7 mmol) in CH$_2$Cl$_2$ (2.5 mLs) containing DMF (0.005 mLs) was added oxalyl chloride (0.450 mLs, 5.1 mmol). After stirring 30 minutes at ambient temperature, the mixture was concentrated to afford 643 as a crude product.

(3S)-2-oxo-3-(1-naphthoyl)amino-5-(2-acetamido)acetyl-2,3,4,5-tetrahydro-1H-1,5-benzodiazepine-1-acetic acid benzyl ester (644), was synthesized from 600b by methods used to make 602d from 600b using 643 to afford 112 mg of 644.

(3S)-3-[(3S)-2-Oxo-3-(1-naphthoyl)amino-5-(2-acetamido)acetyl-2,3,4,5-tetrahydro-1H-1,5-benzodiazepine-1-acetylamino]-4-oxo-butyric acid (645), was synthesized from 644 by methods used to make 605d from 602d to afford 43 mg of 645 as a white solid, $^1$H NMR (CD$_3$OD) δ 1.95 (s, 3H), 2.4 (m, 1H), 2.65 (m, 1H), 3.4 (s, 1H), 3.55 (m, 1H), 3.85 (m, 1H), 4.05 (d, 1H), 4.3 (m, 1H), 4.4-4.6 (m, 2H), 5.0 (m, 1H), 7.4-7.7 (m, 6H), 7.85-8.0 (m, 2H).

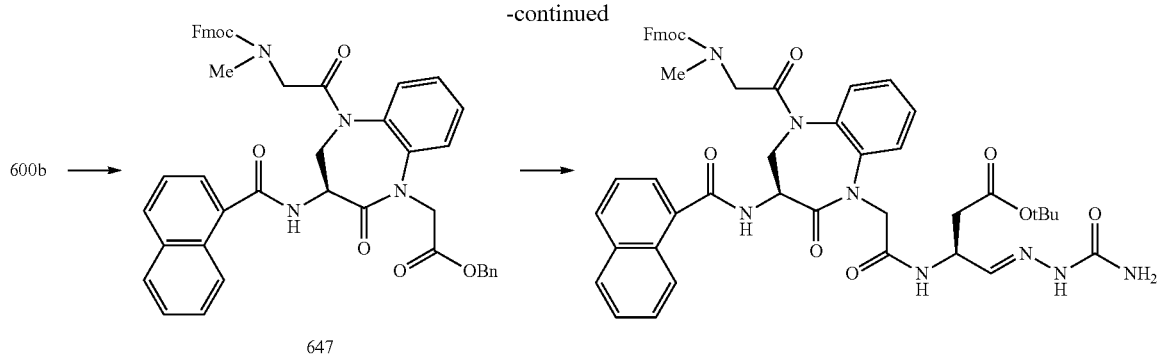

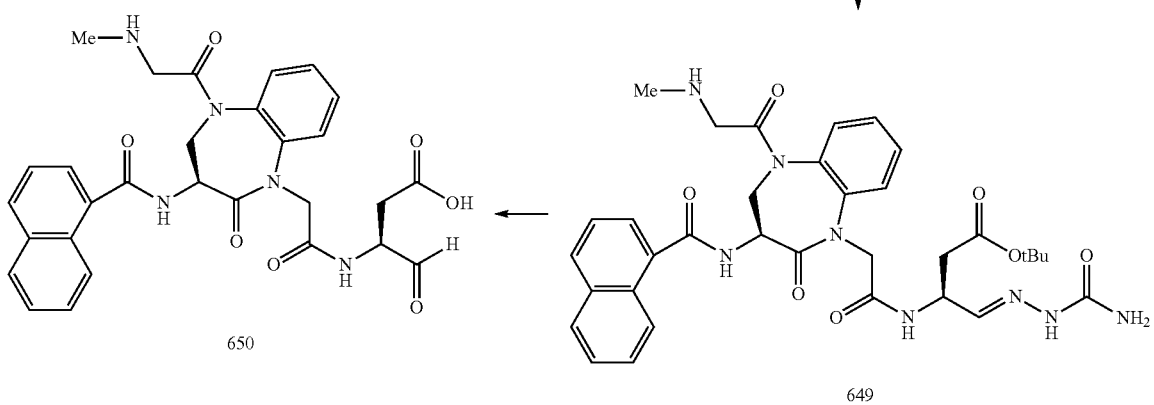

2-(N-Methyl, N-fluorenylmethoxycarbonyl)aminoacetyl chloride (646), was prepared from N-Fmoc-sarcosine by method used to make 643 to afford 646 as a crude product.

(3S)-2-Oxo-3-(1-naphthoyl)amino-5-[2-(N-methyl, N-fluorenylmethoxycarbonyl)amino]acetyl-2,3,4,5-tetrahydro-1H-1,5-benzodiazepine-1-acetic acid benzyl ester (647), was synthesized from 600b by methods used to synthesize 602d from 600b, using 646 to afford 481 mg of 647.

(3S)-3-[(3S)-2-Oxo-3-(1-naphthoyl)amino-5-[2-(N-methyl, N-fluorenylmethoxycarbonyl)amino]acetyl-2,3,4,5-tetrahydro-1H-1,5-benzodiazepine-1-acetylamino]-4-oxo-butyric acid tert-butyl ester semicarbazone (648), was synthesized from 647 by methods used to prepare 604d from 602d to afford 409 mg of 648.

(3S)-3-[(3S)-2-Oxo-3-(1-naphthoyl)amino-5-(2-methyl amino) acetyl-2,3,4,5-tetrahydro-1H-1,5-benzodiazepine-1-acetylamino]-4-oxo-butyric acid tert-butyl ester semicarbazone (649).

A solution of 648 (409 mg, 0.465 mmol) in MeCN:Et$_2$NH (4:1, v/v) was stirred at ambient temperature. After 45 minutes, the reaction mixture was concentrated in vacuo. Flash chromatography (SiO$_2$, 5% to 20% MeOH in CH$_2$Cl$_2$) afforded 241 mg of 649.

(3S)-3-[(3S)-2-Oxo-3-(1-naphthoyl)amino-5-(2-methyl amino) acetyl-2,3,4,5-tetrahydro-1H-1,5-benzodiazepine-1-acetylamino]-4-oxo-butyric acid (650), was synthesized from 649 by methods used to prepare 605d from 604 to afford 179 mg of 650 as a white solid, $^1$H NMR (CD$_3$OD) δ 2.4-2.6 (m, 2H), 2.7 (s, 3H), 3.5 (q, 1H), 3.8 (m, 2H), 4.2-4.4 (m, 2H), 4.3-4.45 (m, 1H), 5.0-5.1 (m, 2H), 7.4-7.7 (m, 6H), 7.85-7.9 (m, 2H), 8.2 (m, 1H).

600b ⟶

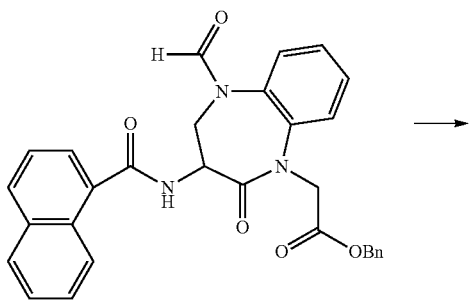

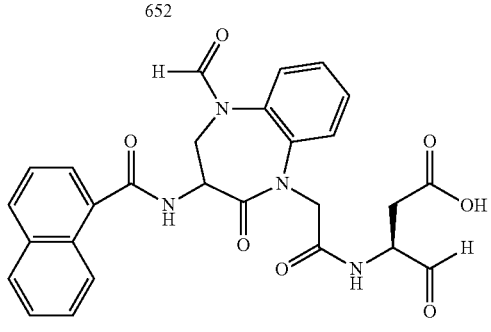

487

(3S)-2-oxo-3-(1-naphthoyl)amino-5-formyl-2,3,4,5-tetrahydro-1H-1,5-benzodiazepine-1-acetic acid benzyl ester (652), was synthesized from 600b by methods similar to those used to make 602n from 600b, using the reagent obtained from reacting DMF with 3 equiv. of oxalyl chloride in a CH$_2$Cl$_2$ solution as R$^3$X, to afford 404 mg of 652.

488

(3S)-3-[(3S)-2-oxo-3-(1-naphthoyl)amino-5-formyl-2,3,4,5-tetrahydro-1H-1,5-benzodiazepine-1-acetylamino]-4-oxo-butyric acid (653), was synthesized from 652 by methods used to prepare 605d from 602d to afford 84 mg of 653 as a white solid, $^1$H NMR (CD$_3$OD) δ 2.3 (m, 1H), 2.55 (dd, 1H), 3.75 (br. s, 1H), 4.25-4.6 (m 5H), 5.15 (m, 1H), 7.2-7.45 (m, 6H), 7.8-7.9 (dd, 3H), 8.1 (s, 1H), 8.2 (m, 2H).

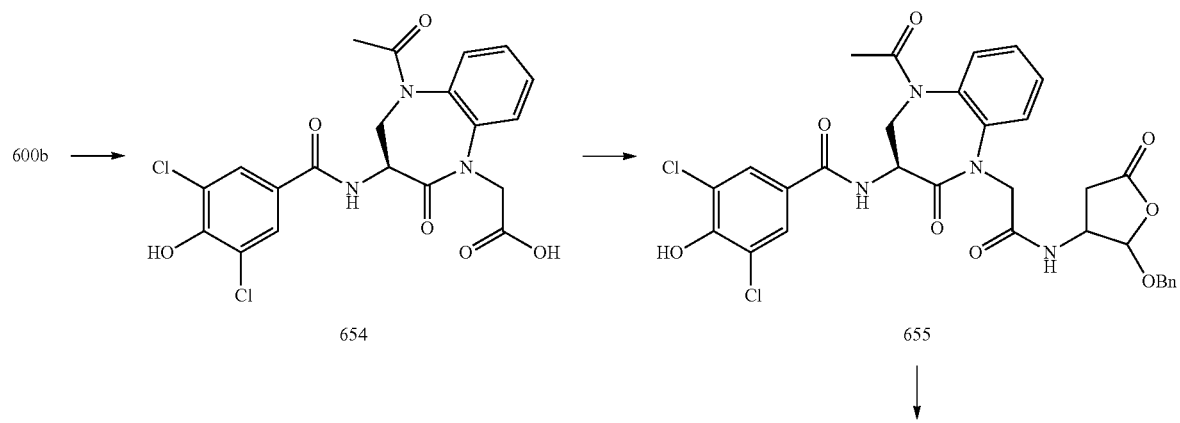

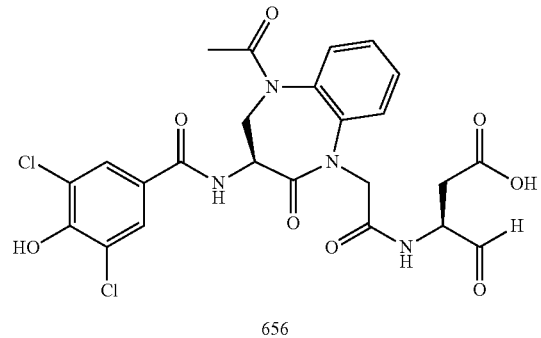

489

(3S)-2-oxo-3-(3,5-dichloro-4-hydroxybenzoyl)amino-5-acetyl-2,3,4,5-tetrahydro-1H-1,5-benzodiazepine-1-acetic acid (654), was synthesized from 600b using methods similar to those used for preparing 603d from 600b to afford 775 mg of 654.

(3S)-2-oxo-3-(3,5-dichloro-4-hydroxybenzoyl)amino-5-acetyl-N-[(2RS,3S)-benzyloxy-5-oxo-tetrahydrofuran-3-yl]-2,3,4,5-tetrahydro-1H-1,5-benzodiazepine-1-acetamide (655), was synthesized from 654 using the method used to prepare 213e to afford 304 mg of 655, $^1$H NMR (CD$_3$OD) δ

490

2.4 (d, 1H), 2.6-2.75 (m, 2H), 3.0 (m, 1H), 3.45 (m, 1H), 3.8 (d, 1H), 4.0 (t, 2H), 4.4 (m, 2H), 4.5-4.55 (m, 2H), 7.2-7.45 (m, 4H), 7.85 (s, 2H).

(3S)-3-[(3S)-2-oxo-3-(3,5-dichloro, 4-hydroxybenzoyl)amino-5-acetyl-2,3,4,5-tetrahydro-1H-1,5-benzodiazepine-1-acetylamino]4-oxo-butyric acid (656), was synthesized from 655 using a method similar to that used to prepare 2002 from 2001 to afford 136 mg of 656 as a white solid, $^1$H NMR (CD$_3$OD). δ 1.85 (s, 3H), 2.5 (m, 1H), 2.65 (m, 1H), 3.7 (m, 1H), 4.3 (m, 1H), 4.55 (m, 2H), 7.4-7.6 (m, 4H), 7.85 (s, 2H).

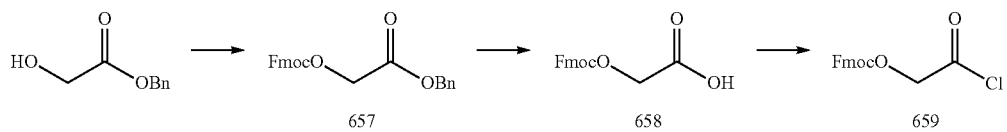

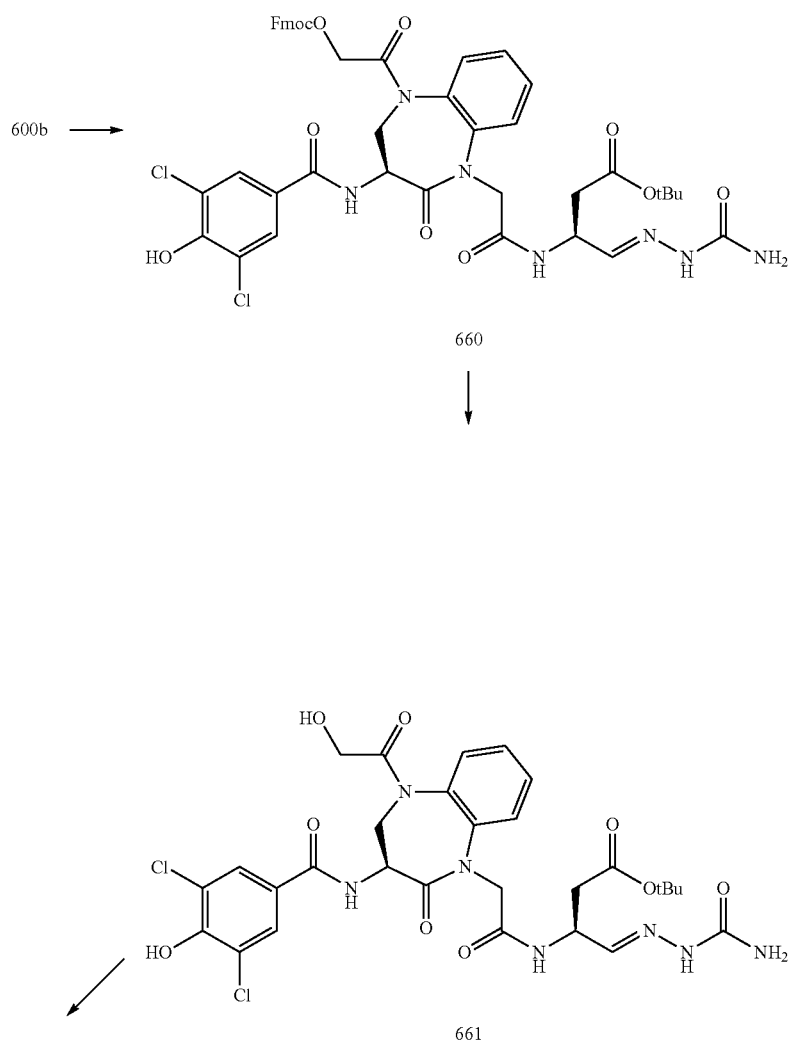

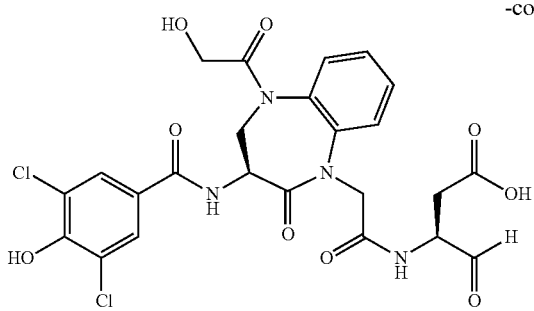

662

2-(Fluorenylmethoxycarbonyl)hydroxyacetic acid benzyl ester (657). To a solution of benzyl glycolate (6.0 g, 36.1 mmol) in CH$_2$Cl$_2$, cooled via ice-water bath, was added fluorenylmethoxy chloroformate (14 g, 1.5 equiv.) then diisopropylethylamine (9 mLs, 1.5 equiv.). After 1 hour, reaction mixture was poured into a saturated aqueous solution of ammonium chloride and extracted with CH$_2$Cl$_2$, dried over Na$_2$SO$_4$ then concentrated in vacuo. The product was triturated from MeOH to obtain 2.2 g of 657 as a first crop of white solid.

2-(Fluorenylmethoxycarbonate) acetic acid (658). To a solution of 657 (2.2 g, 5.93 mmol) in tetrahydrofuran was added 5% Pd/C (220 mg). The resulting suspension was vigorously stirred under hydrogen atmosphere. After 90 min, the reaction mixture was filtered through Celite. The filtrate was poured into saturated aqueous NaHCO$_3$ and washed twice with EtOAc. The aqueous layer was then acidified and the product extracted twice with CH$_2$Cl$_2$, dried over Na$_2$SO$_4$ and concentrated in vacuo to afford 1.46 g (88%) of 658 as a white solid.

2-(Fluorenylmethoxycarbonate) acetyl chloride (659), was prepared from 658 by the method used to prepare 643 to afford 659 as a crude product.

(3S)-3-[(3S)-2-oxo-3-(3,5-dichloro-4-hydroxybenzoyl)amino-5-(2-fluorenylmethoxycarbonate)acetyl-2,3,4,5-tetrahydro-1H-1,5-benzodiazepine-1-acetylamino]-4-oxo-butyric acid tert-butyl ester semicarbazone (660), was synthesized from 600b, using 659, by methods used to prepare 604d from 600b to afford 453 mg of 660.

(3S)-3-[(3S)-2-oxo-3-(3,5-dichloro-4-hydroxybenzoyl)amino-5-(2-hydroxy)acetyl-2,3,4,5-tetrahydro-1H-1,5-benzodiazepine-1-acetylamino]-4-oxo-butyric acid tert-butyl ester semicarbazone (661). A solution of 660 (423 mg) in MeOH:Et$_2$NH (1:1, v/v) was stirred at ambient temperature. After 10 minutes, the reaction mixture was concentrated in vacuo to a small volume. Precipitation by the addition of ether afforded 230 mg of 661.

(3S)-3-[(3S)-2-oxo-3-(3,5-dichloro-4-hydroxybenzoyl)amino-5-(2-hydroxy)acetyl-2,3,4,5-tetrahydro-1H-1,5-benzodiazepine-1-acetylamino]-4-oxo-butyric acid (662), was synthesized from 661 by the methods used to prepare 605d from 604 to afford 37 mg of 662 as a white solid, $^1$H NMR (CD$_3$OD) δ 2.45 (m, 1H), 2.7 (m, 1H), 3.75 (m, 1H), 3.9 (d, 1H), 4.15 (d, 1H), 4.35 (m, 1H), 4.5 (t, 2H), 4.7 (dd, 1H), 7.4-7.6 (m, 4H), 7.85 (s, 2H).

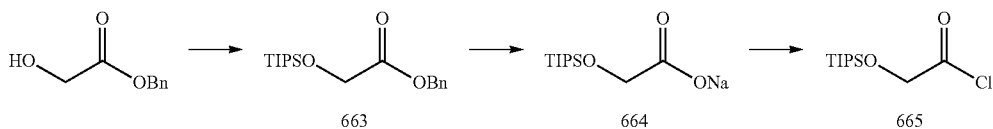

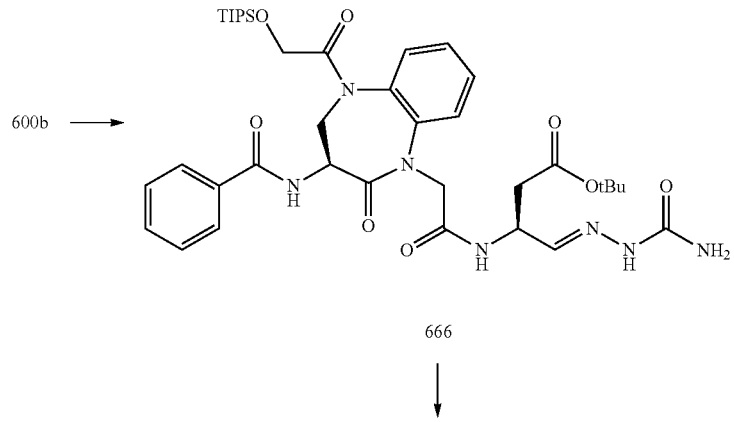

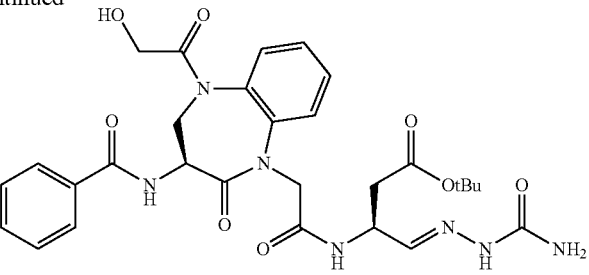

667

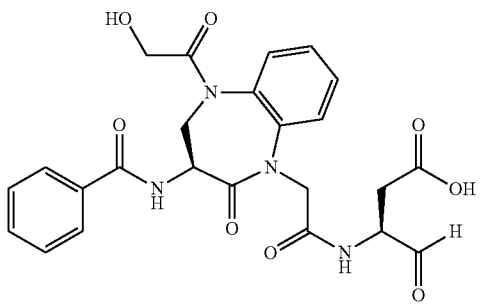

668

2-(Triisopropylsilyloxy)acetic acid benzyl ester (663). To a solution of benzyl glycolate (46.91 g, 0.282 mol) and diisopropylethylamine (74 mLs, 0.423 mol) in CH$_2$Cl$_2$, cooled via water bath, was added a solution of TIPSOTf (95 g, 0.31 mol) in CH$_2$Cl$_2$. The resulting mixture was allowed to warm to ambient temperature then poured into water, washed twice with 10% aqueous NaHSO$_4$, dried over Na$_2$SO$_4$ and concentrated in vacuo. Flash chromatography (SiO$_2$, 0 to 5% EtOAc in hexanes) afforded 71.6 g of 663.

2-(Triisopropylsilyloxy)acetic acid (664). To a solution of 663 (0.4 g, 1.2 mmol) in EtOAc was added 10% Pd/C (33 mg). The resulting suspension was stirred under hydrogen atmosphere. After 15 hours, the reaction mixture was filtered through Celite and the filtrate concentrated in vacuo to afford 0.29 g of an oil. To a solution of this oil in 1,4-dioxane was added NaHCO$_3$ (0.5M, 2.4 mLs). The resulting solution was concentrated in vacuo from toluene to afford 664 as a waxy solid.

2-(Triisopropylsilyloxy)acetyl chloride (665), was synthesized from 664 by a method similar that used to prepare 643 to afford 665 as a crude product.

(3S)-3-[(3S)-2-Oxo-3-benzoylamino-5-(2-triisopropylsilyloxy)acetyl-2,3,4,5-tetrahydro-1H-1,5-benzodiazepine-1-acetylamino]-4-oxo-butyric acid tert-butyl ester semicarbazone (666), was synthesized from 600b, using 665, by methods used to prepare 604d from 600b to afford 131 mg of 666.

(3S)-3-[(3S)-2-oxo-3-benzoylamino-5-(2-hydroxy)acetyl-2,3,4,5-tetrahydro-1H-1,5-benzodiazepine-1-acetylamino]-4-oxo-butyric acid tert-butyl ester semicarbazone (667). To a solution of 666 (131 mg, 0.17 mmol) in tetrahydrofuran, cooled via ice-water bath, was added tetrabutylammonium fluoride (1M, 0.190 mL). After 2 hours the reaction mixture was poured into water, extracted twice with EtOAc, dried over MgSO$_4$ and concentrated in vacuo to afford 63 mg of 667 as a white solid.

(3S)-3-[(3S)-2-Oxo-3-benzoylamino-5-(2-hydroxy)acetyl-2,3,4,5-tetrahydro-1H-1,5-benzodiazepine-1-acetylamino]-4-oxo-butyric acid (668), was synthesized from 667 by the methods used to prepare 605d from 604d to afford 48 mg of 668 as a white solid, $^1$H NMR (CD$_3$OD) δ 2.45 (m, 1H), 2.67 (dddd, 1H), 3.78 (d, 1H), 3.85 (br. m, 1H), 4.05 (d, 1H), 4.28 (m, 1H), 4.5 (m, 2H), 4.65 (m, 1H), 4.95 (br. s, 2H), 7.4-7.5 (m, 4H), 7.52-7.65 (m, 3H), 7.88 (d, 2H).

600b ⟶

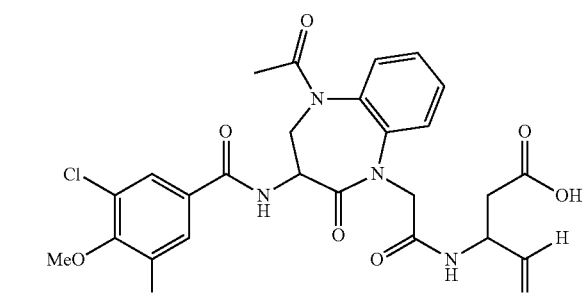

669

(3S)-3-[(3S)-2-oxo-3-(3,5-dichloro-4-methoxybenzoyl)amino-5-acetyl-2,3,4,5-tetrahydro-1H-1,5-benzodiazepine-1-acetylamino]-4-oxo-butyric acid (669), was synthesized from 600b by the methods used to prepare 605d from 600b to afford 63 mg of 669 as a white solid, $^1$H NMR (CD$_3$OD) δ 1.9 (s, 3H), 2.4-2.7 (m, 2H), 3.6-3.7 (m, 2H), 3.9 (s, 3H), 4.2-4.4 (m, 2H), 4.4-4.6 (m, 3H), 7.4-7.8 (m, 4H), 7.9 (s, 2H).

495

600b →

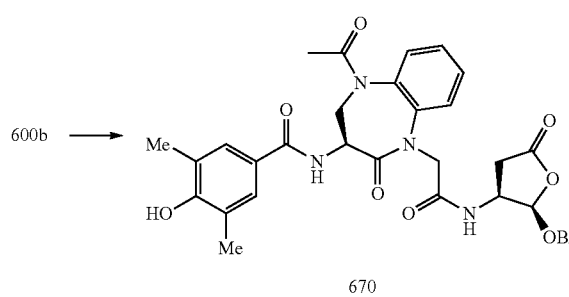

670

↓

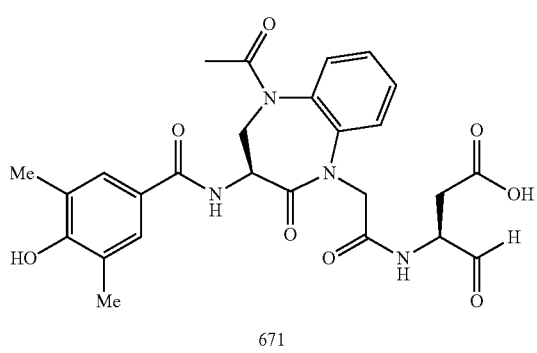

671

496

(3S)-2-oxo-3-(3,5-dimethyl-4-hydroxybenzoyl)amino-5-acetyl-N-[(2RS,3S)-benzyloxy-5-oxo-tetrahydrofuran-3-yl]-2,3,4,5-tetrahydro-1H-1,5-benzodiazepine-1-acetamide (670), was synthesized from 600b by the methods used to prepare 655 from 600b to afford 218 mg of 670 as a white solid, $^1$H NMR (CD$_3$OD) δ 1.7, 1.75 (2s, 3H), 2.15, 2.2 (2s, 6H), 2.4-2.5 (m, 1H), 2.6-2.75 (m, 1H), 3.65-3.75 (m, 2H), 4.2-4.3 (m, 2H), 4.45-4.6 (m, 3H), 7.35-7.6 (m, 4H), 7.5 (s, 2H).

(3S)-3-[(3S)-2-oxo-3-(3,5-dimethyl-4-hydroxybenzoyl)amino-5-acetyl-2,3,4,5-tetrahydro-1H-1,5-benzodiazepine-1-acetylamino]-4-oxo-butyric acid (671), was synthesized from 670 by the methods used to prepare 2002 from 2001 to afford 253 mg of 671 as a white solid, $^1$H NMR (CD$_3$OD) δ 1.9 (s, 3H), 2.25 (s, 6H), 2.4-2.5 (m, 1H), 2.6-2.75 (m, 1H), 3.65-3.75 (m, 2H), 4.2-4.3 (m, 2H), 4.45-4.6 (m, 3H), 7.35-7.6 (m, 4H), 7.5 (s, 2H).

600b →

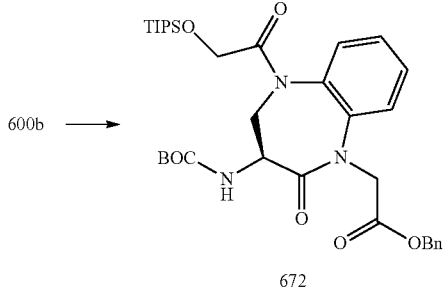

672

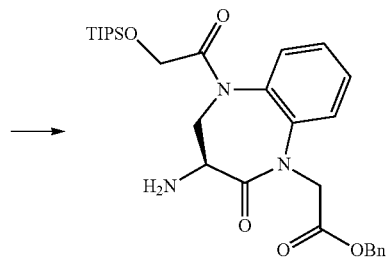

673

↓

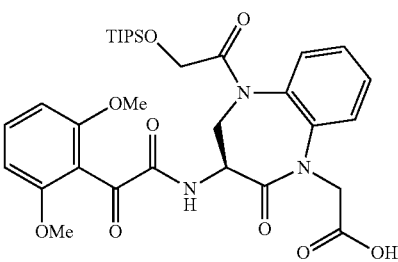

675

↑

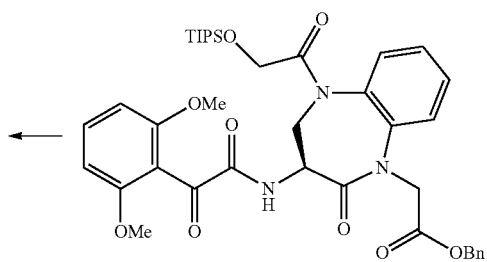

674

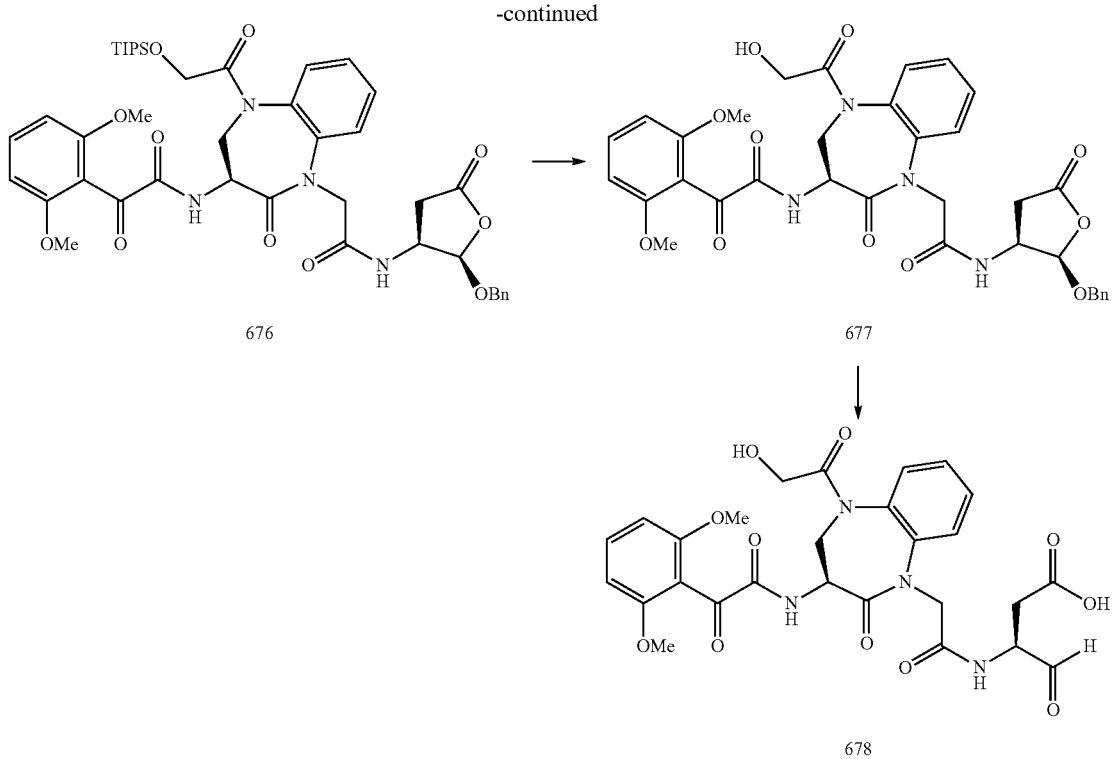

(3S)-2-oxo-3-tert-butoxycarbonylamino-5-(2-triisopropylsilyloxy)acetyl-2,3,4,5-tetrahydro-1H-1,5-benzodiazepine-1-acetic acid benzylester (672), was synthesized from 600b by method 1 used to prepare 602n from 600b using 665 to afford 1.08 g of 672.

(3S)-2-oxo-3-amino-5-(2-triisopropylsilyloxy)acetyl-2,3,4,5-tetrahydro-1H-1,5-benzodiazepine-1-acetic acid benzylester (673). To a solution of 672 (1.08 g, 1.69 mmol) in CH$_2$Cl$_2$ was added 2,6-lutadine (0.8 mL) then TMSOTf (1 mL, 5.1 mmol). After 1 hour, the reaction mixture was poured into NaHCO$_3$ and extracted with CH$_2$Cl$_2$, dried over MgSO$_4$ and concentrated in vacuo to a small volume that was used directly for the next reaction.

(3S)-2-Oxo-3-(1,6-dimethoxybenzoylformyl)amino-5-(2-triisopropylsilyloxy)acetyl-2,3,4,5-tetrahydro-1H-1,5-benzodiazepine-1-acetic acid benzylester (674), was synthesized from 673 by the method used to prepare 602b to afford 0.91 g of 674.

(3S)-2-Oxo-3-(1,6-dimethoxybenzoyl formyl)amino-5-(2-triisopropylsilyloxy)acetyl-2,3,4,5-tetrahydro-1H-1,5-benzodiazepine-1-acetic acid (675). A solution of 674 (0.365 g, 0.5 mmol) in MeOH was stirred with 1N NaOH (1.2 mL, 1.2 mmol). After 16 hours the reaction mixture was concentrated in vacuo then dissolved in water and washed twice with ether. The aqueous layer was acidified with 1N HCl and the product extracted with EtOAc, dried over MgSO$_4$ and concentrated in vacuo to afford 337 mg of 675 as a solid.

(3S)-2-oxo-3-(1,6-dimethoxybenzoylformyl)amino-5-(2-triisopropylsilyloxy)acetyl-N-[(2RS,3S)-benzyloxy-5-oxo-tetrahydrofuran-3-yl]-2,3,4,5-tetrahydro-1H-1,5-benzodiazepine-1-acetamide (676), was synthesized from 675 by the method used to prepare 213e to afford 166 mg of 676 as a white solid.

(3S)-2-oxo-3-(1,6-dimethoxybenzoylformyl)amino-5-(2-hydroxy)acetyl-N-[(2RS,3S)-benzyloxy-5-oxo-tetrahydrofuran-3-yl]-2,3,4,5-tetrahydro-1H-1,5-benzodiazepine-1-acetamide (677). A solution of TBAF (6 mL, 3 mmol) in HOAc (0.46 mL, 8 mmol) was added to 676 (0.213 g, 0.256 mmol). After 16 hours the reaction mixture was poured into EtOAc and washed twice with NaHCO$_3$, once with brine then dried over MgSO$_4$ and concentrated in vacuo to afford 139 mg of 677 as a solid, $^1$H NMR (CDCl$_3$) δ 2.4 (d, 1H), 2.5 (dd, 1H), 2.8 (dd, 1H), 2.92 (dd, 1H), 3.15 (m, 2H), 3.55-3.65 (m, 2H), 3.72 (s, 6H), 3.92 (m, 1H), 4.05 (m, 1H), 4.3 (m, 1H), 4.42 (d, 1H), 4.6 (dd, 1H), 4.65-4.8 (m, 2H), 4.88 (d, 1H), 5.55 (d, 1H), 6.55 (m, 2H), 6.75 (d, 1H), 7.25-7.35 (m, 8H), 7.75 (m, 2H).

(3S)-3-[(3S)-2-oxo-3-(3,5-dimethoxybenzoylformyl)amino-5-(2-hydroxy)acetyl-2,3,4,5-tetrahydro-1H-1,5-benzodiazepine-1-acetylamino]-4-oxo-butyric acid (678), was synthesized by the method used to prepare 667 from 666 to afford 54 mg of 678 as a white solid, $^1$H NMR (CD$_3$OD) δ 2.45 (m, 1H), 2.7 (m, 1H), 3.5 (m, 2H), 3.75 (br. s, 6H), 4.05 (d, 1H), 4.3 (m, 1H), 4.51-4.6 (m, 2H), 4.8 (br. m, 2H), 6.7 (d, 2H), 7.4-7.5 (br. m, 3H), 7.6-7.65 (br. m, 2H).

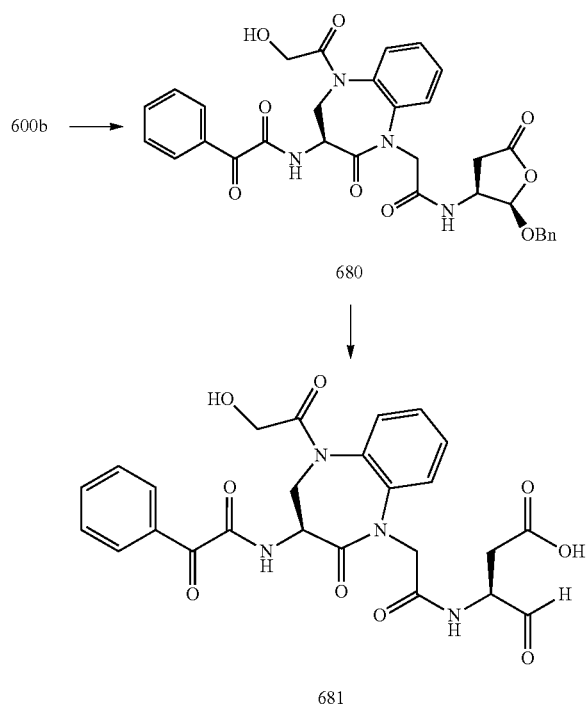

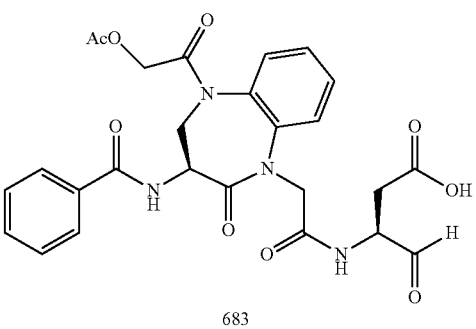

(3S)-2-oxo-3-benzoylamino-5-(2-acetoxy)acetyl-N-[(2RS,3S)-benzyloxy-5-oxo-tetrahydrofuran-3-yl]-2,3,4,5-tetrahydro-1H-1,5-benzodiazepine-1-acetamide (682), was synthesized from 600b by the methods used to prepare 655 from 600b to afford 495 mg of 682 as a white solid, $^1$H NMR (CDCl$_3$) δ 2.00 (s, 3H), 2.05 (s, 3H), 2.47 (d, 1H), 2.58 (dd, 1H), 2.85 (dd, 1H), 2.89 (dd, 1H), 3.9 (m, 2H), 4.05-4.15 (m, 2H), 4.19 (dd, 1H), 4.45 (m, 2H), 4.55-5.05 (m, 8H), 5.55 (d, 1H), 6.85 (d, 1H), 7.15 (d, 1H), 7.25-7.55 (m, 10H), 7.75 (d, 2H).

(3S)-2-oxo-3-benzoylformylamino-5-(2-hydroxy)acetyl-N-(2RS,3S)-benzyloxy-5-oxo-tetrahydrofuran-3-yl]-2,3,4,5-tetrahydro-1H-1,5-benzodiazepine-1-acetamide (680), was synthesized from 600b by the methods used to prepare 677 from 600b to afford 140 mg of 680 as a white solid, $^1$H NMR (CDCl$_3$) δ 2.31 (d, 1H), 2.4 (dd, 2H), 2.75 (dd, 2H), 2.85 (dd, 1H), 3.36 (br. s, 1H), 3.45 (br. s, 1H), 3.6 (br. t, 2H), 3.82 (br. m, 2H), 3.95 (br. d, 2H), 4.35 (m, 2H), 4.42 (d, 1H), 4.55 (m, 1H), 4.70 (d, 1H), 4.82 (br. s, 2H), 5.5 (d, 1H), 6.91 (d, 1H), 7.25 (br. m, 5H), 7.35-7.46 (br. m, 3H), 7.5-7.6 (m, 2H), 8.15 (br. d, 2H).

(3S)-3-[(3S)-2-oxo-3-benzoylamino-5-(2-acetoxy)acetyl-2,3,4,5-tetrahydro-1H-1,5-benzodiazepine-1-acetylamino]-4-oxo-butyric acid (683), was synthesized from 682 by the method used to prepare 2002 from 2001 to afford 82 mg of 683 as a white solid, $^1$H NMR (CD$_3$OD) δ 2.1 (s, 3H), 2.5 (m, 1H), 2.68 (m, 1H), 3.8 (m, 1H), 4.29 (dd, 1H), 4.31 (m, 1H), 4.45 (d, 1H), 4.55 (d, 1H), 4.6 (d, 1H), 4.72 (d, 1H), 4.95 (br. s, 2H), 7.45 (br. m, 2H), 7.52-7.65 (br. m, 5H), 7.88 (d, 2H).

(3S)-3-[(3S)-2-oxo-3-benzoylformylamino-5-(2-hydroxy)acetyl-2,3,4,5-tetrahydro-1H-1,5-benzodiazepine-1-acetylamino]-4-oxo-butyric acid (681), was synthesized from 680 by the method used to prepare 678 from 677 to afford 45 mg of 681 as a grey solid, $^1$H NMR (CD$_3$OD) δ 2.5 (m, 1H), 2.7 (dt, 1H), 3.65-3.85 (br. m, 3H), 4.05 (m, 1H), 4.3 (m, 1H), 4.5-4.7 (br. m, 3H), 4.85 (br. s, 2H), 7.3 (br. m, 2H), 7.4-7.7 (m, 5H), 8.15 (d, 2H).

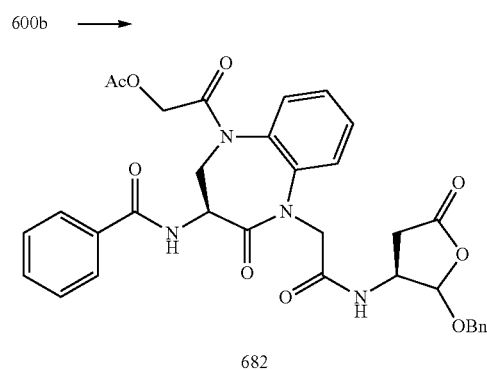

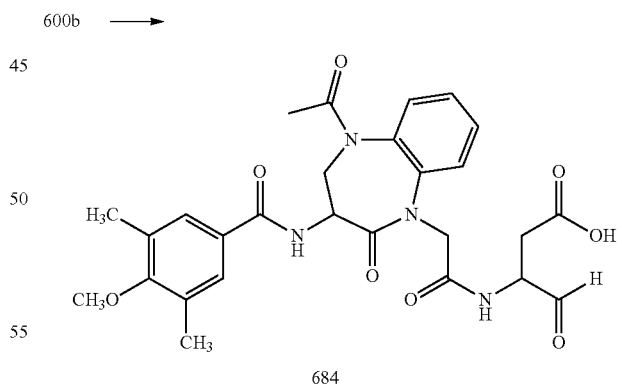

(3S)-3-[(3S)-2-oxo-3-(3,5-dimethyl-4-methoxybenzoyl)amino-5-acetyl-2,3,4,5-tetrahydro-1H-1,5-benzodiazepine-1-acetylamino]-4-oxo-butyric acid (684), was synthesized from 600b by the method used to prepare 605d from 600b to afford 72 mg of 684 as a white solid, $^1$H NMR (CD$_3$OD) δ 1.9 (s, 3H), 2.25 (s, 6H), 2.45 (m, 1H), 2.6 (m, 1H), 3.3 (s, 1H), 3.7 (s, 3H), 4.25 (m, 1H), 4.45-4.6 (m, 3H), 7.4 (br. s, 2H), 7.55 (br. d, 4H).

501

600b →

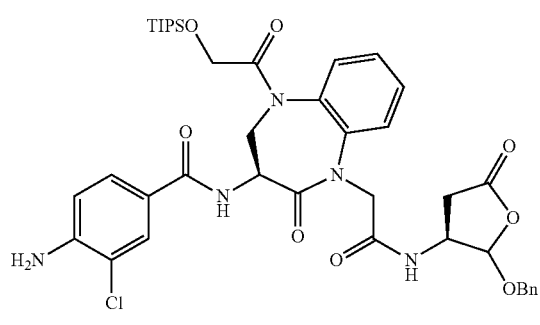

685

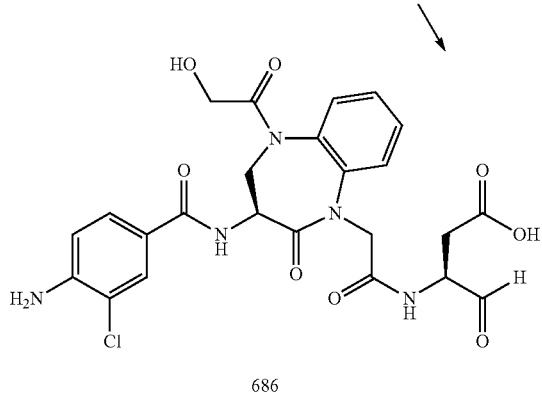

686

(3S)-2-oxo-3-(3-chloro-4-aminobenzoyl)amino-5-(2-tri-isopropylsilyloxy)acetyl-N-[(2RS,3S)-benzyloxy-5-oxo-tetrahydrofuran-3-yl]-2,3,4,5-tetrahydro-1H-1,5-benzodiazepine-1-acetamide (685), was synthesized from 600b by the methods used to prepare 676 from 600b to afford 165 mg of 685.

(3S)-3-[(3S)-2-oxo-3-(3-chloro-4-aminobenzoyl)amino-5-(2-triisopropylsilyloxy)acetyl-2,3,4,5-tetrahydro-1H-1,5-benzodiazepine-1-acetylamino]-4-oxo-butyric acid (686). To a solution of 685 (165 mg, 0.21 mmol) in THF was added a solution of TBAF (1M, 0.21 mL). The product was isolated by filtration after precipitation from reaction mixture. Reverse phase chromatography (10% to 80% MeCN in water/0.1% TFA) afforded 25 mg of 686 as a white solid, $^1$H NMR (CD$_3$OD) δ 2.37-2.42 (m), 2.59-2.70 (m), 3.60-3.89 (m), 4.01 (d), 4.20-4.31 (m), 4.42-4.70 (m), 4.80-5.05 (m), 6.79 (d), 7.32-7.65 (m), 7.81 (s).

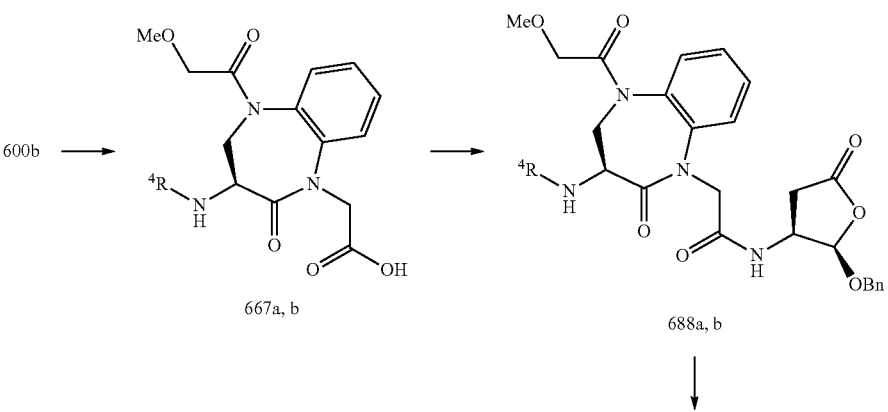

667a, b         688a, b

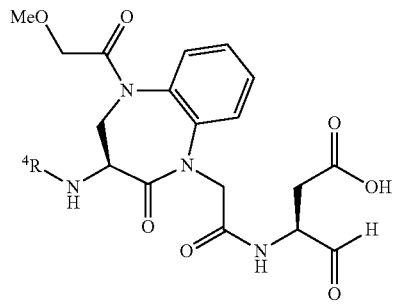

689a, b

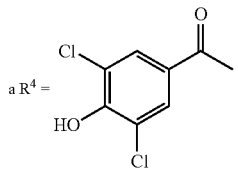

a R⁴ =

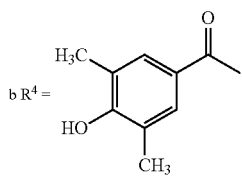

b R⁴ =

(3S)-2-oxo-3-(3,5-dichloro-4-hydroxybenzoyl)amino-5-methoxyacetyl-2,3,4,5-tetrahydro-1H-1,5-benzodiazepine-1-acetic acid (687a), was synthesized from 600b using methods similar to those used for preparing 654 from 600b to afford 1.6 g of 687a.

(3S)-2-oxo-3-(3,5-dimethyl-4-hydroxybenzoyl)amino-5-methoxyacetyl-2,3,4,5-tetrahydro-1H-1,5-benzodiazepine-1-acetic acid (687b), was synthesized from 600b using methods similar to those used for preparing 654 from 600b to afford 1.1 g of 687b.

(3S)-2-oxo-3-(3,5-dichloro-4-hydroxybenzoyl)amino-5-methoxyacetyl-N-[(2RS,3S)-benzyloxy-5-oxo-tetrahydrofuran-3-yl]-2,3,4,5-tetrahydro-1H-1,5-benzodiazepine-1-acetamide (688a). To a solution of (3S,2R,S)-3-alkyloxycarbonylamino-2-benzyloxy-5-oxotetrahydrofuran (Chapman, *Biorg. Med. Chem. Lett.*, 2, pp. 613-618 (1992)) (1.13 g, 1.2 equiv) in CH₂Cl₂ was added triphenylphosphine (423 mg, 0.5 equiv), dimethylbarbituric acid (1.26 g, 2.5 equiv), and tetrakistriphenylphosphine palladium (0) (373 mg, 0.1 equiv). After 5 minutes the reaction mixture was cooled via ice-bath then added a solution of 687a in DMF (1.6 g, 1 equiv), HOBT (480 mg, 1.1 equiv), and EDC (681 mg, 1.1 equiv). The resulting mixture was allowed to stir at ambient temperature. After 16 hours the reaction mixture was poured into NaHSO₄ and extracted twice with EtOAc. The organic layer was washed with NaHCO₃, brine, dried over Na₂SO₄ and concentrated in vacuo. Chromatography (SiO₂, 20% to 100% EtOAc in CH₂Cl₂) afforded 880 mg of 688a as an off-white solid, ¹H NMR (CD₃OD) δ 2.55 (dd, 1H), 2.7 (dd, 1H), 3.0 (m, 1H), 3.6 (m, 1H), 3.75 (d, 1H), 3.9-4.0 (m, 2H), 4.3-4.45 (m, 3H), 4.5-4.6 (m, 3H), 4.7 (m, 2H), 5.35 (s, 1H), 5.55 (d, 1H), 7.1-7.5 (m, 4H), 7.85 (s, 2H).

(3S)-2-oxo-3-(3,5-dimethyl-4-hydroxybenzoyl)amino-5-methoxyacetyl-N-[(2RS,3S)-benzyloxy-5-oxo-tetrahydrofuran-3-yl]-2,3,4,5-tetrahydro-1H-1,5-benzodiazepine-1-acetamide (688b), was synthesized from 687b by the method used to prepare 688a from 687a to afford 960 mg of 688b as an off-white solid, ¹H NMR (CD₃OD) δ 2.6 (dd, 1H), 2.7 (dd, 1H), 3.0 (dd, 1H), 3.2 (s, 3H), 3.7 (m, 3H), 3.9 (m, 2H), 4.4-4.5 (m, 2H), 4.6 (m, 3H), 5.35 (s, 1H), 5.55 (d, 1H), 7.25 (m, 2H), 7.4-7.5 (m, 4H).

(3S)-3-[(3S)-2-oxo-3-(3,5-dichloro-4-hydroxybenzoyl)amino-5-methoxyacetyl-2,3,4,5-tetrahydro-1H-1,5-benzodiazepine-1-acetylamino]-4-oxo-butyric acid (689a), was synthesized from 688a by the method used to prepare 2002 from 2001 to afford 184 mg of 689a as a white solid, ¹H NMR (CD₃OD) δ 2.45 (m, 1H), 2.6 (m 1H), 3.3 (s, 3H), 3.7-3.85 (m, 2H), 4.0 (d, 1H), 4.3 (m, 1H), 4.5-4.6 (m, 3H), 7.3-7.6 (m, 4H), 70.85 (s, 2H).

(3S)-3-[(3S)-2-Oxo-3-(3,5-dimethyl-4-hydroxybenzoyl)amino-5-methoxyacetyl-2,3,4,5-tetrahydro-1H-1,5-benzodiazepine-1-acetylamino]-4-oxo-butyric acid (689b), was synthesized from 688b by the method used to prepare 2002 from 2001 to afford 412 mg of 689b as a white solid, ¹H NMR (CD₃OD) δ 2.5 (m, 1H), 2.7 (m, 1H), 3.3 (s, 3H), 3.7-3.85 (m, 2H), 4.05 (dd, 1H), 4.3 (m, 1H), 4.6 (m, 2H), 7.45-7.4 (m, 2H), 7.5 (s, 2H), 7.55 (m, 2H).

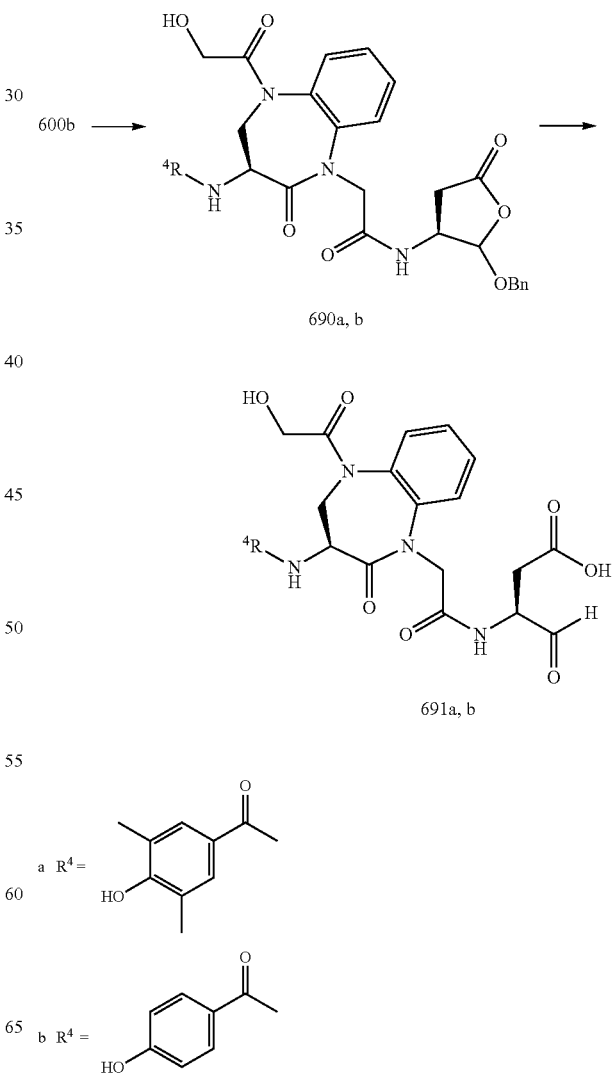

(3S)-2-oxo-3-(3,5-dimethyl-4-hydroxybenzoyl)amino-5-hydroxyacetyl-N-[(2RS,3S)-benzyloxy-5-oxo-tetrahydrofuran-3-yl]-2,3,4,5-tetrahydro-1H-1,5-benzodiazepine-1-acetamide (690a), was synthesized from 600b via methods used to prepare 676 from 600b, 688a from 687a, then 677 from 676 to afford 863 mg of 690a as a white solid, $^1$H NMR (CD$_3$OD) δ 2.2 (s, 6H), 2.45 (d, 0.5H), 2.6-2.9 (m, 1H), 3.05 (dd, 0.5H), 3.65-3.85 (m, 2H), 3.95-4.1 (m, 1H), 4.35-5.0 (m, 7H), 5.35 (s, 0.5H), 5.65 (d, 0.5H), 7.2-7.4 (m, 4H), 7.4-7.7 (m, 7H).

(3S)-2-oxo-3-(4-hydroxybenzoyl)amino-5-hydroxyacetyl-N-[(2RS,3S)-benzyloxy-5-oxo-tetrahydrofuran-3-yl]-2,3,4,5-tetrahydro-1H-1,5-benzodiazepine-1-acetamide (690b), was synthesized from 600b via methods used to prepare 677 from 600b to afford 200 mg of 690b, $^1$H NMR (CD$_3$OD) δ 2.49 (d, 1H), 2.65 (d, 1H), 2.66 (d, 1H), 2.85 (d, 1H), 2.87 (d, 1H), 3.05 (dd, 1H), 3.35 (br. s, 1H), 3.72 (br. s, 2H), 4.01 (m, 2H), 4.45 (br. m, 1H), 4.6 (m, 1H), 4.7 (m, 1H), 4.8 (m, 1H), 4.95 (br. s, 2H), 5.65 (d, 1H), 6.8 (d, 2H), 7.2-7.35 (br. m, 3H), 7.45 (m, 2H), 7.75 (d, 2H).

(3S)-3-[(3S)-2-oxo-3-(3,5-dimethyl-4-hydroxybenzoyl)amino-5-hydroxyacetyl-2,3,4,5-tetrahydro-1H-1,5-benzodiazepine-1-acetylamino]-4-oxo-butyric acid (691a), was synthesized from 690a by the method used to prepare 2002 from 2001 to afford 560 mg of 691a as a white solid, $^1$H NMR (CD$_3$OD) δ 2.15 (s, 6H), 2.45 (m, 1H), 2.65 (m, 1H), 3.55 (m, 1H), 3.7 (d, 1H), 4.0 (d, 1H), 4.25 (m, 1H), 4.5-4.6 (m, 3H), 7.3-7.5 (m, 6H).

(3S)-3-[(3S)-2-oxo-3-(4-hydroxybenzoyl)amino-5-hydroxyacetyl-2,3,4,5-tetrahydro-1H-1,5-benzodiazepine-1-acetylamino]-4-oxo-butyric acid (691b), was synthesized from 690b by the method used to prepare 2002 from 2001 to afford 410 mg of 691b as a white solid, $^1$H NMR (CD$_3$OD) δ 2.5 (m, 1H), 2.65 (m, 1H), 3.75 (m, 1H), 3.8 (d, 1H), 4.05 (d, 1H), 4.25 (m, 1H), 4.5 (m, 1H), 4.6 (m, 1H), 4.95 (br. s, 2H), 6.8 (d, 2H), 7.45 (m, 2H), 7.6 (m, 2H), 7.75 (d, 2H).

(3S)-2-oxo-3-benzoylamino-5-hydroxyacetyl-N-[(2RS,3S)-benzyloxy-5-oxo-tetrahydrofuran-3-yl]-2,3,4,5-tetrahydro-1H-1,5-benzodiazepine-1-acetamide (695a), was synthesized from 600b via methods used to prepare 677 from 600b to afford 75 mg of 695a, $^1$H NMR (CD$_3$OD) δ 2.2 (s, 6H), 2.45 (m, 1H), 2.6 (m, 1H), 3.65 (m, 1H), 3.75 (d, 1H), 4.0 (d, 1H), 4.28 (m, 1H), 4.5 (m, 3H), 7.4-7.6 (m, 6H).

(3S)-2-Oxo-3-(4-acetamidobenzoyl)amino-5-hydroxyacetyl-N-[(2RS,3S)-benzyloxy-5-oxo-tetrahydrofuran-3-yl]-2,3,4,5-tetrahydro-1H-1,5-benzodiazepine-1-acetamide (695b), was synthesized from 600b via methods used to prepare 677 from 600b to afford 880 mg of 695b, $^1$H NMR (CDCl$_3$) δ 2.1 (s, 3H), 2.25-2.5 (m, 2H), 2.8-2.92 (m, 0.5H), 3.15-3.2 (m, 0.5H), 3.45-3.6 (m, 2H), 3.75-3.95 (m, 2H), 4.15-4.25 (m, 1H), 4.35-4.6 (m, 2H), 4.6-4.88 (m, 3H), 5.22 (s, 0.25H), 5.33 (s, 0.25H), 5.52-5.58 (d, 0.5H), 7.15-7.45 (m, 9.5H), 7.5-7.75 (m, 5H), 8.3-8.35 (m, 0.5H), 9.08-9.18 (m, 1H).

(3S)-2RS-Oxo-3-(3,5-dimethyl-4-hydroxybenzoyl)amino-5-hydroxyacetyl-N-(2-benzyloxy-5-oxo-tetrahydrofuran-3-yl)-2,3,4,5-tetrahydro-1H-1,5-benzodiazepine-1-acetamide (695c), was synthesized from 600b via methods used to prepare 677 from 600b to afford 840 mg of 695c, $^1$H NMR (CDCl$_3$) δ 2.23 (s, 3H), 2.26 (s, 3H), 2.45-2.62 (m, 1H), 2.8-2.9 (dd, 0.5H), 2.9-3.05 (dd, 0.5H), 3.45-3.63 (m, 1H), 3.64 (s, 1.5H), 3.68 (s, 1.5H), 3.78-4.05 (m, 2H), 4.2-4.33 (m, 1H), 4.4-4.63 (m, 2H), 4.65-4.94 (m, 2H), 4.95-5.1 (m, 1H), 5.45 (s, 0.5H), 5.5-5.6 (d, 0.5H), 6.9-6.95 (d, 1H), 7.25-7.7 (m, 12H).

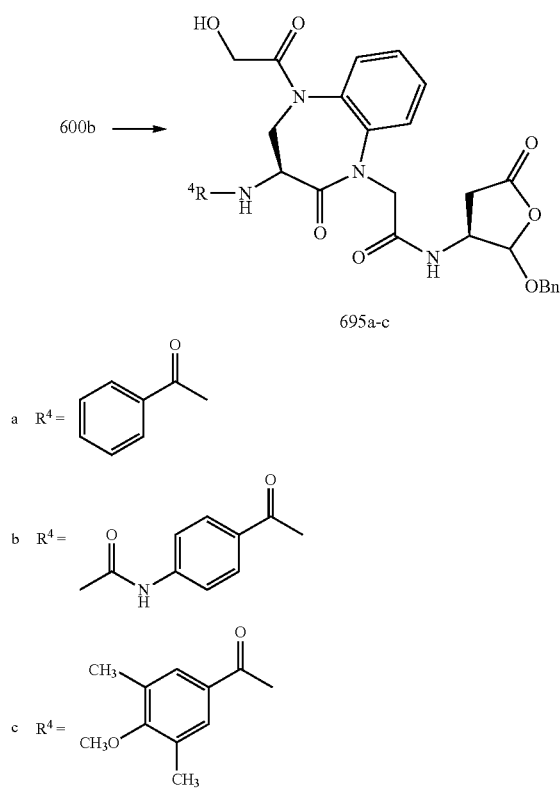

695a-c

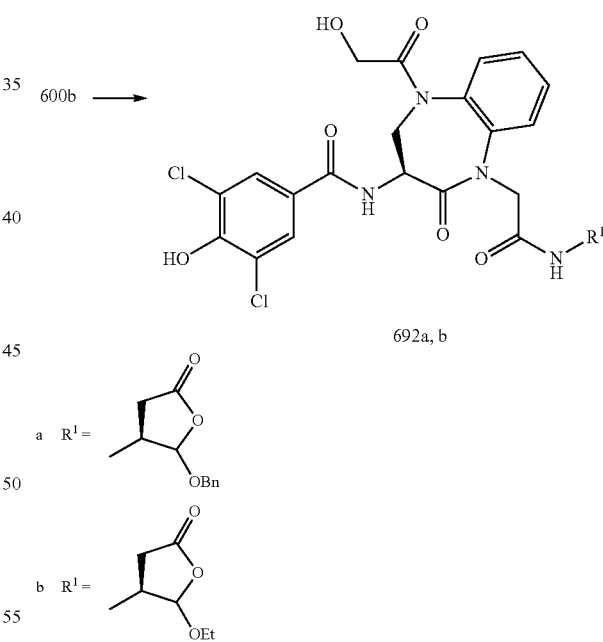

692a, b (3S)-2-oxo-3-(3,5-dichloro-4-hydroxybenzoyl)amino-5-hydroxyacetyl-N-[(2RS,3S)-benzyloxy-5-oxo-tetrahydrofuran-3-yl]-2,3,4,5-tetrahydro-1H-1,5-benzodiazepine-1-acetamide (692a), was synthesized from 600b via methods used to prepare 661 from 600b, excluding steps used to make 604d from 603d, using instead the method to prepare 688a from 687a to afford 854 mg of 692a, $^1$H NMR (CD$_3$OD) δ 2.45 (d, 1H), 2.6 (m, 1H), 2.7 (m, 1H), 3.0 (m, 1H), 3.5-3.7 (m, 4H), 4.0 (q, 2H), 4.45 (m, 3H), 4.55 (m, 4H), 5.35 (s, 1H), 5.6 (d, 1H), 7.2-7.5 (m, 9H), 7.85 (s, 2H).

(3S)-2-Oxo-3-(3,5-dimethyl-4-hydroxybenzoyl)amino-5-hydroxyacetyl-N-[(2RS,3S)-ethoxy-5-oxo-tetrahydrofuran-3-yl]-2,3,4,5-tetrahydro-1H-1,5-benzodiazepine-1-acetamide (692b), was synthesized from 600b via methods used to prepare 661 from 600b, excluding steps used to make 604d from 603d, using instead the method to prepare 688a from 687a to afford 207 mg of 692b, $^1$H NMR (CD$_3$OD) δ 1.05 (t, 3H), 1.15 (t, 3H), 2.45 (d, 1H), 2.55 (m, 1H), 2.7 (m, 1H), 3.55 (m, 2H), 3.6-3.75 (m, 5H), 4.0 (dd, 2H), 4.3 (d, 1H), 4.4-4.7 (m, 5H), 5.25 (s, 1H), 5.5 (d, 1H), 7.25-7.6 (m, 4H), 7.85 (s, 2H).

600b →

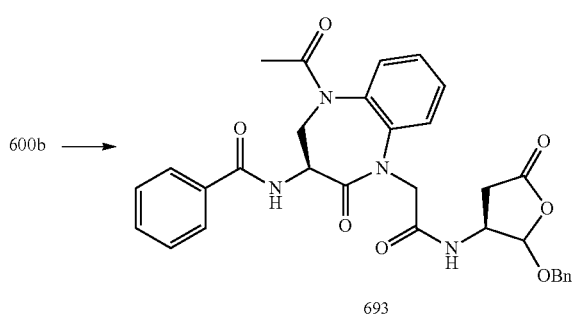

693

(3S)-2-oxo-3-benzoylamino-5-acetyl-N-[(2RS,3S)-benzyloxy-5-oxo-tetrahydrofuran-3-yl]-2,3,4,5-tetrahydro-1H-1,5-benzodiazepine-1-acetamide (693), was synthesized from 600b via methods used to prepare 688a from 600b to afford 30 mg of 693, $^1$H NMR (CD$_3$OD) δ 1.7 (s, 3H), 1.8 (s, 3H), 2.51 (d, 1H), 2.6 (m, 1H), 2.85 (m, 1H), 3.0 (m, 1H), 3.75 (br. d, 2H), 4.0-4.1 (dd, 2H), 4.5-5.0 (m, 6H), 5.45 (s, 1H), 5.55 (s, 1H), 7.15-7.85 (m, 14H).

691c →

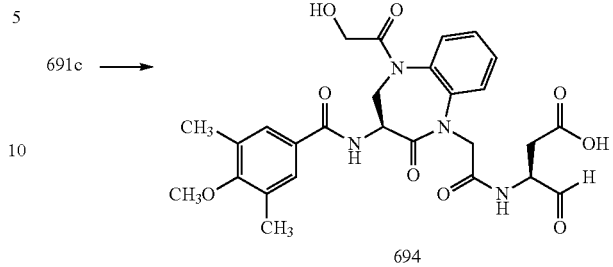

694

(3S)-3-[(3S)-2-oxo-3-(3,5-dimethyl-4-methoxybenzoyl)amino-5-hydroxyacetyl-2,3,4,5-tetrahydro-1H-1,5-benzodiazepine-1-acetylamino)]4-oxo-butyric acid (694), was synthesized from 691c by the method used to prepare 2002 from 2001 to afford 380 mg of 694 as a white solid, $^1$H NMR (CD$_3$OD) δ 2.25 (s, 6H), 2.45 (m, 1H), 2.65 (m, 1H), 3.65 (m, 5H), 4.0 (d, 1H), 4.28 (m, 1H), 4.55 (d, 2H), 4.95 (m, 1H), 7.4-7.6 (m, 6H).

Compounds 700-711 were prepared by methods similar to the methods used to prepare compounds 619-635 (see, Example 13). Physical data for compounds 700-711 is listed in Table 25.

Compounds 910-915 and 918-921 were prepared as described below. Physical data for these compounds is listed in Table 26.

TABLE 25

| Compound | Structure | MF | MW | HPLC RT min (method) Purity | MS (M + Na)+ |
|---|---|---|---|---|---|
| 700 | 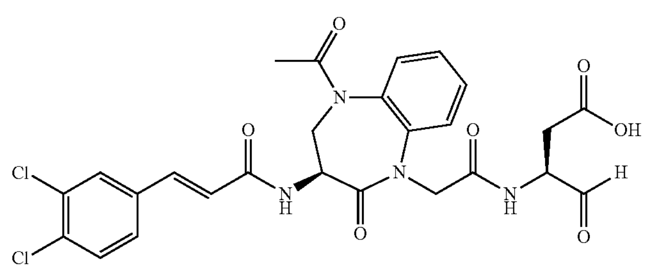 | C26H24Cl2N4O7 | 575.41 | 14.061 (2) 97% | 600 |
| 701 | 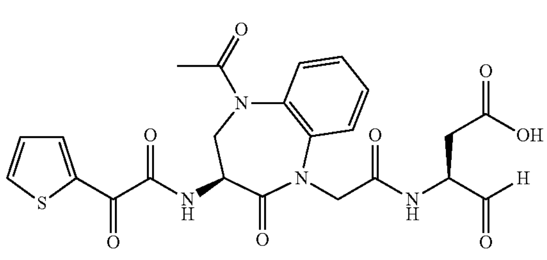 | C23H22N4O8S | 514.52 | 15.589 (1) 97% | 538.8 |

TABLE 25-continued

| Compound | Structure | MF | MW | HPLC RT min (method) Purity | MS (M + Na)+ |
|---|---|---|---|---|---|
| 702 | 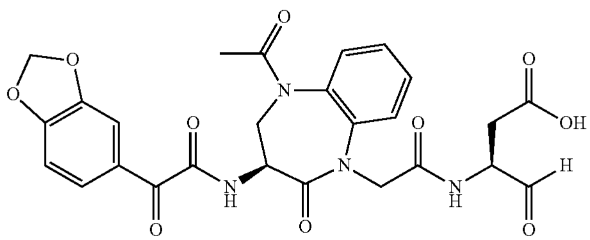 | C26H24N4O10 | 552.50 | 15.855 (1) 98% | 575.9 |
| 703 | 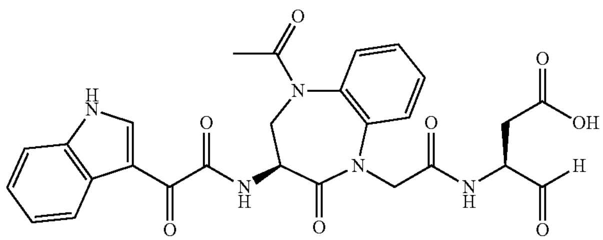 | C27H25N5O8 | 547.53 | 10.315 (2) 97% | 572.1 |
| 704 | 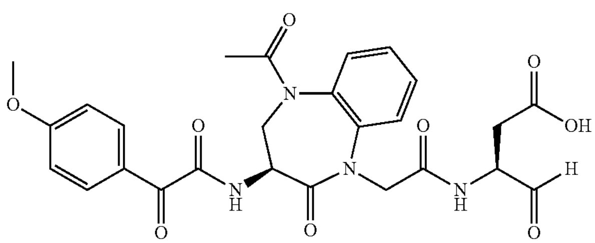 | C26H26N4O9 | 538.52 | 10.475 (2) 96% | 562.1 |
| 705 | 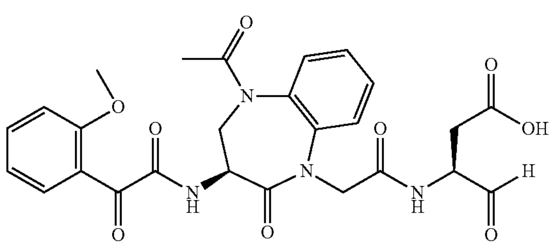 | C26H26N4O9 | 538.52 | 14.260 (1) 72% | 562.1 |
| 706 | 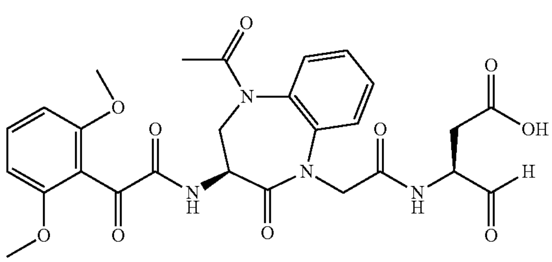 | C27H28N4O10 | 568.55 | 14.836 (1) 97% | 592.4 |
| 707 | 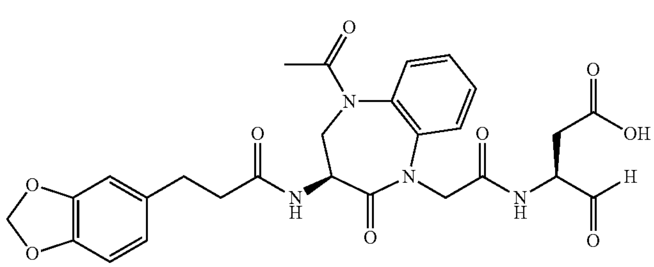 | C27H28N4O9 | 552.55 | 15.952 (1) 98% | 575.9 |

TABLE 25-continued

| Compound | Structure | MF | MW | HPLC RT min (method) Purity | MS (M + Na)+ |
|---|---|---|---|---|---|
| 708 | 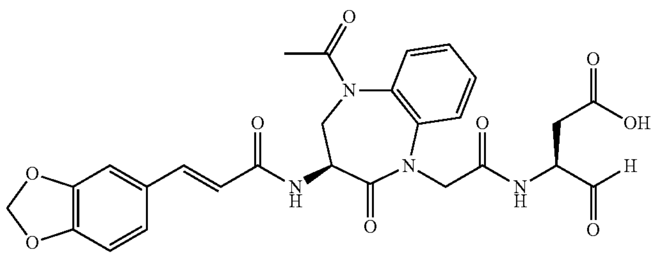 | C27H26N4O9 | 550.53 | 10.731 (2) 93% | 574.6 |
| 709 | 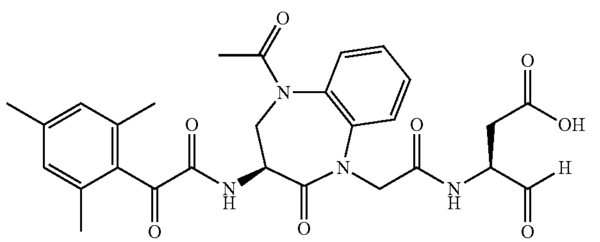 | C28H30N4O8 | 550.57 | 13.192 (2) 95% | 574 |
| 710 | 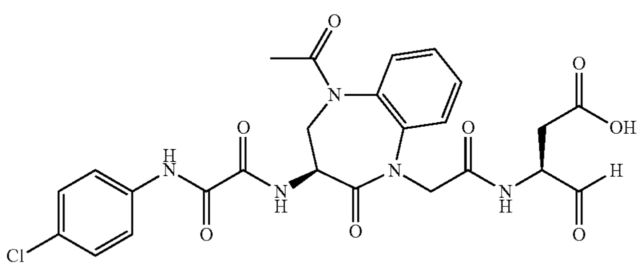 | C25H24ClN5O8 | 557.95 | 12.406 (2) 98% | 582.2 |
| 711 | 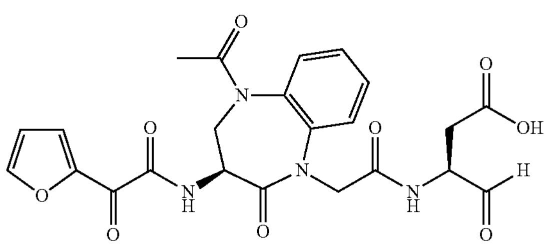 | C23H22N4O9 | 498.45 | 13.072 (1) 99% | 521.9 |

TABLE 26

| Compound | Structure | MF | MW | HPLC RT min (method) Purity | MS (M + Na)+ |
|---|---|---|---|---|---|
| 910 | 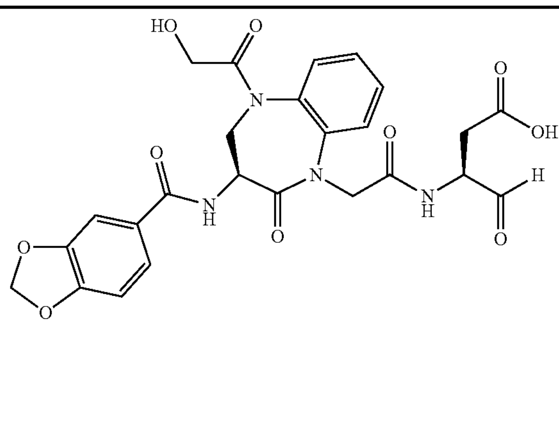 | C25H24N4O10 | 540.49 | 8.172 (2) 99% | 564.4 |

TABLE 26-continued

| Compound | Structure | MF | MW | HPLC RT min (method) Purity | MS (M + Na)+ |
|---|---|---|---|---|---|
| 911 | 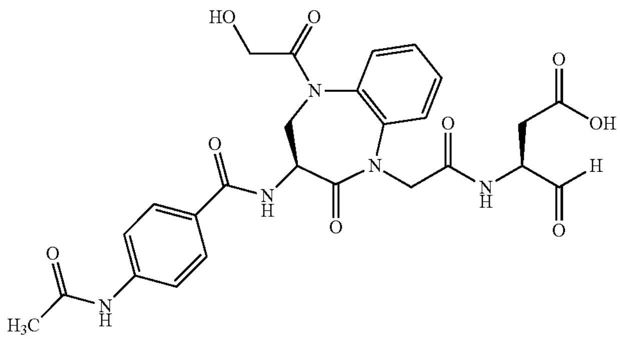 | C26H27N5O9 | 553.53 | 6.949 (2) 99% | 577.5 |
| 912 | 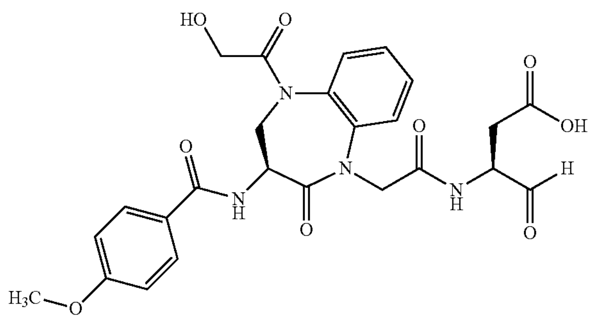 | C25H26N4O9 | 526.51 | 8.317 (2) 99% | 550.7 |
| 913 | 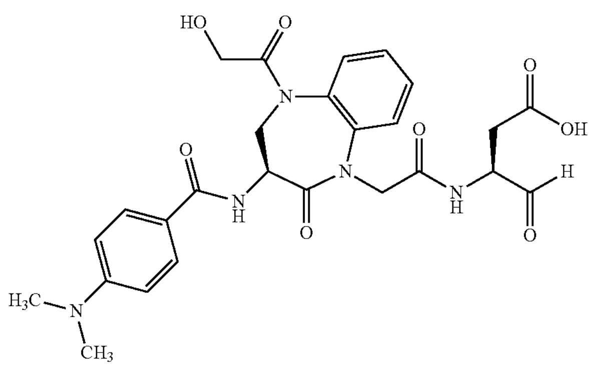 | C26H29NO8 | 539.55 | 6.588 (2) 99% | 563.5 |
| 914 | 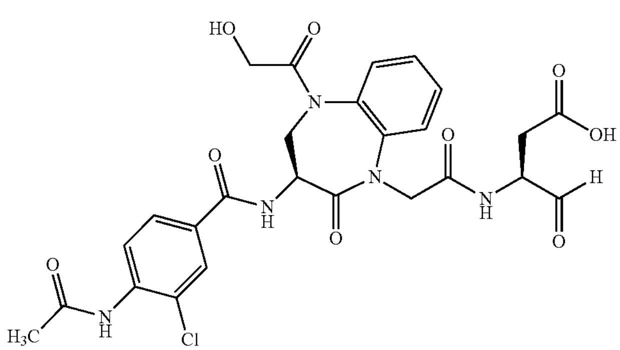 | C26H26ClN5O9 | 587.98 | 7.815 (2) 99% | 612.2 |

TABLE 26-continued

| Compound | Structure | MF | MW | HPLC RT min (method) Purity | MS (M + Na)+ |
|---|---|---|---|---|---|
| 915 | 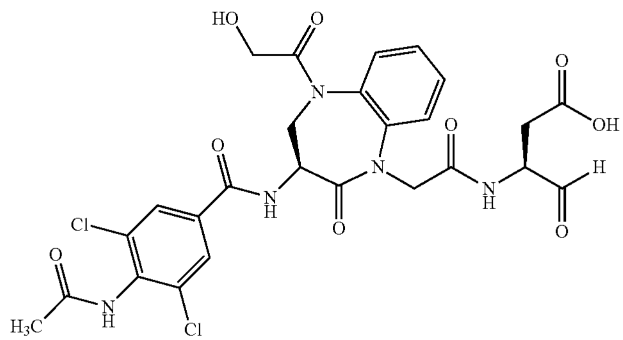 | C26H25Cl2N6O9 | 622.42 | 7.490 (2) 98% | 647 |
| 916/691b | 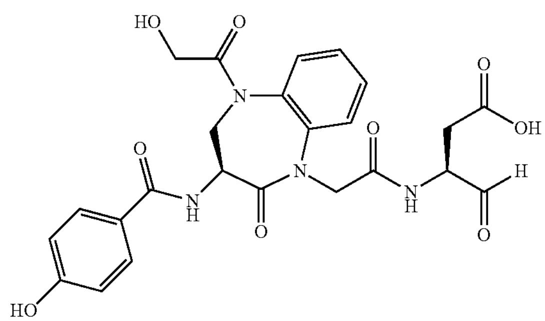 | C24H24N4O9 | 512.48 | 6.331 (2) 98% | 537 |
| 917/691a | 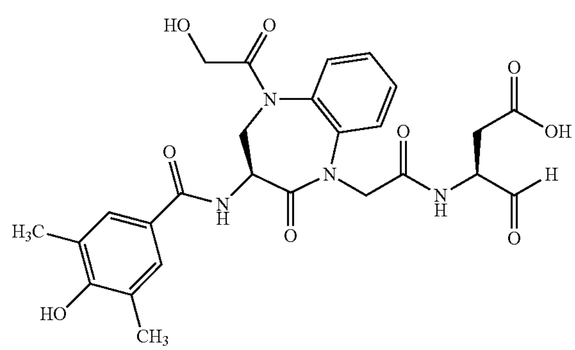 | C26H28N4O9 | 540.53 | 8.114 (2) 99% | 546.9 |
| 918 | 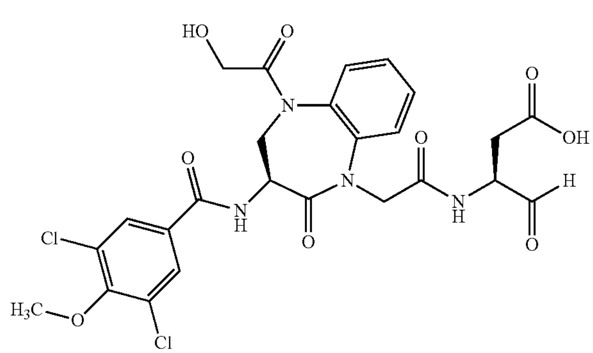 | C25H24Cl2N5O9 | 595.40 | 11.817 (2) 99% | 619.3 |

TABLE 26-continued

| Compound | Structure | MF | MW | HPLC RT min (method) Purity | MS (M + Na)+ |
|---|---|---|---|---|---|
| 919 | 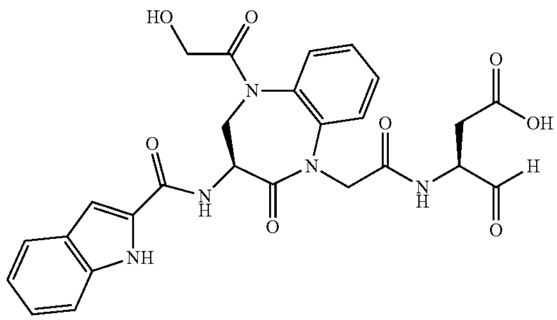 | C26H25N5O8 | 535.52 | 9.709 (2) 91% | 559.7 |
| 920 | 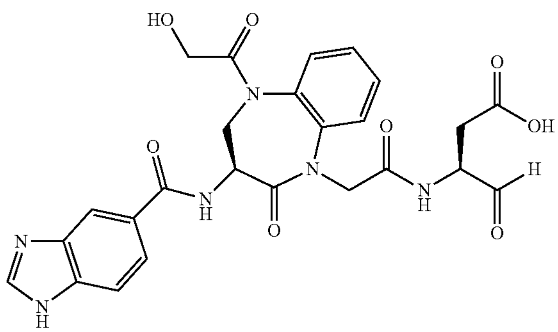 | C25H24N6O8 | 536.51 | 5.494 (2) 98% | 560.6 |
| 921 | 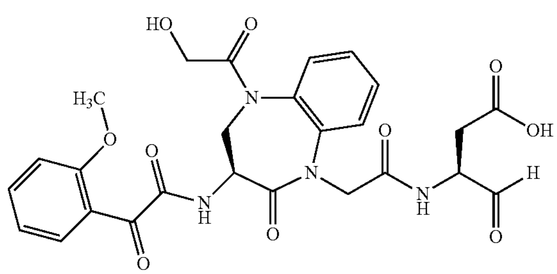 | C26H26N4O10 | 554.52 | 7.827 (2) 96% | 579.1 |
| 922/694 | 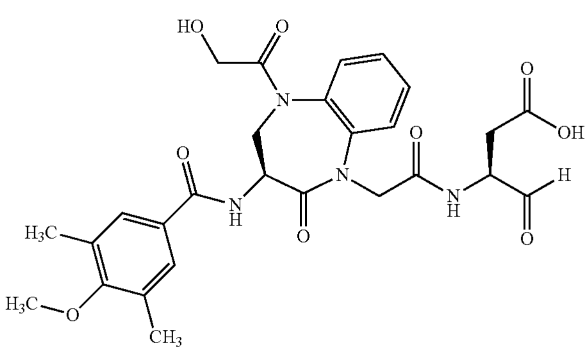 | C27H30N4O9 | 554.56 | 10.024 (2) 99% | 578.8 |

519
520
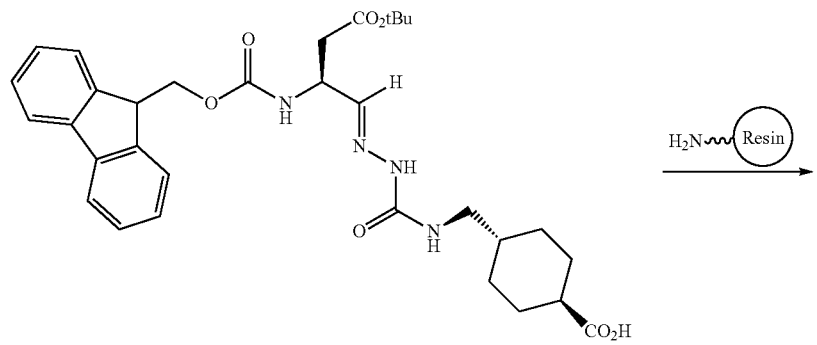
400
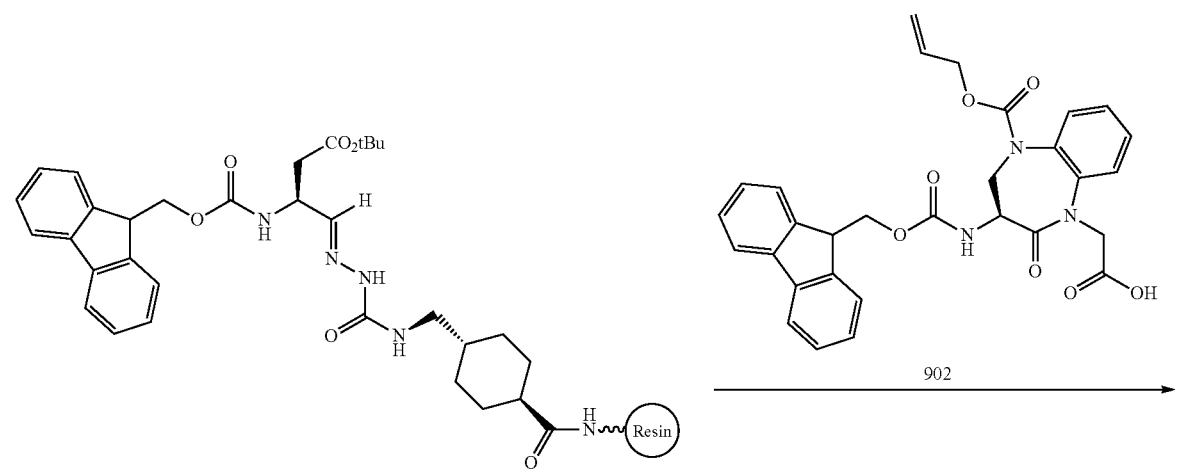
401
902
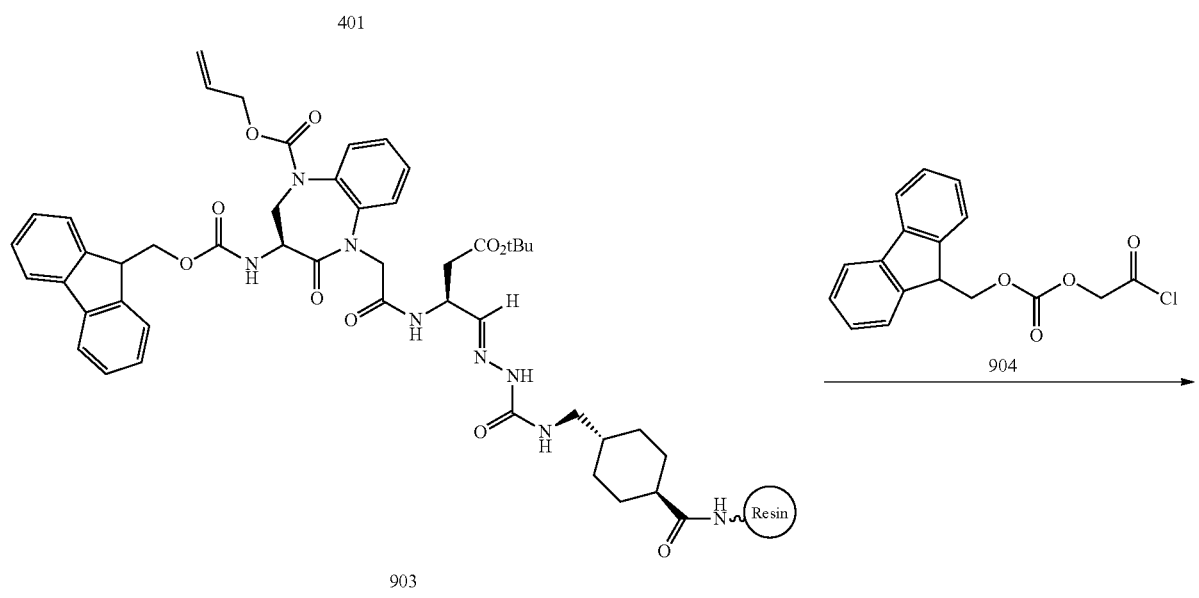
903
904

-continued

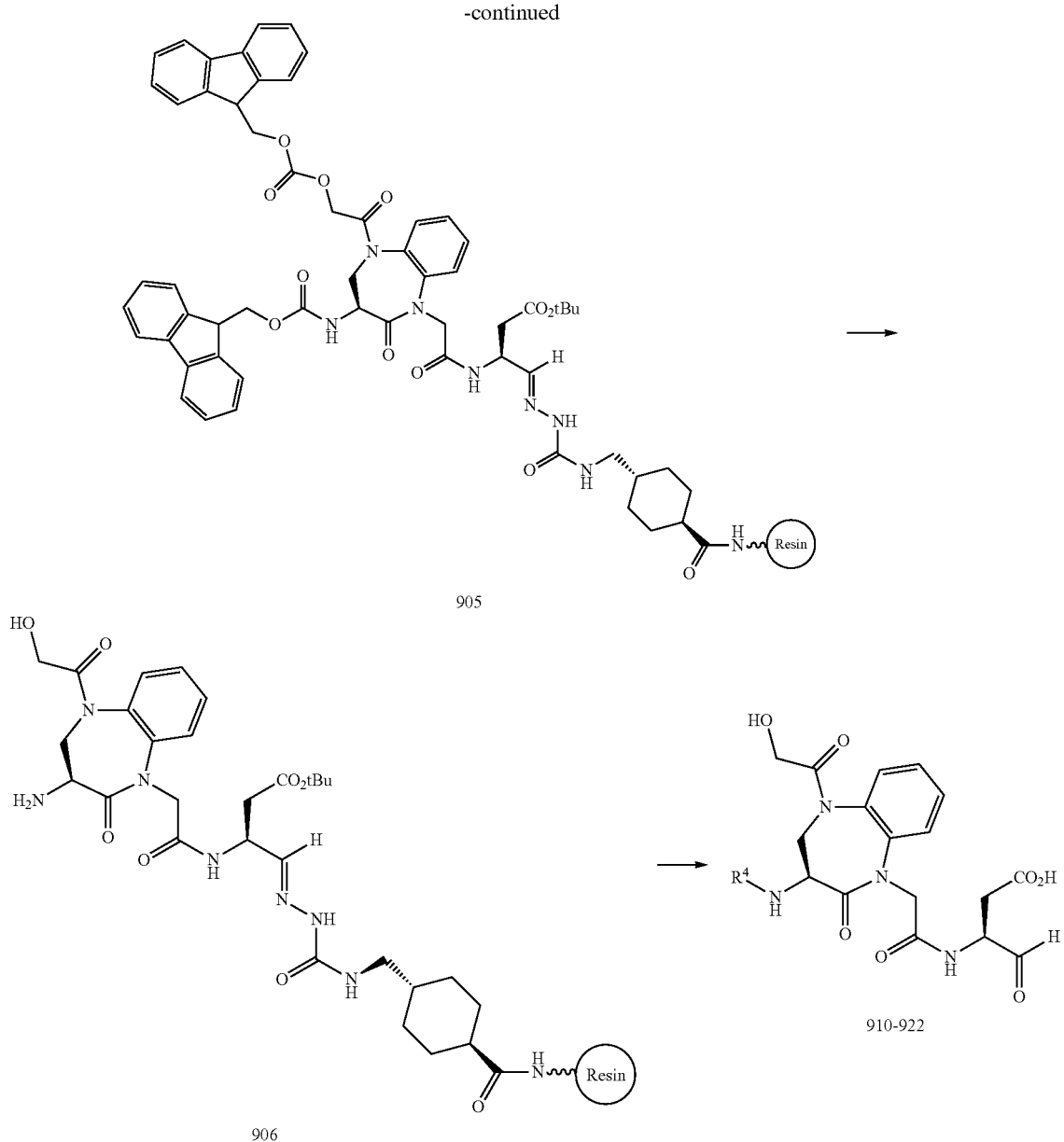

Step A. Synthesis of 401. TentaGel S® NH$_2$ resin (0.25 mmol/g, 6.8 g) was placed in a glass shaker vessel and washed with dimethylacetamide (3×20 mL). To a solution of 400 (1.70 g, 2.9 mmol, prepared from (3S)3-(fluorenylmethyloxycarbonyl)-4-oxobutryic acid t-butyl ester according to A. M. Murphy et. al. *J. Am. Chem. Soc.*, 114, 3156-3157 (1992)) in dimethylacetamide (15 mL) was added O-benzotriazole-N,N,N',N'-tetramethyluronium hexafluorophosphate (HBTU; 1.09 g, 2.9 mmol), and DIEA (1.0 mL, 5.7 mmol). The solution was added to the resin, followed by dimethylacetamide (5 mL). The reaction mixture was agitated for 3 h at room temperature using a wrist arm shaker. The resin was isolated by suction filtration and washed with dimethylacetamide (6×20 mL). A sample of resin (7.4 mg) was thoroughly washed with 50% methanol in dichloromethane and dried under suction. Deprotection of the Fmoc group using 20% piperidine in dimethylacetamide (10.0 mL) and UV analysis of the solution revealed a substitution of 0.19 mmol g$^{-1}$.

Step B. Synthesis of 903. Resin 401 was deprotected with 20% (v/v) piperidine/dimethylacetamide (20 mL) for 10 min (shaking) and then for 10 min with fresh piperidine reagent (20 ml). The resin was then washed with dimethylacetamide (6×20 ml). A solution of 902 (1.52 g, 2.81 mmol) was treated with HBTU (1.07 g, 2.83 mmol) and DIEA (1.0 mL, 5.7 mmol) and transferred to the resin, followed by dimethylacetamide (5 mL). The reaction mixture was agitated for 2.5 h at room temperature using a wrist arm shaker. The resin was isolated by suction filtration and washed with dimethylacetamide (4×20 mL) and dichloromethane (4×20 mL), and dried under nitrogen purge. Resin substitution was performed as described for 401 and determined to be 0.169 mmol g$^{-1}$.

Step C. Synthesis of 905. Resin 903 (7.54 g, 1.27 mmol) and dimedone (2.19 g, 15.6 mmol) were placed in a 100 mL round bottomed flask and freshly distilled anhydrous tetrahydrofuran (60 mL) was added. Tetrakis(triphenylphosphine)palladium (0) (0.32 g, 0.28 mmol) was added and the nitrogen blanketed, sealed reaction was agitated for 15 h on a wrist action shaker. The resin was filtered, washed with dimethylacetamide (4×20 mL), dichloromethane (4×20 mL) and dimethylacetamide (1×20 mL). Sufficient dimethylacetamide was added to the resin to obtain a slurry followed by pyridine (1.5 mL, 18.5 mmol) and a solution of 904 (5.5 mmol) in dichloromethane (10 mL). The reaction was shaken under nitrogen for 8 h, then filtered. The resin was washed with dimethylacetamide (5×20 mL) and dichloromethane (5×20 mL).

Step D. Synthesis of 906. This compound was prepared from resin 905 (0.24 g, 0.038 mmol) using an Advanced ChemTech 396 Multiple Peptide synthesizer. The automated cycles consisted of a resin wash with dimethylformamide (3×1 mL), deprotection with 25% (v/v) piperidine in dimethylformamide (1 mL) for 10 min followed by fresh reagent (1 mL) for 20 min to yield resin 906. The resin was washed with dimethylformamide (3×1 mL) and N-methypyrrolidone (3×1 mL).

Step E. (910-922) Resin 906 was acylated with a solution of 0.4M carboxylic acid and 0.4M HOBT in N-methypyrrolidone (0.5 mL), a solution of 0.4M HBTU in N-methylpyrrolidone (0.5 mL) and a solution of 1.6M DIEA in N-methypyrrolidone (0.25 mL) and the reaction was shaken for 2 hr at room temperature. The resin was washed with N-methylpyrrolidone (1×1 mL), dimethylformamide (4×1 mL), 50% methanol in dichloromethane (5×1 mL) and dried in air. The aldehyde was cleaved from the resin and globally deprotected by treatment with 95% TFA/5% H$_2$O (v/v, 1.5 mL) for 30 min at room temperature. After washing the resin with cleavage reagent (2×1 mL), the combined filtrates were added to cold 1:1 ether:hexane (35 mL) and the resulting precipitate was isolated by centrifugation and decantation. The resulting pellet was dissolved in acetonitrile (0.5 mL) and H$_2$O (0.5 mL) and filtered through 0.45 micron microcentrifuge filters. The compound was purified by semi-preparative RP-HPLC with a Rainin Microsorb™ C18 column (5μ, 21.4×250 mm) eluting with a linear acetonitrile gradient (10%-50%) containing 0.1% TFA (v/v) over 30 min at 12 mL/min. Fractions containing the desired product were pooled and lyophilized to provide 910-922.

Analytical HPLC Methods:
(1) Waters DeltaPak C18, 300 Å (5μ, 3.9×150 mm). Linear acetonitrile gradient (0%-25%) containing 0.1% TFA (v/v) over 14 min at 1 mL/min.
(2) Waters DeltaPak C18, 300 Å (5μ, 3.9×150 mm). Linear acetonitrile gradient (5%-45%) containing 0.1% TFA (v/v) over 14 min at 1 mL/min.

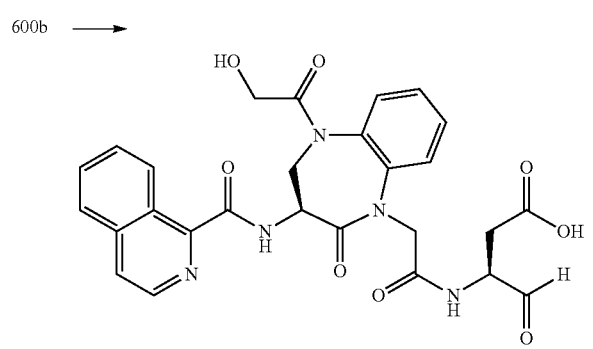

696

(3S)-3-[(3S)-2-oxo-3-(isoquinolin-1-oyl)amino-5-hydroxyacetyl-2,3,4,5-tetrahydro-1H-1,5-benzodiazepine-1-acetylamino]-4-oxo-butyric acid (696) was synthesized from 600b by the method used to prepare 691a from 600b to afford 696. $^1$H NMR (CD$_3$OD) δ 2.45 (m, 1H), 2.7 (m, 1H), 3.75 (d, 1H), 3.95 (q, 1H), 4.05 (d, 1H), 4.3 (m, 1H), 4.45-4.65 (m, 2H), 5.05 (m, 1H), 7.5-7.6 (m, 3H), 7.7 (t, 1H), 7.8 (t, 1H), 7.98 (t, 1H), 8.55 (d, 1H), 9.1 (d, 1H).

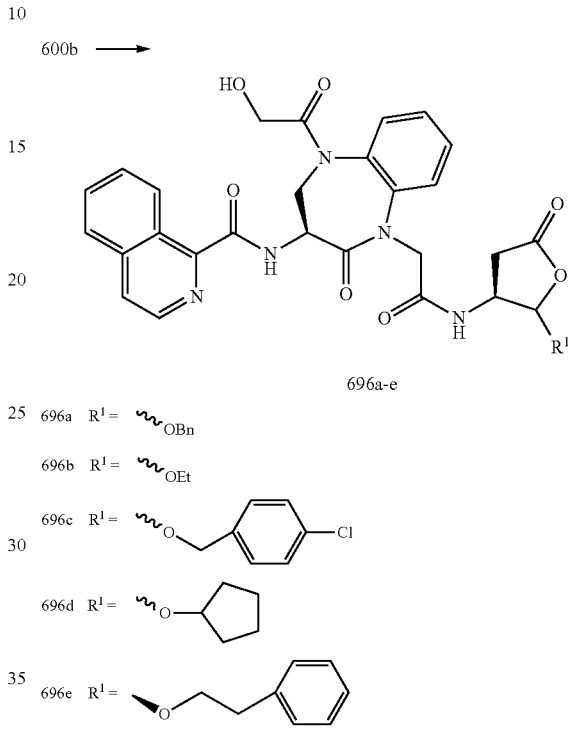

(3S)-2-oxo-3-(isoquinolin-1-oyl)amino-5-hydroxyacetyl-N-[(2RS,3S)-benzyloxy-5-oxo-tetrahydrofuran-3-yl]-2,3,4,5-tetrahydro-1H-1,5-benzodiazepine-1-acetamide (696a) was synthesized from 600b via methods used to prepare 690a from 600b to afford 696a. $^1$H NMR (CDCl$_3$) δ 0.95 (t, 2H), 1.25 (t, 1H), 1.4 (m, 2H), 1.55 (m, 1H), 2.55 (m, 1H), 2.85 (m, 1H), 2.95 (dd, 1H), 3.15 (m, 1H), 3.55 (m, 1H), 3.9 (m, 2H), 4.35 (t, 1H), 4.4-4.55 (m, 2H), 4.75 (m, 1H), 4.8-5.05 (m, 2H), 5.45 (s, 1H), 5.55 (d, 1H), 6.85 (d, 1H), 7.15 (d, 1H), 7.2-7.5 (m, 5H), 7.6-7.8 (m, 3H), 8.45 (d, 1H), 9.05 (d, 1H), 9.35 (d, 1H).

(3S)-2-oxo-3-(isoquinolin-1-oyl)amino-5-hydroxyacetyl-N-[(2RS,3S)-ethoxy-5-oxo-tetrahydrofuran-3-yl]-2,3,4,5-tetrahydro-1H-1,5-benzodiazepine-1-carboxamide (696b) was synthesized from 600b via methods used to prepare 690a from 600b to afford 696b. $^1$H NMR (CDCl$_3$) δ 0.9 (m, 3H), 1.15 (q, 3H), 1.15 (m, 1H), 1.65 (m, 1H), 2.5 (m, 1H), 2.8 (m, 1H), 2.95-3.0 (m, 2H), 3.6 (m, 2H), 3.7-3.85 (m, 4H), 4.0 (m, 2H), 4.3 (m, 1H), 4.55 (m, 1H), 4.65 (m, 1H), 4.85-4.95 (m, 1H), 5.05 (m, 1H), 5.35 (s, 1H), 5.45 (d, 1H), 6.85 (d, 1H), 7.25 (d, 1H), 7.35-7.85 (6H), 8.85 (dd, 2H), 9.05 (m, 1H), 9.35 (dd, 2H).

(3S)-2-oxo-3-(isoquinolin-1-oyl)amino-5-hydroxyacetyl-[2RS-(4-chlorobenzyl)oxy-5-oxo-tetrahydrofuran-3-yl]-2,3,4,5-tetrahydro-1H-1,5-benzodiazepine-1-carboxamide (696c) was synthesized from 600b via methods used to prepare 690a from 600b to afford 696c. $^1$H NMR (CD$_3$OD) δ 1.25 (t, 1H), 1.65 (q, 1H), 1.9 (m, 1H), 2.9 (m, 1H), 3.05 (m, 1H), 3.9 (d, 1H), 4.2 (m, 1H), 4.3 (d, 1H), 4.7-5.0 (m, 3H), 5.25 (m, 1H), 5.7 (s, 1H), 5.9 (d, 1H), 7.5 (d, 2H), 7.7-7.9 (m, 3H), 8.0 (t, 1H), 8.2 (m, 2H), 8.75 (d, 1H), 9.35 (d, 1H).

(3S)-2-oxo-3-(isoquinolin-1-oyl)amino-5-hydroxyacetyl-(2RS-cyclopentyloxy-5-oxo-tetrahydrofuran-3-yl)-2,3,4,5-tetrahydro-1H-1,5-benzodiazepine-1-carboxamide (696d) was synthesized from 600b via methods used to prepare 690a from 600b to afford 696d. $^1$H NMR (CDCl$_3$) δ 0.9 (t, 1H), 1.2 (t, 1H), 1.3-1.45 (m, 2H), 1.6-1.8 (m, 4H), 2.45 (m, 1H), 2.8 (m, 1H), 3.0 (m, 1H), 3.4 (q, 1H), 3.5 (d, 1H), 4.0 (m, 2H), 4.2-4.3 (m, 2H), 4.55 (d, 1H), 4.65 (m, 1H), 4.9 (m, 1H), 5.05 (m, 1H), 5.4 (s, 1H), 5.5 (d, 1H), 6.8 (d, 1H), 7.3-7.9 (m, 6H), 8.5 (d, 1H), 9.05 (d, 1H), 9.4 (d, 1H).

(3S)-2-oxo-3-(isoquinolin-1-oyl)amino-5-hydroxyacetyl-N-[(2R,3S)-phenethoxy-5-oxo-tetrahydrofuran-3-yl]-2,3,4,5-tetrahydro-1H-1,5-benzodiazepine-1-acetamide (696e) was synthesized from 600b via methods used to prepare 690a from 600b to afford 696e. $^1$H NMR (CDCl$_3$) δ 1.2 (t, 1H), 2.4 (m, 1H), 2.8 (m, 2H), 3.6 (d, 1H), 3.7 (q, 1H), 4.0 (m, 2H), 4.3 (d, 2H), 4.65 (m, 1H), 4.85 (t, 1H), 5.0 (m, 1H), 5.35 (d, 1H), 6.5 (d, 1H), 7.15-7.85 (m, 8H), 8.45 (d, 1H), 9.05 (d, 1H), 9.4 (d, 1H).

EXAMPLE 32

TABLE 27

| Compound | UV-Visible Ki (nM) | Cell PBMC avg. IC50 (nM) | Whole human blood IC50 (nM) | Clearance Mouse, i.v. ml/min/kg | Clearance Rat, i.v. ml/min/kg |
|---|---|---|---|---|---|
| 688c | 200 | | | | |
| 689b-1 | 3.5 | | | 2700 | |
| 696-1 | 0.5 | | | | |
| 696-2 | 0.5 | | | | |
| 697 | 1.8 | | 5000 | | |
| 698 | 18 | | 13500 | | |
| 699 | 1.1 | | | | |
| 699a-2 | | | | | |
| 720 | 2.7 | | | | |
| 721 | 1.3 | | 5000 | | |
| 722 | 5 | | 5000 | | |
| 723 | 2.3 | | 2000 | | |
| 724 | 2 | | 1800 | | |
| 725 | 3.7 | | 3000 | | |
| 726 | 300 | | | | |
| 727 | 50 | | 2300 | | |
| 728 | 300 | | | | |
| 729 | 28 | | 2800 | | |
| 730 | 90 | | 8000 | | |
| 731 | 150 | | | | |
| 732 | 5 | | 1800 | | |
| 733 | 5 | | 1500 | | |
| 734 | 9 | | 6000 | | |
| 735 | 6 | | 10000 | | |

EXAMPLE 33

Compounds 684a, 688b-1, 688c, 689b-1, 690a-1, 696-1, 696-2, 696a-2, 696a-1, 697, 697a, 698, 698a, 699, 699a, 699a-1, 699a-2, 800 and 801 were prepared as described below.

TABLE 28

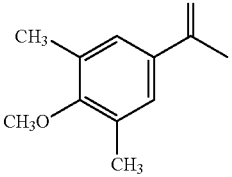

| CIP # | R$^4$ | R$^3$ | R$^5$ | R$^1$ |
|---|---|---|---|---|
| 684a | 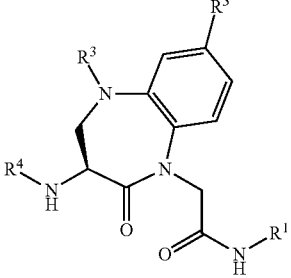 | 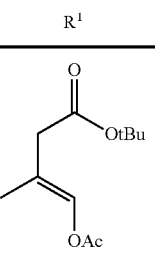 | H | 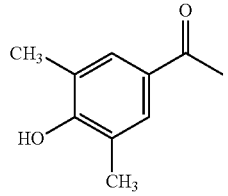 |
| 688b-1 | 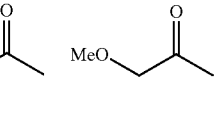 | 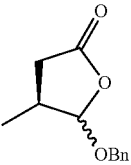 | F |  |

TABLE 28-continued

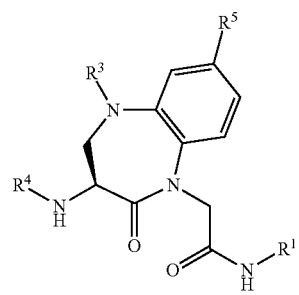

| CIP # | R4 | R3 | R5 | R1 |
|---|---|---|---|---|
| 688c | 3,5-dimethyl-4-hydroxyphenyl C(=O)- | MeOCH2C(=O)- | H | (R)-3-methyl-4-[(2,6-dichlorobenzyl)oxyimino]butanoic acid |
| 689b-1 | 3,5-dimethyl-4-hydroxyphenyl C(=O)- | MeOCH2C(=O)- | F | (R)-3-methyl-4-oxobutanoic acid |
| 690a-1 | 3,5-dimethyl-4-hydroxyphenyl C(=O)- | HOCH2C(=O)- | H | ethyl (R)-3-methyl-4,4-diethoxybutanoate |
| 696-1 | isoquinolin-1-yl C(=O)- | HOCH2C(=O)- | F | (R)-3-methyl-4-oxobutanoic acid |
| 696-2 | isoquinolin-1-yl C(=O)- | HOCH2C(=O)- | Cl | (R)-3-methyl-4-oxobutanoic acid |

TABLE 28-continued
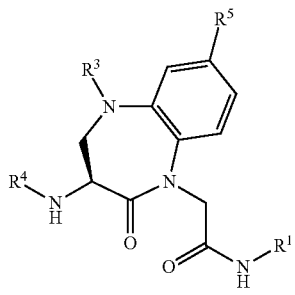
| CIP # | R⁴ | R³ | R⁵ | R¹ |
|---|---|---|---|---|
| 696a-2 | 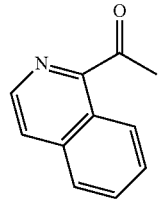 | 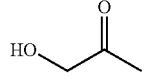 | Cl | 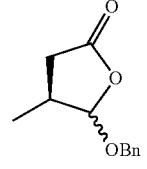 |
| 696a-1 | 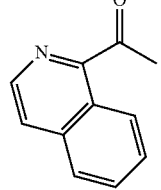 | 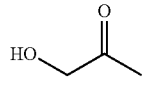 | F | 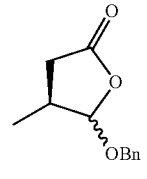 |
| 697 | 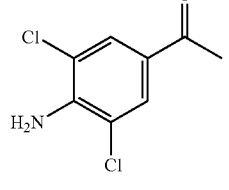 | 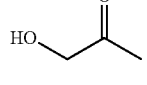 | H | 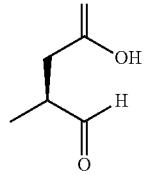 |
| 697a | 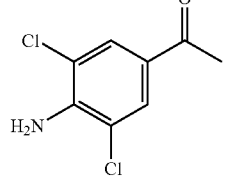 | 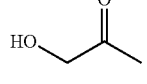 | H | 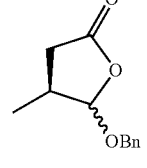 |
| 698 | 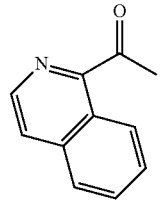 |  | H | 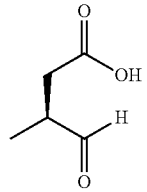 |
| 698a | 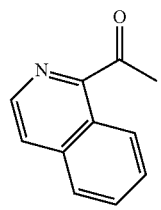 |  | H | 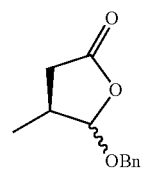 |

TABLE 28-continued

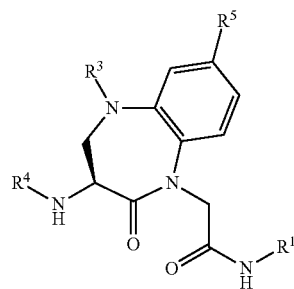

| CIP # | R⁴ | R³ | R⁵ | R¹ |
|---|---|---|---|---|
| 699 | 1-acetylisoquinoline | MeOCH₂C(O)- | H | (R)-3-methyl-4-oxobutanoic acid |
| 699a | 1-acetylisoquinoline | MeOCH₂C(O)- | H | 3-methyl-5-(benzyloxy)dihydrofuran-2(3H)-one |
| 699a-1 | 1-acetylisoquinoline | MeOCH₂C(O)- | F | 3-methyl-5-(benzyloxy)dihydrofuran-2(3H)-one |
| 699a-2 | 1-acetylisoquinoline | MeOCH₂C(O)- | F | (R)-3-methyl-4-oxobutanoic acid |
| 800 | 5-acetyl-2,4-dimethylthiazole | HOCH₂C(O)- | H | 3-methyl-5-(benzyloxy)dihydrofuran-2(3H)-one |
| 801 | 5-acetyl-2,4-dimethylthiazole | HOCH₂C(O)- | H | (R)-3-methyl-4-oxobutanoic acid |

(3S)-3-[(3S)-2-oxo-3-(3,5-dimethyl-4-hydroxybenzoyl) amino-5-hydroxyacetyl-2,3,4,5-tetrahydro-1H-1,5-benzodiazepine-1-acetylamino]-4,4-diethoxybutyric acid ethyl ester (690a-1), was synthesized by the methods used to prepare 690a and 2100b to afford 690a-1, $^1$H NMR (CDCl$_3$) δ 1.15 (t, 6H), 1.3 (t, 3H), 2.25 (s, 6H), 2.60 (d, 2H), 3.50 (m, 2H), 3.70 (m, 4H), 4.05 (m, 2H), 4.15 (m, 2H), 4.30 (d, 1H), 4.45 (m, 1H), 4.50 (d, 1H), 4.55 (d, 1H), 4.70 (t, 1H), 5.05 (m, 1H), 5.30 (s, 1H), 6.70 (d, 1H), 7.10 (d, 2H), 7.30-7.50 (m, 7H)

(3S)-2-oxo-3-(3,5-dichloro-4-aminobenzoyl)amino-5-hydroxyacetyl-N-[(2RS,3S)2-benzyloxy-5-oxo-tetrahydrofuran-3-yl]-2,3,4,5-tetrahydro-1H-1,5-benzodiazepine-1-acetamide (697a) was synthesized via methods used to prepare 677 to afford 840 mg of 697a, $^1$H NMR (CDCl$_3$) δ 1.78 (br. s, 2H), 2.48-2.58 (d, 0.5H), 2.6-2.7 (m, 0.5H), 2.8-2.9 (m, 0.5H), 2.92-3.03 (m, 0.5H), 3.55-3.8 (m, 2H), 3.92-4.02 (d, 1H), 4.25-4.3 (d, 0.5H), 4.37-4.42 (d, 0.5H), 4.43-4.48 (m, 0.5H), 4.55-4.65 (m, 1.5H) 4.7-5.12 (m, 5H), 5.44 (s, 0.5H), 5.58-5.63 (d, 0.5H), 6.95-8.1 (m, 13H).

(3S)-3-[(3S)-2-oxo-3-(3,5-dichloro-4-aminobenzoyl) amino-5-acetyl-2,3,4,5-tetrahydro-1H-1,5-benzodiazepine-1-acetylamino]-4-oxobutyric acid (697) was synthesized via methods used to prepare 2002 from 2001 to afford 140 mg of 697, $^1$H NMR (CD$_3$OD) δ 238-2.5 (m, 1H), 2.55-2.75 (m, 1H), 3.68-3.9 (m, 3H), 3.95-4.03 (m, 1H), 4.2-4.3 (m, 1H), 4.4-4.7 (m, 4H), 7.35-7.8 (m, 6H).

(3S)-3-[(3S)-2-oxo-3-(3,5-dimethyl-4-methoxybenzoyl) amino-5-hydroxyacetyl-2,3,4,5-tetrahydro-1H-1,5-benzodiazepine-1-acetylamino]4-acetoxy-3-butenoic acid ethyl ester (684a), was synthesized by the methods used to prepare 2100j to afford 684a, $^1$H NMR (500 MHz, CDCl$_3$ mixture of diastereomers) δ 1.3 (s, 9H), 1.8 (s, 3H), 2.1 (s, 3H), 2.15 (s, 3H), 2.3 (s, 6H), 3.3-3.5 (m, 3H), 3.65 (s, 3H), 3.9 (m, 1H), 4.1 (d, 1H), 4.3 (d, 1H), 4.6-4.8 (m, 3H), 5.0 (m, 1H), 6.7 (s, 1H), 7.0 (d, 1H), 7.1 (d, 1H), 7.2-7.5 (m, 6H).

(3S)-2-oxo-3-isoquinolin-1-oylamino-5-formyl-N-[(2RS, 3S)2-benzyloxy-5-oxo-tetrahydrofuran-3-yl]-2,3,4,5-tetrahydro-1H-1,5-benzodiazepine-1-acetamide (698a) was synthesized via methods used to prepare 652 to afford 795 mg of 698a $^1$H NMR (500 MHz, CDCl$_3$ mixture of diastereomers) δ 2.8 (m, 2H), 4.0 (m, 1H), 4.5-4.8 (m, 4H), 5.2 (m, 1H), 5.5 (s, 1H), 5.75 (d, 1H), 7.3-7.85 (m, 11H), 7.9 (t, 1H), 8.2 (d, 1H), 8.6 (m, 1H), 9.3 (m, 1H).

(3S)-3-[(3S)-2-oxo-3-isoquinolin-1-oylamino-5-formyl-2,3,4,5-tetrahydro-1H-1,5-benzodiazepine-1-acetylamino]-4-oxobutyric acid (698) was synthesized via methods used to prepare 653 to afford 225 mg of 698 $^1$H NMR (500 MHz, CD$_3$OD) δ 2.4 (m, 1H), 2.6 (m, 1H), 3.9 (m, 1H), 4.2 (m, 1H), 4.3-4.7 (m, 4H), 5.1 (m, 1H), 7.3-7.5 (m, 4H), 7.6-7.8 (m, 2H), 7.8 (m, 2H), 8.2 (d, 1H), 8.5 (d, 1H), 9.0 (d, 1H).

(3S)-2-oxo-3-isoquinolin-1-oylamino-5-methoxyacetyl-N-[(2RS,3S)2-benzyloxy-5-oxo-tetrahydrofuran-3-yl]-2,3,4,5-tetrahydro-1H-1,5-benzodiazepine-1-acetamide (699a) was synthesized via methods used to prepare 655 to afford 820 mg of 699a as a tan solid, $^1$H NMR (500 MHz, CDCl$_3$) δ 2.60 (ddd, 1H), 2.90 (ddd, 1H), 3.20 (s, 3H), 3.25 (s, 3H), 3.70 (t, 1H), 3.90 (m, 2H), 4.20 (dd, 1H), 4.60 (m, 2H), 4.70-5.00 (m, 5H), 5.55 (d, 1H), 7.00 (d, 1H), 7.20-7.50 (m, 7H), 8.45 (dd, 1H), 9.0 (dd, 1H), and 9.35 ppm (dd, 1H).

(3S)-2-oxo-3-(3,5-dimethyl-4-hydroxybenzoyl)amino-5-methoxyacetyl-N-[(2RS,3S)2-benzyloxy-5-oxo-tetrahydrofuran-3-yl]-2,3,4,5-tetrahydro-7-fluoro-1H-1,5-benzodiazepine-1-acetamide (688b-1) was synthesized via methods used to prepare 655 to afford 600 mg of 688b-1, $^1$H NMR (CDCl$_3$; mix. of diastereomers) δ 2.21 (s, 3H), 2.28 (s, 3H), 2.42-2.50 (m, 0.5H), 2.58-2.65 (m, 0.5H), 2.83-2.91 (m, 0.5H), 2.98-3.1 (m, 0.5H), 3.18 (s, 1.5H), 3.22 (s, 1.5H), 3.72-3.78 (d, 1H), 3.78-3.9 (m, 2H), 4.08-4.15 (d, 1H), 4.5-4.69 (m, 3H), 4.7-4.85 (m, 1H), 4.88-5.1 (m, 2H), 5.45 (s, 0.5H), 5.55-5.65 (d, 0.5H), 6.85-6.92 (m, 1H), 7.02-7.13 (m, 2H), 7.24-7.55 (m, 9H).

(3S)-3-[(3S)-2-oxo-3-(3,5-dimethyl-4-hydroxybenzoyl) amino-5-methoxyacetyl-2,3,4,5-tetrahydro-7-fluoro-1H-1,5-benzodiazepine-1-acetylamino]-4-oxobutyric acid (689b-1) was synthesized via methods used to prepare 2002 from 2001 to afford 689b-1, $^1$H NMR (CD$_3$OD) δ 2.18 (s, 6H), 2.36-2.47 (m, 1H), 2.6-2.72 (m, 1H), 3.34 (s, 3H), 3.66-3.88 (m, 2H), 3.95-4.05 (m, 1H), 4.2-4.78 (m, 5H), 4.9 (m, 1H), 7.3-7.41 (m, 2H), 7.48 (s, 2H), 7.5-7.63 (m, 1H).

(3S)-3-[(3S)-2-oxo-3-isoquinolin-1-oylamino-5-methoxyacetyl-2,3,4,5-tetrahydro-1H-1,5-benzodiazepine-1-acetylamino]-4-oxobutyric acid (699) was synthesized via methods used to prepare 2002 from 2001 to afford 699 as a white solid, $^1$H NMR (500 MHz, CD$_3$OD) δ 2.50 (m, 1H), 2.70 (m, 1H), 3.25 (s, 3H), 3.80 (bd, 1H), 3.90 (bd, 1H), 4.00 (bd, 1H), 4.30 (m, 1H), 4.50-4.70 (m, 3H), 4.80-4.85 (bt, 1H), 5.00 (bm, 1H), 7.40-7.55 (m, 5H), 7.70 (bm, 1H), 7.85 (bm, 1H), 8.00 (bm, 1H), 8.55 (bd, 1H), and 9.05 ppm (bd, 1H).

(3S)-2-Oxo-3-isoquinolin-1-oylamino-5-hydroxyacetyl-N-[(2RS,3S)2-benzyloxy-5-oxo-tetrahydrofuran-3-yl]-2,3,4,5-tetrahydro-7-fluoro-1H-1,5-benzodiazepine-1-acetamide (696a-1) was synthesized via methods used to prepare 656 to afford 800 as a yellow solid, $^1$H NMR (500 MHz, CDCl$_3$) δ 2.55 (ddd, 1H), 2.85 (ddd, 1H), 3.70-3.80 (m, 2H), 3.95 (bm, 1H), 4.05 (d, 1H), 4.30 (d, 1H), 4.40-4.60 (m, 4H), 4.70-5.05 (m, 4H), 5.55 (d, 1H), 7.10 (d, 1H), 7.20-7.35 (m, 3H), 7.40-7.50 (m, 1H), 7.60-7.85 (m, 3H), 8.40 (dd, 1H), 9.10 (m, 1H), and 9.30 pp (m, 1H).

(3S)-2-oxo-3-isoquinolin-1-oylamino-5-hydroxyacetyl-N-[(2RS,3S)2-benzyloxy-5-oxo-tetrahydrofuran-3-yl]-2,3,4,5-tetrahydro-7-chloro-1H-1,5-benzodiazepine-1-acetamide (696a-2) was synthesized via methods used to prepare 677, to afford 204 mg of 696a-2 as a white solid, with the exception that the reduction of the nitro-group was done as follows: To a solution of the nitro compound (7.2 g, 20 mmol) in MeOH was added NH$_4$Cl (2.1 g, 39 mmol) and Zn (17 g, 260 mmol). The resulting mixture was heated to reflux 1 hour after which it was cooled and filtered through celite. The filtrated was concentrated in vacuo then treated with cold 1N HCl to afford 3.6 g of a pale red solid. $^1$H NMR (CDCl$_3$) δ 1.85 (s, 1H), 2.45 (d, 0.5H), 2.50-2.65 (m, 0.5H), 2.80-2.90 (m, 0.5H), 2.90-3.00 (m, 0.5H), 3.45 (s, 0.5H), 3.55-3.75 (m, 1H), 3.85-4.15 (m, 2H), 4.25 (d, 1H), 4.40-4.65 (m, 2H), 4.70-4.80 (m, 0.5H), 4.85-5.15 (m, 3H), 5.40 (s, 0.5H), 5.60 (d, 0.5H), 7.00 (d, 0.5H), 7.15-7.90 (m, 12.5H), 8.35-8.45 (m, 1H), 9.00-9.10 (m, 1H), 9.25-9.40 (m, 1H)

(3S)-3-[(3S)-2-Oxo-3-isoquinolin-1-oylamino-5-hydroxyacetyl-2,3,4,5-tetrahydro-7-fluoro-1H-1,5-benzodiazepine-1-acetylamino]-4-oxobutyric acid (696-1) was synthesized via methods used to prepare 2002 from 2001 to afford 140 mg of 696-1 as a white solid, $^1$H NMR (500 MHz, CD$_3$OD) δ 2.50 (m, 1H), 2.70 (m, 1H), 3.85 (d, 1H), 3.95 (m, 1H), 4.10 (d, 1H), 4.35 (m, 1H), 4.50-4.60 (m, 2H), 4.80 (bm, 1H), 5.00 (m, 1H), 7.40-7.48 (m, 3H), 7.65 (m, 1H), 7.75 (t, 1H), 7.85 (t, 1H), 8.00 (d, 1H), 8.55 (d, 1H), and 9.05 ppm (d, 1H).

(3S)-3-[(3S)-2-oxo-3-isoquinolin-1-oylamino-5-hydroxyacetyl-2,3,4,5-tetrahydro-7-chloro-1H-1,5-benzodiazepine-1-acetylamino]-4-oxobutyric acid (696-2) was synthesized via methods used to prepare 2002 from 2001 to afford 250 mg of 696-2 as a white solid, $^1$H NMR (CD$_3$OD) δ 2.40-2.55 (m, 1H), 2.60-2.75 (m, 1H), 3.80-4.00 (m, 2H), 4.05 (d, 1H), 4.20-4.35 (m, 1H), 4.45-4.65 (m, 3H), 4.80-5.10 (m, 2H)

(3S)-2-oxo-3-isoquinolin-1-oylamino-5-methoxyacetyl-N-[(2RS,3S)2-benzyloxy-5-oxo-tetrahydrofuran-3-yl]-2,3,4,5-tetrahydro-7-fluoro-1H-1,5-benzodiazepine-1-acetamide (699a-1) was synthesized via methods used to prepare 655 to afford 699a-1 $^1$H NMR (500 MHz, CDCl$_3$) δ 2.55 (ddd, 1H), 2.90 (ddd, 1H), 3.25 (s, 3H), 3.28 (s, 3H), 3.80 (bt, 2H), 3.95 (bm, 2H), 4.25 (dd, 1H), 4.45-4.90 (m, 3H), 5.60 (d, 1H), 7.05-7.40 (m, 8H), 7.50 (bm, 1H), 7.65-7.85 (m, 2H), 8.45 (d, 1H), 9.1 (m, 1H), and 9.35 ppm (m, 1H)

(3S)-3-[(3S)-2-oxo-3-isoquinolin-1-oylamino-5-methoxyacetyl-2,3,4,5-tetrahydro-7-fluoro-1H-1,5-benzodiazepine-1-acetylamino]-4-oxobutyric acid (699a-2) was synthesized via methods used to prepare 2002 from 2001 to afford 699a-2 $^1$H NMR (500 MHz, CD$_3$OD) δ 2.51 (m, 1H), 2.70 (dt, 1H), 3.31 (bs, 3H), 3.90 (bdt, 1H), 3.95 (bm, 1H), 4.05 (d, 1H), 4.35 (m, 1H), 4.50 (d, 1H), 4.60 (dd, 1H), 4.65 (dt, 1H), 4.80 (m, 1H), 5.05 (m, 1H), 7.35-7.48 (m, 3H), 7.65 (bm, 1H), 7.75 (t, 1H), 7.82 (t, 1H), 8.05 (d, 1H), 8.55 (d, 1H), and 9.05 ppm (d, 1H).

(3S)-3-[(3S)-2-oxo-3-(3,5-dimethyl-4-hydroxybenzoyl)amino-5-methoxyacetyl-2,3,4,5-tetrahydro-1H-1,5-benzodiazepine-1-acetylamino]-4-oxobutyric acid, O-2,6-dichlorobenzyl oxime (688c) was synthesized via methods used to prepare 308d to afford 800, $^1$H NMR (CD$_3$OD) δ 2.2 (s, 6H), 2.58-2.83 (m, 2H), 3.28 (s, 3H), 3.29-3.34 (m, 1H), 3.68-3.80 (m, 2H), 3.95-4.05 (dd, 1H), 4.38-4.48 (dd, 1H), 4.82-5.00 (m, 2H), 5.26-5.36 (m, 2H), 7.22-7.65 (m, 10H).

(3S)-2-oxo-(2,4-dimethylthiazo-5-yl)amino-5-hydroxyacetyl-N-[(2RS,3S)2-benzyloxy-5-oxo-tetrahydrofuran-3-yl]-2,3,4,5-tetrahydro-1H-1,5-benzodiazepine-1-acetamide (800) was synthesized via methods used to prepare 696a-1 to afford 204 mg of 800 as a yellow solid, $^1$H NMR (CDCl$_3$) (mixture of diastereomers) δ 1.70 (s, 1H), 2.40-2.80 (m, 7H), 2.80-2.90 (m, 0.5H), 2.95-3.05 (m, 0.5H), 3.30-3.35 (m, 0.5H), 3.45-3.55 (m, 0.5H), 3.55-3.65 (m, 1H), 3.80-4.05 (m, 2H), 4.30-4.50 (m, 2H), 4.55-4.65 (m, 1H), 4.75-4.95 (m, 3H), 5.45 (s, 0.5H), 5.55 (d, 0.5H), 6.70 (d, 0.5H), 6.90 (d, 0.5H), 7.15-7.80 (m, 10H)

(3S)-3-[(3S)-2-oxo-3-(2,4-dimethylthiazo-1-oyl)amino-5-hydroxyacetyl-2,3,4,5-tetrahydro-1H-1,5-benzodiazepine-1-acetylamino]-4-oxobutyric acid (801) was synthesized via methods used to prepare 2002 from 2001 to afford 801.

EXAMPLE 34

Compounds 720-73 were prepared by methods similar to the methods used to prepare compounds 619-635 (see, Example 13). Physical data for compounds 720-73 is listed in Table 29.

TABLE 29

| Compound | Structure | MF | MW | HPLC RT min Purity | MS (M + Na)+ |
|---|---|---|---|---|---|
| 720 | 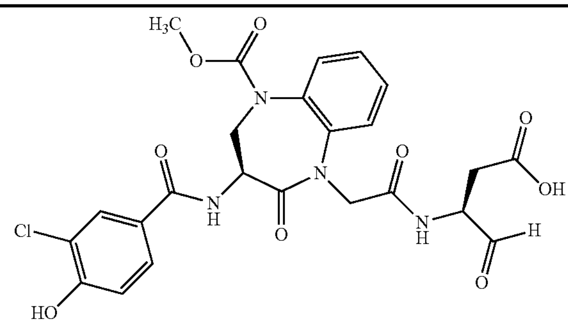 | C24H23ClN4O9 | 546.93 | 10.729 99% | 568.8 |
| 721 | 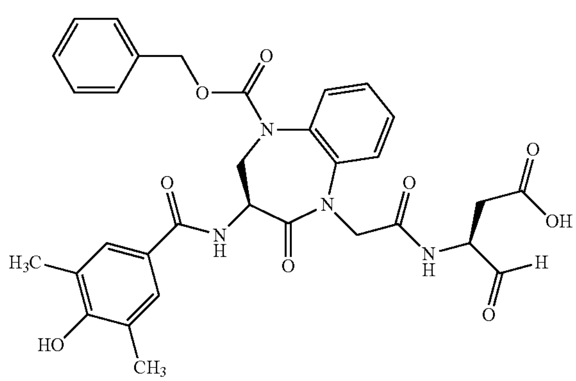 | C32H32N4O9 | 616.63 | 13.241 99% | 640.4 |

TABLE 29-continued

| Compound | Structure | MF | MW | HPLC RT min Purity | MS (M + Na)+ |
|---|---|---|---|---|---|
| 722 | 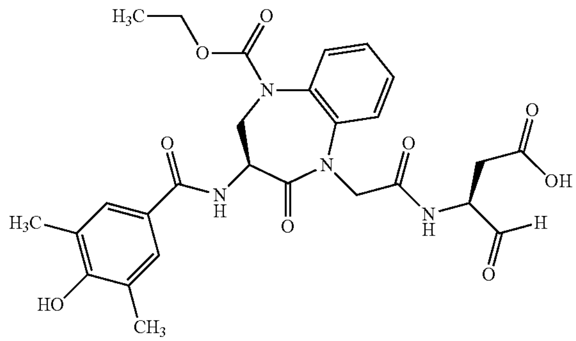 | C27H30N4O9 | 554.56 | 11.761 99% | 578.2 |
| 723 | 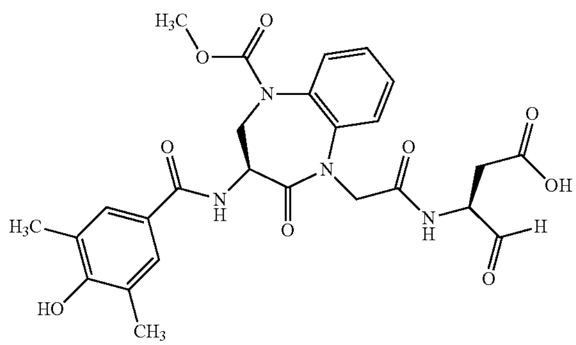 | C26H28N4O9 | 540.53 | 10.655 79% | 564.5 |
| 724 | 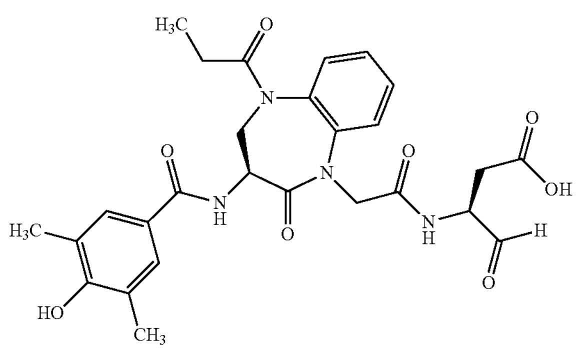 | C27H30N4O8 | 538.56 | 10.584 99% | 563.1 |
| 725 | 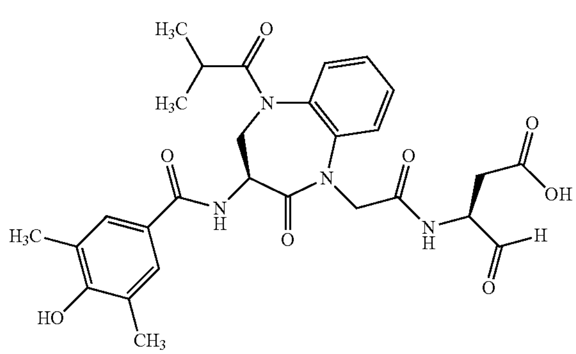 | C28H32N4O8 | 552.59 | 11.329 99% | 577.2 |

TABLE 29-continued

| Compound | Structure | MF | MW | HPLC RT min Purity | MS (M + Na)+ |
|---|---|---|---|---|---|
| 726 | 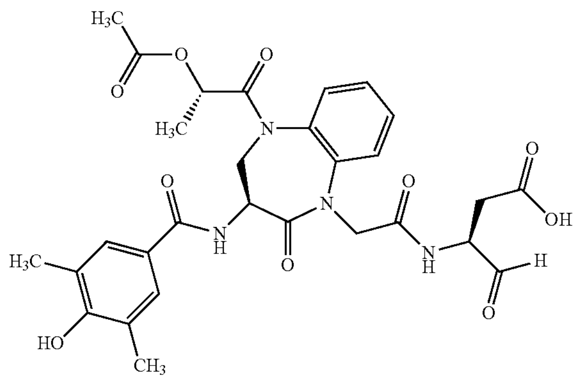 | C29H32N4O10 | 596.60 | 10.667 99% | 620.8 |
| 727 | 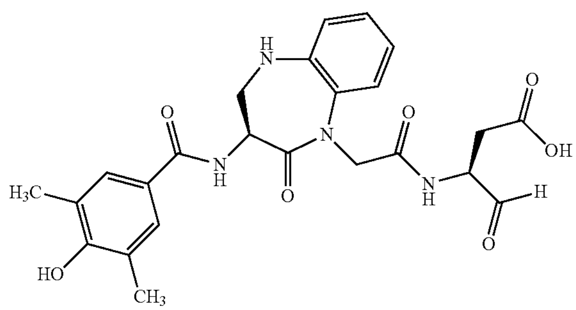 | C24H26N4O7 | 482.50 | 9.085 92% | 506.6 |
| 728 | 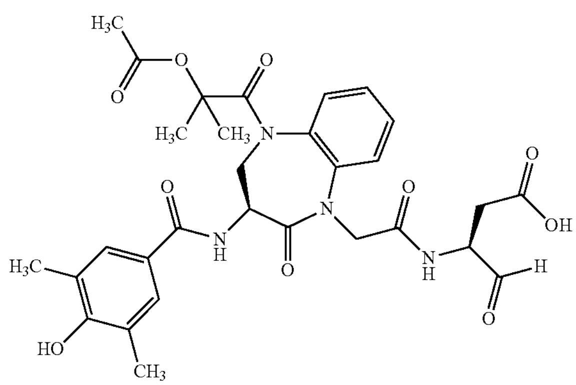 | C30H34N4O10 | 610.63 | 11.556 | 634.9 |
| 729 | 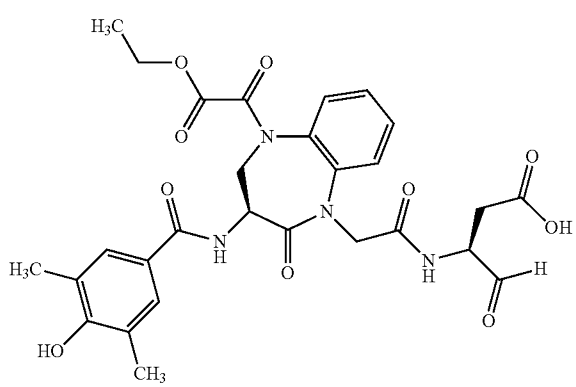 | C28H30N4O10 | 582.57 | 11.611 99% | 607.3 |

TABLE 29-continued

| Compound | Structure | MF | MW | HPLC RT min Purity | MS (M + Na)+ |
|---|---|---|---|---|---|
| 730 | 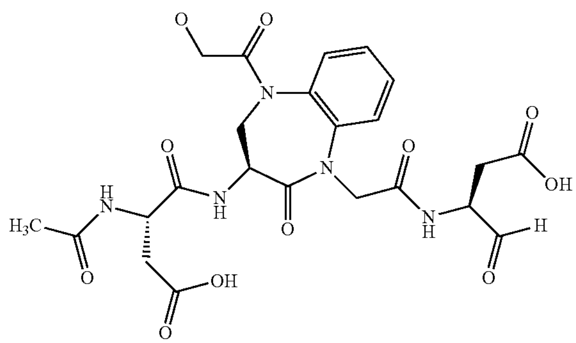 | C23H27N5O11 | 549.50 | 3.939 96% | 572.2 |
| 731 | 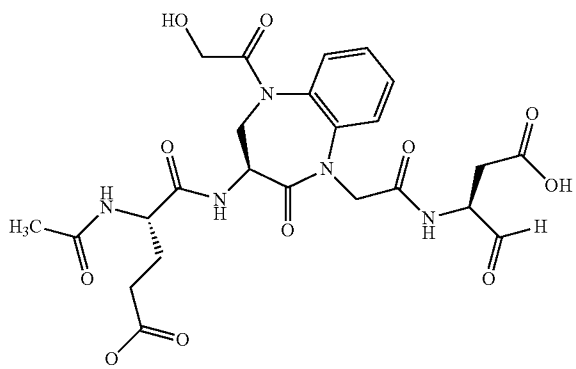 | C24H29N5O11 | 563.53 | 4.298 92% | 587 |
| 732 | 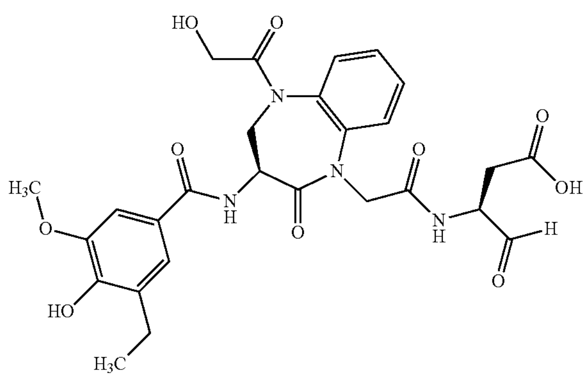 | C26H28N4O11 | 572.53 | 7.640 98% | 595.9 |
| 733 | 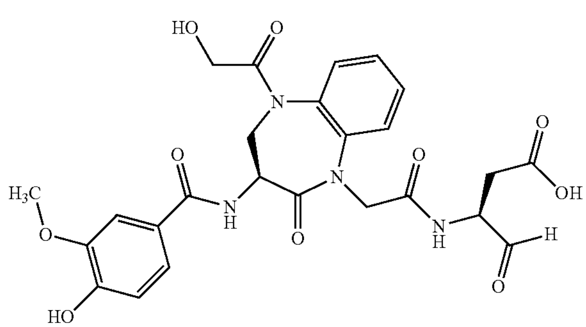 | C25H26N4O10 | 542.51 | 7.375 98% | 565.9 |

TABLE 29-continued

| Compound | Structure | MF | MW | HPLC RT min Purity | MS (M + Na)+ |
|---|---|---|---|---|---|
| 734 | 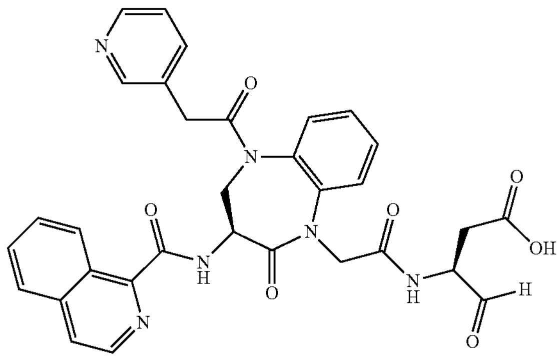 | C32H28N6O7 | 608.62 | 9.656 99% | 630.6 |
| 735 | 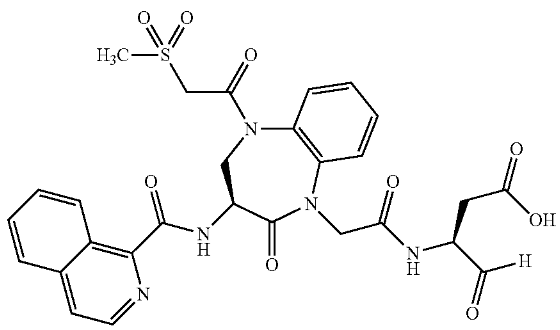 | C28H27N5O9S | 609.62 | 10.887 92% | 632.1 |

EXAMPLE 35

Compounds 736-767 were prepared by methods similar to the methods used to prepare compounds 619-635 (see, Example 13). Physical data for compounds 736-767 is listed in Table 30.

TABLE 30

| Compound | R⁴ | R³ |
|---|---|---|
| 736 | | |
| 737 | | |
| 738 | | |

TABLE 30-continued
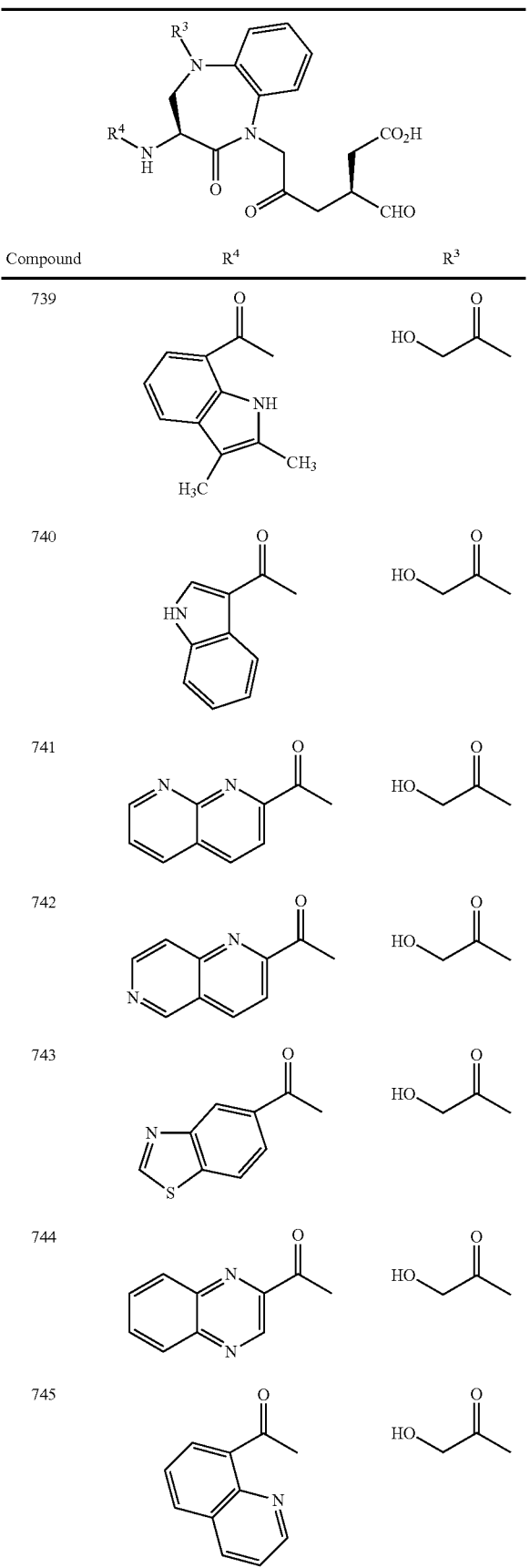
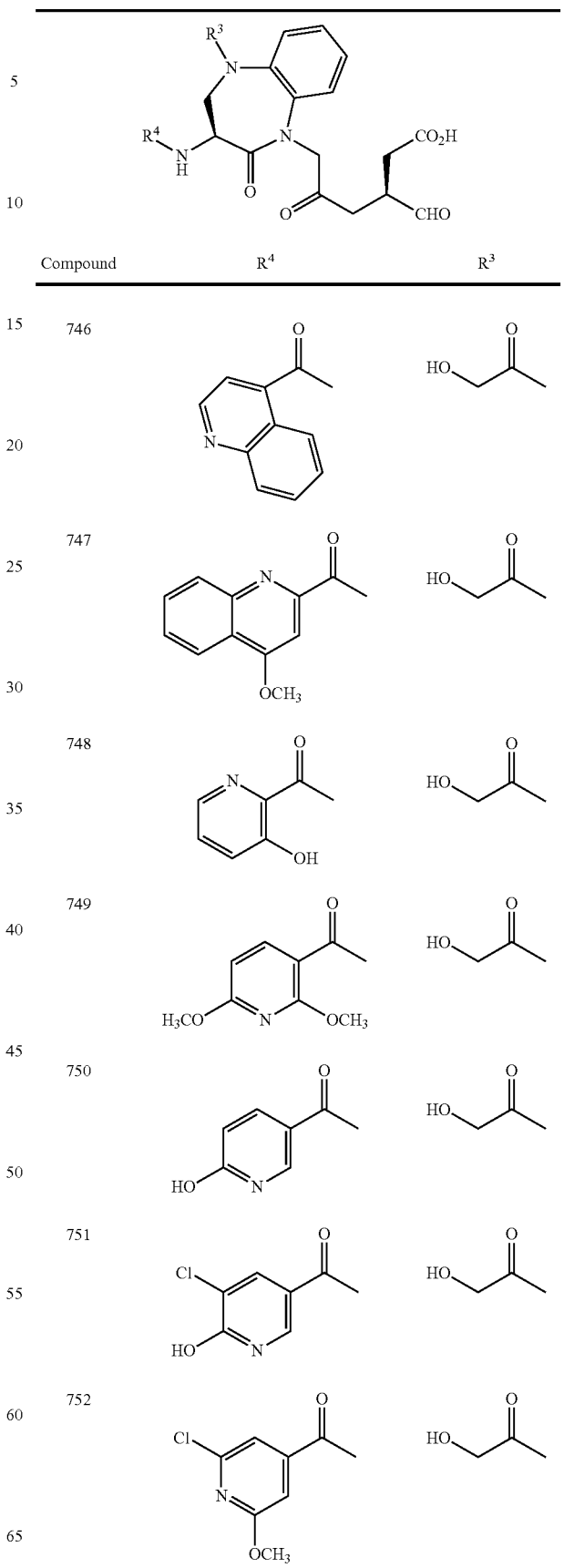

TABLE 30-continued

TABLE 30-continued

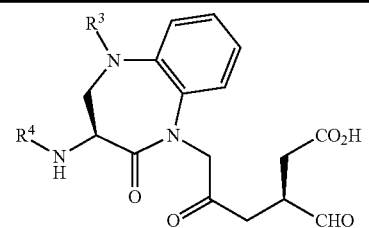

| Compound | R⁴ | R³ |
|---|---|---|
| 767 | (4-hydroxy-2-hydroxy-thiazol-5-yl)-propan-2-one group | hydroxyacetone group |

The data of the examples above demonstrate that compounds according to this invention display inhibitory activity towards IL-1β Converting Enzyme.

Insofar as the compounds of this invention are able to inhibit ICE in vitro and furthermore, may be delivered orally to mammals, they are of evident clinical utility for the treatment of IL-1-, apoptosis-, IGIF-, and IFN-γ mediated diseases. These tests are predictive of the compounds ability to inhibit ICE in vivo.

While we have described a number of embodiments of this invention, it is apparent that our basic constructions may be altered to provide other embodiments which utilize the products and processes of this invention. Therefore, it will be appreciated that the scope of this invention is to be defined by the appended claims, rather than by the specific embodiments which have been presented by way of example.

We claim:

1. A compound represented by the formula:

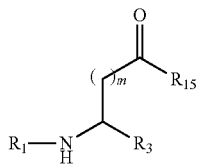
(VII)

wherein:

m is 1 or 2;

$R_1$ is

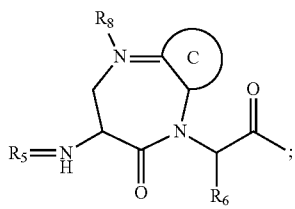
(w2)

C is a ring chosen from the set consisting of benzo, pyrido, thieno, pyrrolo, furano, thiazolo, isothiazolo, oxazolo, isoxazolo, pyrimido, imidazolo, cyclopentyl, and cyclohexyl, the ring optionally being singly or multiply substituted by -$Q_1$;

$R_3$ is selected from the group consisting of:
—CN,
—C(O)—H,
—C(O)—CH$_2$-T$_1$-R$_{11}$,
—C(O)—CH$_2$—F,
—C=N—O—R$_9$, and
—CO—Ar$_2$;

each $R_5$ is independently selected from the group consisting of:
—C(O)—R$_{10}$,
—C(O)O—R$_9$,
—C(O)—N(R$_{10}$)(R$_{10}$)
—S(O)$_2$—R$_9$,
—S(O)$_2$—NH—R$_{10}$,
—C(O)—CH$_2$—O—R$_9$,
—C(O)C(O)—R$_{10}$,
—R$_9$,
—H,
—C(O)C(O)—OR$_{10}$, and
—C(O)C(O)—N(R$_9$)(R$_{10}$);

each $T_1$ is independently selected from the group consisting of —O—, —S—, —S(O)—, and —S(O)$_2$—;

$R_6$ is selected from the group consisting of —H and —CH$_3$;

$R_8$ is selected from the group consisting of:
—C(O)—R$_{10}$,
—C(O)O—R$_9$,
—C(O)—NH—R$_{10}$,
—S(O)$_2$—R$_9$,
—S(O)$_2$—NH—R$_{10}$,
—C(O)—CH$_2$—OR$_{10}$,
—C(O)C(O)—R$_{10}$,
—C(O)—CH$_2$—N(R$_{10}$)(R$_{10}$),
—C(O)—CH$_2$C(O)—O—R$_9$,
—C(O)—CH$_2$C(O)—R$_9$,
and
—C(O)—C(O)—OR$_{10}$;

each $R_9$ is independently selected from the group consisting of —Ar$_3$ and a —C$_{1-6}$ straight or branched alkyl group optionally substituted with —Ar$_3$, wherein the —C$_{1-6}$ alkyl group is optionally unsaturated;

each $R_{10}$ is independently selected from the group consisting of —H, —Ar$_3$, a —C$_{3-6}$ cycloalkyl group, and a —C$_{1-6}$ straight or branched alkyl group optionally substituted with —Ar$_3$, wherein the —C$_{1-6}$ alkyl group is optionally unsaturated;

each $R_{11}$ is independently selected from the group consisting of:
—Ar$_4$,
—(CH$_2$)$_{1-3}$—Ar$_4$,
—H, and
—C(O)—Ar$_4$;

$R_{15}$ is selected from the group consisting of —OH, —OAr$_3$, —N(H)—OH, and —OC$_{1-6}$, wherein C$_{1-6}$ is a straight or branched alkyl group optionally substituted with —Ar$_3$, —CONH$_2$, —OR$_5$, —OH, —OR$_9$, or —CO$_2$H;

Ar$_2$ is independently selected from the following group, in which any ring may optionally be singly or multiply substituted by -$Q_1$ or phenyl, optionally substituted by $Q_1$:

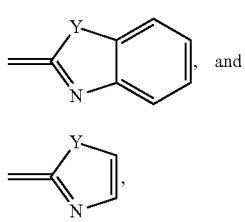
(hh)

and (ii)

wherein each Y is independently selected from the group consisting of O and S;

each Ar$_3$ is a cyclic group independently selected from the set consisting of an aryl group which contains 6, 10, 12, or 14 carbon atoms and between 1 and 3 rings and an aromatic heterocycle group containing between 5 and 15 ring atoms and between 1 and 3 rings, said heterocyclic group containing at least one heteroatom group selected from —O—, —S—, —SO—, SO$_2$, =N—, and —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by -Q$_1$;

each Ar$_4$ is a cyclic group independently selected from the set consisting of an aryl group which contains 6, 10, 12, or 14 carbon atoms and between 1 and 3 rings, and a heterocycle group containing between 5 and 15 ring atoms and between 1 and 3 rings, said heterocyclic group containing at least one heteroatom group selected from —O—, —S—, —SO—, SO$_2$, =N—, —NH—, —N(R$_5$)—, and —N(R$_9$)— said heterocycle group optionally containing one or more double bonds, said heterocycle group optionally comprising one or more aromatic rings, and said cyclic group optionally being singly or multiply substituted by -Q$_1$;

each Q$_1$ is independently selected from the group consisting of —NH$_2$, —CO$_2$H, —Cl, —F, —Br, —I, —NO$_2$, —CN, =O, —OH, -perfluoro C$_{1-3}$ alkyl, R$_5$, —OR$_5$, —NHR$_5$, —OR$_9$, —N(R$_9$)(R$_{10}$), —R$_9$, C(O)—R$_{10}$, and

provided that when —Ar$_3$ is substituted with a Q$_1$ group which comprises one or more additional —Ar$_3$ groups, said additional —Ar$_3$ groups are not substituted with another —Ar$_3$; provided that when:

m is 1; R$_{15}$ is —OH; R$_6$ is H; the C ring is a benzo ring that is unsubstituted by -Q$_1$; R$_3$ is —C(O)—H; and R$_5$ is —C(O)—R$_{10}$, wherein R$_{10}$ is —CH$_2$CH$_2$Ar$_3$ and Ar$_3$ is unsubstituted phenyl; then R$_8$ is not —H or —C(O)—R$_{10}$, wherein R$_{10}$ is —CH$_2$CH$_2$Ar$_3$ and Ar$_3$ is unsubstituted phenyl;

and provided that when:

m is 1; R$_{15}$ is —OH or —OC(CH$_3$)$_3$; R$_6$ is —H; the C ring is a benzo ring that is unsubstituted by -Q$_1$; R$_3$ is —CO—Ar$_2$ and Ar$_2$ is

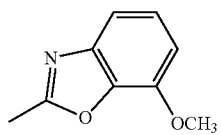 or 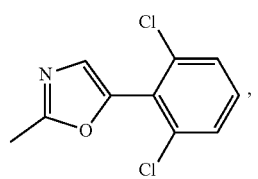, or

R$_3$ is —C(O)—CH$_2$-T$_1$-R$_{11}$, wherein T$_1$ is O and R$_{11}$ is —C(O)—Ar$_4$ and Ar$_4$ is 2,6-dichlorophenyl; and R$_5$ is —C(O)—R$_{10}$, wherein R$_{10}$ is —CH$_2$CH$_2$Ar$_3$ and Ar$_3$ is unsubstituted phenyl; then R$_8$ is not —C(O)—R$_{10}$, wherein R$_{10}$ is —CH$_2$CH$_2$Ar$_3$ and Ar$_3$ is unsubstituted phenyl.

2. The compound according to claim 1, selected from the group consisting of:

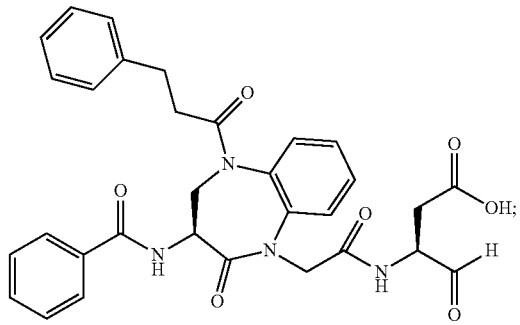

605a

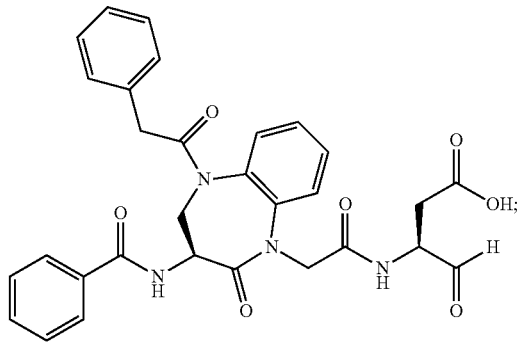

605b

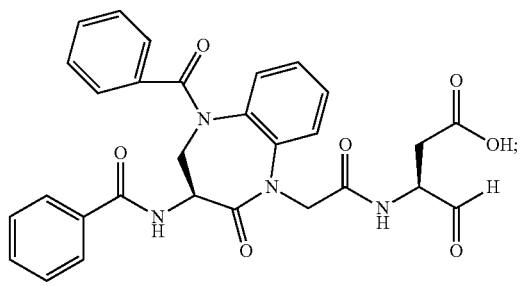

605c

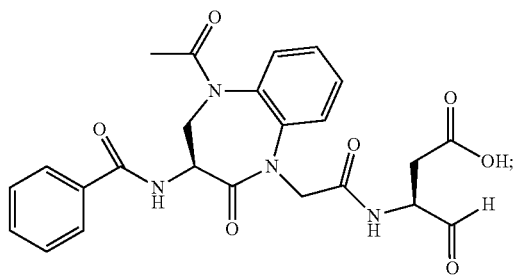

605d

605e 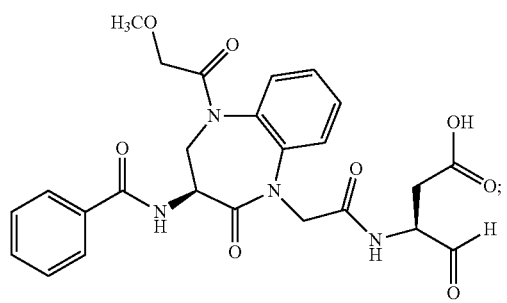
605f 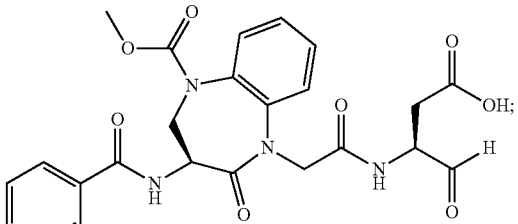
605g 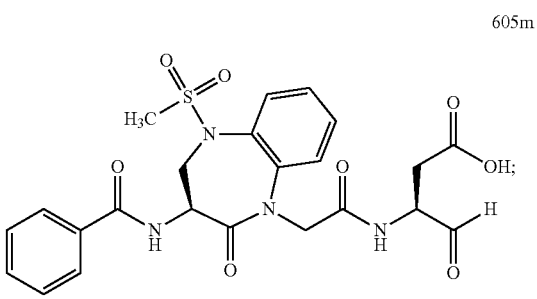
605h 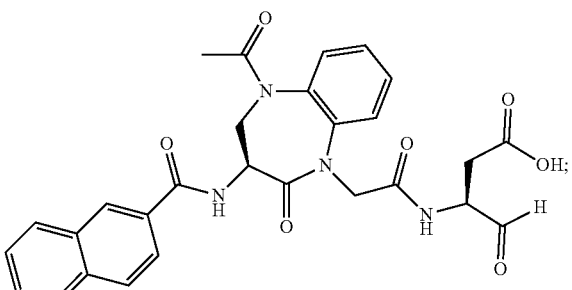
605i
605j 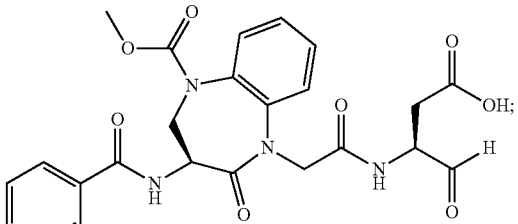
605m 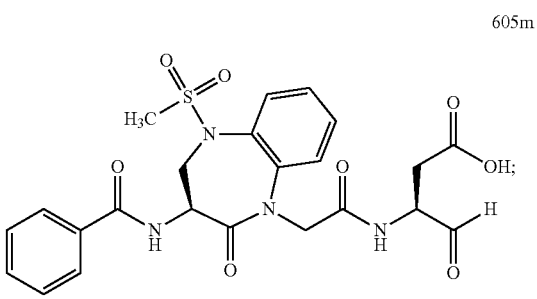
605n 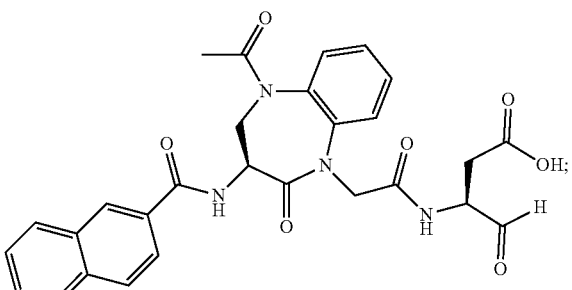
605o 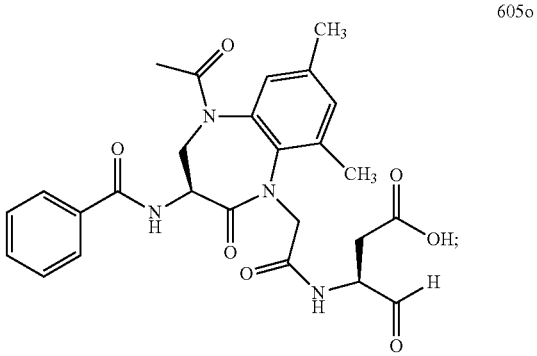
605p 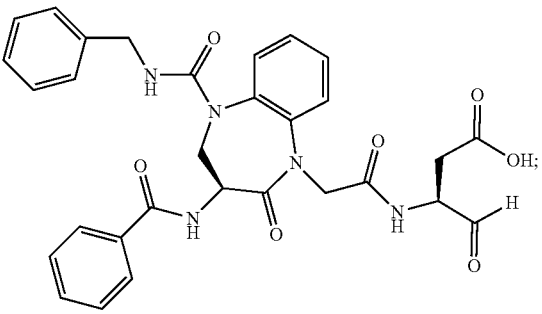

-continued
605s
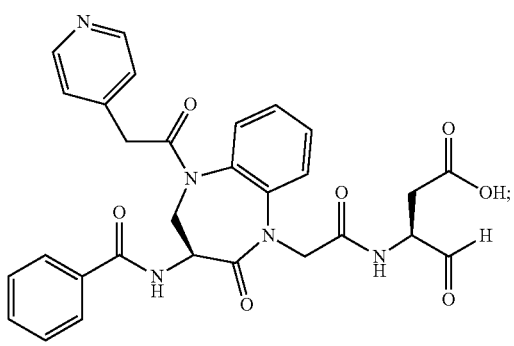
619
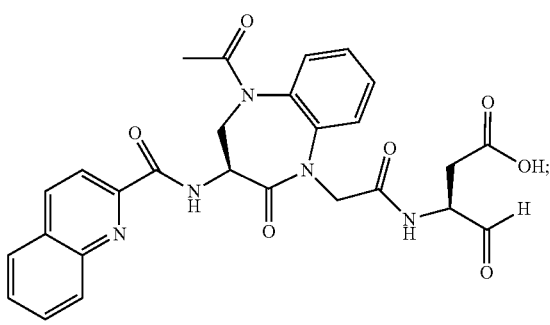
605t
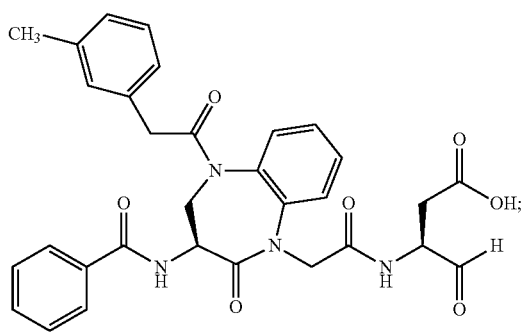
620
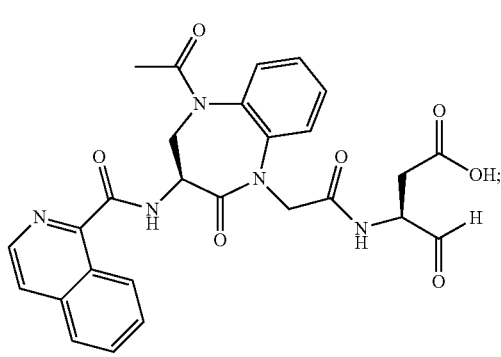
605v
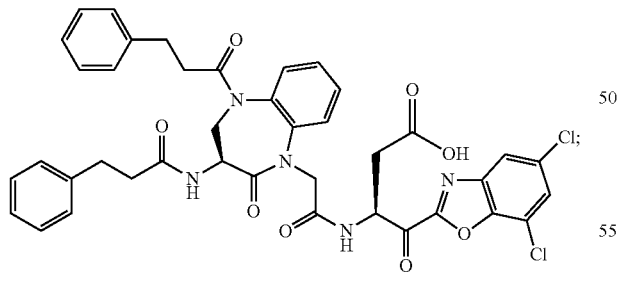
621
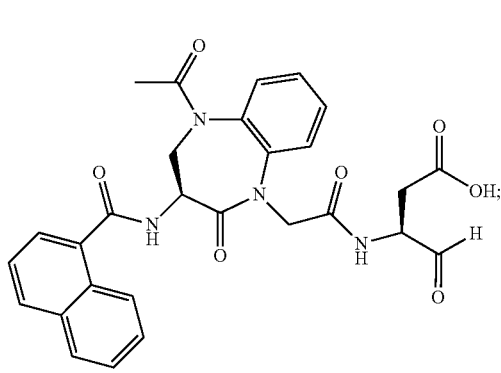
609a
609b
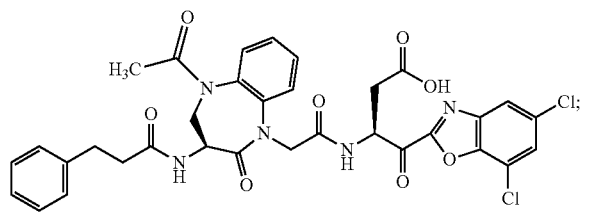
622
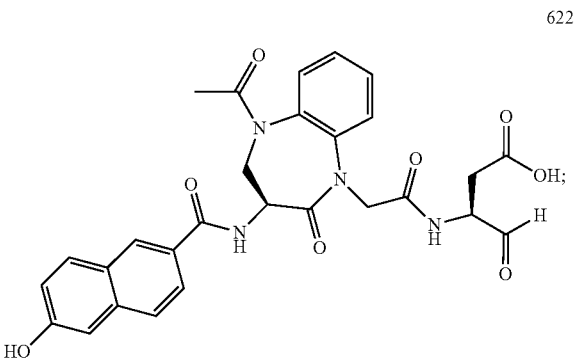

623
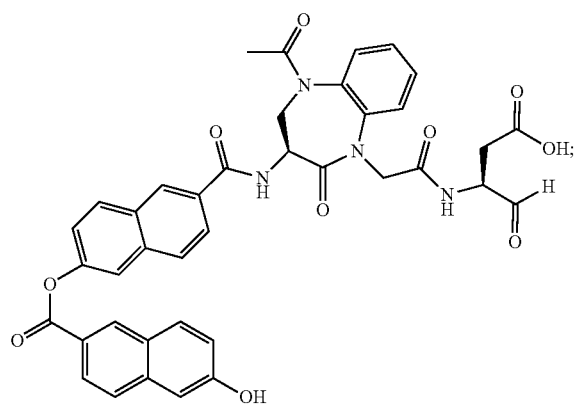
628
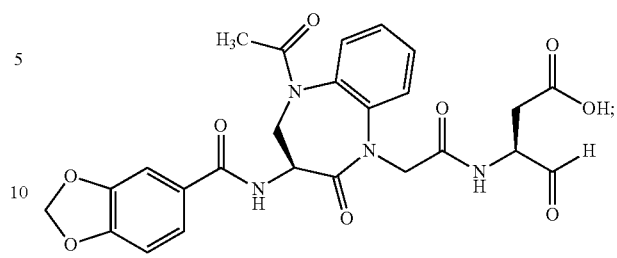
629
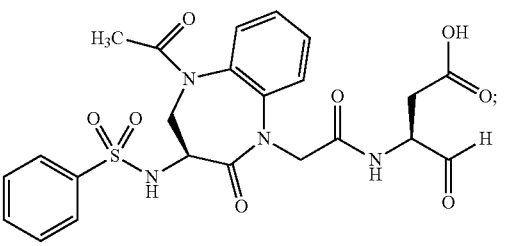
624
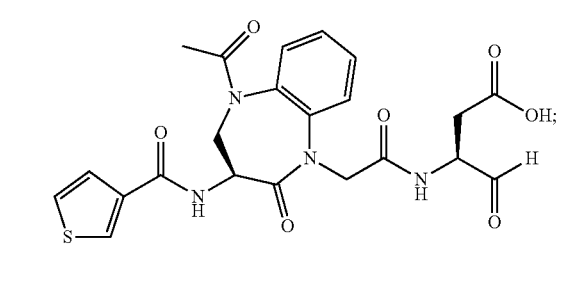
630
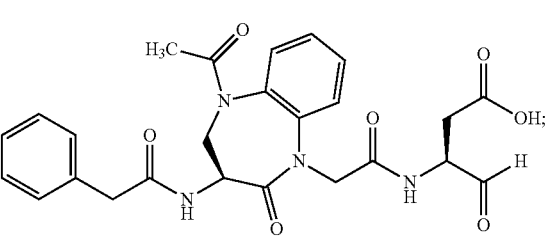
625
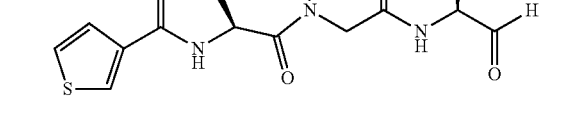
631
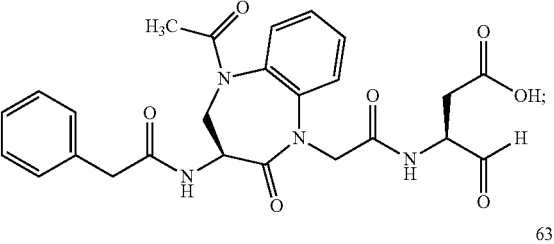
626
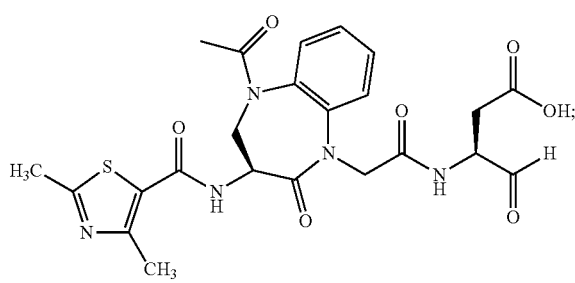
632
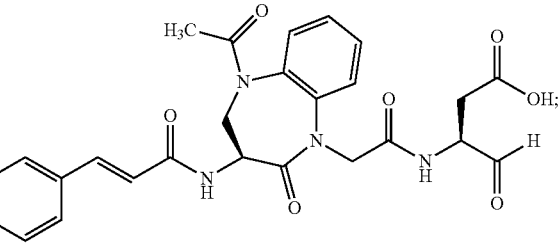
627
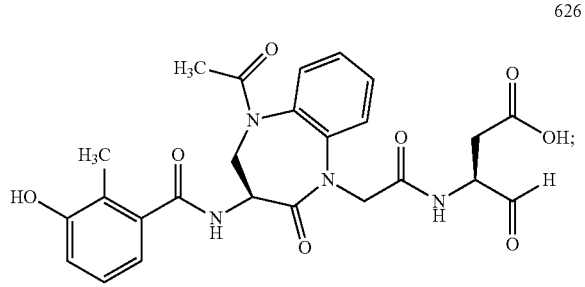
633
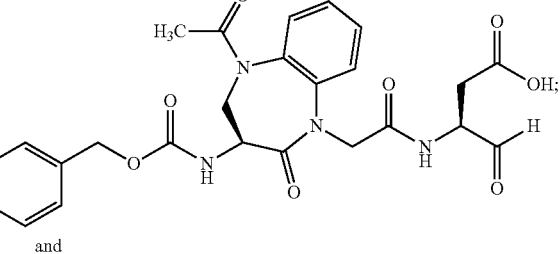
and
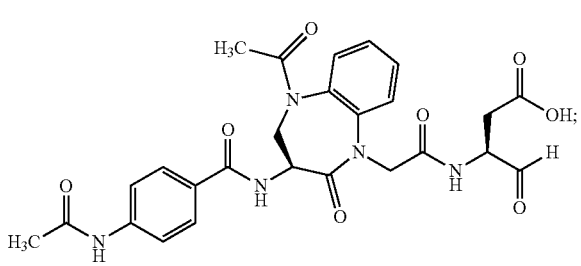

-continued

635

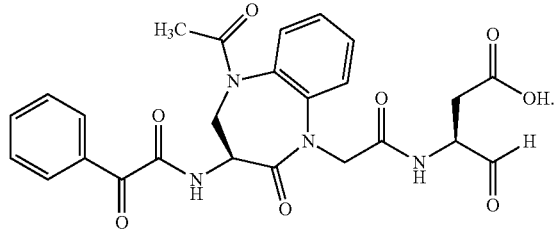

3. The compound according to claim 2, wherein:
m is 1;
C is a ring chosen from the set consisting of benzo, pyrido, and thieno, the ring optionally being singly or multiply substituted by halogen, —NH$_2$, —NH—R$_5$, or —NH—R$_9$, —OR$_{10}$, or —R$_9$, wherein R$_9$ is a straight or branched C$_{1-4}$ alkyl group, and R$_{10}$ is H or a straight or branched C$_{1-4}$ alkyl group;
T$_1$ is O or S;
R$_6$ is H;
R$_{11}$ is selected from the group consisting of —Ar$_4$, —(CH$_2$)$_{1-3}$—Ar$_4$, and —C(O)—Ar$_4$;
Ar$_2$ is (hh);
Y$_2$ is O;
each Ar$_3$ cyclic group is independently selected from the set consisting of phenyl, naphthyl, thienyl, quinolinyl, isoquinolinyl, thiazolyl, benzimidazolyl, thienothienyl, thiadiazolyl, benzotriazolyl, benzo[b]thiophenyl, benzofuranyl, and indolyl, and said cyclic group optionally being singly or multiply substituted by -Q$_1$;
each Ar$_4$ cyclic group is independently selected from the set consisting of phenyl, tetrazolyl, naphthyl, pyridinyl, oxazolyl, pyrimidinyl, or indolyl, and said cyclic group optionally being singly or multiply substituted by -Q$_1$;
each Q$_1$ is independently selected from the group consisting of —NH$_2$, —Cl, —F, —Br, —OH, —R$_9$, —NH—R$_5$ wherein R$_5$ is —C(O)—R$_{10}$ or —S(O)$_2$—R$_9$, —OR$_5$ wherein R$_5$ is
C(O)—R$_{10}$, —OR$_9$, —NHR$_9$, and

wherein each R$_9$ and R$_{10}$ are independently a —C$_{1-6}$ straight or branched alkyl group optionally substituted with —Ar$_3$ wherein Ar$_3$ is phenyl;
provided that when —Ar$_3$ is substituted with a Q$_1$ group which comprises one or more additional —Ar$_3$ groups, said additional —Ar$_3$ groups are not substituted with another —Ar$_3$.

4. The compound according to claim 3, wherein R$_8$ is selected from the group consisting of:
—C(O)—R$_{10}$,
—C(O)O—R$_9$,
—C(O)—CH$_2$—OR$_{10}$, and
—C(O)—CH$_2$C(O)—R$_9$.

5. The compound according to claim 4, wherein R$_8$ is —C(O)—CH$_2$—OR$_{10}$ and R$_{10}$ is —H or —CH$_3$.

6. The compound according to claim 3, wherein R$_3$ is —C(O)—Ar$_2$.

7. The compound according to claim 3, wherein R$_3$ is —C(O)CH$_2$-T$_1$-R$_{11}$.

8. The compound according to claim 3, wherein R$_3$ is —C(O)—H.

9. The compound according to claim 8, wherein R$_8$ is selected from the group consisting of:
—C(O)—R$_{10}$,
—C(O)O—R$_9$,
—C(O)—CH$_2$—OR$_{10}$, and
—C(O)—CH$_2$C(O)—R$_9$.

10. The compound according to claim 9, selected from the group consisting of:

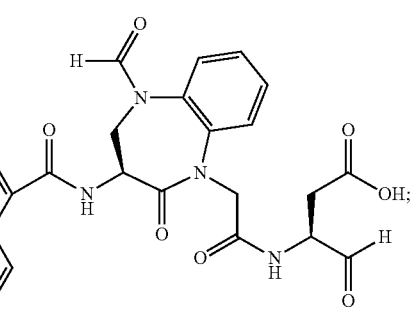

653

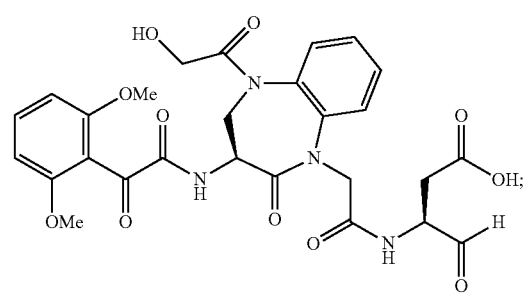

678

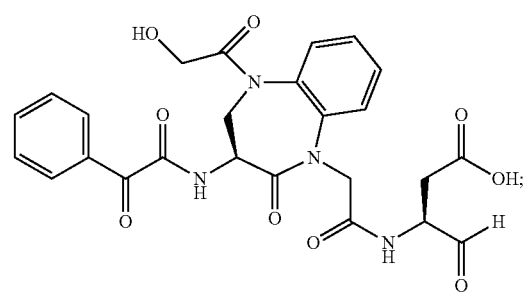

681

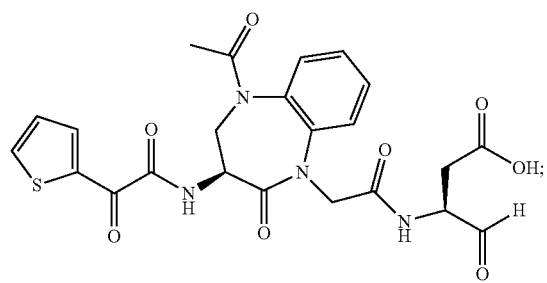

701

567
-continued
702
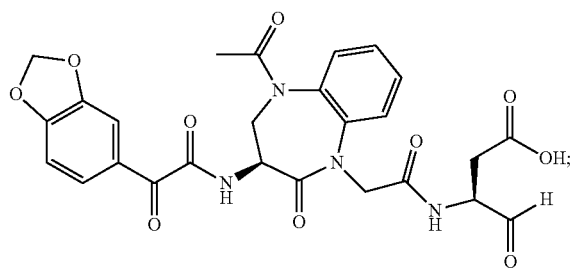
703
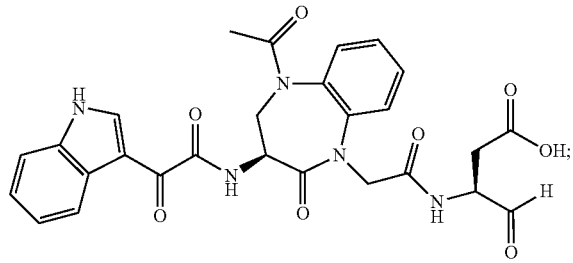
704
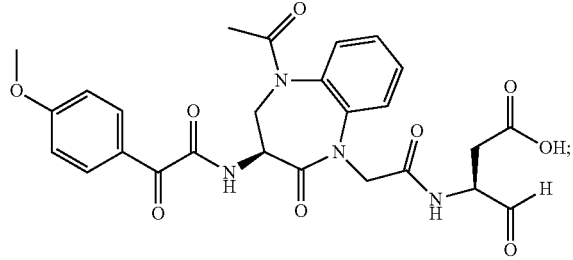
705
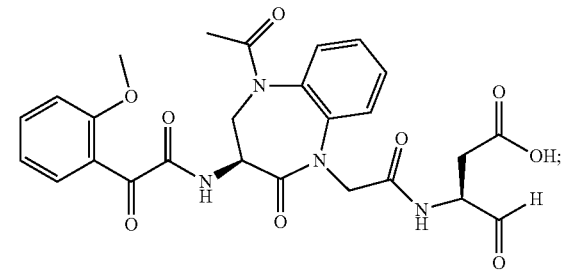
568
-continued
706
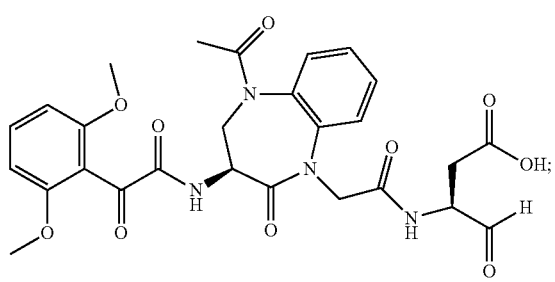
709
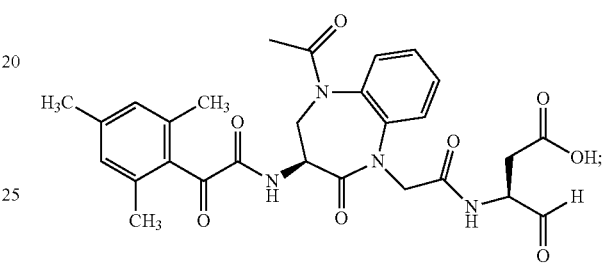
710
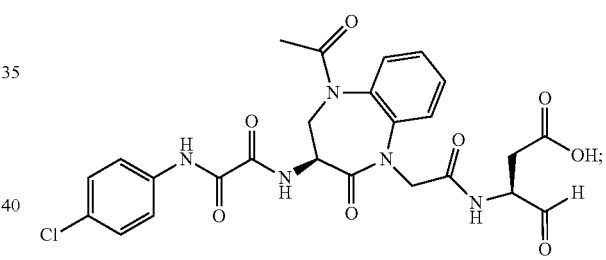
711
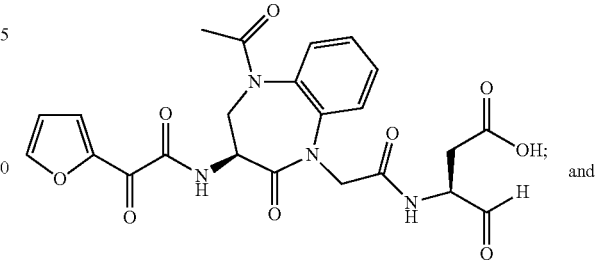
and
921
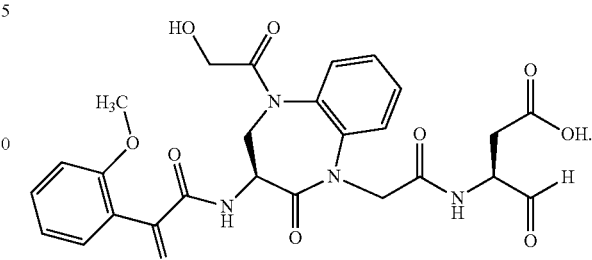

11. The compound according to claim 9, wherein $R_8$ is —C(O)—CH$_2$—OR$_{10}$ and $R_{10}$ is —H or —CH$_3$.

12. The compound according to claim 2, wherein the compound is

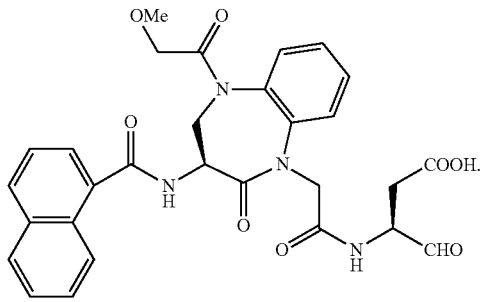

2201

13. A pharmaceutical composition comprising a compound according to any one of claims 1, 2, and 12 and a pharmaceutically acceptable carrier.

14. A method for treating a patient suffering from a disease selected from osteoarthritis, acute pancreatitis, chronic pancreatitis, rheumatoid arthritis, inflammatory bowel disease, Crohn's disease, ulcerative collitis, sepsis, septic shock, glomerulonephritis, multiple sclerosis, psoriasis, graft vs. host disease, and acute myelogenous leukemia comprising the step of administering to said patient a pharmaceutical composition according to claim 13.

15. The method according to claim 14, wherein the disease is selected from acute pancreatitis, rheumatoid arthritis, inflammatory bowel disease, ulcerative collitis, Crohn's disease, glomerulonephritis, psoriasis, and graft vs. host disease.

* * * * *

SEQUENCE LISTING

```
<160> NUMBER OF SEQ ID NOS: 13

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: modified with a chloromethylketone

<400> SEQUENCE: 1

Tyr Val Ala Asp
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: terminal carboxy reduced to aldehyde

<400> SEQUENCE: 2

Tyr Val Ala Asp
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (4)..(4)
<223> OTHER INFORMATION: terminal acid is reduced to an aldehyde

<400> SEQUENCE: 3

Asp Glu Val Asp
1

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 4

Asn Phe Gly Arg Leu
1               5

<210> SEQ ID NO 5
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: Succinylated
<220> FEATURE:
<221> NAME/KEY: MOD_RES
<222> LOCATION: (4)..(4)
<223> OTHER INFORMATION: terminal carboxy is derivatized as a
      p-nitroanilide

<400> SEQUENCE: 5

Tyr Val Ala Asp
1

<210> SEQ ID NO 6
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: terminal carboxy is derivatized with
      amino-4-methylcoumarin

<400> SEQUENCE: 6

Tyr Val Ala Asp
1

<210> SEQ ID NO 7
<211> LENGTH: 23
<212> TYPE: PRT
<213> ORGANISM: Artificial Sequence
<220> FEATURE:
<223> OTHER INFORMATION: Synthetic Peptide

<400> SEQUENCE: 7

Met Gly Ser Ser His His His His His His Ser Ser Gly Leu Val Pro
1               5                   10                  15

Arg Gly Ser His Met Leu Glu
```

```
<210> SEQ ID NO 8
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 8

Leu Val Pro Arg Gly Ser
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: derivatized with amino-4-methylcoumarin

<400> SEQUENCE: 9

Asp Glu Val Asp
1

<210> SEQ ID NO 10
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (4)..(4)
<223> OTHER INFORMATION: derivatized with amino-4-methylcoumarin

<400> SEQUENCE: 10

Tyr Val Ala Asp
1

<210> SEQ ID NO 11
<211> LENGTH: 31
<212> TYPE: DNA
<213> ORGANISM: Artificial Sequence
<220> FEATURE:
<223> OTHER INFORMATION: PCR Primer

<400> SEQUENCE: 11
ggaattccat atggctgcca tgtcagaaga c                              31

<210> SEQ ID NO 12
<211> LENGTH: 37
<212> TYPE: DNA
<213> ORGANISM: Artificial Sequence
<220> FEATURE:
<223> OTHER INFORMATION: PCR Primer

<400> SEQUENCE: 12
ggttaaccat atgctaactt tgatgtaagt tagtgag                        37

<210> SEQ ID NO 13
<211> LENGTH: 21
<212> TYPE: PRT
<213> ORGANISM: Artificial Sequence
<220> FEATURE:
<223> OTHER INFORMATION: Synthetic peptide
```

```
<400> SEQUENCE: 13

Met Gly Ser Ser His His His His His Ser Ser Gly Leu Val Pro
1               5                   10                  15

Arg Gly Ser His Met
            20
```